(12) United States Patent
Wells et al.

(10) Patent No.: US 12,297,457 B2
(45) Date of Patent: May 13, 2025

(54) ESOPHAGEAL TISSUE AND/OR ORGANOID COMPOSITIONS AND METHODS OF MAKING SAME

(71) Applicant: Children's Hospital Medical Center, Cincinnati, OH (US)

(72) Inventors: James M. Wells, Cincinnati, OH (US); Stephen Trisno, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 596 days.

(21) Appl. No.: 16/755,193

(22) PCT Filed: Oct. 5, 2018

(86) PCT No.: PCT/US2018/054635
§ 371 (c)(1),
(2) Date: Apr. 10, 2020

(87) PCT Pub. No.: WO2019/074793
PCT Pub. Date: Apr. 18, 2019

(65) Prior Publication Data
US 2021/0189349 A1    Jun. 24, 2021

Related U.S. Application Data

(60) Provisional application No. 62/570,182, filed on Oct. 10, 2017.

(51) Int. Cl.
| | | |
|---|---|---|
| *C12N 5/071* | (2010.01) | |
| *A01K 67/0271* | (2024.01) | |
| *A61K 35/37* | (2015.01) | |
| *A61P 1/04* | (2006.01) | |
| *C12N 5/00* | (2006.01) | |
| *G01N 33/50* | (2006.01) | |

(52) U.S. Cl.
CPC ........ *C12N 5/0679* (2013.01); *A01K 67/0271* (2013.01); *A61K 35/37* (2013.01); *A61P 1/04* (2018.01); *C12N 5/0062* (2013.01); *G01N 33/5044* (2013.01); *A01K 2207/30* (2013.01); *A01K 2227/105* (2013.01); *A01K 2267/0306* (2013.01); *C12N 2500/38* (2013.01); *C12N 2501/11* (2013.01); *C12N 2501/119* (2013.01); *C12N 2501/155* (2013.01); *C12N 2501/41* (2013.01); *C12N 2501/415* (2013.01); *C12N 2506/02* (2013.01); *C12N 2506/45* (2013.01); *C12N 2513/00* (2013.01); *C12N 2533/54* (2013.01)

(58) Field of Classification Search
None
See application file for complete search history.

(56) References Cited

U.S. PATENT DOCUMENTS

| | | |
|---|---|---|
| 5,912,227 A | 6/1999 | Croom, Jr. et al. |
| 5,942,435 A | 8/1999 | Wheeler |
| 6,607,501 B2 | 8/2003 | Gorsuch |
| 7,160,719 B2 | 1/2007 | Nyberg |
| 7,291,626 B1 | 11/2007 | Beachy et al. |
| 7,326,572 B2 | 2/2008 | Fisk et al. |
| 7,510,876 B2 | 3/2009 | D'Amour et al. |
| 7,514,185 B2 | 4/2009 | Fukushima et al. |
| 7,541,185 B2 | 6/2009 | D'Amour et al. |
| 7,625,753 B2 | 12/2009 | Kelly et al. |
| 7,695,958 B2 | 4/2010 | Funatsu et al. |
| 7,704,738 B2 | 4/2010 | D'Amour et al. |
| 7,727,998 B2 | 6/2010 | Moriya et al. |
| 7,776,592 B2 | 8/2010 | Wandinger-Ness et al. |
| 7,927,869 B2 | 4/2011 | Rosero |
| 7,985,585 B2 | 7/2011 | D'Amour et al. |
| 7,993,916 B2 | 8/2011 | Agulnick et al. |
| 8,187,878 B2 | 5/2012 | Dalton et al. |
| 8,216,826 B2 | 7/2012 | Lee et al. |
| 8,216,836 B2 | 7/2012 | D'Amour et al. |
| 8,298,822 B2 | 10/2012 | Kruse et al. |
| 8,318,492 B2 | 11/2012 | Choo et al. |
| 8,501,476 B2 | 8/2013 | Morgan et al. |
| 8,586,357 B2 | 11/2013 | D'Amour et al. |
| 8,603,809 B2 | 12/2013 | Kruse |
| 8,609,406 B2 | 12/2013 | Subramanian et al. |
| 8,609,413 B2 | 12/2013 | Suter et al. |
| 8,623,645 B2 | 1/2014 | D'Amour et al. |
| 8,632,645 B2 | 1/2014 | Daitou et al. |
| 8,633,024 B2 | 1/2014 | D'Amour et al. |
| 8,642,339 B2 | 2/2014 | Sato et al. |
| 8,647,873 B2 | 2/2014 | D'Amour et al. |

(Continued)

FOREIGN PATENT DOCUMENTS

| | | |
|---|---|---|
| CA | 2968065 A1 | 6/2016 |
| CN | 1299408 A | 6/2001 |

(Continued)

OTHER PUBLICATIONS

Weisenberg, Pathology Outlines, 2023.*

(Continued)

*Primary Examiner* — Ileana Popa
(74) *Attorney, Agent, or Firm* — Norton Rose Fulbright US LLP

(57) ABSTRACT

The instant disclosure relates to methods for converting mammalian definitive endoderm (DE) cells into specific tissue(s) or organ(s) through directed differentiation. In particular, the disclosure relates to formation of esophageal tissue and/or organoids formed from differentiated definitive endoderm.

25 Claims, 85 Drawing Sheets
Specification includes a Sequence Listing.

(56) References Cited

U.S. PATENT DOCUMENTS

| | | |
|---|---|---|
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rajagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,000,740 B2 | 6/2018 | Vallier et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 10,668,108 B2 | 6/2020 | Takebe et al. |
| 10,781,425 B2 | 9/2020 | Wells et al. |
| 11,053,477 B2 | 7/2021 | Wells et al. |
| 11,066,650 B2 | 7/2021 | Wells et al. |
| 2003/0129751 A1 | 7/2003 | Grikscheit et al. |
| 2003/0228685 A1 | 12/2003 | Nyberg |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2008/0195224 A1 | 8/2008 | Teitelbaum et al. |
| 2008/0286366 A1 | 11/2008 | Fischer et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2009/0311765 A1 | 12/2009 | Maguire et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0125286 A1 | 5/2011 | Selden et al. |
| 2011/0151564 A1 | 6/2011 | Menu et al. |
| 2011/0218512 A1 | 9/2011 | Tullis et al. |
| 2011/0231942 A1 | 9/2011 | He et al. |
| 2011/0294735 A1 | 12/2011 | Marsh et al. |
| 2011/0300543 A1 | 12/2011 | Wang |
| 2012/0009086 A1 | 1/2012 | Nyberg et al. |
| 2012/0009618 A1 | 1/2012 | Yu et al. |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0201890 A1 | 8/2012 | Williams et al. |
| 2012/0264209 A1 | 10/2012 | Odorico et al. |
| 2012/0270295 A1 | 10/2012 | Choo et al. |
| 2012/0291096 A1 | 11/2012 | Boldyrev et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2013/0330823 A1 | 12/2013 | Rezania |
| 2014/0038279 A1 | 2/2014 | Ingber et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0328808 A1 | 11/2014 | Watanabe et al. |
| 2014/0336282 A1 | 11/2014 | Ewald et al. |
| 2014/0369973 A1 | 12/2014 | Bernstein et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0185714 A1 | 7/2015 | Geveci |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0247124 A1 | 9/2015 | Snoeck et al. |
| 2015/0273071 A1 | 10/2015 | Green et al. |
| 2015/0273127 A1 | 10/2015 | Flieg et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0046905 A1 | 2/2016 | Inoue et al. |
| 2016/0060707 A1 | 3/2016 | Goldenberg et al. |
| 2016/0068805 A1 | 3/2016 | Martin et al. |

(56) References Cited

U.S. PATENT DOCUMENTS

| | | |
|---|---|---|
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0186140 A1 | 6/2016 | Dalton et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0244724 A1 | 8/2016 | Ferro |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0298087 A1 | 10/2016 | Qu et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0202885 A1 | 7/2017 | Agulnick |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0260509 A1 | 9/2017 | Hung et al. |
| 2017/0266145 A1 | 9/2017 | Nahmias et al. |
| 2017/0266970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0292116 A1 | 10/2017 | Wells et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2017/0362574 A1 | 12/2017 | Sareen et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0043357 A1 | 2/2018 | Bocchi et al. |
| 2018/0059119 A1 | 3/2018 | Tak et al. |
| 2018/0112187 A1 | 4/2018 | Smith et al. |
| 2018/0171302 A1 | 6/2018 | Accili |
| 2018/0179496 A1 | 6/2018 | Rajesh et al. |
| 2018/0193421 A1 | 7/2018 | Soula |
| 2018/0250410 A1 | 9/2018 | Borros Gomez et al. |
| 2018/0258400 A1 | 9/2018 | Ng et al. |
| 2018/0344901 A1 | 12/2018 | Spence et al. |
| 2019/0031992 A1 | 1/2019 | Kerns et al. |
| 2019/0078055 A1 | 3/2019 | Wells et al. |
| 2019/0093076 A1 | 3/2019 | Schulz |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |
| 2020/0040309 A1 | 2/2020 | Takebe et al. |
| 2020/0056157 A1 | 2/2020 | Takebe et al. |
| 2020/0102543 A1 | 4/2020 | Okazaki et al. |
| 2020/0149004 A1 | 5/2020 | Spence et al. |
| 2020/0190478 A1 | 6/2020 | Wells et al. |
| 2020/0199537 A1 | 6/2020 | Takebe et al. |
| 2020/0199538 A1 | 6/2020 | Ng et al. |
| 2021/0008123 A1 | 1/2021 | Takebe et al. |
| 2021/0030811 A1 | 2/2021 | Kim et al. |
| 2021/0096126 A1 | 4/2021 | Takebe et al. |
| 2021/0115366 A1 | 4/2021 | Mahe et al. |
| 2021/0180026 A1 | 6/2021 | Takebe et al. |
| 2021/0292714 A1 | 9/2021 | Takebe et al. |
| 2021/0324334 A1 | 10/2021 | Takebe et al. |
| 2021/0363490 A1 | 11/2021 | Yoshihara et al. |
| 2021/0371815 A1 | 12/2021 | Holloway et al. |
| 2021/0395695 A1 | 12/2021 | Kim et al. |
| 2022/0041684 A1 | 2/2022 | Patterson |
| 2022/0056420 A1 | 2/2022 | Wells et al. |
| 2022/0090011 A1 | 3/2022 | Ngan et al. |
| 2022/0275345 A1 | 9/2022 | Mayhew et al. |

FOREIGN PATENT DOCUMENTS

| | | |
|---|---|---|
| CN | 101600461 A | 12/2009 |
| CN | 101855554 A | 10/2010 |
| CN | 102307990 A | 1/2012 |
| CN | 102439135 A | 5/2012 |
| CN | 102459574 A | 5/2012 |
| CN | 102740888 A | 10/2012 |
| CN | 103068970 A | 4/2013 |
| CN | 103154237 A | 6/2013 |
| CN | 103561751 A | 2/2014 |
| CN | 104387451 A | 3/2015 |
| CN | 105209605 A | 12/2015 |
| CN | 105985395 A | 10/2016 |
| CN | 109415685 A | 3/2019 |
| CN | 110371967 A | 10/2019 |
| CN | 110381967 A | 10/2019 |
| CN | 110582564 A | 12/2019 |
| EP | 1063289 A1 | 12/2000 |
| EP | 2393917 A2 | 12/2011 |
| EP | 2393917 B1 | 4/2016 |
| EP | 3228306 A1 | 10/2017 |
| JP | 2003521673 A | 7/2003 |
| JP | 2004166717 A | 6/2004 |
| JP | 2008503203 A | 2/2008 |
| JP | 2008505638 A | 2/2008 |
| JP | 2012516685 A | 7/2012 |
| JP | 2012254081 A | 12/2012 |
| JP | 2013066414 A | 4/2013 |
| JP | 2013511969 A | 4/2013 |
| JP | 2013521810 A | 6/2013 |
| JP | 2013528397 A | 7/2013 |
| JP | 2013535201 A | 9/2013 |
| JP | 2014516562 A | 7/2014 |
| JP | 2014233281 A | 12/2014 |

(56) References Cited

FOREIGN PATENT DOCUMENTS

| | | |
|---|---|---|
| JP | 2019000014 A | 1/2019 |
| JP | 2020516247 A | 6/2020 |
| JP | 2020523000 A | 8/2020 |
| JP | 7068305 B2 | 5/2022 |
| JP | 7148552 B2 | 10/2022 |
| KR | 20060114355 A | 11/2006 |
| WO | WO-9207615 A1 | 5/1992 |
| WO | WO-9821312 A1 | 5/1998 |
| WO | 9945100 A1 | 9/1999 |
| WO | WO-9949807 A2 | 10/1999 |
| WO | 03046141 A2 | 6/2003 |
| WO | WO-03082201 A2 | 10/2003 |
| WO | WO-2004020614 A1 | 3/2004 |
| WO | WO-2005001072 A1 | 1/2005 |
| WO | 2005063971 A2 | 7/2005 |
| WO | WO-2005081970 A2 | 9/2005 |
| WO | WO-2005097974 A2 | 10/2005 |
| WO | WO-2005113747 A2 | 12/2005 |
| WO | WO-2006126236 A1 | 11/2006 |
| WO | 2008073352 A1 | 6/2008 |
| WO | WO-2008075339 A2 | 6/2008 |
| WO | WO-2009022907 A2 | 2/2009 |
| WO | WO-2009086596 A1 | 7/2009 |
| WO | WO-2009146911 A2 | 12/2009 |
| WO | WO-2010008905 A2 | 1/2010 |
| WO | WO-2010090513 A2 | 8/2010 |
| WO | WO-2010094694 A1 | 8/2010 |
| WO | WO-2010127399 A1 | 11/2010 |
| WO | 2010136583 A2 | 12/2010 |
| WO | WO-2010143747 A1 | 12/2010 |
| WO | WO-2011050672 A1 | 5/2011 |
| WO | 2011064309 A1 | 6/2011 |
| WO | WO-2011116930 A1 | 9/2011 |
| WO | WO-2011139628 A1 | 11/2011 |
| WO | WO-2011140441 A2 | 11/2011 |
| WO | WO-2012014076 A2 | 2/2012 |
| WO | WO-2012027474 A1 | 3/2012 |
| WO | WO-2012089669 A1 | 7/2012 |
| WO | WO-2012118799 A2 | 9/2012 |
| WO | WO-2012154834 A1 | 11/2012 |
| WO | WO-2012155110 A1 | 11/2012 |
| WO | WO-2012166903 A1 | 12/2012 |
| WO | WO-2012168930 A2 | 12/2012 |
| WO | WO-2012178215 A1 | 12/2012 |
| WO | WO-2013040087 A2 | 3/2013 |
| WO | WO-2013067498 A1 | 5/2013 |
| WO | WO-2013086486 A1 | 6/2013 |
| WO | WO-2013086502 A1 | 6/2013 |
| WO | WO-2013093812 A2 | 6/2013 |
| WO | WO-2013096741 A2 | 6/2013 |
| WO | WO-2013127921 A1 | 9/2013 |
| WO | WO-2013155060 A1 | 10/2013 |
| WO | WO-2013174794 A1 | 11/2013 |
| WO | WO-2013176772 A1 | 11/2013 |
| WO | WO-2013192290 A1 | 12/2013 |
| WO | WO-2014013334 A2 | 1/2014 |
| WO | WO-2014018691 A1 | 1/2014 |
| WO | WO-2014048637 A1 | 4/2014 |
| WO | WO-2014053596 A1 | 4/2014 |
| WO | WO-2014062138 A1 | 4/2014 |
| WO | WO-2014082096 A1 | 5/2014 |
| WO | WO-2014083132 A1 | 6/2014 |
| WO | WO-2014090993 A1 | 6/2014 |
| WO | WO-2014093595 A1 | 6/2014 |
| WO | WO-2014093622 A2 | 6/2014 |
| WO | WO-2014093655 A2 | 6/2014 |
| WO | WO-2014093661 A2 | 6/2014 |
| WO | WO-2014093712 A1 | 6/2014 |
| WO | WO-2014127170 A1 | 8/2014 |
| WO | 2014148646 A1 | 9/2014 |
| WO | WO-2014151921 A1 | 9/2014 |
| WO | WO-2014153230 A1 | 9/2014 |
| WO | WO-2014153294 A1 | 9/2014 |
| WO | WO-2014159356 A1 | 10/2014 |
| WO | WO-2014173907 A1 | 10/2014 |
| WO | WO-2014182885 A2 | 11/2014 |
| WO | WO-2014197934 A1 | 12/2014 |
| WO | WO-2014199622 A1 | 12/2014 |
| WO | WO-2014204728 A1 | 12/2014 |
| WO | WO-2014204729 A1 | 12/2014 |
| WO | WO-2015021358 A2 | 2/2015 |
| WO | WO-2015060790 A1 | 4/2015 |
| WO | WO-2015071474 A2 | 5/2015 |
| WO | WO-2015075175 A1 | 5/2015 |
| WO | WO-2015076388 A1 | 5/2015 |
| WO | WO-2015108893 A1 | 7/2015 |
| WO | WO-2015123183 A1 | 8/2015 |
| WO | WO-2015129822 A1 | 9/2015 |
| WO | WO-2015130919 A1 | 9/2015 |
| WO | WO-2015135893 A1 | 9/2015 |
| WO | WO-2015138032 A2 | 9/2015 |
| WO | WO-2015152954 A1 | 10/2015 |
| WO | WO-2015156929 A1 | 10/2015 |
| WO | WO-2015157163 A1 | 10/2015 |
| WO | WO-2015168022 A1 | 11/2015 |
| WO | WO-2015173425 A1 | 11/2015 |
| WO | 2015189320 A1 | 12/2015 |
| WO | WO-2015183920 A2 | 12/2015 |
| WO | WO-2015184273 A1 | 12/2015 |
| WO | WO-2015184375 A2 | 12/2015 |
| WO | WO-2015185714 A1 | 12/2015 |
| WO | WO-2015196012 A1 | 12/2015 |
| WO | WO-2015200901 A1 | 12/2015 |
| WO | WO-2016011377 A1 | 1/2016 |
| WO | WO-2016015158 A1 | 2/2016 |
| WO | WO-2016030525 A1 | 3/2016 |
| WO | WO-2016033163 A1 | 3/2016 |
| WO | WO-2016056999 A1 | 4/2016 |
| WO | WO-2016057571 A1 | 4/2016 |
| WO | WO-2016061464 A1 | 4/2016 |
| WO | WO-2016073989 A2 | 5/2016 |
| WO | WO-2016083612 A1 | 6/2016 |
| WO | WO-2016083613 A2 | 6/2016 |
| WO | WO-2016085765 A1 | 6/2016 |
| WO | WO-2016094948 A1 | 6/2016 |
| WO | WO-2016103002 A1 | 6/2016 |
| WO | WO-2016103269 A1 | 6/2016 |
| WO | WO-2016115326 A1 | 7/2016 |
| WO | WO-2016121512 A1 | 8/2016 |
| WO | 2016141131 A1 | 9/2016 |
| WO | WO-2016140716 A1 | 9/2016 |
| WO | WO-2016141084 A1 | 9/2016 |
| WO | WO-2016141137 A1 | 9/2016 |
| WO | WO-2016141224 A1 | 9/2016 |
| WO | WO-2016144769 A1 | 9/2016 |
| WO | WO-2016164413 A1 | 10/2016 |
| WO | WO-2016168950 A1 | 10/2016 |
| WO | WO-2016174604 A1 | 11/2016 |
| WO | WO-2016176208 A1 | 11/2016 |
| WO | WO-2016183143 A1 | 11/2016 |
| WO | 2016204809 A1 | 12/2016 |
| WO | WO-2016193441 A2 | 12/2016 |
| WO | WO-2016207621 A1 | 12/2016 |
| WO | WO-2016210313 A1 | 12/2016 |
| WO | WO-2016210416 A2 | 12/2016 |
| WO | WO-2017009263 A1 | 1/2017 |
| WO | WO-2017023803 A1 | 2/2017 |
| WO | WO-2017036533 A1 | 3/2017 |
| WO | WO-2017037295 A1 | 3/2017 |
| WO | WO-2017041041 A1 | 3/2017 |
| WO | WO-2017048193 A1 | 3/2017 |
| WO | WO-2017048322 A1 | 3/2017 |
| WO | WO-2017049243 A1 | 3/2017 |
| WO | WO-2017059171 A1 | 4/2017 |
| WO | WO-2017060884 A1 | 4/2017 |
| WO | WO-2017066507 A1 | 4/2017 |
| WO | WO-2017066659 A1 | 4/2017 |
| WO | WO-2017070007 A2 | 4/2017 |
| WO | WO-2017070224 A1 | 4/2017 |
| WO | WO-2017070337 A1 | 4/2017 |
| WO | WO-2017070471 A1 | 4/2017 |
| WO | WO-2017070506 A1 | 4/2017 |
| WO | WO-2017070633 A2 | 4/2017 |
| WO | 2017083696 A1 | 5/2017 |

(56) References Cited

FOREIGN PATENT DOCUMENTS

| | | |
|---|---|---|
| WO | WO-2017075389 A1 | 5/2017 |
| WO | WO-2017077535 A1 | 5/2017 |
| WO | WO-2017079632 A1 | 5/2017 |
| WO | WO-2017083705 A1 | 5/2017 |
| WO | WO-2017083838 A1 | 5/2017 |
| WO | WO-2017096192 A1 | 6/2017 |
| WO | WO-2017096282 A1 | 6/2017 |
| WO | WO-2017112901 A1 | 6/2017 |
| WO | WO-2017115982 A1 | 7/2017 |
| WO | WO-2017117333 A1 | 7/2017 |
| WO | WO-2017117547 A1 | 7/2017 |
| WO | WO-2017117571 A1 | 7/2017 |
| WO | WO-2017120543 A1 | 7/2017 |
| WO | WO-2017121754 A1 | 7/2017 |
| WO | WO-2017123791 A1 | 7/2017 |
| WO | WO-2017136462 A2 | 8/2017 |
| WO | WO-2017136479 A1 | 8/2017 |
| WO | WO-2017139455 A1 | 8/2017 |
| WO | WO-2017139638 A1 | 8/2017 |
| WO | WO-2017142069 A1 | 8/2017 |
| WO | WO-2017143100 A1 | 8/2017 |
| WO | WO-2017149025 A1 | 9/2017 |
| WO | WO-2017153992 A1 | 9/2017 |
| WO | WO-2017160234 A1 | 9/2017 |
| WO | WO-2017160671 A1 | 9/2017 |
| WO | WO-2017172638 A1 | 10/2017 |
| WO | WO-2017174609 A1 | 10/2017 |
| WO | WO-2017175876 A1 | 10/2017 |
| WO | WO-2017176810 A1 | 10/2017 |
| WO | WO-2017184586 A1 | 10/2017 |
| WO | WO-2017192997 A1 | 11/2017 |
| WO | WO-2017205511 A1 | 11/2017 |
| WO | WO-2017218287 A1 | 12/2017 |
| WO | WO-2017220586 A1 | 12/2017 |
| WO | WO-2018011558 A1 | 1/2018 |
| WO | WO-2018019704 A1 | 2/2018 |
| WO | WO-2018026947 A1 | 2/2018 |
| WO | WO-2018027023 A1 | 2/2018 |
| WO | WO-2018027112 A1 | 2/2018 |
| WO | WO-2018035574 A1 | 3/2018 |
| WO | WO-2018038042 A1 | 3/2018 |
| WO | WO-2018044685 A1 | 3/2018 |
| WO | WO-2018044885 A1 | 3/2018 |
| WO | WO-2018044937 A2 | 3/2018 |
| WO | WO-2018044940 A1 | 3/2018 |
| WO | WO-2018085615 A1 | 5/2018 |
| WO | WO-2018085622 A1 | 5/2018 |
| WO | WO-2018085623 A1 | 5/2018 |
| WO | WO-2018091677 A1 | 5/2018 |
| WO | WO-2018094522 A1 | 5/2018 |
| WO | WO-2018106628 A1 | 6/2018 |
| WO | WO-2018115852 A1 | 6/2018 |
| WO | 2018170280 A1 | 9/2018 |
| WO | WO-2018191673 A1 | 10/2018 |
| WO | WO-2018197544 A1 | 11/2018 |
| WO | WO-2018200481 A1 | 11/2018 |
| WO | WO-2018226267 A1 | 12/2018 |
| WO | WO-2018229251 A1 | 12/2018 |
| WO | WO-2019060336 A1 | 3/2019 |
| WO | WO-2019074793 A1 | 4/2019 |
| WO | WO-2019126626 A1 | 6/2019 |
| WO | 2019140151 A1 | 7/2019 |
| WO | WO-2020023245 A1 | 1/2020 |
| WO | WO-2020056158 A1 | 3/2020 |
| WO | WO-2020069285 A1 | 4/2020 |
| WO | WO-2020100481 A1 | 5/2020 |
| WO | WO-2020154374 A1 | 7/2020 |
| WO | WO-2020160371 A1 | 8/2020 |
| WO | WO-2020227711 A1 | 11/2020 |
| WO | WO-2020243633 A1 | 12/2020 |
| WO | WO-2020247528 A1 | 12/2020 |
| WO | WO-2021030373 A1 | 2/2021 |
| WO | WO-2021041443 A2 | 3/2021 |
| WO | WO-2021262676 A1 | 12/2021 |
| WO | 2022261471 A2 | 12/2022 |
| WO | WO-2023030158 A1 | 3/2023 |

OTHER PUBLICATIONS

Bain C.C., et al., "Constant Replenishment from Circulating Monocytes Maintains the Macrophage Pool in Adult Intestine," Nat Immunol, Oct. 2014, vol. 15 (10), pp. 929-937.

Bain C.C., et al., "Resident and Pro-Inflammatory Macrophages in the Colon Represent Alternative Context-Dependent Fates of the Same Ly6Chi Monocyte Precursors," Mucosal Immunology, May 2013, vol. 6 (3), pp. 498-510.

Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.

Bort R., et al., "Hex Homeobox Gene-Dependent Tissue Positioning is Required for Organogenesis of the Ventral Pancreas," Development, Jan. 2004, vol. 131 (4), pp. 797-806.

Bujko A., et al., "Transcriptional and Functional Profiling Defines Human Small Intestinal Macrophage Subsets," Journal of Experimental Medicine, 2018, vol. 215 (2), pp. 441-458.

Bulmer J.N., et al., "Macrophage Populations in the Human Placenta and Amniochorion," Clinical Experimental Immunology, 1984, vol. 57 (2), pp. 393-403.

Camp J.G., et al., "Multilineage Communication Regulates Human Liver Bud Development from Pluripotency," Nature, 2017, vol. 546 (7659), pp. 533-538.

Campbell E.L., et al., "Transmigrating Neutrophils Shape the Mucosal Microenvironment Through Localized Oxygen Depletion to Influence Resolution of Inflammation," Immunity, 2014, vol. 40 (1), pp. 66-77.

Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.

Cumano A., et al., "Lymphoid Potential, Probed before Circulation in Mouse, Is Restricted to Caudal Intraembryonic Splanchnopleura," Cell, Sep. 20, 1996, vol. 86 (6), pp. 907-916.

Davies L.C., et al., "Tissue-Resident Macrophages," Nat Immunol, Oct. 2013, vol. 14 (10), pp. 986-995.

DeSchepper S., et al., "Self-Maintaining Gut Macrophages Are Essential for Intestinal Homeostasis," Cell, Oct. 4, 2018, vol. 175 (2), pp. 400-415.

Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.

Glocker E.O., et al., "Inflammatory Bowel Disease and Mutations Affecting the Interleukin-10 Receptor," N Engl J Med, Nov. 19, 2009, vol. 361 (21), pp. 2033-2045.

Hentsch B., et al., "Hlx Homeo Box Gene is Essential for an Inductive Tissue Interaction that Drives Expansion of Embryonic Liver and Gut," Genes & Development, 1996, vol. 10 (1), pp. 70-79.

Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.

Hoeffel G., et al., "C-Myb+ Erythro-Myeloid Progenitor-Derived Fetal Monocytes Give Rise to Adult Tissue-Resident Macrophages," Immunity, Apr. 21, 2015, vol. 42 (4), pp. 665-678.

Iacovino M., et al., "HoxA3 is an Apical Regulator of Hemogenic Endothelium," Nat Cell Biol, Jan. 2011, vol. 13 (1), pp. 72-78.

Jørgensen M.C., et al., "Neurog3-Dependent Pancreas Dysgenesis Causes Ectopic Pancreas in Hes1 Mutant Mice," Development, 2018, vol. 145 (17), 11 pages.

Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.

Lanctot P.M., et al., "The Glycans of Stem Cells," Curr Opin Chem Biol, Aug. 2007, vol. 11(4), pp. 373-380.

(56) References Cited

OTHER PUBLICATIONS

Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.
Maheshwari A., et al., "TGF-β2 Suppresses Macrophage Cytokine Production and Mucosal Inflammatory Responses In the Developing Intestine," Gastroenterology, 2011, vol. 140 (1), pp. 242-253.
Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.
Martin M.J., et al., "Human Embryonic Stem Cells Express an Immunogenic Nonhuman Sialic Acid," Nature Medicine, Feb. 2005, vol. 11(2), pp. 228-232.
Miller A.J., et al., "Generation of Lung Organoids from Human Pluripotent Stem Cells in Vitro," Nature Protocols, Feb. 28, 2019, vol. 14, No. 2, pp. 518-540.
Montalbano G., et al., "Synthesis of Bioinspired Collagen/Alginate/Fibrin Based Hydrogels for Soft Tissue Engineering," Material Science & Engineering, C 91, 2018, pp. 236-246.
Nissim S., et al., "Iterative Use of Nuclear Receptor Nr5a2 Regulates Multiple Stages of Liver and Pancreas Development," Development Biology, Jul. 26, 2016, vol. 418 (1), pp. 108-123.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Perdiguero E.G., et al., "Development and Maintenance of Resident Macrophages," Nature Immunology, Jan. 2016, vol. 17 (1), pp. 2-8.
Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.
Rankin S.A., et al., "A Retinoic Acid-Hedgehog Cascade Coordinates Mesoderm-Inducing Signals and Endoderm Competence During Lung Specification," Cell Reports, Jun. 28, 2016, vol. 16 (1), pp. 66-78.
San Roman A.K., et al., "Boundaries, Junctions and Transitions in the Gastrointestinal Tract," Exp Cell Res, Nov. 15, 2011, vol. 317 (19), pp. 2711-2718.
Shaw T.N., et al., "Tissue-Resident Macrophages in the Intestine are Long Lived and Defined by Tim-4 and CD4 Expression," Journal of Experimental Medicine, 2018, vol. 215 (6), pp. 1507-1518.
Sheng J., et al., "Most Tissue-Resident Macrophages Except Microglia Are Derived from Fetal Hematopoietic Stem Cells," Immunity, Aug. 18, 2015, vol. 43 (2), pp. 382-393.
Shih H.P., et al., "A Gene Regulatory Network Cooperatively Controlled by Pdx1 and Sox9 Governs Lineage Allocation of Foregut Progenitor Cells," Cell Reports, Oct. 13, 2015, vol. 13 (2), 326-336.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.
Spence J.R., et al., "Sox17 Regulates Organ Lineage Segregation of Ventral Foregut Progenitor Cells," Dev Cell, Jul. 2009, vol. 17 (1), pp. 62-74.
Sturgeon C.M., et al., "Wnt Signaling Controls the Specification of Definitive and Primitive Hematopoiesis from Human Pluripotent Stem Cells," Natural Biotechnology, Jun. 2014, vol. 32 (6), pp. 554-561.
Sumazaki R., et al., "Conversion of Biliary System to Pancreatic Tissue in Hes1-Deficient Mice," Nature Genetics, Jan. 2004, vol. 36 (1), pp. 83-87.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.

Tepass U., et al., "Epithelium Formation in the *Drosophila* Midgut Depends on the Interaction of Endoderm and Mesoderm," Development, 1994, vol. 120 (3), pp. 579-590.
Thamm K., et al., "Notch Signaling During Larval and Juvenile Development in the Polychaete Annelid *Capitella* sp. I," Developmental Biology, 2008, vol. 320 (1), pp. 304-318.
Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Zhang Y., et al., "Development and Stem Cells of the Esophagus," Seminars in Cell & Developmental Biology, Dec. 19, 2016, vol. 66, pp. 25-35.
Zhang Z., et al., "Syndecan4 Coordinates Wnt/JNK and BMP Signaling to Regulate Foregut Progenitor Development," Developmental Biology, 2016, vol. 416 (1), pp. 187-199.
Ader M., et al., "Modeling Human Development in 3D Culture," Current Opinion in Cell Biology, Dec. 2014, vol. 31, pp. 23-28.
Adorini L., et al., "Farnesoid X Receptor Targeting to Treat Non-alcoholic Steatohepatitis," Drug Discovery Today, Sep. 2012, vol. 17 (17/18), pp. 988-997.
Agopian V.G., et al., "Intestinal Stem Cell Organoid Transplantation Generates Neomucosa in Dogs," Journal of Gastrointestinal Surgery, Jan. 23, 2009, vol. 13 (5), pp. 971-982.
Ahnfelt-Ronne J., et al., "An Improved Method for Three-Dimensional Reconstruction of Protein Expression Patterns in Intact Mouse and Chicken Embryos and Organs," Journal of Histochemistry and Cytochemistry, 2007, vol. 55 (9), pp. 925-930.
Ajmera V., et al., "Novel Plasma Biomarkers Associated with Liver Disease Severity in Adults with Nonalcoholic Fatty Liver Disease," Hepatology, Jan. 2017, vol. 65 (1), pp. 65-77.
Aleo M.D., et al., "Human Drug-Induced Liver Injury Severity is Highly Associated with Dual Inhibition of Liver Mitochondrial Function and Bile Salt Export Pump," Hepatology, 2014, vol. 60 (3), pp. 1015-1022.
Alessi D.R., et al., "LKB1-Dependent Signaling Pathways," Annual Review of Biochemistry, 2006, vol. 75, pp. 137-163.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Allard J., et al., "Immunohistochemical Toolkit for Tracking and Quantifying Xenotransplanted Human Stem Cells," Regenerative Medicine, 2014, vol. 9(4), pp. 437-452.
Altman G. H., et al., "Cell Differentiation by Mechanical Stress," The FASEB Journal, 2001, vol. 16 (2), pp. 270-272.
Ameri J., et al., "FGF2 Specifies HESC-Derived Definitive Endoderm into Foregut/Midgut Cell Lineages in a Concentration-Dependent Manner," Stem Cells, Nov. 2009, vol. 28 (1), pp. 45-56.
Amieva M.R., et al., "Helicobacter Pylori Enter and Survive within Multivesicular Vacuoles of Epithelial cells," Cellular Microbiology, Oct. 4, 2002, vol. 4 (10), pp. 677-690.
An W.F., et al., "Discovery of Potent and Highly Selective Inhibitors of GSK3b," Molecular Libraries, Probe Report, May 2014, 115 Pages.
Anderson G., et al., "Loss of Enteric Dopaminergic Neurons and Associated Changes in Colon Motility in an MPTP Mouse Model of Parkinson's Disease," Experimental Neurology, Sep. 2007, vol. 207 (1), 16 pages.
Andrews P.W., et al., "Embryonic Stem (ES) cells and Embryonal Carcinoma (EC) Cells: Opposite Sides of the same Coin," Biochemical Society Transactions, 2005, vol. 33 (6), pp. 1526-1530.
Ang S.L., et al., "The Formation and Maintenance of the Definitive Endoderm Lineage in the Mouse: Involvement of HNF3/Forkhead Proteins," Development, Company of Biologist Limited, 1993, vol. 119, pp. 1301-1315.

(56) References Cited

OTHER PUBLICATIONS

Anlauf M., et al., "Chemical Coding of the Human Gastrointestinal Nervous System: Cholinergic, VIPergic, and Catecholaminergic Phenotypes," The Journal of Comparative Neurology, 2003, vol. 459, pp. 90-111.

Aronson B.E., et al., "GATA4 Represses an ileal Program of Gene Expression in the Proximal Small Intestine by Inhibiting the Acetylation of Histone H3, Lysine 27," Biochimica et Biophysica Acta, Nov. 2014, vol. 1839 (11), pp. 1273-1282.

Arora N., et al., "A Process Engineering Approach to Increase Organoid Yield," Technical and Resources, 2017, vol. 144, pp. 1128-1136.

Arroyo J.D., et al., "Argonaute2 Complexes Carry a Population of Circulating MicroRNAs Independent of Vesicles in Human Plasma," PNAS, 2011, vol. 108 (12), pp. 5003-5008.

Asai A., et al., "Paracrine Signals Regulate Human Liver Organoid Maturation from Induced Pluripotent Stem Cells," Human Development, 2017, vol. 144, pp. 1056-1064.

Aurora M., et al., "hPSC-Derived Lung and Intestinal Organoids as Models of Human Fetal Tissue," Developmental Biology, 2016, vol. 420, pp. 230-238.

Avansino J.R., et al., "Orthotopic Transplantation of Intestinal Mucosal Organoids in Rodents," Surgery, Sep. 2006, vol. 140 (3), pp. 423-434.

Baetge G., et al., "Transient Catecholaminergic (TC) Cells in the Vagus Nerves and Bowel of Fetal Mice: Relationship to the Development of Enteric Neurons," Developmental Biology, 1989, vol. 132, pp. 189-211.

Bain G., "Embryonic Stem Cells Express Neuronal Properties in Vitro," Developmental Biology, 1995, vol. 168, pp. 842-357.

Bajpai R., et al., "CHD7 Cooperates with PBAF to Control Multipotent Neural Crest Formation," Nature, Feb. 18, 2010, vol. 463, pp. 958-962.

Bansal D., et al., "An Ex-Vivo Human Intestinal Model to Study Entamoeba Histolytica Pathogenesis," PLoS Neglected Tropical Diseases, Nov. 17, 2009, vol. 3 (11), 11 pages.

Baptista P.M., et al., "The Use of Whole Organ Decellularization for the Generation of a Vascularized Liver Organoid," Hepatology, 2011, vol. 53 (2), pp. 604-617.

Bar-Ephraim Y.E., et al., "Modelling Cancer Immunomodulation using Epithelial Organoid Cultures," bioRxiv, Aug. 7, 2018, pp. 1-13.

Barker N., et al., "Lgr5(+ve) Stem Cells Drive Self-Renewal in the Stomach and Build Long-Lived Gastric Units In Vitro," Cell Stem Cell, Jan. 8, 2010, vol. 6, pp. 25-36.

Barker N., et al., "Tissue-Resident Adult Stem Cell Populations of Rapidly Self-Renewing Organs," Cell Stem Cell, Dec. 3, 2010, vol. 7, pp. 656-670.

Barlow A.J., et al., "Critical Numbers of Neural Crest Cells are Required in the Pathways from the Neural Tube to the Foregut to Ensure Complete Enteric Nervous System Formation," Development, 2008, vol. 135, pp. 1681-1691.

Bartfeld S., et al., "In Vitro Expansion of Human Gastric Epithelial Stem Cells and Their Responses to Bacterial Infection," Gastroenterology, Jan. 2015, vol. 148 (1), pp. 126-136.

Bartfeld S., et al., "Stem Cell-Derived Organoids and their Application for Medical Research and Patient Treatment," Journal of Molecular Medicine, 2017, vol. 95, pp. 729-738.

Barth C.A., et al., "Transcellular Transport of Fluorescein in Hepatocyte Monolayers: Evidence for Functional Polarity of Cells in Culture," Proceedings of the National Academy of Sciences USA, 1982, vol. 79, pp. 4985-4987.

Bastide P., et al., "Sox9 Regulates Cell Proliferation and is required for Paneth Cell Differentiation in the Intestinal Epithelium," JCB, 2007, vol. 178, Issue 4, pp. 635-648.

Battle M A., et al., "GATA4 is Essential for Jejunal Function in Mice," Gastroenterology, 2008, vol. 135, pp. 1676-1686.

Baumann K., "Colonic Organoids for Drug Testing and Colorectal Disease Modelling," Nature Reviews Molecular Cell Biology, Jul. 2017, vol. 18, No. 8, p. 467.

Beck F., et al., "Expression of Cdx-2 in the Mouse Embryo and Placenta: Possible Role in Patterning of the Extra-Embryonic Membranes," Dev Dyn, 1995, vol. 204, pp. 219-227.

Begriche K., et al., "Drug-induced Toxicity on Mitochondria and Lipid Metabolism: Mechanistic Diversity and Deleterious Consequences for the Liver," Journal of Hepatology, 2011, vol. 54, pp. 773-794.

Bell L.N., et al., "Epidemiology of Idiosyncratic Drug-Induced Liver Injury," Seminars in Liver Disease, 2009, vol. 29, Issue 4, pp. 337-347.

Bergeles C., et al., "From Passive Tool Holders to Microsurgeons: Safer, Smaller, Smarter Surgical Robots," IEEE Transactions on Biomedical Engineering, 2014, vol. 61, Issue 5, pp. 1565-1576.

Bergner A.J., et al., "Birthdating of Myenteric Neuron Subtypes in the Small Intestine of the Mouse," The Journal of Comparative Neurology, 2014, vol. 522, pp. 514-527.

Bernadi P., "The Permeability Transition Pore. Control Points of a Cyclosporin A-Sensitive Mitochondrial Channel Involved in Cell Death," Biochimica et Biophysica Acta, 1996, vol. 1275, pp. 5-9.

Bernstein B.E., et al., "The NIH Roadmap Epigenomics Mapping Consortium," Nature Biotechnology, 2010, vol. 28, Issue 10, pp. 1045-1048.

Beuling E., et al., "Co-Localization of Gata4 and Hnfl alpha in the Gastrointestinal Tract is Restricted to the Distal Stomach and Proximal Small Intestine," Gastroenterology, AGA Abstracts, Abstract T1933, 2007, vol. 132, p. A586.

Beuling E., et al., "Conditional Gata4 Deletion in Mice Induces Bile Acid absorption in the Proximal Small Intestine," Gut, 2010, vol. 59, Issue 7, pp. 888-895.

Beuling E., et al., "Fog Cofactors Partially Mediate Gata4 Function in the Adult Mouse Small Intestine," Gastroenterology, AGA Abstracts, Abstract W1467, 2007, vol. 132, pp. A692-A693.

Beuling E., et al., "GATA4 Mediates Gene Repression in the Mature Mouse Small Intestine through Interactions with Friend of GATA (FOG) Cofactors," Developmental Biology, 2008, vol. 322, Issue 1, pp. 179-189.

Beuling E., et al., "The Absence of GATA4 in the Distal Small Intestine Defines the Ileal Phenotype," Gastroenterology, ABA Abstract, Abstract 602, 2008, vol. 134, pp. A83-A84.

Bharadwaj S., et al., "Current Status of Intestinal and Multivisceral Transplantation," Gastroentrerol Rep (Oxf), 2017, vol. 5, Issue 1, pp. 20-28.

Bhutani N., et al., "Reprogramming towards Pluripotency Requires AID-Dependent DNA Demethylation, " Nature, 2010, vol. 463, Issue 7284, pp. 1042-1047.

Bitar K.N., et al., "Intestinal Tissue Engineering: Current Concepts and Future Vision of Regenerative Medicine in the Gut," Neurogastroenterology & Motility, Jan. 2012, vol. 24, Issue 1, pp. 7-19.

Blaugrund E., et al., "Distinct Subpopulations of Enteric Neuronal Progenitors Defined by Time of Development, Sympathoadrenal Lineage Markers and Mash-1-Dependence," Development, vol. 122, 1996, pp. 309-320.

Bohan T.P., et al., "Effect of L-Carnitine Treatment for Valproate-Induced Hepatotoxicity," Neurology, 2001, vol. 56, pp. 1405-1409.

Bohorquez D.V., et al., "An Enteroendocrine Cell—Enteric Glia Connection Revealed by 3D Electron Microscopy," PLoS One, Feb. 2014, vol. 9, Issue 2, e89881, 13 pages.

Bonilla-Claudio M., et al., "Bmp Signaling Regulates a Dose-Dependent Transcriptional Program to Control Facial Skeletal Development," Development, 2012, vol. 139, pp. 709-719.

Boroviak T., et al., "Single Cell Transcriptome Analysis of Human, Marmoset and Mouse Embryos Reveals Common and Divergent Features of Preimplantation Development," Development, 2018, vol. 145, No. 21, pp. 1-18.

Bort R., et al., "Diclofenac Toxicity to Hepatocytes: A Role for Drug Metabolism in Cell Toxicity," Journal of Pharmacology and Experimental Therapeutics, 1998, vol. 288, Issue 1 , pp. 65-72.

Bosse T., et al., "Gata4 and Hnfl Alpha are partially required for the Expression of Specific Intestinal Genes during Development," American Journal of Physiology: Gastrointestinal and Liver Physiology, May 2007, vol. 292, pp. G1302-G1314.

(56) References Cited

OTHER PUBLICATIONS

Bouchi R., et al., "FOXO1 Inhibition Yields Functional Insulin-Producing Cells in Human Gut Organoid Cultures," Nature Communications, 2014, vol. 5, Issue 4242, 24 pages.
Boullata J.I., et al., "A.S.P.E.N. Clinical Guidelines: Parental Nutrition Ordering, Order Review, Compounding, Labeling and Dispensing," The Journal of Parenteral and Enteral Nutrition, 2014, vol. 38, Issue 3, pp. 334-377.
Bragdon B., et al., "Bone Morphogenetic Proteins: A Critical Review," Cellular Signalling, 2011, vol. 23, pp. 609-620.
Bravo P., et al., "Efficient In Vitro Vectorial Transport of a Fluorescent Conjugated Bile Acid Analogue by Polarized Hepatic Hybrid WIF-B and WIF-B9 Cells," Hepatology, 1998, vol. 27, pp. 576-583.
Brevini T.A.L et al., "No shortcuts to Pig Embryonic Stem Cells," Theriogenology, 2010, vol. 74, pp. 544-550.
Broda T.R., et al., "Generation of Human Antral and Fundic Gastric Organoids from Pluripotent Stem Cells," Nature Protocols, Nov. 2018. vol. 14(1), pp. 28-50.
Browning J.D., et al., "Molecular Mediators of Hepatic Steatosis and Liver Injury," Journal of Clinical Investigation, 2004, vol. 114, Issue 2, pp. 147-152.
Bruens L., et al., "Expanding the Tissue Toolbox: Deriving Colon Tissue from Human Pluripotent Stem Cells," Cell Stem Cell, Jul. 2017, vol. 21, Issue 1, pp. 3-5.
Brugmann S.A., et al., "Building Additional Complexity to in Vitro-Derived Intestinal Tissues," Stem Cell Research & Therapy, 2013, vol. 4, Issue Suppl 1, p. S1, 5 pages.
Burke P., et al., "Towards a Single-Chip, Implantable RFID System: is a Single-Cell Radio Possible?," Biomed Microdevices, 2010, vol. 12, pp. 589-596.
Burn S.F., et al., "Left-right Asymmetry in Gut Development: what happens next?," BioEssays, 2009, vol. 31, pp. 1026-1037.
Burnicka-Turek O., et al., "INSL5-Deficient Mice Display an Alteration in Glucose Homeostasis and an Impaired Fertility," Endocrinology, Oct. 2012, vol. 153, No. 10, pp. 4655-4665.
Burns A J., et al., "In Ovo Transplantation of Enteric Nervous System Precursors From Vagal to Sacral Neural Crest Results in Extensive Hindgut Colonisation," Development, 2002, Issue 129, pp. 2785-2796.
Burns A J., et al., "Neural Stem Cell Therapies for Enteric Nervous System Disorders," Nature Reviews/Gastroenterology & Hepatology, May 2014, Issue11, pp. 317-328.
Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.
Burrin D., et al., "Enteral Obeticholic Acid Prevents Hepatic Cholestasis in Total Parenteral Nutrition-Fed Neonatal Pigs," Hepatology, vol. 62, Oct. 2015, p. 307A.
Buta C., et al., "Reconsidering Pluripotency Tests: Do We Still Need Teratoma Assays?," Stem Cell Research, 2013, vol. 11, pp. 552-562.
Cabezas J., et al., "Nonalcoholic Fatty Liver Disease: A Pathological View," Chapter 8, in Liver Biopsy-Indications, Procedures Results, N. Tagaya (Ed.), InTechOpen, Nov. 21, 2012, pp. 161-188.
Campbell F.C., et al., "Transplantation of Cultured Small Bowel Enterocytes," Gut, Sep. 1993, vol. 34, Issue 9, pp. 1153-1155.
Caneparo L., et al., "Intercellular Bridges in Vertebrate Gastrulation," PloS ONE, 2011, vol. 6, Issue 5, e20230, 6 pages.
Cao L., et al., "Development of Intestinal Organoids as Tissue Surrogates: Cell Composition and the Epigenetic Control of Differentiation," Molecular Carcinogenesis, 2015, vol. 54, pp. 189-202.
Capeling M.M., et al., "Nonadhesive Alginate Hydrogels Support Growth of Pluripotent Stem Cell-Derived Intestinal Organoids," Stem Cell Reports, Feb. 2019, vol. 12, Issue 2, pp. 381-394.
Chai P.R., et al., "Ingestible Biosensors for Real-Time Medical Adherence Monitoring: MyTMed," Processing Hawaii International Conference on System Sciences, Jan. 2016, pp. 3416-3423.
chai P.R., et al., "Utilizing an Ingestible Biosensor to Assess Real-Time Medication Adherence," Journal of Medical Toxicology, 2015, vol. 11, pp. 439-444.
Chang H.M., et al., "BMP15 Suppresses Progesterone Production by Down-Regulating STAR via ALK3 in Human Granulosa Cells," Molecular Endocrinology, 2013, vol. 27, pp. 2093-2104.
Chang J.H., et al., "Evaluating the In Vitro Inhibition of UGT1A1, OATP1B1, OATP1B3, MRP2, and BSEP in Predicting Drug-Induced Hyperbilirubinemia," Molecular Pharmaceutics, 2013, vol. 10, pp. 3067-3075.
Chatterjee S., et al., "Hepatocyte-Based in Vitro Model for Assessment of Drug-Induced Cholestasis," Toxicology and Applied Pharmacology, 2014, vol. 274, pp. 124-136.
Chauhan R.K., et al., "Genetic and Functional Studies of Hirschsprung Disease," Doctoral Thesis: Department of Clinical Genetics, Erasmus University Rotterdam, the Netherlands, 2016, 202 pages.
Chen B., et al., "Dynamic Imaging of Genomic Loci in Living Human Cells by an Optimized CRISPR/Cas System," Cell, 2013, vol. 155, Issue 7, pp. 1479-1491.
Chen C., et al., "Pdx1 Inactivation Restricted to the Intestinal Epithelium in Mice alters Duodenal Gene Expression in Enterocytes and Enteroendocrine Cells," American Journal of Physiology Gastrointestinal and Liver Physiology, 2009, vol. 297, pp. G1126-G1137.
Chen L.Y., et al., "Mass Fabrication and Delivery of 3D Multilayer μTags into Living cells," Scientific Reports, 2013, vol. 3, Issue 2295, 6 pages.
Chen T.W., et al., "Ultrasensitive Fluorescent Proteins for Imaging Neuronal Activity," Nature, Jul. 18, 2013, vol. 499, pp. 295-300.
Chen Y., et al., "Retinoic Acid Signaling is Essential for Pancreas Development and Promotes Endocrine at the Expense of Exocrine Cell Differentiation in Xenopus," Developmental Biology, 2004, vol. 271, pp. 144-160.
Cheng X., et al., "Self-Renewing Endodermal Progenitor Lines Generated from Human Pluripotent Stem Cells," Cell Stem Cell, Apr. 6, 2012, vol. 10, pp. 371-384.
Choi E., et al., "Cell Lineage Distribution Atlas of the Human Stomach Reveals Heterogeneous Gland Populations in the Gastric Antrum," Gut, 2014, vol. 63, Issue 11, pp. 1711-1720.
Choi E., et al., "Expression of Activated Ras in Gastric Chief Cells of Mice Leads to the Full Spectrum of Metaplastic Lineage Transitions," Gastroenterology, Apr. 2016, vol. 150, Issue 4, pp. 918-930.
Christoffersson J., et al., "Developing Organ-on-a-chip Concepts Using Bio-Mechatronic Design Methodology," Biofabrication, May 26, 2017, vol. 9, Issue 2, 025023; 14 pages.
Chughlay M.F., et al., "N-Acetylcysteine for Non-Paracetamol Drug-Induced Liver Injury: a Systematic Review," British Journal of Clinical Pharmacology, 2016, vol. 81, pp. 1021-1029.
Churin Y., et al., "Helicobacter Pylori CagA Protein Targets the c-Met Receptor and Enhances the Motogenic Response," Journal of Cell Biology, 2003, vol. 161, No. 2, pp. 249-255.
Cieslar-Pobuda A., et al., "The Expression Pattern of PFKFB3 Enzyme Distinguishes Between Induced-Pluripotent Stem Cells and Cancer Stem Cells," Oncotarget, Aug. 13, 2015, vol. 6, Issue 30, p. 29753-29770.
Cincinnati Children's Hospital Medical Center, "Scientists Grow Human Esophagus in Lab: Tiny Organoids Enable Personalized Disease Diagnosis, Regenerative Therapies," CCHMC Public Press Release, Sep. 20, 2018, 2 pages.
Clarke L.L., "A Guide to Using Chamber Studies of Mouse Intestine," American Journal of Physiology: Gastrointestinal and Liver Physiology, Jun. 2009, vol. 296, issue 6, pp. G1151-G1166.
Clevers H., "Modeling Development and Disease with Organoids," Cell, Jun. 16, 2016, vol. 165, Issue 7, pp. 1586-1597.
Coghlan M., et al., "Selective Small Molecule Inhibitors of Glycogen Synthase Kinase-3 Modulate Glycogen Metabolism and Gene Transcription," Chemistry & Biology, Oct. 2000, vol. 7, Issue 10, pp. 793-803.
Collier A.J., et al., "Comprehensive Cell Surface Protein Profiling Identifies Specific Markers of Human Naive and Primed Pluripotent States," Cell Stem Cell, Jun. 1, 2017, vol. 20, pp. 874-890.

(56) References Cited

OTHER PUBLICATIONS

Correia C., et al., "Combining Hypoxia and Bioreactor Hydrodynamics Boosts Induced Pluripotent Stem Cell Differentiation towards Cardiomyocytes," Stem Cell Reviews and Reports, Dec. 2014, vol. 10, pp. 786-801.
Cortez A R., et al., "Transplantation of Human Intestinal Organoids into the Mouse Mesentery: A More Physiological and Anatomic Engraftment Site," Surgery, 2018, vol. 164, pp. 643-650.
Costa M., et al., "A Method for Genetic Modification of Human Embryonic Stem Cells using Electroporation," Nature Protocols, Apr. 5, 2007, vol. 2, No. 4, pp. 792-796.
Couzin J., "Small RNAs Make Big Splash," Science, Dec. 20, 2002, vol. 298, pp. 2296-2297.
Covacci A., et al., "Molecular Characterization of the 128-kDa Immunodominant Antigen of Helicobacter Pylori Associated with Cytotoxicity and Duodenal Ulcer," Proceedings of the National Academy of Sciences USA, Jun. 15, 1993, vol. 90, pp. 5791-5795.
Crespo M., et al., "Colonic Organoids Derived from Human Induced Pluripotent Stem Cells for Modeling Colorectal Cancer and Drug Testing," Nature Medicine, Jun. 19, 2017, vol. 23, No. 7, pp. 878-884.
Crocenzi F.A., et al., "Ca(2+)-Dependent Protein Kinase C Isoforms are Critical to Estradiol 17beta-D-Glucuronide-Induced Cholestasis in the Rat," Hepatology, Dec. 2008, vol. 48, pp. 1885-1895.
Cunningham T.J., et al., "Mechanisms of Retinoic Acid Signalling and its Roles in Organ and Limb Development," Nature Reviews Molecular Cell Biology, vol. 16, No. 2, Jan. 5, 2015, pp. 110-123.
Curchoe C.L., et al., "Early Acquisition of Neural Crest Competence During hESCs Neuralization," PloS One, Nov. 2010, vol. 5, pp. 1-17.
Cutrin J.C., et al., "Reperfusion Damage to the Bile Canaliculi in Transplanted Human Liver," Hematology, 1996, vol. 24, pp. 1053-1057.
Dahl A., et al., "Translational Regenerative Medicine-Hepatic Systems," Chapter 34, Clinical Aspects of Regenerative Medicine, eds. A. Atala, M.D. and J. Allickson, PhD, Elsevier, Inc., 2015, pp. 469-484.
D'Amour K A., et al., "Production of Pancreatic Hormone-Expressing Endocrine Cells from Human Embryonic Stem Cells," Nature Biotechnology, 2006, vol. 24, No. 11, pp. 1392-1401.
D'Amour K.A et al., "Efficient Differentiation of Human Embryonic Stem Cells to Definitive Endoderm," Nature Biotechnology, Dec. 2005, vol. 23, No. 12, pp. 1534-1541.
Das R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pages.
Dash A., et al., "Pharmacotoxicology of Clinically-Relevant Concentrations of Obeticholic Acid in an Organotypic Human Hepatocyte System," Toxicol in Vitro, 2017, vol. 39, pp. 93-103.
Date S., et al., "Mini-Gut Organoids: Reconstitution of the Stem Cell Niche," Annual Review of Cell and Developmental Biology, Nov. 2015, vol. 31, pp. 269-289.
Davenport C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, vol. 34, pp. 2635-2647.
Davidson M.D., et al., "Long-Term Exposure to Abnormal Glucose Levels Alters Drug Metabolism Pathways and Insulin Sensitivity in Primary Human Hepatocytes," Scientific Reports, 2016, vol. 6, 28178, 11 pages.
De Santa Barbara P., et al., "Bone Morphogenetic Protein Signaling Pathway Plays Multiple Roles During Gastrointestinal Tract Development," Developmental Dynamics, 2005, vol. 234, pp. 312-322.
De Santa Barbara P., et al., "Development and Differentiation of the Intestinal Epithelium," Cellular and Molecular Life Sciences, 2003, vol. 60, No. 7, pp. 1322-1332.
Dedhia P.H., et al., "Organoid Models of Human Gastrointestinal Development and Disease," Gastroenterology, Jan. 14, 2016, vol. 150, pp. 1098-1112.
Dekaney C.M., et al., "Expansion of Intestinal Stem Cells Associated with Long-Term Adaptation Following Ileocecal Resection in Mice," American Journal of Physiology: Gastrointestinal and Liver Physiology, Sep. 13, 2007, vol. 293, pp. G1013-G1022.
Dekkers J F., et al., "A Functional CFTR Assay Using Primary Cystic Fibrosis Intestinal Organoids," Nature Medicine, Jul. 2013, vol. 19, No. 7, pp. 939-945.
Dekkers R., et al., "A Bioassay Using Intestinal Organoids to Measure CFTR Modulators in Human Plasma," Journal of Cystic Fibrosis, 2015, vol. 14 (2), pp. 178-181.
Demehri F.R., et al., "Development of an Endoluminal Intestinal Attachment for Clinically Applicable Distraction Enterogenesis Device," Journal of Pediatric Surgery, Jan. 2016, vol. 51, pp. 101-106.
Demehri F.R., et al., "Development of an Endoluminal Intestinal Lengthening Device using a Geometric Intestinal Attachment Approach," Surgery, 2015, vol. 158, pp. 802-811.
Deng H., et al., "Effects of All-Trans Retinoic Acid on the Differentiation of Neural Stem Cells and the Expression of c-myc Gene," Chinese Journal of Tissue Engineering Research, Mar. 18, 2007, vol. 11, pp. 2039-2042.
Deng H., "Mechanisms of Retinoic Acid on the Induction of Differentiation of Neural Stem Cells for Newborn Rat Striatum," Chinese Doctoral and Master Dissertations Full-Text Database (Doctoral) Basic Science, Issue 4, May 20, 2005, pp. 1-91. (Translation).
Denham M., et al., "Multipotent Caudal Neural Progenitors derived from Human Pluripotent Stem Cells that give Rise to Lineages of the Central and Peripheral Nervous System," Stem Cells, Mar. 5, 2015, vol. 33, pp. 1759-1770.
Dessimoz J., et al., "FGF Signaling is Necessary for Establishing Gut Tube Domains along the Anterior-Posterior Axis in Vivo," Mech Dev, 2006, vol. 123, pp. 42-55.
DeWard A.D., et al., "Cellular Heterogeneity in the Mouse Esophagus Implicates the Presence of a Nonquiescent Epithelial Stem Cell Population," Cell Reports, Oct. 23, 2014, vol. 9, No. 2, pp. 701-711.
Discher D.E., et al., "Growth Factors, Matrices, and Forces Combine and Control Stem Cells," Science, Jun. 2009, vol. 324, pp. 1673-1677.
Dobreva G., et al., "SATB2 Is a Multifunctional Determinant of Craniofacial Patterning and Osteoblast Differentiation," Cell, 2006, vol. 125, Issue 5, pp. 971-986.
Driver I., et al., "Specification of regional intestinal stem cell identity during *Drosophila* metamorphosis," Development, 2014, vol. 141, pp. 1848-1856.
Duluc I., et al., "Fetal Endoderm Primarily Holds the Temporal and Positional Information Required for Mammalian Intestinal Development," The Journal of Cell Biology, 1994, vol. 126, pp. 211-221.
Dumortier G., et al., "Tolérance hépatique des antipsychotiques atypiques, [Hepatic Tolerance of Atypical Antipsychotic Drugs]," L'Encephale, 2002, vol. 28, pp. 542-551.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501/10?clear=10&p10_accession_num=ucin1544 098242321181; 160 pages.
Dvir-Ginzberg M., et al., "Liver Tissue Engineering within Alginate Scaffolds: Effects of Cell-Seeding Density on Hepatocyte Viability, Morphology, and Function," Tissue Engineering, 2003, vol. 9, pp. 757-766.
Eberhard J., et al., "A Cohort Study of the Prognostic and Treatment Predictive Value of SATB2 Expression in Colorectal Cancer," British Journal of Cancer, 2012, vol. 106, pp. 931-938.
Edling Y., et al., "Increased Sensitivity for Troglitazone-Induced Cytotoxicity using a Human in Vitro Co-Culture Model," Toxicol in Vitro, 2009, vol. 23, pp. 1387-1395.
Eicher A.K., et al., "Translating Developmental Principles to Generate Human Gastric Organoids," Cellular and Molecular Gastroenterology and Hepatology, 2018, vol. 5, pp. 353-363.
Ekser B., et al., "Comparable Outcomes in Intestinal Retransplantation: Single-Center Cohort Study," The Journal of Clinical and Translational Research, 2018, vol. 32, e13290, 10 pages.

(56) References Cited

OTHER PUBLICATIONS

El Kasmi K.C., et al., "Phytosterols Promote Liver Injury and Kupffer Cell Activation in Parenteral Nutrition-Associated Liver Disease," Science Translational Medicine, 2013, vol. 5, Issue 206 206ra137, 10 pages.
El Taghdouini A., et al., "In Vitro Reversion of Activated Primary Human Hepatic Stellate Cells," Fibrogenesis & Tissue Repair, 2015, vol. 8, No. 14, 15 pages.
Elbashir S.M., et al., "Functional Anatomy of siRNAs for Mediating Efficient RNAi in *Drosophila melanogaster* Embryo Lysate," The EMBO Journal, 2001, vol. 20, No. 23, pp. 6877-6888.
Engmann J., et al., "Fluid Mechanics of Eating, Swallowing and Digestion-Overview and Perspectives," Food & Function, 2013, vol. 4, pp. 443-447.
Evans M.J., et al., "Establishment in Culture of Pluripotential Cells from Mouse Embryos," Nature, Jul. 1981, vol. 292, pp. 154-156.
Ezashi T., et al., "Low O2 Tensions and the Prevention of Differentiation of hES Cells," PNAS, Mar. 2005, vol. 102, Issue 13, pp. 4783-4788.
Fagerberg L., et al., "Analysis of the Human Tissue-specific Expression by Genome-wide Integration of Transcriptomics and Antibody-based proteomics," Molecular & Cellular Proteomics, 2014, vol. 13, pp. 397-406.
Fahrmayr C., et al., "Phase I and II Metabolism and MRP2-Mediated Export of Bosentan in a MDCKII-OATP1B1-CYP3A4-UGT1A1-MRP2 quadruple-Transfected Cell Line," British Journal of Pharmacology, 2013, vol. 169, pp. 21-33.
Falasca L., et al., "The Effect of Retinoic Acid on the re-establishment of Differentiated Hepatocyte Phenotype in Primary Culture," Cell Tissue Res, Aug. 1998, vol. 293, pp. 337-347.
Fatehullah A., et al., "Organoids as an in Vitro Model of Human Development and Disease," Nature Cell Biology, Mar. 2016, vol. 18, Issue 3, pp. 246-254.
Feldstein A.E., et al., "Free Fatty Acids Promote Hepatic Lipotoxicity by Stimulating TNF-α Expression via a Lysosomal Pathway," Hepatology, Jul. 2004, vol. 40 (1), pp. 185-194.
Finkbeiner S.R., et al., "A Gutsy Task: Generating Intestinal Tissue from Human Pluripotent Stem Cells," Digestive Diseases and Sciences, 2013, vol. 58, pp. 1176-1184.
Finkbeiner S.R., et al., "Stem Cell-Derived Human Intestinal Organoids as an Infection Model for Rotaviruses," mBio, Jul./Aug. 2012, vol. 3, issue 4, e00159-12, 6 pages.
Finkbeiner S.R., et al., "Transcriptome-wide Analysis Reveals Hallmarks of Human Intestine Development and Maturation in Vitro and In Vivo," Stem Cell Reports, Jun. 3, 2015, vol. 4, pp. 1140-1155.
Finkenzeller K., "RFID Handbook: Fundamentals and Applications in Contactless Smart Cards, Radio Frequency Identification and Near-Field Communication," Third Edition, John Wiley & Sons, Ltd., 2010, 8 pages.
Fisher A., et al., "Entacapone-Induced Hepatotoxicity and Hepatic Dysfunction," Movement Disorders, 2002, vol. 17, pp. 1362-1365.
Fitzpatrick D R., et al., "Identification of SATB2 as the Cleft Palate Gene on 2q32-q33," Human Molecular Genetics, 2003, vol. 12, Issue 19, pp. 2491-2501.
Fon Tacer K., et al., "Research Resource: Comprehensive Expression Atlas of the Fibroblast Growth Factor System in Adult Mouse," Molecular Endocrinology, 2010, vol. 24, No. 10, pp. 2050-2064.
Fordham R.P., et al., "Transplantation of Expanded Fetal Intestinal Progenitors Contributes to Colon Regeneration after Injury," Cell Stem Cell, Dec. 5, 2013, vol. 13, pp. 734-744.
Fromenty B., "Drug-induced liver injury in obesity," Journal of Hepatology, 2013, vol. 58, pp. 824-826.
Fu M., et al., "Embryonic Development of the Ganglion Plexuses and the Concentric Layer Structure of Human Gut: a Topographical Study," Anatomy and Embryology, Feb. 27, 2004, vol. 208, pp. 33-41.
Fu M., et al., "HOXB5 expression is spatially and temporarily Regulated in Human Embryonic Gut during Neural Crest Cell Colonization and Differentiation of Enteric Neuroblasts," Developmental Dynamics, 2003, vol. 228, pp. 1-10.
Furness J.B., "The Enteric Nervous System and Neurogastroenterology," Nature Reviews/Gastroenterology & Hepatology, May 2012, vol. 9, pp. 286-294.
Gafni O., et al., "Derivation of Novel Human Ground State Naive Pluripotent Stem Cells," Nature, Oct. 29, 2013, vol. 504, pp. 282-286; Supplementary Information in 14 pages.
Geerts A., et al., "Formation of Normal Desmin Intermediate Filaments in Mouse Hepatic Stellate Cells Requires Vimentin," Hepatology, Oct. 2001, vol. 33, pp. 177-188.
Genthe J.R., et al., "Ventromorphins: A New Class of Small Molecule Activators of the Canonical BMP Signaling Pathways," ACS Chemical Biology, 2017, vol. 12, Issue 9, pp. 2436-2447.
Georgas K M., et al., "An illustrated Anatomical Ontology of the Developing Mouse Lower Urogenital Tract," Development, May 15, 2015, vol. 142, pp. 1893-1908.
Gerdes H.H., et al., "Tunneling Nanotubes, an Emerging Intercellular Communication Route in Development," 2013, vol. 130, pp. 381-387.
Gessner R.C., et al., "Functional Ultrasound Imaging for Assessment of Extracellular Matrix Scaffolds used for Liver Organoid Formation," Biomaterials, 2013, vol. 34, pp. 9341-9351.
Giles D.A., et al., "Thermoneutral Housing Exacerbates Nonalcoholic Fatty Liver Disease in Mice and Allows for Sex-Independent Disease Modeling," Nature Medicine, 2017, vol. 23, Issue 7, pp. 829-838.
Ginestet C., Book Review in the Journal of the Royal Statistical Society. Series A (Statistics in Society) (2011), of ggplot2: Elegant Graphics for Data Analysis, by H. Wickham, 2009, vol. 174, Issue 1, p. 245 (2 pages).
Glorioso J.M., et al., "Pivotal Preclinical Trial of the Spheroid Reservoir Bioartificial Liver," Journal of Hepatology, 2015, vol. 63, Issue 2, pp. 388-398.
Goldenring J.R., et al., "Differentiation of the Gastric Mucosa: III. Animal Models of Oxyntic Atrophy and Metaplasia," American Journal of Physiology-Gastrointestinal and Liver Physiology, 2006, vol. 291, pp. G999-G1004.
Goldenring J.R., et al., "Overexpression of Transforming Growth Factor-alpha Alters Differentiation of Gastric Cell Lineages," Digestive Diseases and Sciences, 1996, vol. 41, Issue 4, pp. 773-784.
Goldstein A.M., et al., "BMP Signaling is Necessary for Neural Crest Cell Migration and Ganglion Formation in the Enteric Nervous System," Mechanisms of Development, 2005, vol. 122, pp. 821-833.
Gomez M.C., et al., "Derivation of Cat Embryonic Stem-Like Cells from in Vitro-Produced Blastocysts on Homologous and Heterologous Feeder Cells," Theriogenology, Sep. 1, 2010, vol. 74, Issue 4, pp. 498-515.
Gomez-Pinilla P.J., et al., "Ano1 is a Selective Marker of Interstitial Cells of Cajal in the Human and Mouse Gastrointestinal Tract," American Journal of Physiology: Gastrointestinal and Liver Physiology, 2009, vol. 296, Issue 6, pp. G1370-G1381.
Gori M., et al., "Investigating Nonalcoholic Fatty Liver Disease in a Liver-on-a-Chip Microfluidic Device," PLOS One, Jul. 2016, vol. 11, Issue 7, e0159729, 15 pages.
Gouon-Evans V., et al., "BMP-4 is Required for Hepatic Specification of Mouse Embryonic Stem Cell-Derived Definitive Endoderm," Nature Biotechnology, Nov. 2006, vol. 24, Issue 11, pp. 1402-1411.
Gracz A.D., et al., "Brief report: CD24 and CD44 Mark Human Intestinal Epithelial Cell Populations with Characteristics of Active and Facultative Stem Cells," Stem Cells, Apr. 4, 2013, vol. 31, pp. 2024-2030.
Gracz A.D., et al., "Sox9 Expression Marks a Subset of CD24-Expressing Small Intestine Epithelial Stem Cells that Form Organoids in Vitro," American Journal of Physiology: Gastrointestinal and Liver Physiology, 2010, vol. 298, Issue 5, pp. G590-G600.
Gradwohl G., et al., "Neurogenin3 is Required for the Development of the Four Endocrine Cell Lineages of the Pancreas," Proceedings of the National Academy of Sciences USA, Feb. 15, 2000, vol. 97, No. 4, pp. 1607-1611.
Grapin-Botton A., "Three-Dimensional Pancreas Organogenesis Models," Diabetes Obesity and Metabolism, Sep. 2016, vol. 18 (Suppl 1), pp. 33-40.

(56) References Cited

OTHER PUBLICATIONS

Green M.D., et al., "Generation of Anterior Foregut Endoderm from Human Embryonic and Induced pluripotent Stem Cells," Nature Biotechnology, Mar. 2011, vol. 29, Issue 3, pp. 267-272.
Gregersen H., et al., "The Zero-Stress State of the Gastrointestinal Tract: Biomechanical and Functional Implications," Digestive Diseases and Sciences, Dec. 2000, vol. 45(12), pp. 2271-2281.
Gregorieff A., et al., "Wnt Signaling in the Intestinal Epithelium: from Endoderm to Cancer," Genes & Development, 2005, vol. 19, pp. 877-890.
Groneberg D.A., et al., "Intestinal Peptide Transport: Ex Vivo Uptake Studies and Localization of Peptide Carrier PEPT1," American Journal of Physiology: Gastrointestinal and Liver Physiology, Sep. 2001, vol. 281, pp. G697-G704.
Grosse A.S., et al., "Cell Dynamics in Fetal Intestinal Epithelium: Implications for Intestinal Growth and Morphogenesis," Development, 2011, vol. 138, pp. 4423-4432.
Guan Y., et al., "Human Hepatic Organoids for the Analysis of Human Genetic Diseases," JCI Insight, Sep. 7, 2017, vol. 2, Issue 17, e94954; 17 pages.
Guilak F., et al., "Control of Stem Cell Fate by Physical Interactions with the Extracellular Matrix," Cell Stem Cell, Jul. 2009, vol. 5, pp. 17-26.
Guo G., et al., "Epigenetic Resetting of Human Pluripotency," Development, 2017, vol. 144, pp. 2748-2763.
Guo Z., et al., "Injury-Induced BMP Signaling Negatively Regulates Drosophila Midgut Homeostasis," Journal of Cell Biology, 2013, vol. 201, Issue 6, pp. 945-961.
Gurdon J.B., "Adult Frogs Derived from the Nuclei of Single Somatic Cells," Developmental Biology, 1962, vol. 4, pp. 256-273.
Gurken A. "Advances in Small Bowel Transplantation," Turkish Journal of Surgery, 2017, vol. 33, Issue 3, pp. 135-141.
Gyorgy A.B., et al., "SATB2 Interacts with Chromatin-Remodeling Molecules in Differentiating Cortical Neurons," European Journal of Neuroscience, 2008, vol. 27, pp. 865-873.
Haimovich G., et al., "Intercellular mRNA Trafficking via Membrane Nanotube-Like Extensions in Mammalian Cells," PNAS, 2017, vol. 114, Issue 46, pp. E9873-E9882.
Halpern K. B., et al., "Single-cell Spatial Reconstruction Reveals Global Division of Labor in the Mammalian Liver," Nature, 2017, vol. 542, No. 7641, pp. 352-356.
Han B., et al., "Microbiological Safety of a Novel Bio-Artificial Liver support System Based on Porcine Hepatocytes: an Experimental Study," European Journal of Medical Research, 2012, vol. 17, Issue 1, Journal 13, 8 pages.
Han M E., et al., "Gastric Stem Cells and Gastric Cancer Stem Cells," Anatomy & Cell Biology, 2013, vol. 46, Issue 1, pp. 8-18.
Hannon G.J., "RNA Interference," Nature, 2002, vol. 418, Issue 6894, pp. 244-251.
Hannon N.R.F., et al., "Generation of Multipotent Foregut Stem Cells from Human Pluripotent Stem Cells," Stem Cell Reports, Oct. 2013, vol. 1, Issue 4, pp. 293-306.
Hao M.M., et al., "Development of Enteric Neuron Diversity," Journal of Cellular and Molecular Medicine, 2009, vol. 13, Issue 7, pp. 1193-1210.
Haramis A.P.G., et al., "De Novo Crypt Formation and Juvenile Polyposis on BMP Inhibition in Mouse Intestine," Science, 2004, vol. 303, Issue 5664, pp. 1684-1686.
Hardwick J.C.H., et al., "Bone Morphogenetic Protein 2 Is Expressed by, and Acts Upon, Mature Epithelial Cells in the Colon," Gastroenterology, 2004, vol. 126, Issue 1, pp. 111-121.
Hardy T., et al., "Nonalcoholic Fatty Liver Disease: New Treatments," Current Opinion in Gastroenterology, May 2015, vol. 31, Issue 3, pp. 175-183.
Hassan W., et al., "Reduced Oxidative Stress Contributes to the Lipid Lowering Effects of Isoquercitrin in Free Fatty Acids Induced Hepatocytes," Oxidative Medicine and Cellular Longevity, 2014, vol. 2014, 313602, 18 pages.
Haveri H., et al., "Transcription Factors GATA-4 and GATA-6 in Normal and Neoplastic Human Gastrointestinal Mucosa," BMC Gastroenterology, 2008, vol. 8, Issue 9, 13 pages.
He X.C., et al., "BMP Signaling Inhibits Intestinal Stem Cell Self-Renewal through Suppression of Wnt-beta-Catenin Signaling," Nature Genetics, 2004, vol. 36, Issue 10, pp. 1117-1121.
Heidari R., et al., "Factors Affecting Drug-Induced Liver Injury: Antithyroid Drugs as Instances," Clinical and Molecular Hepatology, 2014, vol. 20, Issue 3, pp. 237-248.
Hernandez F., et al., "Refining Indications for Intestinal Retransplantation," International Small Bowel Symposium 2013; Abstract 12.241, retrieved from https://www.tts.org/component/tts/view=presentation &id=13241, Accessed, Jun. 12, 2017, 3 pages.
Higuchi Y., et al., "Gastrointestinal Fibroblasts Have Specialized, Diverse Transcriptional Phenotypes: A Comprehensive Gene Expression Analysis of Human Fibroblasts," PLOS One, Jun. 2015, vol. 10, Issue 6, 19 pages.
Hockemeyer D., et al., "Genetic Engineering of Human ES and iPS Cells using TALE Nucleases," Nature Biotechnology, 2012, vol. 29, Issue 8, pp. 731-734.
Hoffmann W., "Current Status on Stem Cells and Cancers of the Gastric Epithelium," International Journal of Molecular Sciences, 2015, vol. 16, Issue 8, pp. 19153-19169.
Holland P.W.H., et al., "Classification and Nomenclature of all Human Homeobox Genes," BMC Biology, 2007, vol. 5, Issue 47, pp. 1-28.
Hooton D., et al., "The Secretion and Action of Brush Border Enzymes in the Mammalian Small Intestine," Reviews of Physiology, Biochemistry and Pharmacology, 2015, vol. 168, pp. 59-118.
Hou P., et al., "Pluripotent Stem Cells Induced from Mouse Somatic Cells by Small-Molecule Compounds," Science, 2013, vol. 341, Issue 6146, pp. 651-654.
Howell J.C., et al., "Generating Intestinal tissue from Stem Cells: Potential for Research and Therapy," Regenerative Medicine, Nov. 2011, vol. 6, Issue 6, pp. 743-755.
Hsu F., et al., "The UCSC Known Genes," Bioinformatics, 2006, vol. 22, Issue 9, pp. 1036-1046.
Hu H., et al., "Long-Term Expansion of Functional Mouse and Human Hepatocytes as 3D Organoids," Cell, 2018, vol. 175, Issue 6, pp. 1591-1606.
Hu X., et al., "Micrometer-Scale Magnetic-Resonance-Coupled Radio-Frequency Identification and Transceivers for Wireless Sensors in Cells," Physical Review Applied, 2017, vol. 8, Issue 1, 13 pages.
Huang H., "Differentiation of Human Embryonic Stem Cells into Smooth Muscle Cells in Adherent Monolayer Culture," Biochemical and Biophysical Research Communications, 2006, vol. 351 pp. 321-327.
Huch M., et al., "Lgr5+ Liver Stem Cells, Hepatic Organoids and Regenerative medicine," Regenerative Medicine, 2013, vol. 8, Issue 4, pp. 385-387.
Huch M., et al., "Long-Term Culture of Genome-Stable Bipotent Stem Cells from Adult Human Liver," Cell, 2015, Issue 160, pp. 299-312.
Huch M., et al., "Modeling mouse and Human development using Organoid cultures," Development, 2015, Issue 142, pp. 3113-3125.
Huebsch N., et al., "Automated Video-Based Analysis of Contractility and Calcium Flux in Human-Induced Pluripotent Stem Cell-Derived Cardiomyocytes Cultured Over Different Spatial Scales," Tissue Engineering: Part C, 2015, vol. 21, No. 5, pp. 467-479.
Huh W.J., et al., "Ménétrier's Disease: Its Mimickers and Pathogenesis," Journal of Pathology and Translational Medicine, 2016, vol. 50, Issue 1, pp. 10-16.
Hutvagner G., et al., "A microRNA in a Multiple-Turnover RNAi Enzyme Complex," Science, Sep. 20, 2002, vol. 297, No. 5589, pp. 2056-2060.
Hynds R.E., et al., "The Relevance of Human Stem Cell-Derived Organoid Models for Epithelial Translational Medicine," Stem Cells, 2013, vol. 31, No. 3, pp. 417-422.
Ijpenberg., et al., "Wt1 and Retinoic Acid Signaling are Essential for Stellate cell development and Liver Morphogenesis," Developmental Biology, Dec. 2007, vol. 312, No. 1, pp. 157-170.

(56) References Cited

OTHER PUBLICATIONS

Inoue H., et al., "IPS Cells: A game Changer for Future Medicine," The EMBO Journal, 2014, vol. 33, No. 5, pp. 409-417.

Ito K., et al., "Temporal Transition of Mechanical Characteristics of HUVEC/MSC Spheroids Using a Microfluidic Chip with Force Sensor Probes," Micromachines, 2016, vol. 7(221), 14 pages.

Jalan-Sakrikar N., et al., "Hedgehog Signaling Overcomes an EZH2-Dependent Epigenetic Barrier to Promote Cholangiocyte Expansion," PLoS One, 2016, vol. 11, No. 12, 19 pages.

Jean C., et al., "Pluripotent Genes in Avian Stem Cells," Develop. Growth Differ., 2013, vol. 55, pp. 41-51.

Jeejeebhoy K.N., "Short Bowel Syndrome: A Nutritional and Medical Approach," CMAJ, 2002, vol. 166, Issue 10, pp. 1297-1302.

Jenny M., et al., "Neurogenin3 is differentially Required for Endocrine Cell Fate Specification in the Intestinal and Gastric Epithelium," Embo J, 2002, vol. 21, Issue 23, pp. 6338-6347.

Johannesson M., et al., "FGF4 and Retinoic Acid Direct Differentiation of hESCs into PDX1- Expressing Foregut Endoderm in a Time- and Concentration-Dependent Manlier," PLoS One, Mar. 2009, vol. 4, Issue 3, pp. 1-13.

Johansson K.A., et al., "Temporal Control of Neurogenin3 Activity in Pancreas Progenitors Reveals Competence Windows for the Generation of Different Endocrine Cell Types," Dev Cell, 2007, vol. 12, pp. 457-465.

Johnson L.R., et al., "Stimulation of Rat Oxyntic Gland Mucosal Growth by Epidermal Growth Factor," American Journal of Physiology, 1980, vol. 238, Issue G, pp. 45-49.

Johnston T.B., et al., "Extroversion of the Bladder, Complicated by the Presence of Intestinal Openings on the Surface of the Extroverted Area," Journal of Anatomy, 1913, vol. 48, Issue 1, pp. 89-106.

Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.

Jung P., et al., "Isolation and in Vitro Expansion of Human Colonic Stem Cells," Nature Medicine, Oct. 2011, vol. 17, pp. 1225-1227.

Juno R J., et al., "A serum factor(s) after Small Bowel Resection Induces Intestinal Epithelial Cell Proliferation: Effects of Timing, Site, and Extent of Resection," Journal of Pediatric Surgery, Jun. 2003, vol. 38, pp. 868-874.

Juno R.J., et al., "A Serum Factor after Intestinal Resection Stimulates Epidermal Growth Factor Receptor Signaling and Proliferation in Intestinal Epithelial Cells," Surgery, Aug. 2002, vol. 132, pp. 377-383.

Kabouridis P S., et al., "Microbiota Controls the Homeostasis of Glial Cells in the Gut Lamina Propria," Neuron, Jan. 21, 2015, vol. 85, pp. 289-295.

Kaji K., et al., "Virus Free Induction of Pluripotency and Subsequent Excision of Reprogramming Factors," Nature, Apr. 2009, vol. 458, Issue 7239, pp. 771-775.

Kanuri G., et al., "In Vitro and in Vivo Models of Non-Alcoholic Fatty Liver Disease (NAFLD)," International Journal of Molecular Sciences, 2013, vol. 14, pp. 11963-11980.

Karlikow M., et al., "*Drosophila* Cells Use Nanotube-like Structures to Transfer dsRNA and RNAi Machinery Between Cells," Scientific Reports, 2016, vol. 6, Issue 27085, 9 pages.

Katoh M., "WNT Signaling in Stem Cell Biology and Regenerative Medicine," Current Drug Targets, 2008, vol. 9, Issue 7, pp. 565-570.

Kawaguchi J., et al., "Isolation and propagation of enteric neural crest progenitor cells from mouse embryonic stem cells and embryos," Development, 2010, vol. 137, pp. 693-704.

Kawaguchi Y., et al., "The Role of the Transcriptional Regulator Ptf1a in Converting Intestinal to Pancreatic Progenitors," Nature Genetics, 2002, vol. 32, pp. 128-134.

Keeley T.M., et al., "Cytodifferentiation of the postnatal mouse stomach in normal and Huntingtin-interacting protein 1-related-deficient mice," American Journal of Physiology: Gastrointestinal and Liver Physiology, 2010, vol. 299, pp. G1241-G1251.

Keitel V., et al., "De Novo Bile Salt Transporter Antibodies as a Possible Cause of Recurrent Graft Failure after Liver Transplantation: A Novel Mechanism of Cholestasis," Hepatology, 2009, vol. 50, pp. 510-517.

Kelly G.M., et al., "Retinoic Acid and the Development of the Endoderm," Journal Developmental Biology, 2015, vol. 3, pp. 25-56.

Keung A.J., et al., "Presentation Counts: Microenvironmental Regulation of Stem Cells by Biophysical and Material Cues," Annual Review of Cell and Developmental Biology, 2010, vol. 26, pp. 533-556.

Khan F.A., et al., "Overview of Intestinal and Multivisceral Transplantation," UpToDate, Sep. 2018 retrieved from https://www.uptodate.com/contents/overview-of-intestinal-and-multiviscera-I-transplantation/print], 32 pages.

Kilens S., et al., "Parallel Derivation of Isogenic Human Primed and Naive Induced Pluripotent Stem Cells," Nature Communications, 2018, vol. 9, Issue 360, 13 pages.

Kilpinen H., et al., "Common Genetic Variation Drives Molecular Heterogeneity in Human iPSCs," Nature, 2017, vol. 546, Issue 7658, pp. 370-375.

Kim B.M., et al., "Regulation of Mouse Stomach Development and Barx1 Expression by specific microRNAs," Development, 2011, vol. 138, pp. 1081-1086.

Kim B.M., et al., "The Stomach Mesenchymal Transcription Factor Barx1 Specifies Gastric Epithelial Identity through Inhibition of Transient Wnt Signaling," Developmental Cell, 2005, vol. 8, pp. 611-622.

Kim D., et al., "HISAT: a Fast Spliced Aligner with Low Memory Requirements," Nature Methods, 2015, vol. 12, Issue 4, pp. 357-360.

Kim T.H., et al., "Stomach Development, Stem Cells and Disease," Development, 2016, vol. 143, pp. 554-565.

Klimanskaya I., et al., "Human Embryonic Stem Cells Derived without Feeder Cells," Lancet, 2005, vol. 365, Issue 9471, pp. 1636-1641.

Kock K., et al., "A Perspective on Efflux Transport Proteins in the Liver," Clinical Pharmacology & Therapeutics, 2012, vol. 92, Issue 5, pp. 599-612.

Koehler E.M., et al., "Presence of Diabetes Mellitus and Steatosis Is Associated with Liver Stiffness in a General Population: The Rotterdam Study," Hepatology, 2016, vol. 63, pp. 138-147.

Kohlnhofer B.M., et al., "GATA4 Regulates Epithelial Cell Proliferation to Control Intestinal Growth and Development in Mice," Cellular and Molecular Gastroenterology and Hepatology, 2016, vol. 2(2), pp. 189-209.

Koike M., et al., "Effects of mechanical strain on proliferation and differentiation of bone marrow stromal cell line ST2," Journal of Bone and Mineral Metabolism, 2005, vol. 23, pp. 219-225.

Kolahchi A.R., et al., "Microfluidic-Based Multi-Organ Platforms for Drug Discovery," Micromachines, 2016, vol. 7, Issue 162, pp. 1-33.

Kolodny G.M., "Evidence for Transfer of Macromolecular RNA Between Mammalian Cells in Culture," Experimental Cell Research, 1971, vol. 65, pp. 313-324.

Koo B-K., et al., "Controlled Gene Expression in Primary Lgr5 Organoid Cultures," Nature Methods, Jan. 1, 2012, vol. 9, No. 1, Jan. 1, 2012, pp. 81-83.

Kordes C., et al., "Hepatic Stellate Cells Contribute to Progenitor Cells and Liver Regeneration," Journal of Clinical Investigation, 2014, vol. 124, Issue 12, pp. 5503-5515.

Kosinski C., et al., "Indian Hedgehog Regulates Intestinal Stem Cell Fate through Epithelial-Mesenchymal Interactions during Development," Gastroenterology, Sep. 2010, vol. 139, pp. 893-903.

Kostrzewski T., et al., "Three-dimensional Perfused Human in Vitro Model of Non-Alcoholic Fatty Liver Disease," World Journal of Gastroenterology, 2017, vol. 23, Issue 2, pp. 204-215.

Kovalenko P.L., et al., "The Correlation between the Expression of Differentiation Markers in rat Small Intestinal Mucosa and the Transcript Levels of Schlafen 3," JAMA Surgery, Sep. 4, 2013, vol. 148, pp. 1013-1019.

(56) References Cited

OTHER PUBLICATIONS

Krahenbuhl S., et al., "Toxicity of Bile Acids on the Electron Transport Chain of Isolated Rat Liver Mitochondria," Hepatology, 1994, vol. 19, pp. 471-479.
Kraus M.R.C., et al., "Patterning and Shaping the Endoderm in Vivo and in Culture," Current Opinion Genetics & Development, 2012, vol. 22, pp. 347-353.
Krausova M., et al., "Wnt Signaling in Adult Intestinal Stem Cells and Cancer," Cellular Signalling, 2014, vol. 26, pp. 570-579.
Kretzschmar K., et al., "Organoids: Modeling Development and the Stem Cell Niche in a Dish," Developmental Cell, Sep. 2016, vol. 38, pp. 590-600.
Kroon E., et al., "Pancreatic Endoderm Derived From Human Embryonic Stem Cells Generates Glucose-Responsive Insulin Secreting Cells In Vivo," Nature Biotechnology, 2008, vol. 26, Issue 4, pp. 443-452.
Kruitwagen H.S., et al., "SCH-O-5 Long-Term Adult Feline Liver Organoid Cultures For Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis," Stem Cell Reports, Apr. 2017, vol. 8(4), pp. 822-830.
Kubal C.A., et al., "Challenges with Intestine and Multivisceral Re-Transplantation: Importance of Timing of Re-Transplantation and Optimal Immunosuppression," Ann Transplant, 2018, vol. 23, pp. 98-104.
Kubo A., et al., "Development of Definitive Endoderm from Embryonic Stem Cells in Culture," Development, 2004, vol. 131, Issue 7, pp. 1651-1662.
Kuci Z., et al., "Mesenchymal Stromal Cells from Pooled Mononuclear Cells of Multiple Bone Marrow Donors as Rescue Therapy in Pediatric Severe Steroid-Refractory Graft-Versus-Host Disease: A Multicenter Survey," Haematologica, 2016, vol. 101 (8), pp. 985-994.
Kudoh T., et al., "Distinct Roles for Fgf, Wnt and Retinoic Acid in Posteriorizing the Neural Ectoderm," Development, 2002, vol. 129, pp. 4335-4346.
Kullak-Ublick G.A., et al., "Drug-Induced Liver Injury: Recent Advantages in Diagnosis and Risk Assessment," Gut, 2017, vol. 66, pp. 1154-1164.
Kumar J.A., et al., "Controversies in the Mechanism of Total Parenteral Nutrition Induced Pathology," Children, 2015, vol. 2, Issue 3, pp. 358-370.
Kumar M., et al., "Signals from Lateral Plate Mesoderm Instruct Endoderm toward a Pancreatic Fate," Dev Biol, 2003, vol. 259, Issue 1, pp. 109-122.
Kuratnik A., et al., "Intestinal Organoids as Tissue Surrogates for Toxicological and Pharmacological Studies," Biochemical Pharmacology, 2013, vol. 85, Issue 12, pp. 1721-1726.
Kurpios N.A., et al., "The Direction of Gut Looping is Established by Changes in the Extracellular Matrix and in Cell: Cell Adhesion," "PNAS, 2008, vol. 105, Issue 25, pp. 8499-8506.
Lachmann N., et al., "Large-Scale Hematopoietic Differentiation of Human Induced Pluripotent Stem Cells Provides Granulocytes or Macrophages for Cell Replacement Therapies, " Stem Cell Report, Feb. 10, 2015, vol. 4, pp. 282-296.
Lahar N., et al., "Intestinal Subepithelial Myofibroblasts Support in Vitro and in Vivo Growth of Human Small Intestinal Epithelium," PLOS One, Nov. 2011, vol. 6(11), e26898, 9 pages.
Lai F.P-L., et al., "Correction of Hirschsprung-Associated Mutations in Human Induced Pluripotent Stem Cells via Clustered Regularly Interspaced Short Palindromic Repeats/Cas9, Restores Neural Crest Cell Function," Gastroenterology, 2017, vol. 153, No. 1, pp. 139-153.
Lambert P.F., et al., "Using an Immortalized Cell Line to Study the HPV Life Cycle in Organotypic "Raft" Cultures," Methods Molecular Medicine, 2005, vol. 119, pp. 141-155.
Lambrecht N.W.G., et al., "Identification of the K Efflux Channel Coupled to the Gastric H—K-Atpase During Acid Secretion," Physiological Genomics, 2005, vol. 21, Issue 1, pp. 81-91.
Lameris A.L., et al., "Expression Profiling of Claudins in the Human Gastrointestinal Tract in Health and During Inflammatory Bowel Disease," Scandinavian Journal of Gastroenterology, 2013, vol. 48, Issue 1, pp. 58-69.
Lancaster M.A., et al., "Organogenesis in a Dish: Modeling Development and Disease Using Organoid Technologies," Science, 2014, vol. 345, Issue 6194, 1247125, 9 pages.
Langmead G., et al., "Ultrafast and Memory-Efficient Alignment of Short DNA Sequences to the Human Genome," Genome Biology, 2009, vol. 10, 10 pages.
Lavial F., et al., "Chicken Embryonic Stem Cells as a Non-Mammalian Embryonic Stem Cell Model," Development, Growth & Differentiation, 2010, vol. 52, pp. 101-114.
Le Douarin N.M., et al., "Neural Crest Cell Plasticity and its Limits," Development 131, 2004, pp. 4637-4650.
Le S., et al., "FactoMineR: An R Package for Multivariate Analysis," Journal of Statistical Software, 2008, vol. 25, Issue 1, pp. 1-18.
Le Vee M., et al., "Polarized Expression of Drug Transporters in Differentiated Human Hepatoma HepaRG Cells," Toxicology in Vitro, 2013, vol. 27, pp. 1979-1986.
Lechner C., et al., "Development of a Fluorescence-Based Assay for Drug Interactions with Human Multidrug Resistance Related Protein (MRP2; ABCC2) in MDCKII-MRP2 Membrane Vesicles," European Journal of Pharmaceutics and Biopharmaceutics, 2010, vol. 75, pp. 284-290.
Lee C.S., et al., "Neurogenin 3 Is Essential for the Proper Specification of Gastric Enteroendocrine Cells and the Maintenance of Gastric Epithelial Cell Identity," Genes Dev, 2002, vol. 16, pp. 1488-1497.
Lee G., et al., "Isolation And Directed Differentiation of Neural Crest Stem Cells Derived from Human Embryonic Stem Cells," Nature Biotechnology, Dec. 2007, vol. 25, pp. 1468-1475.
Lee W.M., et al., "Intravenous N-Acetylcysteine Improves Transplant-Free Survival in Early Stage Non-Acetaminophen Acute Liver Failure," Gastroenterology, 2009, vol. 137, Issue 3, pp. 856-864.
Lennerz J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, vol. 177, Issue 3, pp. 1514-1533.
Leslie E.M., et al., "Differential Inhibition of Rat and Human Na+-Dependent Taurocholate Cotransporting Polypeptide (NTCP/SLC10A1) by Bosentan: A Mechanism for Species Differences in Hepatotoxicity," Journal of Pharmacology and Experimental Therapeutics, 2007, vol. 321, Issue 3, pp. 1170-1178.
Leung A.A., et al., "Tolerance Testing of Passive Radio Frequency Identification Tags for Solvent, Temperature, And Pressure Conditions Encountered in an Anatomic Pathology or Biorepository Setting," Journal of Pathology Informatics, 2010, vol. 1, 6 pages.
Levin D.E., et al., "Human Tissue-Engineered Small Intestine Forms from Postnatal Progenitor Cells," Journal of Pediatric Surgery, 2013, vol. 48, pp. 129-137.
Li H., et al., "Treefam: A Curated Database of Phylogenetic Trees of Animal Gene Families," Nucleic Acids Research, 2006, vol. 34, pp. D572-D580.
Li L., "BMP Signaling Inhibits Intestinal Stem Cell Self-Renewal through Antagonizing Wnt Signaling," Gastroenterology, AASLD Abstracts, Abstract S1223, 2005, vol. 128, p. A702.
Li N., et al., "A Systematic Assessment of Mitochondrial Function Identified Novel Signatures for Drug-Induced Mitochondrial Disruption in Cells," Toxicological Sciences, 2014, vol. 142, Issue 1, pp. 261-273.
Li Y., et al., "In Vitro Organogenesis from Pluripotent Stem Cells," Organogenesis, Jun. 2014, vol. 10, Issue 2, pp. 159-163.
Li Z., et al., "SATB2 is a Sensitive Marker for Lower Gastrointestinal Well-Differentiated Neuroendocrine Tumors," International Journal of Clinical and Experimental Pathology, vol. 8, No. 6, Jan. 2015, pp. 7072-7082.
Lim D.A., et al., "Noggin Antagonizes BMP Signaling to Create a Niche for Adult Neurogenesis," Neuron, Dec. 2000, vol. 28, pp. 713-726.

(56) References Cited

OTHER PUBLICATIONS

Lin C., et al., "The Application of Engineered Liver Tissues for Novel Drug Discovery," Expert Opinion on Drug Discovery, 2015, vol. 10, Issue 5, pp. 519-540.
Lin Y., et al., "Differentiation, Evaluation, and Application of Human Induced Pluripotent Stem Cell-Derived Endothelial Cells," Arteriosclerosis, Thrombosis, and Vascular Biology, 2017, vol. 37, pp. 2014-2025.
Lindley R.M., et al., "Human and Mouse Enteric Nervous System Neurosphere Transplants Regulate the Function of Aganglionic Embryonic Distal Colon," Gastroenterology, Jul. 2008, vol. 135, No. 1, pp. 205-216.
Liu J., et al., "A Small-Molecule Agonist of the Wnt Signaling Pathway," Angewandte Chemie International Edition Engl., 2005, vol. 44, issue 13, pp. 1987-1990.
Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.
Liu L., et al., "A Review of Locomotion Systems for Capsule Endoscopy," IEEE Reviews in Biomedical Engineering, 2015, vol. 8, pp. 138-151.
Logan C.Y., et al., "The Wnt Signaling Pathway in Development and Disease," Annual Review of Cell and Developmental Biology, 2004, vol. 20, pp. 781-810.
Loike J.D., et al., "Opinion: Develop Organoids, Not Chimeras, for Transplantation," The Scientist Magazine, Aug. 2019, (online: http://www.the-scientist.com/news-opinion/opinion--develop-Organoids--not--chimeras--for-transplantation-66339), 3 pages.
Longmire T.A., et al., "Efficient Derivation of Purified Lung and Thyroid Progenitors from Embryonic Stem Cells," Stem Cell, 2012, vol. 10, pp. 398-411.
Lopez-Diaz L., et al., "Intestinal Neurogenin 3 Directs Differentiation of a Bipotential Secretory Progenitor to Endocrine Cell Rather than Goblet Cell Fate," Developmental Biology, 2007, vol. 309, pp. 298-305.
Love M.I., et al., "Moderated Estimation of Fold Change and Dispersion for RNA-seq Data with DESeq2," Genome Biology, 2014, vol. 15, No. 12, pp. 1-21.
Low L.A., et al., "Organs-on-Chips: Progress, Challenges, and Future Directions," Experimental Biology and Medicine, 2017, vol. 242, pp. 1573-1578.
Lu Y., et al., "A Novel 3D Liver Organoid System for Elucidation of Hepatic Glucose Metabolism," Biotechnology and Bioengineering, Feb. 2012, vol. 109, Issue 2, pp. 595-604.
Ludwig T.E., et al., "Derivation of Human Embryonic Stem Cells in Defined Conditions," Nature Biotechnology, Feb. 2006, vol. 24, pp. 185-187.
Ludwig T.E., et al., "Feeder-Independent Culture of Human Embryonic Stem Cells," Nat Methods, Aug. 2006, vol. 3, pp. 637-646.
Lui V.C.H., et al., "Perturbation of Hoxb5 Signaling in Vagal Neural Crests Down-regulates Ret Leading to Intestinal Hypoganglionosis in Mice," Gastroenterology, Apr. 2008, vol. 134, pp. 1104-1115.
Luntz J., et al., "Mechanical Extension Implants for Short-Bowel Syndrome," Smart Structures and Materials 2006: Smart Structures and Integrated Systems, Proceedings of SPIE, 2006, vol. 6173, p. 617309-1-617309-11.
Luo X., et al., "Generation of Endoderm Lineages from Pluripotent Stem Cells," Regenerative Medicine, 2017, vol. 12, Issue 1, pp. 77-89.
MacParland S.A., et al., "Single Cell RNA Sequencing of Human Liver Reveals Distinct Intrahepatic Macrophage Populations," Nature Communications, Oct. 2018, vol. 9, Issue 4383, 21 pages.
Mahe M.M., et al., "Establishment of Gastrointestinal Epithelial Organoids," Current Protocols in Mouse Biology, 2013, vol. 3, No. 4, 31 pages.
Mahe M.M., et al., "In Vivo Model of Small Intestine," Methods in Molecular Biology, 2017, vol. 1597, pp. 229-245.

Majumdar A.P., "Postnatal Undernutrition: Effect of Epidermal Growth Factor on Growth and Function of the Gastrointestinal Tract in Rats," Journal of Pediatric Gastroenterology and Nutrition, 1984, vol. 3, pp. 618-625.
Makin A.J., et al., "A 7-Year Experience of Severe Acetaminophen-Induced Hepatotoxicity (1987-1993)," Gastroenterology, Dec. 1995, vol. 109, Issue. 6, pp. 1907-1916.
Malinen M.M., et al., "Differentiation of Liver Progenitor Cell Line to Functional Organotypic Cultures in 3D Nanofibrillar Cellulose and Hyaluronan-gelatin Hydrogels," Biomaterials, Jun. 2014, vol. 35, pp. 5110-5121.
Mammoto A., et al., "Mechanosensitive Mechanisms in Transcriptional Regulation," Journal of Cell Science, 2012, vol. 125, pp. 3061-3073.
Marcum Z.A., et al., "Medication Adherence to Multi-Drug Regimens," Clinics in Geriatric Medicine, May 2012, vol. 28, Issue 2, pp. 287-300.
Marini F., et al., "pcaExplorer: an R/Bioconductor Package for Interacting with RNA-seq Principal Components," BMC Bioinformatics, Jun. 2019, vol. 20, Issue 1, pp. 1-8.
Marini F., "pcaExplorer: Interactive Visualization of RNA-seq Data Using a Principal Components Approach," Bioconductor.org, R package version 2.3.0, 2017, 7 pages.
Markova S.M., et al., "Association of CYP2C9*2 with Bosentan-Induced Liver Injury," Clinical Pharmacology & Therapeutics, Dec. 2013, vol. 94, Issue 6, pp. 678-686.
Marsh M.N., et al., "A Study of the Small Intestinal Mucosa Using the Scanning Electron Microscope," Gut, 1969, vol. 10, pp. 940-949.
Martin G.R., "Teratocarcinomas and Mammalian Embryogenesis," Science, Aug. 1980, vol. 209, Issue 4458, pp. 768-776.
Martin M., et al., "Dorsal Pancreas Agenesis in Retinoic Acid-Deficient Raldh2 Mutant Mice," Developmental Biology, Aug. 2005, vol. 284, pp. 399-411.
McCauley H.A., et al., "Pluripotent Stem Cell-derived Organoids: Using Principles of Developmental Biology to Grow Human Tissues in a Dish," Development, Mar. 2017, vol. 144, pp. 958-962.
McCracken K.W., et al., "Erratum: Wnt/B-catenin promotes gastric fundus specification in mice and humans," Nature, 2017, vol. 543, Issue 136, 1 page.
McCracken K.W., et al., "Generating Human Intestinal Tissue from Pluripotent Stem Cells in Vitro," Nature Protocols, Nov. 2011, vol. 6, Issue 12, pp. 1920-1928.
McCracken K.W., et al., "Mechanism of Embryonic Stomach Development," Seminars in Cell & Development Biology, 2017, vol. 66, pp. 36-42.
McCracken K.W., et al., "Modelling Human Development and Disease in Pluripotent Stem-Cell-Derived Gastric Organoids," Nature, Oct. 2014, vol. 516, Issue 7531, pp. 400-404.
McCracken K.W., et al., "Wnt/B-Catenin Promotes Gastric Fundus Specification in Mice and Humans," Nature, Jan. 2017, vol. 541, No. 7636, 31 pages.
McCracken K.W., "Mechanisms of Endoderm Patterning and Directed Differentiation of Human Stem Cells into Foregut Tissues," Dissertation, Graduate School of the University of Cincinnati, Jun. 19, 2014, 185 pages.
McGovern D.P.B., et al., "Genome-Wide Association Identifies Multiple Ulcerative Colitis Susceptibility Loci," Nature Genetics, Apr. 2010, vol. 42, Issue 4, pp. 332-337.
McKenzie T.J., et al., "Artificial and Bioartificial Liver Support," Seminars in Liver Disease, May 2008, vol. 28, Issue 2, pp. 210-217.
McKeown S.J., et al., "Hirschsprung Disease: A Developmental Disorder of the Enteric Nervous System," Wiley Interdisciplinary Reviews Developmental Biology, Jan.-Feb. 2013, vol. 2, pp. 113-129.
McLin V.A., et al., "Repression of Wnt/B-Catenin Signaling in the Anterior Endoderm is Essential for Liver and Pancreas Development," Development, Jun. 2007, vol. 134, pp. 2207-2217.
McLin V.A., et al., "The Role of the Visceral Mesoderm in the Development of the Gastrointestinal Tract," Gastroenterology, Jun. 2009, vol. 136, pp. 2074-2091.

(56) References Cited

OTHER PUBLICATIONS

McMahon J.A., et al., "Noggin-Mediated Antagonism of BMP Signaling is required for Growth and Patterning of the Neural Tube and Somite," Genes & Development, May 1998, vol. 12, pp. 1438-1452.

McManus M.T., et al., "Gene Silencing in Mammals by Small Interfering RNAs," Nature Reviews Genetics, Oct. 2002, vol. 3, pp. 737-747.

Meerbrey K.L., et al., "The pINDUCER Lentiviral Toolkit for Inducible RNA Interference in Vitro and in Vivo," Proceedings of the National Academy of Sciences USA, Mar. 2011, vol. 108, pp. 3665-3670.

Mercaldi C.J., et al., "Methods to Identify and Compare Parenteral Nutrition Administered from Hospital-Compounded and Premixed Multichamber Bags in a Retrospective Hospital Claims Database," Journal of Parenteral and Enteral Nutrition, May 2012, vol. 36, Issue 3, pp. 330-336.

Merker S.R., et al., "Gastrointestinal Organoids: How they Gut it out," Developmental Biology, Dec. 2016, vol. 420, pp. 239-250.

Mica Y., et al., "Modeling Neural Crest Induction, Melanocyte Specification and Disease-Related Pigmentation Defects in hESCs and Patient-Specific iPSCs," Cell Reports, Apr. 25, 2013, vol. 3, pp. 1140-1152.

Micallef S.J., et al., "Endocrine Cells Develop within Pancreatic Bud-like Structures Derived from Mouse ES Cells Differentiated in Response to BMP4 and Retinoic Acid," Stem Cell Research, Oct. 2007, vol. 1, pp. 25-36.

Michaut A., et al., "A Cellular Model to Study Drug-Induced Liver Injury in Nonalcoholic Fatty Liver Disease: Application of Acetaminophen," Toxicology and Applied Pharmacology, Feb. 2016, vol. 292, pp. 40-55.

Miki T., et al., "Hepatic Differentiation of Human Embryonic Stem Cells Is Promoted by Three-Dimensional Dynamic Perfusion Culture Conditions," Tissue Engineering: Part C Methods, May 2011, vol. 17, Issue 5, pp. 557-568.

Mills J C., et al., "Gastric Epithelial Stem Cells," Gastroenterology, Feb. 2011, vol. 140, pp. 412-424.

Miyabayashi T., et al., "Wnt/beta-Catenin/CBP Signaling Maintains Long-Term Murine Embryonic Stem Cell Pluripotency," Proceedings of the National Academy of Sciences USA, Mar. 2007, vol. 104, issue 13, pp. 5668-5673.

Múnera J.O., et al., "Differentiation of Human Pluripotent Stem Cells into Colonic Organoids via Transient Activation of BMP Signaling," Cell Stem Cell, Jul. 6, 2017, vol. 21, No. 1, pp. 51-64.

Molodecky N.A., et al., "Increasing Incidence and Prevalence of the Inflammatory Bowel Diseases With Time, Based on Systematic Review," Gastroenterology, Jan. 2012, vol. 142, pp. 46-54.

Molotkov A., et al., "Retinoic Acid Generated by Raldh2 in Mesoderm is required for Mouse Dorsal Endodermal Pancreas Development," Developmental Dynamics, Apr. 2005, vol. 232, pp. 950-957.

Mori R., et al., "Micropatterned Organoid Culture of Rat Hepatocytes and HepG2 Cells," Journal of Bioscience and Bioengineering, Sep. 2008, vol. 106(3), pp. 237-242.

Mork L.M., et al., "Comparison Culture Media for Bile Acid Transport Studies in Primary Human Hepatocytes," Journal of Clinical and Experimental Hepatology, 2012, vol. 2, pp. 315-322.

Moser A.R., et al., "A Dominant Mutation that Predisposes to Multiple Intestinal Neoplasia in the Mouse," Science, Jan. 1990, vol. 247, Issue 4940, pp. 322-324.

Mosher J T., et al., "Intrinsic Differences among Spatially Distinct Neural Crest Stem Cells in Terms of Migratory Properties, Fate-Determination, and Ability to Colonize the Enteric Nervous System," Developmental Biology, Mar. 2007, vol. 303, issue 1, pp. 1-15.

Mou H., et al., "Generation of Multipotent Lung and Airway Progenitors from Mouse ESCs and Patient-Specific Cystic Fibrosis iPSCs," Stem Cell, Apr. 2012, vol. 10, pp. 385-397.

Mudaliar S., et al., "Efficacy and Safety of the Farnesoid X Receptor Agonist Obeticholic Acid in Patients with Type 2 Diabetes and Nonalcoholic Fatty Liver Disease," Gastroenterology, Sep. 2013, vol. 145, pp. 574-582.

Mullin E., "Tiny Human Esophagus Grown in the Lab-Here's Why: Miniature Version of the Organ that Guides Food to the Stomach could Help Scientists Treat a Variety of Medical Ailments," National Geographic, Sep. 20, 2018, downloaded from https://www.nationalgeographic.com/science/2018/news-human-esophagus-grown-lab-stem-cells-cancer-health.html, 5 pages.

Munera J.O., et al., "Generation of Gastrointestinal Organoids from Human Pluripotent Stem Cells, Organ Regeneration," In: Tsuji T., (eds), Organ Regeneration, Methods in Molecular Biology, Humana Press, New York, NY, 2017, vol. 1597, pp. 167-177.

Munoz M., et al., "Conventional Pluripotency Markers are Unspecific for Bovine Embryonic-Derived Cell-Lines," Theriogenology, 2008, vol. 69, pp. 1159-1164.

Nakamura T., et al., "Advancing Intestinal Organoid Technology toward Regenerative Medicine," Cellular and Molecular Gastroenterology and Hepatology, 2018, vol. 5, pp. 51-60.

Nandivada P., et al., "Treatment of Parenteral Nutrition-Associated Liver Disease: The Role of Lipid Emulsions," Advances in Nutrition, Nov. 2013, vol. 4, No. 6, pp. 711-717.

Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.

Navarro V J., et al., "Drug-Related Hepatotoxicity," New England Journal of Medicine, 2006, vol. 354, pp. 731-739.

Negishi T., et al., "Retinoic Acid Signaling Positively Regulates Liver Specification by Inducing wnt2bb Gene Expression in Medaka," Hepatology, 2010, vol. 51, pp. 1037-1045.

Neiiendam J L., et al., "An NCAM-derived FGF-receptor Agonist, the FGL-peptide, Induces Neurite Outgrowth and Neuronal Survival in Primary Rat Neurons," Journal of Neurochemistry, 2004, vol. 91, issue 4, pp. 920-935.

Nelson B J., et al., "Microrobots for Minimally Invasive Medicine," Annual Review of Biomedical Engineering, 2010, vol. 15, issue 12, pp. 55-85.

Nelson C M., "On Buckling Morphogenesis," Journal of Biomechanical Engineering, 2016, vol. 138, pp. 021005-1-021005-6.

Neuschwander-Tetri B.A., et al., "Farnesoid X Nuclear Receptor Ligand Obeticholic Acid for Non-Cirrhotic, Non-Alcoholic Steatohepatitis (Flint): A Multicentre, Randomised, Placebo-Controlled Trial," Lancet, 2015, vol. 385, No. 9972, 23 pages.

Ni X., et al. "Functional Human Induced Hepatocytes (hiHeps) with Bile Acid Synthesis and Transport Capacities: A Novel in Vitro Cholestatic Model," Scientific Reports, 2016, vol. 6, Issue 38694, 16 pages.

Nielsen C., et al., "Gizzard Formation and the Role of Bapx1," Developmental Biology, 2001, vol. 231, Issue 1, pp. 164-174.

Nishida T., et al., "Rat Liver Canalicular Membrane Vesicles Contain an ATP-Dependent Bile Acid Transport System," Proceedings of the National Academy of Sciences USA, Aug. 1991, vol. 88, Issue 15, pp. 6590-6594.

Noguchi T-A.K., et al., "Generation of Stomach Tissue from Mouse Embryonic Stem Cells," Nature Cell Biology, 2015, vol. 17, Issue 8, pp. 984-993.

Nomura S., et al., "Evidence for Repatterning of the Gastric Fundic Epithelium Associated With Menetrier's Disease and TGFa Overexpression," Gastroenterology, May 2005, vol. 128, Issue 5, pp. 1292-1305.

Obermayr F., et al., "Development and Developmental Disorders of the Enteric Nervous System," Nature Reviews/Gastroenterology & Hepatology, Jan. 2013, vol. 10, Issue 1, pp. 43-57.

Ogaki S., et al., "Wnt and Notch Signals Guide Embryonic Stem Cell Differentiation into the Intestinal Lineages," Stem Cells, Jun. 2013, vol. 31, Issue 6, pp. 1086-1096.

Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.

(56) References Cited

OTHER PUBLICATIONS

Okita K., et al., "An Efficient Nonviral Method to Generate Integration-Free Human-Induced Pluripotent Stem Cells from Cord Blood and Peripheral Blood Cells," Stem Cells, Mar. 2013, vol. 31, Issue 3, pp. 458-466.

Okita K., et al., "Generation of Mouse Induced Pluripotent Stem Cells without Viral Vectors," Science, Nov. 7, 2008, vol. 322, Issue 5903, pp. 949-953.

Olbe L., et al., "A Mechanism by which Helicobacter Pylori Infection of the Antrum Contributes to the Development of Duodenal Ulcer," Gastroenterology, 1996, vol. 110, Issue 5, pp. 1386-1394.

Oorts M., et al., "Drug-induced cholestasis risk assessment in sandwich-cultured human hepatocytes," Toxicol in Vitro, 2016, vol. 34, pp. 179-186.

Ootani A., et al., "Sustained in Vitro Intestinal Epithelial Culture within a Wnt-Dependent Stem Cell Niche," Nature Medicine, 2009, vol. 15, Issue 6, pp. 701-706.

Ornitz D.M., et al., "FGF Signaling Pathways in Endochondral and Intramembranous Bone Development and Human Genetic Disease," Genes & Development, 2002, vol. 16, Issue 12, pp. 1446-1465.

Ornitz D.M., et al., "The Fibroblast Growth Factor Signaling Pathway," Wiley Interdisciplinary Reviews Developmental Biology, 2015, vol. 4, Issue 3, pp. 215-266.

Orso G., et al., "Pediatric Parenteral Nutrition-Associated Liver Disease and Cholestasis: Novel Advances in Pathomechanisms-based Prevention and Treatment," Dig Liver Dis, 2016, vol. 48, Issue 3, pp. 215-222.

Ouchi R., et al., "Modeling Steatohepatitis in Humans with Pluripotent Stem Cell-Derived Organoids," Cell Metabolism, Aug. 6, 2019, vol. 30, Issue 2, pp. 374-384.

Paddison P.J., et al., "Short Hairpin Activated Gene Silencing in Mammalian Cells," Methods in Molecular Biology, 2004, vol. 265, pp. 85-100.

Paddison P.J., et al., "RNA interference: the new somatic cell genetics?," Cancer Cell, 2002, vol. 2, Issue 1, pp. 17-23.

Pai R., et al., "Deoxycholic acid activates beta-catenin Signaling Pathway and Increases Colon Cell Cancer Growth and Invasiveness," Molecular Biology of the Cell, 2004, vol. 15, Issue 5, pp. 2156-2163.

Pan Q., "University of Science and Technology of China Press," Physiology, Jan. 31, 2014, pp. 149-150.

Pardal M.L., et al., "Towards the Internet of Things: An Introduction to RFID Technology," RFID Technology-Concepts, Applications, Challenges, Proceedings of the 4th International Workshop, IWRT 2010, In conjunction with ICEIS, 2010, pp. 69-78.

Paris D.B.B.P., et al., "Equine Embryos and Embryonic Stem Cells: Defining Reliable Markers of Pluripotency," Theriogenology, 2010, vol. 74, Issue 4, pp. 516-524.

Park H.R., et al., "Lipotoxicity of Palmitic Acid on Neural Progenitor Cells and Hippocampal Neurogenesis," Toxicological Research, Jun. 2011, vol. 27, Issue 2, pp. 103-110.

Park J.S., et al., "Differential Effects of Equiaxial and Uniaxial Strain on Mesenchymal Stem Cells," Biotechnology and Bioengineering, 2004, vol. 88, Issue 3, pp. 359-368.

Park J.S., et al., "The effect of Matrix Stiffness on the Differentiation of Mesenchymal Stem Cells in Response to TGF-β," Biomaterials, 2011, vol. 32, Issue 16, pp. 3921-3930.

Park K.I., et al., "Acute Injury Directs the Migration, Proliferation, and Differentiation of Solid Organ Stem Cells: Evidence for the Effect of Hypoxia-Ischemia in the CNS on Clonal "reporter" Neural Stem Cells," Experimental Neurology, 2006, vol. 199, Issue 1, pp. 156-178.

Park Y.H., et al., "Review of Atrophic Gastritis and Intestinal Metaplasia as a Premalignant Lesion of Gastric Cancer," Journal of Cancer Prevention, 2015, vol. 20, Issue 1, pp. 25-40.

Parkin D.M., "The Global Health Burden of Infection-Associated Cancers in the Year 2002," International Journal of Cancer, 2006, vol. 118, Issue 12, pp. 3030-3044.

Pastor W.A., et al., "TFAP2C Regulates Transcription in Human Naive Pluripotency by Opening Enhancers," Nature Cell Biology, 2018, vol. 20, Issue 5, pp. 553-564.

Pastula A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pages.

Patankar J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, vol. 56, p. S496.

Patankar J.V., et al., "Intestinal GATA4 Deficiency Protects from Diet-Induced Hepatic Steatosis," Journal of Hepatology, 2012, vol. 57, Issue 5, pp. 1061-1068.

Peek Jr., R.M., et al., "Helicobacter pylori cagA+ Strains and Dissociation of Gastric Epithelial Cell Proliferation from Apoptosis," Journal of the National Cancer, 1997, vol. 89, Issue 12, pp. 863-868.

Peek Jr., R.M., "Helicobacter Pylori Infection and Disease: from Humans to Animal Models," Disease Models & Mechanisms, 2008, vol. 1, Issue 1, pp. 50-55.

Pennisi C.P., et al., "Uniaxial Cyclic Strain Drives Assembly and Differentiation of Skeletal Myocytes," Tissue Engineering: Part A, 2011, vol. 17, pp. 2543-2550.

Pereira C.F., et al., "Heterokaryon-Based Reprogramming of Human B Lymphocytes for Pluripotency Requires Oct4 but Not Sox2," PLoS Genet, 2008, vol. 4, Issue 9, e1000170, 14 pages.

Pessayre D., et al., "Central Role of Mitochondria in Drug-Induced Liver Injury," Drug Metabolism Reviews, 2012, vol. 44, Issue 1, pp. 34-87.

Pessayre D., et al., "Mitochondrial involvement in Drug-Induced Liver Injury," in Adverse Drug Reaction, J. Uetrecht (ed.). Handbook of Experimental Pharmacology, 2010, pp. 311-365.

Petitte J.N., et al., "Avian Pluripotent Stem Cells," Mechanisms of Development, 2004, vol. 121, Issue 9, pp. 1159-1168.

Poling H.M., et al., "Mechanically Induced Development and Maturation of Human Intestinal Organoids in Vivo," Nature Biomedical Engineering, 2018, vol. 2, Issue 6, pp. 429-442.

Polson J., et al., "AASLD Position Paper: The Management of Acute Liver Failure," Hepatology, 2005, vol. 41, Issue 5, pp. 1179-1197.

Pompaiah M., et al., "Gastric Organoids: An Emerging Model System to Study Helicobacter pylori Pathogenesis," Current Topics in Microbiology and Immunology, 2017, vol. 400, pp. 149-168.

Prakash R., "Regulation of WNT Genes in Stem Cells Development and Organogenesis," IJP, Jun. 2014, vol. 1, Issue 6, pp. 366-372.

Pulikkot S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pages.

Purton L E., et al., "All-Trans Retinoic Acid Enhances the Long-Term Repopulating Activity of Cultured Hematopoietic Stem Cells," Blood, 2000, vol. 95, Issue 2, pp. 470-477.

Qi M-C., et al., "Mechanical Strain induces Osteogenic Differentiation: Cbfa1 and Ets-1 Expression in Stretched Rat Mesenchymal Stem Cells," International Journal of Oral and Maxillofacial Surgery, 2008, vol. 37, pp. 453-458.

Que J., et al., "Morphogenesis of the Trachea and Esophagus: Current Players and New Roles for Noggin and Bmps," Differentiation, 2006, vol. 74, pp. 422-437.

Rachek Li., et al., "Troglitazone, but not Rosiglitazone, Damages Mitochondrial DNA and induces Mitochondrial Dysfunction and Cell Death in Human Hepatocytes," Toxicology and Applied Pharmacology, 2009, vol. 240, Issue 3, pp. 348-354.

Raju R., et al., "A Network Map of FGF-1/FGFR Signaling System," Journal of Signal Transduction, Apr. 2014, Article ID 962962, 16 pages.

Ramachandran S.D., et al., "In Vitro Generation of Functional Liver Organoid-Like Structures Using Adult Human Cells," PLoS One, Oct. 21, 2015, vol. 10, No. 10, pp. 1-14.

Ramalingam S., et al., "Distinct Levels of Sox9 Expression Mark Colon Epithelial Stem Cells that form Colonoids in Culture," The

(56) References Cited

OTHER PUBLICATIONS

American Journal of Physiology: Gastrointestinal and Liver Physiology, 2012, vol. 302, Issue 1, pp. G10-G20.
Ramirez-Weber F.A., et al., "Cytonemes: Cellular Processes that Project to the Principal Signaling Center in Drosophila Imaginal Discs," Cell, May 28, 1999, vol. 97, pp. 599-607.
Ramsey V.G., et al., "The Maturation of Mucus-Secreting Gastric Epithelial Progenitors: into Digestive-Enzyme Secreting Zymogenic Cells Requires Mist1," Development, 2007, vol. 134, Issue 1, pp. 211-222.
Rane A., et al., "Drug Metabolism in the Human Fetus and Newborn Infant," Pediatric Clinics of North America, 1972, vol. 19, Issue 1, pp. 37-49.
Rankin S.A., et al., "A Molecular Atlas of Xenopus Respiratory System Development," Developmental Dynamics, 2015, vol. 244, pp. 69-85.
Rankin S.A., et al., Timing is everything: Reiterative Wnt, BMP and RA Signaling Regulate Developmental Competence during Endoderm Organogenesis, Developmental Biology, Feb. 1, 2018, vol. 434, Issue 1, pp. 121-132.
Rankin S.A., et al., "Suppression of Bmp4 Signaling by the Zinc-Finger Repressors Osr1 and Osr2 is required for Wnt/beta-Catenin-Mediated Lung Specification in Xenopus," Development, 2012, vol. 139, Issue 16, pp. 3010-3020.
Rao R.R., et al., "Gene Expression Profiling of Embryonic Stem Cells Leads to Greater Understanding of Pluripotency and Early Developmental Events," Biology of Reproduction, 2004, vol. 71, pp. 1772-1778.
Ratineau C., et al., "Endoderm- and Mesenchyme-Dependent Commitment of the Differentiated Epithelial Cell Types in the Developing Intestine of Rat," Differentiation, 2003, vol. 71, pp. 163-169.
Ray K., "Engineering Human Intestinal Organoids with a Functional ENS," Nature Reviews Gastroenterology & Hematology, Nov. 2016, 1 page.
Rector, R.S., et al., "Mitochondrial Dysfunction Precedes Insulin Resistance and Hepatic Steatosis and Contributes to the Natural History of Non-Alcoholic Fatty Liver Disease in an Obese Rodent Model," Journal of Hepatology, 2010, vol. 52, Issue 5, pp. 727-736.
Reilly G C., et al., "Intrinsic Extracellular Matrix Properties Regulate Stem Cell Differentiation," Journal of Biomechanics, Jan. 2010, vol. 43, Issue 1, pp. 55-62.
Rennert K., et al., "A Microfluidically Perfused Three Dimensional Human Liver Model," Biomaterials, 2015, vol. 71, pp. 119-131.
Reuben A., et al., "Drug-Induced Acute Liver Failure: Results of a U.S. Multicenter, Prospective Study," Hepatology, 2010, vol. 52, pp. 2065-2076.
Ricchi M., et al., "Differential Effect of Oleic and Palmitic Acid on Lipid Accumulation and Apoptosis in Cultured Hepatocytes," Journal of Gastroenterology and Hepatology, May 2009, vol. 24, Issue 5, pp. 830-840.
Richards M et al., "The Transcriptome Profile of Human Embryonic Stem Cells as Defined by SAGE," Stem Cells, 2004, vol. 22, pp. 51-64.
Riedinger, et al., "Reversible Shutdown of Replicon Initiation by Transient Hypoxia in Ehrlich ascites Cells: Dependence of Initiation on Short-Lived Protein," European Journal of Biochemistry, Dec. 1992, vol. 210, Issue 2, pp. 389-398.
Roberts A., et al., "Identification of Novel Transcripts in Annotated Genomes using RNA-Seq," Bioinformatics, 2011, vol. 27, Issue 17, pp. 2325-2329.
Roberts A., et al., "Improving RNA-Seq Expression Estimates by Correcting for Fragment Bias," Genome Biology, 2011, vol. 12, 14 pages.
Roberts D.J., et al., "Sonic Hedgehog is an Endodermal Signal inducing Bmp-4 and Hox genes during Induction and Regionalization of the Chick hindgut," Development, 1995, vol. 121, pp. 3163-3174.
Rodriguez, P., et al., "BMP Signaling in the Development of the Mouse Esophagus and Forestomach," Development, 2010, vol. 137, Issue 24, pp. 4171-4176.
Rodriguez-Pineiro A.M., et al., "Studies of Mucus in Mouse Stomach, Small Intestine, and Colon. II. Gastrointestinal Mucus Proteome Reveals Muc2 and Muc5ac Accompanied by a set of Core Proteins," American Journal of Physiology: Gastrointestinal and Liver Physiology, 2013, vol. 305, pp. G348-G356.
Rohrschneider, M.R., et al., "Polarity and Cell Fate Specification in the Control of C. Elegans Gastrulation," Developmental Dynamics, 2009, vol. 238, Issue 4, pp. 789-796.
Ronn R.E., et al., "Retinoic Acid Regulates Hematopoietic Development from Human Pluripotent Stem Cells," Stem Cell Reports. 2015, vol. 4, pp. 269-281.
Roth, R.B., et al., "Gene Expression Analyses Reveal Molecular Relationships among 20 Regions of the Human CNS," Neurogenetics, 2006, vol. 7, pp. 67-80.
Rouch J.D., et al., "Scalability of an Endoluminal Spring for Distraction Enterogenesis," Journal of Pediatric Surgery, 2016, vol. 51, pp. 1988-1992.
Roy S., et al., "Cytoneme-Mediated Contact-Dependent Transport of the *Drosophila* Decapentaplegic Signaling Protein," Science, 2014, vol. 343, pp. 1244624-1 to 1244624-10.
Russo M. W., et al., "Liver Transplantation for Acute Liver Failure From Drug Induced Liver Injury in the United States," Liver Transplantation, 2004, vol. 10, Issue 8, pp. 1018-1023.
Sachs N., et al., "A Living Biobank of Breast Cancer Organoids Captures Disease Heterogeneity," Cell, 2018, vol. 172, pp. 373-386.
Saenz J.B., et al., "Stomach Growth in a Dish," Nature, Jan. 2017, vol. 541, No. 7636, pp. 160-161.
Saffrey M J., "Cellular Changes in the Enteric Nervous System During Ageing," Developmental Biology, 2013, vol. 382, pp. 344-355.
Saha S., et al., "Inhibition of Human Embryonic Stem Cell Differentiation by Medical Strain," Journal of Cellular Physiology, 2006, vol. 206, pp. 126-137.
Saini A., "Cystic Fibrosis Patients Benefit from Mini Guts," Cell Stem Cell, 2016, vol. 19, pp. 425-427.
Saito M., et al., "Reconstruction of Liver Organoid using a Bioreactor," World Journal of Gastroenterology, Mar. 2006, vol. 12, Issue 12, pp. 1881-1888.
Salas-Vidal E., et al., "Imaging Filopodia Dynamics in the Mouse Blastocyst," Developmental Biology, 2004, vol. 265, pp. 75-89.
Sampaziotis F., et al., "Potential of Human Induced Pluripotent Stem Cells in Studies of Liver Disease," Hepatology, 2015, vol. 62, Issue 1, pp. 303-311.
Sancho E., et al., "Signaling Pathways in Intestinal Development and Cancer," Annual Review of Cell and Developmental Biology, 2004, vol. 20, pp. 695-723.
Sandoiu A., "Scientists Create Human Esophagus in Stem Cell First," Medical News Today, Downloaded from https://www.medicalnewstoday.com/articles/323118.phpSep. 21, 2018, 4 pages.
Sartori-Rupp A., et al., "Correlative Cryo-Electron Microscopy Reveals the Structure of TNTs in Neuronal Cells," Nature Communications, 2019, vol. 10, 16 pages.
Sasai Y., "Cytosystems Dynamics in Self-Organization of Tissue Architecture," Nature, 2013, vol. 493, pp. 318-326.
Sasai Y., "Next-Generation Regenerative Medicine: Organogenesis from Stem Cells in 3D Culture," Cell Stem Cell, May 2013, vol. 12, pp. 520-530.
Sasselli V., et al., "The Enteric Nervous System," Developmental Biology, Jan. 2012, vol. 366, pp. 64-73.
Sato T., et al., "Single Lgr5 Stem Cells Build Crypt-Villus Structures in Vitro without a Mesenchymal Niche," Nature, 2009, vol. 459, pp. 262-265.
Sato T., et al., "Long-term Expansion of Epithelial Organoids from Human Colon, Adenoma, Adenocarcinoma, and Barrett's Epithelium," Gastroenterology, Nov. 1, 2011, vol. 141, pp. 1762-1772.
Sato T., et al., "Snapshot: Growing Organoids from Stem Cells," Cell, 2015, vol. 161, pp. 1700-1700e1.
Savidge T.C., et al., "Human Intestinal Development in a Severe-Combined Immunodeficient Xenograft model," Differentiation, 1995, vol. 58, pp. 361-371.
Savin T., et al., "On the Growth and Form of the Gut," Nature, Aug. 3, 2011, vol. 476, pp. 57-62.

(56) References Cited

OTHER PUBLICATIONS

Schlieve C.R., et al., "Created of Warm Blood and Nerves: Restoring an Enteric Nervous System in Organoids," Cell Stem Cell, Jan. 2017, vol. 20, pp. 5-7.
Schmelter M., et al., "Embryonic Stem Cells Utilize Reactive Oxygen Species as Transducers of Mechanical Strain-induced Cardiovascular Differentiation," The FASEB Journal, Jun. 2006, vol. 20, Issue 8, pp. 1182-1184.
Schonhoff S E., et al., "Neurogenin 3-Expressing Progenitor Cells in the Gastrointestinal Tract Differentiate into both Endocrine and Non-Endocrine Cell Types," Developmental Biology, Jun. 2004, vol. 270, No. 2, pp. 443-454.
Schumacher M A., et al., "Gastric Sonic Hedgehog Acts as a Macrophage Chemoattractant during the Immune Response to Helicobacter pylori," Gastroenterology, May 2012, vol. 142, Issue 5, pp. 1150-1159.
Schumacher M.A., et al., "The Use of Murine-derived Fundic Organoids in Studies of Gastric Physiology," J. Physiol., Apr. 15, 2015, vol. 593, Issue 8, pp. 1809-1827.
Schuppan D., et al., "Non-alcoholic Steatohepatitis: Pathogenesis and Novel Therapeutic Approaches," Journal of Gastroenterology and Hepatology, Aug. 2013, vol. 28, Suppl. 1, pp. 68-76.
Serviddio G., et al., "Ursodeoxycholic Acid Protects Against Secondary Biliary Cirrhosis in Rats by Preventing Mitochondrial Oxidative Stress," Hepatology, 2004, vol. 39, pp. 711-720.
Shah S.B., et al., "Cellular Self-assembly and Biomaterials-based Organoid Models of Development and Diseases," Acta Biomaterialia, Apr. 15, 2017, vol. 53, pp. 29-45.
Shahbazi M N., et al., "Self-organization of the human embryo in the absence of maternal tissues," Nature Cell Biology, May 4, 2016, vol. 18, Issue 6, pp. 700-708.
Shan J., et al., "Identification of a Specific Inhibitor of the Dishevelled PDZ Domain," Biochemistry, 2005, vol. 44, No. 47, pp. 15495-15503.
Sheehan-Rooney K., et al., "Bmp and Shh Signaling Mediate the Expression of satb2 in the Pharyngeal Arches," PLoS One, Mar. 21, 2013, vol. 8, No. 3, e59533, 10 pages.
Shekherdimian S., et al., "The Feasibility of using an Endoluminal Device for Intestinal Lengthening," Journal of Pediatric Surgery, Aug. 2010, vol. 45, Issue 8, pp. 1575-1580.
Sherwood R I., et al., "Transcriptional Dynamics of Endodermal Organ Formation," Developmental Dynamics, Jan. 2009, vol. 238, Issue 1, pp. 29-42.
Sherwood R I., et al., "Wnt Signaling Specifies and Patterns Intestinal Endoderm," Mechanisms of Development, Sep. 2011, vol. 128, pp. 387-400.
Shi X L., et al., "Evaluation of a Novel Hybrid Bioartificial Liver Based on a Multi-Layer Flat-Plate Bioreactor," World Journal of Gastroenterology, Jul. 28, 2012, vol. 18, Issue 28, pp. 3752-3760.
Shi X-L., et al., "Effects of Membrane Molecular Weight Cut-off on Performance of a Novel Bioartificial Liver," Artificial Organs, Mar. 2011, vol. 35, Issue, 3, pp. E40-E46.
Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.
Shimizu N., et al., "Cyclic Strain Induces Mouse Embryonic Stem Cell Differentiation into Vascular Smooth Muscle Cells by Activating PDGF Receptor Beta," Journal of Applied Physiology, Mar. 2008, vol. 104, pp. 766-772.
Shyer A.E., et al., "Bending Gradients: How the Intestinal Stem Cell Gets Its Home," Cell, Apr. 23, 2015, vol. 161, Issue 3, pp. 569-580.
Shyer A.E., et al., "Villification: How the Gut Gets its Villi," Science, Oct. 11, 2013, vol. 342, pp. 212-218.
Siegel R., et al., "Colorectal Cancer Statistics, 2014," CA Cancer Journal for Clinicians, Apr. 2014, vol. 64, Issue 2, pp. 104-117.
Sigalet D L., "The Role of the Enteric Neuronal System in Controlling Intestinal Function," Clinical Surgery Society Magazine, 2003, vol. 64, p. 214.
Siller R., et al., "Small-Molecule-Driven Hepatocyte Differentiation of Human Pluripotent Stem Cells," Stem Cell Reports, May 2015, vol. 4, No. 5, pp. 939-952.
Sim Y.J., et al., "2i Maintains a Naive Ground State in ESCs through Two Distinct Epigenetic Mechanisms," Stem Cell Reports, May 9, 2017, vol. 8, Issues. 5, pp. 1312-1328.
Simkin J.E., et al., "Retinoic Acid Upregulates Ret and Induces Chain Migration and Population Expansion in Vagal Neural Crest Cells to Colonise the Embryonic Gut," PLoS ONE, May 2013, vol. 8(5), e64077, pp. 1-12.
Simon-Assmann P., et al., "In Vitro Models of Intestinal Epithelial Cell Differentiation," Cell Biology and Toxicology, Jul. 2007, vol. 23, No. 4, pp. 241-256.
Sinagoga K.L., et al., "Generating Human Intestinal Tissues from Pluripotent Stem Cells to Study Development and Disease," The EMBO Journal, May 5, 2015, vol. 34, Issue 9, pp. 1149-1163.
Singh S., et al., "Comparative Effectiveness of Pharmacological Interventions for Nonalcoholic Steatohepatitis: A Systematic Review and Network Meta-analysis," Hepatology, Nov. 2015, vol. 62, Issue 5, pp. 1417-1432.
Si-Tayeb K., et al., "Highly Efficient Generation of Human Hepatocyte-Like Cell from Induced Pluripotent Stem Cells," Hepatology, Jan. 2010, vol. 51, Issue 1, pp. 297-305.
Sitti M., et al., "Biomedical Applications of Untethered Mobile Milli/Microrobots," The Proceedings of the IEEE Institution of Electrical Engineers, Feb. 2015, vol. 103, Issue 2, pp. 205-224.
Skardal A., et al., "Organoid-on-a-Chip and Body-on-a-Chip Systems for Drug Screening and Disease Modeling," Drug Discovery Today, Sep. 2016, vol. 21, Issue 9, pp. 1399-1411.
Slaymaker I M., et al., "Rationally Engineered Cas9 Nucleases with Improved Specificity," Science, Jan. 1, 2016, vol. 351, issue 6268, pp. 84-88.
Sloan C.A., et al., "ENCODE Data at the ENCODE Portal," Nucleic Acids Research, Jan. 4, 2016, vol. 44, Issue. D1, pp. D726-D732.
Sneddon I.N., "The Relation between Load and Penetration in the Axisymmetric Boussinesq Problem for a Punch of Arbitrary Profile," International Journal of Engineering Science, May 1965, vol. 3, Issue 1, pp. 47-57.
Snoeck H W., "Generation of Anterior Foregut Derivatives from Pluripotent Stem Cells," Stem Cells Handbook, S. Sell (ed.), Jul. 3, 2013, pp. 161-175.
Snykers S., et al., "In Vitro Differentiation of Embryonic and Adult Stem Cells into Hepatocytes: State of the Art," Stem Cells, Mar. 2009, vol. 27, No. 3, pp. 577-605.
Soffers J H M., et al., "The Growth Pattern of the Human Intestine and its Mesentery," BMC Developmental Biology, Aug. 22, 2015, vol. 15, Issue 31, 16 pages.
Song W., et al., "Engraftment of Human Induced Pluripotent Stem cell-Derived Hepatocytes in Immunocompetent Mice via 3D Co-aggregation and Encapsulation," Scientific Reports, 2015, vol. 5, Issue 16884, 13 pages.
Song Z., et al., "Efficient Generation of Hepatocyte-like cells from Human Induced Pluripotent Stem Cells," Cell Res, Nov. 2009, vol. 19, Issue 11, pp. 1233-1241.
Sonntag F., et al., "Design and Prototyping of a Chip-based Multi-micro-Organoid Culture System for Substance Testing, Predictive to Human (substance) Exposure," Journal of Biotechnology, Jul. 1, 2010, vol. 148, Issue 1, pp. 70-75.
Soto-Gutierrez A., et al., "Engineering of an Hepatic Organoid to Develop Liver Assist Devices," Cell Transplant, 2010, vol. 19, No. 6, 12 pages.
Spear P C., et al., "Interkinetic Nuclear Migration: A Mysterious Process in Search of a Function," Develop. Growth Differ, Apr. 2012, vol. 54, Issue 3, pp. 306-316.
Speer A L., et al., "Fibroblast Growth Factor 10-Fibroblast Growth Factor Receptor 2b Mediated Signaling is not Required for Adult Glandular Stomach Homeostasis," PLoS ONE, Nov. 2012, vol. 7, Issue 11, e49127, 12 pages.
Speer A L., et al., "Murine Tissue-Engineered Stomach Demonstrates Epithelial Differentiation," Journal of Surgical Research, Mar. 22, 2011, vol. 171, Issue 1, pp. 6-14.

(56) References Cited

OTHER PUBLICATIONS

Spence J R., et al., "Translational Embryology: Using Embryonic Principles to Generate Pancreatic Endocrine cells from Embryonic Stem Cells," Developmental Dynamics, Dec. 2007, vol. 236, issue 12, pp. 3218-3227.
Spence J R., et al., "Vertebrate Intestinal Endoderm Development," Developmental Dynamics, Mar. 2011, vol. 240, Issue 3, pp. 501-520.
Spence J.R., et al., "Directed Differentiation of Human Pluripotent Stem Cells into Intestinal Tissue in Vitro," Nature (London), Feb. 3, 2011, vol. 470, Issue 7332, pp. 105-109.
Stadtfeld M., et al., "Induced Pluripotent Stem Cells Generated without Viral Integration," Science, Nov. 7, 2008, vol. 322, issue 5903, pp. 945-949.
Stafford D., et al., "A Conserved Role for Retinoid Signaling in Vertebrate Pancreas Development," Development Genes and Evolution, Sep. 2004, vol. 214, Issue 9, pp. 432-441.
Stange D E., et al., "Differentiated Troy+ Chief Cells act as 'Reserve' Stem cells to Generate all Lineages of the Stomach Epithelium," Cell, Oct. 10, 2013, vol. 155, Issue 2, pp. 357-368.
Stark R., et al., "Development of an Endoluminal Intestinal Lengthening Capsule," Journal of Pediatric Surgery, Jan. 2012, vol. 47, Issue 1, pp. 136-141.
Stender S., et al., "Adiposity Amplifies the Genetic Risk of Fatty Liver Disease Conferred by Multiple Loci," Nat Genet, Jun. 2017, vol. 49, Issue 6, pp. 842-847.
Stevens J L., et al., "The Future of Drug Safety Testing: Expanding the View and Narrowing the Focus," Drug Discovery Today, Feb. 2009, vol. 14, Issue 3-4, pp. 162-167.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Stuart T., et al., "Comprehensive Integration of Single-Cell Data," Cell, Jun. 13, 2019, vol. 177, pp. 1888-1902.
Su N., et al., "Role of FGF/FGFR Signaling in Skeletal Development and Homeostasis: Learning from Mouse Models," Bone Research, Apr. 29, 2014, vol. 2, No. 1, 24 pages.
Sugawara T., et al., "Organoids Recapitulate Organs?," Stem Cell Investigation, Jan. 2018, vol. 5(3), 4 pages.
Sugimoto S., et al., "Reconstruction of the Human Colon Epithelium in Vivo," Cell Stem Cell, 2018, vol. 22, pp. 171-176, e1-e5.
Sui L., et al., "Signaling Pathways During Maintenance and Definitive Endoderm Differentiation of Embryonic Stem Cells," The International Journal of Developmental Biology, 2013, vol. 57(1), pp. 1-12.
Sun Y., et al., "Genome Engineering of Stem Cell Organoids for Disease Modeling," Protein Cell, May 2017, vol. 8(5), pp. 315-327.
Suzuki A., et al., "Clonal Identification and Characterization of Self-renewing Pluripotent Stem Cells in the Developing Liver," The Journal of Cell Biology, Jan. 7, 2002, vol. 156(1), pp. 173-184.
Tada M., et al., "Embryonic Germ Cells Induce Epigenetic Reprogramming of Somatic Nucleus in Hybrid Cells," EMBO Journal, 1997, vol. 16(21), pp. 6510-6520.
Taipale J., et al., "The Hedgehog and Wnt signalling pathways in cancer," Nature, May 17, 2001, vol. 411, pp. 349-354.
Tait I.S., et al., "Colonic Mucosal Replacement by Syngeneic Small Intestinal Stem Cell Transplantation," The American Journal of Surgery, Jan. 1994, vol. 167(1), pp. 67-72.
Tait I.S., et al., "Generation of Neomucosa in Vivo by Transplantation of Dissociated Rat Postnatal Small Intestinal Epithelium," Differentiation, Apr. 1994 Vol. 56,(1-2), pp. 91-100.
Takahashi K., et al., "Induction of Pluripotent Stem Cells from Adult Human Fibroblasts by Defined Factors," Cell, Nov. 30, 2007, vol. 131(5), pp. 861-872.
Takahashi K., et al., "Induction of Pluripotent Stem Cells from Mouse Embryonic and Adult Fibroblast Cultures by Defined Factors," Cell, Aug. 25, 2006, vol. 126(4), pp. 663-676.
Takahashi S., et al., "Epigenetic Differences between Naive and Primed Pluripotent Stem Cells," Cellular and Molecular Life Sciences, Apr. 2018, vol. 75(7), pp. 1191-1203.
Takaki M., et al., "In Vitro Formation of Enteric Neural Network Structure in a Gut-Like Organ Differentiated from Mouse Embryonic Stem Cells," Stem Cells, Jun. 9, 2006, vol. 24(6), pp. 1414-1422.
Takashima Y., et al., "Resetting Transcription Factor Control Circuitry toward Ground-State Pluripotency in Human," Cell, Sep. 11, 2014, vol. 158(6), pp. 1254-1269.
Takebe T., et al., "Generation of a Vascularized and Functional Human Liver from an iPSC-derived Organ Bud Transplant," Nature Protocols, Feb. 2014, vol. 9(2), pp. 396-409.
Takebe T., et al., "Human iPSC-Derived Miniature Organs: A Tool for Drug Studies," Clinical Pharmacology & Therapeutics, Sep. 2014, vol. 96(3), pp. 310-313.
Takebe T., et al., "Massive and Reproducible Production of Liver Buds Entirely from Human Pluripotent Stem Cells," Cell Reports, Dec. 5, 2017, vol. 21(10), pp. 2661-2670.
Takebe T., et al., "Vascularized and Complex Organ Buds from Diverse Tissues via Mesenchymal Cell-Driven Condensation," Cell Stem Cell, May 7, 2015, vol. 16(5), pp. 556-565.
Takebe T., et al., "Vascularized and Functional Human Liver from an iPSC-derived Organ bud Transplant," Nature, Jul. 25, 2013, vol. 499(7459), pp. 481-484.
Tamm C., et al., "A Comparative Study of Protocols for Mouse Embryonic Stem Cell Culturing," PLoS ONE, Dec. 10, 2013, vol. 8(12), e81156, 10 pages.
Tamminen K., et al., "Intestinal Commitment and Maturation of Human Pluripotent Stem Cells Is Independent for Exogenous FGF4 and R-spondin1," PLOS One, Jul. 31, 2015, vol. 10(7), e0134551, 19 pages.
Tang W., et al., "Faithful Expression of Multiple Proteins via 2A-Peptide Self-processing: a Versatile and Reliable method for Manipulating Brain Circuits," The Journal of Neuroscience, Jul. 8, 2009, vol. 29(27), pp. 8621-8629.
Teo A K.K., et al., "Activin and BMP4 Synergistically Promote Formation of Definitive Endoderm in Human Embryonic Stem Cells," Stem Cells, Apr. 2012, vol. 30(4), pp. 631-642.
Terry B.S., et al., "Preliminary Mechanical Characterization of the Small Bowel for In Vivo Robotic Mobility," Journal of Biomechanical Engineering, Sep. 2011, vol. 133(9), 091010-1-09101-7.
Thanasupawat T., et al., "INSL5 is a Novel Marker for Human Enteroendocrine Cells of the Large Intestine and Neuroendocrine Tumours," Oncology Reports, 2013, vol. 29, No. 1, pp. 149-154.
The ENCODE Project Consortium, "An Integrated Encyclopedia of DNA Elements in the Human Genome," Nature, Sep. 5, 2012, vol. 489, pp. 57-74.
The United States Pharmacopeia: The National Formulary (USP 24 NF 19), United States Pharmacopoeial Convention, Inc., Rockville, MD, 1999, 4 pages.
The WNT Homepage, "Small molecules in Wnt signaling," Nusse Lab, Jan. 2019, 2 pages.
Theunissen T.W., et al., "Systematic Identification of Culture Conditions for Induction and Maintenance of Naive Human Pluripotency," Cell Stem Cell, Oct. 2, 2014, vol. 15(4), pp. 471-487.
Thomson J.A., et al., "Embryonic Stem Cell Lines Derived from Human Blastocysts," Science, Nov. 6, 1998, vol. 282, No. 5391, pp. 1145-1147.
Tian X., et al., "Modulation of Multidrug Resistance-Associated Protein 2 (Mrp2) and Mrp3 Expression and Function with Small Interfering RNA in Sandwich-Cultured Rat Hepatocytes," Molecular Pharmacology, Oct. 2004, vol. 66(4), pp. 1004-1010.
Tiso N., et al., "BMP Signalling Regulates Anteroposterior Endoderm Patterning in Zebrafish," Mech Dev, Oct. 2002, vol. 118, pp. 29-37.
Toivonen S., et al., "Activin A and Wnt-dependent Specification of Human Definitive Endoderm Cells," Experimental Cell Research, Aug. 2013, vol. 319(17), pp. 2535-2544.

(56) References Cited

OTHER PUBLICATIONS

Tran K., et al., "Evaluation of Regional and Whole Gut Motility using the Wireless Motility Capsule: Relevance in Clinical Practice," Therapeutic Advances in Gastroenterology, Jul. 2012, vol. 5(4), pp. 249-260.

Trapnell C., et al., "Differential gene and Transcript Expression Analysis of RNA-seq Experiments with TopHat and Cufflinks," Nature Protocols, 2013, vol. 7(3), pp. 562-578.

Trapnell C., et al., "Transcript Assembly and Quantification by RNA-Seq reveals Unannotated Transcripts and Isoform Switching during Cell Differentiation," Nature Biotechnology, May 2, 2010, vol. 28(5), pp. 511-515.

Trisno S.L., et al., "Esophageal Organoids from Human Pluripotent Stem Cells Delineate Sox2 Functions during Esophageal Specification," Cell Stem Cell, Oct. 4, 2018, vol. 23(4), pp. 501-515.

Troy D.B., et al., "Remington: The Science and Practice of Pharmacy," 21st Edition, Lippincott Williams & Wilkens, 2006, Table of Contents, 6 pages.

Tsakmaki A., et al., "3D Intestinal Organoids in Metabolic Research: Virtual Reality in a Dish," Current Opinion in Pharmacology, 2017, vol. 37, pp. 51-58.

Tsedensodnom O., et al., "ROS: Redux and Paradox in Fatty Liver Disease," Hepatology, Oct. 2013, vol. 58, No. 4, pp. 1210-1212.

Tsukada N., et al., "The Structure and Organization of the Bile Canalicular Cytoskeleton with Special Reference to Actin and Actin-Binding Proteins," Hepatology, 1995, vol. 21, No. 4, pp. 1106-1113.

Tuschl T et al., "Targeted mRNA degradation by Double-Stranded RNA in vitro," Genes & Development., 1999, vol. 13, pp. 3191-3197.

Tyml K., et al., "Lipopolysaccharide Reduces Intercellular Coupling in Vitro and Arteriolar Conducted Response in Vivo," American Journal of Physiology—Heart and Circulatory Physiology, 2001, vol. 281, pp. H1397-H1406.

Uppal K., et al., "Meckel's Diverticulum: A Review," Clinical Anatomy, 2011, vol. 24, pp. 416-422.

Valadi H., et al., "Exosome-Mediated Transfer of mRNAs and MicroRNAs is a Novel mechanism of Genetic Exchange between Cells," Nature Cell Biology, 2007, vol. 9, No. 6, pp. 654-659.

Van Breemen R.B., et al., "Caco-2 Cell Permeability Assays to Measure Drug Absorption," Expert Opinion on Drug Metabolism & Toxicology, Aug. 2005, vol. 1, No. 2, pp. 175-185.

Van De Garde M.D., et al., "Liver Monocytes and Kupffer Cells Remain Transcriptionally Distinct during Chronic Viral Infection," PLoS One, Nov. 3, 2016, vol. 11, No. 11, 16 pages.

Van Dop W.A., et al., "Depletion of the Colonic Epithelial Precursor Cell Compartment upon Conditional Activation of the Hedgehog Pathway," Gastroenterology, 2009, vol. 136, No. 7, pp. 2195-2203.

Van Klinken B.J.W., et al., "MUC5B is the Prominent Mucin in Human Gallbladder and is also Expressed in a Subset of Colonic Goblet Cells," The American Journal of Physiology, 1998, vol. 274, pp. G871-G878.

Venick, R.S., et al., "Unique Technical and Patient Characteristics of Retransplantation: A Detailed Single-Center Analysis of Intestinal Transplantation," International Small Bowel Symposium 2013; Abstract 5.203, retrieved from https://www.tts.org/component/ts/?view=presentation&id=13190, accessed Jun. 12, 2017, 4 pages.

Verma S., et al., "Diagnosis, Management and Prevention of Drug-Induced Liver Injury," Gut, 2009, vol. 58, pp. 1555-1564.

Verzi M.P., et al., "Role of the Homeodomain Transcription Factor Bapx1 in Mouse Distal Stomach Development," Gastroenterology, 2009, vol. 136, No. 5, pp. 1701-1710.

Vosough M., et al. "Generation of Functional Hepatocyte-Like Cells from Human Pluripotent Stem Cells in a Scalable Suspension Culture," Stem Cells and Development, 2013, vol. 22, No. 20, pp. 2693-2705.

Vu J., et al., "Regulation of Appetite, Body Composition and Metabolic Hormones by Vasoactive Intestinal Polypeptide (VIP)," Journal of Molecular Neuroscience, Apr. 23, 2015, vol. 56, No. 2, pp. 377-387.

Wakayama T., et al., "Full-term Development of Mice from Enucleated Oocytes Injected with Cumulus Cell Nuclei," Nature, Jul. 23, 1998, vol. 394, pp. 369-374.

Walker E.M., et al., "GATA4 and GATA6 Regulate Intestinal Epithelial Cytodifferentiation during Development," Developmental Biology, 2014, vol. 392, pp. 283-294.

Wallace A S., et al., "Development of the Enteric Nervous System, Smooth Muscle and Interstitial cells of Cajal in the Human Gastrointestinal Tract," Cell and Tissue Research, Jan. 26, 2005, vol. 319, pp. 367-382.

Walton K.D., et al., "Epithelial Hedgehog Signals Direct Mesenchymal Villus Patterning through BMP," Abstracts / Developmental Biology, 2009, vol. 331, Abstract #354, p. 489.

Walton K.D., et al., "Hedgehog-Responsive Mesenchymal Clusters Direct Patterning and Emergence of Intestinal Villi," PNAS, Sep. 25, 2012, vol. 109, No. 39, p. 15817-15822.

Walton K.D., et al., "Villification in the Mouse: Bmp Signals Control Intestinal Villus Patterning," Development, 2016, vol. 143, pp. 427-436.

Wan W., et al., "The Role of wnt Signaling in the Development of Alzheimer's disease: A Potential Therapeutic Target?," BioMed Research International, 2014, vol. 2014, pp. 1-9.

Wang A., et al., "Generating Cells of the Gastrointestinal system: Current Approaches and Applications for the Differentiation of Human Pluripotent Stem Cells," Journal of Molecular Medicine, Jun. 20, 2012, vol. 90, pp. 763-771.

Wang F., et al., "Isolation and Characterization of Intestinal Stem Cells based on Surface Marker Combinations and Colony-Formation Assay," Gastroenterology, 2013, vol. 145, No. 2, pp. 383-395.

Wang J., et al., "Mutant Neurogenin-3 in Congenital Malabsorptive Diarrhea," New England Journal of Medicine, Jul. 20, 2006, vol. 355, pp. 270-280.

Wang S., (Ed.), "The role of Homologous Genes in the Development of Appendages," in Basis of Developmental Biology, Press of East China University of Science and Technology, 2014, pp. 184-185.

Wang X., et al., "Cloning and Variation of Ground State Intestinal Stem Cells," Nature, Jun. 11, 2015, vol. 522, 18 pages.

Wang Y., et al., "Hepatic Stellate Cells, Liver Innate Immunity, and Hepatitis C Virus," Journal of Gastroenterology and Hepatology, 2013, vol. 28(1), pp. 112-115.

Wang Z., et al., "Retinoic Acid Regulates Morphogenesis and Patterning of Posterior Foregut Derivatives," Developmental Biology, May 23, 2006, vol. 297, pp. 433-445.

Want R., "An Introduction to RFID Technology," IEEE Pervasive Computing, 2006, vol. 5, pp. 25-33.

Ward D.F Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, vol. 16, pp. 467-479.

Ware C.B., "Concise Review: Lessons from Naive Human Pluripotent Cells," Stem Cells, 2017, vol. 35, pp. 35-41.

Warlich E., et al., "Lentiviral Vector Design and Imaging Approaches to Visualize the Early Stages of Cellular Reprogramming," Molecular Therapy, Apr. 2011, vol. 19, No. 4, pp. 782-789.

Warren C.R., et al., "Induced Pluripotent Stem Cell Differentiation Enables Functional Validation of GWAS Variants in Metabolic Disease," Cell Stem Cell, Apr. 6, 2017, vol. 20, pp. 547-557.

Warren C.R., et al., "The NextGen Genetic Association Studies Consortium: A Foray into In Vitro Population Genetics," Cell Stem Cell, 2017, vol. 20, pp. 431-433.

Watson C.L., et al., "An In Vivo Model of Human Small Intestine Using Pluripotent Stem Cells," Nature Medicine, Oct. 19, 2014, vol. 20, No. 11, 16 pages.

Wehkamp J., et al., "Paneth Cell Antimicrobial Peptides: Topographical Distribution and Quantification in Human Gastrointestinal Tissues," FEBS Letters, 2006, vol. 580, pp. 5344-5350.

Weis V.G., et al., "Current Understanding of SPEM and its Standing in the Preneoplastic Process," Gastric Cancer, 2009, vol. 12, pp. 189-197.

(56) References Cited

OTHER PUBLICATIONS

Wells J.M., et al., "Early Mouse Endoderm is Patterned by Soluble Factors from Adjacent Germ Layers," Development, Mar. 21, 2000, vol. 127, pp. 1563-1572.
Wells J.M., et al., "How to Make and Intestine," Development, vol. 141, No. 4, Feb. 15, 2014, pp. 752-760.
Wen S., et al., "Helicobacter Pylori Virulence Factors in Gastric Carcinogenesis," Cancer Letters, 2009, vol. 282, pp. 1-8.
Wernig M., et al., "In Vitro Reprogramming of Fibroblasts into a Pluripotent ES-cell-like State," Nature, 2007, vol. 448, pp. 318-324.
Whissell G., et al., "The Transcription Factor GATA6 Enables Self-Renewal of Colon Adenoma Stem Cells by Repressing BMP Gene Expression," Nature Cell Biology, 2014, vol. 16, No. 7, pp. 695-707.
Wieck M.M., et al., "Prolonged Absence of Mechanoluminal Stimulation in Human Intestine Alters the Transcriptome and Intestinal Stem Cell Niche," Cell Mol Gastroenterol Hepatol, 2017, vol. 3, No. 3, pp. 367-388.
Wiley L.A., et al., "cGMP Production of Patient-Specific iPSCs and Photoreceptor Precursor Cells to Treat Retinal Degenerative Blindness," Scientific Reports, 2016, vol. 6(30742), 16 pages.
Willet S.G., et al., "Stomach Organ and Cell Lineage Differentiation: From Embryogenesis to Adult Homeostasis," Cellular and Molecular Gastroenterology and Hepatology, Sep. 2016, vol. 2, pp. 546-559.
Williamson R.C.N., et al., "Humoral Stimulation of Cell Proliferation in Small Bowel after Transection and Resection in Rats," Gastroenterology, 1978, vol. 75, No. 2, pp. 249-254.
Wills A., et al., "Bmp Signaling is necessary and sufficient for Ventrolateral Endoderm Specification in Xenopus," Developmental Dynamics, 2008, vol. 237(8), pp. 2177-2186.
Wilmut I., et al., "Viable Offspring Derived from Fetal and Adult Mammalian Cells," Nature, Feb. 27, 1997, vol. 385, pp. 810-813.
Woltjen K., et al., "piggyBac transposition reprograms fibroblasts to induced pluripotent stem cells," Nature, Apr. 9, 2009, vol. 458, pp. 766-770.
Workman M.J., et al., "Engineered Human Pluripotent-Stem-Cell-derived Intestinal tissues with a functional Enteric Nervous System," Nature Medicine, Jan. 2017, vol. 23(1), pp. 49-59.
Workman M.J., "Generating 3D Human Intestinal Organoids with an Enteric Nervous System," Thesis, Graduate School of the University of Cincinnati, 2014, 61 pages.
Xia H.H.X., et al., "Antral-Type Mucosa in the Gastric Incisura, Body, and Fundus (Antralization): A Link Between Helicobacter pylori Infection and Intestinal Metaplasia?," American Journal of Gastroenterology, 2000, vol. 95, No. 1, pp. 114-121.
Xinaris C., et al., "Organoid Models and Applications in Biomedical Research," Nephron Jun. 25, 2015, Issue 130, pp. 191-199.
Xu R., et al., "Association between Patatin-Like Phospholipase Domain Containing 3 Gene (PNPLA3) Polymorphisms and Nonalcoholic Fatty Liver Disease: A Huge Review and Meta- Analysis," Scientific Reports, Mar. 20, 2015, vol. 5(9284), 11 pages.
Xu R., et al. (Eds), "Retinoic Acid Receptor" in Basis and Clinic of Receptor, Shanghai Science and Technology Press, 1992, pp. 129-131.
Xue X., et al., "Endothelial PAS Domain Protein 1 Activates the Inflammatory Response in the Intestinal Epithelium to Promote Colitis in Mice," Gastroenterology, 2013, vol. 145, No. 4, pp. 831-841.
Yahagi N., et al., "Position-Specific Expression of Hox Genes along the Gastrointestinal Tract," Congenital Anomalies, 2004, vol. 44, pp. 18-26.
Yamada S., et al. "Differentiation of Immature Enterocytes into Enteroendocrine Cells by Pdx1 Overexpression," American Journal of Physiology: Gastrointestinal and Liver Physiology, 2001, vol. 281, No. 1, pp. G229-G236.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.

Yanagimachi M.D., et al., "Robust and Highly-Efficient Differentiation of Functional Monocytic Cells from Human Pluripotent Stem Cells Under Serum- and Feeder Cell-Free Conditions," PLOS One, 2013, vol. 8(4), e59243, 9 pages.
Yanagita M., "Modulator of Bone Morphogenetic Protein Activity in the Progression of Kidney Diseases," Kidney International, 2006, vol. 70, pp. 989-993.
Yang K., et al., "Systems Pharmacology Modeling Predicts Delayed Presentation and Species Differences in Bile Acid-Mediated Troglitazone Hepatotoxicity," Clinical Pharmacology & Therapeutics, 2014, vol. 96(5), pp. 589-598.
Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.
Yin C., et al., "Hepatic Stellate Cells in Liver Development, Regeneration, and Cancer," The Journal of Clinical Investigation, May 2013, vol. 123, No. 5, pp. 1902-1910.
Yoneda M., et al., "Noninvasive Assessment of Liver Fibrosis by Measurement of Stiffness in Patients with Nonalcoholic Fatty Liver Disease (NAFLD)," Dig Liver Dis, 2008, vol. 40, pp. 371-378.
Young H.M., et al., "Expression of Ret-, p75(NTR)-, Phox2a-, Phox2b-, and Tyrosine Hydroxylase-Immunoreactivity by Undifferentiated Neural Crest-Derived Cells and Different Classes of Enteric Neurons in the Embryonic Mouse Gut," Developmental Dynamics, 1999, vol. 216, pp. 137-152.
Young H.M., et al., "GDNF is a Chemoattractant for Enteric Neural Cells," Developmental biology, Dec. 19, 2000, vol. 229, pp. 503-516.
Yu H., et al., "The Contributions of Human Mini-Intestines to the Study of Intestinal Physiology and Pathophysiology," Annual Review of Physiology, Feb. 10, 2017, vol. 79, pp. 291-312.
Yuan Y., et al., "Peptic ulcer disease today," Nature Clinical Practice Gastroenterology & Hepatology, Feb. 2006, vol. 3, No. 2, pp. 80-89.
Yui S., et al., "Functional Engraftment of Colon Epithelium Expanded in Vitro from a Single Adult Lgr5(+) stem cell," Nature Medicine, Mar. 11, 2012, vol. 18, No. 4, pp. 618-623.
Zachos N.C., et al., "Human Enteroids/Colonoids and Intestinal Organoids Functionally Recapitulate Normal Intestinal Physiology and Pathophysiology," The Journal of Biological Chemistry, Feb. 19, 2016, vol. 29, No. 18, pp. 3759-3766.
Zain S.M., et al., "A Common Variant in the Glucokinase Regulatory Gene rs780094 and Risk of Nonalcoholic Fatty Liver Disease: A Meta-Analysis," Journal of Gastroenterology & Hepatology, 2015, vol. 30, pp. 21-27.
Zambrano E., et al., "Total parenteral Nutrition Induced Liver Pathology: An Autopsy Series of 24 Newborn Cases," Pediatric and Developmental Pathology, 2004, vol. 7, pp. 425-432.
Zborowski J., et al., "Induction of Swelling of Liver Mitochondria by Fatty Acids of Various Chain Length," Biochimica et Biophysica Acta, Oct. 22, 1963, vol. 70, pp. 596-598.
Zbuk K.M., et al., "Hamartomatous polyposis syndromes," Nature Clinical Practice Gastroenterology & Hepatology, 2007, vol. 4, No. 9, pp. 492-502.
Zhang D., et al., "Neural Crest Regionalisation for Enteric Nervous System Formation: Implications for Hirschsprung's Disease and Stem Cell Therapy," Developmental Biology, Mar. 15, 2010, vol. 339, pp. 280-294.
Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.
Zhang Q., et al., "Small-Molecule Synergist of the Wnt/β-catenin Signaling Pathway," PNAS, May 1, 2007, vol. 104, No. 18, pp. 7444-7448.
Zhang R.R., et al., "Human iPSC-Derived Posterior Gut Progenitors are Expandable and Capable of Forming Gut and Liver Organoids," Stem Cell Reports, Mar. 13, 2018, vol. 10, pp. 780-793.
Zhang W., et al., "Elastomeric Free-Form Blood Vessels for Interconnecting Organs on Chip Systems," Lab Chip, Apr. 26, 2016, vol. 16, No. 9, pp. 1579-1586.

(56) References Cited

OTHER PUBLICATIONS

Zhang Y., et al., "Palmitic and Linoleic Acids Induce ER Stress and Apoptosis in Hepatoma Cells," Lipids in Health and Disease, 2012, vol. 11 (1), 8 pages.

Zhang Y.S., et al., "Seeking the Right Context for Evaluating Nanomedicine: from Tissue Models in Petri Dishes to Microfluidic Organs-on-a-chip," Nanomedicine (Lond.), 2015, vol. 10, No. 5, pp. 685-688.

Zhang Y.S., et al., "Multisensor-Integrated Organs-on-Chips Platform for Automated and Continual in Situ Monitoring of Organoid behaviors," Proceedings of the National Academy of Sciences USA, 2017, vol. 114, pp. E2293-E2302.

Zhao Y., et al., "A XEN-like State Bridges Somatic Cells to Pluripotency during Chemical Reprogramming," Cell, 2015, vol. 163, pp. 1678-1691.

Zhong J., et al., "Continuous-Wave Laser-Assisted Injection of Single Magnetic Nanobeads into Living Cells," Sensors and Actuators B: Chemical, 2016, vol. 230, pp. 298-305.

Zhou H., et al., "Generation of Induced Pluripotent Stem Cells Using Recombinant Proteins," Cell Stem Cell, May 8, 2009, vol. 4, pp. 381-384.

Zhou J., et al., "The Potential for Gut Organoid Derived Interstitial Cells of Cajal in Replacement Therapy," International Journal of Molecular Sciences, Sep. 26, 2017, vol. 18, No. 10, p. 2059 in 17 pages.

Zhou Q., et al., "In Vivo Reprogramming of Adult Pancreatic Exocrine Cells to β-Cells," Nature, 2008, vol. 455, pp. 627-632.

Zorn A.M., et al., "Vertebrate Endoderm Development and Organ Formation," Annual Review of Cell and Developmental Biology, 2009, vol. 25, pp. 221-251.

Abe T., et al., "Reporter Mouse Lines for Fluorescence Imaging," Development, Growth & Differentiation, May 2013, vol. 55, No. 4, pp. 390-405.

Adam M., et al., Psychrophilic Proteases Dramatically Reduce Single-Cell RNA-Seq Artifacts: a Molecular Atlas of Kidney Development, Development, Oct. 1, 2017, vol. 144, No. 19, pp. 3625-3632.

Arora R., et al., Multiple Roles and Interactions of Tbx4 and Tbx5 in Development of the Respiratory System, PLOS Genetics, Aug. 2, 2012, vol. 8, No. 8, e1002866, 14 pages.

Asahina K., et al., Septum Transversum-Derived Mesothelium gives rise to Hepatic Stellate Cells and Perivascular Mesenchymal Cells in Developing Mouse Liver, Hepatology, Mar. 2011, vol. 53, No. 3, pp. 983-995.

Baptista P.M., et al., "Transplantable Liver Organoids, Too Many Cell Types to Choose: a Need for Scientific Self-Organization," Current Transplantation Reports, Feb. 15, 2020, vol. 7, pp. 18-23.

Barnes R.M., et al., "Analysis of the Hand1 Cell Lineage Reveals Novel Contributions to Cardiovascular, Neural Crest, Extra-Embryonic, and Lateral Mesoderm Derivatives," Developmental Dynamics, vol. 239, 2010, pp. 3086-3097.

Baron M., et al., A Single-Cell Transcriptomic Map of the Human and Mouse Pancreas Reveals Inter- and Intra-cell Population Structure, Cell Systems, Oct. 26, 2016, vol. 3, No. 4, pp. 346-360.

Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.

Brandenberg N., et al., "High-Throughput Automated Organoid Culture via Stem-Cell Aggregation in Microcavity Arrays," Nature Biomedical Engineering, 2020, vol. 4, pp. 863-874.

Briggs J.A., et al., The Dynamics of Gene Expression in Vertebrate Embryogenesis at SingleCell Resolution, Science, Jun. 1, 2018, vol. 360, No. 6392, eaar5780, 23 pages.

Bult C.J., et al., Mouse Genome Database (MGD) 2019, Nucleic Acids Research, Jan. 8, 2019, vol. 47, No. D1, pp. D801-D806.

Calder, L.E., Retinoic Acid-mediated Regulation of GLI3 Enables High Yield Motoneuron Derivation from Human Embryonic Stem Cells Independent of Extrinsic Activation of SHH Signaling, Dissertation, Jan. 2015, 24 pages.

Cao J., et al., The Single-Cell Transcriptional Landscape of Mammalian Organogenesis, Nature, Feb. 2019, vol. 566, No. 7745, pp. 496-502.

Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.

Carpenedo R.L., et al., "Rotary Suspension Culture Enhances the Efficiency, Yield, and Homogeneity of Embryoid Body Differentiation," Stem Cells, 2007, vol. 25, pp. 2224-2234.

Carpenedo R.L., "Microsphere-Mediated Control of Embryoid Body Microenvironments," May 2010, 24 pages.

Chambers M. S., et al., "Highly Efficient Neural Conversion of Human ES and IPS Cells by Dual Inhibition of SMAD Signaling, Nature Biotechnol., Mar. 2009, vol. 27(3), pp. 275-280.

Chen Y., et al., "Robust Bioengineered 3D Functional Human Intestinal Epithelium," Scientific Reports, vol. 5 (13708), Sep. 16, 2015, XP055454950, DOI: 10.1038/srep13708, 11 pages.

Chua C.C., et al., "Single Luminal Epithelial Progenitors Can Generate Prostate Organoids in Culture," Nature Cell Biology, Oct. 2014, vol. 16(10), 26 pages.

Cohen M., et al., Lung Single-Cell Signaling Interaction Map Reveals Basophil Role in Macrophage Imprinting, Cell, Nov. 1, 2018, vol. 175, No. 4, pp. 1031-1044.

Conley B.J., et al., "Derivation, Propagation and Differentiation of Human Embryonic Stem Cells," The International Journal of Biochemistry & Cell Biology, 2004, vol. 36, pp. 555-567.

De Soysa T.Y., et al., Single-cell Analysis of Cardiogenesis Reveals Basis for Organ-level Developmental Defects, Nature, Aug. 2019, vol. 572, No. 7767, pp. 120-124.

Dolle L., et al., "EpCAM and the Biology of Hepatic Stem/Progenitor Cells," American Journal of physiology gastrointestinal liver physiology, 2015, vol. 308, pp. G233-G250.

Duh G., et al., "EGF Regulates Early Embryonic Mouse Gut Development in Chemically Defined Organ Culture," International Pediatric Research Foundation, 2000, vol. 48, No. 6, pp. 794-802.

Dye B.R., et al., "Take a Deep Breath and Digest the Material: Organoids and Biomaterials of the Respiratory and Digestive Systems," Materials Research Society, Sep. 2017, vol. 7, No. 3, pp. 502-514.

Ei Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.

Erkan M., et al., Organ-, Inflammation- and Cancer Specific Transcriptional Fingerprints of Pancreatic and Hepatic Stellate Cells,. Molecular Cancer, Dec. 2010, vol. 9, No. 1, pp. 1-15.

Farrell J.A., et al., Single-Cell Reconstruction of Developmental Trajectories During Zebrafish Embryogenesis, Science, Jun. 1, 2018, vol. 360, No. 6392, eaar3131, 18 pages.

Fattahi F., et al., Deriving Human ENS Lineages for Cell Therapy and Drug Discovery in Hirschsprung Disease, Nature, Feb. 2016, vol. 531 (7592), pp. 105-109.

Ferretti E., et al., Mesoderm Specification and Diversification: From Single Cells to Emergent Tissues,. Current Opinion in Cell Biology, Dec. 2019, vol. 61, pp. 110-116.

Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.

Foulke-Abel J., et al., Human Enteroids as a Model of Upper Small Intestinal Ion Transport Physiology and Pathophysiology, Gastroenterology, Mar. 2016, vol. 150, No. 3, pp. 638-649.

Francou A., et al., Second Heart Field Cardiac Progenitor Cells in the Early Mouse Embryo, Biochimica et Biophysica Acta, Apr. 1, 2013, vol. 1833, No. 4, pp. 795-798.

Franklin V., et al., Regionalisation of the Endoderm Progenitors and Morphogenesis of the Gut Portals of the Mouse Embryo,. Mechanisms of Development, Jul. 1, 2008, vol. 125, No. 7, pp. 587-600.

Gao S., et al., Fetal Liver: An Ideal Niche for Hematopoietic Stem Cell Expansion, Science China, Life Sciences, Review, Aug. 2018, vol. 61 (8), pp. 885-892.

(56) References Cited

OTHER PUBLICATIONS

Gissen P et al., "Structural and Functional Hepatocyte Polarity and Liver Disease," Journal of Hepatology, 2015, vol. 63, pp. 1023-1037.

Godoy P., et al., "Recent Advances in 2D and 3D in vitro Systems Using Primary Hepatocytes, Alternative Hepatocyte Sources and Non-parenchymal Liver Cells and their use in Investigating Mechanisms of Hepatotoxicity Cell Signaling and ADME," Arch Toxicol, Aug. 2013, vol. 87, 216 pages.

Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.

Grand R. J., et al., "Development of the Human Gastrointestinal Tract—A Review," Gastroenterology, May 1976, vol. 70, No. 5, pp. 790-810.

Grapin-Botton A., Antero-posterior Patterning of the Vertebrate Digestive Tract: 40 Years After Nicole Le Douarin's PhD Thesis, The International Journal of Developmental Biology, Jan. 1, 2005, vol. 49, Nos. 2-3, pp. 335-347.

Griffin O.D., et al., "Human B1 Cells in Umbilical Cord and Adult Peripheral Blood Express the Novel Phenotype CD20+CD27+CD43+ CD70−," Journal of Experimental Medicine, 2011, vol. 208(1), pp. 67-80.

Han L., et al., Single Cell Transcriptomics Identifies a Signaling Network Coordinating Endoderm and Mesoderm Diversification during Foregut Organogenesis, Nature Communications, Aug. 2020, vol. 11, No. 4158, pp. 1-16.

Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132,35 pages.

Hoffmann A.D., et al., Sonic Hedgehog Is required in Pulmonary Endoderm for Atrial Septation, Development, 2009, vol. 136, p. 1761 1770.

Horie M., et al., TBX4 is involved in the Super-Enhancer-Driven Transcriptional Programs Underlying Features Specific to Lung Fibroblasts,. The American Journal of Physiology-Lung Cellular and Molecular Physiology, Jan. 1, 2018, vol. 314, No. 1, pp. L177-L191.

Huss J. M., et al., "Constitutive Activities of Estrogen-Related Receptors: Transcriptional Regulation of Metabolism by the ERR Pathways in Health and Disease," Biochimica et Biophysica Acta, 2015, vol. 1852, 2015, pp. 1912-1927.

Huynh N., et al., "61.06 Feasibility and Scalability of Spring Parameters in Distraction Enterogenesis in a Murine Model," 2017, 3 pages, Retrieved from Internet: URL: https://www.asc-abstracts.org/abs2017/61-06-feasibility-and-scalability-of-spring-parameters-in-distraction-enterogenesis-in-a-murine-model/, Retrieved on Jun. 4, 2022.

Ibarra-Soria X. et al., Defining Murine Organogenesis at Single-Cell Resolution Reveals a Role for the Leukotriene Pathway in Regulating Blood Progenitor Formation,. Nature Cell Biology, Feb. 2018, vol. 20, No. 2, pp. 127-134.

Khan J.A., et al., "Fetal Liver Hematopoietic Stem Cell Niches Associate With Portal Vessels," Science, Jan. 8, 2016, vol. 351 (6269), pp. 176-180.

Kharchenko V. P., et al., Bayesian Approach to Single-cell Differential Expression Analysis, Nature Methods, Jul. 2014, vol. 11, No. 7, pp. 740-742.

Kim E., et al., Isl1 Regulation of Nkx2.1 in the Early Foregut Epithelium Is Required for Trachea-Esophageal Separation and Lung Lobation, Developmental Cell, Dec. 16, 2019, vol. 51, No. 6, pp. 675-683.

Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.

Kiselev Y. V., et al., SCmap—A Tool for Unsupervised Projection of Single Cell RNA-seq data, Nature Methods, May 2018, vol. 15 (5), pp. 359-362.

Koike H., et al., "Engineering Human Hepato-Biliary-Pancreatic Organoids from Pluripotent Stem Cells," Nature Protocols, Feb. 2021, vol. 16(2), pp. 919-936.

Koike H., et al., Modeling human hepato-biliary-pancreatic organogenesis from the foregutmidgut boundary, Nature, Oct. 2019, vol. 574(7776), pp. 112-116.

Langfelder P., et al., WGCNA: An R package for weighted correlation network analysis, BMC Bioinformatics, Dec. 2008, vol. 9 (1), pp. 1-13.

Langmead B., et al., Fast Gapped-read Alignment with Bowtie 2, Nature Methods, Apr. 2012, vol. 9 (4), pp. 357-359.

Le Douarin N., et al., Role of the Mesoderm in the Induction of the Synthesis of Glycogen During Differentiation of the Hepatic Endoderm, CR Acad Hebd Seances Acad Sci D, 1967, vol. 264, pp. 1872-1874.

Lee G., et al., "Derivation of Neural Crest Cells From Human Pluripotent Stem Cells," Nature Protocols, Mar. 18, 2010, vol. 5(4), pp. 688-701.

Li et al., RSEM: Accurate Transcript Quantification from RNA-Seq data with or without a Reference Genome, BMC Bioinformatics Aug. 2011, vol. 12, No. 323, 16 pages.

Li L.C., et al., Single-Cell Transcriptomic Analyses Reveal Distinct Dorsal/Ventral Pancreatic Programs,. EMBO Reports, Oct. 2018, vol. 19, No. 10, e46148, 14 pages.

Lis R., et al., "Conversion of Adult Endothelium to Immunocompetent Haematopoietic Stem Cells," Nature, May 2017, vol. 545 (7655), pp. 439-445.

Loh K. M., et al., Mapping the Pairwise Choices Leading From Pluripotency to Human Bone, Heart, and Other Mesoderm Cell Types, Cell, Jul. 14, 2016, vol. 166, No. 2, pp. 451-467.

Manno L. G., et al., Molecular Diversity of Midbrain Development in Mouse, Human and Stem Cells, Cell, Oct. 6, 2016, vol. 167, (2), pp. 566-580.

Mashima H., et al., INSL5 may be a Unique Marker of Colorectal Endocrine Cells and Neuroendocrine Tumors, Biochemical and Biophysical Research Communications, 2013, vol. 432, pp. 586-592.

McCann C.J., et al., "Enteric Neural Stem Cell Therapies for Enteric Neuropathies," Neurogastroenterology and Motility, vol. 30, e13369, 2018, doi: 10.1111/nmo. 13369, pp. 1-9.

McGrath P.S., et al., The Basic Helix-Loop-Helix Transcription Factor NEUROG3 Is Required for Development of the Human Endocrine Pancreas, Diabetes, Jul. 2015, vol. 64, pp. 2497-2505.

McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.

McKimpson W.M., et al., "A Fluorescent Reporter Assay of Differential Gene Expression Response to Insulin in Hepatocytes," Methods in Cell Physiology, American Journal of Physiology Cell Physiology, May 15, 2019, vol. 317, pp. C143-C151.

Menendez L., et al., Directed differentiation of human pluripotent cells to neural crest stem cells, Nature Protocols, Jan. 2013, vol. 8 (1), pp. 203-212.

Mitaka T., "Reconstruction of Hepatic Organoid by Hepatic Stem Cells," Journal of Hepatobiliary Pancreatic Surgery, 2002, vol. 9 (6), pp. 697-703.

Moignard V., et al., Decoding the Regulatory Network of Early Blood Development From Single-Cell Gene Expression Measurements, Nature Biotechnology, Mar. 2015, vol. 33, No. 3, pp. 269-276.

Montecino-Rodriguez E., et al., "Identification of a B-1 B Cell-Specified Progenitor," Natural Immunology, Mar. 2006, vol. 7(3), pp. 293-301.

Morrison A. J., et al., Single-cell transcriptome analysis of avian neural crest migration reveals signatures of invasion and molecular transitions, eLife., Dec. 2017, vol. 6, 27 pages.

(56) References Cited

OTHER PUBLICATIONS

Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.
Nantasanti S., et al., Disease Modeling and Gene Therapy of Copper Storage Disease in Canine Hepatic Organoids, Stem Cell Reports, 2015, vol. 5, pp. 895-907.
Nasr T., et al., Endosome-Mediated Epithelial Remodeling Downstream of Hedgehog-Gli Is Required for Tracheoesophageal Separation, Developmental Cell, Dec. 16, 2019, vol. 51, No. 6, pp. 665-674.
Naujok O., et al., Cytotoxicity and Activation of the WNT/Beta-Catenin Pathway in Mouse Embryonic Stem Cells Treated with Four GSK3 Inhibitors, BMC Research Notes, 2014, vol. 7, No. 273, pp. 1-8.
Ng S., et al., "Human iPSC-Derived Hepatocyte-Like Cells Support Plasmodium Liver-Stage Infection In Vitro," Stem cell reports, Mar. 10, 2015, vol. 4, pp. 348-359.
Nowotschin S., et al., The Emergent Landscape of the Mouse Gut Endoderm at Single-Cell Resolution, Nature, May 2019, vol. 569, No. 7756, pp. 361-367.
Ogaki S., et al., A Cost-Effective System for Differentiation of Intestinal Epithelium from Human Induced Pluripotent Stem Cells, Scientific Reports, Nov. 30, 2015, 11 pages.
Payushina O.V., Hematopoietic Microenvironment in the Fetal Liver: Roles of Different Cell Populations, Review Article, International Scholarly Research Network Cell Biology, 2012, 8 pages.
Pedersen J.K., et al., Endodermal Expression of Nkx6 Genes depends differentially on Pdx1, Developmental Biology, Dec. 15, 2005, vol. 288, No. 2, pp. 487-501.
Peng T., et al., Coordination of Heart and Lung Co-development by a Multipotent Cardiopulmonary Progenitor, Nature, Aug. 2013, vol. 500, No. 7464, pp. 589-592.
Pijuan-Sala B., et al., A Single-Cell Molecular Map of Mouse Gastrulation and Early Organogenesis, Nature, Feb. 2019, vol. 566, No. 7745, pp. 490-495.
Que J., et al., Mesothelium Contributes to Vascular Smooth Muscle and Mesenchyme During Lung Development, Proceedings of the National Academy of Sciences USA, Oct. 28, 2008, vol. 105, No. 43, pp. 16626-16630.
Rana M.S., et al., A Molecular and Genetic Outline of Cardiac Morphogenesis, Acta Physiologica (Oxf), Apr. 2013, vol. 207, No. 4, pp. 588-615.
Riehl T., et al., "CD44 and TLR4 Mediate Hyaluronic Acid Regulation of Lgr5+ Stem Cell Proliferation, Crypt Fission, and Intestinal Growth in Postnatal and Adult Mice," The American Journal of Physiology-Gastrointestinal and Liver Physiology, Dec. 1, 2015, vol. 309, No. 11, pp. G874-G887.
Robert-Moreno A., et al., "Impaired Embryonic Haematopoiesis Yet Normal Arterial Development in the Absence of the Notch ligand Jagged1 ," EMBO Journal, 2008, vol. 27(13), pp. 1886-1895.
Robert-Moreno A., et al., "RBPj?-dependent Notch Function Regulates Gata2 and is Essential for the Formation of Intra-embryonic Hematopoietic Cells," Development and disease, 2005, vol. 132(5), pp. 1117-1126.
Rothstein L.T., et al., "Human B-1 cells take the stage," Annals of the New York Academy of Sciences, May 2013, vol. 1285, pp. 97-114.
Rubin L.L., et al., Targeting the Hedgehog Pathway in Cancer, Nature Reviews Drug Discovery, 2006, vol. 5, pp. 1026-1033.
Sanchez-Valle V., et al., "Role of Oxidative Stress and Molecular Changes in Liver Fibrosis: A Review," Current Medicinal Chemistry, 2012, vol. 19, No. 28, pp. 4850-4860.
Sander M., et al., Homeobox Gene Nkx6.1 lies Downstream of Nkx2.2 in the major Pathway of Beta-Cell formation in the Pancreas, Development, Dec. 15, 2000, vol. 127, No. 24, pp. 5533-5540.
Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.
Sauka-Spengler T et al., Snapshot: Neural Crest, Cell, Oct. 2010, vol. 143, No. 3, 486-486. e1.
Schlieve C. R., et al., Neural Crest Cell Implantation Restores Enteric Nervous System Function and Alters the Gastrointestinal Transcriptome in Human Tissue-Engineered Small Intestine, Stem Cell Reports, ISSCR, Sep. 12, 2017, vol. 9, pp. 883-896.
Scialdone A., et al., Resolving Early Mesoderm Diversification Through Single-Cell Expression Profiling, Nature, Jul. 2016, vol. 535, No. 7611, pp. 289-293.
Scott A., et al., "Repeated Mechanical Lengthening of Intestinal Segments in a Novel Model," Journal of Pediatric Surgery, Jun. 2015, vol. 50, No. 6, pp. 954-957.
Seet C.S., et al., Generation of Mature T Cells from Human Hematopoietic Stem/Progenitor Cells in Artificial Thymic Organoids, Nature Methods, May 2017, vol. 14 (5), pp. 521-530.
Semrau S., et al., Dynamics of lineage commitment revealed by single-cell transcriptomics of differentiating embryonic stem cells, Nature Communications, Oct. 2017, vol. 8 (1), pp. 1-16.
Simões F.C., et al., "The Ontogeny, Activation and Function of the Epicardium During Heart Development and Regeneration," Development, Apr. 1, 2018, vol. 145, No. 7, dev155994; 13 pages.
Simian M., et al., Organoids: A Historical Perspective of Thinking In Three Dimensions, Journal of Cell Biology, 2017, vol. 216, No. 1, pp. 31-40.
Soldatow V. Y., et al., "In Vitro Models for Liver Toxicity Testing," Toxicology Research 2.1, 2013, vol. 2, pp. 23-39.
Sugimura R., et al., "Haemotopoietic Stem and Progenitor Cells from Human Pluripotent Stem Cells," Nature, May 25, 2017, vol. 545 (7655), pp. 432-438.
Sullins V. F., et al., "Intestinal Lengthening in an Innovative Rodent Surgical Model," Journal of Pediatric Surgery, Dec. 2014, vol. 49, No. 12, pp. 1791-1794.
Sweetman D., et al., The Migration of Paraxial and Lateral Plate Mesoderm Cells Emerging From the Late Primitive Streak Is Controlled by Different Wnt Signals, BMC Developmental Biology, Dec. 2008, vol. 8, No. 1, pp. 1-15.
Tanaka M., "Molecular and Evolutionary Basis of Limb Field Specification and Limb Initiation," Development, Growth & Differentiation, Jan. 2013, vol. 55, No. 1, pp. 149-163.
Tang X. et al. Transcriptome Regulation and Chromatin Occupancy by E2F3 and MYC in Mice, Scientific Data, Feb. 16, 2016, vol. 3, No. 1, pp. 1-8.
Testaz S., et al., Sonic hedgehog restricts adhesion and migration of neural crest cells independently of the Patched-Smoothened-Gli signaling pathway, PNAS, Oct. 23, 2001, vol. 98 (22), pp. 12521-12526.
Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.
Uenishi I.G., et al., "NOTCH Signaling Specifies Arterial-type Definitive Hemogenic Endothelium from Human Pluripotent Stem Cells," Nature Communication, 2018, 14 pages.
Wagner D.E., et al., Lineage Tracing Meets Single-cell Omics: Opportunities and Challenges, Nature Reviews Genetics, Jul. 2020, vol. 21, No. 7, pp. 410-427.
Wang, et al., "Spatially Monitoring Oxygen Level in 3D Microfabricated Cell Culture Systems Using Optical Oxygen Sensing Beads," Lab on a Chip, 2013, vol. 13, pp. 1586-1592.
Wang J., et al., WebGestalt 2017: A more comprehensive, powerful, flexible and interactive gene set enrichment analysis toolkit, Nucleic Acids Research, Jul. 2017, vol. 45, 8 pages.
Wang L., et al., "The Maintenance and Generation of Membrane Polarity in Hepatocytes," Hepatology, 2004, vol. 39, No. 4, pp. 892-899.
Weinreb C., et al., Lineage tracing on transcriptional landscapes links state to fate during differentiation, Science, Feb. 14, 2020, vol. 367, (6479), 48 pages.

(56) References Cited

OTHER PUBLICATIONS

Weinreb C., et al., SPRING: A Kinetic Interface for Visualizing High Dimensional Single-cell Expression Data, Bioinformatics, Apr. 2018, vol. 34 (7), pp. 1246-1248.
Wilkinson C. A., et al., "Long-term Ex-vivo Haematopoietic-stem-Cell Expansion Allows Nonconditioned Transplantation," Nature, 2019, vol. 571 (7763), pp. 117-121.
Xie T., et al., Single-Cell Deconvolution of Fibroblast Heterogeneity in Mouse Pulmonary Fibrosis, Cell Reports, Mar. 27, 2018, vol. 22, No. 13, pp. 3625-3640.
Yao S., et al., Long-Term Self-Renewal and Directed Differentiation of Human Embryonic Stem Cells in Chemically Defined Conditions, PNAS, 2006, vol. 103, No. 18, pp. 6907-6912.
Yu G., et al., ClusterProfiler: An R package for Comparing Biological Themes Among Gene Clusters, Omics: A Journal Integrative Biology, May 2012, vol. 16 (5), pp. 284-287.
Yuelei C., et al., BMP Signaling Pathway and Colon Cancer, CNKI, Oct. 15, 2009, 1 page.
Zaret K.S., From Endoderm to Liver Bud: Paradigms of Cell Type Specification and Tissue Morphogenesis, Current Topics in Developmental Biology, Jan. 2016, vol. 117, pp. 647-669.
Zeltner N., et al., Feeder-free derivation of neural crest progenitor cells from human pluripotent stem cells, Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.
Zhang X., et al., A Comprehensive Structure-Function Study of Neurogenin3 Disease-Causing Alleles during Human Pancreas and Intestinal Organoid Development, Developmental Cell, Aug. 5, 2019, vol. 50, pp. 367-380.
Abo., K.M., et al., Human iPSC-Derived Alveolar and Airway Epithelial Cells Can Be Cultured at Air-liquid Interface and Express SARS-COV-2 Host Factors. Biorxiv, Jun. 4, 2020, 27 pages.
Adachi S., et al., "Three Distinctive Steps in Peyer's Patch Formation of Murine Embryo," International Immunology, Apr. 1997, vol. 9(4), pp. 507-514.
Anderson C.M.H., et al., "Inhibition of Intestinal Dipeptide Transport by the Neuropeptide VIP is an Anti-absorptive Effect via the VPAC1 Receptor in a Human Enterocyte-like Cell Line (Caco-2)," British Journal of Pharmacology, 2003, vol. 138, No. 4, pp. 564-573.
Ang L.T., et al., "A Roadmap for Human Liver Differentiation from Pluripotent Stem Cells," Cell Reports, Feb. 20, 2018, vol. 22, pp. 2190-2205.
Baker C., et al., "Hypoganglionosis in the Gastric Antrum Causes Delayed Gastric Emptying," Neurogastroenterology and Motility, May 2020, vol. 32(5): e13766, 18 pages.
Balbinot C., et al., "Fine-tuning and Autoregulation of the Intestinal Determinant and Tumor Suppressor Homeobox Gene CDX2 by Alternative Splicing," Cell Death and Differentiation, 2017, vol. 24, No. 12, pp. 2173-2186.
Barber K., et al., "Derivation of Enteric Neuron Lineages from Human Pluripotent Stem Cells," Nature Protocols, Apr. 2019, vol. 14, No. 4, pp. 1261-1279.
Bar-Ephraim Y.E., et al., "Organoids in Immunological Research,". Nature Reviews Immunology, May 2020, vol. 20(5), pp. 279-293.
Barkauskas C. E et al. "Lung Organoids: Current Uses and Future Promise," Development, Mar. 15; 2017, vol. 144(6), pp. 986-997.
Barkauskas C.E., et al., Type 2 alveolar Cells Are Stem Cells in Adult Lung. The Journal of Clinical Investigation, Jul. 1, 2013, vol. 123(7), pp. 3025-3036.
Barnes P.J., et al., "Chronic Lung Diseases: Prospects for Regeneration and Repair," European Respiratory Review, Mar. 31, 2021, vol. 30(159), 14 pages.
Basil, M. C., et al., "The Cellular and Physiological Basis for Lung Repair and Regeneration: Past, Present, and Future," Apr. 2, 2020, vol. 26(4, pp. 482-502.
Batterham R.L., et al., "Gut Hormone PYY3-36 Physiologically Inhibits Food Intake," Nature, Aug. 8, 2002, vol. 418, pp. 650-654.
Beckett E.A.H., et al., "Inhibitory Responses Mediated by Vagal Nerve Stimulation are Diminished in Stomachs of Mice with Reduced Intramuscular Interstitial Cells of Cajal," Mar. 20, 2017, Scientific Reports, vol. 7, No. 44759, 11 pages.
Beers M.F., et al., "Alveolar Type 2 Epithelial Cell Quality Control Responses to Pulmonary Fibrosis Related SFTPC Mutations Are Dysfunctional And Substrate Specific," The FASEB Journal, Apr. 2020, vol. 34(S1), 1 page (Abstract Only).
Bergen V., et al., "Generalizing RNA Velocity to Transient Cell States Through Dynamical Modeling," Nature Biotechnology, Oct. 28, 2019, vol. 38(12), 26 pages.
Bharat A., et al., "Lung Transplantation for Patients with Severe COVID-19," Science Translational Medicine, Dec. 16, 2020, vol. 12(574):eabe4282, 13 pages.
Blanchard J.W., et al., "Reconstruction of the Human Blood-Brain Barrier in vitro reveals a Pathogenic Mechanism of APOE4 in Pericytes," Nature Medicine, Jun. 2020, vol. 26, No. 6, pp. 952-963.
Bohorquez D.V., et al., "Neuroepithelial Circuit Formed by Innervation of Sensory Enteroendocrine Cells," The Journal of Clinical Investigation, 2015, vol. 125, No. 2, pp. 782-786.
Bolte C., et al., "FOXF1 Transcription Factor Promotes Lung Regeneration After Partial Pneumonectomy," Scientific Reports, Sep. 6, 2017, vol. 7(1):10690, 14 pages.
Braegger C.P., et al., "Ontogenetic Aspects of the Intestinal Immune System in Man," International Journal of Clinical and Laboratory Research, 1992, vol. 22(1), pp. 1-4.
Breit S., et al., "Vagus Nerve as Modulator of the Brain-Gut Axis in Psychiatric and Inflammatory Disorders," Frontiers in Psychiatry, Mar. 13, 2018, vol. 9, Article. 44, 15 pages.
Brookes S.J.H., et al., "Extrinsic Primary Afferent Signaling in the Gut," Nature Rev Gastroenter Hepatol., 2013, vol. 10, No. 5, pp. 286-296.
Brosch M., et al., "Epigenomic Map of Human Liver Reveals Principles of Zonated Morphogenic and Metabolic Control," Nature Communications, 2018, vol. 9, Article. 4150, 13 pages.
Buning J.W., et al., "Higher Hydrocortisone Dose Increases Bilirubin in Hypopituitary Patients—results from an RCT," European Journal of Clinical Investigation, 2016, vol. 46, No. 5, pp. 475-480.
Burleigh D.E., et al., "Stimulation of Intestinal Secretion by Vasoactive Intestinal Peptide and Cholera Toxin," Autonomic Neuroscience: Basic and Clinical, 2007, vol. 133, pp. 64-75.
Bykov V.L., "Paneth Cells: History of Discovery, Structural and Functional Characteristics and the Role in the Maintenance of Homeostasis in the Small Intestine," Morfologiia, 2014, vol. 145, No. 1, pp. 67-80.
Cakir B., et al., "Development of Human Brain Organoids with Functional Vascular-like System," Nature Methods, Nov. 2019, vol. 16, No. 11, pp. 1169-1176.
Cao J., et al., "A Human Cell Atlas of Fetal Gene Expression," Science, Nov. 13, 2020, vol. 370(6518), 42 pages.
Cardenas-Diaz F. L., et al., Temporal and Spatial Staging of Lung Alveolar Regeneration Is Determined by the Grainyhead Transcription Factor Tfcp2l1, Cell Reports, May 30; 2023, vol. 42(5), 21 pages.
Cardoso W.V., et al., "Regulation of Early Lung Morphogenesis: Questions, Facts and Controversies," Development, 2006, vol. 133, pp. 1611-1624.
Chandrasekaran A., et al., "Astrocyte Differentiation of Human Pluripotent Stem Cells: New Tools for Neurological Disorder Research," Frontiers in Cellular Neuroscience, Sep. 26, 2016, vol. 10, Article. 215, 27 pages.
Chassaing B., et al., "Mammalian Gut Immunity," Biomedical Journal, Sep. 2014, vol. 37(5) p. 246 in 22 pages.
Chen M., et al., "Gene Ablation for PEPT1 in Mice Abolishes the Effects of Dipeptides on Small Intestinal Fluid Absorption, Short Circuit Current and Intracellular pH," American Journal of Physiology—Gastrointestinal and Liver Physiology, Apr. 29, 2010, 33 pages.
Cheng Y., et al., "Current Development Status of MEK Inhibitors," Molecules, 2017, vol. 22, pp. 1-20.

(56) References Cited

OTHER PUBLICATIONS

Choi J., et al., "Inflammatory Signals Induce AT2 Cell-Derived Damage-Associated Transient Progenitors that Mediate Alveolar Regeneration," Cell stem cell, Sep. 3, 2020, vol. 27(3), pp. 366-382.
Chung C., et al., "Hippo-Foxa2 Signaling Pathway Plays a Role in Peripheral Lung Maturation and Surfactant Homeostasis." Proceedings of the National Academy of Sciences of the United States of America, May 7, 2013, vol. 110(19), pp. 7732-7737.
Chung, M. I., et al., "Niche-mediated BMP/SMAD Signaling Regulates Lung Alveolar Stem Cell Proliferation and Differentiation," Development, May 1, 2018, vol. 145(9):dev 163014, 23 pages.
Cox H.M., et al., "Peptide YY Is Critical for Acylethanolamine Receptor Gpr119-Induced Activation of Gastrointestinal Mucosal Responses," Cell Metabolism, Jun. 9, 2010, vol. 11, pp. 532-542.
Cox H.M., "Neuroendocrine Peptide Mechanisms Controlling Intestinal Epithelial Function," Current Opinion in Pharmacology, 2016, vol. 31, pp. 50-56.
Creeden J.F., et al., "Bilirubin as a Metabolic Hormone: the Physiological Relevance of Low Levels," American Journal of Physiology-Endocrinology and Metabolism, 2021, vol. 320, No. 2, 59 pages.
Daviaud N., et al., "Vascularization and Engraftment of Transplanted Human Cerebral Organoids in Mouse Cortex," Disorders of the Nervous System, Nov./Dec. 2018, vol. 5, No. 6, 18 pages.
De Carvalho A.L.R.T., et al., "Glycogen Synthase Kinase 3 Induces Multilineage Maturation of Human Pluripotent Stem Cell-derived Lung Progenitors in 3D Culture," Development. Jan. 15, 2019, vol. 146(2):dev171652, 34 pages.
De Carvalho A.L.R.T et al., "The in Vitro Multi-Lineage Differentiation and Maturation of Lung and Airway Cells from Human Pluripotent Stem Cell-derived Lung Progenitors in 3D," Nature Protocols, Apr. 2021, 16(4), pp. 1802-1829.
De Lau W., et al., "Peyer's Patch M Cells Derived from Lgr5+ Stem Cells Require SpiB and are Induced by RankL in Cultured Miniguts,". Molecular and Cellular Biology, Sep. 2012, vol. 32(18), pp. 3639-3647.
De Souza H.S.P., et al., "Immunopathogenesis of IBD: Current State of the Art," Nature Reviews Gastroenterology & Hepatology, Jan. 2016, vol. 13(1), pp. 13-27.
Dekkers J.F., et al., "High-resolution 3D Imaging of Fixed and Cleared Organoids," Nature protocol, Jun. 2019, vol. 14(6), pp. 1756-1771.
Duren Z., et al., "Modeling Gene Regulation from Paired Expression and Chromatin Accessibility Data,". Proceedings of the National Academy of Sciences of the United States of America, Jun. 2, 2017, vol. 114(25), pp. E4914-E4923.
Eberl G., et al., "An Essential Function for the Nuclear Receptor RORgamma(t) in the Generation of Fetal Lymphoid Tissue Inducer Cells," Nature Immunology, Dec. 21, 2003, vol. 5(1), pp. 64-73.
Egerod K.L., et al., "A Major Lineage of Enteroendocrine Cells Coexpress CCK, Secretin, GIP, GLP-1, PYY, and Neurotensin but Not Somatostatin," Endocrinology, Dec. 1, 2012, vol. 153, No. 12, pp. 5782-5795.
Egerod K.L., et al., "Profiling of G Protein-coupled Receptors in Vagal Afferents Reveals Novel Gut-to-brain Sensing Mechanisms," Molecular Metabolism, 2018, vol. 12, pp. 62-75.
Faure S., et al., "Endogenous Patterns of BMP Signaling During Early Chick Development," Developmental Biology, Apr. 1, 2002, vol. 244(1), pp. 44-65.
Faure S., et al., "Enteric Neural Crest Cells Regulate Vertebrate Stomach Patterning and Differentiation," Development, 2015, vol. 142, pp. 331-342.
Faure S., et al., "Expression Pattern of the Homeotic Gene Bapx1 During Early Chick Gastrointestinal Tract Development," Gene Expression Patterns, Dec. 2013, vol. 13(8), 7 pages.
Finn J., et al., DIk1-Mediated Temporal Regulation of Notch Signaling Is Required for Differentiation of Alveolar Type II to Type I Cells during Repair, Cell Reports, Mar. 12, 2019, vol. 26(11), pp. 2942-2954.

Flodby P., et al., "Cell-Specific Expression of Aquaporin-5 (Aqp5) in Alveolar Epithelium Is Directed by GATA6/Spl via Histone Acetylation," Scientific Reports, Jun. 14, 2017, vol. 7(1):3473, 12 pages.
Fomin M.E., et al., "Human Fetal Liver Cultures Support Multiple Cell Lineages That Can Engraft Immunodeficient Mice," Open Biology, 2017, 16 pages.
Frank D. B., et al., "Emergence of a Wave of Wnt Signaling that Regulates Lung Alveologenesis by Controlling Epithelial Self-Renewal and Differentiation," Cell Reports, Nov. 22, 2016, vol. 17(9), pp. 2312-2325.
Freddo A.M., et al., "Coordination of Signaling and Tissue Mechanics During Morphogenesis of Murine Intestinal Villi: A Role for Mitotic Cell Rounding," Integrative Biol., Sep. 1, 20162;8(9): 918-928.
Fukuda M., et al., "Small Intestinal Stem Cell Identity Is Maintained with Functional Paneth Cells in Heterotopically Grafted Epithelium Onto the Colon," Genes & Development, 2014, vol. 28, No. 16, pp. 1752-1757.
Furness J.B., et al., "The Identification of Neuronal Control Pathways Supplying Effector Tissues in the Stomach," Cell and Tissue Research, Dec. 2020, vol. 382, No. 3, pp. 433-445.
Gage B.K., et al., "Generation of Functional Liver Sinusoidal Endothelial Cells from Human Pluripotent Stem-Cell Derived Venous Angioblasts," Cell Stem Cell, Aug. 6, 2020, vol. 27, pp. 254-269.
Galand G., "Brush Border Membrane Sucrase-Isomaltase, Maltase-Glucoamylase and Trehalase in Mammals. Comparative Development, Effects of Glucocorticoids, Molecular Mechanisms, and Phylogenetic Implications," Comparative Biochemistry & Physiology, 1989, vol. 94B, No. 1, 11 pages.
Gaskill C.F., et al., "Disruption of Lineage Specification in Adult Pulmonary Mesenchymal Progenitor Cells Promotes Microvascular Dysfunction," Journal of Clinical Investigation, Jun. 1, 2017, vol. 127(6), pp. 2262-2276.
Gerdes H-H., et al., "Intercellular Transfer Mediated by Tunneling Nanotubes," Current Opinion in Cell Biology, 2008, vol. 20, pp. 470-475.
Gibbs C.S., et al., "High-performance Single-cell Gene Regulatory Network Inference at Scale: the Inferelator 3.0," Bioinformatics, May 1, 2022, vol. 38(9), pp. 2519-2528.
Gilbert M.A., et al., "Protein-Elongating Mutations in MYH11 Are Implicated in a Dominantly Inherited Smooth Muscle Dysmotility Syndrome with Severe Esophageal, Gastric, and Intestinal Disease," Human Mutation, 2020, vol. 41, pp. 973-982.
Gillich A., et al., "Capillary Cell Type Specialization in the Alveolus," Nature, Oct. 2020, 586(7831), pp. 785-789.
Gokey J.J., et al., "Active Epithelial Hippo Signaling in Idiopathic Pulmonary Fibrosis," JCI insight, Mar. 3, 2018, vol. 3(6), 14 pages.
Gonzales L.W., et al., "Differentiation of Human Pulmonary Type II Cells in Vitro by Glucocorticoid Plus Cyclic Amp," AJP-Lung Articles in Press, 2002, 45 pages.
Goodwin K., et al., "Smooth Muscle Differentiation Shapes Domain Branches During Mouse Lung Development," Development, Nov. 15, 2019, 146(22), 37 pages.
Gorin G., et al., "Protein Velocity and Acceleration from Single-cell Multiomics Experiments," Genome Biology, (2020)21:39, 6 pages.
Gorin G., et al., "RNA Velocity Unraveled," PLOS Computational Biology, Sep. 12, 2022, vol. 18(9) :e1010492, 55 pages.
Granja J.M., et al., "ArchR is a Scalable Software Package for Integrative Single-Cell Chromatin Accessibility Analysis," Nature Genetics, Mar. 2021, vol. 53(3), pp. 403-411.
Grant R.A., et al., "Circuits Between Infected Macrophages and T cells in Sars- COV-2 Pneumonia," Nature, Feb. 25, 2021, vol. 590(7847), pp. 635-641.
Green J., et al., "Diversity of Interstitial Lung Fibroblasts Is Regulated by Platelet-derived Growth Factor Receptor Alpha Kinase Activity," American Journal of Respiratory Cell and Molecular Biology, Apr. 2016, vol. 54(4), pp. 532-545.
Gribble F.M., et al., "Function and Mechanisms of Enteroendocrine Cells and Gut Hormones in Metabolism," Reviews, Apr. 2019, vol. 15, pp. 226-237.

(56) References Cited

OTHER PUBLICATIONS

Guo M., et al., "Single Cell RNA Analysis Identifies Cellular Heterogeneity and Adaptive Responses of the Lung at Birth," Nature Communications, Jan. 3, 2019; vol. 10(1):37, 16 pages.
Guye P., et al., "Genetically Engineering Self-organization of Human Pluripotent Stem Cells into a Liver Bud-like Tissue Using Gata6," Nature Communications, Jan. 6, 2016, 12 pages.
Ham O., et al., "Blood Vessel Formation in Cerebral Organoids Formed From Human Embryonic Stem Cells," Biochemical and Biophysical Research Communications, 2020, vol. 521, pp. 84-90.
Hamilton T.G., et al., "Evolutionary Divergence of Platelet-derived Growth Factor Alpha Receptor Signaling Mechanisms," Molecular and Cellular Biology, Jun. 1, 2003, vol. 23(11), pp. 4013-4025.
Hao Y., et al., "Integrated Analysis of Multimodal Single-cell Data," Cell, Jun. 24, 2021, ;vol. 184(13), pp. 3573-3587.
Harrison S.P., et al., "Liver Organoids: Recent Developments, Limitations and Potential," Frontiers in Medicine, May 2021, vol. 8, 18 pages.
Hawkins F., et al., "Prospective Isolation of NKX2-1-Expressing Human Lung Progenitors Derived from Pluripotent Stem Cells," The Journal of Clinical Investigation, Jun. 1, 2017; 127(6), pp. 2277-2294.
He B., et al., "Understanding Transcriptional Regulatory Networks Using Computational Models," Current Opinion in Genetics & Development, Apr. 1, 2016, vol. 37, pp. 101-108.
Herriges M.J., et al., "Long Noncoding RNAs are Spatially Correlated with Transcription Factors and Regulate Lung Development," Genes & Development, Jun. 15, 2014, vol. 28(12), pp. 1363-1379.
Holloway E.M., et al., "Differentiation of Human Intestinal Organoids with Endogenous Vascular Endothelial Cells," Developmental Cell, 2020, vol. 54, pp. 516-528.
Homan K.A., et al., "Flow-Enhanced Vascularization and Maturation of Kidney Organoids in Vitro," Nature Methods, 2019, 16(3), pp. 255-262.
Hu S., et al., "Wnt/β-Catenin Signaling and Liver Regeneration: Circuit, Biology, and Opportunities," Gene expression, 2021, vol. 20(3), pp. 189-199.
Hu Y., et al., "Wnt/β-Catenin Signaling Is Critical for Regenerative Potential of Distal Lung Epithelial Progenitor Cells in Homeostasis and Emphysema," Stem Cells, Nov. 2020, vol. 38(11), pp. 1467-1478.
Huang W-K., et al., "Generation of Hypothalamic Arcuate Organoids From Human Induced Pluripotent Stem Cells," Cell Stem Cell, 2021, pp. 1657-1670.
Huycke T.R., et al., "Genetic and Mechanical Regulation of Intestinal Smooth Muscle Development," Cell, 2019, vol. 179, No. 1, pp. 90-105.
Hyland N.P., et al., "Functional Consequences of Neuropeptide Y Y2 Receptor Knockout and Y2 Antagonism in Mouse and Human Colonic Tissues," British Journal of Pharmacology, 2003, vol. 139, pp. 863-871.
Iino S., et al., "Interstitial Cells of Cajal Are Involved in Neurotransmission in the Gastrointestinal Tract," The Japan Society of Histochemistry and Cytochemistry, 2006, 39 (6), pp. 145-153.
Ikegami., M et al. "Surfactant Protein D Influences Surfactant Ultrastructure and Uptake by Alveolar Type II Cells," American Journal of Physiology—Lung Cellular and Molecular Physiology, Mar. 2005, vol. 288(3), pp. L552-L561.
Jacob A., et al., "Derivation of Self-Renewing Lung Alveolar Epithelial Type II Cells From Human Pluripotent Stem Cells," Nature Protocols, 2019, 14(12), pp. 3303-3332.
Jacob A., et al., "Differentiation of Human Pluripotent Stem Cells into Functional Lung Alveolar Epithelial Cells," Cell Stem Cell, Oct. 5, 2017, vol. 21(4), pp. 472-488.
Jacob F., et al., "Human Pluripotent Stem Cell-Derived Neural Cells and Brain Organoids Reveal SARS-COV-2 Neurotropism Predominates in Choroid Plexus Epithelium," Cell Stem Cell, 2020, vol. 27, pp. 937-950.
Jain R., et al., "Plasticity of Hopx (+) Type I Alveolar Cells to Regenerate Type II Cells in the Lung," Nature Communications, 2015, vol. 13;6(1):6727, 20 pages.
Jin S., et al., "Inference and Analysis of Cell-cell Communication Using Cellchat," Nature Communications, Feb. 17, 2021, vol. 12(1):1088, 20 pages.
Kaelberer M.M., et al., "A Gut-Brain Neural Circuit for Nutrient Sensory Transduction," Science, Sep. 2, 20181, vol. 361, No. 6408, 18 pages.
Kalucka J., et al., "Single-Cell Transcriptome Atlas of Murine Endothelial Cells," Cell, 2020, vol. 180, pp. 764-779.
Kathiriya, J.J., et al., "Human Alveolar Type 2 Epithelium Transdifferentiates into Metaplastic KRT5+ Basal Cells," Nature Cell Biology, Jan. 2022, vol. 24(1), pp. 10-23.
Khalil H.A., et al., "Intestinal Epithelial Replacement by Transplantation of Cultured Murine and Human Cells Into the Small Intestine," Plos One, May 31, 2019, vol. 14, No. 5, 13 pages.
Kim S., et al., "Engraftment Potential of Spheroid-Forming Hepatic Endoderm Derived from Human Embryonic Stem Cells," Stem Cells Development. Jun. 15, 2013, vol. 22(12), pp. 1818-1829.
Kinchen J., et al., "Structural Remodeling of the Human Colonic Mesenchyme in Inflammatory Bowel Disease," Cell, 2018, vol. 175, No. 2, pp. 372-388.
Kitano K., et al., "Bioengineering of Functional Human Induced Pluripotent Stem Cell-derived Intestinal Grafts," Nature Communications, 2017, vol. 8, No. 765, 13 pages.
Knox S.M., et al., "Parasympathetic Innervation Maintains Epithelial Progenitor Cells During Salivary Organogenesis," Science, Sep. 24, 2010, vol. 329, No. 5999, pp. 1645-1647.
Kobayashi Y., et al., "Persistence of a Regeneration-associated, Transitional Alveolar Epithelial Cell State in Pulmonary Fibrosis," Nature Cell Biology, Aug. 2020, vol. 22(8), pp. 934-946.
Koboziev I., et al., "Use of Humanized Mice to Study the Pathogenesis of Autoimmune and Inflammatory Diseases," Inflammatory Bowel Diseases, Jul. 1, 2015, 21 (7), pp. 1652-1673.
Koslowski M., et al., "MS4A12 Is a Colon-Selective Store-Operated Calcium Channel Promoting Malignant Cell Processes," Cancer Research, May 1, 2008, vol. 68, No. 9, 3458-3466.
Kotobank, "Encyclopedia—Basement Membrane," Machine translated by Google, 2023, 6 pages.
Kuna L., et al., "Peptic Ulcer Disease: A Brief Review of Conventional Therapy and Herbal Treatment Options," Journal of Clinical Medicine, 2019, vol. 8, No. 2, 19 pages.
Kusakabe T., et al., "Thyroid-Specific Enhancer-binding Protein/NKX2.1 is Required for the Maintenance of Ordered Architecture and Function of the Differentiated Thyroid," Molecular Endocrinology, Aug. 2006, vol. 20(8), pp. 1796-1809.
Lacanna R., et al., "Yap/Taz Regulate Alveolar Regeneration and Resolution of Lung Inflammation," Journal of Clinical Investigation, May 1, 2019, vol. 129(5), pp. 2107-2122.
Lanas A., et al., "Peptic Ulcer Disease," vol. 390, Aug. 5, 2017, pp. 613-624.
Lange M., et al., "CellRank for Directed Single-cell Fate Mapping," Nature Methods, Feb. 2022, vol. 19(2), pp. 159-170.
Lasrado R., et al., "Lineage-Dependent Spatial and Functional Organization of the Mammalian Enteric Nervous System," Science, 2017, vol. 356, No. 6339, pp. 722-726.
Laughney A.M., et al., "Regenerative Lineages and Immune-mediated Pruning in Lung Cancer Metastasis," Nature Medicine, Feb. 2020, vol. 26(2), pp. 259-269.
Le Guen L., et al., "Mesenchymal-Epithelial Interactions During Digestive Tract Development and Epithelial Stem Cell Regeneration," Cellular and Molecular Life Sciences, 2015, vol. 72, No. 20, pp. 3883-3896.
Lee J., et al., "IL-25 and CD4(+) TH2 Cells Enhance Type 2 Innate Lymphoid Cell-derived IL-13 Production, Which Promotes IgE-mediated Experimental Food Allergy," The Journal of Allergy and Clinical Immunology, Apr. 1, 2016, vol. 137(4), pp. 1216-1225.
Lee J.H. et al., "Anatomically and Functionally Distinct Lung Mesenchymal Populations Marked by Lgr5 and Lgr6," Cell, Sep. 7, 2017, vol. 170(6), pp. 1149-1163.

(56) References Cited

OTHER PUBLICATIONS

Li N., et al., Early-Life Compartmentalization of Immune Cells in Human Fetal Tissues Revealed by High-Dimensional Mass Cytometry, Frontiers in Immunology, Aug. 14, 2019; vol. 10(1932), 13 pages.
Li N., et al., Mass cytometry reveals innate lymphoid cell differentiation pathways in the human fetal intestine. Journal of Experimental Medicine, May 7, 2018, vol. 215(5), pp. 1383-1396.
Li N., et al., "Memory CD4+ T Cells Are Generated in the Human Fetal Intestine," Nature Immunology, Mar. 2019, vol. 20(3), pp. 301-312.
Li Z., et al., "Essential Roles of Enteric Neuronal Serotonin in Gastrointestinal Motility and the Development/Survival of Enteric Dopaminergic Neurons," The Journal of Neuroscience, Jun. 15, 2011, vol. 31, No. 24, pp. 8998-9009.
Lian X., et al., "Robust Cardiomyocyte Differentiation from Human Pluripotent Stem Cells via Temporal Modulation of Canonical Wnt Signaling," PNAS, May 29, 2012, pp. E1848-E1857.
Liang, W., et al., "MEF2C Alleviates Acute Lung Injury in Cecal Ligation and Puncture (CLP)-induced Sepsis Rats by Up-regulating AQP1," Allergologia et Immunopathologia, Sep. 1, 2021, vol. 49(5), pp. 117-124.
Lignitto L., et al., "Nrf2 Activation Promotes Lung Cancer Metastasis by Inhibiting the Degradation of Bach 1," Cell, Jul. 11, 2019, vol. 178(2), pp. 316-329.
Lippmann E.S., et al., "Human Blood-Brain Barrier Endothelial Cells Derived from Pluripotent Stem Cells," Nature Biotechnology, Aug. 2012, 30(8), pp. 783-791.
Little D.R., et al., "Differential Chromatin Binding of the Lung Lineage Transcription Factor NKX2-1 Resolves Opposing Murine Alveolar Cell Fates in Vivo," Nat Comm. May 2021; vol. 12, No. 1, 18 pages.
Loh K.M., et al., "Efficient Endoderm Induction from Human Pluripotent Stem Cells by Logically Directing Signals Controlling Lineage Bifurcations," Cell Stem Cell, Feb. 6, 2014, vol. 14(2), pp. 237-252.
Ma T.Y., et al., "IEC-18, A Nontransformed Small Intestinal Cell Line for Studying Epithelial Permeability," Journal of Laboratory and Clinical Medicine, Aug. 1992, vol. 120, No. 2, pp. 329-341.
Mabbott N.A., et al., "Microfold (M) Cells: Important Immunosurveillance Posts in the Intestinal Epithelium," Mucosal Immunology, Jul. 1, 2013, vol. 6(4), pp. 666-677.
Maeda Y., et al., Kras(G12D) and Nkx2-1 Haploinsufficiency Induce Mucinous Adenocarcinoma of the Lung. Journal of Clinical Investigation, Dec. 3, 2012, vol. 122(12), pp. 4388-4400.
Mahe M., et al., "Establishment of Human Epithelial Enteroids and Colonoids from Whole Tissue and Biopsy," Journal of Visualized Experiments, Mar. 6, 2015, vol. 97, 13 pages.
Manno., L.G., et al., "RNA Velocity of Single Cells," Nature, Aug. 2018, vol. 560 (7719), pp. 494-498.
Mansour A.A., et al., "An In Vivo Model of Functional and Vascularized Human Brain Organoids," Nature Biotechnology, Jun. 2018, 36(5), pp. 432-441.
Maruyama E.O., et al., "Cell-Specific Cre Strains for Genetic Manipulation in Salivary Glands," PLOS ONE, Jan. 11, 2016, vol. 11(1):e0146711, 12 pages.
McCauley H.A., "Enteroendocrine Regulation of Nutrient Absorption," The Journal of Nutrition, 2019, pp. 10-21.
McCauley H.A., et al., "Enteroendocrine Cells Couple Nutrient Sensing to Nutrient Absorption by Regulating Ion Transport," Nature Communications, 2020, vol. 11,10 pages.
McCauley K.B., et al., "Efficient Derivation of Functional Human Airway Epithelium from Pluripotent Stem Cells via Temporal Regulation of Wnt Signaling," Cell Stem Cell, 2017, vol. 20, pp. 844-857.
McCauley K.B., et al., "Single-Cell Transcriptomic Profiling of Pluripotent Stem Cell-Derived SCGB3A2+ Airway Epithelium," Stem Cell Reports, 2018, vol. 10, pp. 1579-1595.
McGinnis C.S., et al., "DoubletFinder: Doublet Detection in Single-Cell RNA Sequencing Data Using Artificial Nearest Neighbors," Cell Systems, Apr. 24, 2019, vol. 8(4), pp. 329-337.
Mellitzer G., et al., "Loss of Enteroendocrine Cells in Mice Alters Lipid Absorption and Glucose Homeostasis and Impairs Postnatal Survival," The Journal of Clinical Investigation, vol. 120, No. 5, May 2010, pp. 1708-1721.
Menoret S., et al., "Generation of Immunodeficient Rats With Rag1 and Il2rg Gene Deletions and Human Tissue Grafting Models," Transplantation, Aug. 2018, vol. 102, No. 8, pp. 1271-1278.
Mentlein R., et al., "Proteolytic Processing of Neuropeptide Y and Peptide YY by Dipeptidyl Peptidase IV," Regulatory Peptides, 1993, vol. 49, pp. 133-144.
Miraldi E.R., et al., Leveraging Chromatin Accessibility for Transcriptional Regulatory Network Inference in T Helper 17 Cells. Genome Research, Mar. 1, 2019, vol. 29(3), pp. 449-463.
Miranda J., et al., "A Novel Mutation in FOXF1 Gene Associated with Alveolar Capillary Dysplasia with Misalignment of Pulmonary Veins, Intestinal Malrotation and Annular Pancreas," Neonatology, 2013, vol. 103, pp. 241-245.
MITAKA., et al., "Characterization of Hepatic-organoid Cultures," Drug Metabolism Reviews, 2010, vol. 42, No. 3, pp. 472-481.
Mizumoto H., et al., "Hybrid Artificial Liver Using Hepatocyte Organoids," Regenerative Medicine, 2006, vol. 5 No. 3, pp. 81-86.
Mollaoglu G., et al., "The Lineage-Defining Transcription Factors SOX2 and NKX2-1 Determine Lung Cancer Cell Fate and Shape the Tumor Immune Microenvironment," Immunity, Oct. 16, 2018, vol. 49(4), pp. 764-779.
Moniot B., et al., "SOX9 Specifies the Pyloric Sphincter Epithelium Through Mesenchymal-epithelial Signals," Development, Aug. 2004, vol. 131, No. 15, pp. 3795-3804.
Moodaley R., et al., "Agonism of Free Fatty Acid Receptors 1 and 4 Generates Peptide YY-Mediated Inhibitory Responses in Mouse Colon," British journal of Pharmacology, 2017, vol. 174, pp. 4508-4522.
Morrisey E.E., et al., "Preparing for the First Breath: Genetic and Cellular Mechanisms in Lung Development," Developmental Cell, Jan. 19, 2010, vol. 18, pp. 8-23.
Mowat A., et al., "Regional Specialization Within the Intestinal Immune System," Nature Reviews Immunology, Oct. 2014, vol. 14(10), pp. 667-685.
Nabhan A., et al., "A Single Cell Wnt Signaling Niche Maintains Stemness of Alveolar Type 2 Cells," Science, Mar. 9, 2018; vol. 359(6380), pp. 1118-1123.
Nagy N., et al., "Enteric Nervous System Development: a Crest Cell's Journey From Neural Tube to Colon," Seminars in Cell & Developmental Biology, 2017, vol. 66, pp. 94-106.
Nagy N., et al., "Sonic Hedgehog Controls Enteric Nervous System Development by Patterning the Extracellular Matrix," Development, 2016, 143(2), pp. 264-275.
Nakahara T., et al., "Human Papillomavirus Type 16 E1 E4 Contributes to Multiple Facets of the Papillomavirus Life Cycle," Journal of Virology, Oct. 31, 2005, vol. 79, No. 20, pp. 13150-13165.
Nakamura T., et al., "Intestinal Stem Cell Transplantation," Journal of Gastroenterology, 2017, vol. 52, pp. 151-157.
Nedvetsky P.I., et al., "Parasympathetic Innervation Regulates Tubulogenesis in the Developing Salivary Gland," Developmental Cell, 2014, vol. 30, pp. 449-462.
Negretti N. M., et al., "A Single-cell Atlas of Mouse Lung Development," Development Dec. 15, 2021, vol. 148(24), 30 pages.
Nguyen J., et al., "The Next Generation of Endothelial Differentiation: Tissue-Specific ECs," Cell Stem Cell, Jul. 1, 2021, vol. 28(7), pp. 1188-1204.
Nochi T., et al., "Cryptopatches are essential for the development of human GALT," Cell Reports, Jun. 27, 2013, vol. 3(6), vol. 1874-1884.
Noel G., et al., "A Primary Human Macrophage-enteroid Co-culture Model to Investigate Mucosal Gut Physiology and Host-pathogen Interactions," Scientific Reports, Mar. 27, 2017, vol. 7(45270), 13 pages.
Norlen P., et al., "The Vagus Regulates Histamine Mobilization from Rat Stomach ECL Cells by Controlling Their Sensitivity to Gastrin," The Journal of Physiology, 2005, 564(Pt 3), pp. 895-905.

(56) References Cited

OTHER PUBLICATIONS

Oceguera-Yanez F., et al., "Engineering the AAVS1 Locus for Consistent and Scalable Transgene Expression in Human iPSCs and their Differentiated Derivatives," Methods, 2015, 13 pages.

Ohashi S., et al., "Epidermal Growth Factor Receptor and Mutant p53 Expand an Esophageal Cellular Subpopulation Capable of Epithelial-to-Mesenchymal Transition through ZEB Transcription Factors," Tumor and Stem Cell Biology, Apr. 27, 2010, vol. 70, No. 10, pp. 4147-4184.

Ostrin E. J., et al., "β-Catenin Maintains Lung Epithelial Progenitors After Lung Specification," Development, Mar. 1, 2018, vol. 145(5), 32 pages.

Paik D.T., et al., "Single-cell RNA-Seq Unveils Unique Transcriptomic Signatures of Organ-Specific Endothelial Cells," Circulation, Nov. 10, 2020, 142(19), pp. 1848-1862.

Palikuqi B., et al., "Adaptable Haemodynamic Endothelial Cells for Organogenesis and Tumorigenesis," Nature, Sep. 17, 2020, vol. 585, 33 pages.

Panaro B.L., et al., "The Melanocortin-4 Receptor Is Expressed in Enteroendocrine L Cells and Regulates the Release of Peptide YY and Glucagon-like Peptide 1 In Vivo," Cell Metabolism, Dec. 2, 2014, vol. 20, pp. 1018-1029.

Paris A.J., et al., "STAT3-BDNF-TrkB Signaling Promotes Alveolar Epithelial Regeneration After Lung Injury," Nature Cell Biology, Oct. 2020, vol. 22(10), pp. 1197-1210.

Park B., et al., "Hematopoietic Stem Cell Expansion and Generation: the Ways to Make a Breakthrough," Blood Research, Dec. 2015, vol. 50, No. 4, 10 pages.

Penkala I.J., et al., "Age-Dependent Alveolar Epithelial Plasticity Orchestrates Lung Homeostasis and Regeneration," Cell Stem Cell, Oct. 7, 2021, vol. 28, pp. 1775-1789.

Perriot S., et al., "Differentiation of Functional Astrocytes From Human-Induced Pluripotent Stem Cells in Chemically Defined Media," STAR Protocols, Dec. 17, 2021, 2(4):100902, 13 pages.

Perriot S., et al., "Human Induced Pluripotent Stem Cell-Derived Astrocytes Are Differentially Activated by Multiple Sclerosis-Associated Cytokines," Stem Cell Reports, Nov. 13, 2018, vol. 11, pp. 1199-1210.

Pradhan A., et al., "The S52F FOXF1 Mutation Inhibits STAT3 Signaling and Causes Alveolar Capillary Dysplasia," American Journal of Respiratory and Critical Care Medicine, Oct. 15, 2019, vol. 200, No. 8, pp. 1045-1056.

Qian X., et al., "Brain-Region-Specific Organoids Using Minibioreactors for Modeling ZIKV Exposure," Cell, 2016, vol. 165, pp. 1238-1254.

Qian X., et al., "Generation of Human Brain Region-specific Organoids Using a Miniaturized Spinning Bioreactor," Nature Protocols, Mar. 2018, 13(3), pp. 565-580.

Qin X., "Why is Damage Limited to the Mucosa in Ulcerative Colitis but Transmural in Crohn's Disease", World Journal of Gastrointestinal Pathophysiology, Aug. 15, 2013, vol. 4, No. 3, pp. 63-64.

Rakhilin N., et al., "Simultaneous Optical and Electrical in Vivo Analysis of the Enteric Nervous System," Nature Communications, Jun. 7, 2016, 7:11800, 7 pages.

Ran F.A., et al., "Genome Engineering using the CRISPR-Cas9 System," Nature Protocols, Nov. 2013, 8(11), pp. 2281-2308.

Ranganathan S., et al., "Evaluating *Shigella flexneri* Pathogenesis in the Human Enteroid Model," Infection and Immunity, Apr. 2019, vol. 87(4), 14 pages.

Rice A.C., et al., "A New Animal Model of Hemolytic Hyperbilirubinemia-Induced Bilirubin Encephalopathy (Kernicterus)," Pediatric Research, 2008, vol. 64, No. 3, pp. 265-269.

Riemondy K. A., et al., "Single Cell RNA Sequencing Identifies TGF-β as a Key Regenerative Cue Following LPS-induced Lung Injury," JCI Insight, Apr. 4, 2019, vol. 4(8), 18 pages.

Rindler T.N., et al., "Efficient Transduction of Alveolar Type 2 Cells with Adeno-associated Virus for the Study of Lung Regeneration," American Journal of Respiratory Cell and Molecular Biology, Jul. 2021, vol. 65(1), pp. 118-121.

Roberts D.J., et al., "Epithelial-mesenchymal Signaling During the Regionalization of the Chick Gut," Development, 1998, vol. 125, No. 15, pp. 2791-2801.

Rodriguez-Castillo J. A., et al., "Understanding Alveolarization to Induce Lung Regeneration," Respiratory Research, Dec. 2018, vol. 19:1-1, 11 pages.

Rouch J.D., et al., "Development of Functional Microfold (M) Cells from Intestinal Stem Cells in Primary Human Enteroids," PLOS One. Jan. 28, 2016, vol. 11(1), 16 pages.

Ruppert C.. et al., "Role of HGF in the healthy and injured lung," European Respiratory Journal, 2015, vol. 46, 2 pages.

Rydning A., et al., "Mast Cell Derived Histamine is Involved in Gastric Vasodilation During Acid Back Diffusion via Activation of Sensory Neurons," Am J Physiol Gastrointest Liver Physiol., Sep. 1, 2002, vol. 283, vol. 3, 36 pages.

Salahudeen A. A., et al., "Progenitor Identification and SARS-CoV-2 Infection in Human Distal Lung Organoids," Nature, Dec. 24, 2020, vol. 588(7839), pp. 670-675.

Scavuzzo M.A., et al., "Organotypic Pancreatoids with Native Mesenchyme Develop Insulin Producing Endocrine Cells," Scientific Reports, Sep. 7, 2017, pp. 1-12.

Serra M., et al., "Pluripotent Stem Cell Differentiation Reveals Distinct Developmental Pathways Regulating Lung-Versus Thyroid-lineage Specification," Development, Nov. 1, 2017, vol. 144(21), pp. 3879-3893.

Shacham-Silverberg V., et al., "Generation of Esophageal Organoids and Organotypic Raft Cultures from Human Pluripotent Stem Cells," Methods of Cell Biology, May 13, 2020, vol. 159, pp. 1-23.

Shaylor L.A., et al., "Convergence of Inhibitory Neural Inputs Regulate Motor Activity in the Murine and Monkey Stomach," Am J Physiol Gastrointest Liver Physiol., Nov. 1, 2016, vol. 311, No. 5, pp. G838-G851.

Shi Y., et al., "Vascularized Human Cortical Organoids (vOrganoids) Model Cortical Development in Vivo," PloS Biology, 2020, 8(5), 29 pages.

Shin Y., et al., "Blood-Brain Barrier Dysfunction in a 3D In Vitro Model of Alzheimer's Disease," Advanced Science, 2019, 6(20), 10 pages.

Shinozawa T., et al., "High-Fidelity Drug-Induced Liver Injury Screen Using Human Pluripotent Stem Cell-Derived Organoids," Gastroenterology. Feb. 2021, vol. 160(3), pp. 831-846.

Singh A., et al., "Evaluation of Transplantation Sites for Human Intestinal Organoids," Plos One, Aug. 27, 2020, 15(8), 12 pages.

Singh A., et al., "Gastrointestinal Organoids: a Next-Generation Tool for Modeling Human Development," American Journal of Physiology-gastrointestinal and Liver Physiology, 2020, 319(3), pp. G375-G381.

Smith D.M., et al., "BMP Signaling Specifies the Pyloric Sphincter," Nature, Dec. 16, 1999, vol. 402, No. 6763, pp. 748-749.

Song L., et al., "Assembly of Human Stem Cell Derived Cortical Spheroids and Vascular Spheroids to Model 3-D Brain-like Tissues," 2019, Scientific Reports, vol. 9, No. 5977, 16 pages.

Spencer J., et al., "T Cell Subclasses in Fetal Human Ileum," Clinical and Experimental Immunology, 1986, pp. 553-558.

Spencer J., et al., "The Development of Gut Associated Lymphoid Tissue in the Terminal Ileum of Fetal Human Intestine," Clinical and Experimental Immunology, 1986, pp. 536-543.

Srinivas S., et al., "Cre Reporter Strains Produced by Targeted Insertion of EYFP and ECFP into the ROSA26 Locus," BMC Developmental Biology, Dec. 2001, vol. 1 (4), 8 pages.

Srinivasan B., et al., "TEER Measurement Techniques for in Vitro Barrier Model Systems," Journal of Laboratory Automation, 2015, 20 (2), 20 pages.

Staab J.F., et al., "Co-Culture System of Human Enteroids/Colonoids with Innate Immune Cells,". Current Protocols in Immunology, Dec. 2020, vol. 131(1), 23 pages.

Stevens M.L., et al., "Genomic Integration of Wnt/-catenin and BMP/smad1 Signaling Coordinates Foregut and Hindgut Transcriptional Programs," Development, 2017, 144(7), pp. 1283-1295.

Stras., et al., "Maturation of the Human Intestinal Immune System Occurs Early in Fetal Development," Developmental Cell, Nov. 4, 2019, vol. 51(3), pp. 357-373.

(56) References Cited

OTHER PUBLICATIONS

Strauss K.A., et al., "Crigler-Najjar Syndrome Type 1: Pathophysiology, Natural History, and Therapeutic Frontier," Hepatology, 2020, 71(6), pp. 1923-1939.
Street K., et al., "Slingshot: Cell Lineage and Pseudotime Inference for Single-cell Transcriptomics," BMC Genomics, Dec. 2018, vol. 19, pp. 1-16.
Strikoudis A., et al., "Modeling of Fibrotic Lung Disease Using 3D Organoids Derived from Human Pluripotent Stem Cells," Cell Reports, Jun. 18, 2019, vol. 27(12), pp. 3709-3723.
Strunz M., et al., "Alveolar Regeneration Through a Krt8+ Transitional Stem Cell State That Persists in Human Lung Fibrosis," Nature Communications, Jul. 16, 2020, vol. 11(1):3559, 20 pages.
Sucre J. M.S., et al., "Hyperoxia Injury in the Developing Lung is Mediated by Mesenchymal Expression of Wnt5A," American Journal of Respiratory and Critical Care Medicine, May 15, 2020, vol. 201(10), pp. 1249-1262.
Sugimoto S., et al., "An Organoid-based Organ-Repurposing Approach to Treat Short Bowel Syndrome," Nature, Apr. 2021, vol. 99, 26 pages.
Sun X., et al., "A Census of the Lung: CellCards from LungMAP," Developmental Cell, Jan. 10, 2022, vol. 57(1), pp. 112-145.
Sun X-Y., et al., "Generation of Vascularized Brain Organoids to Study Neurovascular Interactions," eLife, 2022, vol. 11,28 pages.
Sung T.S., et al., "The Cells and Conductance Mediating Cholinergic Neurotransmission in the Murine Proximal Stomach," The Journal of Physiology, 2018, 596(9), pp. 1549-1574.
Tan S.H., et al., "AQP5 Enriches for Stem Cells and Cancer Origins in the Distal Stomach," Nature, 2020, 578 (7795), pp. 437-443.
Tanimizu N., et al., "Generation of Functional Liver Organoids on Combining Hepatocytes and Cholangiocytes with Hepatobiliary Connections Ex Vivo," Nature Communications, Jun. 2021, 12 pages.
Tanimizu N., et al., "Tissue Structure Formation by Liver Epithelial Cells," 2012, vol. 84, No. 8, pp. 658-665.
Tata P.R., et al., "Developmental History Provides a Roadmap for the Emergence of Tumor Plasticity," Developmental Cell, Mar. 26, 2018, vol. 44(6), pp. 679-693.
Tcw J. et al., "An Efficient Platform for Astrocyte Differentiation from Human Induced Pluripotent Stem Cells," Stem Cell Reports, vol. 9, 2017, pp. 600-614.
Teixeira V., et al., "Neonatal Vitamin C and Cysteine Deficiencies Program Adult Hepatic Glutathione and Specific Activities of Glucokinase, Phosphofructokinase, and Acetyl-CoA Carboxylase in Guinea Pigs' Livers," 2021, Antioxidants, 10, 953, 17 pages.
Theodosiou N.A., et al., "Sox9 and Nkx2. 5 Determine the Pyloric Sphincter Epithelium Under the Control of BMP Signaling," Developmental Biology, 2005, 279, pp. 481-490.
Thompson C.A., et al., "GATA4 Is Sufficient to Establish Jejunal Versus Ileal Identity in the Small Intestine," Cellular and Molecular Gastroenterology and Hepatology, May 2017, 3(3), pp. 422-446.
Thwaites D.T., et al., "H+/Dipeptide Absorption Across the Human Intestinal Epithelium Is Controlled Indirectly via a Functional Na+/H+ Exchanger," Gastroenterology, 2002, vol. 122, pp. 1322-1333.
Toth A., et al., "Alveolar Epithelial Progenitor Cells Drive Lung Regeneration via Dynamic Changes in Chromatin Topology Modulated by Lineage-specific Nkx2-1 Activity," bioRxiv, 2022, 31 pages.
Toth A., et al., "Alveolar Epithelial Stem Cells in Homeostasis and Repair," Chapter 10 in Lung Stem Cells in Development, Health and Disease, European Respiratory Society, 2021, pp. 122-133.
Tough I.R., et al., "Endogenous Peptide YY and Neuropeptide Y Inhibit Colonic Ion Transport, Contractility and Transit Differentially via Y1 and Y2 Receptors," British journal of Pharmacology, 2011, vol. 164, pp. 471-484.
Traber M.G., et al., "Vitamins C and E: Beneficial Effects from a Mechanistic Perspective," Free Radical Biology and Medicine, 2011,51 (5), pp. 1000-1013.

Travaglini K.J., et al., "A Molecular Cell Atlas of the Human Lung from Single-cell RNA Sequencing," Nature, Nov. 26, 2020, vol. 587(7835), pp. 619-625.
Tsai Y-H., et al., "In Vitro Patterning of Pluripotent Stem Cell-Derived Intestine Recapitulates in Vivo Human Development," Development, 2016, 144(6), 57 pages.
Ustiyan V., et al., "FOXF1 Transcription Factor Promotes Lung Morphogenesis by Inducing Cellular Proliferation in Fetal Lung Mesenchyme," Developmental Biology, 2018, 443(1), pp. 50-63.
Vallicelli C., et al., "Small Bowel Emergency Surgery: Literature's Review," World Journal of Emergency Surgery, 2011, vol. 6, No. 1,8 pages.
Van De Steeg E., et al., "Complete OATP1B1 and OATP1B3 Deficiency Causes Human Rotor Syndrome by Interrupting Conjugated Bilirubin Reuptake Into the Liver," The Journal of Clinical Investigation, 2012, vol. 122, No. 2, pp. 519-528.
Van Lieshout., L.P., et al., "A Novel Triple-Mutant AAV6 Capsid Induces Rapid and Potent Transgene Expression in the Muscle and Respiratory Tract of Mice," Molecular Therapy- Methods and Clinical Development, Open Access Jun. 15, 2018, vol. 9, pp. 323-329.
Vannucchi M.G., "The Telocytes: Ten Years after Their Introduction in the Scientific Literature. An Update on Their Morphology, Distribution, and Potential Roles in the Gut," International Journal of Molecular Sciences, 2020, vol. 21, 15 pages.
Verheyden J.M., et al., "A Transitional Stem Cell State in the Lung," Nature Cell Biology, Sep. 2020, vol. 22(9), pp. 1025-1026.
Vila Ellis L., et al., "Epithelial Vegfa Specifies a Distinct Endothelial Population in the Mouse Lung," Developmental Cell, 2020, 52, pp. 617-630.
Walsh K.T., et al., "The Enteric Nervous System for Epithelial Researchers: Basic Anatomy, Techniques, and Interactions with the Epithelium," Cellular and Molecular Gastroenterology and Hepatology, 2019, vol. 8, No. 3, pp. 369-378.
Wang Y., et al., "Loss of Lrig1 Leads to Expansion of Brunner Glands Followed by Duodenal Adenomas with Gastric Metaplasia," Am J Pathol., Apr. 2015, vol. 185, No. 4, pp. 1123-1134.
Ward S.M., et al., "Involvement of Intramuscular Interstitial Cells of Cajal in Neuroeffector Transmission in the Gastrointestinal Tract," The Journal of Physiology, 2006, vol. 576, pp. 675-682.
Weigmann B., et al., Isolation and Subsequent Analysis of Murine Lamina Propria Mononuclear Cells from Colonic Tissue, Nature Protocols, Oct. 2007, vol. 2(10), 2307-2311.
Weng A., et al., "Lung Injury Induces Alveolar Type 2 Cell Hypertrophy and Polyploidy with Implications for Repair and Regeneration," American Journal of Respiratory Cell and Molecular Biology, May 2022, vol. 66(5), pp. 564-576.
Westfal M.L., et al., "Pediatric Enteric Neuropathies: Diagnosis and Current Management," Current Opinion in Pediatrics, 2017, 29(3), pp. 347-353.
Wiel C., et al., "BACH1 Stabilization by Antioxidants Stimulates Lung Cancer Metastasis," Cell, Jul. 11, 2019, vol. 178(2), pp. 330-345.
Wimmer R.A., et al., "Generation of Blood Vessel Organoids from Human Pluripotent Stem Cells," Nature Protocols, 2019, vol. 14, pp. 3082-3100.
Wimmer R.A., et al., "Human Blood Vessel Organoids as a Model of Diabetic Vasculopathy," Nature, 2019, 565(7740), 41 pages.
Wong G.L.H., et al., "High Incidence of Mortality and Recurrent Bleeding in Patients With Helicobacter Pylori-Negative Idiopathic Bleeding Ulcers," Gastroenterology, 2009, vol. 137, pp. 525-531.
Wright E.M., et al., "Biology of Human Sodium Glucose Transporters," Physiological Reviews, 2011, vol. 91,62 pages.
Wright E.M., et al., "Regulation of Na+/Glucose Cotransporters," The Journal of Experimental Biology, 1997, vol. 200, pp. 287-293.
Wunderlich M., et al., "AML Xenograft Efficiency Is Significantly Improved in NOD/SCID-IL2RG Mice Constitutively Expressing Human SCF, GM-CSF and IL-3," Leukemia, Oct. 2010, vol. 24(10) pp. 1785-1788.
Wunderlich M., et al., "Improved Multilineage Human Hematopoietic Reconstitution and Function in NSGS Mice," PLOS One, Dec. 12, 2018, vol. 13(12), 20 pages.

(56) References Cited

OTHER PUBLICATIONS

Yamaguchi T., et al., "NKX2-1/TTF-1: An Enigmatic Oncogene That Functions as a Double- edged Sword for Cancer Cell Survival and Progression," Cancer Cell, Jun. 10, 2013, vol. 23(6), pp. 718-723.

Yang Y., et al., "Transcription Factor C/EBP Homologous Protein in Health and Diseases," Frontiers in Immunology, Nov. 27, 2017, vol. 8:1612, 18 pages.

Yu Q., et al., "Charting Human Development Using a Multi-Endodermal Organ Atlas and Organoid Models," Cell, 2021, vol. 184, pp. 3281-3298.

Yuan T., et al., "Fgf10 Signaling in Lung Development, Homeostasis, Disease, and Repair After Injury," Frontiers in Genetics, Sep. 25, 2018, vol. 9(418), 8 pages.

Yun C.H.C., et al., "CAMP-mediated Inhibition of the Epithelial Brush Border Na +/H+ exchanger, NHE3, requires an Associated Regulatory Protein," PNAS, 1997, vol. 94, pp. 3010-3015.

Zacharias W.J., et al., "Regeneration of the Lung Alveolus by an Evolutionarily Conserved Epithelial Progenitor," Nature, Mar. 8, 2018, vol. 555(7695), pp. 251-255.

Zepp J.A., et al., "Distinct Mesenchymal Lineages and Niches Promote Epithelial Self-Renewal and Myofibrogenesis in the Lung," Cell, Sep. 7, 2017, vol. 170(6), pp. 1134-1148.

Zhang S., et al., "Vascularized Organoids on a Chip: Strategies for Engineering Organoids with Functional Vasculature," Lab Chip, 2021,21 (3), pp. 473-488.

Zhao C-M., et al., "Control of Gastric Acid Secretion in Somatostatin Receptor 2 Deficient Mice: Shift from Endocrine/Paracrine to Neurocrine Pathways," Endocrinology, 2008, 149(2), pp. 498-505.

Zhou B., et al., "Comprehensive Epigenomic Profiling of Human Alveolar Epithelial Differentiation Identifies Key Epigenetic States and Transcription Factor Co-regulatory Networks for Maintenance of Distal Lung Identity," BMC Genomics, Dec. 2021, vol. 22(906), 25 pages.

Ross M.G et al., "Development of ingestive behavior.," Am J Physiol, 1998, 274, R879-893.

Rossi J.M. et al., "Distinct mesodermal signals, including BMPs from the septum transversum mesenchyme, arc required in combination for hepatogenesis from the endoderm," Genes Dev, 2001, 15, 1998-2009.

Rubio-Cabezas O., et al., "Permanent Neonatal Diabetes and Enteric Anendocrinosis Associated with Biallelic Mutations in NEUROG3," Diabetes, 2011, vol. 60, pp. 1349-1353.

Sahdeo S., et al., "High-Throughput Screening of FDA-Approved Drugs Using Oxygen Biosensor Plates Reveals Secondary Mitofunctional Effects," Mitochondrion, 2014, vol. 17, pp. 116-125.

Saili K. S., et al., "Blood-Brain Barrier Development: Systems Modeling and Predictive Toxicology," Birth Defects Research, 2017, vol. 109, pp. 1680-1710.

Sajiki T., et al., "Transmission Electron Microscopic Study of Hepatocytes in Bioartificial Liver," Tissue Engineering, 2000, vol. 6, No. 6, pp. 627-640.

Samson A et al., "Effect of somatostatin on electrogenic ion transport in the duodenum and colon of the mouse, *Mus domesticus*," Comparative Biochemistry and Physiology Part A: Molecular Integrative Physiology, 2000, 125, 459-468.

Samuel, V.T., et al., "Nonalcoholic Fatty Liver Disease, Insulin Resistance, and Ceramides," New England Journal of Medicine, 2019, vol. 381, pp. 1866-1869.

Sankoda N., et al., "Epithelial Expression of Gata4 and Sox2 Regulates Specification of the Squamous-columnar Junction via MAPK/ERK Signaling in Mice," Nature Communications, 2021, vol. 12, pp. 1-15.

Santoro N., et al., "Variant in the Glucokinase Regulatory Protein (GCKR) Gene Is Associated with Fatty Liver in Obese Children and Adolescents," Hepatology, 2012, vol. 55, pp. 781-789.

Sarkar A., et al., "Sox2 Suppresses Gastric Tumorigenesis in Mice," Cell Reports, 2016, 16(7), pp. 1929-1941.

Sato T., et al., "Growing Self-Organizing Mini-Guts from a Single Intestinal Stem Cell: Mechanism and Applications," Science, 2013, vol. 340, pp. 1190-1194. DOI: 10.1126/science.1234852.

Saunders N. R., et al., "Barrier Mechanisms in the Developing Brain," Frontiers in Pharmacology, 2012, vol. 3, Article 46, 18 pages.

Sayar E., et al., "Chromogranin-A Staining Reveals Enteric Anendocrinosis in Unexplained Congenital Diarrhea," Journal of Pediatric Gastroenterology and Nutrition, 2013, vol. 57, No. 4, pp. e21.

Sayar E., et al., "Extremely Rare Cause of Congenital Diarrhea: Enteric Anendocrinosis," Pediatrics International, 2013, vol. 55, pp. 661-663.

Scheidecker, B., et al., "Induction of in vitro Metabolic Zonation in Primary Hepatocytes Requires Both Near-Physiological Oxygen Concentration and Flux," Frontiers in Bioengineering and Biotechnology, 2020, vol. 8.

Schreiber R., et al., "Inherited Renal Tubular Dysgenesis May Not Be Universally Fatal," Pediatric Nephrology, 2010, vol. 25, pp. 2531-2534.

Schreiber R., et al., "Renal Tubular Dysgenesis Secondary to Mutations in Genes Encoding the Renin-Angiotensin System," Harefuah, 2021, vol. 160, pp. 822-826.

Schuldiner et al. "Induced Neuronal Differentiation of Human Embryonic Stem Cells," Brain Research 2001, Sep. 21, 2001, vol. 913(2):201-205.

Schupp J.C., et al., "Integrated Single-Cell Atlas of Endothelial Cells of the Human Lung," Circulation, May 2021, vol. 144, No. 4, 286-302. doi: 10.1161/CIRCULATIONAHA.120.052318.

Sebrell T.A., et al., "Live Imaging Analysis of Human Gastric Epithelial Spheroids Reveals Spontaneous Rupture, Rotation and Fusion Events,". Cell and Tissue Research, 2018, vol. 371, pp. 293-307.

Sekar R. and Chow B. K. C., "Secrelin Receptor-Knockout Mice Are Resistant to High-Fat Diet-Induced Obesity and Exhibit Impaired Intestinal Lipid Absorption," The FASEB Journal, 2014, vol. 28, pp. 3494-3505.

Self M et al., "Six2 activity is required for the formation of the mammalian pyloric sphincter," Dev Biol, 2009, 334, 409-417.

Shaham O. et al., "Pax6 is essential for lens fiber cell differentiation," Development (Cambridge, England), 2009, 136 (15), 2567-2578.

Shankar A.S., et al., "Human Kidney Organoids Produce Functional Renin," Kidney International, 2021, vol. 99, pp. 134-147.

Shao Z et al., "MAnorm: a robust model for quantitative comparison of ChIP-Seq data sets," Genome Biol, 2012, 13, R16, 17 pages.

Shapiro E., et al., "Single-cell Sequencing-based Technologies will Revolutionize Whole Organism Science," Nature Reviews Genetics, 2013, vol. 14(9), pp. 618-630.

Shen H., et al., "Glucokinase Regulatory Protein Gene Polymorphism Affects Postprandial Lipemic Response in a Dietary Intervention Study," Human Genetics, 2009, vol. 126, pp. 567-574.

Shoyaib A.A., et al., "Intraperitoneal Route of Drug Administration: Should it Be Used in Experimental Animal Studies?," Pharm Res, Dec. 23, 2019, vol. 37(1):12.

Simon, M., et al., "Expression of Vascular Endothelial Growth Factor and Its Receptors in Human Renal Ontogenesis and in Adult Kidney." American Journal of Physiology, vol. 268, No. 2, Feb. 1995, pp. F240-F250.

Simon T.G., et al., "Mortality in Biopsy-Confirmed Nonalcoholic Fatty Liver Disease: Results from a Nationwide Cohort," Gut, 2021, vol. 70, pp. 1375-1382. doi: 10.1136/gutjnl-2020-322786.

Sinagoga K. L., et al., "Distinct Roles for the mTOR Pathway in Postnatal Morphogenesis, Maturation and Function of Pancreatic Islets," Development, 2017, vol. 144, pp. 2402-2414.

Sinagoga K.L., et al., "Deriving Functional Human Enteroendocrine Cells from Pluripotent Stem Cells," Development, 2018, vol. 145.

Singh A., et al., "Transplanted Human Intestinal Organoids: A Resource for Modeling Human Intestinal Development," Development, 2023, vol. 150, dev201416. doi: 10.1242/dev.201416.

Singh S. K., et al., "Glucose-Dependent Insulinotropic Polypeptide (GIP) Stimulates Transepithelial Glucose Transport," Obesity, 2008, vol. 16, pp. 2412-2416.

(56) References Cited

OTHER PUBLICATIONS

Sinner D. et al. "Sox17 and Sox4 differentially regulate beta-catenin/ T-cell factor activity and proliferation of colon carcinoma cells," Molecular and Cellular Biology, 27(22), 2007, 7802-7815.

Sloan S. A., et al., "Human Astrocyte Maturation Captured in 3D Cerebral Cortical Spheroids Derived from Pluripotent Stem Cells," Neuron, 2017, vol. 95, pp. 779-790.e1-e6.

Sloth B et al., "Effect of subcutaneous injections of PYY1-36 and PYY3-36 on appetite, ad libitum energy intake, and plasma free fatty acid concentration in obese males," American Journal of Physiology Endocrinology and Metabolism, 2007, 293, E604-E609.

Sluch V.M., et al., "Highly Efficient Scarless Knock-in of Reporter Genes into Human and Mouse Pluripotent Stem Cells via Transient Antibiotic Selection", PLOS ONE, vol. 13, No. 11, Nov. 29, 2018. Retrieved from the Internet: URL :https://www.ncbi.nlm.nih.gov/pmc/articles/PMC6264506/pdf/ pone.0201683.pdf.

Smith, S.M., et al., "Obeticholic Acid: A Farnesoid X Receptor Agonist for Primary Biliary Cholangitis," Journal of Pharmacy Technology, 2017, vol. 33 (2), pp. 66-71.

Snellings D.A., et al., "Cerebral Cavernous Malformation: From Mechanism to Therapy," Circulation Research, 2021, vol. 129, pp. 195-215. doi: 10.1161/CIRCRESAHA.121.318174.

Snowball J. et al., "Endodermal Wnt signaling is required for tracheal cartilage formation," Dev Biol 405, 56-70 (2015).

Soneson C., et al., "Differential Analyses for RNA-Seq: Transcript-Level Estimates Improve Gene-Level Inferences," F1000Research, 2015, vol. 4, p. 1521.

Song H.W., et al., "Transcriptomic Comparison of Human and Mouse Brain Microvessels," Scientific Reports, 2020, vol. 10, 12358. doi: 10.1038/s41598-020-69096-7.

Spangle, J. M., et al., "The Human Papillomavirus Type 16 E6 Oncoprotein Activates mTORC1 Signaling and Increases Protein Synthesis." Journal of Virology, vol. 84, No. 18, Sep. 2010, pp. 9398-9407.

Sparrow D. B., et al., "A Mechanism for Gene-Environment Interaction in the Etiology of Congenital Scoliosis," Cell, 2012, vol. 149, pp. 295-306.

Speliotes E. K., et al., "Genome-Wide Association Analysis Identifies Variants Associated with Nonalcoholic Fatty Liver Disease That Have Distinct Effects on Metabolic Traits," PLoS Genetics, 2011, vol. 7, e1001324.

Spencer-Dene B et al., "Stomach development is dependent on fibroblast growth factor 10/fibroblast growth factor receptor 2b-mediated signaling," Gastroenterology, 2006, 130, 1233-1244.

Sreter K.B., et al., "Plasma Brain-Derived Neurotrophic Factor (BDNF) Concentration and BDNF/TrkB Gene Polymorphisms in Croatian Adults with Asthma," Journal of Personalized Medicine, Oct. 2020, vol. 10, No. 4, doi: 10.3390/jpm10040189.

Stoeckius M., et al., "Cell Hashing with Barcoded antibodies enables Multiplexing and Doublet Detection for Single Cell Genomics," Genome Biology, 2018, vol. 19(1), pp. 1-12.

Blanchard C., et al., "Coordinate Interaction between IL-13 and Epithelial Differentiation Cluster Genes in Eosinophilic Esophagitis," The Journal of Immunology 2010, 184(7), 4033-4041.

Bochkis I.M et al., "Genome-wide location analysis reveals distinct transcriptional circuitry by paralogous regulators Foxa1 and Foxa2," PLoS genetics, 2012, 8, 6, e1002770, 10 pages.

Boj S.F., et al., "Forskolin-induced Swelling in Intestinal Organoids: An In Vitro Assay for Assessing Drug Response in Cystic Fibrosis Patients," J Vis Exp, Feb. 11, 2017, (120):55159.

Bolger A. M et al., "Trimmomatic: a flexible trimmer for Illumina sequence data," Bioinformatics, 2014, 30, 2114-2120.

Bolte C., et al., "Nanoparticle Delivery of Proangiogenic Transcription Factors into the Neonatal Neurotrophic Factor- Mediated Alveolar Capillary Injury and Repair Circulation Inhibits Alveolar Simplification Caused by Hyperoxia," American Journal of Respiratory and Critical Care Medicine, Jul. 2020, vol. 202, No. 1, pp. 100-111. doi: 10.1164/rccm.201906-12320C.

Boon et al., "Amino Acid Levels Determine Metabolism and CYP450 Function in Hepatocytes and Hepatoma Cell Lines," Nature Communications, 2020, vol. 11, 1393.

Bordi C et al., "Classification of gastric endocrine cells at the light and electron microscopical levels," Microsc. Res. Tech., 2000, 48, 258-271.

Bray N. L., et al., "Near-Optimal Probabilistic RNA-Seq Quantification," Nature Biotechnology, 2016, vol. 34, pp. 525-527.

Buettner et al., "Computational Analysis of Cell-to-cell Heterogeneity in Single-cell RNA-sequencing Data reveals Hidden Subpopulations of cells", Nature Biotech, 2015, vol. 33(2), pp. 155-160.

Buske P., et al., "On the Biomechanics of Stem Cell Niche Formation in the Gut—Modelling Growing Organoids," The FEBS Journal, 2012, vol. 279, pp. 3475-3487.

Butler, A., et al. Integrating Single-Cell Transcriptomic Data Across Different Conditions, Technologies, and Species,. Nature Biotechnology, 2018, 36(4), pp. 411-420.

Cai, W., et al., "Genetic polymorphisms associated with nonalcoholic fatty liver disease in Uyghur population: a case-control study and meta-analysis," Lipids in Health and Disease, 2019, vol. 18, 14.

Cain M.P., et al., "Quantitative Single-Cell Interactomes in Normal and Virus-Infected Mouse Lungs," Disease Models Mechanisms, May 2020, vol. 13, No. 6, doi: 10.1242/dmm.044404.

Cakir, et al., "Engineering of Human Brain Organoids with a Functional Vascular-Like System," Nature Methods, 2019, vol. 16, No. 11, 1169-1175.

Caldwell J. M., et al., "Novel Immunologic Mechanisms in Eosinophilic Esophagitis," Current Opinion in Immunology, 2017, vol. 48, pp. 114-121.

Candi E. et al., "Differential roles of p63 isoforms in epidermal development: selective genetic complementation in p63 null mice," Cell Death Differ, 2006, 13, 1037-1047.

Capeling M. M. et al., "Suspension culture promotes serosal mesothelial development in human intestingal organoids," Cell Reports, 2002, 38, 110379, 33 pages.

Carmona R., et al., "Conditional Deletion of WT1 in the Septum Transversum Mesenchyme Causes Congenital Diaphragmatic Hernia in Mice,". eLife, Sep. 19, 2016, vol. 5, No. e16009, pp. 1-17.

Chambers J. C., et al., "Genome-Wide Association Study Identifies Loci Influencing Concentrations of Liver Enzymes in Plasma," Nature Genetics, 2011, vol. 43, pp. 1131-1138.

Chance W.T., et al., "Preservation of Intestine Protein by Peptide YY During Total Parenteral Nutrition," Life Sciences 1996, vol. 58, No. 21, pp. 1785-1794.

Chandran S., et al., "Necrotising Enterocolitis in a Newborn Infant Treated with Octreotide for Chylous Effusion: Is Octreotide Safe?," BMJ Case Reports, 2020, 13, e232062. doi: 10.1136/bcr-2019-232062.

Char V.C. et al., "Digestion and absorption of carbohydrates by the fetal lamb in utero," Pediatr Res, 1979, 13, 1018-1023.

Charlton, V. E., et al., "Effects of Gastric Nutritional Supplementation on Fetal Umbilical Uptake of Nutrients," Am J Physiol, 1981, vol. 241, pp. E178-E185.

Chatterjee S., et al., "Tissue-Specific Gene Expression during Productive Human Papillomavirus 16 Infection of Cervical, Foreskin, and Tonsil Epithelium." Journal of Virology, 93(17), 2019, e00915-19.

Chen et al., "A Versatile Polypharmacology Platform Promotes Cryoprotection and Viability of Human Pluripotent and Differentiated Cells," Nature Methods, 2021, vol. 18, pp. 528-541.

Chen, F., et al., "Inhibition of Tgf beta signaling by endogenous retinoic acid is essential for primary lung bud induction," Development, 2007, vol. 134, pp. 2969-2979.

Chen H., et al., "Single-Cell Trajectories Reconstruction, Exploration and Mapping of Omics Data with STREAM," Nature Communications, 2019, vol. 10, Article 1903. doi: 10.1038/s41467-019-09670-4, 14 pages.

Chen H. et al., "Transcript profiling identifies dynamic gene expression patterns and an important role for Nrf2/Keap1 pathway in the developing mouse esophagus," PloS One 2012, 7(5), e36504, 10 pages.

(56) References Cited

OTHER PUBLICATIONS

Chen J., et al., "Improved Human Disease Candidate Gene Prioritization Using Mouse Phenotype," BMC Bioinformatics, 2007, vol. 8, p. 392.
Chen J., et al., "ToppGene Suite for Gene List Enrichment Analysis and Candidate Gene Prioritization," Nucleic Acids Research, 2009, vol. 37, pp. W305-W311.
Chen S., et al., "fastp: An Ultra-Fast All-in-One FASTQ Preprocessor," Bioinformatics, 2018, vol. 34, pp. 1884-1890.
Chen X., "Aberrant expression of Wnt and Notch signal pathways in Barrett's esophagus," Clinics and Research in Hepatology and Gastroenterology, 2012, 36(5), 473-483.
Chen Y., et al., "A Three-Dimensional Model of Human Lung Development and Disease from Pluripotent Stem Cells," Nature Cell Biology, May 2017, vol. 19, No. 5, pp. 542-557.
Chen Y. et al., "BMP Signaling pathway and colon cancer," Journal of Cell Biology 2009, 5, 6 pages (Chinese with machine translation).
Chen, Y., et al., "SOX2 expression inhibits terminal epidermal differentiation," Exp. Dermatol., 2015, vol. 24, pp. 966-982.
Chen Y., et al., "Regulation of Angiogenesis Through a MicroRNA (miR-130a) That Down-Regulates Antiangiogenic Homeobox Genes GAX and HOXA5," Blood, 2008, vol. 111, pp. 1217-1226.
Chen Y. et al., "The Molecular Mechanism Governing the Oncogenic Potential of SOX2 in Breast Cancer," Journal of Biological Chemistry 2008, 283(26), 17969-17978.
Cheung K.C.P., et al., "Preservation of Microvascular Barrier Function Requires CD31 Receptor-Induced Metabolic Reprogramming," Nature Communications, Jul. 2020, vol. 11, No. 1, doi: 10.1038/s41467-020-17329-8.
Chey, W. Y., et al., "Secretin: historical perspective and current status," Pancreas, 2014, vol. 43, pp. 162-182.
Chin, A. M., et al., "Morphogenesis and maturation of the embryonic and postnatal intestine," Seminars in Cell Developmental Biology, 2017, vol. 66, pp. 81-93.
Cho C., et al., "Reck and Gpr124 Are Essential Receptor Cofactors for Wnt7a/Wnt7b-Specific Signaling in Mammalian CNS Angiogenesis and Blood-Brain Barrier Regulation," Neuron, 2017, vol. 95, pp. 1221-1225.
Cho C. F., et al., "Blood-Brain-Barrier Spheroids as an In Vitro Screening Platform for Brain-Penetrating Agents," Nature Communications, 2017, vol. 8, p. 15623.
Choi K., et al., "iGEAK: An Interactive Gene Expression Analysis Kit for Seamless Workflow Using the R/Shiny Platform," BMC Genomics, 2019, vol. 20, p. 177.
Choudhary S., et al., "Comparison and Evaluation of Statistical Error Models for scRNA-seq," Genome Biology, 2022, vol. 23, 27. doi: 10.1186/s13059-021-02584-9.
Claesson-Welsh L., et al., "Permeability of the Endothelial Barrier: Identifying and Reconciling Controversies," Trends in Molecular Medicine, Apr. 2021, vol. 27, No. 4, pp. 314-331.
Claeys, W., et al., "A mouse model of hepatic encephalopathy: bile duct ligation induces brain ammonia overload, glial cell activation and neuroinflammation," Scientific Reports, 2022, vol. 12, 17558.
Clemmensen, C. et al., "Emerging Hormonal-Based Combination Pharmacotherapies for the Treatment of Metabolic Diseases". Nat Rev Endocrinol, 2018, 14(10), pp. 670-684.
Collier et al., "Identifying Human Naïve Pluripotent Stem Cells—Evaluating State-Specific Reporter Lines and Cell-Surface Markers", BioEssays. May 2018, 40(5): 1700239 in 12 pages.
Concepcion J. P., et al., "Neonatal Diabetes, Gallbladder Agenesis, Duodenal Atresia, and Intestinal Malrotation Caused by a Novel Homozygous Mutation in RFX6," Pediatric Diabetes, 2014, vol. 15, pp. 67-72.
Coon S. D et al., "Glucose-dependent insulinotropic polypeptide-mediated signaling pathways enhance apical PepT1 expression in intestinal epithelial cells," Am J Physiol Gastrointest Liver Physiol, 2015, 308, G56-62.

Marino G. et al., "Self-consumption: the interplay of autophagy and apoptosis", Nature reviews Molecular cell biology, 2014, vol. 15, No. 2, pp. 81-94.
Mariotti, V., et al., "Animal models of biliary injury and altered bile acid metabolism," Biochimica et Biophysica Acta (BBA)—Molecular Basis of Disease, 2018, vol. 1864, pp. 1254-1261.
Martin M. "Cutadapt Removes Adapter Sequences From High-Throughput Sequencing Reads," EMBnet.journal, 2011 17, 10-12.
Martindale J.L., et al., "Ribonucleoprotein Immunoprecipitation (RIP) Analysis," Bio Protoc, 2020, vol. 10, No. 2, e3488. doi: 10.21769/BioProtoc.3488.
Matrka M. C., et al., "Overexpression of the Human DEK Oncogene Reprograms Cellular Metabolism and Promotes Glycolysis," PLoS One, 2017, vol. 12, e0177952.
Matsuda S., et al., "Brain-Derived Neurotrophic Factor Induces Migration of Endothelial Cells Through a TrkB-ERK-Integrin $\alpha V\beta 3$-FAK Cascade." Journal of Cellular Physiology, 227, 2012, pp. 2123-2129.
Matt N. et al., "Retinoic acid-induced developmental defects are mediated by RARI3/RXR heterodimers in the pharyngeal endoderm," Development, 2003, 130(10), 2083-2093.
Mayor S., et al., "Pathways of Clathrin-independent Endocytosis," Nature Reviews, Molecular Cell Biology, 2007, vol. 8(8), pp. 603-612.
McCarty, W. J., et al., "A Microfabricated Platform for Generating Physiologically-Relevant Hepatocyte Zonation," Scientific Reports, 2016, vol. 6, 26868, 10 Pages.
McMahon H.T., et al., "Molecular Mechanism and Physiological Functions of Clathrin-mediated Endocytosis," Nature Reviews Molecular Cell Biology, Aug. 2011, vol. 12(8), pp. 517-533.
McNaughton, L., et al., "Distribution of nitric oxide synthase in normal and cirrhotic human liver," Proceedings of the National Academy of Sciences, 2002, vol. 99, pp. 17161-17166.
Mendelsohn C et al., "Developmental analsyis of the retinoic acid-inducible RARb2 promoter in transgenic animals," Development, 1991,113, 723-734.
Miao Y., et al., "Enhancer-Associated Long Non-Coding RNA LEENE Regulates Endothelial Nitric Oxide Synthase and Endothelial Function," Nature Communications, Jan. 2018, vol. 9, No. 1, doi: 10.1038/s41467-017-02113-y.
Miao Y., et al., "Intrinsic Endocardial Defects in Hypoplastic Left Heart Syndrome," Cell Stem Cell, Jul. 2020. doi: 10.1016/j.stem.2020.07.015.
Miao Z., et al., "Single Cell Regulatory Landscape of the Mouse Kidney Highlights Cellular Differentiation Programs and Disease Targets," Nature Communications, 2021, vol. 12, No. 2277.
Midendorp S., et al., "Adult Stem Cells in the Small Intestine Are Intrinsically Programmed with Their Location-Specific Function," Stem Cells, 2014, vol. 32, pp. 1083-1091. DOI: 10.1002/stem.1655.
Miller J. L., et al., "Emergence of Oropharyngeal, Laryngeal and Swallowing Activity in the Developing Fetal Upper Aerodigestive Tract: An Ultrasound Evaluation." Early Human Development, 71, 2003, pp. 61-87.
Minoo P. et al., "Defects in tracheoesophageal and lung morphogenesis in Nkx2.1 (−/−) mouse embryos," Dev. Biol., 1999, 209, 60-71.
Mitani, S., et al., "Human ESC/iPSC-Derived Hepatocyte-like Cells Achieve Zone-Specific Hepatic Properties by Modulation of WNT Signaling," Mol Ther, 2017, vol. 25, pp. 1420-1433.
Miyoshi H., et al., "In Vitro Expansion and Genetic Modification of Gastrointestinal Stem Cells in Spheroid Culture," Nature Protocols, 2013, vol. 8(12), pp. 2471-2482.
Moffett, J.R., et al., "Acetate Revisited: A Key Biomolecule at the Nexus of Metabolism, Epigenetics and Oncogenesis—Part 1: Acetyl-CoA, Acetogenesis and Acyl-CoA Short-Chain Synthetases," Frontiers in Physiology, 2020, vol. 11.
Moon C. et al., "Development of a primary mouse intestinal epithelial cell monolayer culture system to evaluate factors that modulate IgA transcytosis," Mucosal Immunol, 2014, 7, 818-828.
Moorefield E.C., et al., "Generation of renewable mouse intestinal epithelial cell monolayers and organoids for functional analyses," BMC Cell Biol, Aug. 15, 2018, vol. 19(1):15.

(56) References Cited

OTHER PUBLICATIONS

Mootha V.K. et al., "PGC-1alpha-responsive genes involved in oxidative phosphorylation are coordinately downregulated in human diabetes," Nat Genet 34, 267-273 (2003).

Morizane R., et al., "Differentiation of Murine Embryonic Stem and Induced Pluripotent Stem Cells to Renal Lineage In Vitro." Biochemical and Biophysical Research Communications, 390, 2009, pp. 1334-1339.

Morizane R., et al., "Generation of Nephron Progenitor Cells and Kidney Organoids from Human Pluripotent Stem Cells," Nature Protocols, 2017, vol. 12, pp. 195-207.

Morizane R., et al., "Kidney Organoids: A Translational Journey," Trends in Molecular Medicine, 2017, vol. 23, pp. 246-263.

Morizane R., et al., "Nephron Organoids Derived from Human Pluripotent Stem Cells Model Kidney Development and Injury." Nature Biotechnology, 33(11), 2015, pp. 1193-1200. https://doi.org/10.1038/nbt.3392.

Morris M. E., et al., "SLC and ABC Transporters: Expression, Localization, and Species Differences at the Blood-Brain and the Blood-Cerebrospinal Fluid Barriers," AAPS Journal, 2017, vol. 19, pp. 1317-1331.

Mounier F., et al., "Ontogenesis of Angiotensin-I Converting Enzyme in Human Kidney," Kidney International, 1987, vol. 32, pp. 684-690.

Murphy C. L., et al., "HIF-Mediated Articular Chondrocyte Function: Prospects for Cartilage Repair," Arthritis Research & Therapy, 2009, vol. 11, p. 213. DOI: 10.1186/ar2574.

Murphy P.A., et al., "Alternative RNA Splicing in the Endothelium Mediated in Part by Rbfox2 Regulates the Arterial Response to Low Flow," eLife, Jan. 2018, vol. 7, e29494. doi: 10.7554/eLife.29494.

Navin N., et al., "Tumor Evolution Inferred by Single-cell Sequencing," Nature, Apr. 7, 2011, vol. 472(7341), pp. 90-94.

Neal E.H., et al., "A Simplified, Fully Defined Differentiation Scheme for Producing Blood-Brain Barrier Endothelial Cells from Human iPSCs," Stem Cell Reports, 2019, vol. 12, pp. 1380-1388.

Nebert D. W., et al., "Letter to the Editor for 'Update of the Human and Mouse Fanconi Anemia Genes,'" Human Genomics, 2016, vol. 10, No. 1, 25 pages.

Nejak-Bowen, K., et al., "Beta-catenin regulates vitamin C biosynthesis and cell survival in murine liver," J Biol Chem, 2009, vol. 284, pp. 28115-28127.

Nelson L.J., et al., "Low-Shear Modelled Microgravity Environment Maintains Morphology and Differentiated Functionality of Primary Porcine Hepatocyte Cultures," Cells Tissues Organs, 2010, vol. 192, pp. 125-140.

Niederreither K. "Embryonic retinoic acid synthesis is essential for early mouse post-implantation development," Nature Genetics, 1999, 21(4), 444-448.

Niethamer T.K., et al., "Defining the Role of Pulmonary Endothelial Cell Heterogeneity in the Response to Acute Lung Injury," eLife, Feb. 2020, vol. 9, No. e53072. doi: 10.7554/eLife.53072.

Nishinakamura R., "Human Kidney Organoids: Progress and Remaining Challenges," Nature Reviews Nephrology, 2019, vol. 15, pp. 613-624.

Nonn, O., et al., "Maternal Angiotensin Increases Placental Leptin in Early Gestation via an Alternative Renin- Angiotensin System Pathway: Suggesting a Link to Preeclampsia," Hypertension, 2021, vol. 77, pp. 1723-1736.

Nozaki, Y., et al., "Metabolic Control Analysis of Hepatic Glycogen Synthesis In Vivo," Proceedings of the National Academy of Sciences of the United States of America, 2020, vol. 117, pp. 8166-8176.

Nyeng P. et al., FGF10 signaling controls stomach morphogenesis. Developmental Biology, 2007, 303, 295-310.

Oberg, K. C., et al., "Renal Tubular Dysgenesis in Twin-Twin Transfusion Syndrome." Pediatric Developmental Pathology, vol. 2, No. 1, 1999, pp. 25-32.

Offield M.F. et al., "PDX-1 is required for pancreatic outgrowth and differentiation of the rostral duodenum," Development, 1996, 122(3), 983-995.

Ohashi T., "Enzyme replacement therapy for lysosomal storage diseases," Pediatr Endocrinol Rev. Oct. 1, 2012;10(supp 1):26 34.

Ohmori T et al. "Efficient expression of a transgene in platelets using simian immunodeficiency virus based vector harboring glycoprotein Iba promoter: in vivo model for platelet targeting gene therapy," FASEB J. (2006); 20(9):1522 4.

Ohsie S. et al., "A paucity of colonic enteroendocrine and/or enterochromaffin cells characterizes a subset of patients with chronic unexplained diarrhea/malabsorption," Hum Pathol , 2009, 40(7), 1006-1014.

Ohta et al., "Hemogenic endothelium differentiation from human pluripotent stem cells in a feeder and xeno free defined condition," Journal of Visualized Experiments. Jun. 16, 2019; 148:e59823 in 6 pages.

Oliverio M. I., et al., "Reduced Growth, Abnormal Kidney Structure, and Type 2 (AT2) Angiotensin Receptor-Mediated Blood Pressure Regulation in Mice Lacking Both AT1A and AT1B Receptors for Angiotensin II," Proceedings of the National Academy of Sciences USA, 1998, vol. 95, pp. 15496-15501.

Zeng, Q., et al., "O-Linked GlcNAcylation Elevated by Hpv E6 Mediates Viral Oncogenesis." Proceedings of the National Academy of Sciences, vol. 113, No. 33, Aug. 16, 2016, pp. 9333-9338.

Zhang, D., et al., "Highly efficient differentiation of human ES cells and iPS cells into mature pancreatic insulin- producing cells," Cell Res., 2009, vol. 19, pp. 429-438.

Zhang H., et al., "Generation of Quiescent Cardiac Fibroblasts From Human Induced Pluripotent Stem Cells for In Vitro Modeling of Cardiac Fibrosis," Circulation Research, Sep. 2019, vol. 125, No. 5, pp. 552-566.

Zhang S. L., et al., "Angiotensin II Stimulates Pax-2 in Rat Kidney Proximal Tubular Cells: Impact on Proliferation and Apoptosis," Kidney International, 2004, vol. 66, pp. 2181-2192.

Zhao Z., et al., "Establishment and Dysfunction of the Blood-Brain Barrier," Cell, 2015, vol. 163(5), pp. 1064-1078.

Zheng G.X.Y., et al., "Massively Parallel Digital Transcriptional Profiling of Single Cells," Nature Communications, 2017, vol. 8(1), pp. 1-12.

Zheng, Y., et al., pH- and Temperature-Senstive PCL-Grafted Poly (R-amino ester)-Poly (ethylene glycol)-Poly (R-amino ester) Copolymer Hydrogels, Macromolecular Research, 2010, vol. 18, No. 11, pp. 1096-1102.

Zhou C., et al., "Comprehensive Profiling Reveals Mechanisms of SOX2-Mediated Cell Fate Specification in Human ESCs and NPCs," Cell Research, 2016, 26(2), pp. 171-189. DOI: 10.1038/cr.2016.15.

Zhou H. J., et al., "Endothelial Exocytosis of Angiopoietin-2 Resulting from CCM3 Deficiency Contributes to Cerebral Cavernous Malformation," Nature Medicine, 2016, vol. 22, pp. 1033-1042.

Zhou Y., et al., "A Subtype of Oral, Laryngeal, Esophageal, and Lung Squamous Cell Carcinoma with High Levels of TrkB-T1 Neurotrophin Receptor mRNA," BMC Cancer, Jun. 2019, vol. 19, No. 1, doi: 10.1186/s12885-019-5789-8.

Zhou Z., et al., "Cerebral Cavernous Malformations Arise from Endothelial Gain of MEKK3-KLF2/4 Signaling," Nature, 2016, vol. 532, pp. 122-126.

Zhu, S., et al., "Liver Endothelial Heg Regulates Vascular/Biliary Network Patterning and Metabolic Zonation Via Wnt Signaling," Cell Molecular Gastroenterology and Hepatology, 2022, vol. 13, pp. 1757-1783.

Zhu Z et al., "Human pluripotent stem cells: an emerging model in developmental biology," Development 140, 705-717 (2013).

Zhuo J. L., et al., "Proximal Nephron," Comprehensive Physiology, 2013, vol. 3, No. 3, pp. 1079-1123.

Ziegler B. L., et al., "KDR Receptor: A Key Marker Defining Hematopoietic Stem Cells," Science, vol. 285, No. 5433, Sep. 3, 1999, pp. 1553-1558.

Zwerschke, W., et al., "Modulation of Type M2 Pyruvate Kinase Activity by the Human Papillomavirus Type 16 E7 Oncoprotein." Proceedings of the National Academy of Sciences USA, vol. 96, Feb. 1999, pp. 1291-1296.

Habib A. M. et al., "Overlap of endocrine hormone expression in the mouse intestine revealed by transcriptional profiling and flow cytometry," Endocrinology, 2012, 153, 3054-3065.

(56) References Cited

OTHER PUBLICATIONS

Haeussler M., et al., "Evaluation of Off-Target and On-Target Scoring Algorithms and Integration into the Guide RNA Selection Tool CRISPOR," Genome Biology, 2016, vol. 17, No. 148, 12 pages.
Hagan D.M. et al., "Mutation analysis and embryonic expression of the HLXB9 Currarino syndrome gene," Am. J. Hum. Genet., 2000, 66, 1504-1515.
Haigh J. J., et al., "Cortical and Retinal Defects Caused by Dosage-Dependent Reductions in VEGF-A Paracrine Signaling," Developmental Biology, 2003, vol. 262, pp. 225-241.
Hajal C., et al., "Biology and Models of the Blood-Brain Barrier," Annual Review of Biomedical Engineering, 2021, vol. 23, pp. 359-384.
Hale, C., et al., "Molecular Targeting of the GK-GKRP Pathway in Diabetes." Expert Opinion on Therapeutic Targets, vol. 19, No. 1, 2015, pp. 129-139.
Han L., et al., "Osr1 Functions Downstream of Hedgehog Pathway to Regulate Foregut Development," Developmental Biology, 2017, 427, pp. 72-83.
Hansmann G., et al., "Pulmonary Hypertension in Bronchopulmonary Dysplasia," Pediatric Research, Jun. 2020, No. 10.1038/s41390-020-0993-4.
Harris-Johnson K.S et al., "13-Catenin promotes respiratory progenitor identity in mouse foregut," Proc. Natl. Acad. Sci. U. S. A., 2009, 106, 16287-16292.
Harrison S.A., et al., "Selonsertib for Patients with Bridging Fibrosis or Compensated Cirrhosis Due to NASH: Results from Randomized Phase III STELLAR Trials," Journal of Hepatology, 2020, vol. 73, pp. 26-39.
Haussinger, D., "Nitrogen metabolism in liver: structural and functional organization and physiological relevance," Biochem J, 1990, vol. 267, pp. 281-290.
He, L., et al., "Proliferation tracing reveals regional hepatocyte generation in liver homeostasis and repair," Science, 2021, vol. 371, eabc4346.
Heinz S. et al., "Simple combinations of lineage-determining transcription factors prime cis-regulatory elements required for macrophage and B cell identities," Mol Cell, 2010, 38, 576-589.
Hernaez R., et al., "Association Between Variants in or near PNPLA3, Gckr, and PPP1R3B with Ultrasound-Defined Steatosis Based on Data from the Third National Health and Nutrition Examination Survey," Clinical Gastroenterology and Hepatology, 2013, vol. 11, pp. 1183-1190.e1182.
Hilgers K. F., et al., "Aberrant Renal Vascular Morphology and Renin Expression in Mutant Mice Lacking Angiotensin-Converting Enzyme," Hypertension, 1997, vol. 29, pp. 216-221.
Hill, D. R., et al., "Gastrointestinal Organoids: Understanding the Molecular Basis of the Host-Microbe Interface," Cell Mol Gastroenterol Hepatol, 2017, vol. 3, pp. 138-149.
Hirschhorn, J. N., et al., "Genome-Wide Association Studies for Common Diseases and Complex Traits." Nature Reviews Genetics, vol. 6, 2005, pp. 95-108.
Hirsh A. J., et al., "Effect of Cholecystokinin and Related Peptides on Jejunal Transepithelial Hexose Transport in the Sprague-Dawley Rat," American Journal of Physiology-Gastrointestinal and Liver Physiology, 1996, vol. 271, No. G755-G761.
Hoffmeister K.M., "Desialylated Platelets: A Missing Link in Hepatic Thrombopoietin Regulation," The Hematologist 2015; 12(3), 7 pages.
Hoffmeister K.M., "The role of lectins and glycans in platelet clearance," Journal of Thrombosis and Haemostasis. Jul. 2011;9 (supp1), pp. 35-43.
Hohwieler H., et al., "Human Pluripotent Stem Cell-Derived Acinar/Ductal Organoids Generate Human Pancreas upon Orthotopic Transplantation and Allow Disease Modelling," Gut, 2017, vol. 66, pp. 473-486.
Holt L.M., et al., "Astrocyte Morphogenesis is Dependent on BDNF Signaling via Astrocytic TrkB.T1," eLife, Aug. 2019, vol. 8, No. e44667. doi: 10.7554/eLife.44667.
Homayun B., et al., "Challenges and Recent Progress in Oral Drug Delivery Systems for Biopharmaceuticals," Pharmaceutics, Mar. 1, 20199, vol. 11(3):129.
Hoskins E. E., et al., Fanconi anemia deficiency stimulates HPV-associated hyperplastic growth in organotypic epithelial raft culture. Oncogene, 2009, 28(5), 674-685.
Hotta K., et al., "Association of the rs738409 Polymorphism in PNPLA3 with Liver Damage and the Development of Nonalcoholic Fatty Liver Disease," BMC Medical Genetics, 2010, vol. 11, p. 172.
Hu H., et al., "AnimalTFDB 3.0: A Comprehensive Resource for Annotation and Prediction of Animal Transcription Factors," Nucleic Acids Research, 2019, 47(D1), pp. D33-D38.
Hu Y. et al., "Targeted disruption of peptide transporter Pept1 gene in mice significantly reduces dipeptide absorption in intestine," Molecular pharmaceutics, 2008, 5(6), 1122-1130.
Hu Z. et al., "Generation of Naivetropic Induced Pluripotent Stem Cells from Parkinson's Desease Patients for High-Efficiency Genetic Manipulation oand Disease Modeling," Stem Cells and Development, 2015, vol. 24, No. 21, 2591-2604.
Huang H., et al., "p300-Mediated Lysine 2-Hydroxyisobutyrylation Regulates Glycolysis," Molecular Cell, 2018, vol. 70, pp. 663-678. e666. doi: 10.1016/j.molcel.2018.04.011.
Huang J., et al., "Activation of Wnt/B-Catenin Signalling via GSK3 Inhibitors Direct Differentiation of Human Adipose Stem Cells into Functional Hepatocytes," Nature Scientific Reports, 2017, 7, Article No. 40716, 12 pages.
Huang, S. X. L., et al., "Efficient generation of lung and airway epithelial cells from human pluripotent stem cells," Nat. Biotechnol., 2014, vol. 32, No. 1, pp. 84-91.
Hudert, C. A., et al., "Genetic Determinants of Steatosis and Fibrosis Progression in Paediatric Non-Alcoholic Fatty Liver Disease." Liver International, vol. 39, 2019, pp. 540-556.
Huo X et al., "Acid and Bile Salt-Induced CDX2 Expression Differs in Esophageal Squamous Cells From Patients With and Without Barrett's Esophagus," Gastroenterology, 2010, 139(1), 194-203.e1.
Hurr, C., et al., "Liver Sympathetic Denervation Reverses Obesity-Induced Hepatic Steatosis." The Journal of Physiology, vol. 597, No. 17, Sep. 2019, pp. 4565-4580.
Hurskainen M., et al., "Single Cell Transcriptomic Analysis of Murine Lung Development on Hyperoxia-Induced Damage," Nature Communications, Mar. 2021, vol. 12, No. 1565. doi: 10.1038/s41467-021-21865-2.
Husson, A., et al., "Argininosuccinate synthetase from the urea cycle to the citrulline-NO cycle," European Journal of Biochemistry, 2003, vol. 270, pp. 1887-1899.
Huynh N., et al., "Feasibility and Scalability of Spring Parameters in Distraction Enterogenesis in a Murine Model," Journal of Surgical Research, 2017, vol. 215, pp. 219-224.
Iansante, V., et al., "Human hepatocyte transplantation for liver disease: current status and future perspectives," Pediatric Research, 2018, vol. 83, pp. 232-240.
Ikeda, Y., et al., "Bilirubin exerts pro-angiogenic property through Akt-eNOS787 dependent pathway," Hypertension Research, 2015, vol. 38, pp. 733-740.
Illig R et al., "Spatio-temporal expression of HOX genes in human hindgut development," Developmental dynamics: an official publication of the American Association of Anatomists, 2013, 242, 53-66.
Isosaari L., et al., "Simultaneous Induction of Vasculature and Neuronal Network Formation on a Chip Reveals a Dynamic Interrelationship Between Cell Types," Cell Communication and Signaling, 2023, vol. 21, 132. doi: 10.1186/s12964-023-01159-4.
Iwafuchi-Doi, M. et al., "Pioneer transcription factors in cell reprogramming," Genes Dev 2014, 28, 2679-2692.
Iwasawa K., et al., "Organogenesis In Vitro," Current Opinion in Cell Biology, 2021, 73, pp. 84-91.
Jackerott M. et al., "Immunocytochemical localization of the NPY/PYY Y1 receptor in enteric neurons, endothelial cells, and endocrine-like cells of the rat intestinal tract," J Histochem Cytochem, 1997, 45(12), 1643-1650.

(56) References Cited

OTHER PUBLICATIONS

Jang S. W., et al., "A Selective TrkB Agonist with Potent Neurotrophic Activities by 7,8-Dihydroxyflavone," Proceedings of the National Academy of Sciences of the United States of America, 2010, vol. 107, pp. 2687-2692.
Jaramillo M., et al., "Endothelial Cells Mediate Islet-Specific Maturation of Human Embryonic Stem Cell-Derived Pancreatic Progenitor Cells," Tissue Engineering Part A, 2015, vol. 21, pp. 14-25.
Jarmas, A.E., et al., "Progenitor translatome changes coordinated by Tsc1 increase perception of Wnt signals to end nephrogenesis," Nature Communications, 2021, vol. 12.LOW, J.H., et al., "Generation of Human PSC-Derived Kidney Organoids with Patterned Nephron Segments and a De Novo Vascular Network," Cell Stem Cell, 2019, vol. 25, pp. 373-387.
Jennings R. E., et al., "Development of the Human Pancreas from Foregut to Endocrine Commitment," Diabetes, 2013, vol. 62, pp. 3514-3522.
Jennings R. E., et al., "Human Pancreas Development," Development, 2015, vol. 142, pp. 3126-3137.
Jensen E. A., et al., "Epidemiology of Bronchopulmonary Dysplasia," Birth Defects Research Part A: Clinical and Molecular Teratology, 2014, vol. 100, pp. 145-157.
Jensen K. J., et al., "Hepatic Nervous System and Neurobiology of the Liver," Comprehensive Physiology, 2013, vol. 3, pp. 655-665.
Jeong, Y., et al., "Identification and genetic manipulation of human and mouse oesophageal stem cells," Gut, 2015, pp. 1-10.
Jho E. et al., "Wnt/beta-catenin/Tcf signaling induces the transcription of Axin2, a negative regulator of the signaling pathway," Molecular and Cellular Biology, 2002, 22(4), 1172-83.
Jiang C., et al., "Comparative Transcriptomics Analyses in Livers of Mice, Humans, and Humanized Mice Define Human-Specific Gene Networks," Cells, Nov. 2020, vol. 9, No. 2566.
Jiang H., et al., "Tyrosine Kinase Receptor B Protects Against Coronary Artery Disease and Promotes Adult Vasculature Integrity by Regulating Ets1-Mediated VE-Cadherin Expression," Arteriosclerosis, Thrombosis, and Vascular Biology, 2015, vol. 35, pp. 580-588.
Jiang M et al., "BMP-driven NRF2 activation in esophageal basal cell differentiation and eosinophilic esophagitis," The Journal of Clinical Investigation, 2015, 125(14), 1-12.
Jiang M., et al., "Transitional Basal Cells at the Squamous-Columnar Junction Generate Barrett's Oesophagus," Nature, 2017, 550(7677), pp. 529-533.
Jin W., et al., "Regulation of BDNF-TrkB Signaling and Potential Therapeutic Strategies for Parkinson's Disease," Journal of Clinical Medicine, Jan. 2020, vol. 9, No. 1, doi: 10.3390/jcm9010257.
Jonatan D., et al., "Sox17 regulates insulin secretion in the normal and pathologic mouse beta cell," PloS one, 2014, 9, e104675, 16 pages.
Kaczmarek J. C., et al., "Polymer-Lipid Nanoparticles for Systemic Delivery of mRNA to the Lungs," Angewandte Chemie International Edition, 2016, vol. 55, pp. 13808-13812.
Kaczmarek J.C., et al., "Optimization of a Degradable Polymer-Lipid Nanoparticle for Potent Systemic Delivery of mRNA to the Lung Endothelium and Immune Cells," Nano Letters, 2018, vol. 18, No. 10, 6449-6454. doi: 10.1021/acs.nanolett.8b02917.
Kaiser J., Virus used in gene therapies may pose cancer risk, dog study hints, Science—Jan. 6, 2020 doi: 10.1126/science.aba7696 in 3 pages.
Kajiwara, K., et al., "Molecular Mechanisms Underlying Twin-to-Twin Transfusion Syndrome," Cells, 2022, vol. 11, 18 pages.
Kalabis J. et al., "A subpopulation of mouse esophageal basal cells has properties of stem cells with the capacity for self-renewal and lineage specification," Journal of Clinical Investigation, 2008, (118), 3860-3869.
Kalabis J. et al., "Isolation and characterization of mouse and human esophageal epithelial cells in 3D organotypic culture," Nature Protocols, 2012, 7(2), 235-246.
Kang, J., et al., "Simultaneous deletion of the methylcytosine oxidases Tet1 and Tet3 increases transcriptome variability in early embryogenesis," Proceedings of the National Academy of Sciences, 2015, vol. 112, pp. E4236-E4245.
Kang, S. D., et al., "Effect of Productive Human Papillomavirus 16 Infection on Global Gene Expression in Cervical Epithelium." Journal of Virology, vol. 92, No. 20, Oct. 15, 2018, e01261-18.
Kapadia, B., et al., "PIMT regulates Hepatic Gluconeogenesis in Mice," iScience, 2023, 106120.
Kawaguchi T., et al., "Genetic Polymorphisms of the Human PNPLA3 Gene Are Strongly Associated with Severity of Non-Alcoholic Fatty Liver Disease in Japanese," PLoS One, 2012, vol. 7, e38322.
Kazumori H. et al., "Bile acids directly augment caudal related homeobox gene Cdx2 expression in oesophageal keratinocytes in Barrett's epithelium," Gut, 2006, 55(1), 16-25.
Kazumori H. et al., "Roles of caudal-related homeobox gene Cdx1 in oesophageal epithelial cells in Barrett's epithelium development," Gut, 2009, 58(5), 620-628.
Kc K et al., "In vitro model for studying esophageal epithelial differentiation and allergic inflammatory responses identifies keratin involvement in eosinophilic esophagitis," PloS One, 2015, 10(6), e0127755.
Kearns N. A. et al., "Generation of organized anterior foregut epithelia from pluripotent stem cells using small molecules," Stem Cell Res., 2013, 11, 1003-1012.
Kebschull et al., "High-throughput mapping of single-neuron projections by sequencing of barcoded RNA", Neuron, 2016, vol. 91(5), pp. 975-987.
Keebler M. E., et al., "Fine-Mapping in African Americans of 8 Recently Discovered Genetic Loci for Plasma Lipids: The Jackson Heart Study," Circulation: Cardiovascular Genetics, 2010, vol. 3, pp. 358-364.
Keeley, T.P., et al., "Defining Physiological Normoxia for Improved Translation of Cell Physiology to Animal Models and Humans," Physiological Reviews, 2019, vol. 99, pp. 161-234.
Kennedy D., et al., "Optimal Absorptive Transport of the Dipeptide Glycylsarcosine Is Dependent on Functional Na?/H? Exchange Activity," Pflugers Archiv, 2002, vol. 445, pp. 139-146.
Kermani P., et al., "Neurotrophins Promote Revascularization by Local Recruitment of TrkB+ Endothelial Cells and Systemic Mobilization of Hematopoietic Progenitors," Journal of Clinical Investigation, 2005, vol. 115, pp. 653-663.
Kietzmann, T., et al., "Metabolic zonation of the liver: The oxygen gradient revisited," Redox Biol, 2017, vol. 11, pp. 622-630.
Kim et al., "Recent progress in development of siRNA delivery vehicles for cancer therapy", Advanced Drug Delivery Reviews, 2016, vol. 104, pp. 61-77.
Kim M., et al., "O-Linked N-Acetylglucosamine Transferase Promotes Cervical Cancer Tumorigenesis through Human Papillomavirus E6 and E7 Oncogenes." Oncotarget, 7(28), 2016, 44596-44607.
Kim, S. G., et al., "Bilirubin Activates Transcription of HIF-1a in Human Proximal Tubular Cells Cultured in the Physiologic Oxygen Content," J Korean Med Sci, 2014, vol. 29, pp. S146-S154.
Kim Y. K., et al., "Gene-Edited Human Kidney Organoids Reveal Mechanisms of Disease in Podocyte Development," Stem Cells, 2017, vol. 35, pp. 2366-2378.
Kimura M., et al., "En Masse Organoid Phenotyping Informs Metabolic-Associated Genetic Susceptibility to NASH," Cell, Jun. 2022, vol. 185, No. 12, pp. 4216-4232.e4216.
Kitamoto A., et al., "Association of Polymorphisms in GCKR and TRIB1 with Nonalcoholic Fatty Liver Disease and Metabolic Syndrome Traits," Endocrine Journal, 2014, vol. 61, pp. 683-689.
Kleshchevnikov V., et al., "Comprehensive Mapping of Tissue Cell Architecture via Integrated Single Cell and Spatial Transcriptomics," bioRxiv, Nov. 2020, doi: 10.1101/2020.11.15.378125.
Kligerman S. J., et al., "From the Radiologic Pathology Archives: Organization and Fibrosis as a Response to Lung Injury in Diffuse Alveolar Damage, Organizing Pneumonia, and Acute Fibrinous and Organizing Pneumonia," Radiographics, 2013, 33, doi:10.1148/rg.337130057. PMID—24224590.

(56) References Cited

OTHER PUBLICATIONS

Kolbe E., et al., "Mutual Zonated Interactions of Wnt and Hh Signaling Are Orchestrating the Metabolism of the Adult Liver in Mice and Human," Cell Reports, Nov. 2019, vol. 29, No. 11, pp. 4553-4567.e4557.
Kong J. et al., "Ectopic Cdx2 expression in murine esophagus models an intermediate stage in the emergence of Barrett's esophagus," PLoS ONE, 2011, 6(4), 1-12.
Kong J. et al., "Induction of intestinalization in human esophageal keratinocytes is a multistep process," Carcinogenesis, 2009, 30(1), 122-130.
Kormish J.D. et al., "Interactions between SOX factors and Wnt/beta-catenin signaling in development and disease," Developmental Dynamics: An Official Publication of the American Association of Anatomists, 2010, 239, 56-68.
Koui Y., et al., "An In Vitro Human Liver Model by iPSC-Derived Parenchymal and Non-Parenchymal Cells," Stem Cell Reports, 2017, 9, pp. 490-498.
Kouznetsova I. et al., Self-renewal of the human gastric epithelium: new insights from expression profiling using laser microdissection. Mol Biosyst, 2011, 7, 1105-1112.
Kowalski P.S., et al., "Delivering the messenger: Advances in Technologies for Therapeutic mRNA delivery," Molecular Therapy . Apr. 10, 2019;27(4):710-728.
Kozyra M., et al., "Human Hepatic D Spheroids as a Model for Steatosis and Insulin Resistance", Scientific Reports, vol. 8, No. 1, Sep. 24, 2018, Retrieved from the Internet: URL: https://www.nature.com/articles/s41598-018-32722-6.
Krishnan, U., et al., "Evaluation and Management of Pulmonary Hypertension in Children with Bronchopulmonary Dysplasia." The Journal of Pediatrics, vol. 188, Sep. 2017, pp. 24-34.e1.
Kuhnert F. et al., "Essential regulation of CNS angiogenesis by the orphan G protein-coupled receptor GPR124," Science, 2010, 330, 985-989. 10.1126/science.1196554.
Kumagai et al., "A bilirubin-inducible fluorescent protein from eel muscle," Cell (2013) 153(7):1602-11.
Kumar A., et al., "Specification and Diversification of Pericytes and Smooth Muscle Cells from Mesenchymoangioblasts," Cell Reports, 2017, vol. 19, pp. 1902-1916.
Kumari, D., "States of Pluripotency: Naïve and Primed Pluripotent Stem Cells," InTech Open, vol. 1, Chapter 3, 2016, pp. 31-45.
Stoffers D. A., et al., "Pancreatic Agenesis Attributable to a Single Nucleotide Deletion in the Human IPF1 Gene Coding Sequence," Nature Genetics, 1997, vol. 15, pp. 106-110.
Stoll B. J., et al., "Neonatal Outcomes of Extremely Preterm Infants from the NICHD Neonatal Research Network," Pediatrics, 2010, vol. 126, pp. 443-456.
Subramanian, A. et al., "Gene set enrichment analysis: A knowledge-based approach for interpreting genome-wide expression profiles," Proceedings of the National Academy of Sciences, 2005, 102(43), 15545-15550.
Sunshine J.C., "Effects of Base Polymer Hydrophobicity and End-Group Modification on Polymeric Gene Delivery," Biomacromolecules 2011, 12, pp. 3592-3600.
Suprynowicz, F. A., et al., "HPV-16 E5 Oncoprotein Upregulates Lipid Raft Components Caveolin-1 and Ganglioside GM1 at the Plasma Membrane of Cervical Cells." Oncogene, vol. 27, 2008, pp. 1071-1078.
Suzuki, et al., "Directed differentiation of human induced pluripotent stem cells into mature stratified bladder urothelium," Scientific Reports, 2019, vol. 9, 10506.
Takasato M., et al., "Kidney Organoids from Human iPS Cells Contain Multiple Lineages and Model Human Nephrogenesis," Nature, 2016, vol. 536, p. 238.
Tam P. P., and Loebel D. A., "Gene Function in Mouse Embryogenesis: Get Set for Gastrulation," Nature Reviews Genetics, 2007, 8, pp. 368-381.
Tanaka K., et al., "Structure and Functional Expression of the Cloned Rat Neurotensin Receptor," Neuron, 1990, vol. 4, pp. 847-854.
Tanii, H., et al., "Induction of Cytochrome P450 2A6 by Bilirubin in Human Hepatocytes," Pharmacology & Pharmacy, 2013, vol. 04, pp. 182-190.
Tannenbaum, S.E. et al., "Derivation of Xeno-Free and GMP-Grade Human Embryonic Stem Cells—Platforms for Future Clinical Applications," PLoS ONE, Jun. 2012, vol. 7, No. 6, 16 pages.
Tanwar S. et al., "Validation of terminal peptide of procollagen III for the detection and assessment of nonalcoholic steatohepatitis in patients with nonalcoholic fatty liver disease," Hepatology, 2013, 57, 103-111.
Tarlungeanu D. C., et al., "Impaired Amino Acid Transport at the Blood Brain Barrier Is a Cause of Autism Spectrum Disorder," Cell, 2016, vol. 167, pp. 1481-1494.e1418.
Terry, N. A. et al., "Lipid Malabsorption from Altered Hormonal Signaling Changes Early Gut Microbial Responses". Am J Physiol-Gastrointest Liver Physiol, 2018, 315(6), pp. G990-G1000.
Terry N.A. et al., "Dysgenesis of enteroendocrine cells in Aristaless-Related Homeobox polyalanine expansion mutationsm," J Pediatr Gastroenterol Nutr, 2015, 60, 2, 192-199.
Tessarollo L., et al., "TrkB Truncated Isoform Receptors as Transducers and Determinants of BDNF Functions," Frontiers in Neuroscience, Mar. 2022, vol. 16, doi: 10.3389/fnins.2022.847572.
Thakur, A., et al., "Hepatocyte Nuclear Factor 4-Alpha Is Essential for the Active Epigenetic State at Enhancers in Mouse Liver," Hepatology, 2019, vol. 70, pp. 1360-1376.
The Lancet Gastroenterology, "Headway and hurdles in non-alcoholic fatty liver disease," Lancet Gastroenterology Hepatology, 2020, vol. 5, 93.
Thebaud B., et al., "Vascular Endothelial Growth Factor Gene Therapy Increases Survival, Promotes Lung Angiogenesis, and Prevents Alveolar Damage in Hyperoxia-Induced Lung Injury: Evidence that Angiogenesis Participates in Alveolarization," Circulation, 2005, vol. 112, pp. 2477-2486.
Thommensen L. et al., "Molecular mechanisms involved in gastrin-mediated regulation of cAMP-responsive promoter elements," Am J Physiol Endocrinol Metab, 2001, 281, E1316-1325.
Thompson F.M., et al., "Epithelial Growth of the Small Intestine Occurs by Both Crypt Fission and Crypt Hyperplasia During Infancy and Childhood in Humans," Journal of Gastroenterology and Hepatology, 2001, 2 Pages.
Tomassoni-Ardori F., et al., "Rbfox1 Up-Regulation Impairs BDNF-Dependent Hippocampal LTP by Dysregulating TrkB Isoform Expression Levels," eLife, Aug. 2019, vol. 8, e49673. doi: 10.7554/eLife.49673.
Totoson P., et al., "Activation of endothelial TrkB receptors induces relaxation of resistance arteries." Vascular Pharmacology, 106, 2018, pp. 46-53.
Touboul T et al., "Generation of functional hepatocytes from human embryonic stem cells under chemically defined conditions that recapitulate liver development," Hepatology, 2010, 51, 1754-1765.
Traag V.A., et al., "From Louvain to Leiden: Guaranteeing Well-Connected Communities," Scientific Reports, 2019, vol. 9, 5233. doi: 10.1038/s41598-019-41695-z.
Tran M., et al., "Spatial Analysis of Ligand-Receptor Interaction in Skin Cancer at Genome-Wide and Single-Cell Resolution," bioRxiv, Sep. 2021, doi: 10.1101/2020.09.10.290833.
Trapnell C. et al., "The dynamics and regulators of cell fate decisions are revealed by pseudotemporal ordering of single cells," Nat Biotechnol, 2014, 32, 381-386.
Tsakmaki A., et al., "Diabetes Through a 3D Lens: Organoid Models," Diabetologia, Springer Berlin Heidelberg, Berlin/heidelberg, vol. 63, No. 6, Mar. 27, 2020, pp. 1093-1102.
Tsankov A. M et al., "Transcription factor binding dynamics during human ES cell differentiation," Nature, 2015, 518 (7539), 344-9.
Tufro-Mcreddie, A., et al., "Angiotensin II Regulates Nephrogenesis and Renal Vascular Development." American Journal of Physiology, vol. 269, No. 1, 1995, pp. F110-F115.
Uchida H., et al., "A Xenogeneic-free System Generating Functional Human Gut Organoids from Pluripotent Stem Cells," JCI Insight, Jan. 12, 2017, vol. 2, No. 1, 13 pages.
Uchimura, K., et al., "Human Pluripotent Stem Cell-Derived Kidney Organoids with Improved Collecting Duct Maturation and Injury Modeling," Cell Reports, 2020, vol. 33, 108514.

(56) References Cited

OTHER PUBLICATIONS

Vales, S., et al., "In Vivo Human PSC-Derived Intestinal Organoids to Study Stem Cell Maintenance." In Methods in Molecular Biology, vol. 2171, Chapter 12, 2020, pp. 201-214.
Van Den Berg C.W., et al., "Renal Subcapsular Transplantation of PSC-Derived Kidney Organoids Induces Neo- vasculogenesis and Significant Glomerular and Tubular Maturation In Vivo," Stem Cell Reports, 2018, vol. 10, pp. 751-765. doi: 10.1016/j.stemcr.2018.01.041.
Van Dop W. A., et al., "Hedgehog Signalling Stimulates Precursor Cell Accumulation and Impairs Epithelial Maturation in the Murine Oesophagus," Gut, 2012, 62(3), pp. 348-357.
Van Hoecke et al., "How mRNA therapeutics are entering the monoclonal antibody field," Journal of Translational Medicine . Feb. 22, 2019;17(1):54 in 14 pages.
Van Raay T. J. et al., "Frizzled 5 signaling governs the neural potential of progenitors in the developing Xenopus retina," Neuron, 2005, 46(1), 23-36.
Van Straten, G., et al., "Aberrant Expression and Distribution of Enzymes of the Urea Cycle and Other Ammonia Metabolizing Pathways in Dogs with Congenital Portosystemic Shunts," PLOS ONE, 2014, vol. 9, e100077, 11 pages.
Vatine G. D., et al., "Modeling Psychomotor Retardation Using iPSCs from MCT8-Deficient Patients Indicates a Prominent Role for the Blood-Brain Barrier," Cell Stem Cell, 2017, vol. 20, pp. 831-843.e835.
Vatine G.D., et al., "Human iPSC-Derived Blood-Brain Barrier Chips Enable Disease Modeling and Personalized Medicine Applications," Cell Stem Cell, 2019, vol. 24, pp. 995-1005.
Vega M. E. et al., "Inhibition of notch signaling enhances transdifferentiation of the esophageal squamous epithelium towards a Barrett's-like metaplasia via KLF4," Cell Cycle, 2014, 13(24), 3857-3866.
Veldman, T., et al., "Human Papillomavirus E6 and Myc Proteins Associate In Vivo and Bind to and Cooperatively Activate the Telomerase Reverse Transcriptase Promoter." Proceedings of the National Academy of Sciences, vol. 100, No. 14, Jul. 8, 2003, pp. 8211-8216.
Verdera H,C., et al., AAV vector immunogenicity in humans: A long journey to successful gene transfer, Mol Thera. Mar. 4, 2020;28(3):723-746.
Verma S.K., et al., "RBFOX2 is Required for Establishing RNA Regulatory Networks Essential for Heart Development," Nucleic Acids Research, 2022, vol. 50, No. 4, 2270-2286. doi: 10.1093/nar/gkac055.
Verscheijden L.F.M., et al., "Differences in P-Glycoprotein Activity in Human and Rodent Blood-Brain Barrier Assessed by Mechanistic Modelling," Archives of Toxicology, 2021, vol. 95, pp. 3015-3029.
Vincent K.M., et al., "Expanding the Clinical Spectrum of Autosomal-Recessive Renal Tubular Dysgenesis: Two Siblings with Neonatal Survival and Review of the Literature," Molecular Genetics and Genomic Medicine, 2022, vol. 10, e1920.
Vohwinkel C.U., et al., "Bronchopulmonary Dysplasia: Endothelial Cells in the Driver's Seat," American Journal of Respiratory Cell and Molecular Biology, Apr. 2021, vol. 65, No. 1, pp. 6-7. doi: 10.1165/rcmb.2021-0145ED.
Wagner N., et al., "Coronary Vessel Development Requires Activation of the TrkB Neurotrophin Receptor by the Wilms' Tumor Transcription Factor Wt1," Genes Development, 2005, vol. 19, pp. 2631-2642.
Wahlestedt C. et al., "Neuropeptide Y Receptor Subtypes, Y1 and Y2," Annals of the New York Academy of Sciences, 1990, 611, 7-26.
Wahlicht, T., et al., "Controlled Functional Zonation of Hepatocytes In Vitro by Engineering of Wnt Signaling." ACS Synthetic Biology, vol. 9, 2020, pp. 1638-1649.
Omer, D., et al., "Human Kidney Spheroids and Monolayers Provide Insights into SARS-CoV-2 Renal Interactions," Journal of the American Society of Nephrology, 2021, vol. 32, pp. 2242-2254.

Onaga T., et al., "Multiple Regulation of Peptide YY Secretion in the Digestive Tract," Peptides, 2002, vol. 23, pp. 279-290.
Onlilsoy Aksu A., et al., "Mutant Neurogenin-3 in a Turkish Boy with Congenital Malabsorptive Diarrhea," Pediatrics International, 2016, vol. 58, pp. 379-382.
Orho-Melander M., et al., "Common Missense Variant in the Glucokinase Regulatory Protein Gene Is Associated with Increased Plasma Triglyceride and C-Reactive Protein but Lower Fasting Glucose Concentrations," Diabetes, 2008, vol. 57, pp. 3112-3121.
Orskov C. et al., "GLP-2 stimulates colonic growth via KGF, released by subepithelial myofibroblasts with GLP-2 receptors," Regulatory peptides, 2005, 124, 105-112.
Ortiz-Meoz, R. F., et al., "A Small Molecule that Inhibits OGT Activity in Cells." ACS Chemical Biology, vol. 10, No. 6, Jun. 19, 2015, pp. 1392-1397.
Pan S., "Physiology," Science and Technology of China Press, Chapter 6, "Digestion within Large Intestine," 149-150, Jan. 2014.
Pankevich D.E. et al., "Improving and accelerating drug development for nervous system disorders," Neuron, 2014, 84, 546-553.
Paris, J., et al., "Liver zonation, revisited," Hepatology, 2022, vol. 76.
Park E.J. et al., "System for tamoxifen-inducible expression of Cre-recombinase from the Foxa2 locus in mice," Developmental Dynamics, 2008, 237(2), 447-453.
Patel Y. C., "Somatostatin and Its Receptor Family," Frontiers in Neuroendocrinology, 1999, 20, 157-198.
Patro R., et al., "Salmon Provides Fast and Bias-Aware Quantification of Transcript Expression using Dual-Phase Inference," Nature Methods, 2017, vol. 14, pp. 417-419.
Pedersen J. et al., "The glucagon-like peptide 2 receptor is expressed in enteric neurons and not in the epithelium of the intestine," Peptides, 2015, 67, 20-28.
Peng K., et al., "Regulation of O-Linked N-Acetyl Glucosamine Transferase (OGT) Through E6 Stimulation of the Ubiquitin Ligase Activity of E6AP." Journal of Molecular Sciences, 22, 2021, 10286. https://doi.org/10.3390/ ijms221910286.
Perdomo J., et al., "Megakaryocyte differentiation and platelet formation from human cord blood derived CD34+ cells," Journal of Visualized Experiments. Dec. 27, 2017;130:e56420 in 8 pages.
Petta S., et al., "Glucokinase Regulatory Protein Gene Polymorphism Affects Liver Fibrosis in Non-Alcoholic Fatty Liver Disease," PLoS One, 2014, vol. 9, e87523.
Pham D., et al., "stLearn: Integrating Spatial Location, Tissue Morphology and Gene Expression to Find Cell Types, Cell-Cell Interactions and Spatial Trajectories Within Undissociated Tissues," bioRxiv, May 2020, doi: 10.1101/2020.05.31.125658.
Picelli S., et al., "Smart-seq2 for Sensitive Full-length Transcriptome Profiling in Single Cells," Nature Methods, Nov. 2013, vol. 10(11), pp. 1096-1098.
Pierre C., et al., "Can We Live Without a Functional Renin-Angiotensin System?" Clinical and Experimental Pharmacology and Physiology, 2008, vol. 35, pp. 431-433.
Pinney S. E. et al., "Neonatal diabetes and congenital malabsorptive diarrhea attributable to a novel mutation in the human neurogenin-3 gene coding sequence," The Journal of clinical endocrinology and metabolism, 2011, 96, 1960-1965.
Pirola, C.J., et al., "A Rare Nonsense Mutation in the Glucokinase Regulator Gene Is Associated with a Rapidly Progressive Clinical Form of Nonalcoholic Steatohepatitis," Hepatology Communications, 2018, vol. 2, pp. 1030-1036.
Pless G., "Artificial and Bioartificial Liver Support," Organogenesis, Jan. 2007, vol. 3(1), pp. 20-24.
Podolsky D. K., "Healing the Epithelium: Solving the Problem from Two Sides," Journal of Gastroenterology, 1997, vol. 32, pp. 122-126. DOI: 10.1007/BF01213309.
Pollin T. I., et al., "Triglyceride Response to an Intensive Lifestyle Intervention Is Enhanced in Carriers of the GCKR Pro446Leu Polymorphism," Journal of Clinical Endocrinology Metabolism, 2011, vol. 96, pp. E1142-1147.
Powell D. W., et al., "Myofibroblasts. II. Intestinal Subepithelial Myofibroblasts," American Journal of Physiology, 1999, vol. 277, pp. C183-C201. DOI: 10.1152/ajpcell. 1999.277.2.C183.

(56) References Cited

OTHER PUBLICATIONS

Prakash Y., et al., "Neurotrophins in Lung Health and Disease," Expert Review of Respiratory Medicine, 2010, vol. 4, pp. 395-411.
Prakash Y. S., et al., "Brain-Derived Neurotrophic Factor in the Airways," Pharmacology Therapeutics, 2014, vol. 143, pp. 74-86.
Pupilli C., et al., "Angiotensin II Stimulates the Synthesis and Secretion of Vascular Permeability Factor/Vascular Endothelial Growth Factor in Human Mesangial Cells," Journal of the American Society of Nephrology, 1999, vol. 10, pp. 245-255.
Pyke C., et al., "GLP-1 Receptor Localization in Monkey and Human Tissue: Novel Distribution Revealed With Extensively Validated Monoclonal Antibody," Endocrinology, 2014, 155, 1280-1290.
Qian T., et al., "Directed Differentiation of Human Pluripotent Stem Cells to Blood-Brain Barrier Endothelial Cells," Science Advances, 2017, vol. 3, e1701679.
Qiu X., et al., "Single-Cell mRNA Quantification and Differential Analysis with Census," Nature Methods, 2017, vol. 14, pp. 309-315.
Qiu X., et al., "Reversed Graph Embedding Resolves Complex Single-Cell Trajectories," Nature Methods, 2017, vol. 14, pp. 979-982.
Que J. et al., "Multiple dose-dependent roles for Sox2 in the patterning and differentiation of anterior foregut endoderm," Development (Cambridge, England), 2007, 134(13), 2521-31.
Que J. et al., "Multiple roles for Sox2 in the developing and adult mouse trachea," Development (Cambridge, England), 2009,136(11), 1899-1907.
Que J., "The initial establishment and epithelial morphogenesis of the esophagus: a new model of tracheal-esophageal separation and transition of simple columnar into stratified squamous epithelium in the developing esophagus," Wiley Interdiscip. Rev. Dev. Biol., 2015, 4(4), 419-430.
Raisner, R., et al., "Enhancer Activity Requires CBP/P300 Bromodomain-Dependent Histone H3K27 Acetylation," Cell Reports, 2018, vol. 24, pp. 1722-1729.
Ramilowski J. A., et al., "A Draft Network of Ligand-Receptor-Mediated Multicellular Signalling in Human," Nature Communications, 2015, vol. 6, Article 7866, 11 pages.
Raredon M.S.B., et al., "Computation and Visualization of Cell-Cell Signaling Topologies in Single-Cell Systems Data Using Connectome," Scientific Reports, 2022, vol. 12, 4187. doi: 10.1038/s41598-022-07959-x.
Ren, X., et al., "Postnatal Alveologenesis Depends on FOXF1 Signaling in c-KIT+ Endothelial Progenitor Cells." American Journal of Respiratory and Critical Care Medicine, vol. 200, No. 9, 2019, pp. 1164-1176.
Revencu N. et al. "Cerebral cavernous malformation: new molecular and clinical insights," J Med Genet, 2006, 43, 716-721.
Reyes-Palomares A., et al., "Remodeling of Active Endothelial Enhancers is Associated with Aberrant Gene Regulatory Networks in Pulmonary Arterial Hypertension," Nature Communications, Apr. 2020, vol. 11, No. 1, 1673. doi: 10.1038/s41467-020-15463-x.
Reza H.A., et al., "Organoid Transplant Approaches for the Liver," Transplant International, Nov. 2021, vol. 34, No. 11, pp. 2031-2045.
Reza, H.A., et al., "Synthetic augmentation of bilirubin metabolism in human pluripotent stem cell-derived liver organoids," Stem Cell Reports, 2023.
Rhoads, K., et al., "A Role for Hox A5 in Regulating Angiogenesis and Vascular Patterning." Lymphatic Research and Biology, vol. 3, No. 4, 2005, pp. 240-252.
Rich, N.E., et al., "Racial and Ethnic Disparities in Nonalcoholic Fatty Liver Disease Prevalence, Severity, and Outcomes in the United States: A Systematic Review and Meta-Analysis," Clinical Gastroenterology and Hepatology, 2018, vol. 16, pp. 198-210 e192.
Robbins D. J. et al., "The Hedgehog Signal Transduction Network," Science Signaling 2012, 5(246), re6-re6, 28 pages.
Robinson B.D., et al., "Measurement of Microvascular Endothelial Barrier Dysfunction and Hyperpermeability In Vitro," Methods in Molecular Biology, Feb. 2018, vol. 1717, pp. 237-242.

Rochman M., et al., "Profound Loss of Esophageal Tissue Differentiation in Patients with Eosinophilic Esophagitis," Journal of Allergy and Clinical Immunology, 2017, 140(3), pp. 738-749.e3.
Roitbak T., et al., "Neural Stem/Progenitor Cells Promote Endothelial Cell Morphogenesis and Protect Endothelial Cells against Ischemia via HIF-1a-Regulated VEGF Signaling," Journal of Cerebral Blood Flow Metabolism, 2008, vol. 28, pp. 1530-1542.
Rosekrans S. L. et al., "Esophageal development and epithelial homeostasis," American Journal of Physiology—Gastrointestinal and Liver Physiology, 2015, 309(4), G216-228.
Cortina, G., et al., "Enteroendocrine Cell Dysgenesis and Malabsorption, a Histopathologic and Immunohistochemical Characterization," Human Pathology, 2007, vol. 38, pp. 570-580.
Coskun T. et al., "Activation of Prostaglandin E Receptor 4 Triggers Secretion of Gut Hormone Peptides GLP-1, GLP-2, and PYY," Endocrinology, 2013, 154, 45-53.
Cox H. M., "Endogenous PYY and NPY mediate tonic Y(1)- and Y(2)-mediated absorption in human and mouse colon," Nutrition, 2008, 24, 900-906.
Creane M., et al., "Biodistribution and Retention of Locally Administered Human Mesenchymal Stromal Cells: Quantitative Polymerase Chain Reaction-Based Detection of Human DNA in Murine Organs," Cytotherapy, 2017, vol. 19, pp. 384-394. DOI: 10.1016/j.jcyt.2016.12.003.
Crisera C. A., et al., "Expression and Role of Laminin-1 in Mouse Pancreatic Organogenesis," Diabetes, 2000, vol. 49, pp. 936-944.
Cruz, N. M., et al., "Differentiation of Human Kidney Organoids from Pluripotent Stem Cells." In Methods in Cell Biology, vol. 153, Chapter 7, 2019, pp. 133-150.
Cucullo L., et al., "The role of shear stress in Blood-Brain Barrier endothelial physiology," BMC Neurosci, 2011, 40, 15 pages.
Cuevas I., et al., "Sustained Endothelial Expression of HoxA5 In Vivo Impairs Pathological Angiogenesis and Tumor Progression," PLoS One, 2015, vol. 10, e0121720.
Cui, J., et al., "Progressive Pseudogenization: Vitamin C Synthesis and Its Loss in Bats," Molecular Biology and Evolution, 2011, vol. 28, No. 4, pp. 1025-1031.
Cunningham, R.P., et al., "Liver Zonation—Revisiting Old Questions With New Technologies," Frontiers in Physiology, 2021, vol. 12, 732929.
Dahlman et al., "Barcoded Nanoparticles for High Throughput in Vivo Discovery of Targeted Therapeutics", PNAS, U.S.A., 2017, vol. 114(8), pp. 2060-2065.
Daneman R., et al., "The Blood-Brain Barrier," Cold Spring Harbor Perspectives in Biology, 2015, vol. 7, a020412.
Daniely Y. et al., "Critical role of p63 in the development of a normal esophageal and tracheobronchial epithelium," American Journal of Physiology, Cell Physiology, 2004, 287(1), C171-C181.
Dathan N. et al., "Distribution of the titf2/foxe1 gene product is consistent with an important role in the development of foregut endoderm, palate, and hair," Dev. Dyn., 2002, 224, 450-456.
Davidson L. M., et al., "Bronchopulmonary Dysplasia: Chronic Lung Disease of Infancy and Long-Term Pulmonary Outcomes," Journal of Clinical Medicine, 2017, vol. 6, p. 20.
Davis B. P., et al., "Eosinophilic Esophagitis-Linked Calpain 14 is an IL-13-Induced Protease that Mediates Esophageal Epithelial Barrier Impairment," JCI Insight, 2016, 1(4), 11 pages.
Dawkins H.J.S., et al., "Progress in rare diseases research 2010-2016: An IRDiRC Perspective," Clinical and Translational Science. Jan. 2018;11(1):11-20.
De Felice, M et al., "A mouse model for hereditary thyroid dysgenesis and cleft palate," Nat. Genet., 1998, 19, 395-398.
De Jong E. M et al., "Etiology of esophageal atresia and tracheoesophageal fistula: 'Mind the gap', Current Gastroenterology Reports, 2010, 12(3), 215-222.
De Paepe M. E., et al., "Growth of Pulmonary Microvasculature in Ventilated Preterm Infants," American Journal of Respiratory and Critical Care Medicine, 2006, vol. 173, pp. 204-211.
De Santa Barbara P., et al., "Molecular Etiology of Gut Malformations and Diseases," American Journal of Medical Genetics, Dec. 3, 20020; vol. 115(4), pp. 221-230.

(56) References Cited

OTHER PUBLICATIONS

De Santa Barbara, P., et al., "Tail gut endoderm and gut/genitourinary/tail development: a new tissue-specific role for Hoxa13," Development, 2002, vol. 129, pp. 551-561.
Demirgan E.B., et al., "AGTR1-related Renal Tubular Dysgeneses May Not Be Fatal," Kidney International Reports, 2021, vol. 6, pp. 846-852.
Distefano P.V et al., "KRIT1 protein depletion modifies endothelial cell behavior via increased vascular endothelial growth factor (VEGF)signaling," J Biol Chem, 2014, 289, 33054-33065.
D'Mello R. J., et al., "LRRC31 is Induced by IL-13 and Regulates Kallikrein Expression and Barrier Function in the Esophageal Epithelium," Mucosal Immunology, 2016, 9(3), pp. 744-756.
Dolinay T., et al., "Integrated Stress Response Mediates Epithelial Injury in Mechanical Ventilation," American Journal of Respiratory Cell and Molecular Biology, 2017, 57, pp. 193-203.
Dollard S. C., et al., "Production of Human Papillomavirus and Modulation of the Infectious Program in Epithelial Raft Cultures." Genes & Development, 6, 1992, pp. 1131-1142.
Domyan E.T et al., "Signaling through BMP receptors promotes respiratory identity in the foregut via repression of Sox2," Development (Cambridge, England), 2011, 138(5), 971-981.
Donati, B., et al., "The rs2294918 E434K Variant Modulates Patatin-Like Phospholipase Domain-Containing 3 Expression and Liver Damage." Hepatology, vol. 63, No. 3, Mar. 2016, pp. 787-798.
Dong R., et al., "SpatialDWLS: Accurate Deconvolution of Spatial Transcriptomic Data." Genome Biology, 22, 145, 2021, 10 pages. https://doi.org/10.1186/s13059-021-02362-7.
Dorison A., et al., "What Can We Learn from Kidney Organoids?" Kidney International, 102, 2022, pp. 1013-1029. https://doi.org/10.1016/j.kint.2022.06.032.
Dougherty, E., "Tackling the common denominator in liver disease," Novartis, Jun. 16, 2016, https://www.novartis.com/stories/tackling-common-denominator-liver-disease.
Doupe D. P. et al., "A Single Progenitor Population Switches Behavior to Maintain and Repair Esophageal Epithelium," Science, 2012, 337(6098), 1091-1093.
Draheim K. M., et al., "Cerebral Cavernous Malformation Proteins at a Glance," Journal of Cell Science, 2014, vol. 127(4), pp. 701-707.
Drukcer, D. J., "Evolving Concepts and Translational Relevance of Enteroendocrine Cell Biology," J Clin Endocrinol Metab, 2016, vol. 101, No. 3, pp. 778-786.
Du A. et al., "Arx is required for normal enteroendocrine cell development in mice and humans," Developmental biology, 2012, 365, 175-188.
Du Y., et al., "Lung Gene Expression Analysis (LGEA): An Integrative Web Portal for Comprehensive Gene Expression Data Analysis in Lung Development," Thorax, 2017, 72, pp. 481-484.
Du Y et al., "'LungGENS': a web-based tool for mapping single-cell gene expression in the developing lung," Thorax, 2015, 70, 1092-1094.
Dubrovskyi O., et al., "Measurement of Local Permeability at Subcellular Level in Cell Models of Agonist- and Ventilator-Induced Lung Injury," Laboratory Investigation, 2013, vol. 93, pp. 254-263.
Duluc I., et al., "Changing Intestinal Connective Tissue Interactions Alters Homeobox Gene Expression in Epithelial Cells," Journal of Cell Science, 1997, vol. 110, pp. 1317-1324.
Dunn A., et al., "POLY seq: A poly(J3-amino ester)-based Vector for Multifunctional Cellular Barcoding," Stem Cell Reports. Sep. 2021, vol. 14(2), pp. 2149-2158.
Dunn A., et al., "Polymeric Vectors for Strategic Delivery of Nucleic Acids," Nano Life, 2017, vol. 7, No. 02, 1730003, 12 pages.
Dunn et al., "Highly Efficient In Vivo Targeting of the Pulmonary Endothelium Using Novel Modifications of Polyethylenimine: An Importance of Charge", Advan Health Mater. 2018, vol. 7(23): 1800876, 25 pages.

Duval, K., et al., "Revisiting the role of Notch in nephron segmentation confirms a role for proximal fate selection during mouse and human nephrogenesis," Development, 2022, vol. 149.
Dye B. R., et al., "A Bioengineered Niche Promotes In Vivo Engraftment and Maturation of Pluripotent Stem Cell Derived Human Lung Organoids," eLife 5, 2016, 18 pages.
Dye B.R. et al., "In vitro generation of human pluripotent stem cell derived lung organoids," Elife 4:e05098 (2015), 25 pages.
Efremova I., et al., "CellPhoneDB: Inferring Cell-Cell Communication from Combined Expression of Multi-Subunit Receptor-Ligand Complexes," Nature Protocols, 2020, vol. 15, pp. 1484-1506.
Eicher A.K., et al., "Functional Human Gastrointestinal Organoids Can Be Engineered from Three Primary Germ Layers Derived Separately from Pluripotent Stem Cells," Cell Stem Cell, 2022, vol. 29, pp. 36-51.e6. doi: 10.1016/j.stem.2021.10.010.
Engelstoft, M. S. et al., "Enteroendocrine Cell Types Revisited". Current Opinion in Pharmacology, 2013, vol. 13, pp. 912-921.
Everhart J. E., et al., "Fatty Liver: Think Globally," Hepatology, 2010, vol. 51, pp. 1491-1493.
Fan Y., et al., "Bioengineering Thymus Organoids to Restore Thymic Function and Induce Donor-Specific Immune Tolerance to Allografts", The American Society of Gene Cell Therapy, vol. 23, No. 7, Jul. 2015, pp. 1262-1277.
Fang M., et al., "Ulinastatin Ameliorates Pulmonary Capillary Endothelial Permeability Induced by Sepsis Through Protection of Tight Junctions via Inhibition of TNFalpha and Related Pathways," Frontiers in Pharmacology, Sep. 2018, vol. 9, doi: 10.3389/fphar.2018.00823.
Fantes J et al., "Mutations in SOX2 cause anophthalmia," Nature Genetics, 2003, 33(4), 461-463.
Fausett S. R. et al., "Compartmentalization of the foregut tube: developmental origins of the trachea and esophagus," Wiley Interdisciplinary eviews. Developmental Biology, 2012, (2), 184-202.
Fausett S.R., et al., "BMP antagonism by Noggin is required in presumptive notochord cells for mammalian foregut morphogenesis," Developmental Biology, 2014, 391(1), 111-24.
Feliers D., et al., "Mechanism of VEGF Expression by High Glucose in Proximal Tubule Epithelial Cells," Molecular and Cellular Endocrinology, 2010, vol. 314, pp. 136-142.
Ferguson, D., et al., "Emerging Therapeutic Approaches for the Treatment of NAFLD and Type 2 Diabetes Mellitus," Nature Reviews Endocrinology, 2021, vol. 17, pp. 484-495.
Fermini, B., et al., "Clinical Trials in a Dish: A Perspective on the Coming Revolution in Drug Development," SLAS Discovery, 2018, vol. 23, pp. 765-776.
Fischer B., et al., "Oxygen Tension in the Oviduct and Uterus of Rhesus Monkeys, Hamsters and Rabbits," Journal of Reproduction and Fertility, 1993, vol. 99, pp. 673-679.
Freedman B.S., "Physiology Assays in Human Kidney Organoids," American Journal of Physiology—Renal Physiology, 2022, vol. 322, pp. F625-F638.
Freund J.B. et al., "Fluid flows and forces in development: functions, features and biophysical principles," Development, 2012, 139(7), 1229-1245.
Fujita Y et al., "Pax6 and Pdx1 are required for production of glucose-dependent insulinotropic polypeptide in proglucagon-expressing L cells," Am J Physiol Endocrinol Metab, 2008, 295, E648-657.
Funakoshi, K., et al., "Highly Sensitive and Specific Alu-Based Quantification of Human Cells Among Rodent Cells," Scientific Reports, 2017, vol. 7, Article 13202. DOI: 10.1038/s41598-017-13402-3.
Furuta G. T. et al., "Eosinophilic Esophagitis," New England Journal of Medicine, 2015, 373(17), 1640-1648.
Gang, X., et al., "P300 Acetyltransferase Regulates Fatty Acid Synthase Expression, Lipid Metabolism and Prostate Cancer Growth," Oncotarget, 2016, vol. 7, No. 11, pp. 15135-15149.
Gao C., et al., "RBFox1-Mediated RNA Splicing Regulates Cardiac Hypertrophy and Heart Failure," Journal of Clinical Investigation, 2016, vol. 126, pp. 195-206.
Gao et al., "Highly Branched Poly (β-amino esters) for Non-Viral Gene Delivery: High Transfection Efficiency and Low Toxicity

(56) References Cited

OTHER PUBLICATIONS

Achieved by Increasing Molecular Weight", Biomacromolecules, 2016, vol. 17(11), pp. 3640-3647.

Gao, H., et al., "Association of GCKR Gene Polymorphisms with the Risk of Nonalcoholic Fatty Liver Disease and Coronary Artery Disease in a Chinese Northern Han Population," Journal of Clinical and Translational Hepatology, 2019, vol. 7, pp. 297-303.

García-Suárez, O., et al., "TrkB is Necessary for the Normal Development of the Lung." Respiratory Physiology Neurobiology, vol. 167, No. 3, Jul. 31, 2009, pp. 281-291.

Garcia-Martinez, S., et al., "Mimicking physiological O2 tension in the female reproductive tract improves assisted reproduction outcomes in pig," Molecular Human Reproduction, 2018, vol. 24, pp. 260-270.

Garlanda C. et al., "Heterogeneity of endothelial cells. Specific markers" Arterioscler Thromb Vasc Biol, 1997, 17, 1193-1202.

Gazzin, S., et al., "Bilirubin Accumulation and Cyp mRNA Expression in Selected Brain Regions of Jaundiced Gunn Rat Pups," Pediatric Research, 2012, vol. 71, No. 6, pp. 653-660.

German-Diaz, M., et al., "A New Case of Congenital Malabsorptive Diarrhea and Diabetes Secondary to Mutant Neurogenin," Pediatrics, 2017, vol. 140, No. 2, 8 pages.

Ghatak S. et al., "Bile acid at low pH reduces squamous differentiation and activates EGFR signaling in esophageal squamous cells in 3-D culture," Journal of Gastrointestinal Surgery: Official Journal of the Society for Surgery of the Alimentary Tract, 2013, 17(10), 1723-31.

Ginestet C., "ggplot2: Elegant Graphics for Data Analysis," J R Stat Soc a Stat, 2011 174, 245,245.

Glass, L. L., et al., "Single-cell RNA-sequencing reveals a distinct population of proglucagon-expressing cells specific to the mouse upper small intestine," Molecular Metabolism, 2017, vol. 6, pp. 1296-1303.

Gololow N., et al., "Epitheliomesenchymal Interaction in Pancreatic Morphogenesis," Developmental Biology, 1962, vol. 4, pp. 242-255.

Gordillo M., et al., "Orchestrating liver development," Development, Jun. 2015, vol. 142(12), pp. 2094-2108.

Goss A.M., "Wnt2/2b and beta-catenin signaling are necessary and sufficient to specify lung progenitors in the foregut," Developmental Cell, 2009, 17(2), 290-8.

Gotoh S. et al. "Generation of Alveolar Epithelial Spheroids via Isolated Progenitor Cells from Human Pluripotent Stem cells" Stem Cell Reports (2014) 3(3):394-403.

Greene, A. S., et al., "Microvascular Angiogenesis and the Renin-Angiotensin System." Current Hypertension Reports, vol. 4, No. 1, Feb. 2002, pp. 56-62.

Greene Y. J., et al., "Ascorbic Acid Regulation of 3-Hydroxy-3-Methylglutaryl Coenzyme A Reductase Activity and Cholesterol Synthesis in Guinea Pig Liver." Biochimica et Biophysica Acta, 834(1), 1985, pp. 134-138.

Greggio C., et al., "Artificial Three-Dimensional Niches Deconstruct Pancreas Development In Vitro," Development, 2013, vol. 140, pp. 4452-4462.

Gribble, F. M., et al., "Enteroendocrine Cells: Chemosensors in the Intestinal Epithelium," Annu Rev Physiol, 2016, vol. 78, pp. 277-299.

Gribouval O., et al., "Mutations in Genes in the Renin-Angiotensin System Are Associated with Autosomal Recessive Renal Tubular Dysgenesis," Nature Genetics, 2005, vol. 37, pp. 964-968.

Gribouval, O., et al., "Spectrum of Mutations in the Renin-Angiotensin System Genes in Autosomal Recessive Renal Tubular Dysgenesis." Human Mutation, vol. 33, No. 2, Feb. 2012, pp. 316-326.

Gu G., et al., "Global expression analysis of gene regulatory pathways during endocrine pancreatic development," Development, 2004, 131, 165-179.

Gu M., et al., "iPSC-Endothelial Cell Phenotypic Drug Screening and In Silico Analyses Identify Tyrphostin-AG1296 for Pulmonary Arterial Hypertension," Science Translational Medicine, 2021, vol. 13, No. 592. doi: 10.1126/scitranslmed.aba6480.

Gu M., et al., "Microfluidic Single-Cell Analysis Shows That Porcine Induced Pluripotent Stem Cell-Derived Endothelial Cells Improve Myocardial Function by Paracrine Activation," Circulation Research, 2012, vol. 111, pp. 882-893.

Gu M., et al., "Patient-Specific iPSC-Derived Endothelial Cells Uncover Pathways that Protect Against Pulmonary Hypertension in BMPR2 Mutation Carriers," Cell Stem Cell, 2017, vol. 20, pp. 490-504.

Gualdi R. et al., "Hepatic specification of the gut endoderm in vitro: cell signaling and transcriptional control," Genes Dev, 1996, 10, 1670-1682.

Guan X. et al., "GLP-2 receptor localizes to enteric neurons and endocrine cells expressing vasoactive peptides and mediates increased blood flow," Gastroenterology, 2006, 130, 150-164.

Guarino, M., et al., "Nicotinamide and NAFLD: Is There Nothing New Under the Sun?" Metabolites, 2019, vol. 9.

Gubler M. C., et al., "Renin-Angiotensin System in Kidney Development: Renal Tubular Dysgenesis," Kidney International, 2010, vol. 77, pp. 400-406.

Gubler M. C., "Renal Tubular Dysgenesis," Pediatric Nephrology, 2014, vol. 29, pp. 51-59.

Guo L., et al., "The Adrenal Stress Response is an Essential Host Response Against Therapy-Induced Lethal Immune Activation," Science Signaling, 2023, vol. 16, eadd4900. doi: 10.1126/scisignal.add4900.

Guo M., et al., "Guided Construction of Single Cell Reference for Human and Mouse Lung," Nature Communications, Jul. 29, 2023, 14:4566, 20 pages.

Gupta A. et al., "The great divide: septation and malformation of the cloaca, and its implications for surgeons," Pediatr Surg Int, 2014, 30, 1089-1095.

Ha, T. Y., et al., "Ascorbate Indirectly Stimulates Fatty Acid Utilization in Primary Cultured Guinea Pig Hepatocytes by Enhancing Carnitine Synthesis," The Journal of Nutrition, 1994, vol. 124, pp. 732-737.

Haasdijk R. A., et al., "Cerebral Cavernous Malformations: From Molecular Pathogenesis to Genetic Counselling and Clinical Management," European Journal of Human Genetics, 2012, vol. 20, pp. 134-140.

Aakerlund, L., et al., "Y1 receptors for neuropeptide Y are coupled to mobilization of intracellular calcium and inhibition of adenylate cyclase," FEBS Letters, 1990, vol. 260, pp. 73-78.

Abbott N.J., "Astrocyte-Endothelial Interactions and Blood-Brain Barrier Permeability," Journal of Anatomy, 2002, vol. 200, pp. 629-638.

Adams S. H. et al., "Effects of peptide YY [3-36] on short-term food intake in mice are not affected by prevailing plasma ghrelin levels," Endocrinology, 2004, 145, 4967-4975.

Aday S., et al., "Stem Cell-Based Human Blood-Brain Barrier Models for Drug Discovery and Delivery," Trends in Biotechnology, 2016, vol. 34, pp. 382-393.

Afgan E., et al., "The Galaxy Platform for Accessible, Reproducible and Collaborative Biomedical Analyses: 2016 Update," Nucleic Acids Research, 2016, vol. 44, pp. W3-W10.

Ager E. I., et al., "The Renin-Angiotensin System and Malignancy," Carcinogenesis, 2008, vol. 29, pp. 1675-1684.

Aird W.C. et al., "Endothelial cell heterogeneity," Cold Spring Harb Perspect Med, 2012, 2, a006429, 14 pages.

Aizarani N., et al., "A Human Liver Cell Atlas Reveals Heterogeneity and Epithelial Progenitors," Nature, Aug. 2019, vol. 572, No. 7770, pp. 199-204.

Akbari S., et al., "Next-Generation Liver Medicine Using Organoid Models", Frontiers in Cell and Developmental Biology, vol. 7, Dec. 20, 2019.

Akers A., et al., "Synopsis of Guidelines for the Clinical Management of Cerebral Cavernous Malformations: Consensus Recommendations Based on Systematic Literature Review by the Angioma Alliance Scientific Advisory Board Clinical Experts Panel," Neurosurgery, 2017, vol. 80, pp. 665-680.

(56) References Cited

OTHER PUBLICATIONS

Al Alam D., et al., "Contrasting expression of canonical Wnt signaling reporters Topgal, Batgal and Axin2(LacZ) during murine lung development and repair," PLoS One, 2011, 6, 8, e23139, 11 pages.

Alber A.B., et al., "Directed Differentiation of Mouse Pluripotent Stem Cells into Functional Lung-Specific Mesenchyme," bioRxiv, Aug. 2022, doi: 10.1101/2022.08.12.502651.

Alber A.B., et al., "Directed Differentiation of Mouse Pluripotent Stem Cells into Functional Lung-specific Mesenchyme," Nature Communications, Jun. 13, 2023, vol. 14:3488. 18 pages.

Allanson J.E., et al., "Possible New Autosomal Recessive Syndrome With Unusual Renal Histopathological Changes," American Journal of Medical Genetics, 1983, vol. 16, pp. 57-60.

Almeida, L. F., et al., "Role of the Renin-Angiotensin System in Kidney Development and Programming of Adult Blood Pressure." Clinical Science, vol. 134, No. 6, Mar. 27, 2020, pp. 641-656.

Alvira C. M., "Aberrant Pulmonary Vascular Growth and Remodeling in Bronchopulmonary Dysplasia," Frontiers in Medicine (Lausanne), 2016, vol. 3, p. 21.

Alvira C. M., "Nuclear Factor-Kappa-B Signaling in Lung Development and Disease: One Pathway, Numerous Functions," Birth Defects Research Part A: Clinical and Molecular Teratology, 2014, vol. 100, pp. 202-216.

Amir et al., "Comparing the Cellular Phenotype of Naïve and Primed Human Embryonic Stem Cells," Fertility and Sterility, Sep. 1, 2018 110(4):e36 Abstract.

Amir M., et al., "Hepatic Autonomic Nervous System and Neurotrophic Factors Regulate the Pathogenesis and Progression of Non-Alcoholic Fatty Liver Disease," Frontiers in Medicine (Lausanne), 2020, vol. 7, Article 62. doi: 10.3389/fmed.2020.00062.

Amireddy N., et al., "The Unintended Mitochondrial Uncoupling Effects of the FDA-Approved Anti-Helminth Drug Nitazoxanide Mitigates Experimental Parkinsonism in Mice," Journal of Biological Chemistry, 2017, vol. 292, pp. 15731-15743.

Andl C.D. et al., "Epidermal growth factor receptor mediates increased cell proliferation, migration, and aggregation in esophageal keratinocytes in vitro and in vivo," Journal of Biological Chemistry, 2003, 278(3), 1824-1830.

Andrews T.S., et al., "Single-Cell, Single-Nucleus, and Spatial RNA Sequencing of the Human Liver Identifies Cholangiocyte and Mesenchymal Heterogeneity," Hepatology Communications, Nov. 2022, vol. 6, No. 11, pp. 821-840.

Anstee, Q.M., et al., "Genome-wide association study of nonalcoholic fatty liver and steatohepatitis in a histologically characterised cohort," Journal of Hepatology, 2020, vol. 73, pp. 505-515.

Appuhn S.V., et al., "Capillary Changes Precede Disordered Alveolarization in a Mouse Model of Bronchopulmonary Dysplasia," American Journal of Respiratory Cell and Molecular Biology, Mar. 2021, vol. 65, No. 1, pp. 81-91. doi: 10.1165/rcmb.2021-0004OC.

Arnold K. et al., "Sox2+ Adult Stem and Progenitor Cells Are Important for Tissue Regeneration and Survival of Mice," Cell Stem Cell, 2011, 9(4), 317-329.

Artegiani B., et al., "Fast and Efficient Generation of Knock-in Human Organoids Using Homology-independent CRISPR-Cas9 Precision Genome Editing", Nature Cell Biology, 2020, vol. 22, No. 3, pp. 321-331.

Auerbach A. D., "Fanconi anemia and its diagnosis," Mutation Research—Fundamental and Molecular Mechanisms of Mutagenesis, 2009, 668(1-2), 4-10.

Aven L., et al., "An NT4/TrkB Dependent Increase in Innervation Links Early-Life Allergen Exposure to Persistent Airway Hyperreactivity," FASEB Journal, 2014, vol. 28, pp. 897-907.

Bagnat M. et al., "Genetic control of single lumen formation in the zebrafish gut," Nat Cell Biol, 2007, 9, 954-960.

Bakker S. T. et al., "Learning from a paradox: recent insights into Fanconi anaemia through studying mouse models," Disease Models Mechanisms, 2013, 6(1), 40-47.

Baldelli, S., et al., "Glutathione and Nitric Oxide: Key Team Players in Use and Disuse of Skeletal Muscle," Nutrients, 2019, vol. 11.

Ballermann B. J., "Dependence of Renal Microvessel Density on Angiotensin II: Only in the Fetus?" Journal of the American Society of Nephrology, 2010, vol. 21, pp. 386-388.

Bamberger C. et al., "Retinoic acid inhibits downregulation of DeltaNp63alpha expression during terminal differentiation of human primary keratinocytes," The Journal of Investigative Dermatology, 2002, 118(1), 133-8.

Bandara, N., et al., "Molecular Control of Nitric Oxide Synthesis through eNOS and Caveolin-1 Interaction Regulates Osteogenic Differentiation of Adipose-Derived Stem Cells by Modulation of Wnt/ß-Catenin Signaling," Stem Cell Research Therapy, 2016, vol. 7, No. 182, pp. 1-15.

Barbera M. et al., "The human squamous oesophagus has widespread capacity for clonal expansion from cells at diverse stages of differentiation," Gut, 2015, 64, 11-19.

Bartl, M., et al., "Optimality in the Zonation of Ammonia Detoxification in Rodent Liver." Archives of Toxicology, vol. 89, 2015, pp. 2069-2078.

Basu-Roy U. et al., "Sox2 maintains self renewal of tumor-initiating cells in osteosarcomas," Oncogene, 2012, 31 (18), 2270-2282.

Batra S., et al., "Cavernous Malformations: Natural History, Diagnosis and Treatment." Nature Reviews Neurology, 2009, vol. 5, pp. 659-670.

Beer N. L., et al., "The P446L Variant in GCKR Associated with Fasting Plasma Glucose and Triglyceride Levels Exerts Its Effect through Increased Glucokinase Activity in Liver," Human Molecular Genetics, 2009, vol. 18, pp. 4081-4088.

Belalcazar L. M., et al., "Lifestyle Intervention for Weight Loss and Cardiometabolic Changes in the Setting of Glucokinase Regulatory Protein Inhibition: Glucokinase Regulatory Protein-Leu446Pro Variant in Look AHEAD," Circulation: Cardiovascular Genetics, 2016, vol. 9, pp. 71-78.

Bellentani, S., et al., "Epidemiology of Non-Alcoholic Fatty Liver Disease." Digestive Diseases, vol. 28, 2010, pp. 155-161.

Bergers G. et al., "The role of pericytes in blood-vessel formation and maintenance," Neuro Oncol, 2005, 7, 452-464.

Besserer-Offroy, E., et al., "The signaling signature of the neurotensin type 1 receptor with endogenous ligands," Eur J Pharmacol, 2017, vol. 805, pp. 1-13.

Beucher A., et al., "The homeodomain-containing transcription factors Arx and Pax4 control enteroendocrine subtype specification in mice," PLoS One, 2012, 7(5), e36449, 11 pages.

Bhatt A. J., et al., "Disrupted Pulmonary Vasculature and Decreased Vascular Endothelial Growth Factor, Flt-1, and TIE-2 in Human Infants Dying with Bronchopulmonary Dysplasia," American Journal of Respiratory and Critical Care Medicine, 2001, vol. 164, pp. 1971-1980.

Biancalani T., et al., "Deep Learning and Alignment of Spatially Resolved Single-Cell Transcriptomes with Tangram," Nature Methods, Nov. 2021, vol. 18, No. 11, pp. 1352-1362.

Bilchik A. J., et al., "Peptide YY Augments Postprandial Small Intestinal Absorption in the Conscious Dog," The American Journal of Surgery, 1994, vol. 167, pp. 570-574.

Biology Stack Exchange., "Are there situations where in vivo results work better than in vitro results would have shown?", Forum post, reply on Sep. 28, 2018; Retrieved Jul. 25, 2024 from https://biology.stackexchange.com/questions/77736/are-there-situations-where-in-vivo-results-work-better-th (Year: 2018).

Blair T.A., et al., "Mass cytometry reveals distinct platelet subtypes in healthy subjects and novel alterations in surface glycoproteins in Glanzmann thrombasthenia," Scientific Reports. Jul. 9, 2018; 8(1):10300 in 13 pages.

Blakenberg D. et al., "Manipulation of FASTQ data with Galaxy," Bioinformatics, 2010, 26(14), 1783-1785.

Walker E.M. et al., "Characterization of the developing small intestine in the absence of either GATA4 or GATA6," BMC Res Notes, 2014, 7, 902, 12 pages.

Wang D. H., et al., "Regulation of Angiotensin Type 1 Receptor and Its Gene Expression: Role in Renal Growth," Journal of the American Society of Nephrology, 1997, vol. 8, pp. 193-198.

Wang D.H. et al., "Aberrant Epithelial-Mesenchymal Hedgehog Signaling Characterizes Barrett's Metaplasia," Gastroenterology 2010, 138(5), 1810-1822.e2.

(56) References Cited

OTHER PUBLICATIONS

Wang H., et al., "Recent Progress in microRNA Delivery for Cancer Therapy by Non-Viral Synthetic Vectors," Advanced Drug Delivery Reviews, 2015, vol. 81, pp. 142-160.
Wang K., et al., "ANNOVAR: Functional Annotation of Genetic Variants from High-Throughput Sequencing Data," Nucleic Acids Research, 2010, vol. 38, e164.
Wang Q. et al., "Regulatable in vivo biotinylation expression system in mouse embryonic stem cells," PloS One, 2013, 8, 5, e63532, 7 pages.
Wang S., "Fundamentals of developmental biology", edited by , East China University of 25 Technology Press, Feb. 2014, 1st edition, pp. 184-185 "Role of homologous genes in development of appendages", published on Feb. 28, 2014).
Wang T. et al."Polypeptide Growth Factor and Spinal Cord Injury". Xinjiang Science and Technology Press, Yunnan Science and Technology Press, "Biological Effects of EGF", pp. 88-89, published on Apr. 30, 2003).
Wang X., et al., "A Tropomyosin Receptor Kinase Family Protein, NTRK2, is a Potential Predictive Biomarker for Lung Adenocarcinoma," PeerJ, Jun. 2019, vol. 7, doi: 10.7717/peerj.7125.
Wang, Y., et al., "Metformin Improves Mitochondrial Respiratory Activity through Activation of AMPK," Cell Reports, 2019, vol. 29, pp. 1511-1523 e1515.
Wang, Y., et al., "Transcriptional regulation of hepatic lipogenesis," Nat Rev Mol Cell Biol, 2015, vol. 16, pp. 678-689.
Watanabe H., et al., "SOX2 and p63 colocalize at genetic loci in squamous cell carcinomas," Journal of Clinical Investigation, 2014, 124(4), 1636-1645.
Watanabe M., et al., "Feasibility Study of NMR-Based Serum Metabolomic Profiling to Animal Health Monitoring: A Case Study on Iron Storage Disease in Captive Sumatran Rhinoceros (*Dicerorhinus sumatrensis*)," PLoS One, 2016, vol. 11, e0156318.
Weber R.J., et al., "Efficient Targeting of Fatty-acid modified Oligonucleotides to live Cell Membranes through Stepwise Assembly," Biomacromolecules, 2014, vol. 15(12), pp. 4621-4626.
Wei Y., et al., "Liver Homeostasis is Maintained by Midlobular Zone 2 Hepatocytes," Science, Feb. 2021, vol. 371, No. eabb1625.
Weirauch M. T. et al., "Determination and inference of eukaryotic transcription factor sequence specificity," Cell, 2014, 158, 1431-1443.
Wells J.M. et al., "Wnt/beta-catenin signaling is required for development of the exocrine pancreas," BMC Dev Biol, 2007, 7, 4, 18 pages.
Wesley, B. T., et al., "Single-Cell Atlas of Human Liver Development Reveals Pathways Directing Hepatic Cell Fates," Nature Cell Biology, 2022, vol. 24, No. 10, pp. 1487-1498.
Wessel J., et al., "Do Genes Determine Our Health? Implications for Designing Lifestyle Interventions and Drug Trials," Circulation: Cardiovascular Genetics, 2016, vol. 9, pp. 2-3.
Wesson, D., et al., "The effect of intrauterine esophageal ligation on growth of fetal rabbits," J Pediatr Surg, 1984, vol. 19, pp. 398-399.
Whitehead K. J., et al., "The Cerebral Cavernous Malformation Signaling Pathway Promotes Vascular Integrity via Rho GTPases," Nature Medicine, 2009, vol. 15, pp. 177-184.
Wieland H.A., et al., "Subtype selectivity of the novel nonpeptide neuropeptide YY1 receptor antagonist BIBO3304 and its effect on feeding in rodents," Br J Pharmacol, Oct. 1998, vol. 125(3), pp. 549-555.
Williamson K. A., et al., "Mutations in SOX2 Cause Anophthalmia-Esophageal-Genital (AEG) Syndrome," Human Molecular Genetics, 2006, 15(9), pp. 1413-1422.
Woo J. et al., "Band -mediated inhibition of Wnt signaling in the mouse thoracic foregut controls tracheo-esophageal septation and epithelial differentiation," PloS One, 2011, 6(7), e22493, 8 pages.
Wu H., et al., "Advantages of Single-Nucleus over Single-Cell RNA Sequencing of Adult Kidney: Rare Cell Types and Novel Cell States Revealed in Fibrosis," Journal of the American Society of Nephrology, Jan. 2019, vol. 30, No. 1, pp. 23-32.

Wu H., et al., "Comparative Analysis and Refinement of Human PSC-Derived Kidney Organoid Differentiation with Single-Cell Transcriptomics," Cell Stem Cell, 2018, vol. 23, pp. 869-881.e868.
Wu X., et al., "Modeling Drug-induced Liver Injury and Screening for Anti-hepatofibrotic Compounds Using Human PSC-derived Organoids,", Cell Regeneration, Biomed Central, vol. 12, No. 1, Mar. 3, 2023, pp. 1-13.
Xia, M.F., et al., "NAFLD and Diabetes: Two Sides of the Same Coin? Rationale for Gene-Based Personalized NAFLD Treatment," Frontiers in Pharmacology, 2019, vol. 10, 877.
Xia Y., et al., "Angiotensin Receptors, Autoimmunity, and Preeclampsia," Journal of Immunology, 2007, vol. 179, pp. 3391-3395.
Xiang Y., et al., "Fusion of Regionally Specified hPSC-Derived Organoids Models Human Brain Development and Interneuron Migration,". Cell Stem Cell, 2017, vol. 21, pp. 383-398.
Xiao C. et al., "Gut peptides are novel regulators of intestinal lipoprotein secretion: experimental and pharmacological manipulation of lipoprotein metabolism," Diabetes, 2015, 64, 2310-2318.
Xiao S., et al., "Gastric Stem Cells: Physiological and Pathological Perspectives," Frontiers in Cell and Developmental Biology, 2020, vol. 8, pp. 1-13.
Xu, C.-R., et al., "Chromatin 'Prepattern' and Histone Modifiers in a Fate Choice for Liver and Pancreas," Science, 2011, vol. 332, pp. 963-966.
Xu R., "Basis and Clinical Applications of Receptors", edited by et al. Shanghai Science and Technology Press, 1st edition, Feb. 1992, Section of "Retinoic Acid Receptors" on pp. 129-131, published on Feb. 29, 1992.
Xu, W., et al., "Hypoxia activates Wnt/ß-catenin signaling by regulating the expression of BCL9 in human hepatocellular carcinoma," Scientific Reports, 2017, vol. 7, 40446, 13 pages.
Xu, Y., et al., "Ascorbate protects liver from metabolic disorder through inhibition of lipogenesis and suppressor of cytokine signaling 3 (SOCS3)," Nutrition Metabolism, 2020, vol. 17, 17.
Yanan Y., et al., "Research Progress on Hedgehog Signaling Pathway and Liver Fibrosis," Chinese Journal of Anatomy, 06, Dec. 25. 2019, pp. 589-592.
Yang M., et al., "Angiogenesis-Related Genes May Be a More Important Factor than Matrix Metalloproteinases in Bronchopulmonary Dysplasia Development," Oncotarget, 2017, vol. 8, pp. 18670-18679.
Ye D.Z. et al., "Foxa1 and Foxa2 control the differentiation of goblet and enteroendocrine L- and D-cells in mice," Gastroenterology, 2009, 137, 2052-2062.
Ye F., et al., "Fibroblast Growth Factors 7 and 10 Are Expressed in the Human Embryonic Pancreatic Mesenchyme and Promote the Proliferation of Embryonic Pancreatic Epithelial Cells," Diabetologia, 2005, vol. 48, pp. 277-281.
Yin H., et al., "Non-viral Vectors for Gene-based Therapy," Nature Reviews Genetics, 2014, vol. 15(8), pp. 541-555.
Yokobori, T., et al., "Intestinal epithelial culture under an air-liquid interface: a tool for studying human and mouse esophagi," Dis. Esophagus, 2016, vol. 29, pp. 843-847.
Younossi, Z.M., et al., "Economic and Clinical Burden of Nonalcoholic Steatohepatitis in Patients With Type 2 Diabetes in the U.S.," Diabetes Care, 2020, vol. 43, pp. 283-289.
Yu J., et al., "Induced Pluripotent Stem Cell Lines Derived from Human Somatic Cells," Science, 2007, vol. 318, pp. 1917-1920.
Yu X. et al., "Lentiviral vectors with two independent internal promoters transfer highlevel expression of multiple transgenes to human hematopoietic stem-progenitor cells," Mol Ther, 2003, 7, 827-838.
Yu, Y., Chinese Studies on Disease Signaling Pathway and Targeted Therapy, Anhui Science and Technology Press, May 31, 2013, p. 363 [Reference unavailable, citing referencing Search Report, 3 pgs.].
Yu, Y., et al., "A comparative analysis of liver transcriptome suggests divergent liver function among human, mouse and rat," Genomics, 2010, vol. 96, pp. 281-289.
Yusta B. et al., "Enteroendocrine localization of GLP-2 receptor expression in humans and rodents," Gastroenterology, 2000, 119, 744-755.

(56) References Cited

OTHER PUBLICATIONS

Zanini F., et al., "Developmental Diversity and Unique Sensitivity to Injury of Lung Endothelial Subtypes During Postnatal Growth," iScience, Mar. 2023, vol. 26, No. 3, doi: 10.1016/j.isci.2023.106097.

Zanini F., et al., "Phenotypic Diversity and Sensitivity to Injury of the Pulmonary Endothelium During a Period of Rapid Postnatal Growth," bioRxiv, Apr. 2021, doi: 10.1101/2021.04.27.441649.

Kurz H., "Cell Lineages and Early Patterns of Embryonic CNS Vascularization," Cell Adhesion & Migration, 2009, vol. 3, pp. 205-210.

Kuzmichev A. N. et al., "Sox2 acts through Sox21 to regulate transcription in pluripotent and differentiated cells," Current Biology, 22(18), 2012, 1705-1710.

Kwapiszewska G., et al., "BDNF/TrkB Signaling Augments Smooth Muscle Cell Proliferation in Pulmonary Hypertension," American Journal of Pathology, 2012, vol. 181, pp. 2018-2029.

L. Landsman, et al., "Pancreatic Mesenchyme Regulates Epithelial Organogenesis Throughout Development," PLoS Biology, 2011, vol. 9, Article e1001143, 14 pages.

Lammert E., "Induction of Pancreatic Differentiation by Signals from Blood Vessels," Science, 2001, vol. 294, pp. 564-567.

Lancaster M. A., et al., "Cerebral Organoids Model Human Brain Development and Microcephaly," Nature, 2013, vol. 501(7467), pp. 373-379.

Landin, B. H., et al., "Labeled Lectin Studies of Renal Tubular Dysgenesis and Renal Tubular Atrophy of Postnatal Renal Ischemia and End-Stage Kidney Disease." Pediatric Pathology, vol. 14, No. 1, 1994, pp. 87-99.

Langen U.H., et al., "Development and Cell Biology of the Blood-Brain Barrier," Annual Review of Cell and Developmental Biology, 2019, vol. 35, pp. 591-613.

Langer R., "Tissue Engineering," Science, 1990, vol. 249, pp. 1527-1533.

Lau J. Y., et al., "Systematic Review of the Epidemiology of Complicated Peptic Ulcer Disease: Incidence, Recurrence, Risk Factors and Mortality," Digestion, 2011, vol. 84, pp. 102-113. DOI: 10.1159/000323958.

Leblanc G. G., et al., "Biology of Vascular Malformations of the Brain," Stroke, 2009, vol. 40, pp. e694-702.

Leedham S. J. et al., "Individual crypt genetic heterogeneity and the origin of metaplastic glandular epithelium in human Barrett's oesophagus," Gut, 2008, 57(8), 1041-1048.

Lehner, R et al., "A Comparison of Plasmid DNA Delivery Efficiency and Cytotoxicity of Two Cationic Diblock Polyoxazoline Copolymers", Nanotechnology, 28, 2017, pp. 111.

Li B., et al., "Benchmarking Spatial and Single-Cell Transcriptomics Integration Methods for Transcript Distribution Prediction and Cell Type Deconvolution," Nature Methods, Jun. 2022, vol. 19, No. 6, pp. 662-670.

Li H., et al., "Directed Differentiation of Human Embryonic Stem Cells into Keratinocyte Progenitors In Vitro: An Attempt with Promise of Clinical Use," In Vitro Cellular Developmental Biology—Animal, 2016, 52(8), pp. 885-893.

Li H. et al., "Fast and accurate short read alignment with Burrows-Wheeler transform," Bioinformatics, 2009, 25(14), 1754-1760.

Li H.J. et al., Basic helix-loop-helix transcription factors and enteroendocrine cell differentiation. Diabetes Obes Metab, 2011, 13(01), Suppl 1, 5-12, 16 pages.

Li J., et al., "An Obligatory Role for Neurotensin in High Fat Diet-Induced Obesity," Nature, 2016, vol. 533, No. 7603, pp. 411-415.

Li, Y., et al., "The Renin-Angiotensin-Aldosterone System (RAAS) Is One of the Effectors by Which Vascular Endothelial Growth Factor (VEGF)/Anti-VEGF Controls the Endothelial Cell Barrier," American Journal of Pathology, 2020, vol. 190, pp. 1971-1981.

Li Y., et al., "Synthesis and Characterization of an Amphiphilic Graft Polymer and its Potential as a pH-Sensitive Drug Carrier", Polymer, vol. 58, No. 15, Jul. 2011, pp. 3304-3310.

Lin Y. C., et al., "Genetic Variants in GCKR and PNPLA3 Confer Susceptibility to Nonalcoholic Fatty Liver Disease in Obese Individuals," American Journal of Clinical Nutrition, 2014, vol. 99, pp. 869-874.

Lindström N. O., et al., "Integrated B-catenin, BMP, PTEN, and Notch signalling patterns the nephron." eLife, 4, e04000. 2015, 29 pages. https://doi.org/10.7554/eLife.04000.

Lindström N. O., et al., "Spatial Transcriptional Mapping of the Human Nephrogenic Program." Developmental Cell, 56(16), 2021, pp. 2381-2398.e6. https://doi.org/10.1016/j.devcel.2021.07.017.

Lindstrom N.O., et al., "Integrated Beta-Catenin, BMP, PTEN, and Notch Signalling Patterns the Nephron," eLife, 2015, vol. 3, e04000.

Liu D., Chinese Encyclopedia of Medicine—Pathophysiology, "China Signal Pathway and Targeted Therapeutics", edited by Yu Yuanxun, Anhui Science and Technology Press, May 2013, 1st edition.

Liu K., et al., "Sox2 Cooperates with Inflammation-Mediated Stat3 Activation in the Malignant Transformation of Foregut Basal Progenitor Cells," Cell Stem Cell, 2013, 12(3), 304-315.

Liu T., et al., "Regulation of Cdx2 expression by promoter methylation, and effects of Cdx2 transfection on morphology and gene expression of human esophageal epithelial cells," Carcinogenesis, 2007, 28(2), 488-496.

Lloyd D. J., et al., "Antidiabetic Effects of Glucokinase Regulatory Protein Small-Molecule Disruptors." Nature, 504, 2013, 16 pages.

Lois C. et al., "Germline transmission and tissue-specific expression of transgenes delivered by lentiviral vectors," Science, 2002, 295, 868-872.

Loomba, R., et al., "Combination Therapies Including Cilofexor and Firsocostat for Bridging Fibrosis and Cirrhosis Attributable to NASH." Hepatology, vol. 73, No. 2, Feb. 2021, pp. 625-643.

Loomba R., et al., "Heritability of Hepatic Fibrosis and Steatosis Based on a Prospective Twin Study," Gastroenterology, 2015, vol. 149, pp. 1784-1793.

Loquet PH., et al., "Influence of Raising Maternal Blood Pressure With Angiotensin II on Utero-Placental and Feto-Placental Blood Velocity Indices In The Human," Clinical Science, 1990, vol. 78, pp. 95-100.

Low, J.H., et al., "Generation of Human PSC-Derived Kidney Organoids with Patterned Nephron Segments and a De Novo Vascular Network," Cell Stem Cell, 2019, vol. 25, pp. 373-387 e379.

Lu T.M., et al., "Pluripotent Stem Cell-Derived Epithelium Misidentified as Brain Microvascular Endothelium Requires ETS Factors to Acquire Vascular Fate," Proceedings of the National Academy of Sciences of the United States of America, 2021, vol. 118.

Lubinsky M. Sonic Hedgehog, VACTERL, and Fanconi anemia: Pathogenetic connections and therapeutic implications. American Journal of Medical Genetics, Part A, 2015, 167(11), 2594-2598.

Lucía Selfa, I., et al., "Directed Differentiation of Human Pluripotent Stem Cells for the Generation of High-Order Kidney Organoids." Methods in Molecular Biology, vol. 2258, 2021, pp. 171-189.

Lustig B. et al., "Negative feedback loop of Wnt signaling through upregulation of conductin/axin2 in colorectal and liver tumors," Molecular and Cellular Biology, 2002, 22(4), 1184-93.

Luzio J.P. et al., "Lysosomes: fusion and function", Nature reviews Molecular cell biology, 2007, vol. 8, No. 8, pp. 622-632.

Ma, R., et al., "Metabolic and non-metabolic liver zonation is established non-synchronously and requires sinusoidal Wnts," eLife, 2020, vol. 9, e46206.

Mace O. J. et al., "Pharmacology and physiology of gastrointestinal enteroendocrine cells," Pharmacol Res Perspect, 2015 3(4), e00155, 26 pages.

Maddaluno L., et al., "EndMT Contributes to the Onset and Progression of Cerebral Cavernous Malformations." Nature, vol. 498, 2013, 7 pages.

Madisen L. et al., "A robust and high-throughput Cre reporting and characterization system for the whole mouse brain," Nat Neurosci, 2020, 13, 133-140.

Madsen K., et al., "Angiotensin II Promotes Development of the Renal Microcirculation through AT1 Receptors," Journal of the American Society of Nephrology, 2010, vol. 21, pp. 448-459.

(56) References Cited

OTHER PUBLICATIONS

Mahieu-Caputo D., et al., "Twin-to-Twin Transfusion Syndrome: Role of the Fetal Renin-Angiotensin System," American Journal of Pathology, 2000, vol. 156, pp. 629-636.

Mammen J. M., et al., "Mucosal Repair in the Gastrointestinal Tract," Critical Care Medicine, 2003, vol. 31, pp. S532-537. DOI: 10.1097/01.CCM.0000081429.89277.AF.

Mammoto A., et al., "Vascular Niche in Lung Alveolar Development, Homeostasis, and Regeneration," Frontiers in Bioengineering and Biotechnology, Nov. 2019, vol. 7, No. 318. doi: 10.3389/fbioe.2019.00318.

Mammoto, T., et al., "Mechanical control of tissue and organ development," Development, 2010, vol. 137, No. 9, pp. 1407-1420.

Mandegar M. A., et al., "CRISPR Interference Efficiently Induces Specific and Reversible Gene Silencing in Human iPSCs," Cell Stem Cell, 2016, 18(4), pp. 541-553.

Marable, S.S., et al., "Hnf4a deletion in the mouse kidney phenocopies Fanconi renotubular syndrome," JCI Insight, 2018, vol. 3, 12 Pages.

Mari L. et al., "A pSMAD/CDX2 complex is essential for the intestinalization of epithelial metaplasia," Cell Reports, 2014, 7(4), 1197-1210.

\* cited by examiner

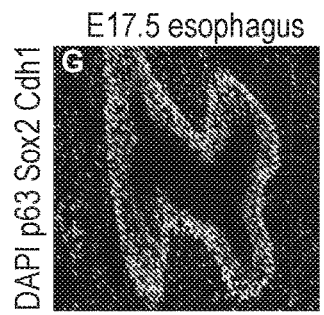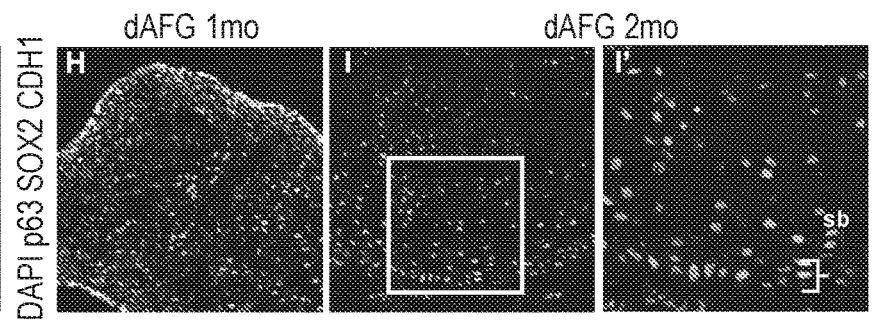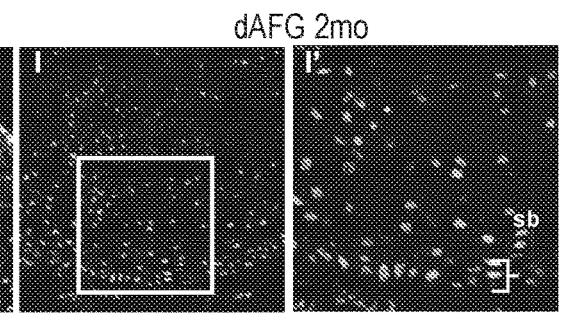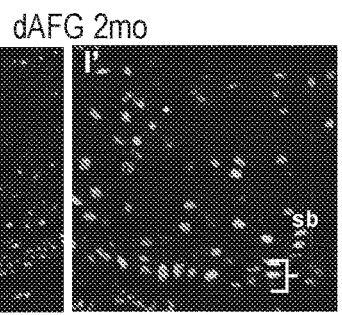
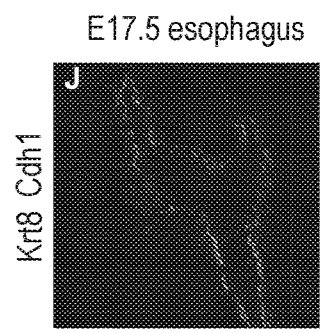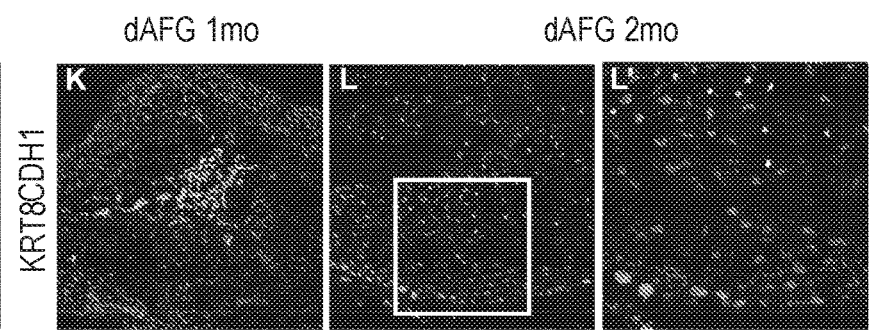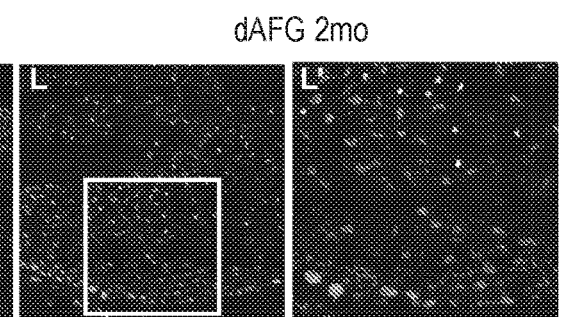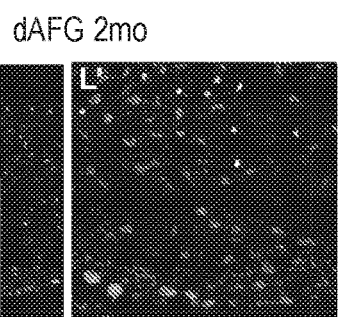
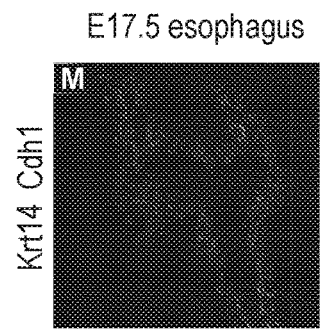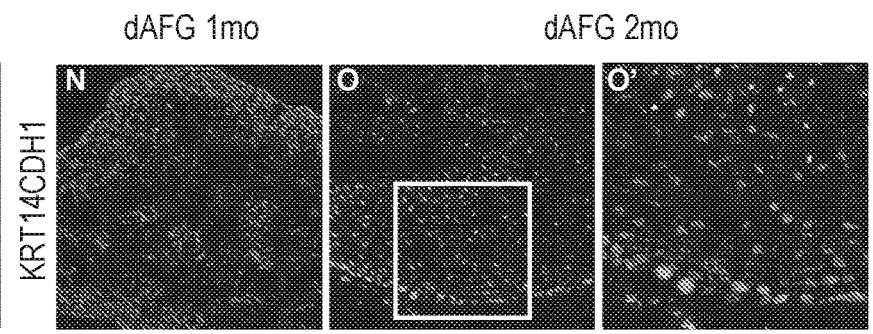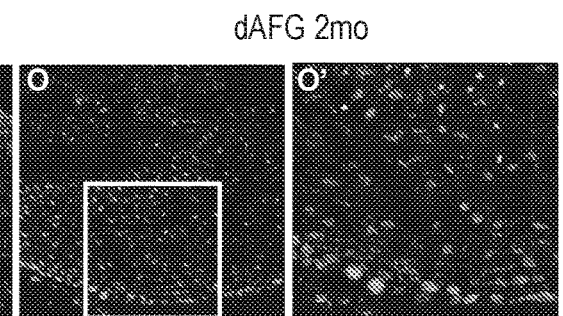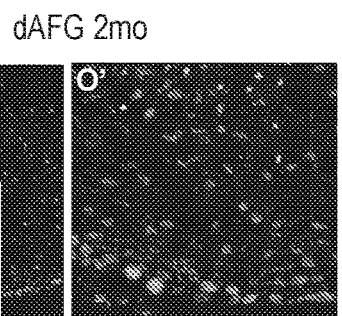
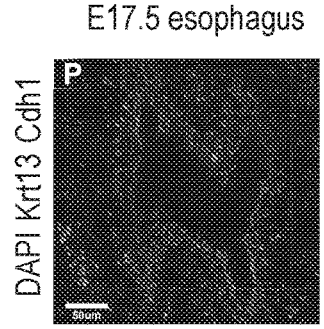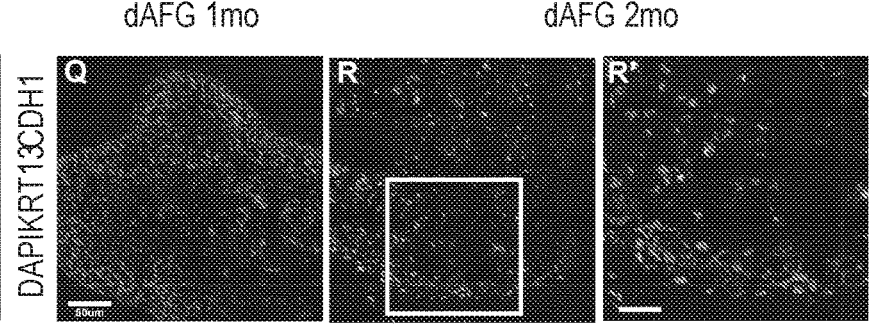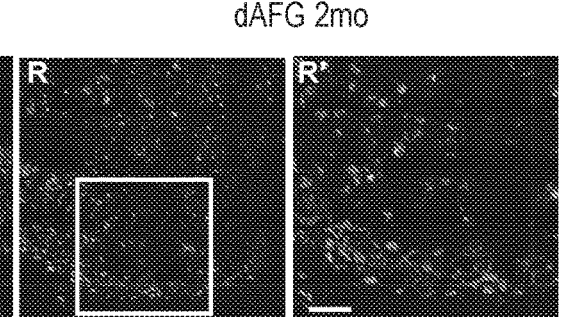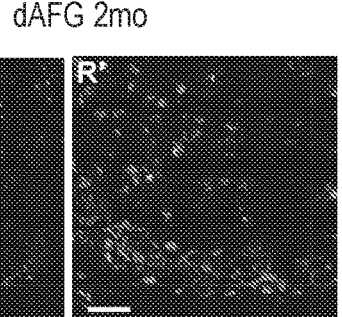
FIG. 3G  FIG. 3H  FIG. 3I  FIG. 3I-1
FIG. 3J  FIG. 3K  FIG. 3L  FIG. 3L-1
FIG. 3M  FIG. 3N  FIG. 3O  FIG. 3O-1
FIG. 3P  FIG. 3Q  FIG. 3R  FIG. 3R-1

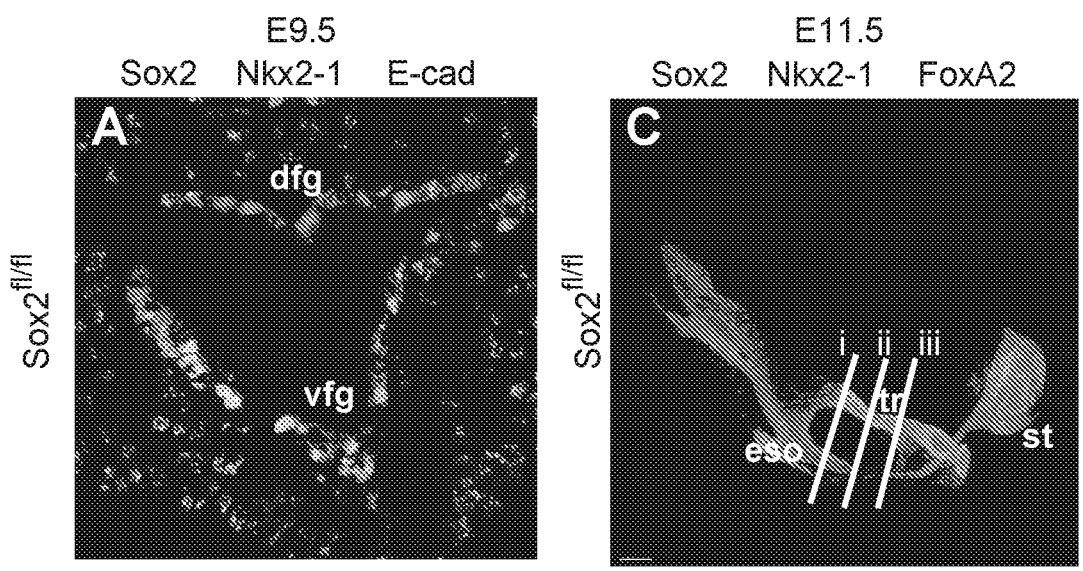
FIG. 5A
FIG. 5C
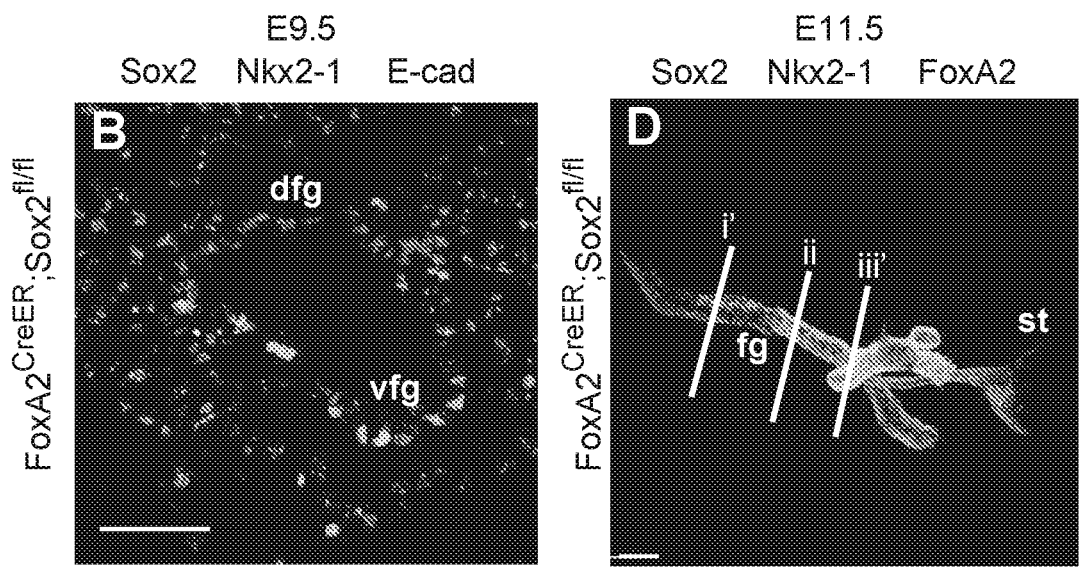
FIG. 5B
FIG. 5D

|                              | dAFG (Nog) | vAFG (BMP) |
|------------------------------|------------|------------|
| SOX2 independent             | 410        | 331        |
| Positively Regulated by SOX2 | 93         | 38         |
| Negatively Regulated by SOX2 | 39         | 5          |

FIG. 7D d6 (nascent) spheroids d6 (nascent) spheroids d6 (nascent) spheroids

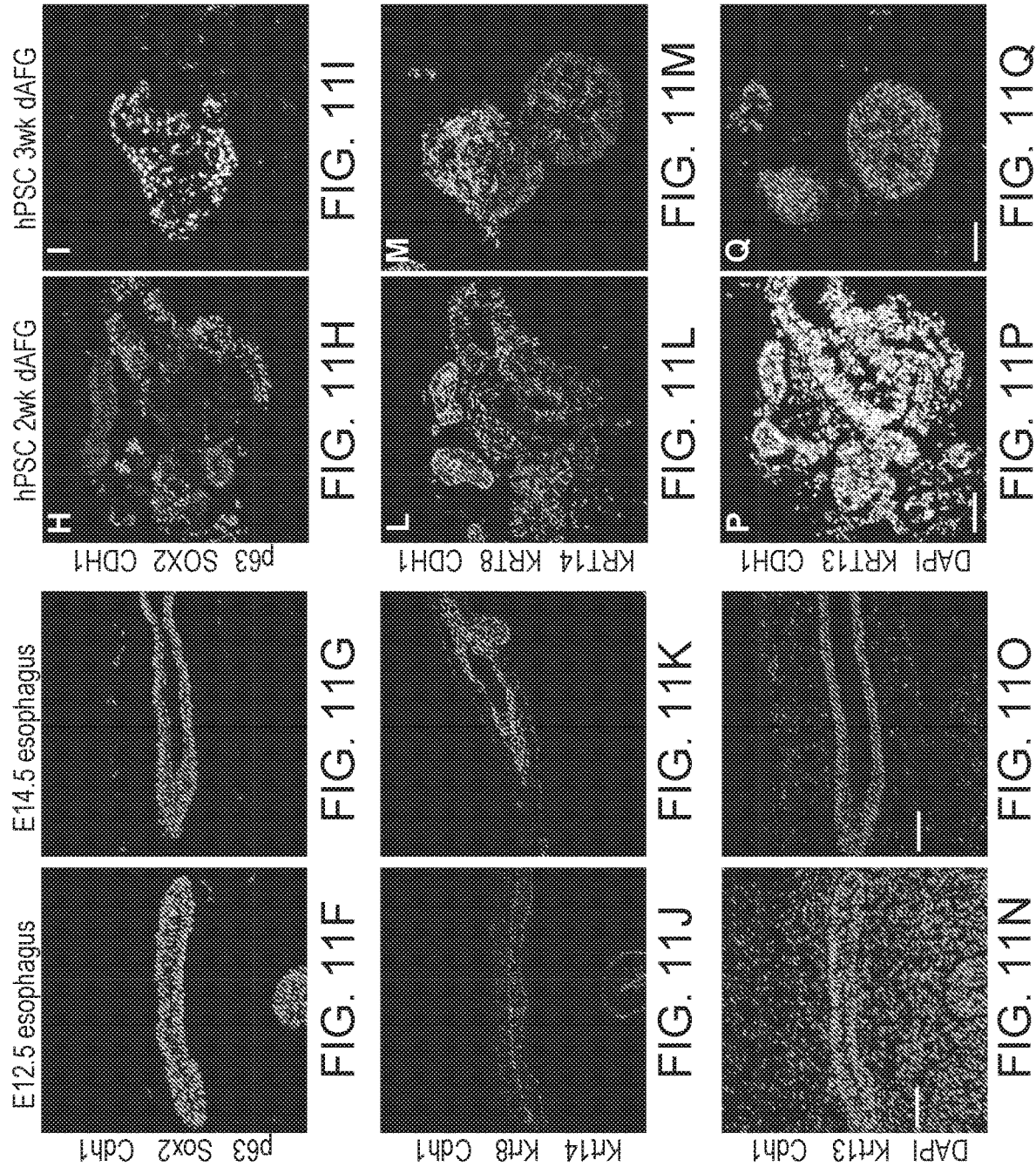

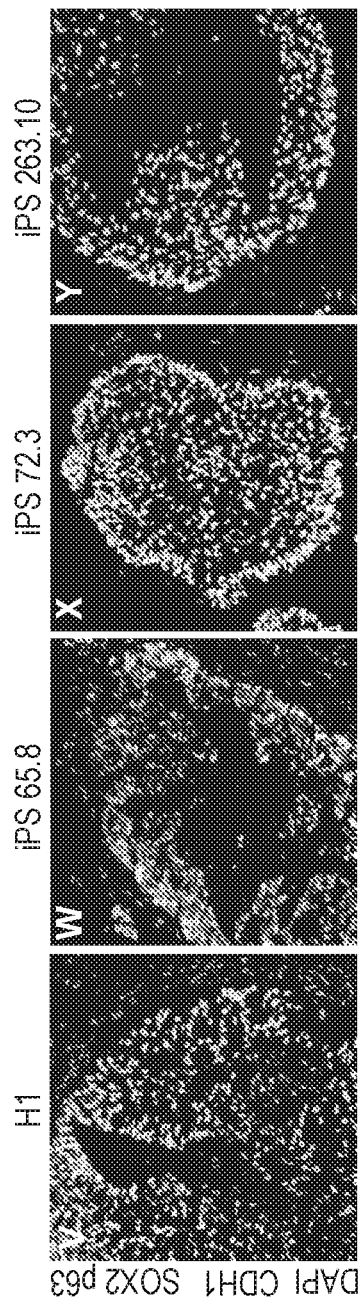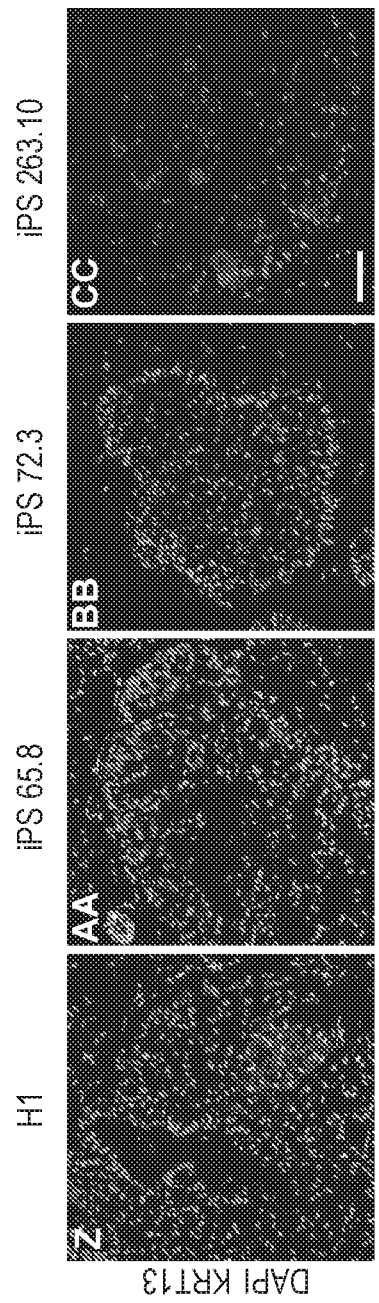

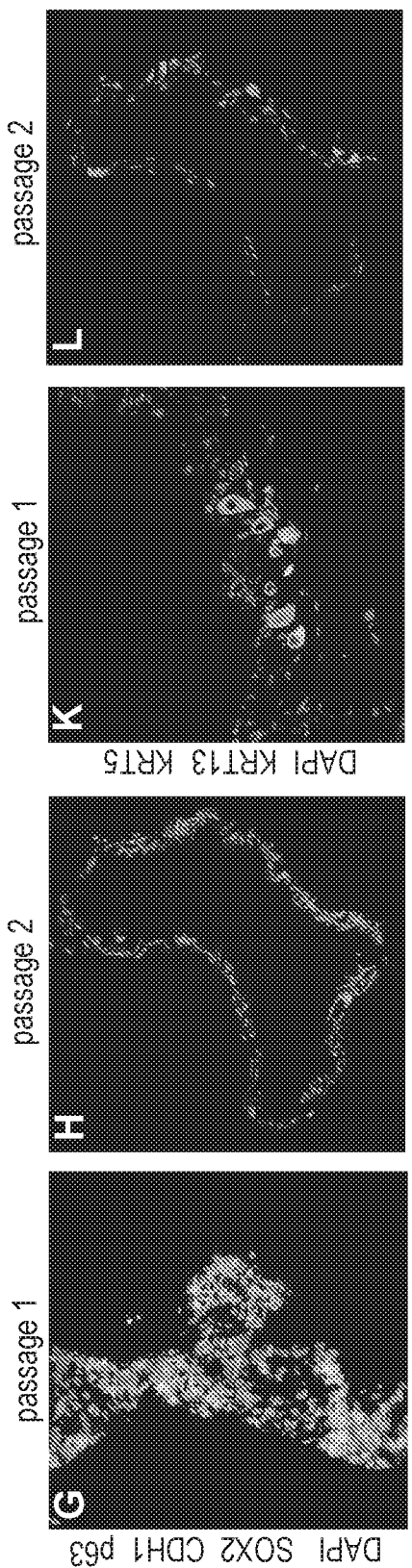
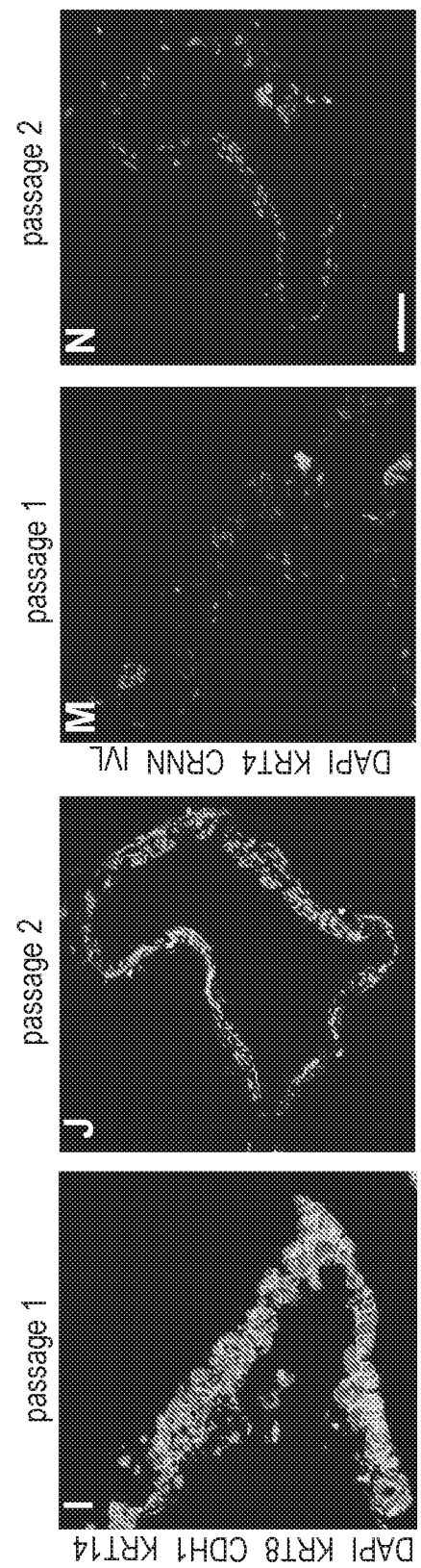
FIG. 12G  FIG. 12H  FIG. 12K  FIG. 12L
FIG. 12I  FIG. 12J  FIG. 12M  FIG. 12N

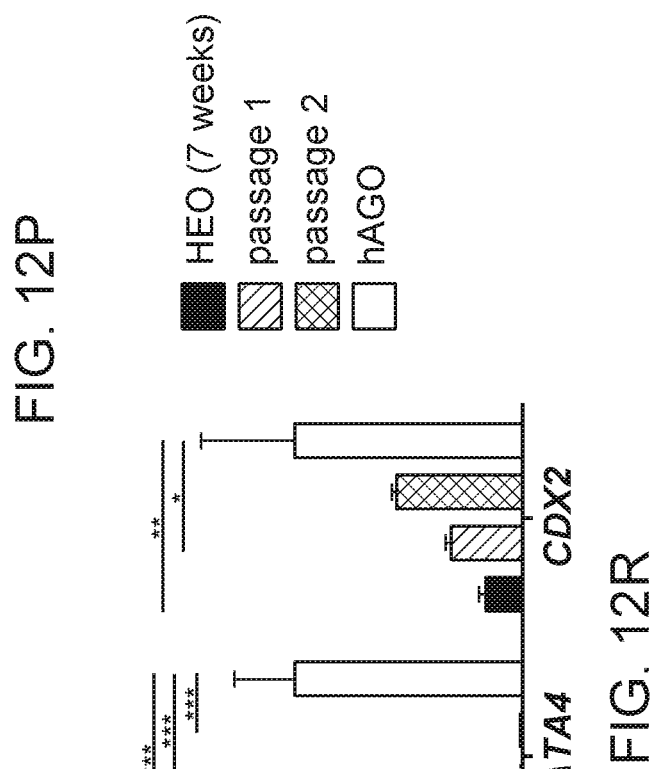
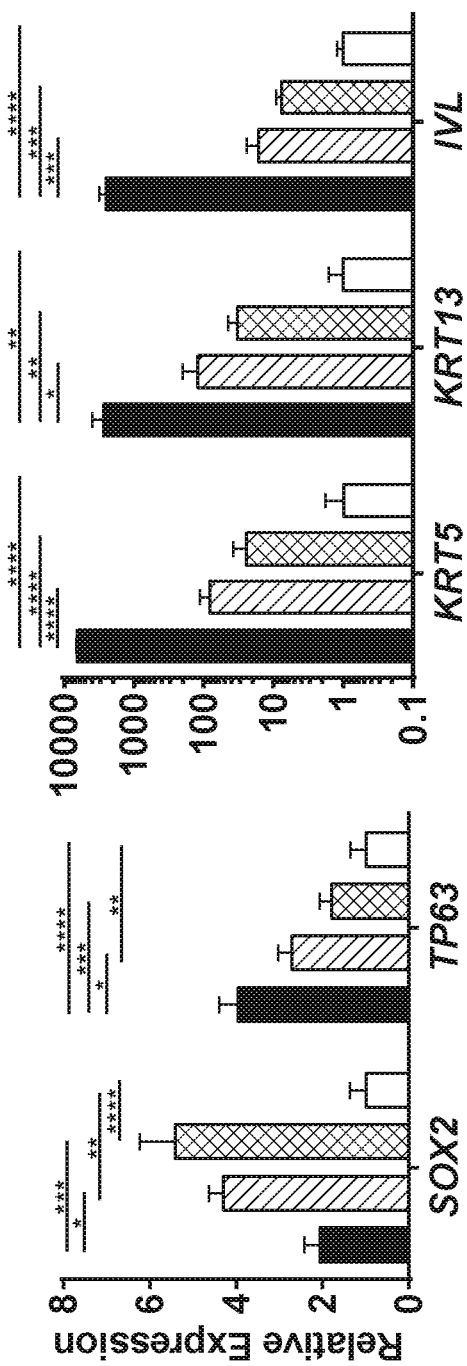
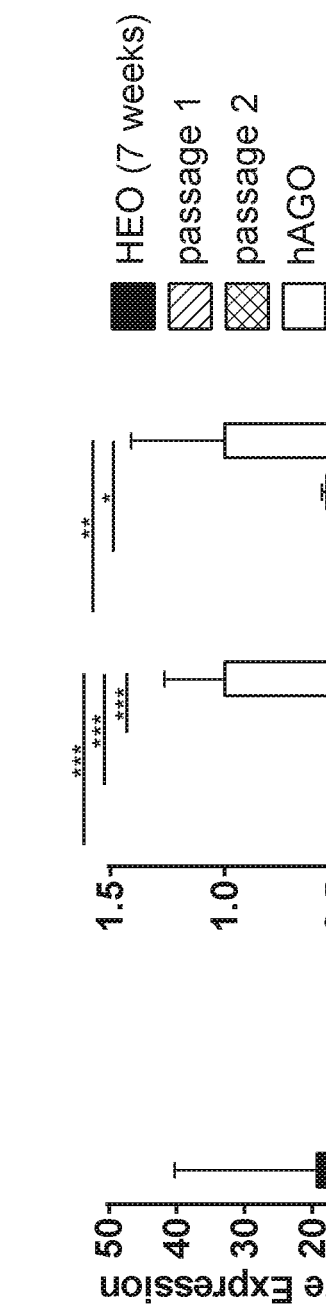
FIG. 12P
FIG. 12R
FIG. 12O
FIG. 12Q

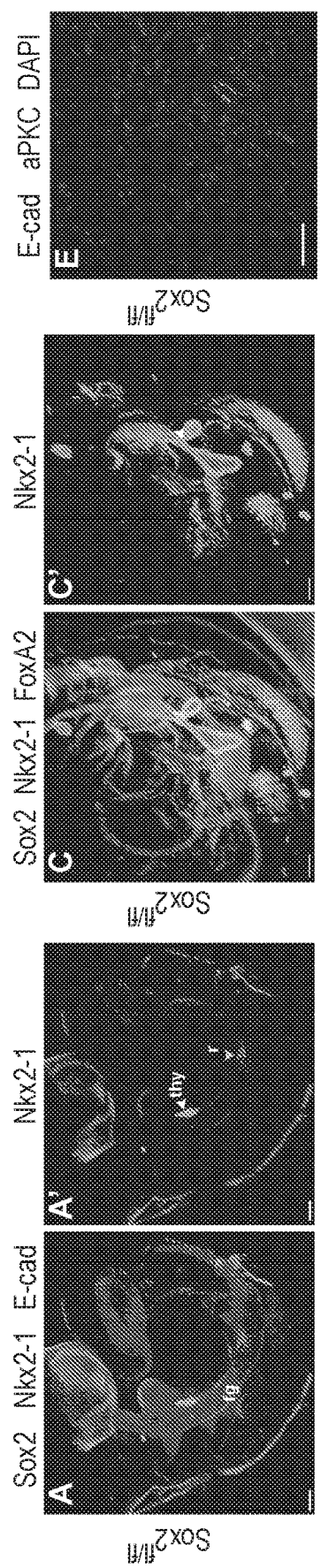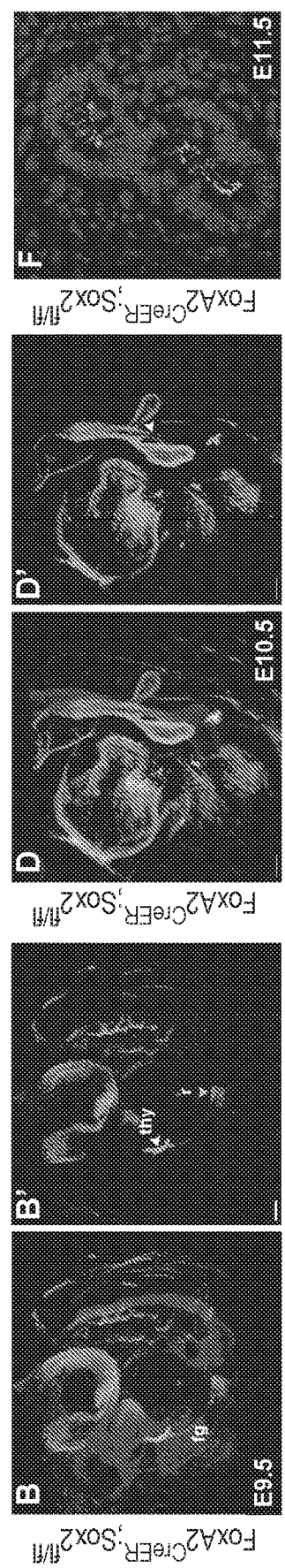

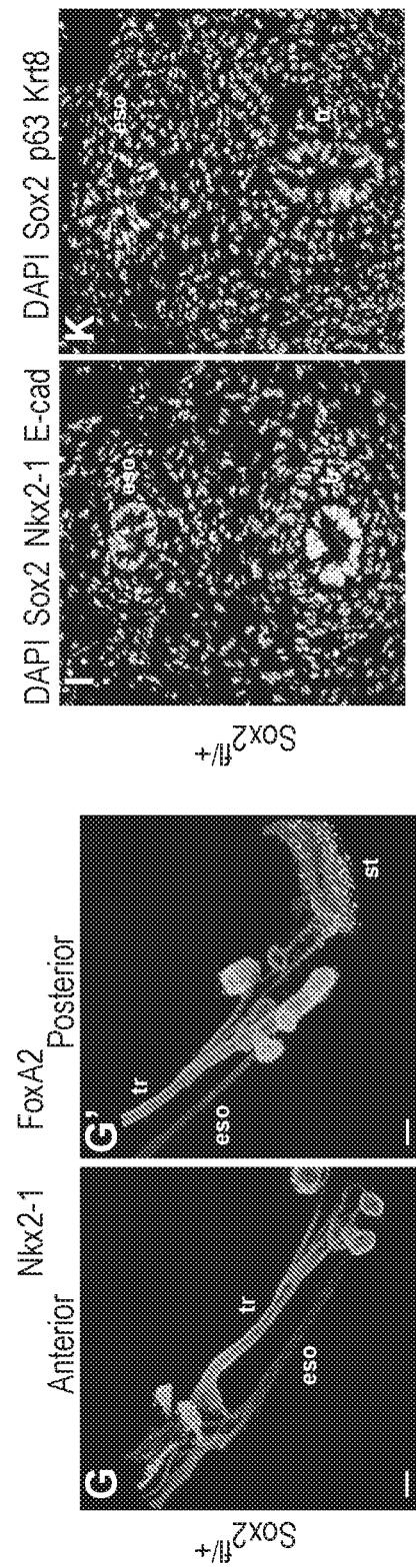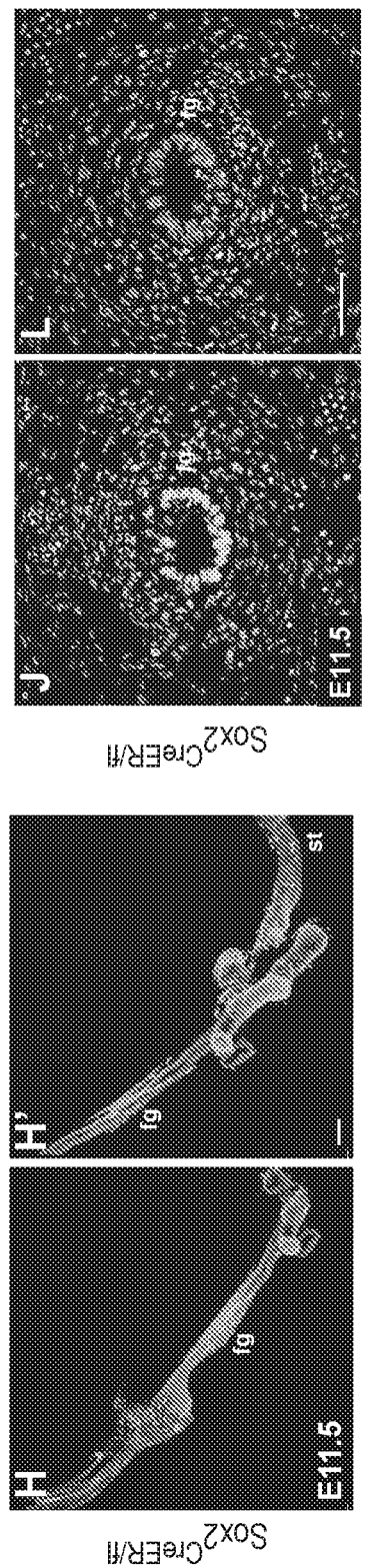

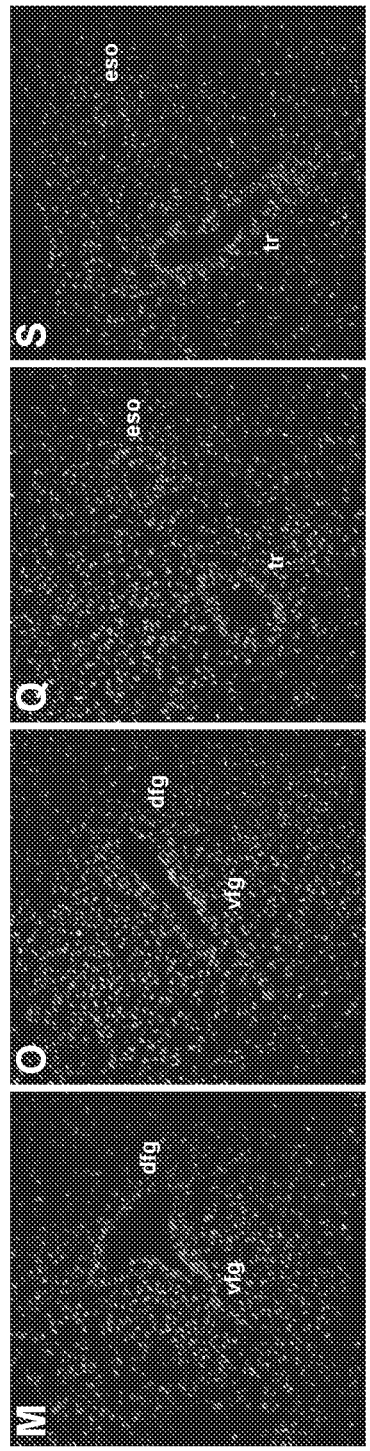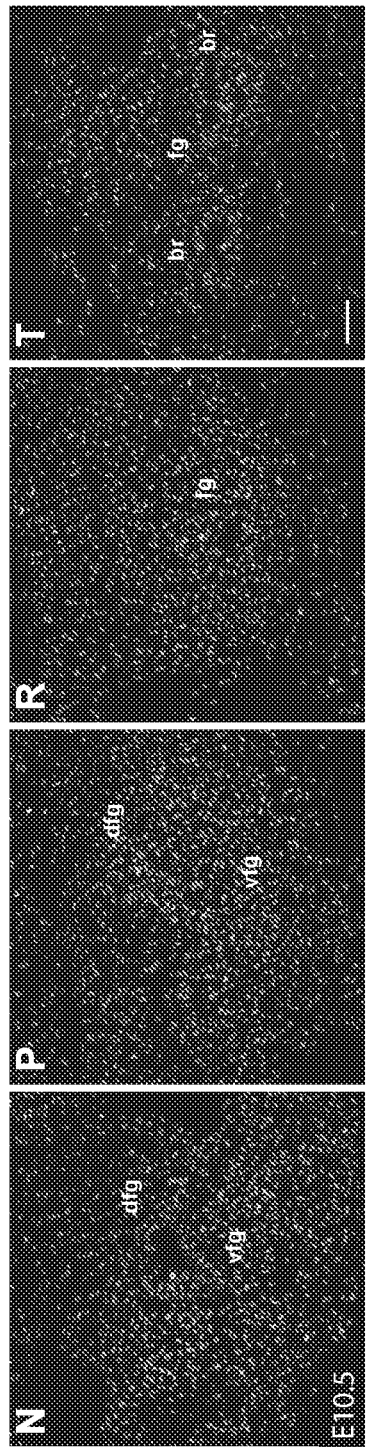

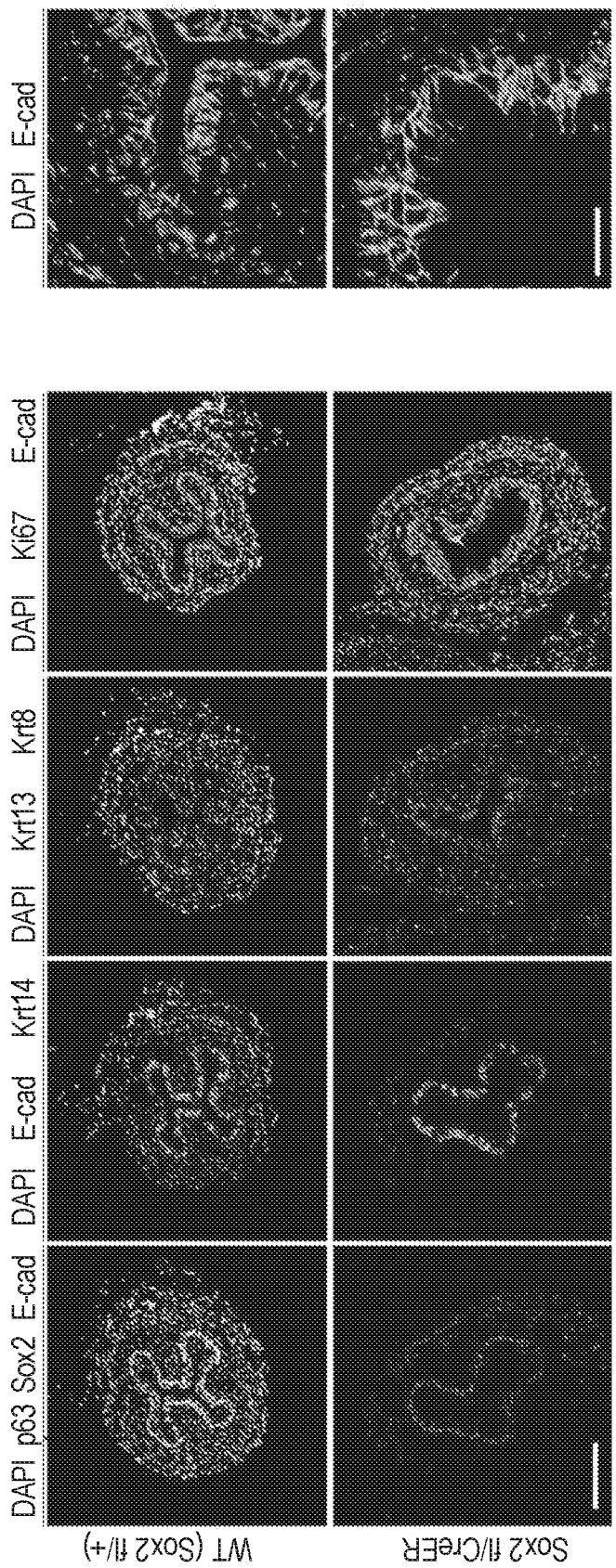

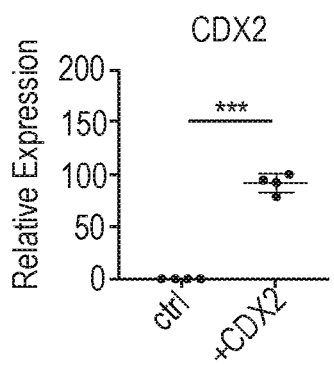
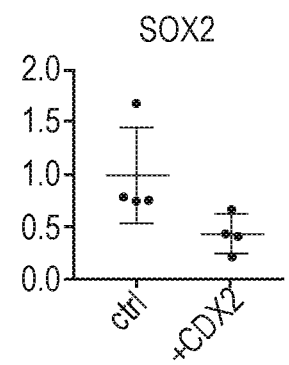
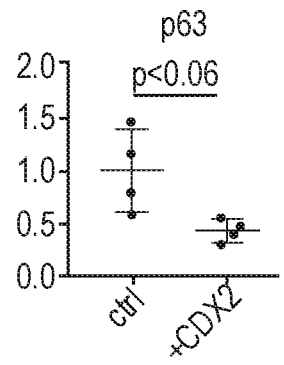
FIG. 18C        FIG. 18D        FIG. 18E
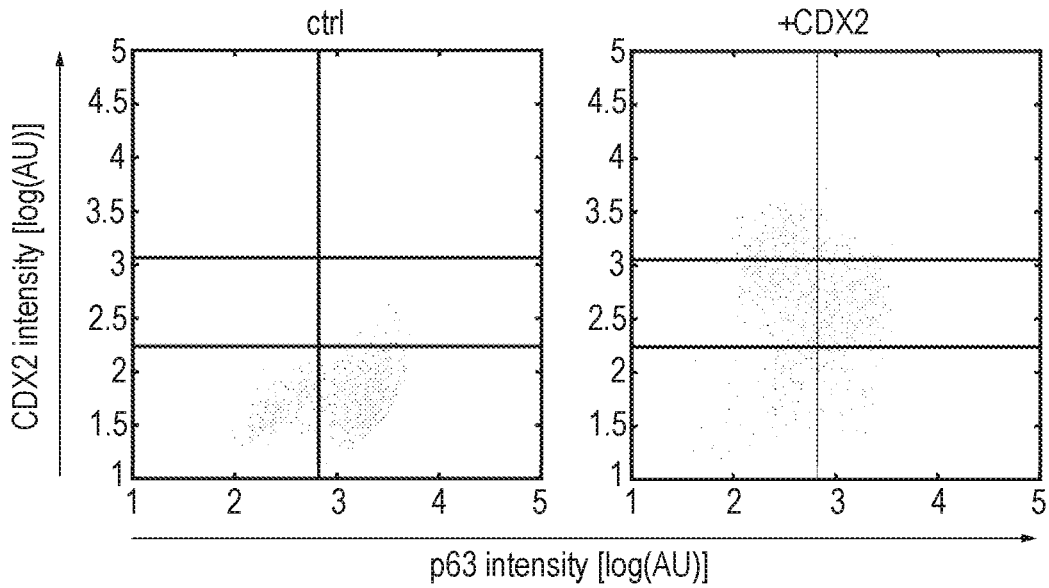
FIG. 18F
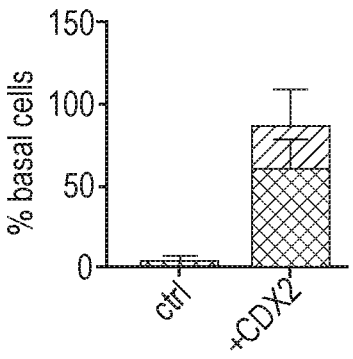
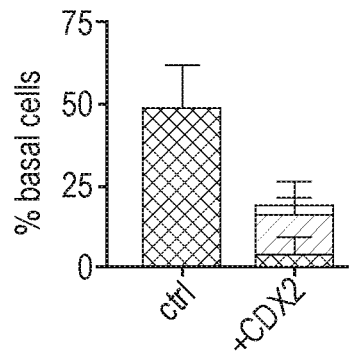
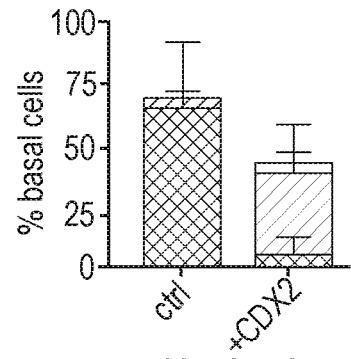
FIG. 18G        FIG. 18H        FIG. 18I

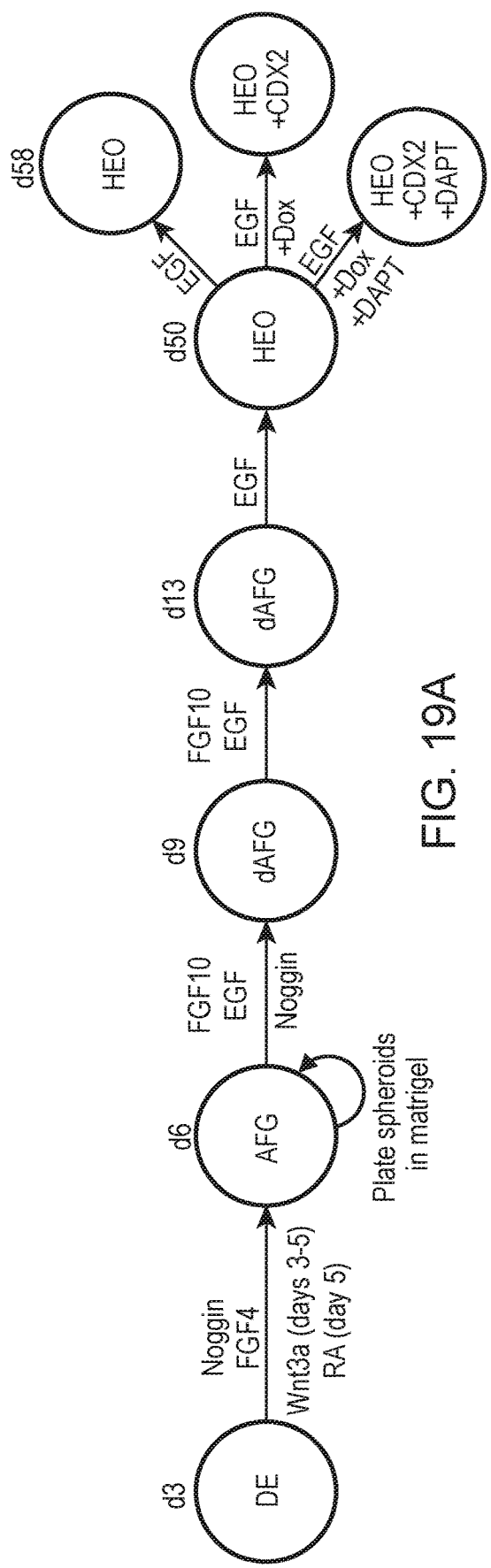
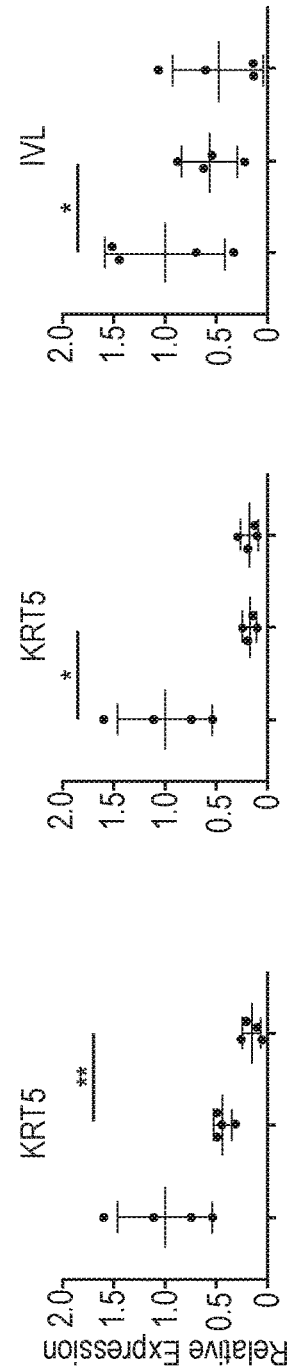
FIG. 19A
FIG. 19B
FIG. 19C
FIG. 19D

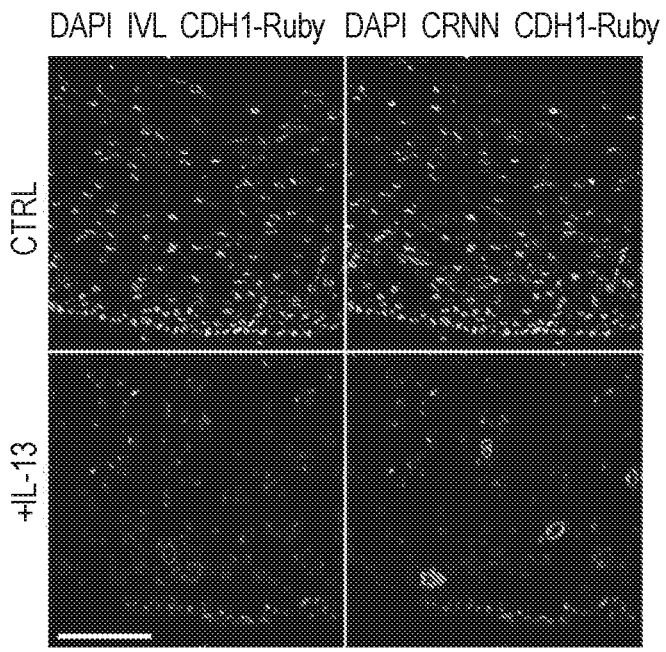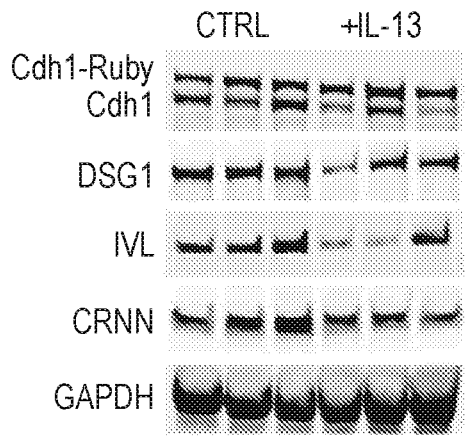
FIG. 21A
FIG. 21B
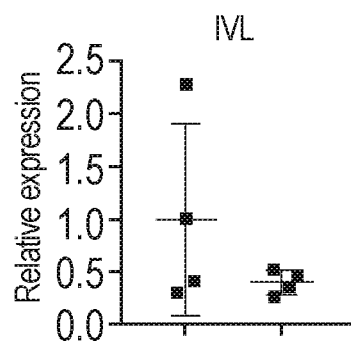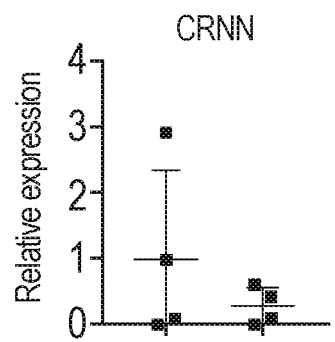
FIG. 21C
FIG. 21D
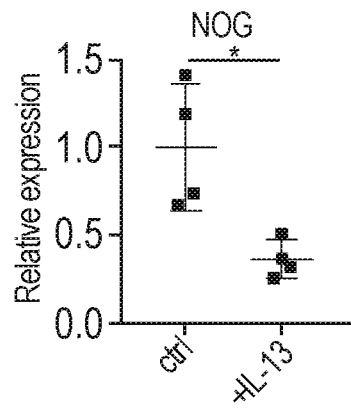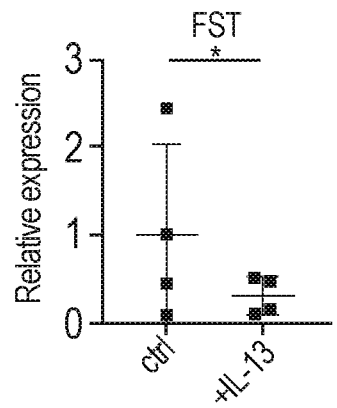
FIG. 21E
FIG. 21F

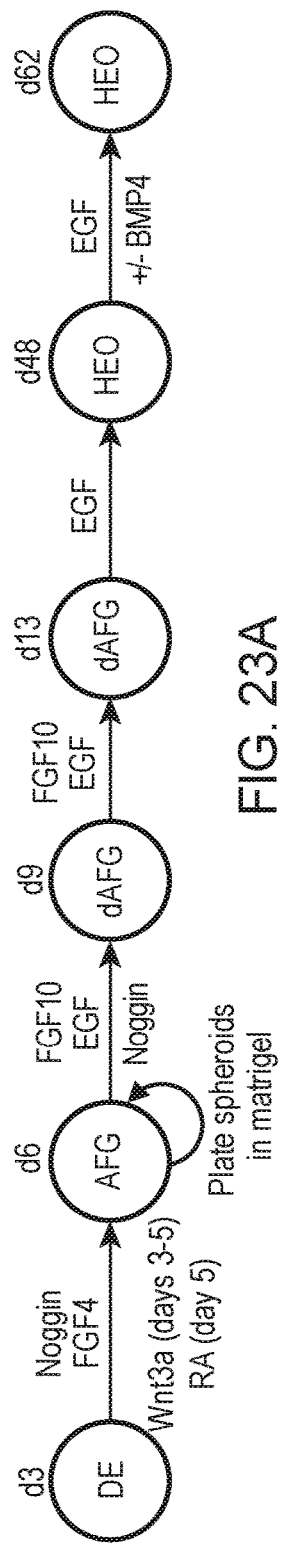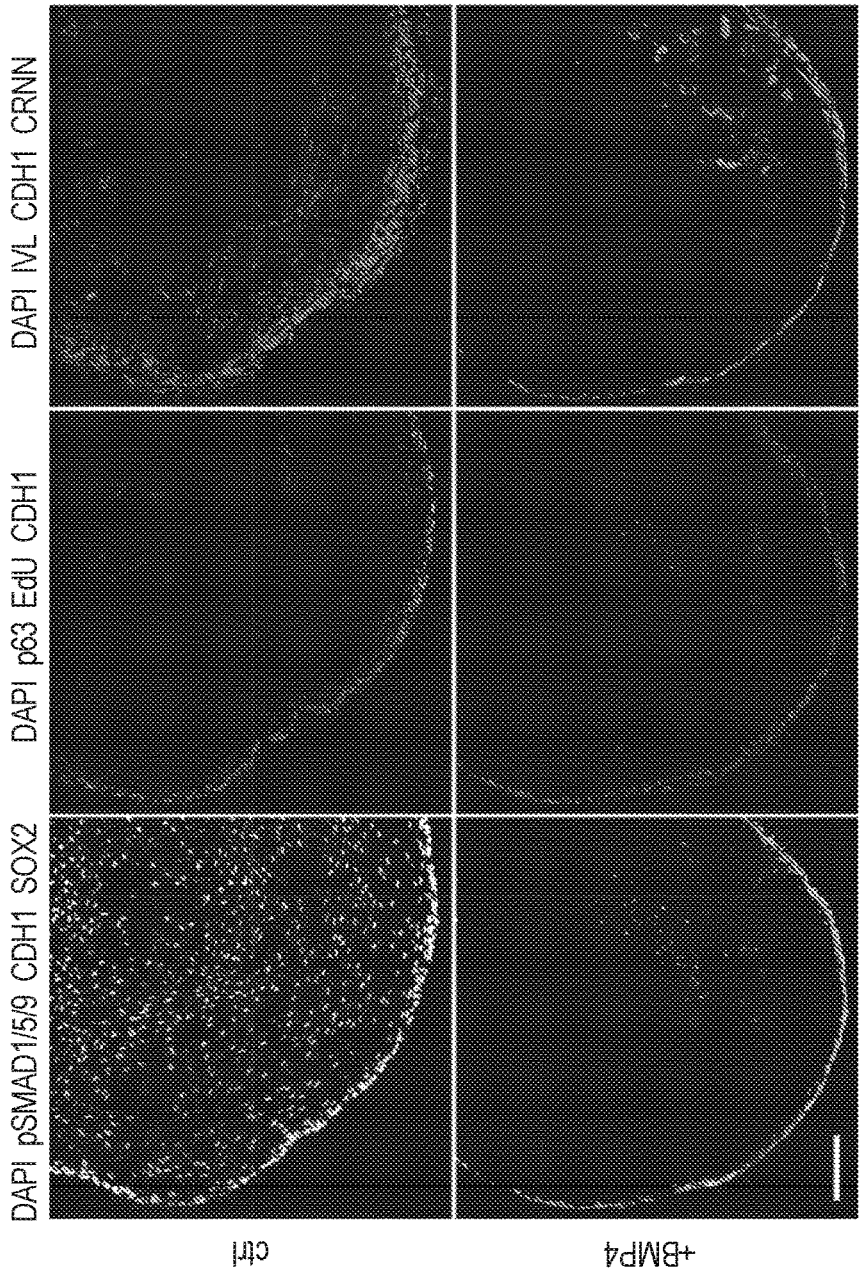
FIG. 23A
FIG. 23B

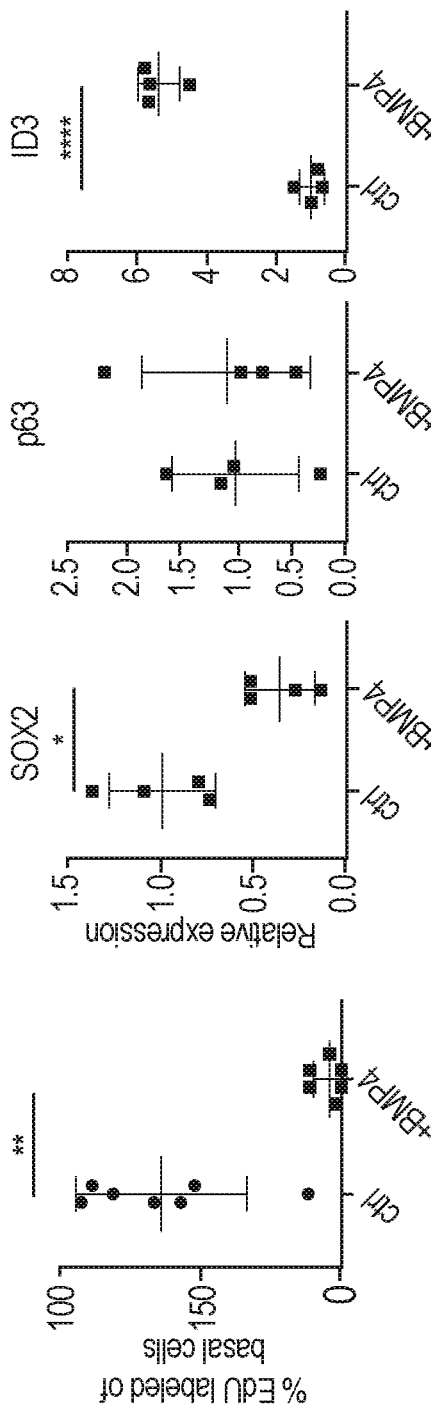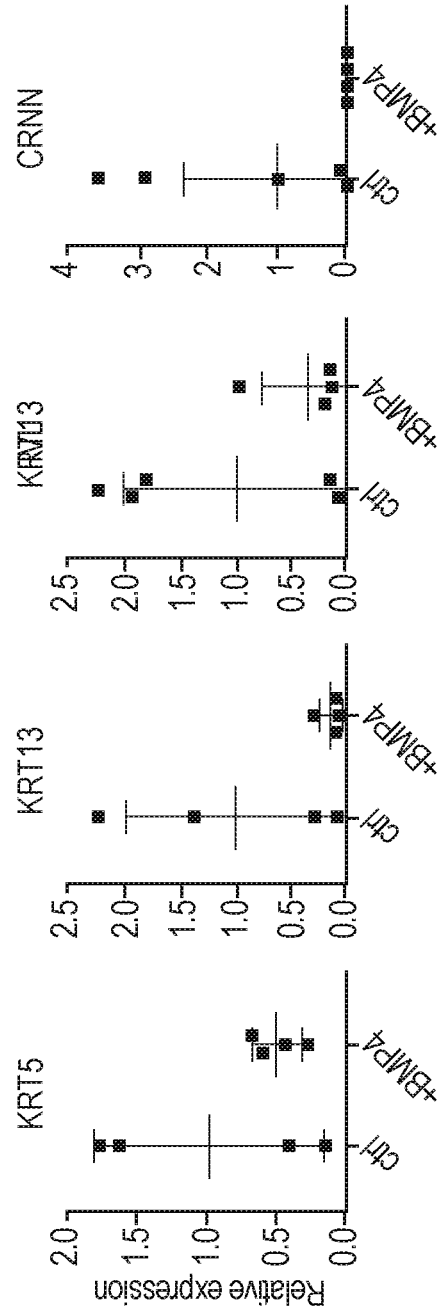

ESOPHAGEAL TISSUE AND/OR ORGANOID COMPOSITIONS AND METHODS OF MAKING SAME

CROSS-REFERENCE TO RELATED APPLICATIONS

This application claims priority to and benefit of International Application No. PCT/US18/54635 entitled "Esophageal Tissue and/or Organoid Compositions and Methods of Making Same," filed Oct. 5, 2018, which claims priority to and benefit of U.S. Provisional Application 62/570,182, to James Wells, filed Oct. 10, 2017, the contents of which are incorporated in their entirety for all purposes.

STATEMENT REGARDING FEDERALLY-SPONSORED RESEARCH

This invention was made with U.S. government support NIH grant number P01HD093363. The U.S. government has certain rights in this invention.

BACKGROUND

The esophagus actively facilitates the passing of food from the oral cavity and pharynx to the stomach. It consists of a stratified squamous epithelium, muscle layers, and an enteric nervous system to sense stretch and control peristalsis. Congenital diseases such as esophageal atresia are caused by gene mutations that result in luminal narrowing or discontinuity. Other diseases affect the esophagus later in life, such as esophageal carcinoma, eosinophilic esophagitis, achalasia and other motility disorders. Tracheal and esophageal disorders are prevalent in humans and are difficult to accurately model in mice. Despite the prevalence of the aforementioned disease states, and because there are substantial differences in tissue architecture between mouse and human esophagus, there is a need in the art for human esophageal tissue models for research. The instant disclosure addresses one or more of the aforementioned needs in the art.

BRIEF SUMMARY

The instant disclosure relates to methods for converting mammalian definitive endoderm (DE) cells into specific tissue(s) or organ(s) through directed differentiation. In particular, the disclosure relates to formation of esophageal tissue and/or organoids formed from differentiated definitive endoderm.

BRIEF DESCRIPTION OF THE DRAWINGS

Those of skill in the art will understand that the drawings, described below, are for illustrative purposes only. The drawings are not intended to limit the scope of the present teachings in any way.

FIGS. 5A-5L. Early endodermal deletion of Sox2 results in esophageal agenesis in mouse. (5A-5D) IF analysis for Sox2 and Nkx2-1 in control embryos (Sox2$^{fl/fl}$) and Sox2 conditional endodermal knockout embryos (Sox2-DE-LOF, FoxA2$^{CreER}$; Sox2$^{fl/fl}$) from pregnant dams gavaged with tamoxifen at 6.5 dpc. Embryo sections at E9.5 (5A-5B) and whole-mount IF at E11.5 (5C-5D) in which the image is masked highlight the endoderm. (5E-5F) IF images of sections with the relative section indicated in the whole-mount images (5C-5D) for Nkx2-1 (5E) and p63 (5F). Insets show only the Sox2 channel (left) and the green/right (Nkx2-1 or p63) channel (5G-5H) Analysis of cell death by cleaved Caspase 3 staining in E10.5 Sox2 cKO (Sox2$^{CreER/fl}$) embryos from pregnant dams gavaged at 8.5 dpc. The boxed region is magnified and shown in (5G-1-5H-1), with the endoderm is outlined in white and displays only the cleaved Caspase 3. (5I-5L) IF analysis of E11.5 mouse control and Sox2 cKO embryos (Sox2$^{CreER/fl}$) from pregnant dams gavaged at 9.5 dpc. (5I and 5J) Whole-mount IF for Nkx2-1 and Foxa2 of the foregut from a side and frontal projection. (5K and 5L) Sections of the E11.5 foregut corresponding to their relative position in the whole-mount IF projections (5I-5J), stained for Nkx2-1 (5K) and p63 (5J), with the yellow arrowhead pointing at the mutant esophagus. Scale bar=50 μm in all IF sections, and 100 μm in all IF whole-mount projections. See quantification and statistical analysis section for details. fg=foregut, dfg=dorsal foregut, vfg=ventral foregut, eso=esophagus, tr=trachea, br=bronchi, st=stomach. See also FIG. 13A-13F.

FIGS. 7A-7L. Sox2 regulates expression of secreted Wnt antagonists and Wnt signaling activity in the dorsal foregut endoderm. (7A) Clustered heatmap of differentially expressed genes from RNA sequencing of day 9 dorsal (+Noggin) or ventral (+BMP4) AFG cultures with (+dox) and without SOX2 CRISPR interference (CRISPRi). (7B) Venn diagram analysis of genes upregulated in dorsal and ventral cultures compared to genes that are elevated or decreased following SOX2 knockdown by CRISPRi. (7C) Gene ontology (GO) term analysis on biological processes for genes positively regulated by SOX2. (7D) Number of genes enriched in dorsal and ventral cultures and whether their expression was SOX2-dependent. (7E) Gene set enrichment analysis of the gene ontology term "Regulation of Wnt signaling pathway", red indicating higher expression while blue indicates low expression. (7F-7G) In situ hybridization for the Wnt-responsive gene Axin2 on E9.5 mouse anterior foreguts in (7F) control (Sox2$^{fl/fl}$) and (7G) Sox2-DE-LOF (FoxA2$^{CreER}$; Sox2$^{fl/fl}$) embryos. (7H-7I) In situ hybridization for Axin2 in E10.5 mouse embryonic foregut of (7H) control (Sox2$^{fl/+}$) and (7I) Sox2 cKO (Sox2$^{CreER/fl}$) embryos taken from dams gavaged at 8.5 dpc. Numbers of embryos analyzed is shown in the upper left. Boxed regions (7F-7I) highlight the dorsal foregut region. (7J) qPCR analysis for AXIN2 in day 9 dorsal and ventral foregut cultures with or without SOX2 exogenously expressed. (7K) Plotted TPM values for Wnt antagonists SFRP1, SFRP2, and DKK1 from RNA-seq of AFG cultures. (7L) Proposed model on role of Sox2 in dorsal-ventral patterning of the anterior foregut. Scale bar=100 μm. See materials and methods & quantification and statistical analysis section for details. See also FIG. 14A-14D.

FIGS. 15A-15E. The role of Sox2 in the development of the esophagus after anterior foregut separation. (15A) Schematic of mouse breeding and tamoxifen administration scheme. (15B) Confocal immunofluorescence (IF) images of E14.5 (left), E17.5 (middle), and P7 (right) esophageal sections with pregnant dams gavaged at 11.5 dpc (left), 14.5 dpc (middle), and pups gavaged at P1 (right), respectively. Sections were stained for E-cadherin to visualize the epithelium, Sox2, and Nkx2-1 for respiratory identity. (15C) IF images of E17.5 esophagus from pregnant dams gavaged at 11.5 dpc for various markers: p63 and Sox2 to confirm esophageal identity, the basal marker Krt14, the suprabasal marker Krt13, the immature or columnar marker Krt8, the proliferation marker Ki67. The green arrowhead in the bottom middle right panel highlights suprabasal Ki67 staining (15D) High magnification IF image of E17.5 esophagus from pregnant dams gavaged at 11.5 dpc for E-cadherin. (15E) IF images of E17.5 esophagus from pregnant dams gavaged at 11.5 dpc for patterning markers: the intestinal marker Cdx2, the gastric/intestinal markers Gata4 and Pdx1, the respiratory marker Nkx2-1, and smooth muscle marker Desmin. The yellow arrowhead highlights the rare Nkx2-1 positive cells in the mutant esophagus. Scale bar=100 μm in (15B, 15C, 15E), and 25 μm in (15D).

FIGS. 18A-18I. 18A) Late induction of CDX2 in HEOs result in repression of esophageal transcription factors SOX2 and p63. 18A. Schematic depicting experimental protocol to induce CDX2 in more mature HEOs (6-7 weeks old). 18B IF images of day 58 HEOs with (+CDX2) or without doxycycline treatment for stratified squamous markers SOX2 and p63 and hindgut marker CDX2. (18C-18E) qPCR analysis of day 58 HEOs for (18C) CDX2, (18D) SOX2, and (18E) p63. (18F) Analysis of IF images (such as 18B) by scatter plot of HEO basal epithelial cells for CDX2 versus p63 intensity. Vertical line divides the p63-negative (left) and p63 positive (right) cells. Horizontal lines divide the CDX2-negative (bottom), CDX2-low (middle), and CDX2-high (top) cells (18G-18I) Quantification of IF analysis (see 18B and 18F) for (18G) all CDX2-high and CDX2-low basal cells (18H) CDX2-high and CDX2-low basal cells that are SOX2+, (18I) CDX2-high and CDX2-low basal cells that are p63+. Scale bar=100 um. ***p≤0.0001 for Student's t-test with 2-tailed distribution not assuming equal variance. DE=definitive endoderm; AFG=anterior foregut; dAFG=dorsal anterior foregut; HEO=human esophageal organoid.

FIGS. 19A-19H. Loss of esophageal differentiation in CDX2-induced HEOs. (19A) Schematic of the experimental protocol to induce CDX2 with or without Notch inhibition in HEOs. (19B-19G) qPCR analysis of d58 HEOs for the stratified squamous markers (19B) KRT5, (19C) KRT13, and (19D) IVL, (19E) the intestinal epithelial marker CDH17, (19F) the Notch target HESS, and (19G) the BMP target ID1. (19H) IF images of HEOs treated with doxycycline and γ-secretase (Notch) inhibitor DAPT for CDH17, KRT5, and KRT13 (top row); and the differentiated stratified squamous markers CRNN and IVL (bottom row). Scale bar=100 μm. *p≤0.05, p≤0.01, and *p≤0.001 for Student's t-test with 2-tailed distribution not assuming equal variance. DE=definitive endoderm; AFG=anterior foregut; dAFG=dorsal anterior foregut; HEO=human esophageal organoid.

FIGS. 21A-L. Impaired differentiation and altered morphology of HEOs treated with IL-13. (21A) IF analysis of day 62 HEOs treated with IL-13 (100 ng/mL) for 2 weeks prior to harvest. (21B) Western blot analysis of day 56 HEOs treated with IL-13 (100 ng/mL) for 1 week prior to harvest for structural and differentiated proteins. (21C-21F) qPCR analysis of day 62 HEOs treated with IL-13 (100 ng/mL) for 2 weeks prior to harvest for (21C) IVL, (21D) CRNN, and the BMP antagonists (21E) NOG and (21F) FST. (21G) Structural analysis of day 62 HEOs treated with IL-13 (100 ng/mL) for 2 weeks prior to fixation by H&E staining (left column) and electron micrographs (right column) (21H-21L) qPCR analysis of day 62 HEOs treated with IL-13 (100 ng/mL) and BMP4 (100 ng/mL) for (21H) SOX2, (21I) CCL26, (21J) CDH26, (21K) the hedgehog target PTCH1, and (21L) the BMP target ID3. Scale bar=100 μm for IF and H&E images, and 6 μm for electron micrographs. *p≤0.05, p≤0.01, *p≤0.001, and ****p≤0.0001 for Student's t-test with 2-tailed distribution not assuming equal variance.

Figure 1A:
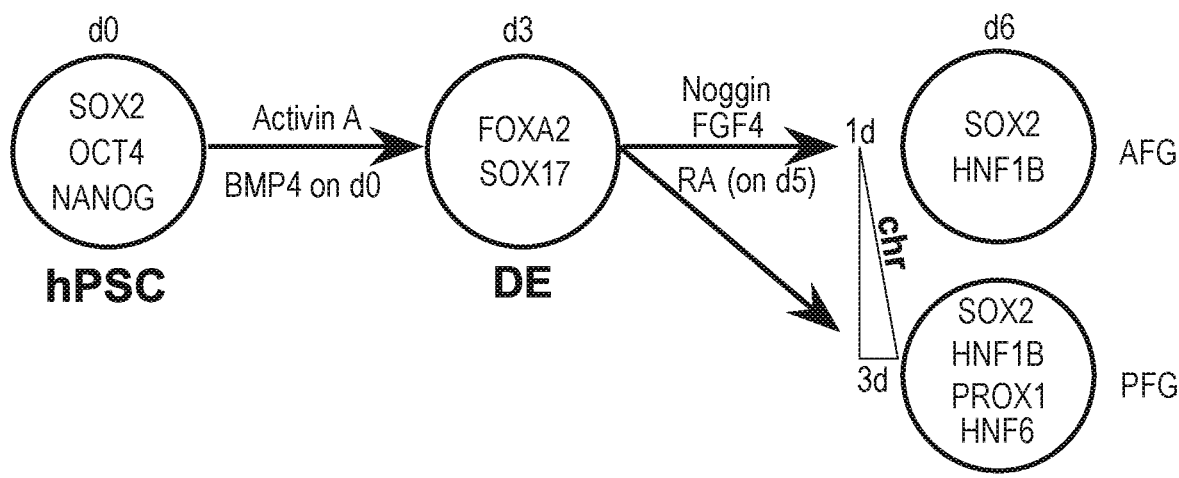
FIGS. 1A-1K. Specifying anterior foregut fate by modulating Wnt and retinoic acid signaling during foregut spheroid development. (1A) The experimental protocol to pattern foregut spheroids along anterior-posterior axis by manipulating the duration of Wnt activation (chiron-chr). (1B-1C) qPCR analysis of varying chiron treatment duration on patterning of foregut spheroids as measured by (1B) the foregut marker SOX2 and mid/hindgut marker CDX2, and (1C) the anterior foregut ("AFG") marker HNF1B, and the posterior foregut markers PROX1 and HNF6. (D-E) Whole-mount immunofluorescence ("IF") analysis with HNF1B, SOX2 and CTNNB1 of nascent spheroids (day 6) treated with 1 day (1D) and 3 days (1E) of chiron. (1F) The experimental protocol to pattern foregut spheroids along anterior-posterior axis using retinoic acid (RA). (1G) Effects of varying the duration of RA treatment on 3-day-old foregut spheroids as measured by SOX2, TP63 (ΔN isoform), GATA4, and PDX1. (1J-1K) IF analysis on early esophageal markers SOX2 and p63 in untreated spheroids (H), and spheroids treated with RA for 1 day (1J) or 4 days (1K). 1I-1, 1J-1, and 1K-1 show p63 staining alone (1H) Quantification of the percent of SOX2+ and p63+ epithelial cells per spheroid. Scale bar=25 µm. See quantification and statistical analysis section for details. See also FIG. 8 and FIG. 9A-R.

FIGS. 22A-22H. SOX2-induction in human intestinal organoids (HIOs) upregulate stratified squamous markers. (22A) Schematic depicting experimental protocol to induce SOX2 in HIOs. (22B) Schematic of the transduced lentiviral vector to induce HA-tagged SOX2 upon administration of doxycycline (22C) IF images of day 36 HIOs treated with or without doxycycline for (top) the foregut marker SOX2 and hindgut marker CDX2 (middle) anterior foregut marker p63, gastric/intestinal marker PDX1, and the HA-tag; (bottom) the intestinal marker CDH17 and gastric marker CLDN18 (22D-22H) qPCR analysis for various regional markers (22D) SOX2, (22E) p63, (22F) PDX1, and (22G) CDX2, and (22H) the suprabasal stratified squamous marker KRT13. Scale bar=100 um. *p≤0.05, p≤0.01, and **p≤0.0001 for Student's t-test with 2-tailed distribution not assuming equal variance. DE=definitive endoderm; HG=hindgut; HIO=human intestinal organoid.

FIGS. 23A-23J. BMP activation in HEOs result in loss of proliferation and differentiation. (23A) Schematic depicting the experimental protocol to activate BMP signaling in late stage HEOs. (23B) IF images of day 62 HEOs treated with or without BMP4 (100 ng/mL) for: (left) pSMAD1/5/9 and SOX2, (middle) p63 and EdU, (right) IVL and CRNN. (23C) Quantification for the percent EdU labeled of all basal-most epithelial cells in HEOs with or without BMP4. (23D-23J) qPCR analysis of day 62 HEOs for various markers: (D) SOX2, (23E) p63, (23F) ID3, (23G) KRT5, (23H) KRT13, (23I) IVL, and (23J) CRNN. Scale bar=100 μm. For qPCR data, *p≤0.05 and **p≤0.0001 for Student's t-test with 2-tailed distribution not assuming equal variance. For organoid EdU incorporation quantification (23C), p≤0.01 for Mann-Whitney non-parametric test. DE=definitive endoderm; AFG=anterior foregut; dAFG=dorsal anterior foregut; HEO=human esophageal organoid.

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

As used herein, the term "definitive endoderm (DE) cell" means one of the three primary germ layers produced by the process of gastrulation.

As used herein the term "wnt signalling pathway" means the wnt/beta-catenin pathway and is a signal transduction pathway that is mediated by Wnt ligands and frizzled cell surface receptors that acts through the beta-catenin protein.

As used herein the term "activator" with respect to a pathway, such as a "wnt pathway" means a substance that activates the Wnt/beta-catenin pathway such that Wnt/beta-catenin targets are increased.

As used herein, the term "FGF signaling pathway activator" means a substance that activates the FGF pathway such that FGF targets are increased.

As used herein, the term "BMP signaling pathway inhibitor" a substance that interferes with the BMP pathway and causes BMP targets to be decreased.

As used herein, the term "growth factor" means a substance capable of stimulating cellular processes including but not limited to growth, proliferation, morphogenesis or differentiation.

As used herein, the term "stable expression" of a marker means expression that does not change upon modification of the growth environment.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryos (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent stem cell; a pluripotent stem cell (induced or non-induced); a multipotent stem cell; and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

Pluripotent Stem Cells Derived from Embryonic Cells

In some embodiments, an important step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UCO1 (HSF1); UCO6 (HSF6); WA01 (H1); WA07 (H7); WA09 (H9); WA13 (H13); WA14 (H14).

More details on embryonic stem cells can be found in, for example, Thomson et al., 1998, "Embryonic Stem Cell Lines Derived from Human Blastocysts," Science 282 (5391):1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458):768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," Nature 458:771-775; Woltjen et al., 2009, "piggyBac transposition reprograms fibroblasts to induced pluripotent stem cells," Nature 458:766-770; Okita et al., 2008, "Generation of Mouse Induced Pluripotent Stem Cells Without Viral Vectors," Science 322(5903):949-953; Stadtfeld et al., 2008, "Induced Pluripotent Stem Cells Generated without Viral Integration," Science 322(5903):945-949; and Zhou et al., 2009, "Generation of Induced Pluripotent Stem Cells Using Recombinant Proteins," Cell Stem Cell 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

More details on the functions of signaling pathways relating to DE development can be found in, for example, Zorn and Wells, 2009, "Vertebrate endoderm development and organ formation," Annu Rev Cell Dev Biol 25:221-251; Dessimoz et al., 2006, "FGF signaling is necessary for establishing gut tube domains along the anterior-posterior axis in vivo," Mech Dev 123:42-55; McLin et al., 2007, "Repression of Wnt/β-catenin signaling in the anterior endoderm is essential for liver and pancreas development. Development," 134:2207-2217; Wells and Melton, 2000, Development 127:1563-1572; de Santa Barbara et al., 2003, "Development and differentiation of the intestinal epithelium," Cell Mol Life Sci 60(7): 1322-1332; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

Tracheal and esophageal disorders are prevalent in humans and are difficult to accurately model in mice. Applicant therefore established a three-dimensional organoid model of esophageal development through directed differentiation of human pluripotent stem cells. Sequential manipulation of BMP, WNT, and RA signaling pathways allowed pattern definitive endoderm into foregut, anterior foregut (AFG), and dorsal AFG spheroids. Dorsal AFG spheroids grown in a 3D matrix formed human esophageal organoids (HEOs), and HEO cells could be transitioned into two-dimensional cultures and grown as esophageal organotypic rafts. In both configurations, esophageal tissues had proliferative basal progenitors and a differentiated stratified squamous epithelium. Using HEO cultures to model human esophageal birth defects, Applicant identified that Sox2 promotes esophageal specification in part through repressing Wnt signaling in dorsal AFG and promoting survival. Consistently, Sox2 ablation in mice causes esophageal agenesis. Thus, HEOs present a powerful platform for modeling human pathologies and tissue engineering.

Human tissue organoids, differentiated from pluripotent stem cells (PSCs) or obtained directly from organs, have proven to be excellent models of tissue physiology and pathology (McCauley and Wells, 2017). In general, the process of converting PSCs into organ cell types relies on step-wise differentiation that recapitulates organogenesis, including formation of definitive endoderm (DE), anterior-posterior patterning into foregut, midgut, and hindgut, organ specification, and differentiation into organ specific lineages. This approach has been used to generate human anterior and posterior endoderm organoids including respiratory, gastric, small intestine and colon (Chen et al., 2017; Dye et al., 2015, 2016, McCracken et al., 2014, 2017; Múnera et al., 2017; Spence et al., 2011). However, human PSC-derived esophageal tissues have not been reported. Dual BMP and TGFβ inhibition after DE induction generates anterior foregut (AFG); however, this yielded a mix of tissues including pharyngeal, esophageal and respiratory endoderm (Green et al., 2011; Kearns et al., 2013; Longmire et al., 2012). This suggests that a more refined patterning approach based on pathways that control esophageal development is required to direct differentiation of PSCs specifically into esophagus.

Several signaling pathways guide differentiation and morphogenesis of the developing esophagus. The esophageal epithelium derives from definitive endoderm (DE), a 2-dimensional sheet of cells that forms during gastrulation (Zorn and Wells, 2007). The DE then is patterned along the anterior-posterior axis by Wnt, BMP and FGF signaling and forms a primitive gut tube, divided broadly into the foregut, midgut, and hindgut (Dessimoz et al., 2006; McLin et al., 2007; Stevens et al., 2017; Zorn and Wells, 2009). The foregut is further patterned into posterior foregut by retinoic acid (RA) (Bayha et al., 2009; Niederreither et al., 1999; Wang et al., 2006). The anterior foregut (AFG) gives rise to the esophagus and respiratory tract. Respiratory specification in response to Wnt and BMP activation results in expression of the transcription factor Nkx2-1 whereas inhibition of BMP in the dorsal foregut promotes development of Sox2-expressing esophageal epithelium (Domyan et al., 2011; Goss et al., 2009; Harris-Johnson et al., 2009; Que et al., 2006; Rankin et al., 2016). The esophagus starts as a simple cuboidal epithelium but develops into a stratified squamous epithelium that expresses multiple keratin proteins and a basal layer that expresses Sox2 and p63 (Rosekrans et al., 2015; Zhang et al., 2016).

Disclosed herein is the temporal manipulation of the above signaling pathways to differentiate human PSCs into esophageal organoids. Following DE formation, Applicant identified that precise temporal manipulation of BMP, WNT, and RA pathways direct formation of AFG spheroids. Consistent with in vivo data, AFG spheroids acquired a respiratory fate through activation of WNT and BMP pathways whereas BMP inhibition promoted formation of dorsal foregut spheroids that upon continued growth for 1-2 months formed human esophageal organoids (HEOs). HEOs contained stratified squamous epithelium, with distinct basal and luminal cell layers, and harbored proliferative esophageal progenitors that could be expanded and differentiated into esophageal epithelium in organotypic raft cultures. HEOs, used in parallel with mouse embryos, can be used to identify molecular pathways that are affected by SOX2 loss-of-function, one cause of esophageal atresia in humans and mice (Domyan et al., 2011; Que et al., 2007). While reduced Sox2 function leads to esophageal atresia in mice, complete loss of Sox2 in mouse foregut endoderm results in esophageal agenesis. Loss of SOX2 function and transcriptional profiling of human and mouse foregut identified that SOX2 regulates the dorsal expression of Wnt antagonists such as SFRP2, suggesting that SOX2 represses the ability of Wnt to induce a respiratory fate in the dorsal foregut. Net, Applicant has found that the disclosed HEOs provide a complementary platform to study human esophageal organogenesis, birth defects, and disease.

In one aspect, a method of making an esophageal organoid (EO) is disclosed. The method may comprise the steps of contacting a definitive endoderm with a BMP inhibitor, a Wnt activator, an FGF activator, and retinoic acid (RA). This contacting step may be for a first period of time sufficient to form an anterior foregut culture. In one aspect, the anterior foregut culture expresses SOX2 and HNF1B after such first period of time, and does not substantially express PROX1 and HNF6. The method may further comprise the step of contacting the anterior foregut culture with a BMP inhibitor (Noggin), and an EGF activator for a second period of time sufficient to form a dorsal anterior foregut ("dAFG") spheroid, wherein the dAFG may express SOX2 and TP63 but not PDX1, PAX9, or NKX2.1. The method may further comprise the step of culturing the dAFG for a third period of time sufficient to allow formation of an esophageal organoid (EO), wherein said culturing is carried out in the presence of EGF, further optionally including an FGF signaling pathway activator, preferably FGF10. In one aspect, the EO is a human esophageal organoid (HEO).

Exemplary gene (or mRNA when gene is not available) accession numbers are provided as follows: SOX2 (NG_009080.1); HNF1B (NG_013019.2), PROX1 (NC_000001.11); HNF6 (NM_214659.1); TP63 (NG_007550.1); PDX1 (NG_008183.1), PAX9 (NG_013357.1); and NKX2.1 (NG_013365.1). It is to be noted that the Gene Name as listed above (i.e., "SOX2, HNF1B, etc.) is sufficient for one of ordinary skill in the art to identify the recited gene. The named genes are intended to encompass variations of the gene and are not intended to be limited by the naming of exemplary accession numbers provided. That is, the provided accession numbers are not intended to limit the scope of the gene and/or claims, is but one of many identifiers for these genes/mRNA/protein, and is solely exemplary in nature. That is, the identifiers may only refer to specific isoform/variant which may be one of many. This distinction will be readily appreciated by one of ordinary skill in the art, and one of ordinary skill in the art will appreciate that the recited genes encompass variants and genes having sequences different from that associated with the accession numbers above.

In one aspect, the definitive endoderm may be derived from a precursor cell selected from an embryonic stem cell, an embryonic germ cell, an induced pluripotent stem cell, a mesoderm cell, a definitive endoderm cell, a posterior endoderm cell, a posterior endoderm cell, and a hindgut cell. In one aspect, the definitive endoderm may be derived from a pluripotent stem cell. In one aspect, the definitive endoderm may be derived from a pluripotent stem cell selected from an embryonic stem cell, an adult stem cell, or an induced pluripotent stem cell. In one aspect, the DE may be a DE monolayer, wherein greater than 90% of the cells in the DE monolayer co-express FOXA2 and SOX17.

In one aspect, the definitive endoderm may be derived from contacting a pluripotent stem cell with one or more molecules selected from Activin, the BMP subgroups of the TGF-beta superfamily of growth factors; Nodal, Activin A, Activin B, BMP4, Wnt3a, and combinations thereof.

In one aspect, the BMP signaling pathway inhibitor may be selected from Noggin, Dorsomorphin, LDN189, DMH-1, and combinations thereof. In one aspect, the BMP signaling pathway inhibitor is Noggin. The BMP inhibitor may be present at a concentration of between from about 50 to about 1500 ng/ml.

In one aspect, the WNT activator may be selected from one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSKβ inhibitor (e.g., CHIR99021, i.e. "CHIRON"), BIO, LY2090314, SB-216763, lithium, porcupine inhibitors IWP, LGK974, C59, SFRP inhibitor WAY-316606, beta-catenin activator DCA. The concentration of the Wnt pathway activator may be, for example, used at a concentration between about 50 to about 1500 ng/ml. There are many ways to activate the Wnt/beta-catenin pathway (see http://web.stanford.edu/group/nusselab/cgi-bin/wnt/). Suitable Some existing wnt signalling pathway activators include but are not limited to protein-based activators, which may include Wnt ligands including but not limited to Wnt1, Wnt2, Wnt2b, Wnt3, Wnt3a, Wnt8, et al; modifiers of Wnt ligand activity including but not limited to activated Wnt frizzled receptors, (LRP) co-receptors, R-spondin proteins, Dkk proteins, regulators of Wnt ligand secretion and trafficking (Wnt1ess, Porcupine), inhibiting beta-catenin degradation APC and GSK3beta inhibition, activated beta-catenin, constitutively active TCF/Lef proteins and chemical activators, which may include over 28 known chemicals that either activate or inhibit Wnt/beta-catenin signaling. Some activators include but are not limited to GSK3-beta inhibitors CHIR99021 (CHIRON), BIO, LY2090314, SB-216763, lithium, porcupine inhibitors IWP, LGK974, C59, SFRP inhibitor WAY-316606, beta-catenin activator DCA.

In one aspect, the FGF activator may be one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, FGF23, and combinations thereof, preferably FGF4 or FGF10, or a combination thereof. In one aspect, the concentration of the FGF pathway activator may be used at a concentration between about 50 to about 1500 ng/ml. Proteins and chemicals that stimulate the FGF receptor and signaling components downstream of the receptors including MAPK, MEK, ERK proteins and chemicals that modulate their activity. FGF signaling can be activated by inhibiting inhibitors of FGF signaling pathways including but not limited to Sprouty protein family members.

In one aspect, the retinoic acid of step a may be contacted with the DE for a period of time of from about 12 hours to about 48 hours, or about 20 hours to about 40 hours, or about 24 hours, or until treatment results in PDX expression and loss of p63 expression.

In one aspect, said step c may be carried out for a period of time sufficient for formation of a stratified epithelium lacking KRT8. In one aspect, step c may be carried out for a period of time sufficient for formation a stratified squamous epithelium expressing regional keratins. In one aspect, step c may be carried out for a period of time sufficient for said HEO to express INV.

In one aspect, the first period may be a period of about three days ±24 hours. In one aspect, the second period may be a period of about three days ±24 hours. In one aspect, the third period may be a period of about 28 days ±48 hours, or about 21 days to about 90 days, or about 30 days to about 60 days. In one aspect, steps a through c may be conducted in vitro.

In one aspect, the method may further comprise the step of contacting the anterior foregut culture of step a) or the spheroid of step b) with a matrix selected from collagen, basement membrane matrix (Matrigel), or a combination thereof.

In one aspect, the esophageal compositions described herein may be characterized by being free of innervation and/or blood vessels. In one aspect, the composition is a human esophageal organoid (HEO) composition, wherein the HEO composition is substantially free of one or more of submucosal glands, transition zones, vasculature, immune cells, or submucosal layers.

In one aspect, an esophogeal progenitor cell capable of organizing into an organotypic culture is disclosed. The esophageal progenitor cell may be derived from the method disclosed herein.

In one aspect, a method of making a stratified squamous epithelium is disclosed. The method may comprise the steps of enzymatically dissociating an HEO as described herein to release progenitor cells, wherein the HEO is at an age of about 3 weeks to about 10 weeks, or about 4 weeks to about 8 weeks, or about 5 weeks of age; expanding said progenitor cells in a monolayer; and re-differentiating the dissociated HEOs into a stratified squamous epithelium on a collagen coated membrane for a period of time sufficient to give rise to a non-keratinized stratified squamous epithelium, wherein the non-keratinized stratified squamous epithelium expresses keratins and one or more markers selected from IVL, CRNN, and FLG. In one aspect, stratified squamous epithelium may comprise esophageal cells organized substantially in the form of a sheet.

In one aspect, a method of treating a disease of the esophagus in an individual in need thereof is disclosed. The disease may be selected from a congenital disease (atresia), a functional disease (achalasia and other motility disorders) an immunological disease (eosinophilic esophagitis), pathological disease (Barrett's esophagus and esophageal carcinoma), and combination thereof, comprising the step of contacting an esophageal composition (such as an HEO or esophageal sheet) as disclosed herein, with said individual.

In one aspect, the disease may comprise an ulcer or ulcerated tissue of the esophagus, and the disclosed esophageal compositions may be used to contact and repair the ulcerated tissue. For example, in one aspect, the esophageal composition may comprise esophageal cells organized substantially in the form of a sheet, which may be contacted with the patient.

In one aspect, a method of identifying a treatment for eosinophilic esophagitis is disclosed. In this aspect, the method may comprise the step of contacting a potential therapeutic agent of interest with an organoid or esophageal tissue as described herein, detecting a measure of eosinophilic esophagitis activity, and determining whether the potential therapeutic agent of interest improves a measure of eosinophilic esophagitis activity.

In one aspect, a method of making a Fanconi's anemia disease model is disclosed. In this aspect, the disclosed methods of making and HEO or an esophageal sheet are carried out as described herein, wherein the DE is obtained from a precursor cell deficient in FANCA.

In one aspect, a method of making a Barrett's metaplasia disease model is disclosed. In this aspect, the method may comprise the step of inducing CDX2 and activating BMP in an HEO or esophageal sheet made according to the methods disclosed herein.

In one aspect, A method of making an eosinophilic esophagitis disease model is disclosed. In this aspect, the method may comprise the step of contacting an HEO or esophageal sheet made according to the methods disclosed herein with IL-13 for a period of time sufficient to increase expression of CCL26 and CAPN14 and decrease expression of CRNN and IVL In one aspect, A method of identifying an active agent capable of treating an esophageal disease state is disclosed. comprising the step of contacting a test agent with an HEO or esophageal sheet made according to the methods disclosed herein for a period of time sufficient to elicit a physiological change in said disease model; and detecting a decrease in expression of CCL26 and CAPN14 and an increase in expression of CRNN and IVL for EoE; or detecting an increase in esophageal gene expression such as SOX2, p63, KRT13, CRNN, IVL and a loss of intestinal genes for Barrett's.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Wnt and Retinoic Acid Signaling Control Anterior Versus Posterior Foregut Fate

Figure 1B:
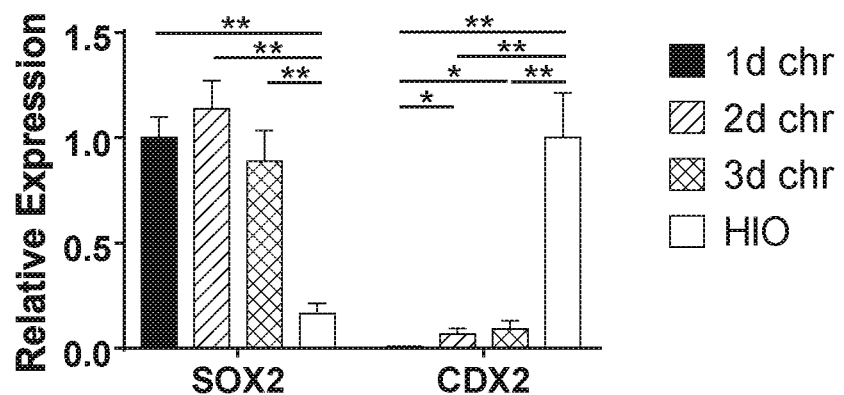
Figure 1C:
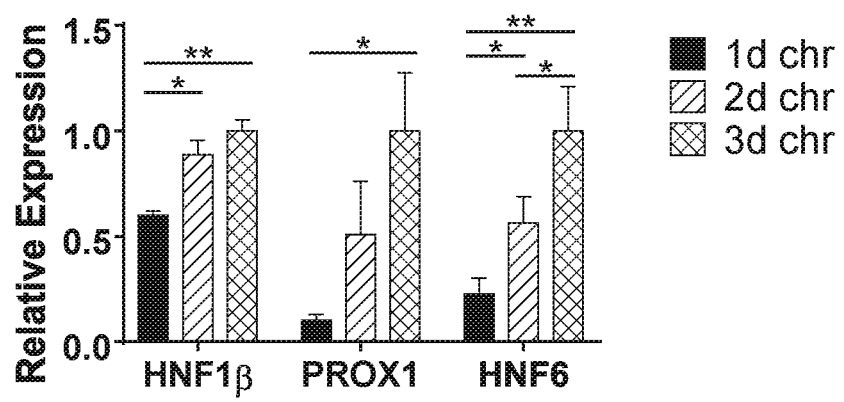
Figures 1, 1D:
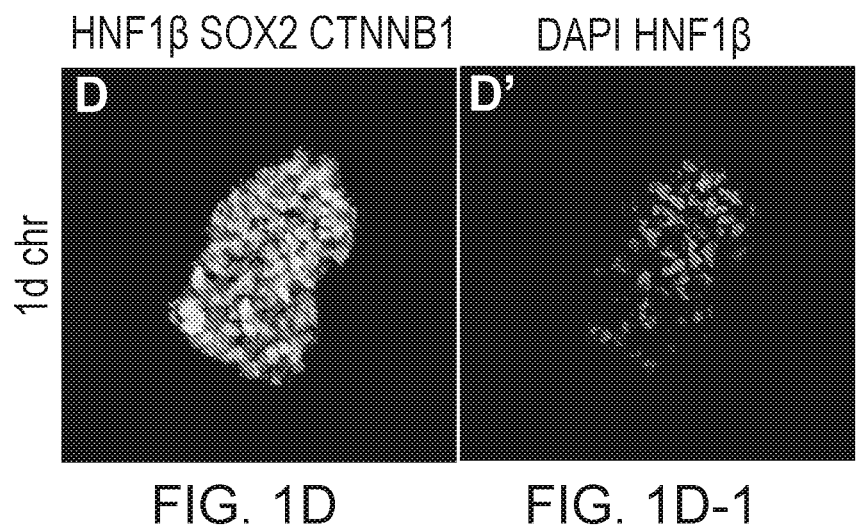
Figures 1, 1E:
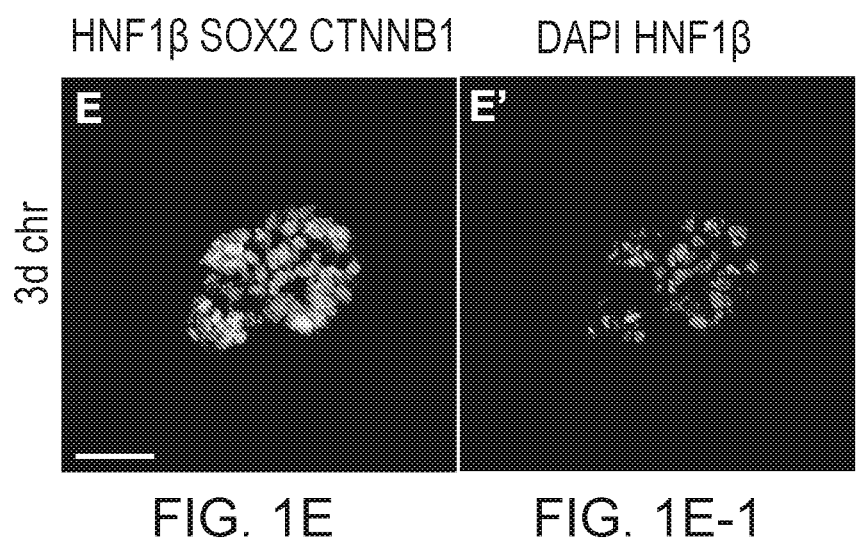
Figure 1F:
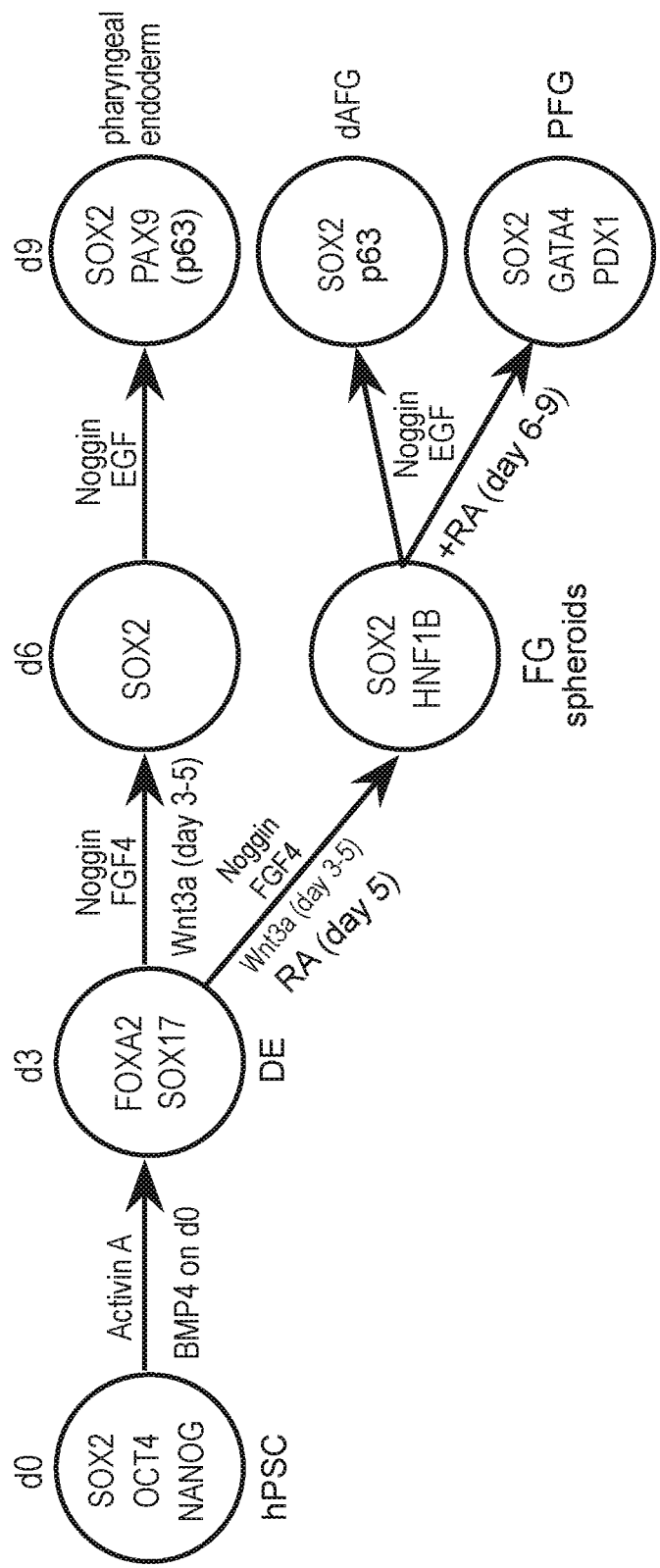
Figure 1G:
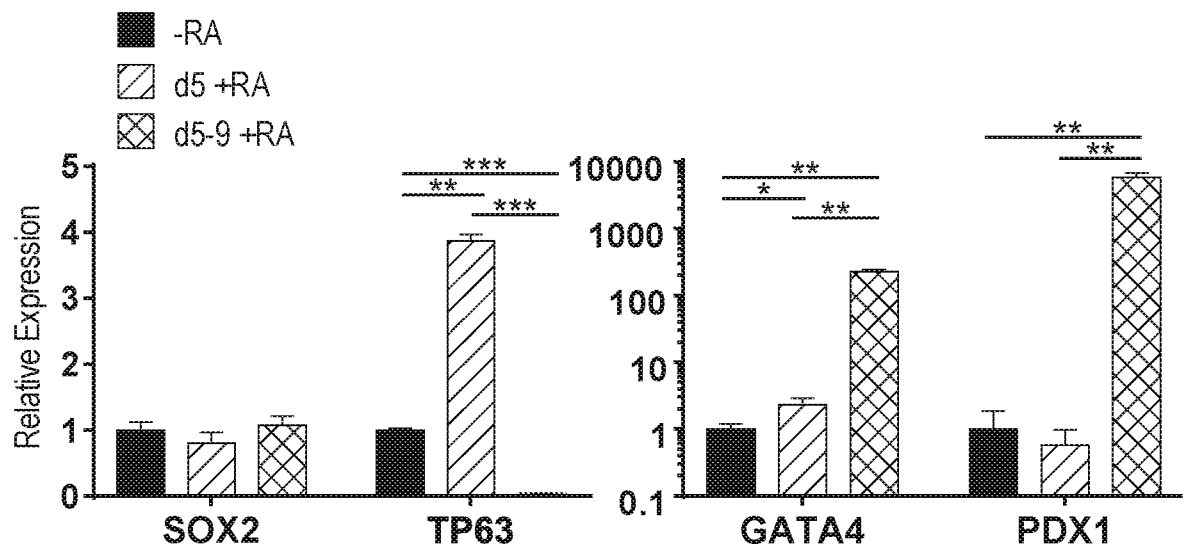
Figure 1H:
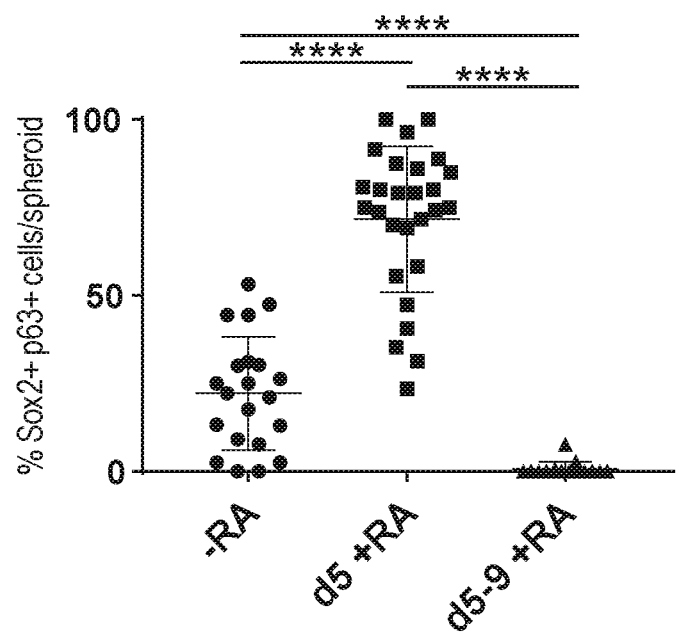
Figures 1I, 1J, 1K:
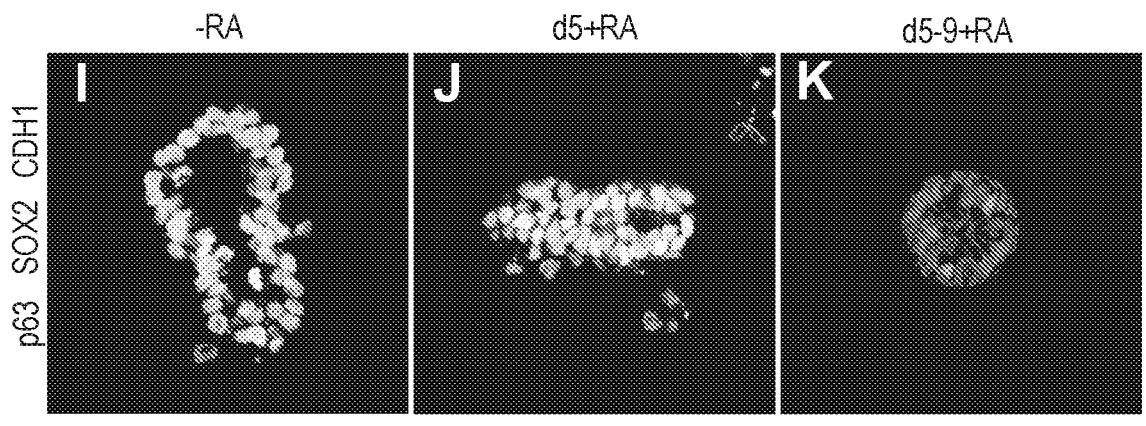
Figures 1, 1I, 1J, 1K:
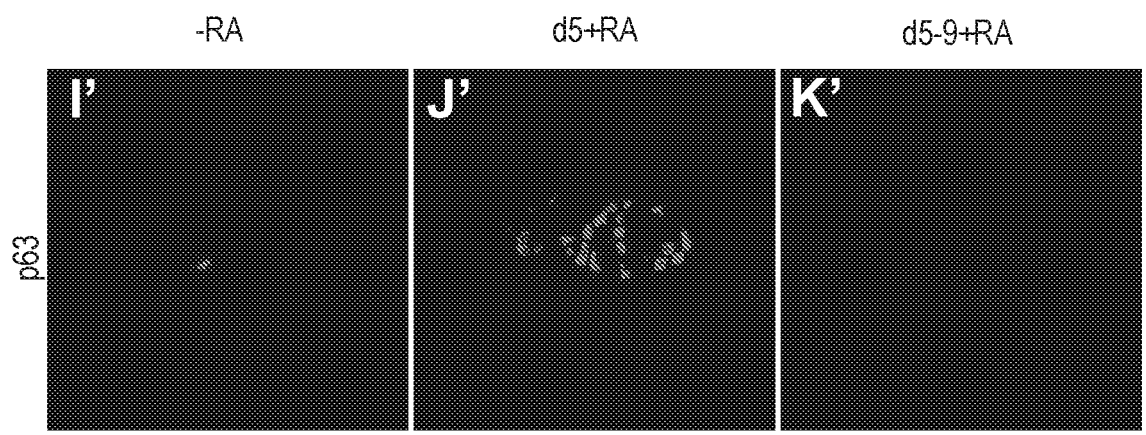

To generate foregut derivatives, hPSCs were first induced into DE and then three-dimensional (3D) SOX2-expressing foregut spheroids as previously described (FIG. 1) (D'Amour et al., 2005; Dye et al., 2016; McCracken et al., 2014, 2017). In attempting to generate esophageal organoids, the primary challenge was to generate foregut tissue of the correct regional identity. Endoderm patterning is regulated by differential BMP, WNT and RA signaling, where the highest levels of activation of these pathways promoting a mid- and hindgut fate and lower levels promoting a foregut fate (Bayha et al., 2009; Davenport et al., 2016; Matt et al., 2003; McLin et al., 2007; Tiso et al., 2002; Wang et al., 2006). Based on our previous studies indicating that the duration of signaling is important for differentiation, Applicant tested the effects of duration of Wnt activation during foregut spheroid formation on anterior-posterior identity (Spence et al., 2011). Applicant found that shorter duration of chiron, a canonical Wnt pathway activator (through GSK3β inhibition), or Wnt3a treatment following DE formation resulted in formation of anterior foregut (AFG) spheroids expressing HNF1β and SOX2, with low levels of posterior foregut markers PROX1 and HNF6 (FIG. 1A-1E, 8A-8G). HN1β is not expressed in pharyngeal endoderm indicating that AFG spheroids were not pharyngeal (FIG. 1C-1E, 8B). CDX2, a mid/hindgut marker, is not expressed (FIG. 1B, 1D, 1E). From this, Applicant concluded that the regional identity of these foregut spheroids (HNF1B+/SOX2+, PROX1-/HNF6-) are distal to the pharynx and proximal to the posterior foregut.

Four days of RA treatment is also known to posteriorize foregut spheroids (McCracken et al., 2014), and loss of RA signaling results in abnormal development of posterior foregut organs (Bayha et al., 2009; Wang et al., 2006). Applicant therefore investigated whether shortening the duration of RA signaling in foregut cultures would promote a more anterior fate. Foregut cultures treated with RA for 4 days express posterior foregut markers, GATA4 and PDX1, whereas 1 day of RA treatment resulted in spheroids that express TP63, a marker expressed in the developing esophagus (FIG. 1F-K, 8O-8R). Cultures lacking RA, or containing DEAB, an aldehyde dehydrogenase inhibitor (blocking RA synthesis) yielded spheroids with minimal TP63 expression and increased levels of the pharyngeal markers PAX9 and OTX2 (FIG. 1G-1K, 8F-8G; 8S-8V). Together, the data suggests that brief activation of RA promotes foregut regional identity consistent with the presumptive esophageal domain.

Figure 2A:
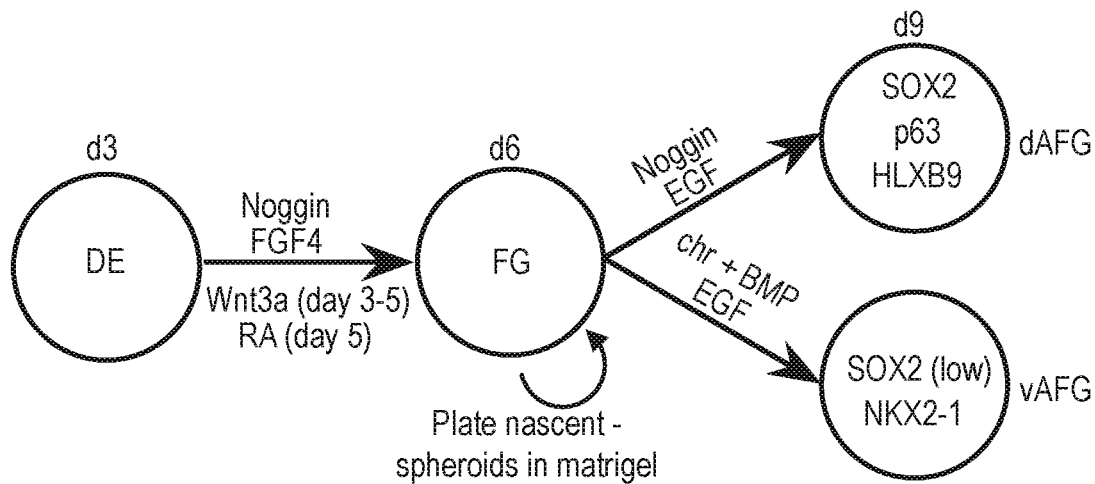
FIGS. 2A-2I. Anterior foregut spheroids have esophageal-respiratory competence. (2A) Schematic depicting experimental protocol to pattern AFG spheroids along the dorsal-ventral axis. (2B) Current simplified model of the cues guiding dorsal-ventral patterning of the AFG of mouse and frog embryos. (2C-2G) qPCR analysis of 3-day-old spheroids (day 9) treated for 3 days with Noggin, untreated (−ctrl), or chiron and BMP4 (10 ng/mL) using dorsal markers SOX2 and MNX1 (2C+2E), the respiratory marker NKX2-1 (2D), ΔN splice variant of TP63 (2F), and the stratified squamous epithelium marker KRT4 (2G). (2H-2I) IF staining for SOX2, NKX2-1, CDH1, and nuclei (DAPI) in Noggin (2H) versus chiron+BMP4 (2I) treated spheroids. Scale bar=25 µm. See quantification and statistical analysis section for details. See also FIG. 10A-10J.
Figure 2B:
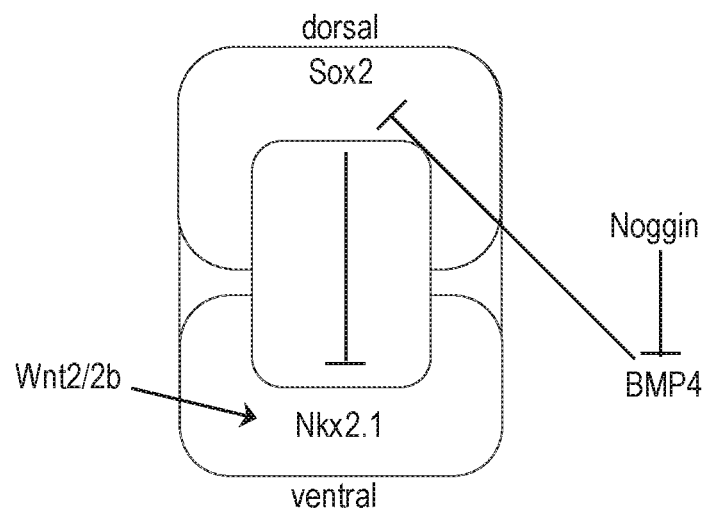

Anterior Foregut Spheroids are Competent to Form Esophagus or Respiratory Lineages The presumptive esophageal/respiratory region of the foregut is patterned along the dorsal-ventral (D-V) axis, resulting in specification of the esophageal and respiratory fates respectively. Applicant predicted that AFG spheroids would respond to D-V patterning cues to acquire either an esophageal or respiratory fate. Studies in vertebrate embryos demonstrate that BMP and Wnt signaling promote a respiratory fate (NKX2-1+SOX2-), while Noggin-mediated inhibition of BMP signaling in the dorsal foregut tube is required for esophageal development (Domyan et al., 2011; Fausett et al., 2014; Goss et al., 2009; Harris-Johnson et al., 2009; Que et al., 2006). Thus, Applicant treated day 6 AFG spheroids with either 3 days of chiron and BMP4 or alternatively with Noggin (to inhibit BMP signaling) (FIG. 2A-2B). Treatment with chiron+BMP4 resulted in induction of NKX2-1 and repression of SOX2, whereas treatment with Noggin dorsalized spheroids, as marked by elevated levels of SOX2, MNX1, KRT4, and TP63 (FIG. 2C-I) (Daniely et al., 2004; Sherwood et al., 2009). Taken together, inhibition of BMP signaling in cultures of AFG spheroids promoted a dorsal anterior foregut identity.

Formation of Esophageal Organoids with a Stratified Squamous Epithelium

To determine if dorsally-patterned AFG spheroids were competent to grow into esophageal organoids, Applicant cultured them suspended in matrigel with EGF alone or in the context of manipulation of other pathways predicted to promote esophageal development including Wnt activation (chiron), extended BMP inhibition (Noggin), activation of hedgehog (SAG, a smoothened agonist), and FGF10. While most of these manipulations had no effect on growth (data not shown), Applicant found that addition of FGF10 to cultures from day 6 to day 13 resulted in improved efficiency of spheroid to organoid outgrowth (FIG. 11A-11E) and did not affect the patterning and differentiation into esophageal organoids (data not shown).

Next, Applicant compared the morphologic and molecular development of putative human esophageal organoids (HEOs) to normal development of the embryonic mouse esophagus. During embryonic growth and development, the esophagus transitions from simple cuboidal epithelium at E12.5 to a multilayered/stratified epithelium between E14.5 and E17.5 (FIG. 3G, 3J, 3M, 3P, 11F-11O, 11R) (Chen et al., 2012). Similarly, over the course of one month, HEOs expanded in size from approximately 50 μm to 200-400 μm in diameter (FIG. 3B-3F). Moreover, the organoid epithelium transitioned from a simple epithelium that was largely SOX2, p63 double-positive to a multilayered epithelium expressing markers of esophageal stratified squamous epithelium (FIG. 11H-11Q, 11S). At one month, HEOs expressed basal markers p63 and KRT14 as well as the suprabasal marker KRT13 (FIG. 3H, 3K, 3N, 3Q). This expression pattern is similar to an E17.5 esophagus composed of multilayered epithelium (FIG. 3G, 3J, 3M, 3P).

Figure 3A:
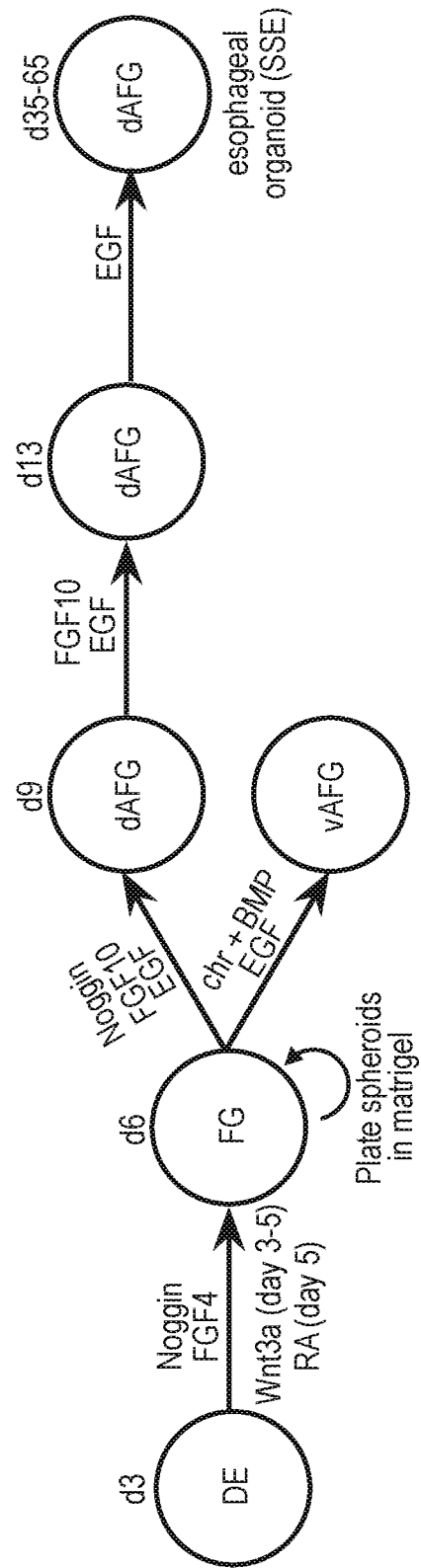
FIGS. 3A-3Y. Dorsal anterior foregut spheroids form organoids comprised of a stratified squamous epithelium that expresses esophageal markers. (3A) Schematic depicting differentiation of DE into human esophageal organoids (HEOs). (3B-3F) Brightfield images depicting growth of nascent spheroids into HEOs. (G-R) Comparison of E17.5 esophagi (G,J,M,K) to 1- and 2-month-old HEOs (3H-3I, 3K-3L, 3N-3O, 3Q-3R), by IF analysis of the transcription factors Sox2 and p63 (3G-3I), epithelial markers Krt8 versus Krt14 (3J-3O), and the suprabasal marker Krt13 (3P-3R). (3S-3V) qPCR analysis of the identity and maturation of esophageal organoids at 1- and 2-months of age compared to human gastric and intestinal organoids (HGO and HIO) and pediatric esophageal biopsies by the stratified squamous epithelial markers p63, KRT5, KRT13, IVL, CRNN. (3W) Unsupervised hierarchical clustering of 2-month HEOs compared to various biopsies of the GI tract. (3X) Principal component analysis of 1-month old HIOs, HGOs, and HEOs. (3Y) Heat map of log 2-transformed normalized TPM values of selected genes (esophageal, gastric, intestinal) averaged across replicates. SSE=stratified squamous epithelium; b=basal; sb=suprabasal. Scale bar=500 µm (3B-3F), 50 µm (3G-3L), 100 µm (3O-3R), and 25 µm (3O-1-3R-1). See quantification and statistical analysis section for details. See also FIG. 11A-11CC.
Figures 4A, 4B:
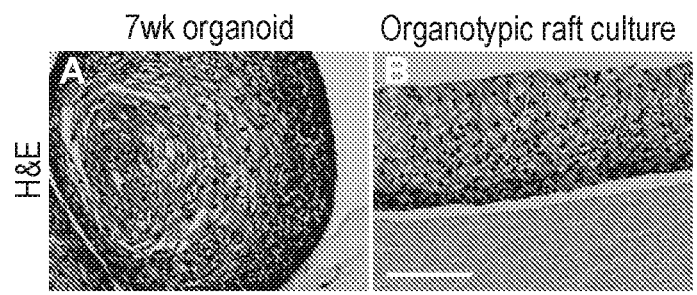
FIGS. 4A-4BB. HEOs contain progenitors that give rise to differentiated stratified squamous epithelium. (4A-4B) H&E staining comparing 7-week HEOs to organotypic rafts generated using HEO-derived from keratinocytes. (4C-4N) Comparison of 7-week HEOs to organotypic rafts by IF analysis of transcription factors SOX2 and p63 (4C-4D), basal marker KRT14 (4E-4F), suprabasal keratins KRT4 (4G-4H) and KRT13 (4I-4J), and differentiated markers IVL, CRNN, and FLG (4K-4N). (4O-4U) qPCR analysis of esophageal biopsies, 7-week HEOs, HEO-derived keratinocytes, and organotypic rafts for SOX2 and TP63 (4O), KRT5 (4P), KRT14 (4Q), KRT4 and KRT13 (4R), IVL (4S), CRNN (4T), and esophageal specific markers TMPRSS11A/D (4U). (4V) Protocol for EdU pulse-chase labeling experiment in HEOs. (4W-4Z) IF images of HEOs at various time-points post-labeling. (4AA-4BB) Analysis of IF images using a 2D histogram of P63 intensity versus EdU intensity. (4AA) and a 1D histogram of percent of total EdU labeled cells versus distance from the epithelial base (4BB). b=basal; sb=suprabasal. Scale bar=50 μm (C-N), 100 μm (4A-4B, 4S-4V). See quantification and statistical analysis section for details. See also FIG. 12A-12R.
Figures 4C, 4D:
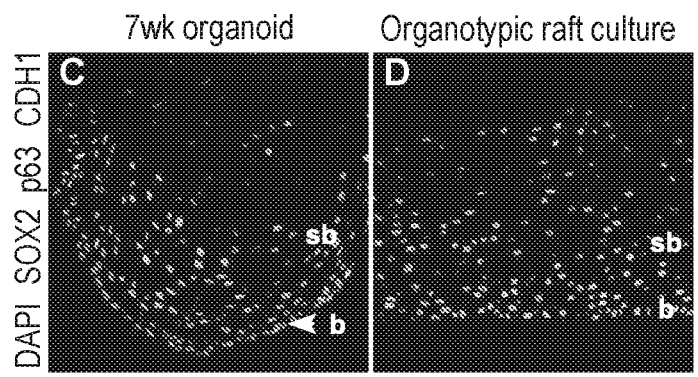

One-month HEOs were still relatively immature as evidenced by broad SOX2 epithelial expression and expression of KRT8, a marker of immature esophagus (FIG. 3J, 11L-11M). Applicant therefore extended the culture period out to 2 months, which resulted in additional growth and formation of a stratified epithelium that lacked KRT8. Applicant observed robust expression of KRT14 throughout the basal layer and KRT13 and IVL throughout the differentiated suprabasal layers, demonstrating the presence of a stratified squamous epithelium (FIG. 3I, 3L, 3O, 3R). Histologically, 2-month HEOs had a more defined basal layer as well as squamous cells suprabasally, with no evidence of cornification (FIG. 4A). The epithelial morphology of HEOs was easily distinguished from other organoids including gastric (HGO), intestinal (HIO) or colonic organoids, with each organoid having an epithelial morphology that is unique to that organ type (McCracken et al., 2014, 2017; Múnera et al., 2017; Spence et al., 2011).

Figures 3B, 3C, 3D, 3E, 3F:
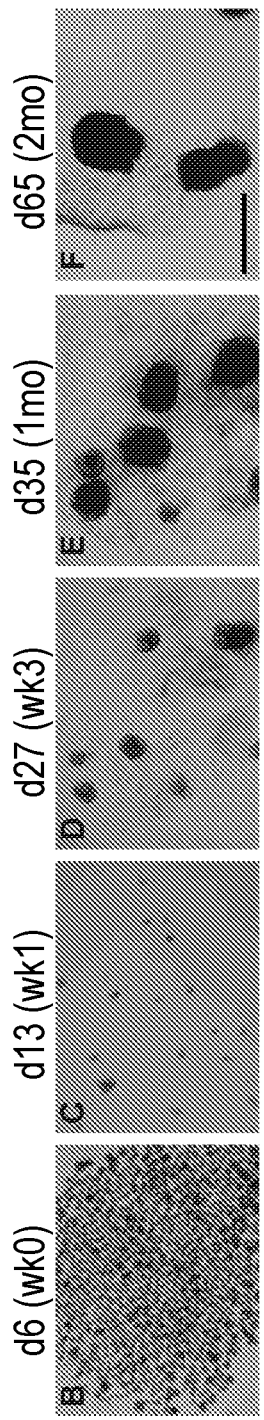
Figure 3S:
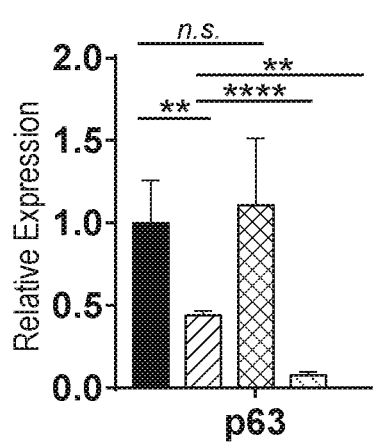
Figure 3T:
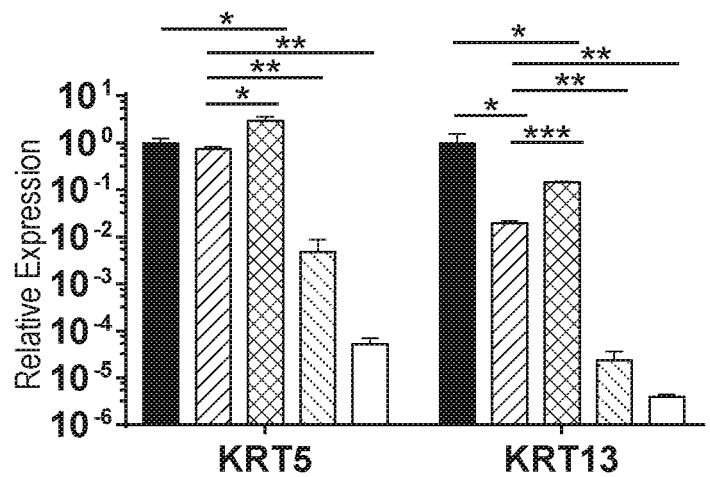
Figure 3U:
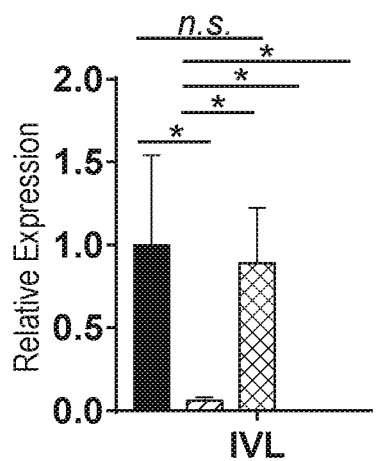
Figure 3V:
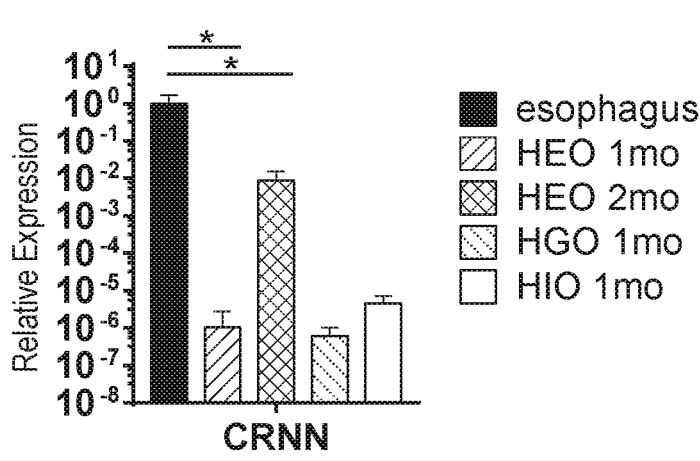
Figure 3W:
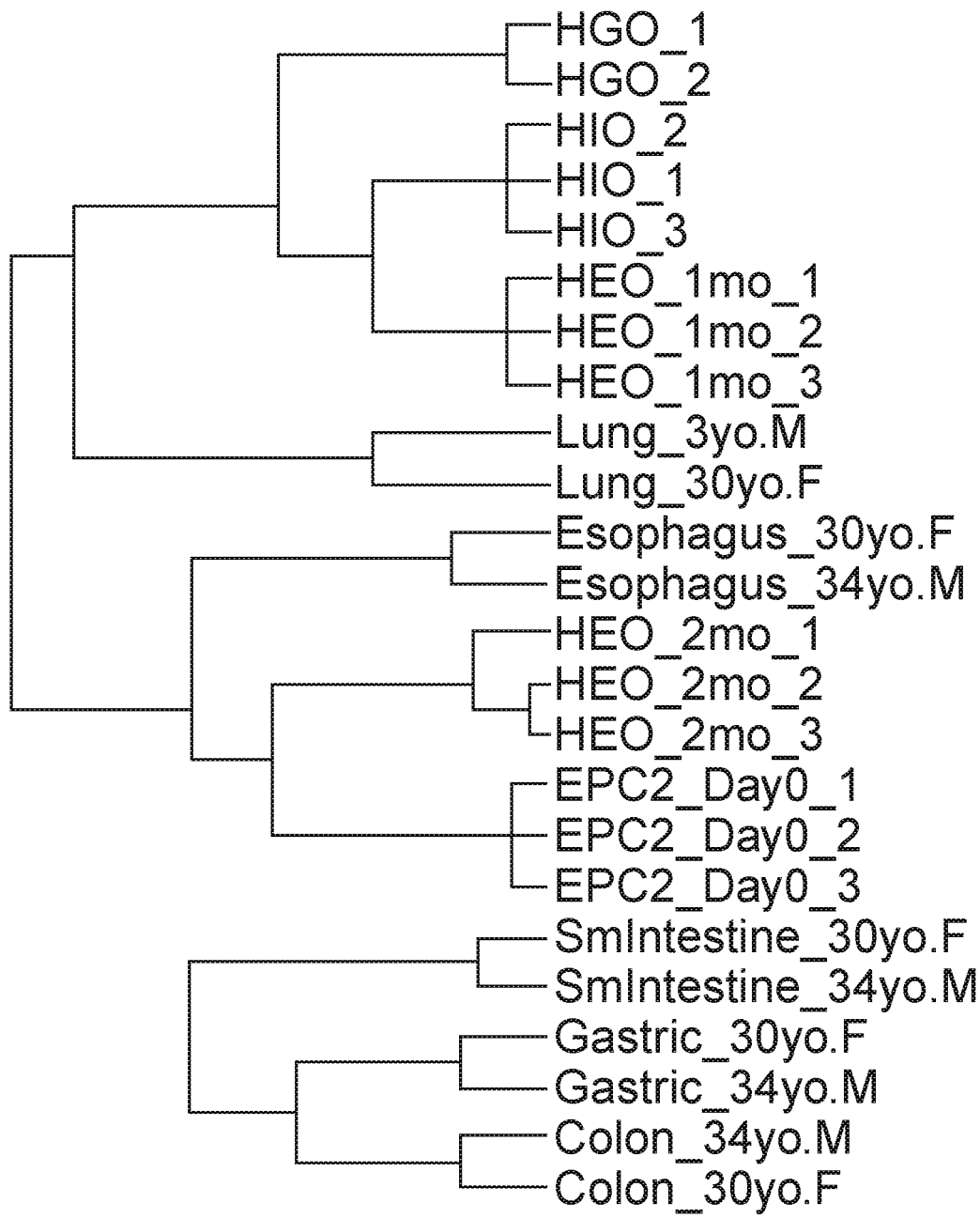
Figure 3X:
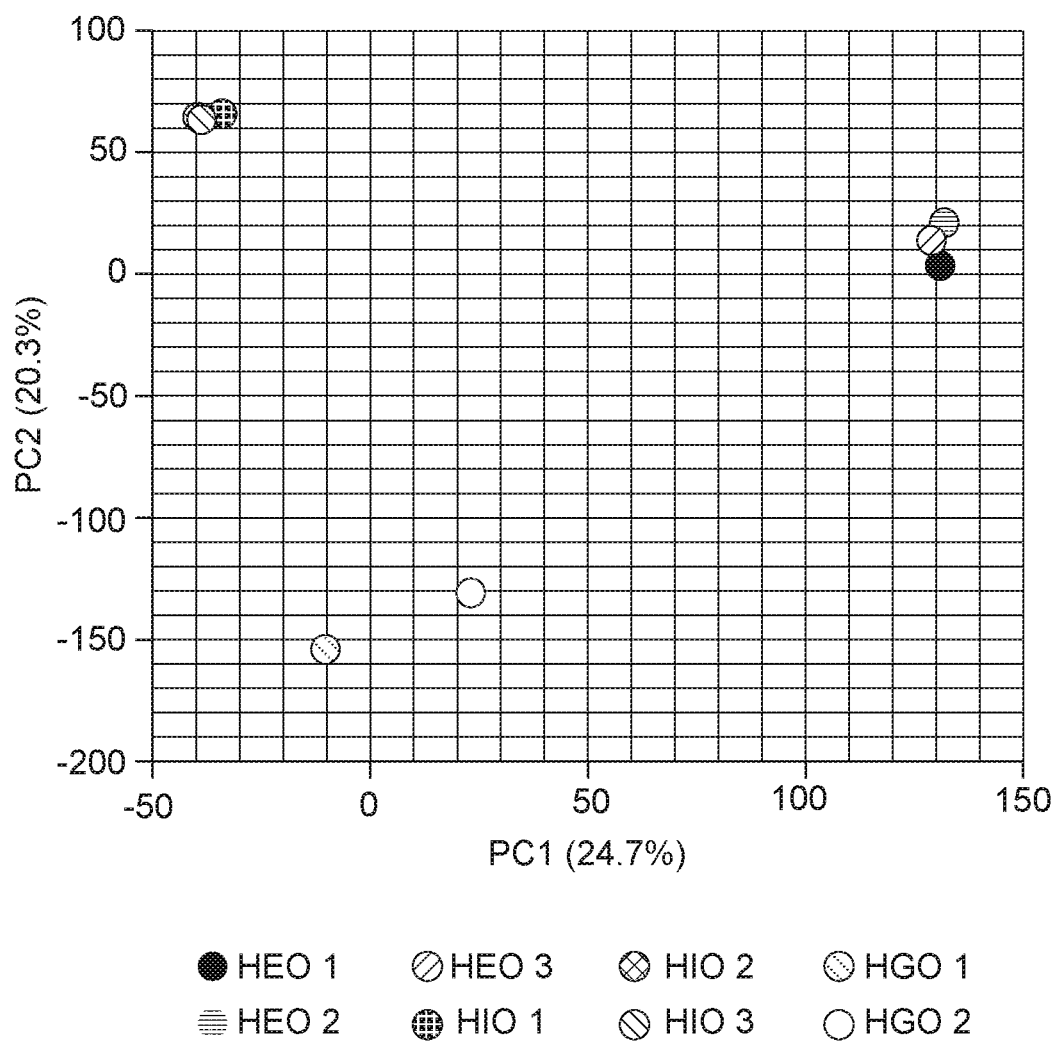
Figure 3Y:
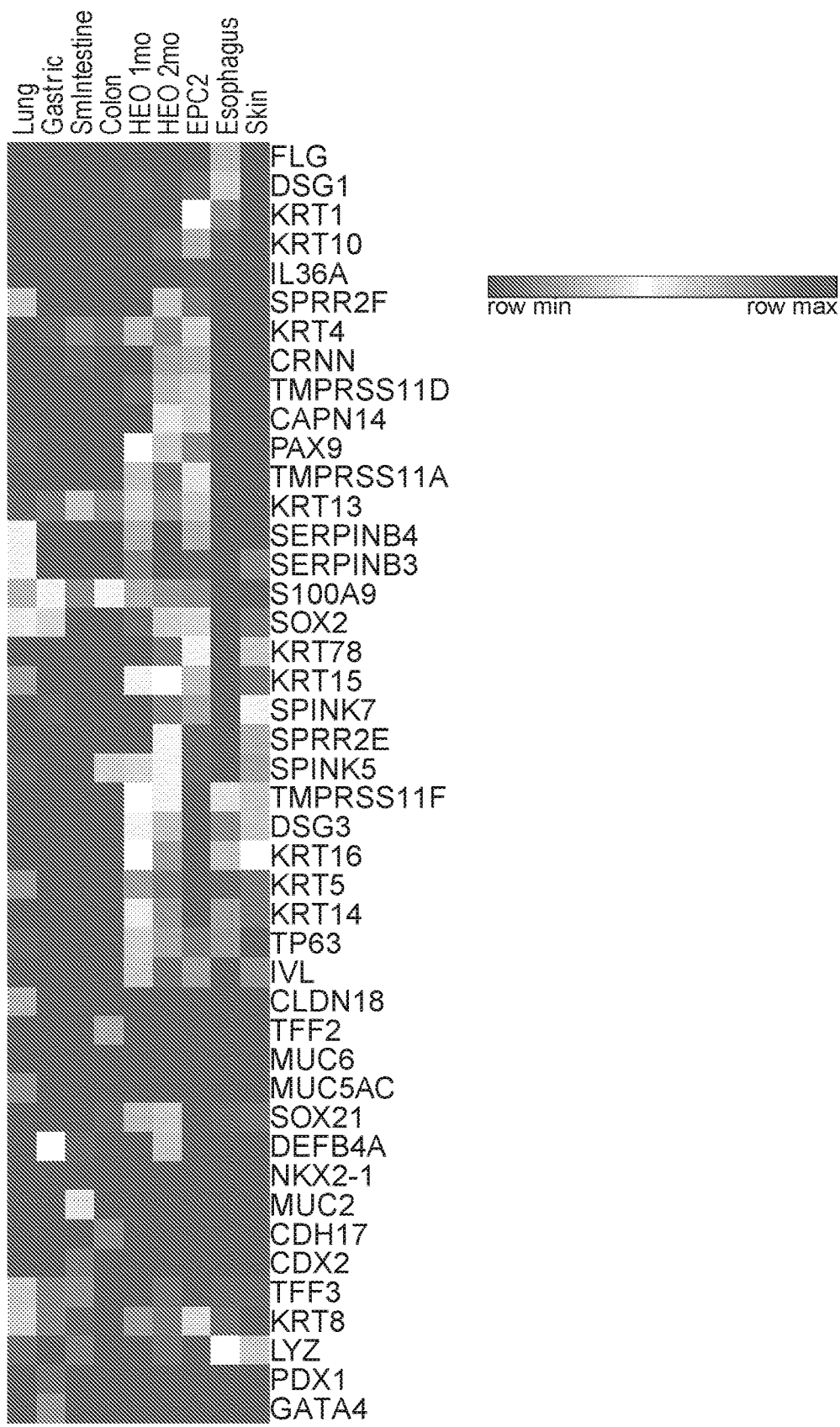

To show that HEOs were human esophageal epithelium, Applicant compared 1 and 2-month HEOs to human esophageal biopsies as well as 1-month HGOs and HIOs by qPCR. Key stratified squamous epithelial markers p63, KRT5, KRT13, IVL, and CRNN were expressed highest in human esophageal biopsies and 2-month HEOs, whereas HGOs and HIOs negligibly expressed these transcripts (FIG. 3S-3V). Additionally, Applicant compared the entire transcriptome of HEOs with that of other human epithelial tissues isolated from esophagus, lung, skin, stomach, small intestine, colon, HGOs, and HIOs. Clustering analyses of RNA sequencing data revealed that HEOs are most closely related to human esophagus and EPC2, an esophageal keratinocyte cell line, as opposed to the stomach, small intestine, and colon (FIG. 3W). Applicant used principal component analyses to compare HEOs with HIOs and HGOs and found that even one-month HEOs were entirely distinct from the other gastrointestinal organoids (FIG. 3X). A comparison of markers of esophagus, skin, stomach, and colon revealed that HEOs were highly similar to human esophagus, reaffirming the qPCR analysis. While there was significant overlap between skin and esophagus, there were also distinct differences including KRT1 in the skin and KRT4 and 13 in the esophagus. Of note, HEOs did not express gastric or intestinal markers TFF2, CLDN18, GATA4, PDX1, CDX2, and CDH17 (FIG. 3Y).

Given that growth of PSC-derived organoids in vivo has been shown to promote further maturation and function, Applicant utilized three different transplantation-based approaches to study HEOs in vivo. Applicant first engrafted 1-month old HEOs into the kidney capsule of immunodeficient (NSG) mice and allowed them to grow for 8 weeks, which resulted in maturation in a subset of the organoids transplanted (2/5) (FIG. 12A-12F). Applicant used two other transplantation approaches that were unsuccessful: seeding HEOs onto biodegradable PEG scaffolds and transplanting them into the fat pad of mice; or engrafting HEOs into the forestomach of NSG mice (data not shown) (Dye et al., 2016). Overall, the generation of spheroids and organoid outgrowth is robust across various ES and iPS lines, with each generation resulting in a large majority of organoids expressing stratified squamous markers (FIG T-11CC). Together, the data demonstrates that PSC-derived dorsal foregut spheroids form esophageal organoids with a well-differentiated, non-keratinized stratified squamous epithelium.

Figures 4E, 4F:
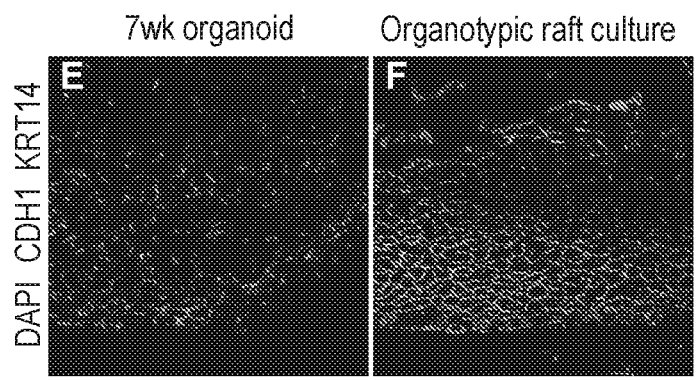
Figures 4G, 4H:
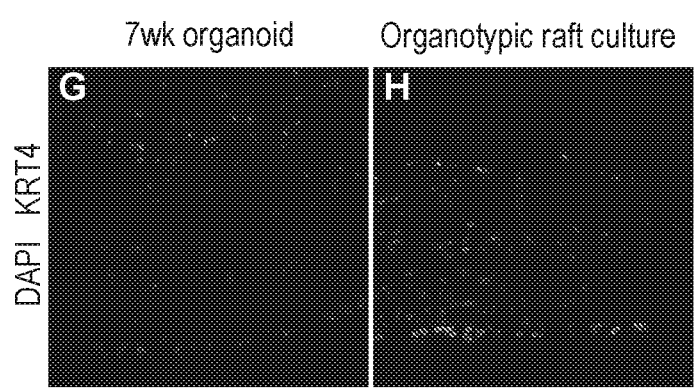
Figures 4I, 4J:
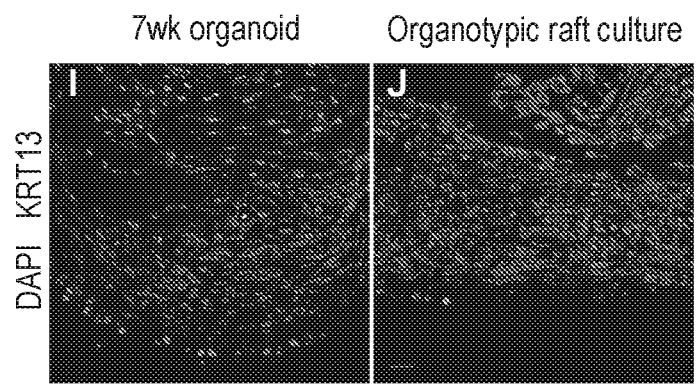
Figures 4K, 4L:
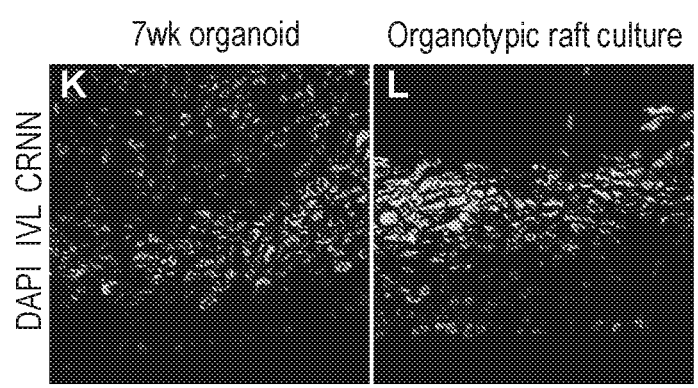
Figures 4M, 4N:
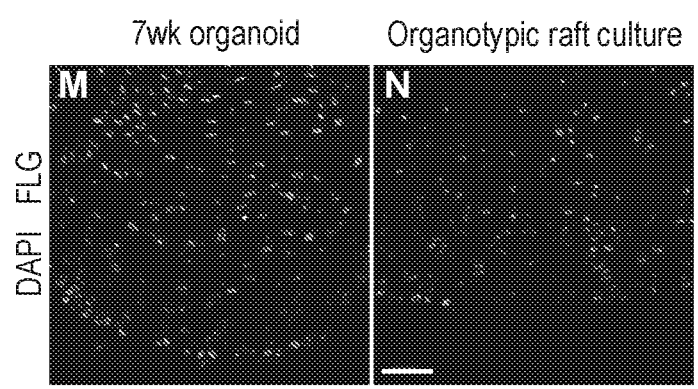
Figures 4O, 4P, 4Q:
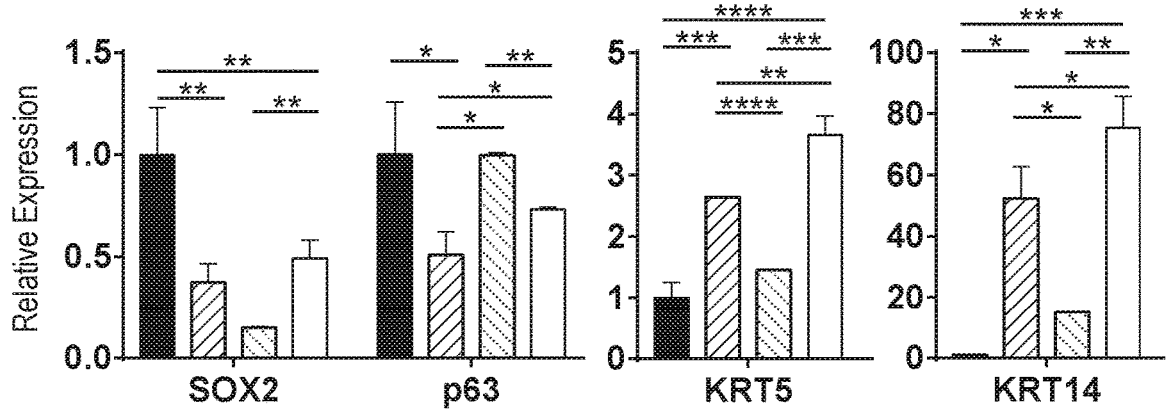
Figures 4R, 4S, 4T:
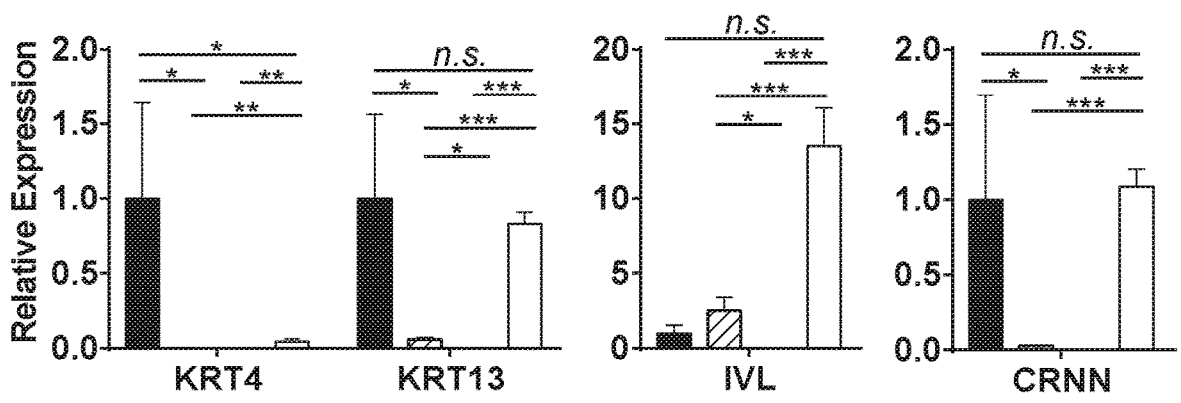
Figure 4U:
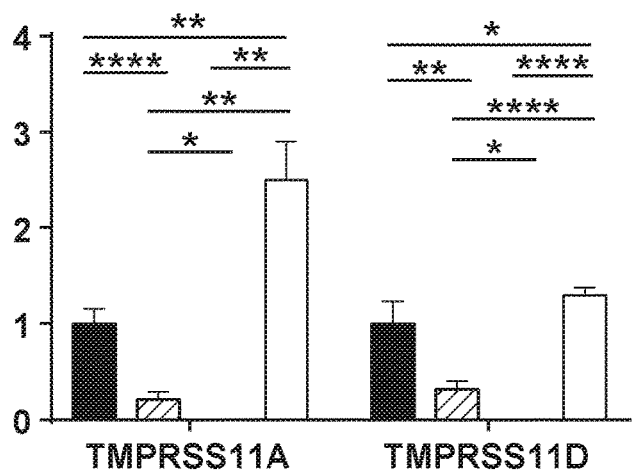

HEOs Contain Progenitors Capable of Reconstituting a Stratified Squamous Epithelium The esophagus contains basal progenitors that can give rise to all of the differentiated stratified layers (DeWard et al., 2014; Doupe et al., 2012; Kalabis et al., 2008). This property allows esophageal cells to be isolated, expanded in culture, and then re-differentiated into a stratified squamous epithelium. Applicant first tested if HEOs contain esophageal progenitors by enzymatically dissociating 5-week HEOs into single cells, expanding them in monolayer cultures, and then testing their ability to re-differentiate into a stratified squamous epithelium using an organotypic raft culture method (Hoskins et al., 2009). After 14 days of organotypic culture, the HEO-derived keratinocytes gave rise to a non-keratinized stratified squamous epithelium, expressing the appropriate keratins and differentiated markers IVL, CRNN, FLG. (FIG. 4A-4N). HEOs, HEO-derived keratinocytes and organotypic raft cultures all expressed high levels of the basal markers p63, KRT5, and KRT14 (FIG. 4O-Q), whereas organotypic rafts were the most differentiated, expressing CRNN, IVL, KRT13, TMPRSS11A and D at levels comparable to human esophageal biopsies (FIG. 4R-4U). However, efforts to expand these progenitors long-term in 3D organoid cultures were unsuccessful. Dissociated organoids re-plated in 3D-matrigel grew over several weeks, maintained patterning (SOX2+p63+), and were passaged (re-dissociated) several times (FIG. 12G-12H, 12O, 12Q-12R). However, passaging efficiency diminished over time, and Applicant was unable to induce differentiation or stratification in these passaged organoids (FIG. 12I-N, 12P). This result is similar to esophageal progenitors derived from human esophagus, demonstrating a general inability to culture these cells long-term (Kasagi et al., 2018).

Figure 4V:
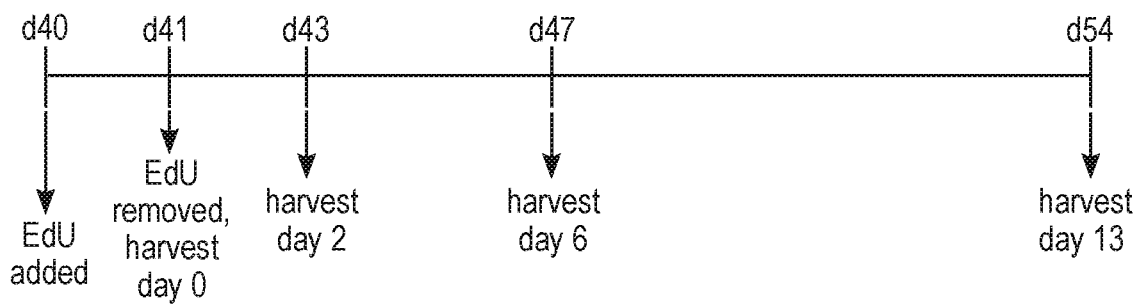
Figures 4W, 4X, 4Y, 4Z:
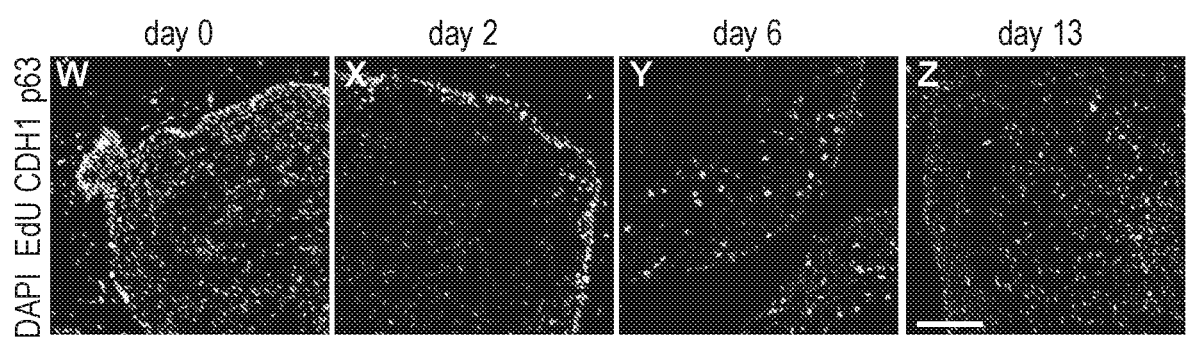
Figure 4A:
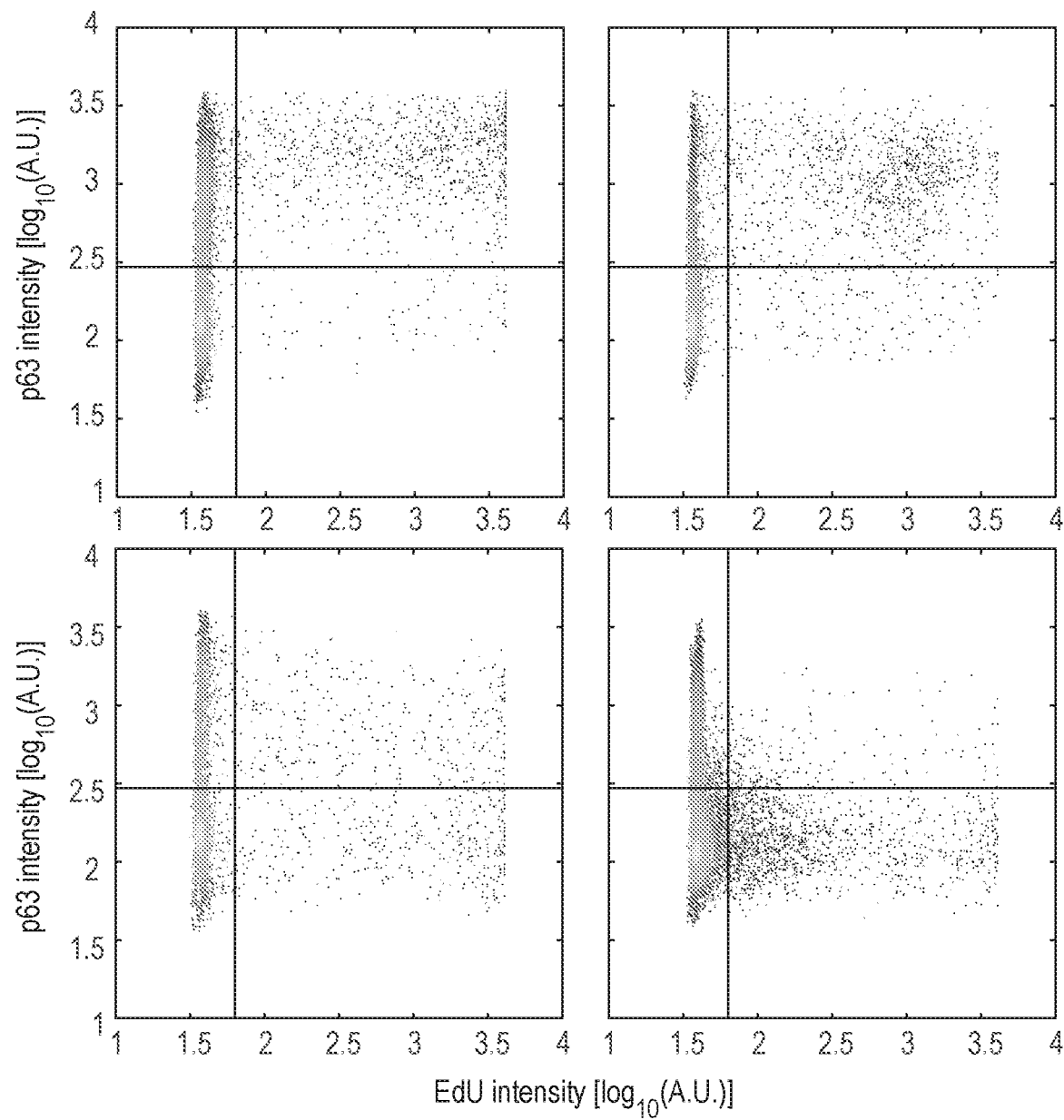
Figure 4B:
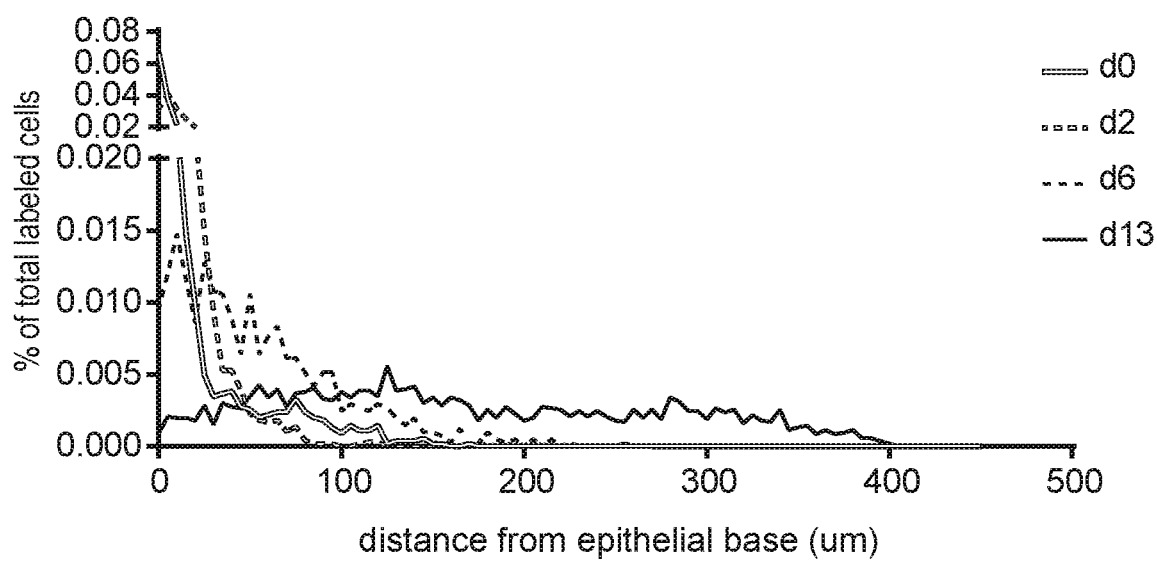

Another method to study basal progenitor differentiation is through pulse-chase labeling of proliferating basal progenitors and following labeled cells as they differentiate into stratified layers over time. Applicant labeled proliferating cells in day 40 HEOs by one day treatment of EdU and analyzed them immediately (day 0) or following a chase period for 2, 6, and 13 days post-label (FIG. 4V-4BB). EdU labeled cells initially appeared in p63-expressing basal cells, but over time, these cells moved into the suprabasal compartment, lost p63 expression, and were eventually shed into the lumen by 13 days post-label (FIG. 4W-4BB). Thus, it is believed that HEOs contain basal progenitors that differentiate and migrate into the stratified layers, similar to esophageal epithelium.

Using HEOs and Mouse Genetics to Identify Mechanisms of Esophageal Development While establishing a PSC-derived HEO model system is an important advance, there is a need to demonstrate that HEOs could be used to study human development and disease. Applicant chose to use HEOs, in parallel with two well-established vertebrate model systems, mouse and *Xenopus*, to model esophageal birth defects by studying loss-of-function of SOX2. First, Applicant determined the consequences of complete loss of Sox2, since partial loss of SOX2 function in humans and mice leads to partial loss of the esophagus (atresia) (OMIM 206900, Fantes et al., 2003; Que et al., 2007; Williamson et al., 2006). Applicant generated two mouse models to inducibly delete Sox2 in the foregut endoderm prior to initiation of esophageal development (FoxA2$^{CreER}$; Sox2$^{fl/fl}$ and Sox2$^{CreER/fl}$) (Arnold et al., 2011; Park et al., 2008; Shaham et al., 2009). In both models, early deletion of Sox2 in the foregut resulted in complete esophageal agenesis, with the foregut region between the pharynx and stomach remaining as one tube lacking p63 and broadly expressing the respiratory marker Nkx2-1 (FIG. 5C-5F, 13A-13D). The lung buds were largely similar to control embryos, and cell polarity was unaffected (FIG. 13E-F). Deletion of Sox2 after initiation of esophageal development resulted in partial loss of esophageal tissue, with regions of the esophagus being severely hypoplastic at E11.5. In some regions, the esophagus is only 2-3 cells wide, remains a simple cuboidal epithelium, lacks p63 expression, and expresses Nkx2-1 in some cells (FIG. 5I-5L). These data suggest that Sox2 function is required for initiating esophageal development whereas loss of Sox2 one day later results in reduced esophageal tissue and identity.

Figure 5E:
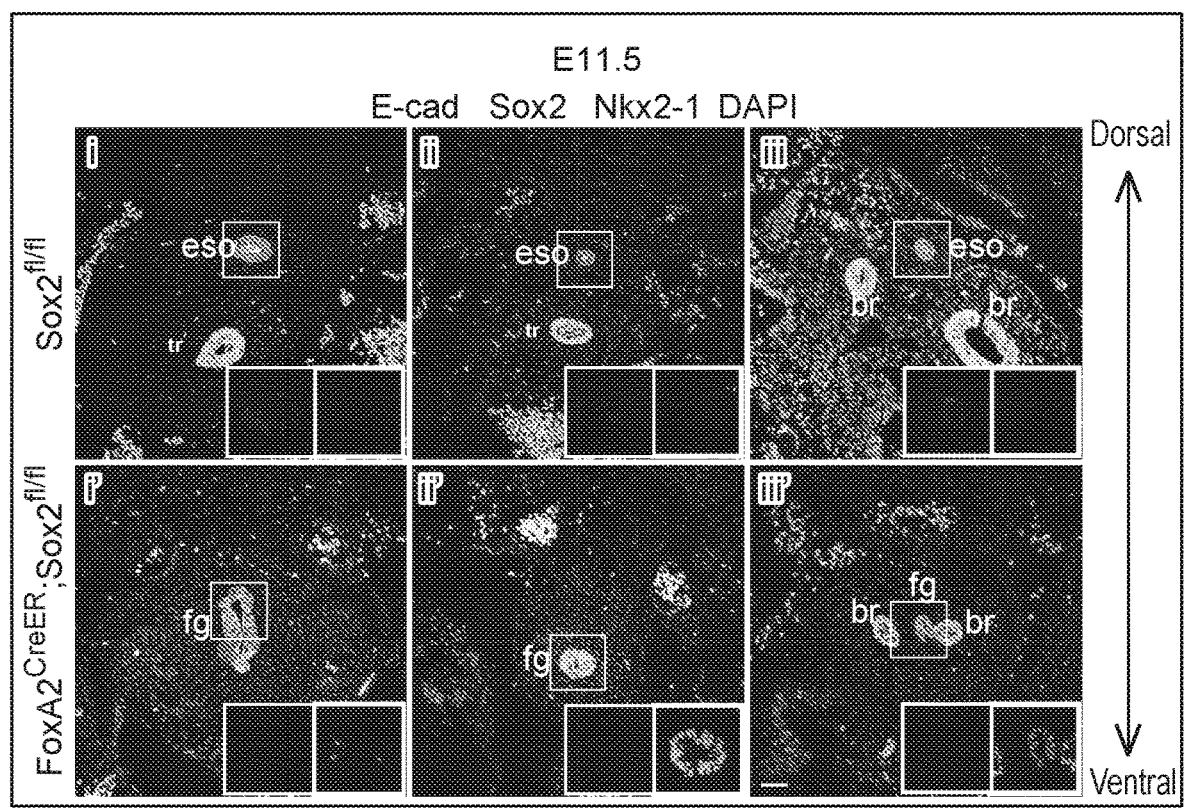
Figure 5F:
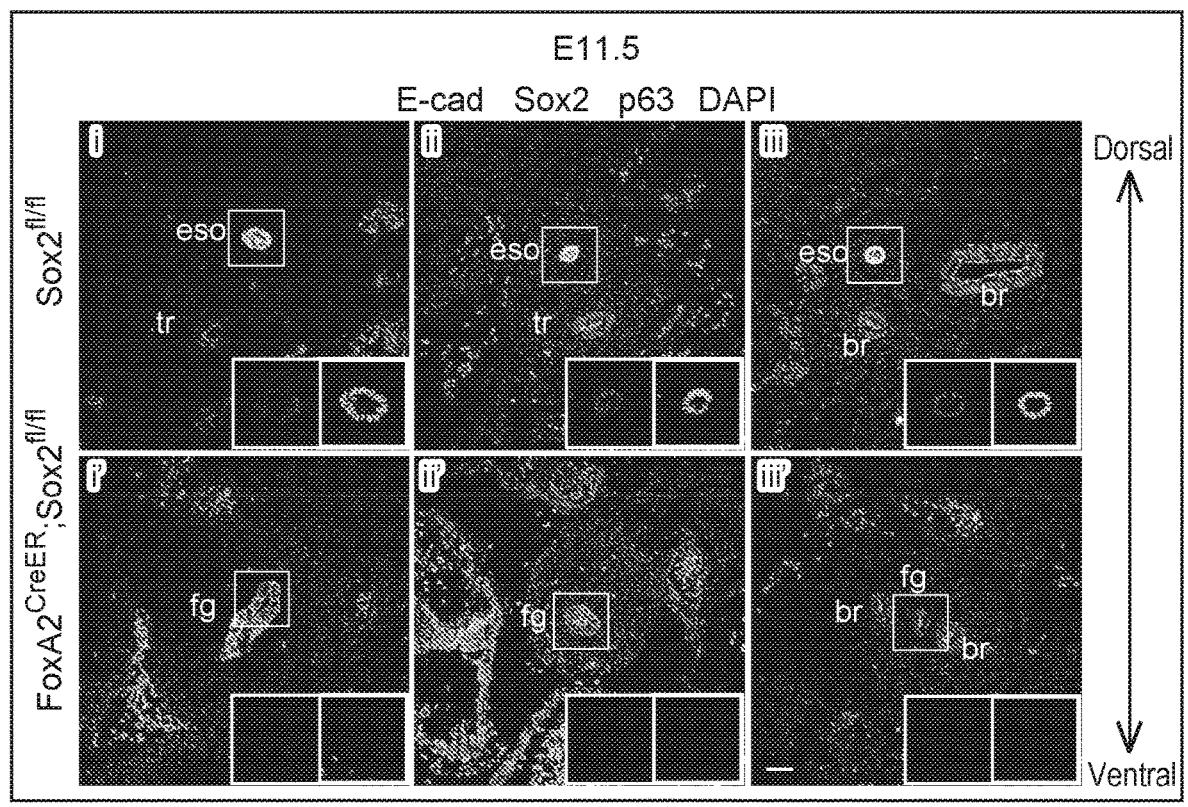
Figures 1, 5G:
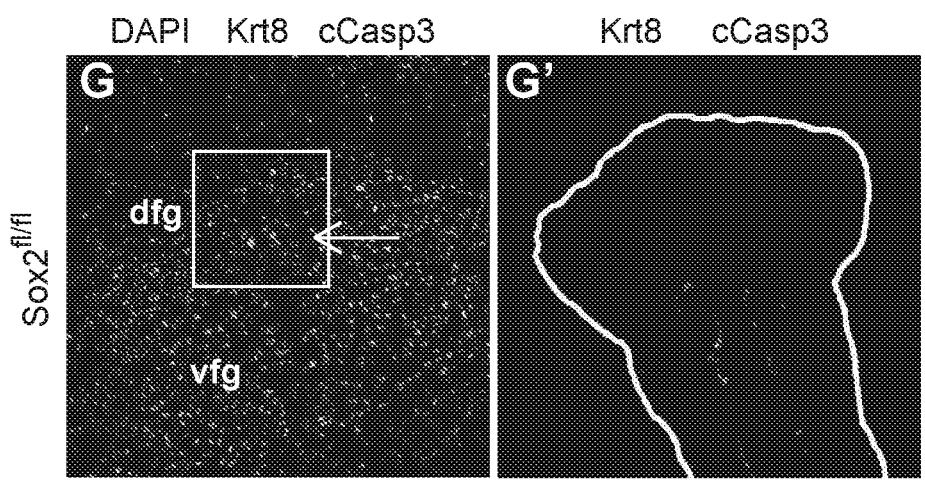
Figures 1, 5H:
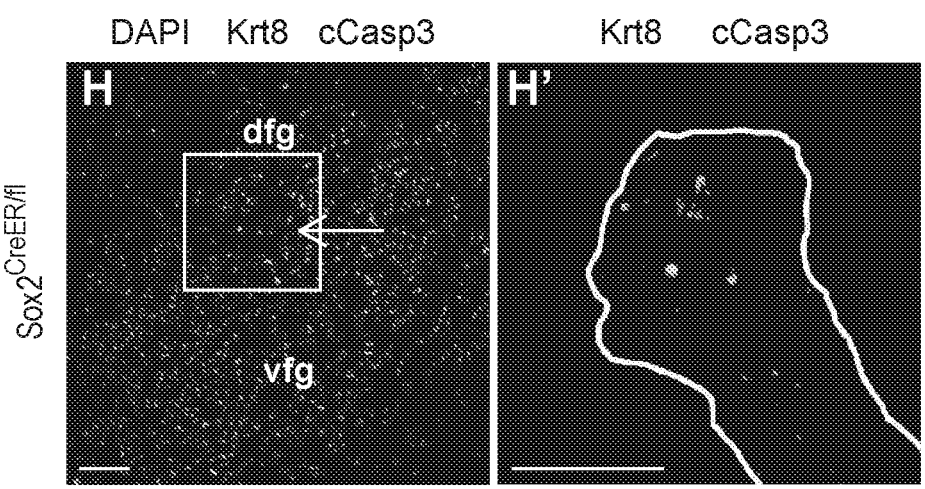
Figures 1, 5I, 5J, 5K, 5L:
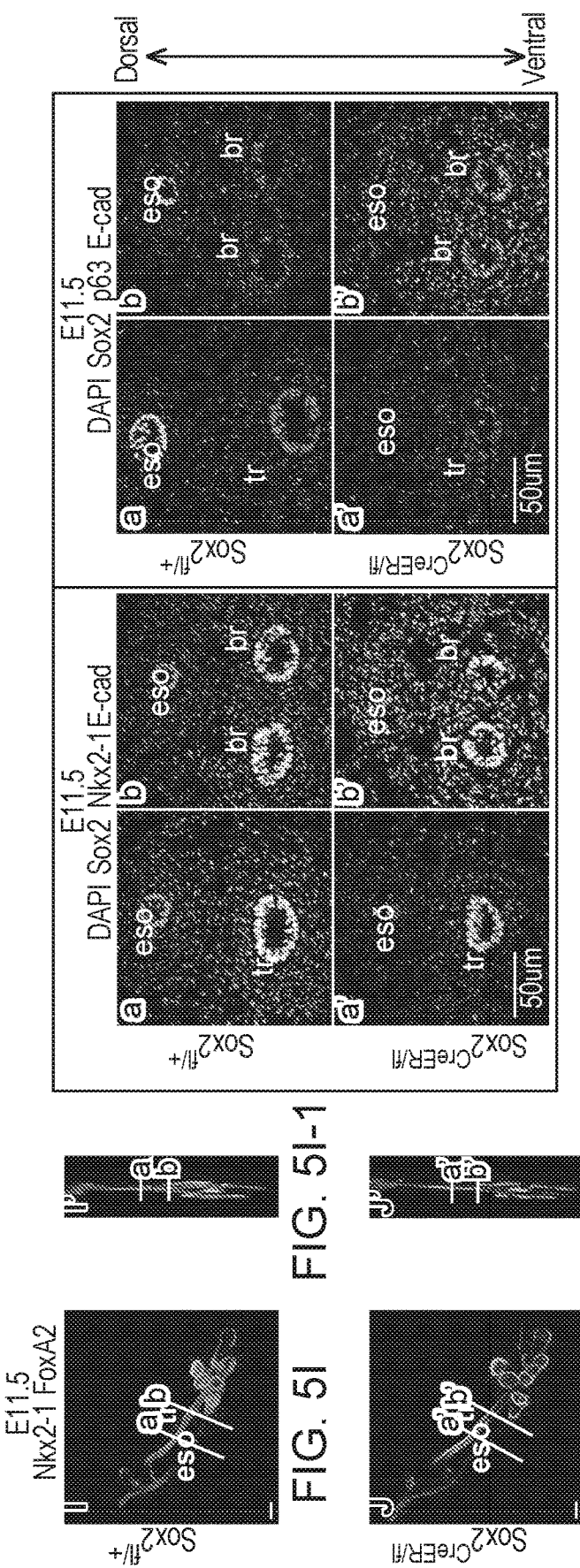
Figure 13U:
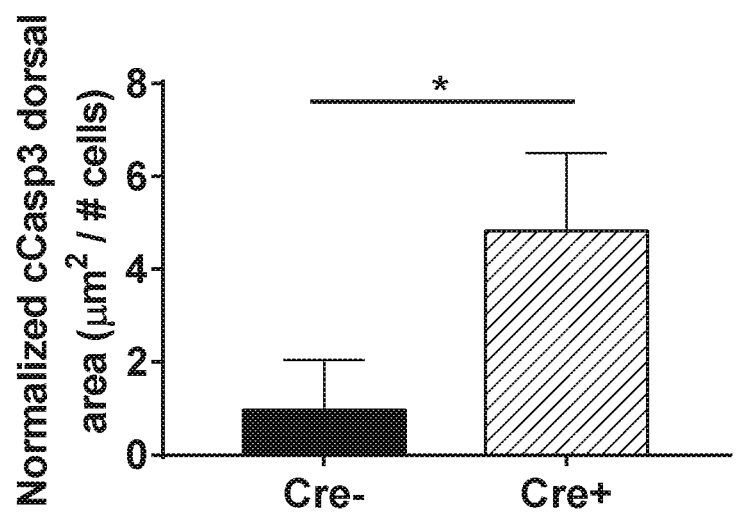
FIGS. 13A-13V. Post-gastrulation endodermal or broad Sox2 knockout results in a similar phenotype of esophageal agenesis. (13A-13B) Wholemount immunofluorescence (IF) analysis for dorsal marker Sox2 (red), respiratory marker Nkx2-1 (green) in E9.5 control ($Sox2^{fl/fl}$) and Sox2-DE-LOF ($FoxA2^{CreER}$; $Sox2^{fl/fl}$) embryos. (13C-13D) Wholemount IF analysis for Sox2, Nkx2-1 in E10.5 control ($Sox2^{fl/fl}$) and Sox2-DE-LOF ($FoxA2^{CreER}$; $Sox2^{fl/fl}$) embryos. White arrowheads highlight normal versus ectopic Nkx2-1 expression. (13E-13F) IF analysis of foregut sections of E11.5 embryos for the apical marker aPKC (green). (G-H) Wholemount IF analysis for Nkx2-1 of E11.5 control ($Sox2^{fl/+}$) and Sox2-cKO ($Sox2^{CreER/fl}$) embryos taken from dams gavaged at 8.5 dpc. (13I-13L) Immunofluorescence analysis of E11.5 embryos (similar as in 13E-13F) for (13I-13J) Sox2 and Nkx2-1, and (13K-13L) Sox2 and p63. (13M-13T) IF analysis of E10.5 control ($Sox2^{fl/+}$) and Sox2-cKO ($Sox2^{CreER/fl}$) embryos taken from dams gavaged at 8.5 dpc for epithelial morphology across the anterior (13M, 13N) to posterior (13S, 13T) axis. (13S, 13T) Quantification of (13U) cleaved Caspase 3 and (13V) Ki67 IF staining in E10.5 mouse embryonic foregut for cell death at the point of segregation of the dorsal and ventral foreguts in control (Cre-, $Sox2^{fl/+}$) and Sox2 cKO (Cre+, $Sox2^{CreER/fl}$) embryos taken from dams gavaged at 8.5 dpc. Scale bar=100 μm for (13A-13D, 13G-13H), 50 μm for (13I-13T), and 25 μm for (13E-13F). For Sox2-DE-LOF embryos, n=3 embryos of each genotype at E9.5, and n=2 embryos for each analysis for each genotype at E11.5 (a minimum of 2 litters were harvested for each analysis and time point). For Sox2-driven Sox2 cKO embryos, n=3 embryos for each genotype. Error bars indicate SD. *p≤0.05 for two-tailed t-test. fg=foregut, dfg=dorsal foregut, vfg=ventral foregut, ph=pharyngeal endoderm, eso=esophagus, r=respiratory progenitor, thy=thyroid, tr=trachea, br=bronchi, st=stomach.
Figure 13V:
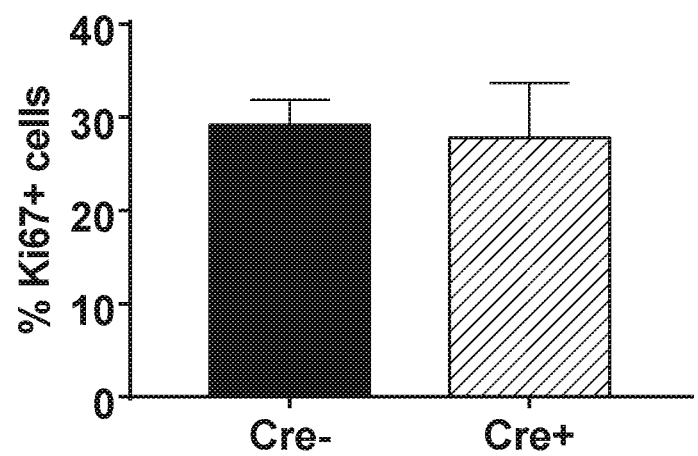

To investigate if esophageal agenesis was caused by changes in cell death and proliferation, or merely absence of septation from the common foregut, Applicant analyzed E10.5 embryos at the start of septation. Sox2$^{CreER/fl}$ embryos had increased cleaved Caspase 3 staining in the dorsal foregut at the level where separation would normally be occurring, suggesting that cells of the presumptive esophagus were undergoing cell death (FIG. 5G-5H, 13U). Proliferation, as marked by Ki67+ cells, was unchanged (FIG. 13V). In both control and Sox2 knockout foreguts, there appears to be a point where the epithelium narrows midway along the dorsal-ventral axis, suggesting that the epithelium is attempting to separate into the two tubes regardless of the presence of Sox2 protein (FIG S6M-T). The results in mouse demonstrate Sox2 is required in the foregut for esophageal development, survival and for restricting Nkx2-1 to the ventral/respiratory domain.

BMP-Independent Roles for Sox2 in Repressing Nkx2-1 Expression

Applicant next wanted to exploit the in vitro advantages of human and *Xenopus* foregut cultures to mechanistically explore how Sox2 initiates esophageal development. From previous studies, Sox2 is believed to repress respiratory (ventral) development and promote esophageal (dorsal) development. In order to promote ventral identity, BMP signaling is believed to repress Sox2 in the ventral foregut, thus allowing for Wnt-mediated induction of Nkx2-1 expression (Domyan et al., 2011). Applicant tested if the sole function of BMP is to inhibit Sox2 by inhibiting Sox2 and then activating Wnt, which is predicted to be sufficient to activate Nkx2-1 in the absence of BMP. Knocking down sox2 using morpholino injections in *Xenopus* endoderm explants and activating canonical Wnt signaling with Bio did not activate nkx2-1 expression in the absence of BMP4 (FIG. 6A-B, 6E-6F). However, treatment with Bio and BMP4 expanded the nkx2-1 domain upon sox2 knock down as it was in the mouse Sox2 knockout (FIG. 6C-6D). These data suggest two things: one, BMP signaling is required for Nkx2-1 expression independent of Sox2 inhibition; and two, Sox2 is required for repressing ectopic Nkx2-1 expression outside of the respiratory domain.

To determine if human SOX2 is required to prevent ectopic expression of NKX2-1, Applicant used an iPSC line to inducibly express a repressor form of CRISPR protein that represses transcription at the SOX2 locus (CRISPRi-SOX2) (Mandegar et al., 2016). SOX2 knockdown in human dorsal anterior foregut cultures (dAFG) resulted in ectopic expression of NKX2-1 mRNA and protein (FIG. 6G-6J,6L-6M). Optimal NKX2-1 induction in ventral anterior foregut (vAFG) was still dependent on the presence of BMP (FIG. 6K-6N). To determine if SOX2 expression was sufficient to repress NKX2-1, Applicant generated a stable tet-inducible hPSC line to express HA-tagged SOX2 in the ventral foregut during respiratory induction. Expression of SOX2 in the ventral foregut resulted in significant down-regulation of NKX2-1 mRNA and protein (FIG. 6Q-6T). Together, these data suggest that BMP has additional functions for respiratory induction and confirm that in all contexts Wnt signaling is required for NKX2-1 expression. In addition, SOX2 expression is sufficient to repress NKX2-1 expression through unknown mechanisms.

Figure 7A:
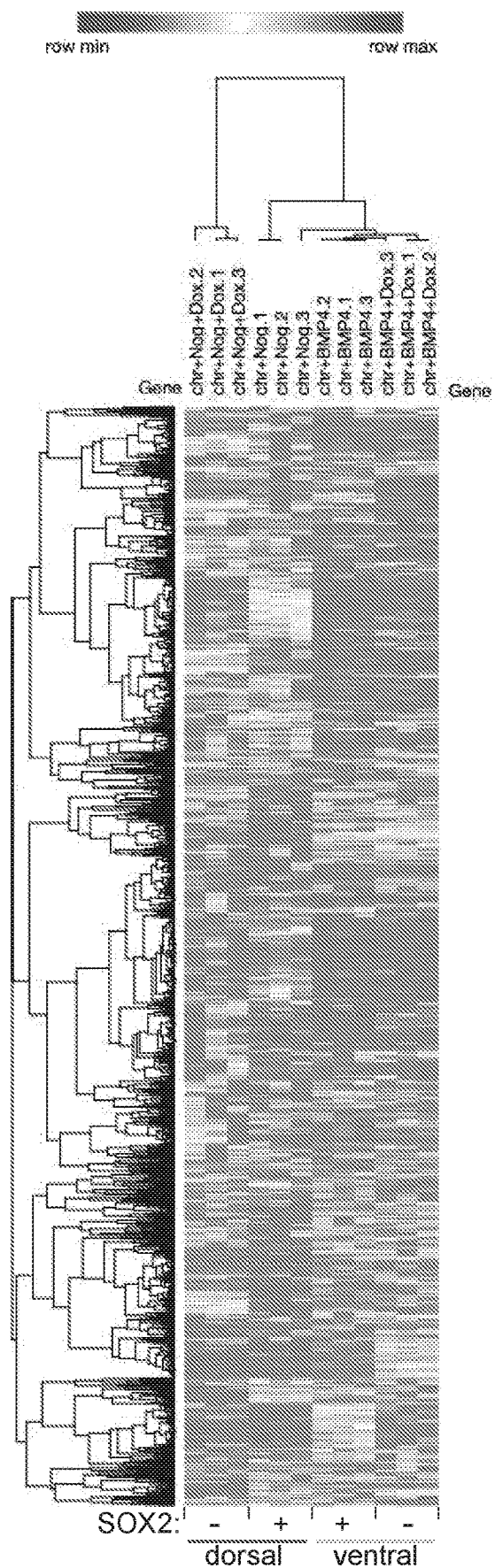
Figure 14A:
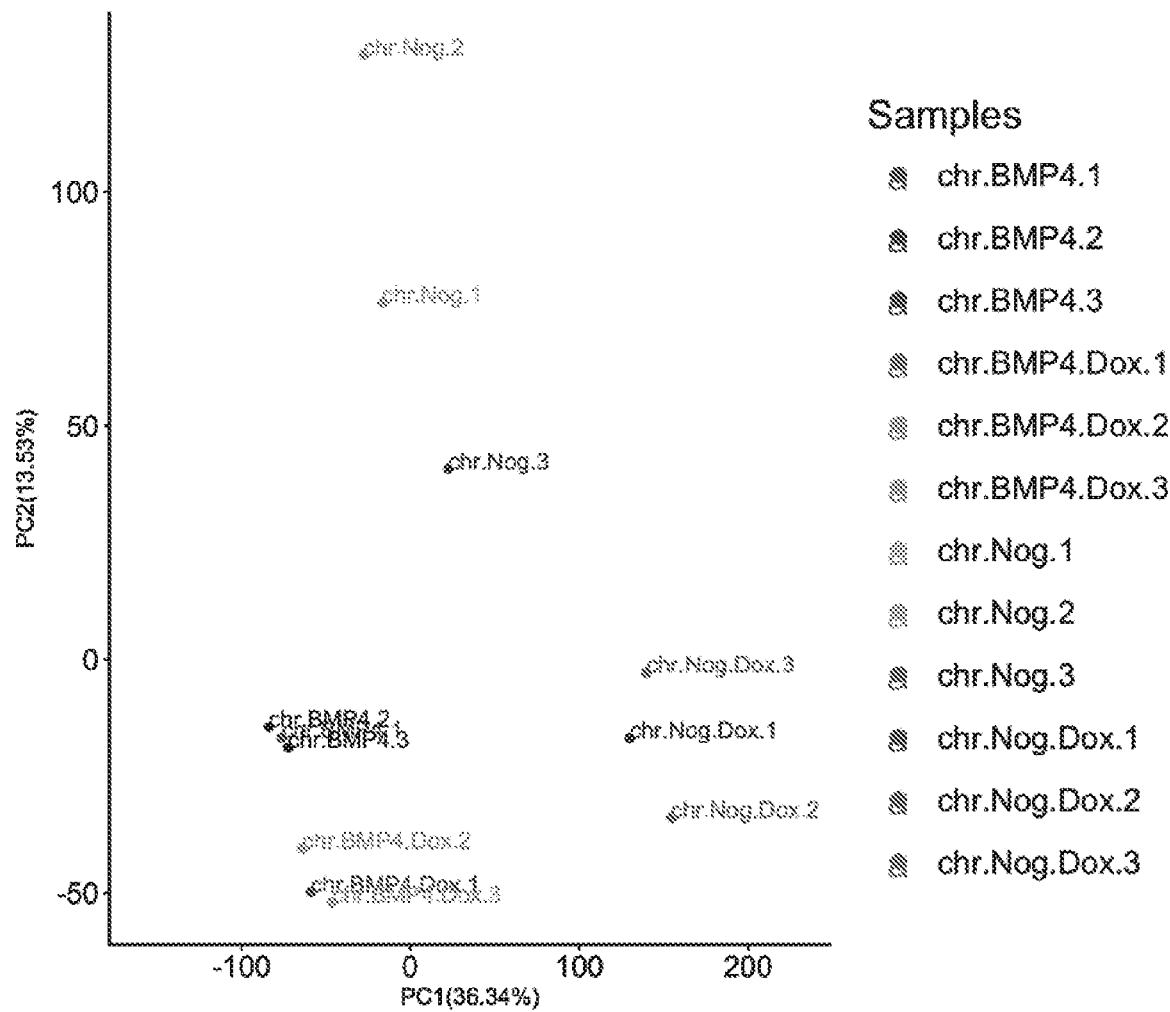
FIGS. 14A-14D. Analysis of loss or gain of function on Sox2 in human cultures. (14A) Principal component analysis of the transcriptome resulting from day 9 anterior foregut cultures patterned along the dorsal-ventral axis with and without SOX2 (without or with Dox treatment to activate the CRISPR interference construct). Dorsal vs. ventral anterior foregut (dAFG vs. vAFG) is indicated as chr+Nog and chr+BMP4, respectively. Knockdown is indicated by the +Dox. (14B) TPM values for SOX2 and NKX2-1. (14C) qPCR analysis for SFRP2 on day 9 anterior foregut cultures patterned along the dorsal (dAFG) and ventral (vAFG) axis, including inducing exogenous HA-tagged SOX2 in ventral cultures by Dox treatment on day 8. (14D) Genome browser view of Sox2 peaks at the SFRP2 locus in hPSC-derived endoderm (GSM1505764) and mesendoderm (GSM1505767) from GEO dataset GSE61475 (Tsankov et al., 2015). Scale bar=500 μm. Error bars indicate SD. *p≤0.05 for two-tailed t-test.
Figure 14B:
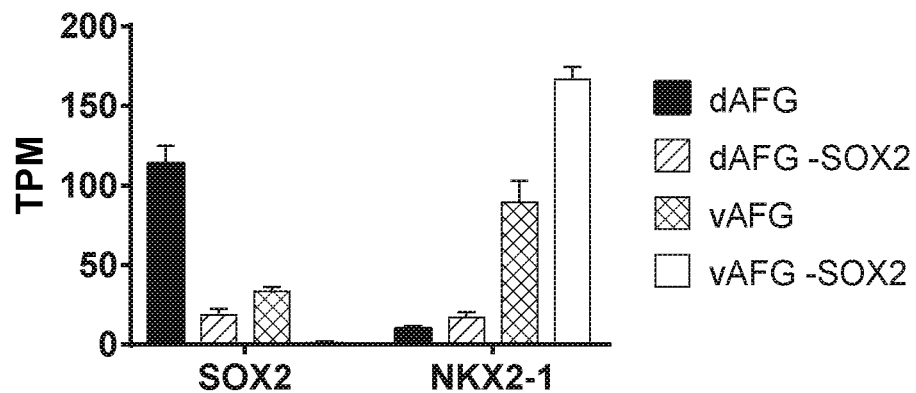

Sox2 Regulates Expression of Wnt Antagonists During Dorsal-Ventral Patterning The ease of manipulation and scalability of foregut cultures are ideally suited for "omic" approaches. Applicant therefore took an RNA sequencing-based approach to identify genes that are regulated by SOX2 and/or BMP signaling during dorsal-ventral (esophageal-respiratory) patterning. Principal component analysis (PCA) identified that the largest groups of regulated genes were for dorsal-ventral patterning (±BMP4 or Noggin) and for SOX2-regulated genes (±dox-SOX2 CRISPRi) (FIG. 14A). Moreover, SOX2 regulates a distinct set of genes in dorsal (Noggin) cultures as compared to ventral (BMP4) cultures, as indicated in the cluster heatmap and in the PCA along principal component axis 1 (FIG. 7A, 14A). The use of either BMP4 or Noggin resulted in the expected changes in dorsal-ventral patterning markers, such as upregulation of NKX2-1 and repression of SOX2, MNX1, KRT4, PAX9 in the ventral (BMP-high) cultures. The loss of SOX2, however, resulted in many transcriptional changes in the dorsal foregut and relatively few in the ventral foregut, including increased expression of NKX2-1 and reduced expression of FOXE1, NTN1, and GDNF (FIG. 7A-7B, 7D, 14B).

Figure 7B:
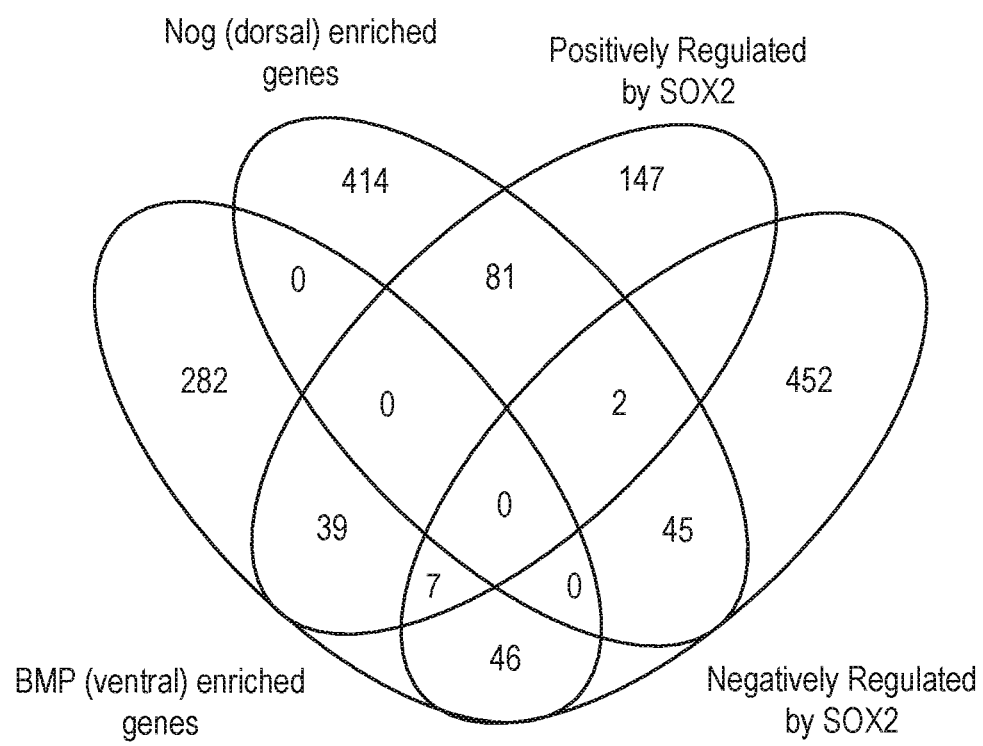

Of the dorsal and ventral genes, there were transcripts that changed in response to the CRISPRi-SOX2 (either elevated or reduced) and genes that were not (SOX2-independent). For example, of the 542 genes enriched in the dorsal foregut, 75.6% (410 genes) are SOX2-independent. 17.2% (93 genes) in the dorsal foregut were downregulated upon SOX2 knockdown, referred to by Applicant as "positively regulated by SOX2". There were 39 transcripts that were elevated in response to SOX2 knockdown, suggesting that these are "negatively regulated by SOX2". In the ventral cultures, 374 genes are upregulated by BMP treatment, and of these, 38 were decreased and 5 were increased in response to loss of SOX2 (FIG. 7D). Not surprisingly, more genes were regulated by SOX2 in the dorsal foregut as ventral SOX2 expression is already significantly downregulated in response to BMP. Applicant used intersectional analysis to identify genes that BMP likely regulates through repression of SOX2 and found 46 genes (12.3%) that are both upregulated by both BMP treatment and SOX2 knockdown ("Genes negatively regulated by SOX2"). Applicant also found 81 genes (14.9%) that are both downregulated by both BMP treatment and SOX2 knockdown ("Genes positively regulated by SOX2") (FIG. 7B). In addition, >80% of BMP-regulated transcripts were unchanged in response to SOX2 knockdown, consistent with the conclusion that BMP has a role in ventral foregut specification independent of SOX2 repression.

Figure 7C:
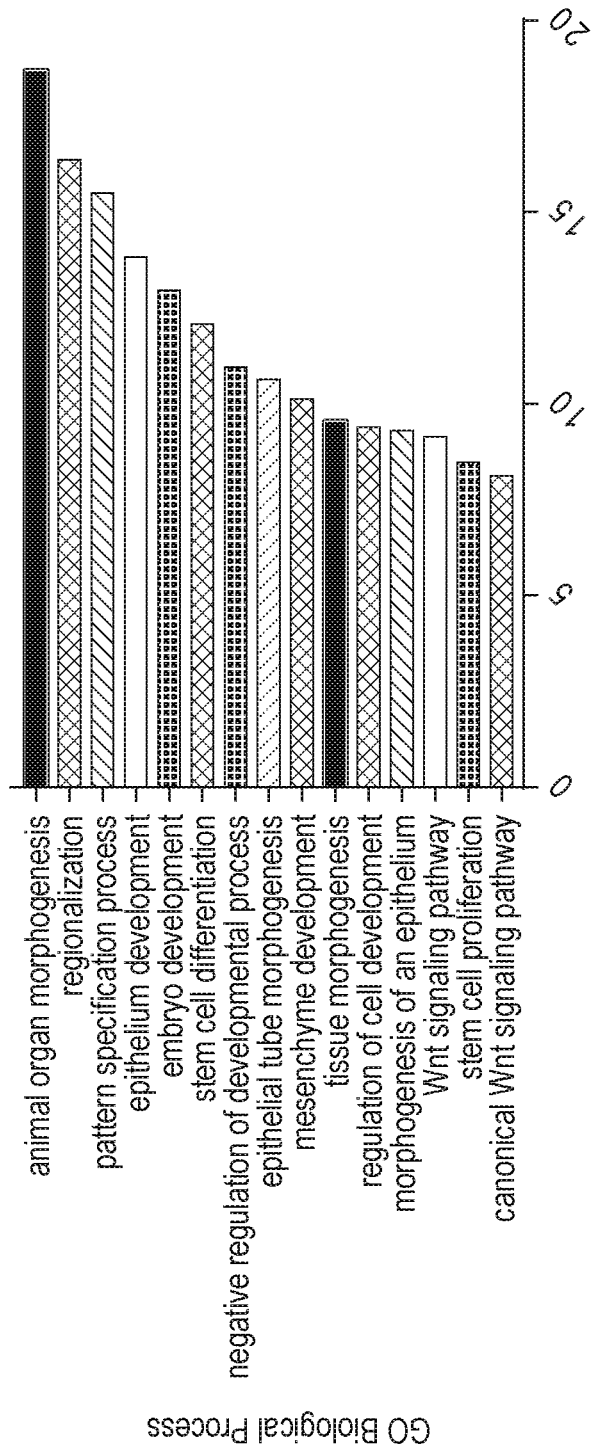
Figure 7E:
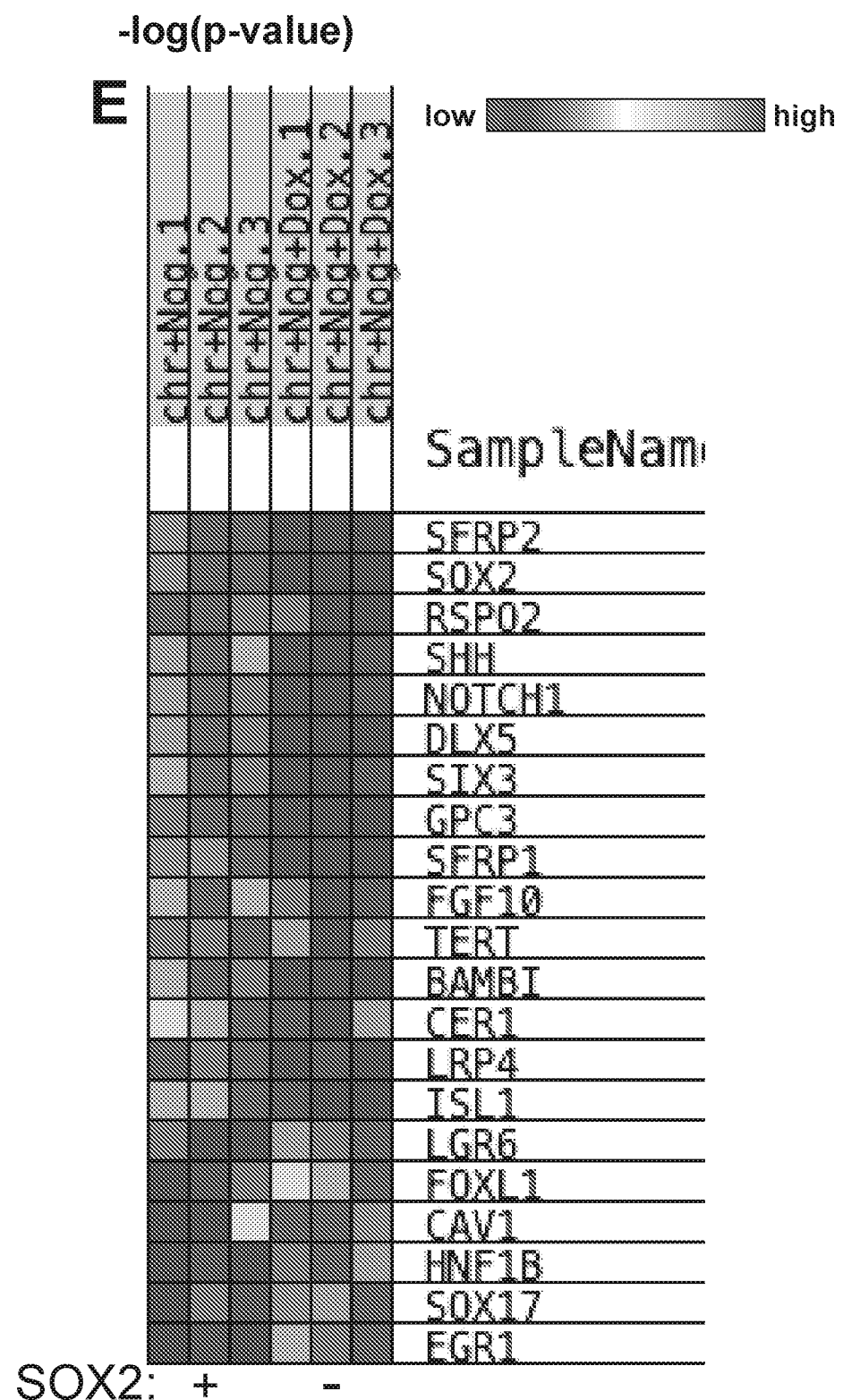
Figures 7F, 7G:
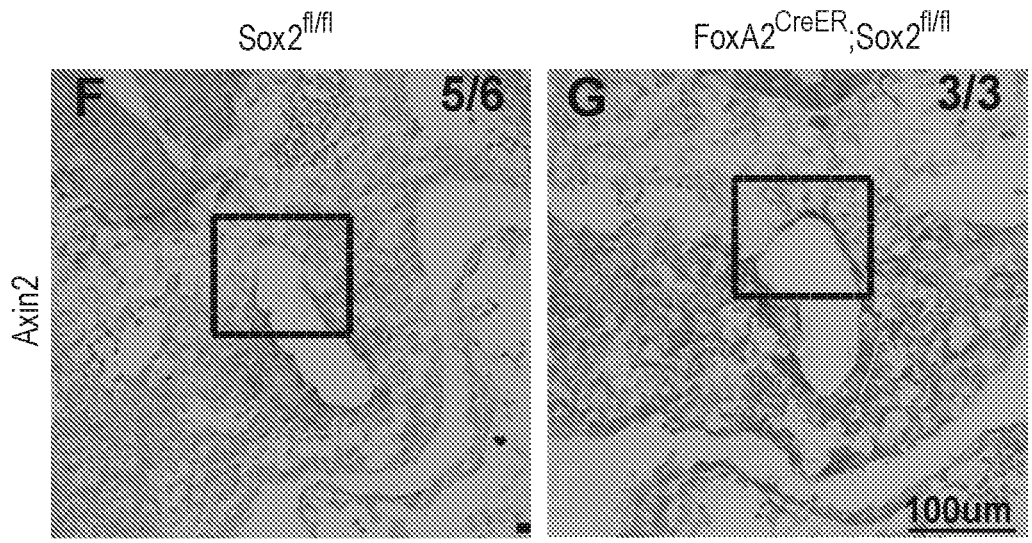
Figures 7H, 7I:
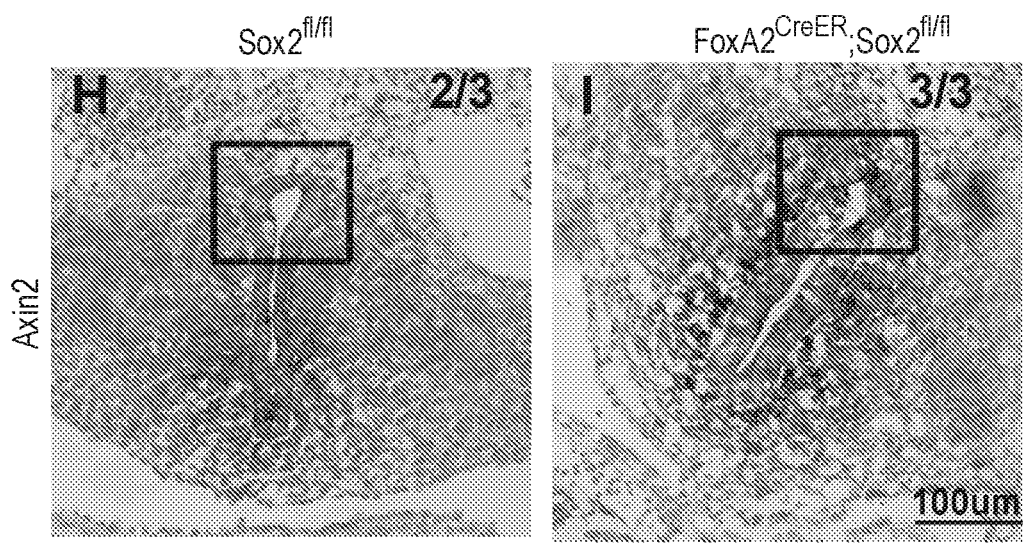
Figure 7J:
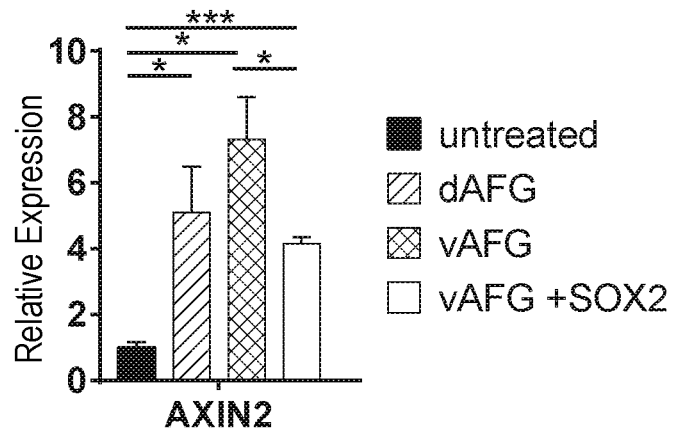
Figure 7K:
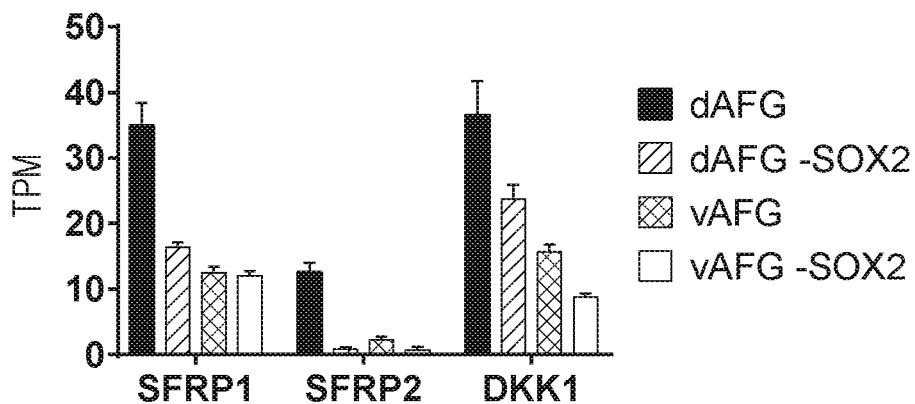
Figure 14C:
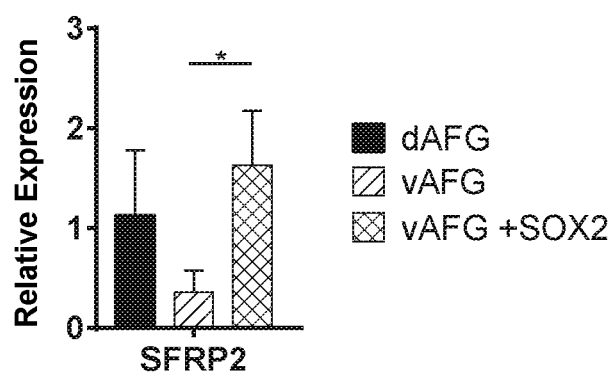
Figure 14D:
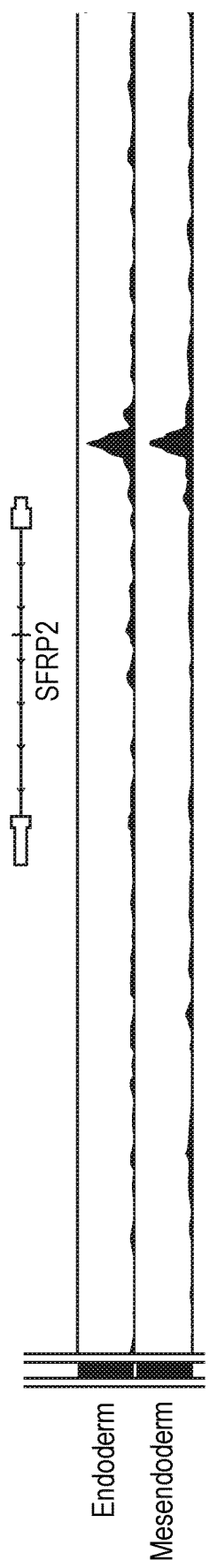
Figure 15A:
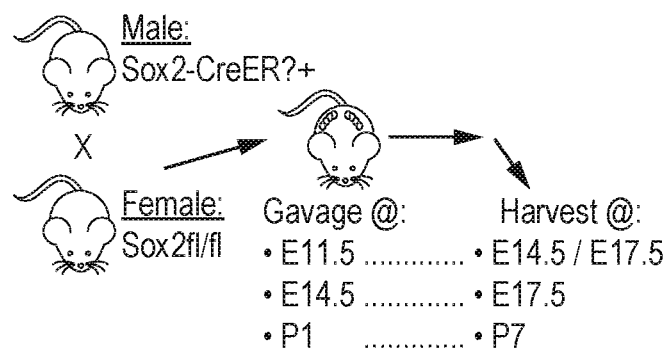
Figure 15B:
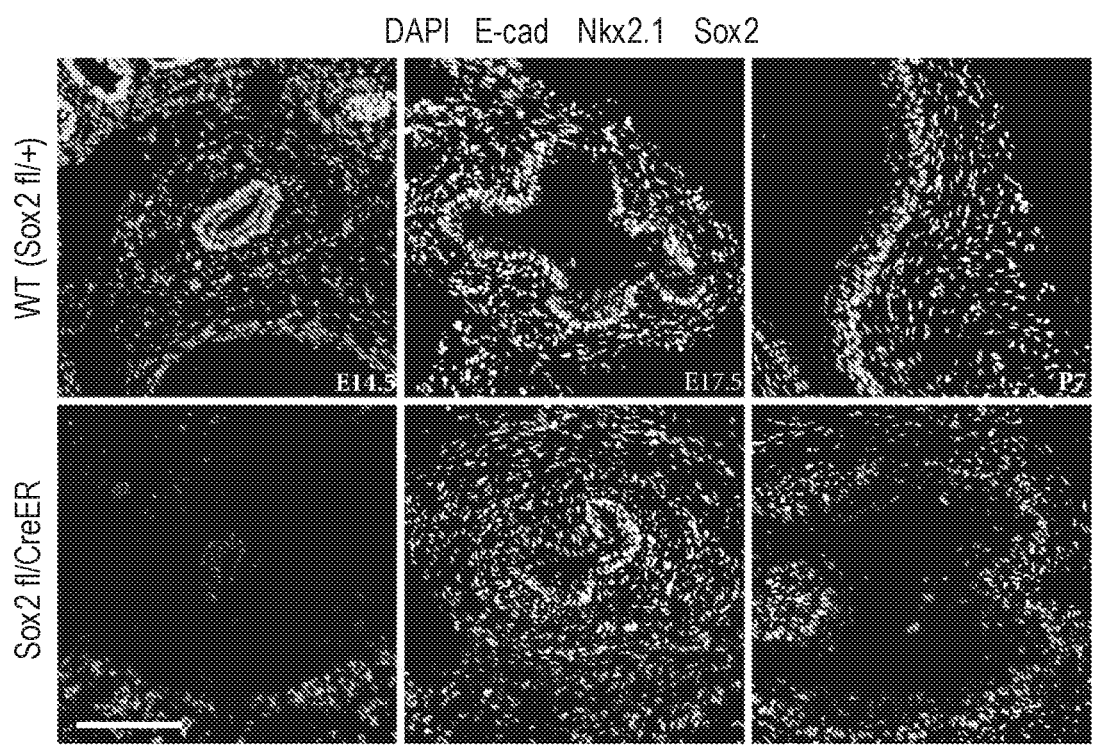
Figure 15E:
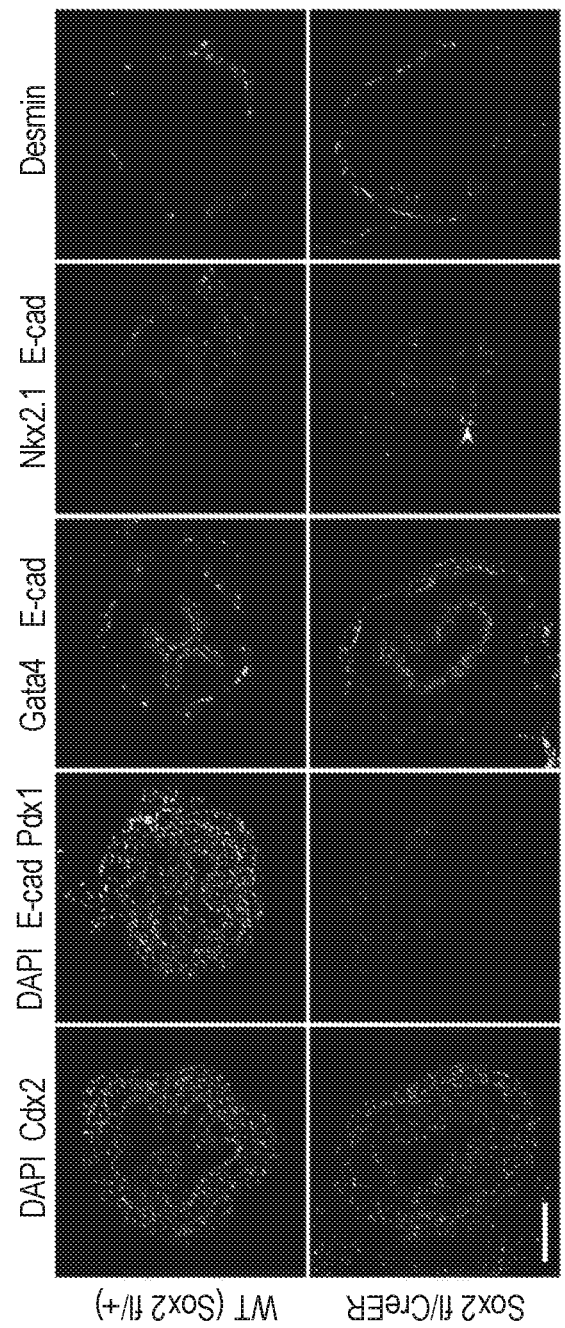
Figure 16A:
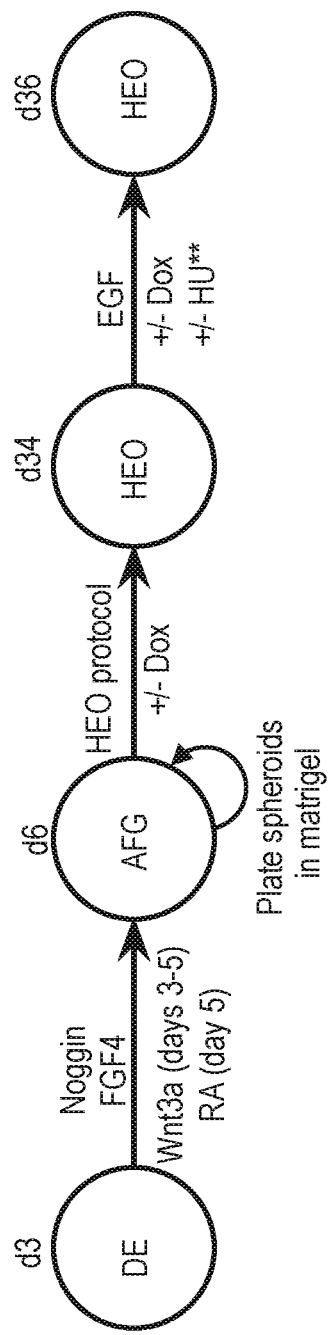
FIGS. 16A-16G. Modeling the effects of Fanconi anemia (FANCA loss) in HEOs. (16A) Schematic depicting the experimental protocol to generate HEOs with (+dox) or without FANCA. **Note: Hydroxyurea (HU) is used for Western blot analysis in (16E). (16B) IF images of day 6 AFG monolayer stained for the foregut marker SOX2 (green) and hindgut marker CDX2 (red). (16C) Brightfield images of HEOs grown with or without doxycycline treatment at week 0 (day 6), week 2 (day 20), and week 4 (day 35) of organoid growth. (16D) IF images of HEOs for SOX2 and the proliferation marker KI67. (16E) Western blot analysis for FANCA and FANCD2 to confirm expression and function of dox-induced FANCA protein. (16F) Size quantification of 2-week-old HEOs from brightfield images. (16G) Quantification of proliferative (KI67+) epithelial cells in 1 month (day 36) old HEOs. Scale bar=100 μm for (16B, 16D), and 250 μm in (16C). *p≤0.05 and **p≤0.01 for Mann-Whitney non-parametric test. DE=definitive endoderm; AFG=anterior foregut; HEO=human esophageal organoid.
Figure 16B:
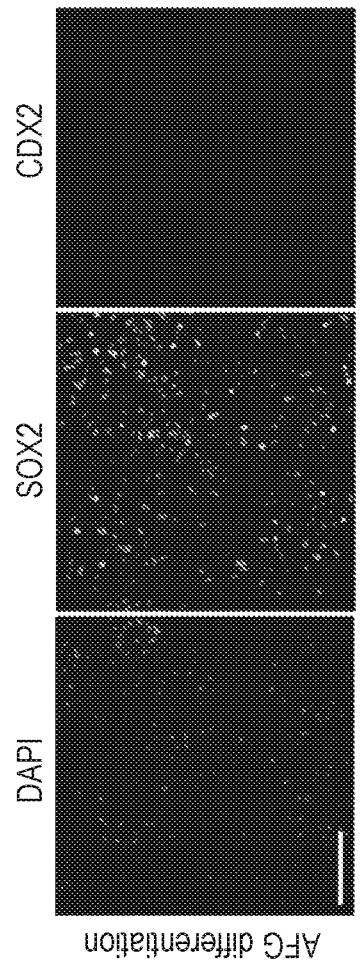
Figure 16C:
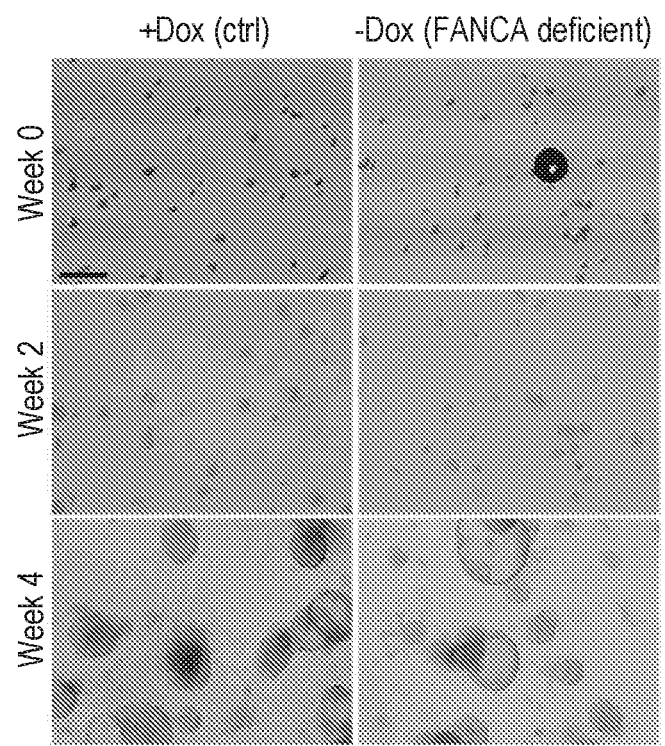
Figure 16D:
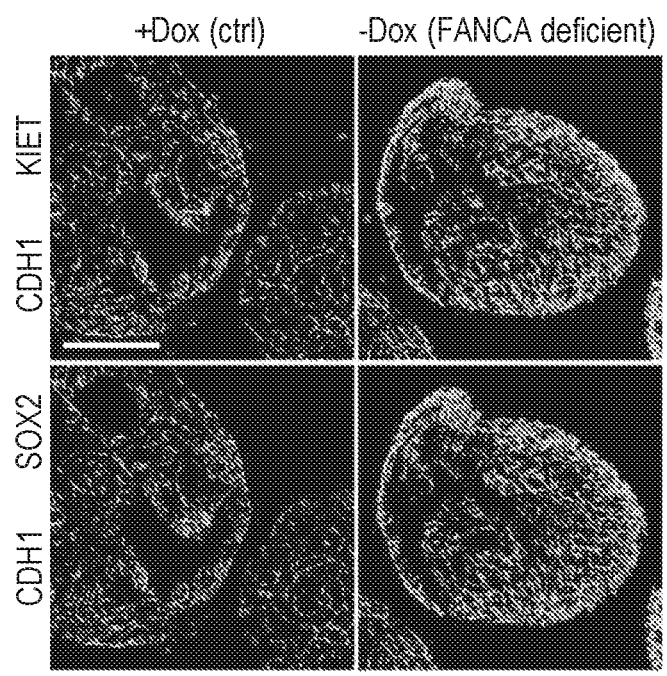
Figure 16E:
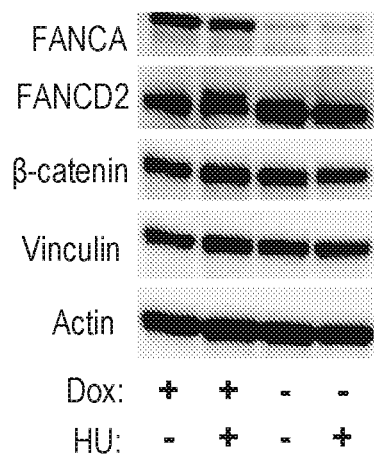
Figure 16F:
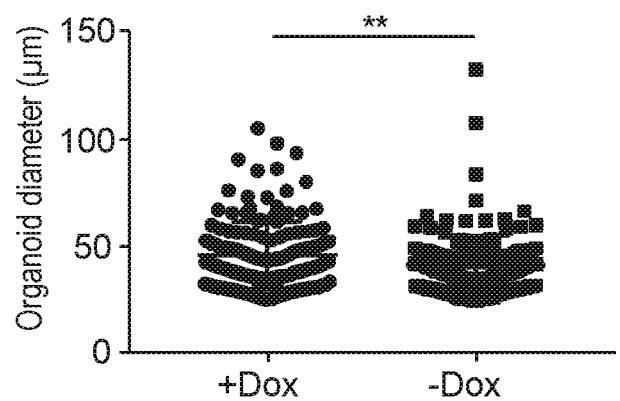
Figure 16G:
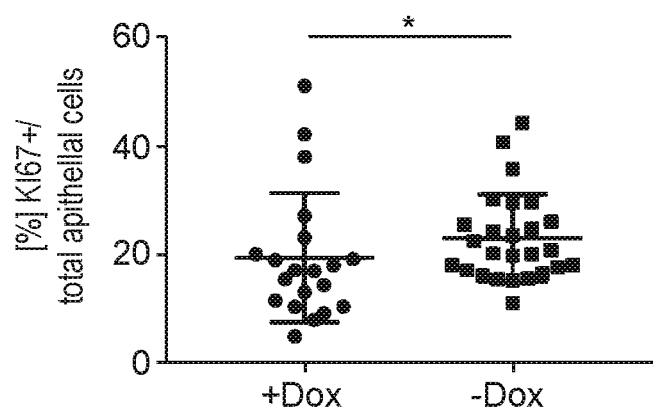
Figure 17A:
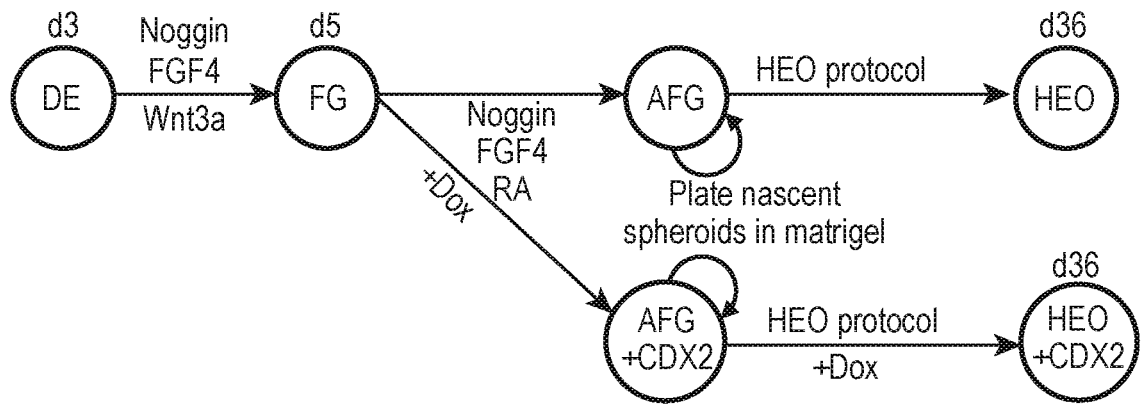
FIGS. 17A-17L. Induction of CDX2 in human foregut and HEO cultures. (17A) Schematic depicting the experimental protocol to induce CDX2 in foregut and HEO cultures. (17B) Schematic of the transduced lentiviral vector to induce CDX2 upon administration of doxycycline. (17C) IF analysis of day 6 anterior foregut monolayers treated with various levels of doxycycline (20, 100, and 500 ng/mL) for the foregut marker SOX2 and hindgut marker CDX2. (17D+17E) Quantification of IF images (as in 17C) by (17D) scatter plot for SOX2 versus CDX2 intensity. Vertical line within scatter plot is the "gate" to define CDX2+ versus CDX2− cells. (17E) Bar graph of percent CDX2+ cells. (17F) IF analysis of 1-month HEOs treated with or without doxycycline for the stratified squamous markers SOX2 and p63, and hindgut (induced) marker CDX2. (17G-17L) qPCR analysis of hindgut markers (17G) CDX1, (17H) CDX2, (17I) CDH17, (17J) MUC2, and foregut/stratified squamous markers (17K) SOX2 and (17L) p63. Scale bar=100 μm. p≤0.01, *p≤0.001, and ****p≤0.0001 for Student's t-test with 2-tailed distribution not assuming equal variance. DE=definitive endoderm; FG=foregut; AFG=anterior foregut; HEO=human esophageal organoid.
Figure 17B:
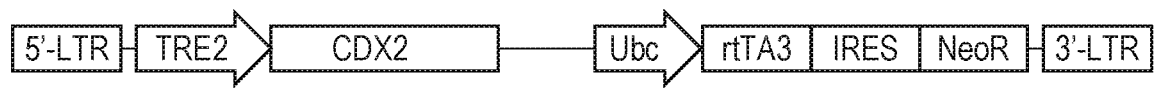
Figure 17C:
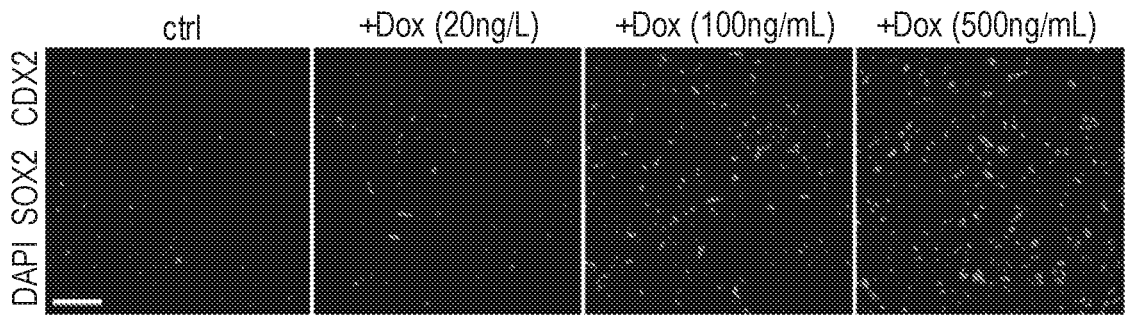
Figure 17D:
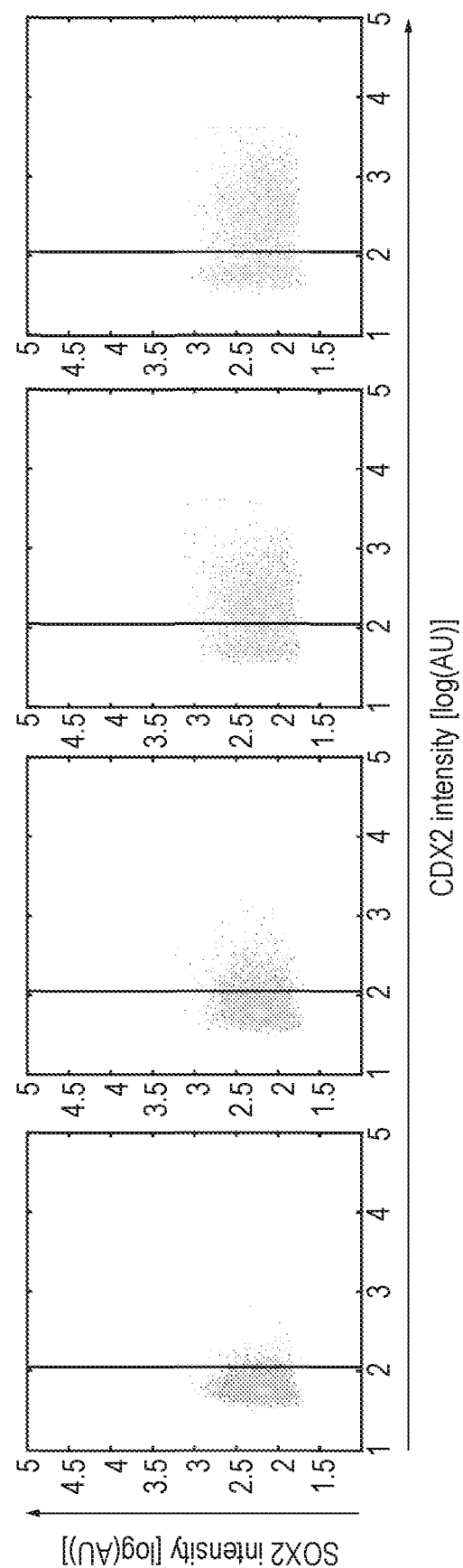
Figure 17E:
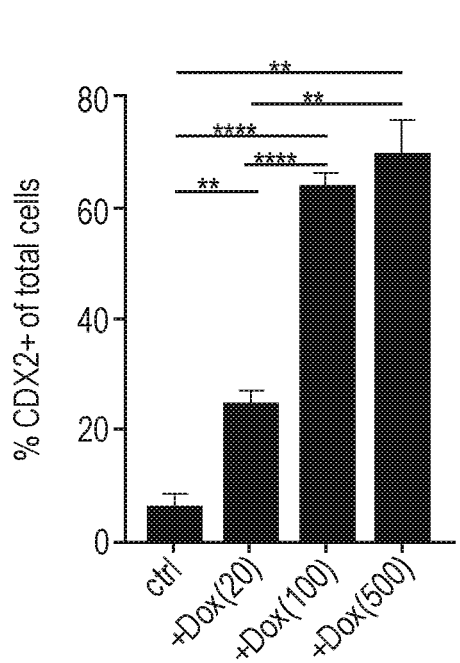
Figure 17F:
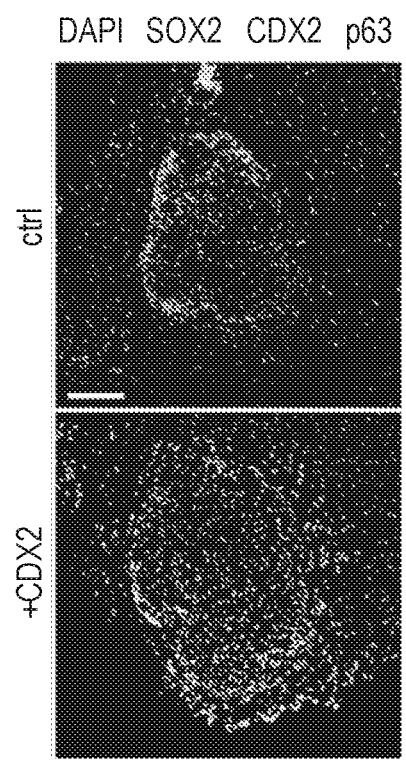
Figure 17G:
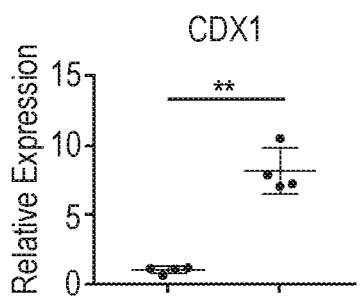
Figure 17I:
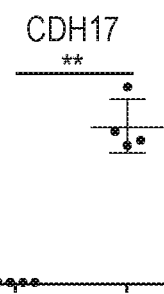
Figure 17K:
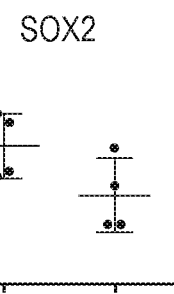
Figure 17H:
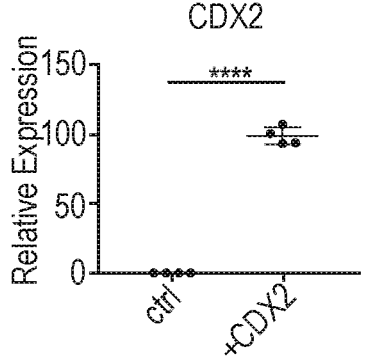
Figure 17J:
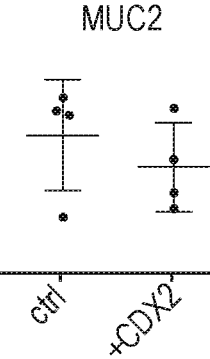
Figure 17L:
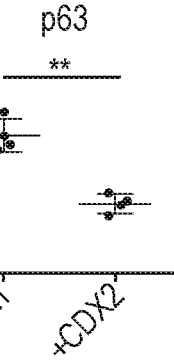
Figure 18A:
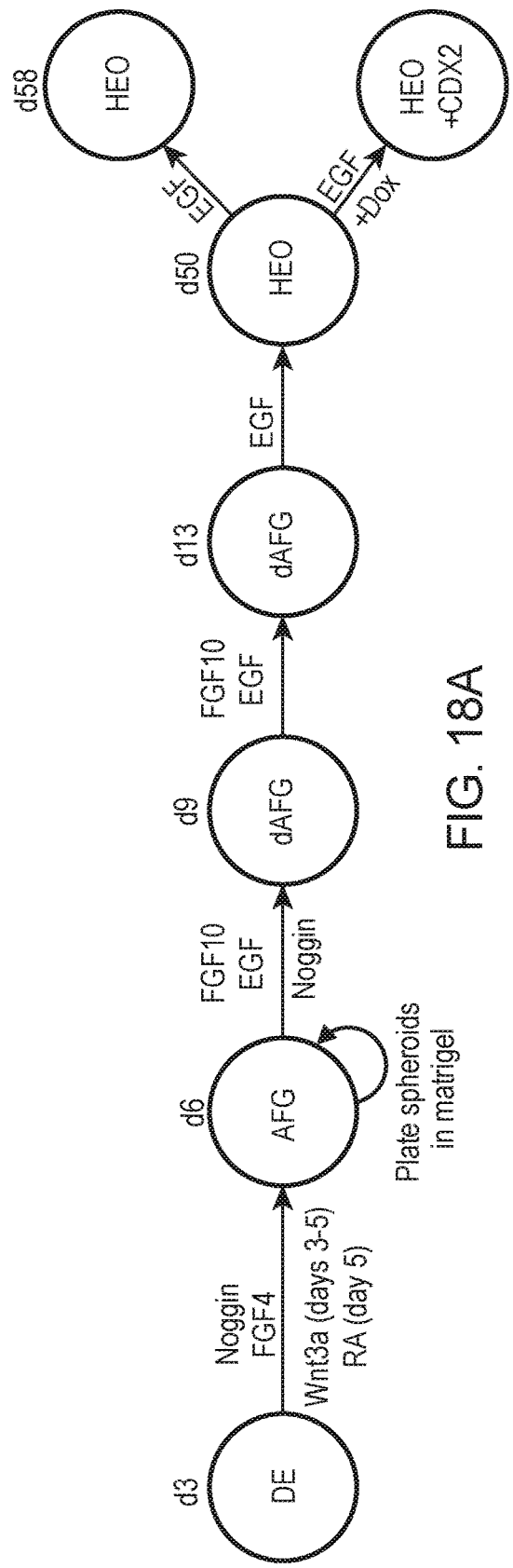
Figure 18B:
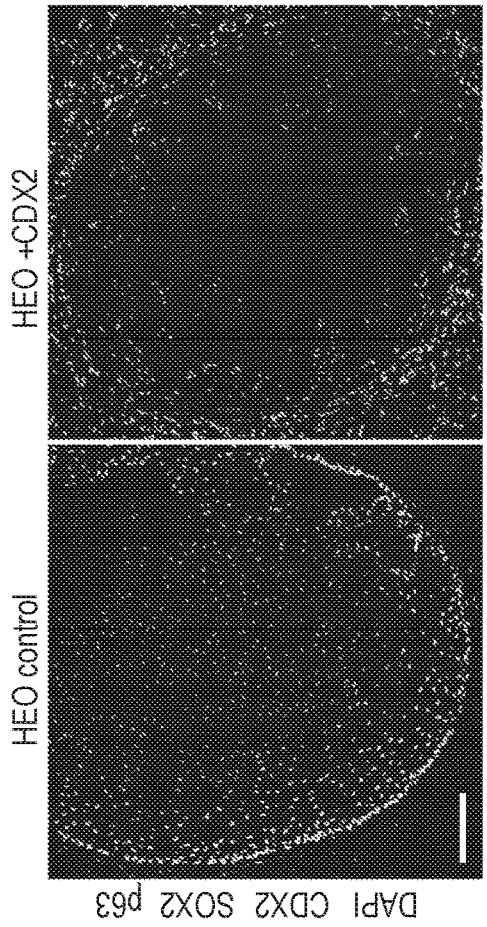
Figures 19E, 19F, 19G:
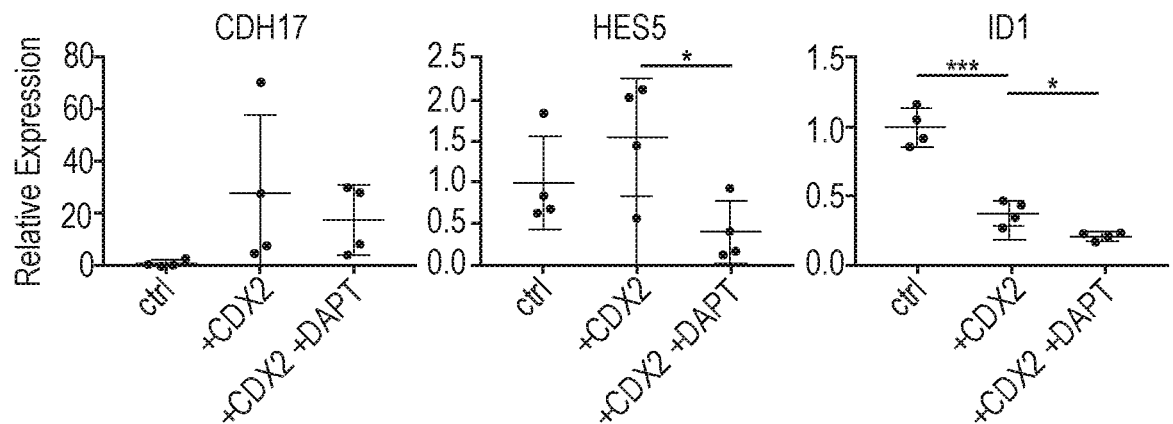
Figure 19H:
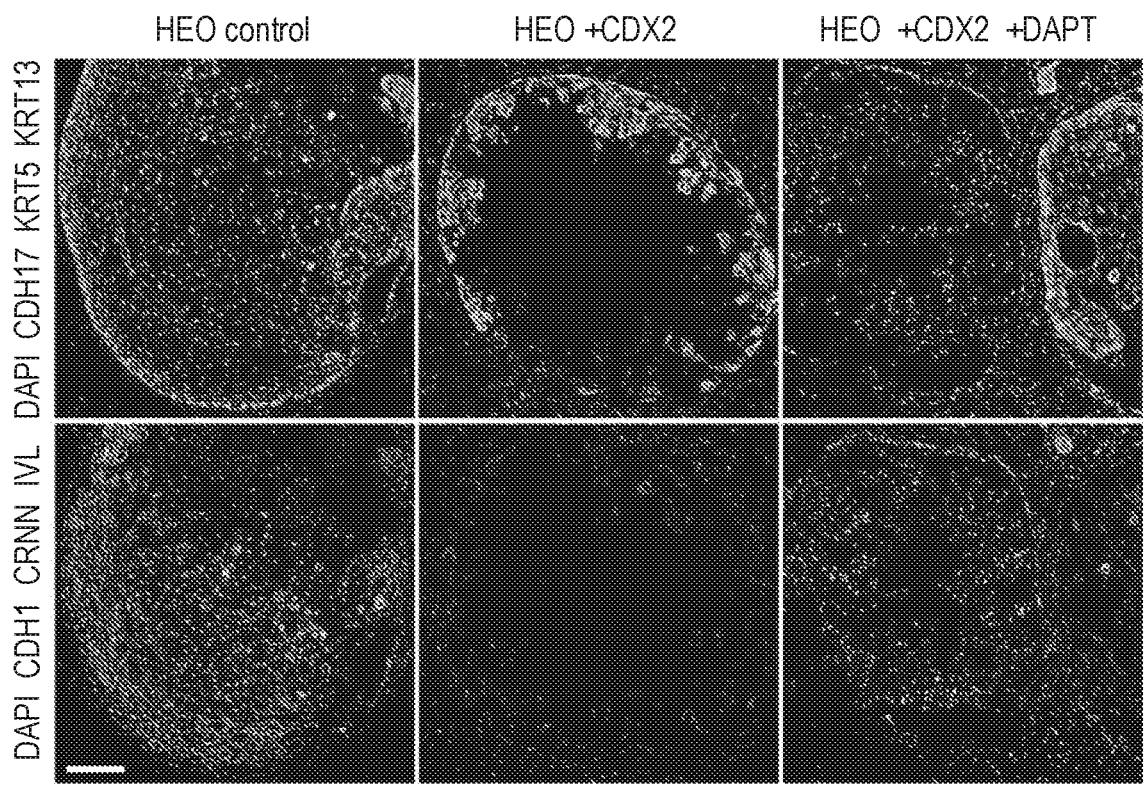
Figure 20A:
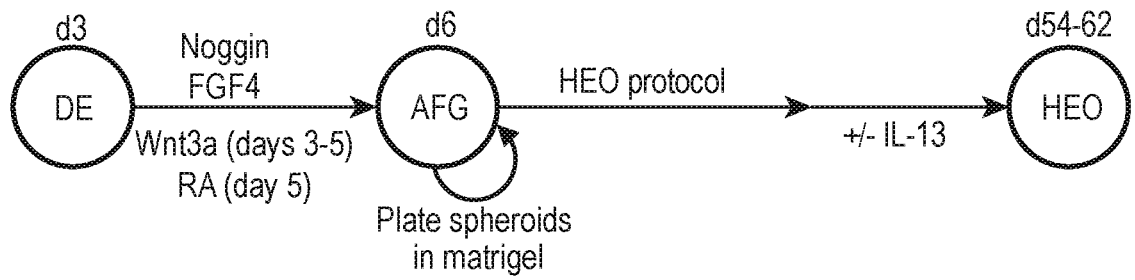
FIGS. 20A-20H. IL-13 treated HEOs upregulate IL-13 target genes and increase proliferation. (20A) Schematic depicting the experimental protocol to treat IL-13 in late stage HEOs. (20B-20E) qPCR analysis of day 62 HEOs treated with IL-13 for 2 days prior to harvest for known IL-13 target genes (20B) CCL26, (20C) CDS26, (20D) CAPN14, and (20E) SERPINB4. (20F) Western blot analysis of day 50 HEOs treated with IL-13 (100 ng/mL) for 1 week prior to harvest for SERPINB13, CDH26, and a housekeeping protein GAPDS. (20G) IF images of day 62 HEOs treated with IL-13 (100 ng/mL) for 2 weeks and EdU (10 uM) for 2 days prior to harvest. (20H) quantification (of 20G) for the percent EdU labeled of all basal-most p63 cells. For qPCR data, *p≤0.05 and **p≤0.01 for Student's t-test with 2-tailed distribution not assuming equal variance. For organoid EdU incorporation quantification, *p<0.05 for Mann-Whitney non-parametric test. Scale bar=100 μm. DE=definitive endoderm; AFG=anterior foregut; HEO=human esophageal organoid.
Figures 20B, 20C:
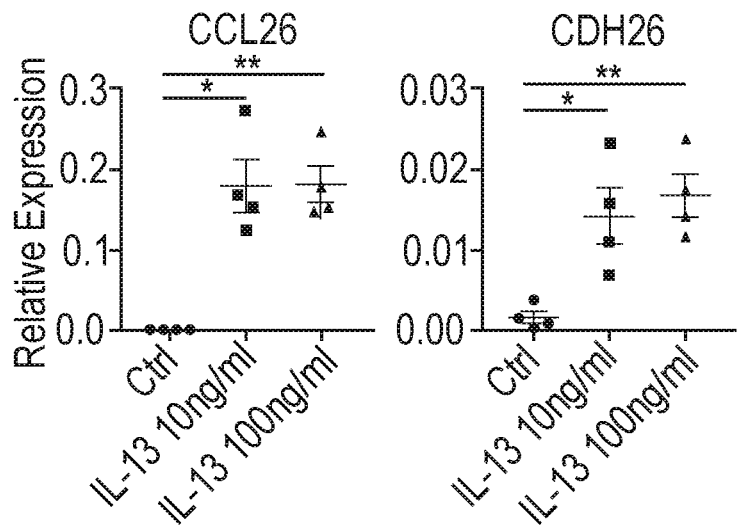
Figures 20D, 20E:
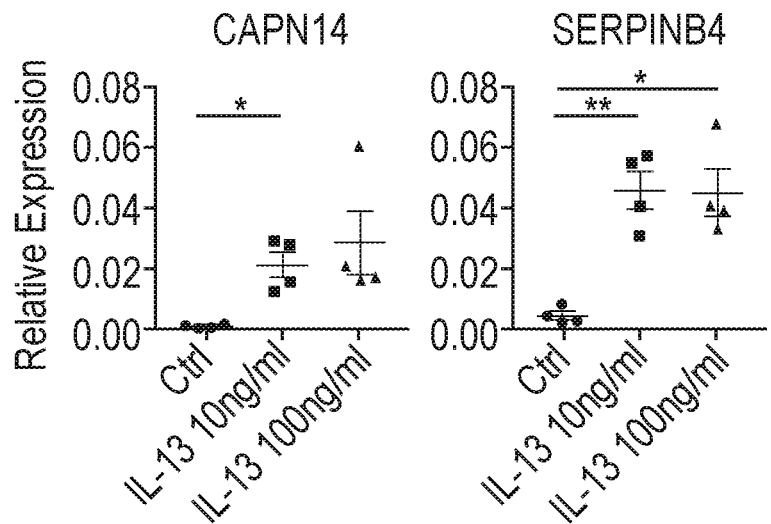
Figure 20F:
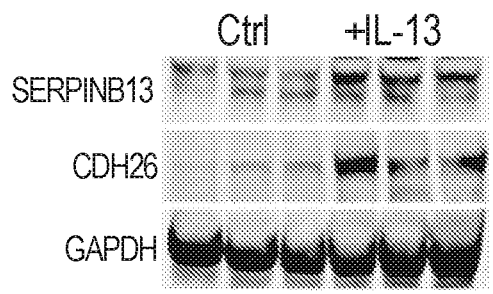
Figure 20G:
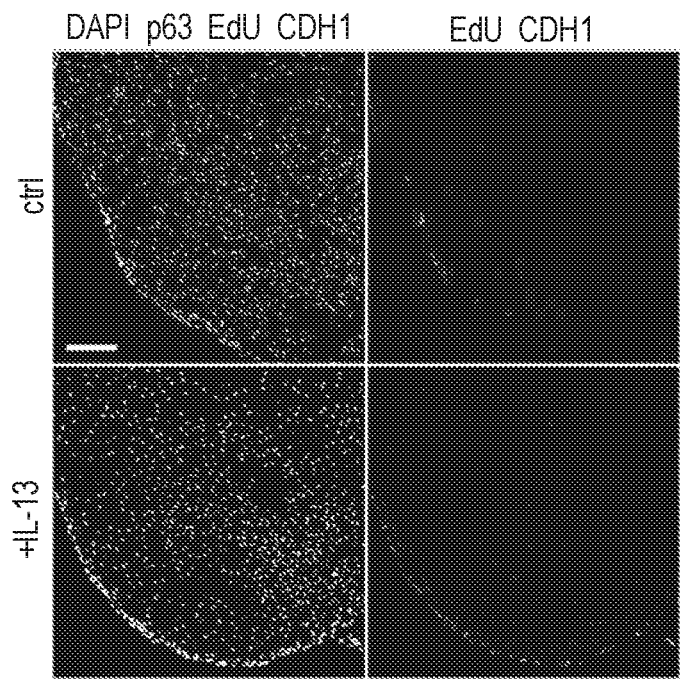
Figure 20H:
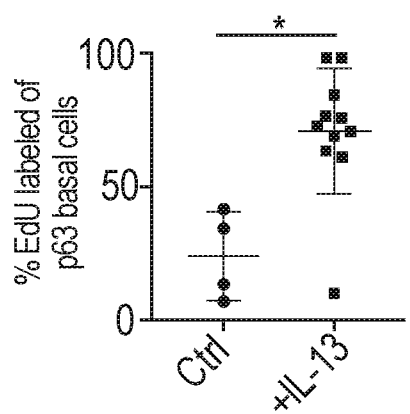
Figure 21G:
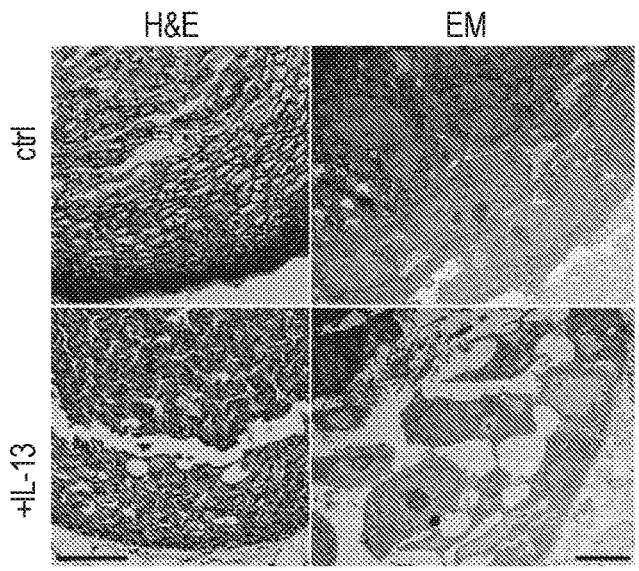
Figure 21H:
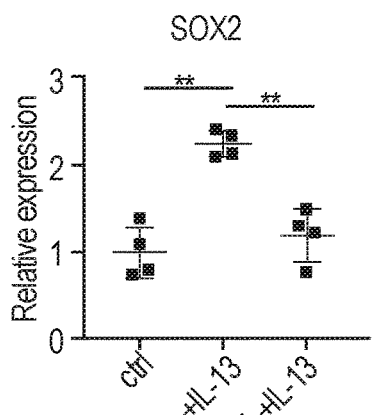
Figure 21I:
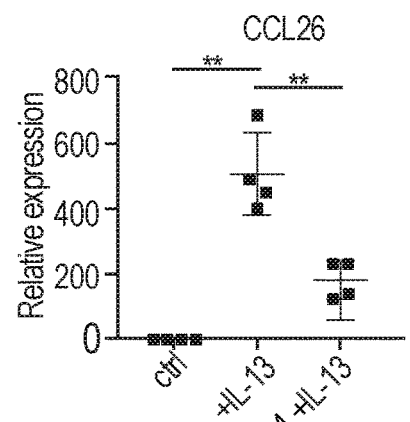
Figure 21J:
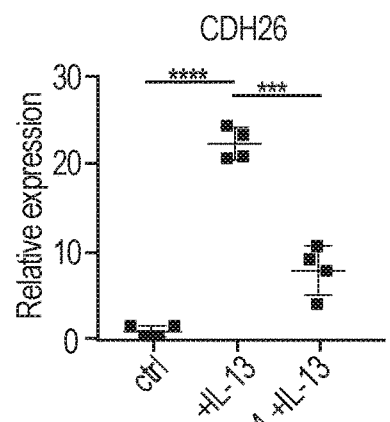
Figure 21K:
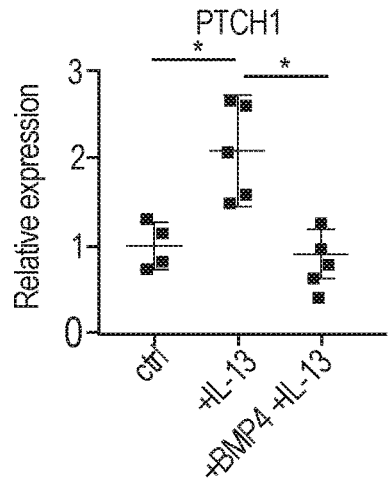
Figure 21L:
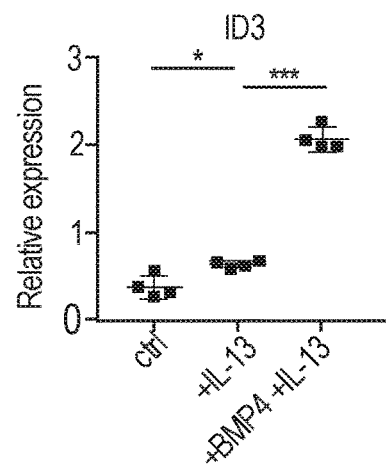
Figure 22A:
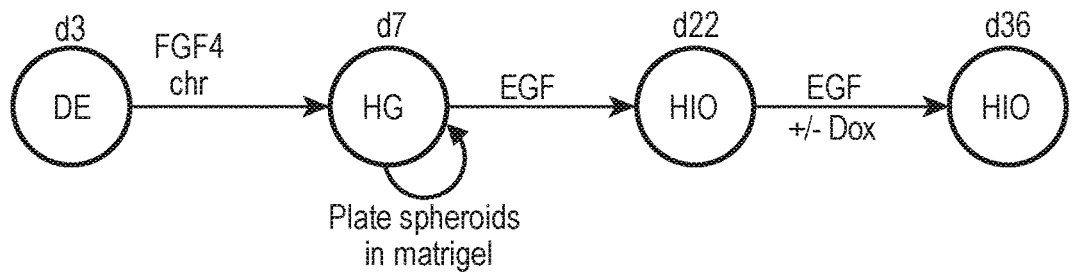
Figure 22B:
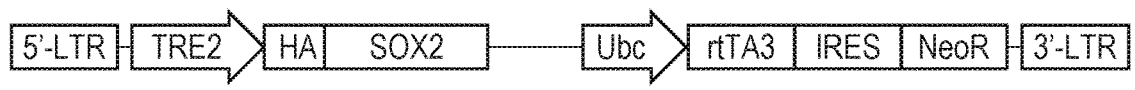
Figure 22C:
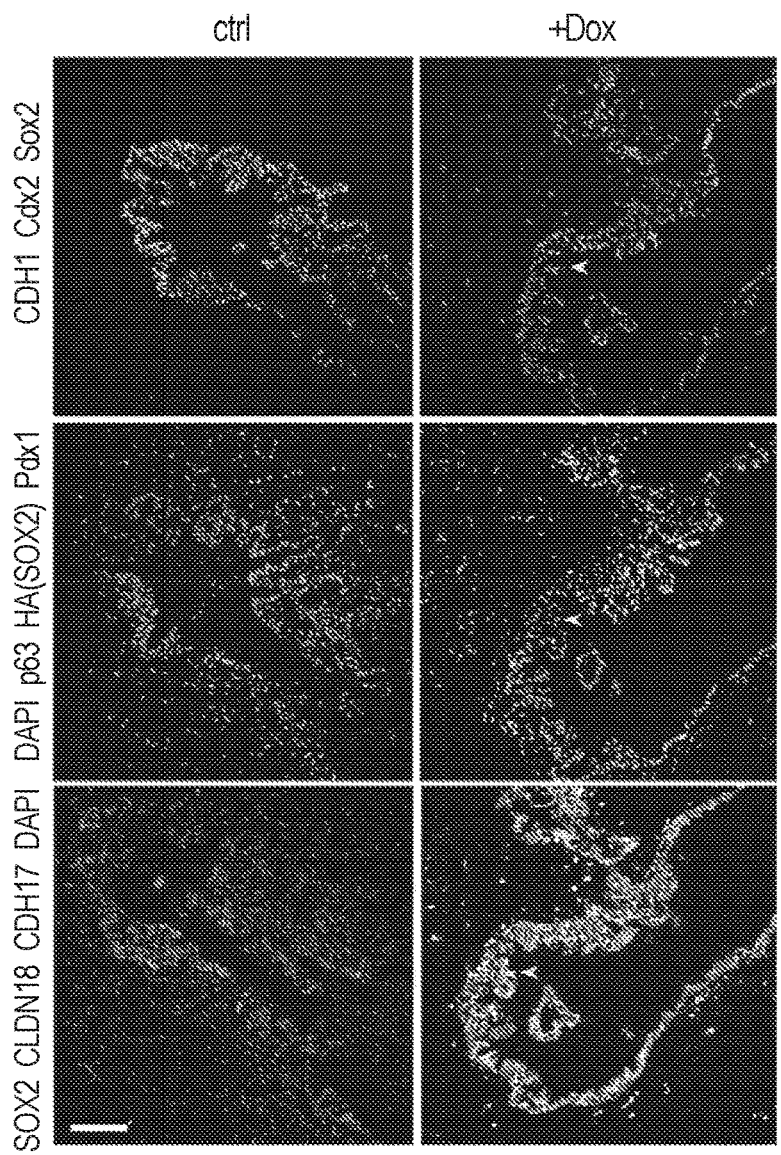
Figure 22D:
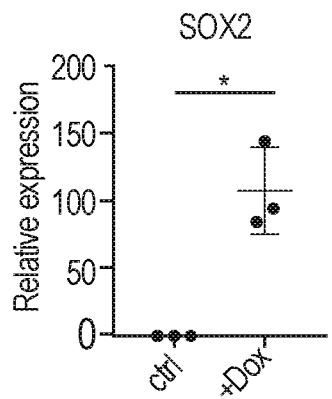
Figure 22E:
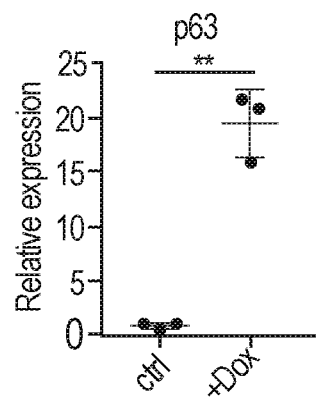
Figure 22F:
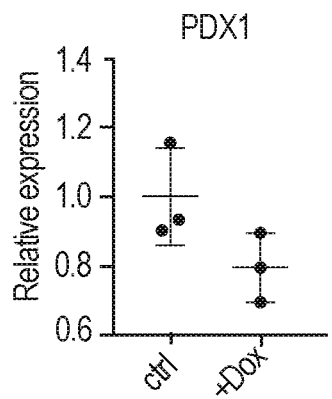
Figure 22G:
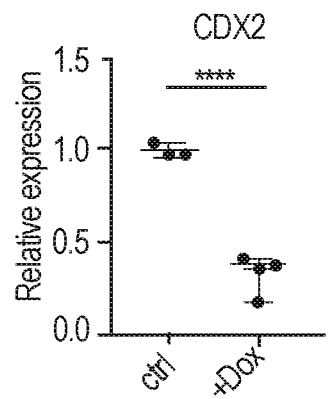
Figure 22H:
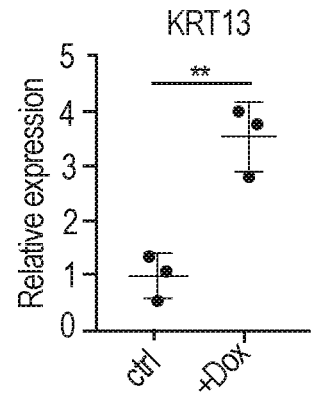

Performing gene ontology analysis of all 404 unique genes whose expression was reduced in dAFG in response to SOX2 knockdown yielded in many significant gene ontology terms, including two terms involving the Wnt signaling pathway (FIG. 7C). Gene set enrichment analysis also found several Wnt signaling components to be significantly altered in response to SOX2 knockdown (FIG. 7E). The secreted canonical Wnt signaling inhibitors SFRP1, SFRP2, DKK1, were all downregulated upon SOX2 loss (FIG. 7E, 7K). Moreover, over-expression of SOX2 in ventral cultures upregulated SFRP2, which is consistent with published ChIP-seq data in hPSC-derived mesendoderm and endoderm showing a SOX2 binding peak at the SFRP2 locus (FIG. 14C-14D) (Tsankov et al., 2015).

Figure 6G:
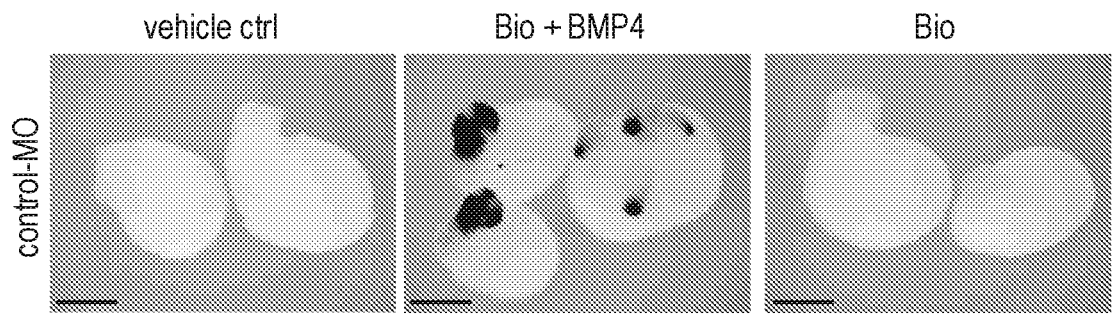
FIGS. 6A-6T. Sox2 represses the respiratory fate and promotes the dorsal (esophageal) lineage. (6A-6F) In situ hybridization for nkx2-1 of control (6A, 6C, 6E) or Sox2 MO-injected (6B, 6D, 6F) Xenopus endoderm explants analyzed at stage NF35 treated with Bio (GSK3β inhibitor) and Bio+BMP4. (6G) Schematic depicting experimental protocol to generate human dorsal (Noggin) and ventral (BMP) AFG cultures. +SOX2 indicates tet-inducible SOX2, while −SOX2 indicates SOX2 CRISPRi. (6H-6N) Analysis of day 9 AFG cultures patterned along the dorsal-ventral axis, with or without SOX2 knockdown in the dorsal cultures using Dox-inducible CRISPRi on day 3-9; (6H-6K) IF staining of cultures for SOX2 and NKX2-1 and quantification in (6L). (6M-6N) qPCR analysis for SOX2 and NKX2-1 in response to these patterning conditions. (6O-6T) Doxycycline-induced expression of exogenous SOX2 in ventral cultures on day 8 and analysis on day 9. (6O-6R) IF staining of cultures for NKX2-1 and HA-SOX2; and (6S-6T) qPCR analysis for SOX2 and NKX2-1 in response to patterning conditions. Scale bar=50 μm for IF images, and 200 μm for Xenopus explant images. See quantification and statistical analysis section for details.
Figure 6G:
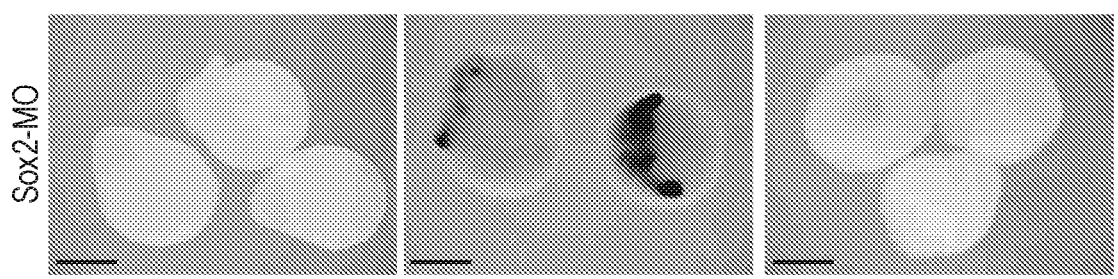
Figure 6G:
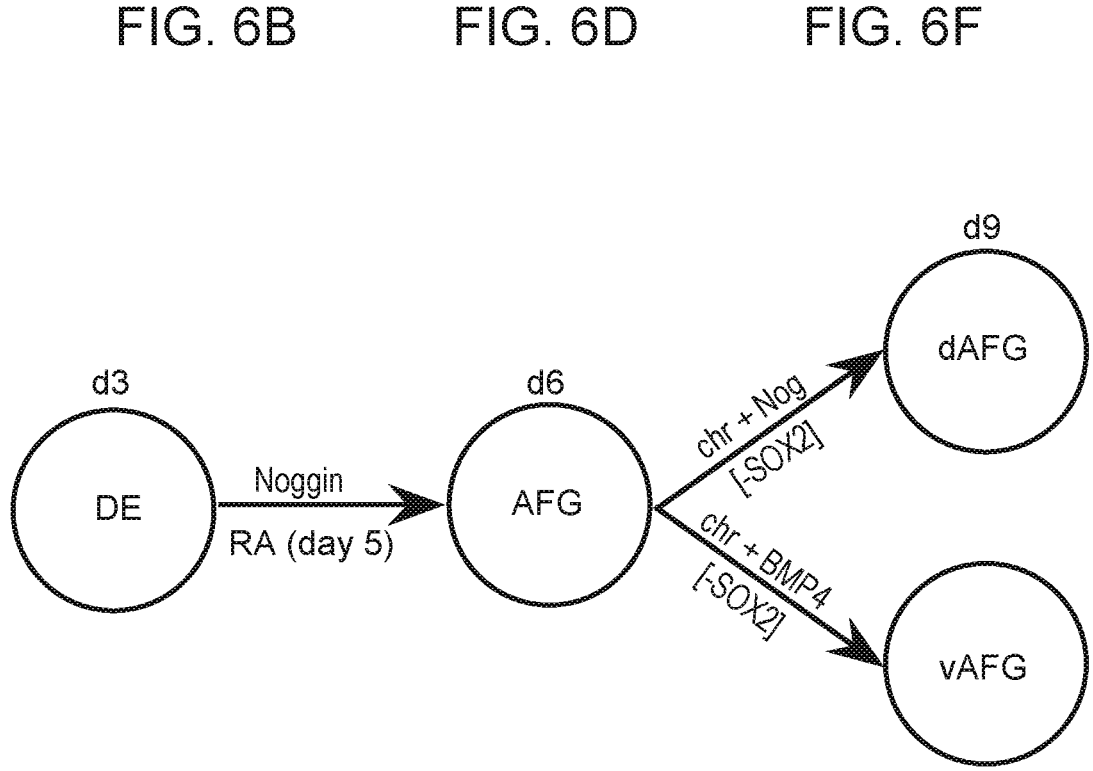

Since SOX2 positively regulates expression of Wnt antagonists, Applicant hypothesized that SOX2 may inhibit canonical Wnt signaling in the dorsal foregut. To investigate this, Applicant deleted Sox2 from the mouse foregut using two genetic models, Foxa2$^{CreER}$; Sox2$^{fl/fl}$ and Sox2$^{CreER/fl}$ and measured canonical Wnt/β-catenin activity by analyzing expression of the Wnt target gene Axin2 (Jho et al., 2002; Lustig et al., 2002). In situ hybridization revealed high levels of Axin2 mRNA in the ventral foregut endoderm and low levels in the dorsal foregut endoderm of control embryos. In contrast, the dorsal foregut had increased Axin2 staining when Sox2 was deleted (FIG. 7F-7I). Similarly, AXIN2 transcript levels were reduced in human ventral foregut cultures with SOX2 exogenously expressed (FIG. 6G, 7J). In addition to increased expression of canonical Wnt genes, the Nkx2-1 expression domain was expanded into the dorsal foregut (FIG. 5E, 13C-13D). Together with the data from human foregut cultures, Applicant proposes a model in which Sox2 positively regulates expression of secreted Wnt antagonists in the dorsal foregut, which represses canonical Wnt signaling in the dorsal foregut and restricts expression of Nkx2-1 to the ventral foregut.

DISCUSSION

Generation of HEOs and organotypic raft cultures has been described from primary esophageal cells and cell lines (Andl et al., 2003; Kalabis et al., 2012; Kasagi et al., 2018). In addition, human PSC-derived anterior foregut (AFG) endoderm cultures give rise to a heterogeneous mix of multiple AFG derivatives (Green et al., 2011; Kearns et al., 2013; Longmire et al., 2012). To enrich for esophageal endoderm with this sort of approach, one must rely on cell sorting and subsequent culture, as achieved by Zhang et al. Alternatively, directed differentiation into specific foregut derivatives, like the esophagus, has benefited from a more granular recapitulation of early organ development. Here, Applicant has differentiated human PSCs specifically into HEOs using a step-wise manner approximating DE formation, foregut patterning and morphogenesis, AFG patterning into the presumptive esophageal-respiratory domain, and finally dorsal foregut patterning. This approach gradually restricts endodermal differentiation potential such that one is left with dorsal AFG endoderm that grows out into esophageal organoids.

One challenge was to find conditions that generate the respiratory-esophageal anterior region of the foregut but not the anterior-most pharyngeal region. BMP inhibition is essential for foregut specification, and Applicant found that transient Wnt and RA activation patterns foregut into esophageal-respiratory rather than pharyngeal endoderm. Moreover, Applicant found that 1 day of RA promotes expression of TP63 and KRT4 and not posterior foregut markers GATA4 and PDX1. Without intending to be limited by theory, this effect of RA could be direct as RA promotes expression of KRT4 and TP63 in keratinocytes (Bamberger et al., 2002). Due to the lack of specific esophageal markers, Applicant relied on the presence or absence of regionally expressed markers to determine early anterior foregut endoderm identity and exclude pharyngeal, respiratory, hepatic, pancreatic, and gastric endoderm.

Applicant also used a functional assay to show that the esophageal-respiratory region of the foregut had been generated. This anterior-posterior level of the foregut should be competent to give rise to the esophagus and respiratory lineage. Applicant showed that AFG spheroids could respond to respiratory-inducing signals (BMP4 and Wnt activation by chiron) by upregulating NKX2-1. Conversely, repression of BMP signaling dorsalizes spheroids based on expression of SOX2, TP63, and MNX1. Interestingly, in Applicant's culture conditions, addition of a TGFβ inhibitor during foregut induction causes an increase in posterior foregut markers and reduces upregulation of NKX2-1, in contrast to other protocols (FIG. 10A-J), exemplifying how timing and combinatorial signaling pathways manipulation can result in different outcomes.

The final proof of esophageal lineage commitment from dorsal foregut spheroids was their growth into three-dimensional HEOs with a stratified squamous epithelium expressing regional keratins. Upon extended culture or in vivo transplantation, HEOs significantly increase in maturity, both morphologically and by analysis of later-stage esophageal markers (IVL, CRNN, FLG). Additionally, HEOs could be dissociated, expanded as keratinocytes, and differentiated into stratified squamous epithelium in organotypic raft cultures, demonstrating that HEOs have basal progenitor cells similar to human esophagus (Doupe et al., 2012; Kalabis et al., 2008). In fact, the expression level of differentiation markers in organotypic raft cultures approached that of human esophagus. Generation of fully differentiated and mature cell types from human PSCs has been a challenge across organ systems, and our data suggest that PSC-derived esophageal epithelium is among the most highly differentiated tissues derived to date.

HEOs will undoubtedly facilitate studies of human esophageal disease. As one example, Applicant showed how HEOs model human esophageal birth defects. Since SOX2 mutations can cause esophageal atresia in mice and humans, Applicant used HEOs to identify how SOX2 may control human esophageal development since the mechanism underlying its action was unclear (Fantes et al., 2003; Que et al., 2007; Williamson et al., 2006). Applicant first identified transcriptional changes that occur upon loss of SOX2. The current model suggests that the primary role of BMP signaling is to repress Sox2, which represses Nkx2-1; however, Applicant has identified that BMP signaling modulates many transcriptional changes independently of SOX2, suggesting that the current model is oversimplified (Domyan et al., 2011; Rankin et al., 2012) (FIG. 2B). Moreover, the data suggests that SOX2 represses canonical Wnt signaling and promotes dorsal endoderm survival. In other contexts, Sox2 can both repress and promote Wnt signaling by a variety of mechanisms including direct binding to TCF/LEF as well as regulating secreted Wnt antagonists (Chen et al., 2008; Kormish et al., 2010; Li et al., 2016; Sinner et al., 2007; Zhou et al., 2016). A role for secreted Wnt antagonists, Sfrp1 and Sfrp2, in tracheoesophageal septation has been shown using Barx1 knockout mice (Woo et al., 2011). In human foregut cultures, SOX2 also regulates transcript levels of SFRP2, and loss of SOX2 causes increased Wnt activity in the dorsal foregut. From this, Applicant concludes that SOX2 restricts the respiratory lineage from the dorsal foregut endoderm, possibly by repressing canonical Wnt signaling.

In summary, Applicant has developed a method to generate human PSC-derived HEOs based on temporal manipulation of signals that pattern the early endoderm and foregut. HEO development is strikingly similar to mouse esophageal development and results in a patterned stratified squamous epithelium. Applicant used human foregut cultures and genetic approaches in mice and frogs to identify molecular pathways that are regulated by Sox2 during dorsal-ventral patterning and esophageal specification. Applicant identified that in both humans and mice, SOX2 represses Wnt activity and that failure to do so results in inappropriate dorsal activation of the respiratory program. Thus, HEOs provide a powerful model to study esophageal development and disease.

EXPERIMENTAL MODEL AND SUBJECT DETAILS

Animals

All mice and frogs were housed in the animal facility at Cincinnati Children's Hospital Medical Center (CCHMC) in accordance with NIH Guidelines for the Care and Use of Laboratory animals Animals were maintained on a 12-hour light-dark cycle with access to water and standard chow ad libitum. Wild-type and mutant mice and *Xenopus laevis* were used for studies on foregut and esophageal embryonic development. The sexes of the embryos were not determined. Male immune deficient NSG (NOD.Cg-Prkdc$^{-scid}$Il2rg$^{tm1Wjl}$/SzJ) mice, aged 8-16 weeks old, were used for transplantation experiments. Healthy animals were used for all experiments. All experiments were performed under the approval of the Institutional Animal Care and Use Committee of CCHMC (protocols IACUC2016-0004 and IACUC2016-0059).

Human ESC/IPSC

Human embryonic stem cell (ESC) line H1 (WA01) were purchased from WiCell. Unmodified iPSC lines 65.8, 72.3, and 263.10 were generated and obtained from either the CCHMC Pluripotent Stem Cell Facilities and approved by the institutional review board at CCHMC. CRISPR interference iPSC lines (WTC11 genetic background) were generated and obtained from the Conklin lab at University of California, San Francisco (Mandegar et al., 2016). The H1 line is male, iPSC65.8 line is female, iPSC72.3 line is male, the iPSC263.10 line is male, and the SOX2 CRISPR interference line (CRISPRi-SOX2) is male. All the iPSC lines were checked for and determined to have a normal karyotype, and iPSC65.8 and iPSC72.3 have been tested with an in vivo teratoma assay.

Human Biopsy Tissue

Human esophageal tissue was collected at time of endoscopy in pediatric patients (all male, ages 3 to 13 years old) that consented to provide esophageal biopsy specimens for research purposes, which is approved by the Institutional Review Board of Cincinnati Children's Hospital Medical Center (protocol 2008-0090). Samples were used as positive controls for esophageal tissue identity by RNA quantification.

Method Details

Experimental Design

Pluripotent Stem Cell Lines and Maintenance

Both human embryonic and induced pluripotent stem cells (hESCs and hiPSCs) were maintained on feeder-free cultures. Cells are plated on hESC-qualified Matrigel (BD Biosciences, San Jose, Calif.) and maintained at 37° C. with 5% $CO_2$ with daily replacement of mTeSR1 media (STEMCELL Technologies, Vancouver, Canada); cells were passaged routinely every 4 days using Dispase (STEMCELL Technologies). The H1 HA-tagged SOX2 dox-inducible line was generated by cloning the human SOX2 ORF into pINDUCER20 (Addgene #44012, Meerbrey et al., 2011), generating lentivirus with help of the Viral Vector Core Facility at CCHMC, and transducing hESCs with 2 µL of virus; this line was maintained on selection with mTeSR1 and G418 (500 µg mL-1, ThermoFisher Scientific).

Differentiation of Anterior Foregut Cultures and Spheroids

Confluent hPSC cultures were treated with Acutase (STEMCELL Technologies) to resuspend as single cells in mTeSR1 and Y-27632 (10 µM, Tocris) and plated on Matrigel. On the following day, differentiation into definitive endoderm was carried out as previously described (McCracken et al., 2014). Briefly, cells were treated with Activin A (100 ng mL-1, R&D systems, Minneapolis, Minn.) and BMP4 (50 ng mL-1, R&D systems) on the first day in RPMI 1640 media (Life Technologies). Cells in the following two days were treated with only Activin A (100 ng mL-1) in RPMI 1640 with increasing concentrations 0.2% and 2% of HyClone defined fetal bovine serum (dFBS, GE Healthcare Life Sciences).

For anterior foregut monolayer cultures, cells were treated for 3 days in Noggin (200 ng mL-1) in RPMI 1640 with 2% dFBS, with all-trans retinoic acid (2 µM, Sigma, St. Louis, Mo.) the 3rd day.

Alternately, for the generation of anterior foregut spheroids, from definitive endoderm, cells were treated with FGF4 (500 ng mL-1, R&D systems), Noggin (200 ng mL-1) for 3 days in RPMI 1640 with 2% dFBS. Additional factors were tested during this time (described in results), such as CHIR99021 ("chiron" or "chr", 2 µM, Tocris), Wnt3a (500 ng mL-1, R&D systems), SB431542 (10 µM, Tocris), DEAB (10 µM, Sigma), and retinoic acid (2 µM).

Three-Dimensional Culture and Differentiation of Anterior Foregut Spheroids into Human Esophageal Organoids Anterior foregut spheroids were transferred into 50 µL droplets of Matrigel, and are cultured for 3-58 days in the base ("Gut") media of Advanced DMEM/F12 (ThermoFisher Scientific) supplemented with B27 supplement (1x, ThermoFisher Scientific), N2 supplement (1x, ThermoFisher Scientific), HEPES (13 mM, ThermoFisher Scientific), L-Glutamine (2 mM ThermoFisher Scientific), penicillin/streptomycin (1x, ThermoFisher Scientific), and EGF (100 ng $mL^{-1}$, R&D systems). In addition to this base media, the first three days were supplemented with Noggin (200 ng $mL^{-1}$), FGF10 (50 ng $mL^{-1}$), and CultureOne supplement (1x, ThermoFisher Scientific). FGF10 and CultureOne supplementation is continued until the end of the first week in three-dimensional culture. Media was replaced every 3-4 days. For EdU labeling, media was supplemented with EdU (10 µM Invitrogen) for a defined period of time, and was removed by washing with sterile PBS twice before replacing with media without EdU.

Keratinocyte and Organotypic Raft Culture

Day 41 HEOs were dissociated using TrypLE Select (Gibco) at 37C for 30-40 minutes, during which they triturated with a 22½ & 27½ gauge needle. After dissociation, cells were reconstituted in complete keratinocyte serum free media (K-SFM, Gibco) supplemented with Y-27632 (10 µM), EGF (10 ng $mL^{-1}$), and penicillin/streptomycin (1x) and subsequently plated onto collagen IV (Sigma) coated plates (1.5 µg $cm^{-2}$) at approximately $1.5 \times 10^4$ cells $cm^{-2}$. After reaching 90% confluency, HEO-derived keratinocytes were dissociated to single-cells with TrypLE Select and transferred into organotypic rafts cultures. Organotypic rafts were generated as previously described with minor modifications (Hoskins et al., 2009). Briefly, $1.2 \times 10^6$ HEO-derived keratinocytes were plated on a 24 mm collagen matrix (rat tail, EMD Millipore) harboring embedded mouse fibroblasts (J2-3T3 cells). Rafts were initially cultured for 4 days with the addition of Y-27632 (10 µM) prior to exposure to the liquid-air interface to generate a stratified epithelium. After 14 days, rafts were fixed in 4% PFA and embedded into paraffin. Sections were stained with H&E and examined for histopathology by routine microscopy.

Mouse Models

All animal experiments performed were approved by the Institutional Animal Care and Use Committee (IACUC) of Cincinnati Children's Hospital Medical Center (CCHMC). FoxA2$^{CreER}$ mice were obtained from Anne Moon's lab (Park et al., 2008), Sox2$^{fl/fl}$ mice were obtained from Richard Lang's lab (Shaham et al., 2009), and Sox2$^{CreER}$ (stock #017593, Arnold et al., 2011) were obtained from The Jackson Laboratory. Mice were housed at the CCHMC animal facility, and timed matings were used to obtain embryos at the relevant stages. Pregnant dams were gavaged at various stages with tamoxifen at 0.12 mg/g mouse to activate the CreER at appropriate stages. Specifically, pregnant dams in FoxA2$^{CreER}$ experiments were gavaged at 6.5 dpc to achieve efficient recombination. In Sox2$^{CreER}$ experiments, pregnant dams were gavaged at 8.5 dpc to knockout Sox2 prior to tracheoesophageal separation, and 9.5 dpc to knockout Sox2 during/after tracheoesophageal separation.

Xenopus Experiments

Xenopus laevis adults were purchased from the Nasco (Fort Atkinson, Wis.), and housed according to CCHMC IACUC protocols. Ovulation, in vitro fertilization, and de-jellying of embryos were performed as described (Sive et al., 2000). A mixture of previously validated Sox2 morpholinos (MOs; Van Raay et al., 2005) targeting the 5'UTR (Sox2-UTR MO) and the ATG start codon (Sox2-ATG MO) were injected at the 8-cell stage into each vegetal blastomere (2 ng total MO per blastomere, 8 ng total per embryo) to target endoderm. MOs were synthesized and purchased from GeneTools. Equal amount of control MO was used in control injections.

For Xenopus explant studies, stage NF20 foregut endoderm tissue was micro-dissected in 1×MBS (Modified Barth's Saline; Sive et al., 2000)+50 ug/mL gentamycin sulfate (MP Biochemicals), +4% Ficoll-400 (Sigma) and explants were then cultured in 0.5×MBS+0.1% Fatty Acid Free BSA (Fisher)+50 ug/mL gentamycin sulfate with or without the following concentrations of small molecules or recombinant proteins from stages NF25-NF38 (approximately 48 hours): 3.5 µM Bio (Tocris), 50 ng/mL recombinant human BMP4 (R&D systems).

In Situ Hybridization

In situ hybridization on mouse sections was performed by generating DIG-labeled probes from linearized mouse cDNA plasmids. Probes were allowed to hybridize overnight at 65° C., and on the next day, probes were thoroughly washed before blocking and incubating with anti-DIG alkaline phosphatase antibody (Sigma) in a 1:5,000 dilution in MAB buffer (maleic acid buffer, 100 mM Maleic acid, 150 mM NaCl, pH7.5)+10% heat-inactivated lamb serum (Gibco)+2% blocking reagent (Sigma) overnight at 4° C. Several washes were done before developing the slides using BM purple. In situ hybridization of Xenopus explants was performed mostly as described in (Sive et al., 2000). Briefly, embryos and explants were fixed overnight at 40 C in MEMFA (0.1M MOPS, 2 mM EGTA, 1 mM MgSO$_4$, 3.7% formaldehyde), dehydrated directly into 100% ethanol, and stored at −20° C. The following minor modifications to the in-situ protocol were used: proteinase K (ThermoFisher) on day 1 was used at 2 ug/mL for 10 minutes on explants; the RNAse A step was omitted on day 2; and finally the anti-DIG-alkaline phosphatase antibody was used at a 1:5,000 dilution in MAB buffer+10% heat-inactivated lamb serum+2% blocking reagent on day 2/3.

In situ hybridization on whole-mount Xenopus embryos was performed by generating anti-sense DIG labeled nkx2-1 in-situ probe was generated using linearized plasmid full-length nkx2-1 cDNA template (Small et al 2000; XbaI for linearization, T7 to synthesize antisense RNA) with the 10×DIG RNA labeling mix (Sigma) according to manufacturer's instructions.

Immunofluorescence Analysis

Tissue cultures were fixed with 4% paraformaldehyde at either room temperature for 15 minutes, 4° C. for 2 hours for cryosectioning, or 4° C. overnight for paraffin embedding/sectioning and mouse embryos. For paraffin embedding and sectioning, following fixation, tissues were dehydrated and embedded into paraffin blocks. Afterwards, paraffin-sectioned slides were deparaffinized and subjected to antigen retrieval in 10 mM sodium citrate for 30 minutes prior to staining. For cryosectioning, tissues were thoroughly washed in PBS, left in 30% sucrose overnight, embedded in OCT compound (VWR), and sectioned at a thickness of 8 µm. Commonly, slides were then permeabilized with 0.5% TritonX-100 in PBS for 10 minutes, blocked in 5% normal donkey serum (Jackson ImmunoResearch) for 1 hour, and incubated in primary antibody overnight at 4° C. On the next day, slides were thoroughly washed in PBS, incubated in secondary antibody (at 1:500) for 1 hour, and then thoroughly washed again. For EdU visualization, Applicant used the Click-iT EdU Alexa Fluor 488 Imaging Kit (Invitrogen) prior to blocking. For wholemount immunofluorescence staining, embryos were placed in 100% methanol immediately after fixation. Embryos were then permeabilized with Dent's Bleach (4:1:1 MeOH:DMSO:30% $H_2O_2$) for 2 hours at room temperature, rehydrated with methanol washes, and blocked for several hours at room temperature to overnight at 4° C. Primary antibodies were applied and embryos incubated overnight at 4° C. Then, embryos were thoroughly washed in 0.1% TritonX-100 in PBS before incubating in secondary antibodies overnight at 4° C. Finally, embryos were washed again, dehydrated with methanol washes, and cleared with Murray's Clear (2:1 benzyl benzoate:benzyl alcohol, Sigma) at least 15 minutes prior to imaging. For a list of antibodies and dilutions used, please see Table 2.

RNA Isolation and qPCR

Spheroid and organoids were harvested in total, including the embedding matrigel. Collagen plugs from the organotypic raft cultures were first removed from the transwell on day 14, and subsequently harvested in total. Total RNA was isolated using the NucleoSpin RNA kit (Macherey-Nagel) and reverse transcribed to cDNA using the SuperScript VILO cDNA synthesis kit (ThermoFisher Scientific). For qRT-PCR, Applicant used Quantitect SYBR-Green master mix (Qiagen) and ran the reaction on a QuantStudio 6 machine (ThermoFisher Scientific). For a list of primers used, please see Table 1.

TABLE 1

List of primers used for qPCR analysis.
Related to FIG. 1-7.

| Gene | Specie | Strand | Sequence |
|------|--------|--------|----------|
| DSG3 | human | forward | CGT GGT TGT CTC CGC TAG AA |
|      | human | reverse | CCG AGG TAG CAT TGA GGG TT |
| KRT5 | human | forward | CTG GTC CAA CTC CTT CTC CA |
|      | human | reverse | GGA GCT CAT GAA CAC CAA GC |

TABLE 1-continued

List of primers used for qPCR analysis.
Related to FIG. 1-7.

| Gene | Specie | Strand | Sequence |
|---|---|---|---|
| FOXE1 | human | forward | CGA CAA CCC CAA AAA GTG GC |
| | human | reverse | GCC CAG TAG TTG CCC TTA CC |
| TBX1 | human | forward | GTC TAT GTG GAC CCA CGC AA |
| | human | reverse | CTG CGT GAT CCG ATG GTT CT |
| SFRP2 | human | forward | CCA CCG AGG AAG CTC CAA A |
| | human | reverse | TTC AGG TCC CTT TCG GAC AC |
| SOX2 | human | forward | GCT TAG CCT CGT CGA TGA AC |
| | human | reverse | AAC CCC AAG ATG CAC AAC TC |
| PAX9 | human | forward | GGT AGG GTA AGG AGC CAT GC |
| | human | reverse | CTG GAG CAG GAA GCC AAG TA |
| GATA4 | human | forward | TAG CCC CAC AGT TGA CAC AC |
| | human | reverse | GTC CTG CAC AGC CTG CC |
| KRT13 | human | forward | AGG TGA AGA TCC GTG ACT GG |
| | human | reverse | GTT GTT TTC AAT GGT GGC G |
| KRT14 | human | forward | GGC CTG CTG AGA TCA AAG AC |
| | human | reverse | TCT GCA GAA GGA CAT TGG C |
| IVL | human | forward | CTG CCT CAG CCT TAC TGT GA |
| | human | reverse | GGA GGA GGA ACA GTC TTG AGG |
| LEF1 | human | forward | CAC TGT AAG TGA TGA GGG GG |
| | human | reverse | TGG ATC TCT TTC TCC ACC CA |
| TCF1 | human | forward | GAC TTG ACC ATC TTC GCC AC |
| | human | reverse | CCT CAA AGA GCT GGA GAA CCT |
| HNF1B | human | forward | TCA CAG ATA CCA GCA GCA TCA GT |
| | human | reverse | GGG CAT CAC CAG GCT TGT A |
| PROX1 | human | forward | GGC ATT GAA AAA CTC CCG TA |
| | human | reverse | ACA GGG CTC TGA ACA TGC AC |
| HNF6 | human | forward | TGT TGC CTC TAT CCT TCC CA |
| | human | reverse | GGA GGA TGT GGA AGT GGC T |
| PDX1 | human | forward | CGT CCG CTT GTT CTC CTC |
| | human | reverse | CCT TTC CCA TGG ATG AAG TC |
| (ΔN isoform) TP63 | human | forward | AGC CAG AAG AAA GGA CAG CA |
| | human | reverse | TCG TGT ACT GTG GCT CAC TAA |
| RFX6 | human | forward | CCA GTT TTT GAG CTA AGC GAA |
| | human | reverse | TGG CAT CAA AGA GAG CAG TG |
| MNX1 | human | forward | CTG CCT AAG ATG CCC GAC T |
| | human | reverse | AGC TGC TGG CTG GTG AAG |
| NKX2-1 (TTF1) | human | forward | CTC ATG TTC ATG CCG CTC |
| | human | reverse | GAC ACC ATG AGG AAC AGC G |
| CDH1 (E-CAD) | human | forward | GAC CGG TGC AAT CTT CAA A |
| | human | reverse | TTG ACG CCG AGA GCT ACA C |
| AXIN2 | human | forward | CTG GTG CAA AGA CAT AGC CA |
| | human | reverse | AGT GTG AGG TCC ACG GAA AC |
| KRT4 | human | forward | CCT GAG ATC AGA AAG TC CG |
| | human | reverse | TTC CAT TTG GTC TCC AGG AC |
| CDX2 | human | forward | CTG GAG CTG GAG AAG GAG TTT C |
| | human | reverse | ATT TTA ACC TGC CTC TCA GAG AGC |
| NESTIN | human | forward | GAG GGA AGT CTT GGA GCC AC |
| | human | reverse | AAG ATG TCC CTC AGC CTG G |
| HOXA1 | human | forward | GTA CGG CTA CCT GGG TCA AC |
| | human | reverse | ACT GGG TCT CGT TGA GCT G |

TABLE 1-continued

List of primers used for qPCR analysis.
Related to FIG. 1-7.

| Gene | Specie | Strand | Sequence |
|---|---|---|---|
| HOXB1 | human | forward | AAC CCA CCC AAG ACA GCG AA |
|  | human | reverse | CGC GCT TCT TCT GCT TCA TTC |
| CYP26C1 | human | forward | GTT CCC TTC AGT GGC CTA CG |
|  | human | reverse | ACA GCC GAC TCC TTC AGC TC |
| OTX2 | human | forward | GGA AGC ACT GTT TGC CAA GAC C |
|  | human | reverse | CTG TTG TTG GCG GCA CTT AGC T |
| CRNN | human | forward | TGT GAT TGT GAA ACC CCA CGA |
|  | human | reverse | GCA CTC TCG CTC AGT GTC TT |
| TMPRSS11A | human | forward | GTC TCC TGG TTC ACT TCC TAG T |
|  | human | reverse | GTG TTG CTT TGT CCG AAA TTG T |
| TMPRSS11D | human | forward | GCA GTC ACC ATA GCT CTA CTT G |
|  | human | reverse | CCA CTC AAA GTC CTG TAT TCC TG |
| CPHA (PPIA) | human | forward | CCC ACC GTG TTC TTC GAC ATT |
|  | human | reverse | GGA CCC GTA TGC TTT AGG ATG A |
| ID1 | human | forward | CTG CTC TAC GAC ATG AAC GG |
|  | human | reverse | GAA GGT CCC TGA TGT AGT CGA T |
| ID3 | human | forward | GAG AGG CAC TCA GCT TAG CC |
|  | human | reverse | TCC TTT TGT CGT TGG AGA TGA C |
| HES5 | human | forward | GAA AAA CCG ACT GCG GAA GC |
|  | human | reverse | GAC GAA GGC TTT GCT GTG CT |
| FST | human | forward | TGC CAC CTG AGA AAG GCT AC |
|  | human | reverse | TCT TCA CAG GAC TTT GCT TTG ATA C |
| NOG | human | forward | TGG TGG ACC TCA TCG AAC AC |
|  | human | reverse | ATG AAG CCT GGG TCG TAG TG |
| CCL26 | human | forward | AAC TCC GAA ACA ATT GTG ACT CAG CTG |
|  | human | reverse | GTA ACT CTG GGA GGA AAC ACC CTC TCC |
| CDH26 | human | forward | TGC TTT TTC TGT TGC GAT GCT |
|  | human | reverse | CTT GCC ATA ACC CCA GCT C |

TABLE 2

List of antibodies used for immunofluorescence staining.
Related to FIGS. 1-7.

| Antibody | Company | Catalog | RRID Number | Dilutio |
|---|---|---|---|---|
| Goat anti-Sox2 | Santa Cruz Biotechnology | #sc-17320 (Y-17) | RRID:AB_2286684 | 1:250 |
| rabbit anti-Sox2 | Abcam | #ab97959 | RRID:AB_2341193 | 1:1000 |
| rabbit anti-p63 | Santa Cruz Biotechnology | #sc-8343 | RRID:AB_653763 | 1:200 |
| mouse anti-HNF1b | BD Transduction Laboratories | #612504 | RRID:AB_399805 | 1:500 |
| rat anti-E-cadherin | R&D Systems | #MAB7481 | RRID:AB_2076679 | 1:1000 |
| goat anti-E-cadherin | R&D Systems | #AF648 | RRID:AB_355504 | 1:1000 |
| mouse anti-E-cadherin | BD Transduction Laboratories | #610182 | RRID:AB_397581 | 1:500 |
| rabbit anti-Nkx2.1 | Abcam | #ab76013 | RRID:AB_1310784 | 1:1000 |
| rat anti-Krt8 | DSHB | #TROMA-I-S | RRID:AB_531826 | 1:100 |
| mouse anti-Krt4 | Abcam | #ab9004 | RRID:AB_306932 | 1:200 |
| rabbit anti-Krt13 | Abcam | #ab92551 | RRID:AB_2134681 | 1:1000 |
| rabbit anti-Krt14 | BioLegend | #905301 (PRB-155P) | RRID:AB_2565048 | 1:2000 |
| rabbit anti-Ki67 | Cell Marque | #275R-15 (SP6) | RRID:AB_1158037 | 1:100 |

TABLE 2-continued

List of antibodies used for immunofluorescence staining.
Related to FIGS. 1-7.

| Antibody | Company | Catalog | RRID Number | Dilutio |
|---|---|---|---|---|
| rabbit anti-Ivl | Atlas Antibodies | #HPA055211 | RRID:AB_2682739 | 1:250 |
| rabbit anti-Dsg3 | Cell Marque | #436R-15 | | 1:200 |
| goat anti-FoxA2 | Santa Cruz Biotechnology | #sc-6554 | RRID:AB_2262810 | 1:500 |
| rat anti-HA-Biotin | Sigma-Aldrich (Roche) | #12158167001 (3F10) | RRID:AB_390915 | 1:300 |
| goat anti-Pdx1 | Abcam | #ab47383 | RRID:AB_2162359 | 1:5000 |
| goat anti-Gata4 | Santa Cruz Biotechnology | #sc-1237 | RRID:AB_2108747 | 1:200 |
| rabbit anti-Caspase 3 (cleaved) | Cell Signaling | #9661 | RRID:AB_2341188 | 1:200 |
| rabbit anti-Cdx2 | Cell Marque | #235R-15 (EPR2764Y) | RRID:AB_1516799 | 1:200 |
| mouse anti-Cdx2 | BioGenex | #cdx2-88 | RRID:AB_2650531 | 1:300 |
| rabbit anti-B-catenin | Santa Cruz | #sc-7199 | RRID:AB_634603 | 1:100 |
| mouse anti-Filaggrin | Santa Cruz | #sc-66192 | RRID:AB_1122916 | 1:200 |
| goat anti-Cornulin | R&D Systems | #AF3607 | RRID:AB_2085498 | 1:200 |
| anti-DIG alkaline phosphatase | Sigma-Aldrich | #11093274910 | RRID:AB_514497 | 1:5000 |
| AlexaFluor Donkey anti-goat 488 | Thermo Fisher Scientific | #A11055 | RRID:AB_2534102 | 1:500 |
| AlexaFluor Donkey anti-goat 568 | Thermo Fisher Scientific | #A11057 | RRID:AB_2534104 | 1:500 |
| AffiniPure Donkey anti-mouse 647 | Jackson ImmunoResearch laboratories | #715-605-150 | RRID:AB_2340862 | 1:500 |
| AlexaFluor Donkey anti-mouse 568 | Thermo Fisher Scientific | #A10037 | RRID:AB_2534013 | 1:500 |
| AlexaFluor Donkey anti-rabbit 647 | Thermo Fisher Scientific | #A31573 | RRID:AB_2536183 | 1:500 |
| AlexaFluor Donkey anti-rabbit 546 | Thermo Fisher Scientific | #A10040 | RRID:AB_2534016 | 1:500 |
| AffiniPure Donkey Anti-Rat 647 IgG | Jackson ImmunoResearch laboratories | #712-605-153 | RRID:AB_2340694 | 1:500 |
| Mouse anti-CDH17 | R&D Systems | #MAB1032 | — | 1:200 |
| Rabbit anti-CLDN18 | Atlas Antibodies | #HPA018446 | — | 1:100 |

Resources Table

Bacterial and Virus Stains
Biological Samples

| | | |
|---|---|---|
| Human Esophageal Biopsies | Rothenberg Lab CCHMC | CB2096, CB2394, CB3027, CB3082, and CB3103 |

Chemicals, Peptides, and Recombinant Proteins

| | | |
|---|---|---|
| recombinant human FGF4 | R&D Systems | Cat#235-F4 |
| recombinant human EGF | R&D Systems | Cat#236-EGF |
| recombinant human Noggin | R&D Systems | Cat#6057-NG |
| recombinant human BMP4 | R&D Systems | Cat#314-BP |
| recombinant human FGF10 | R&D Systems | Cat#345-FG |
| recombinant human Wnt3a | R&D Systems | Cat#5036-WN |
| Activin A | Cell Guidance Systems | Cat#GFH6 |
| CHIR99021 | Stemgent | Cat#04-0004 |
| BIO | Tocris | Cat#3194 |
| Y-27632 dihydrchloride | Tocris | Cat#1254 |
| SB431542 | Tocris | Cat#1614 |
| Doxycycline | Sigma-Aldrich | Cat#3447 |
| Tamoxifen | Sigma-Aldrich | Cat#T5648 |
| hESC-qualified Matrigel | BD Biosciences | Cat#354277 |
| mTeSR1 media | Stem Cell Technologies | Cat#5850 |
| Advanced DMEM:F12 | Thermo Fisher Scientific | Cat#12634-010 |
| Matrigel | BD Biosciences | Cat#354234 |
| Defined fetal bovine serum dFBS) | Hyclone | Cat#SH30070.02 |
| Proteinase K | Thermo Fisher Scientific | Cat#AM2548 |
| Normal donkey serum | Jackson Immuno-research Labs | Cat#017-000-121 |
| Heat-inactivated lamb serum | Gibco | Cat#16070096 |
| Blocking Reagent | Sigma-Aldrith | Cat#11096176001 |

Resources Table

| | | |
|---|---|---|
| L-glutamine | Thermo Fisher Scientific | Cat#25030-081 |
| Pen/Strep (100x) | Thermo Fisher Scientific | Cat#15140-122 |
| 50x B27 supplement w/o Vitamin A | Thermo Fisher Scientific | Ca#12587-010 |
| Non-essential Amino Acids (100x) | Thermo Fisher Scientific | Cat#11140050 |
| HEPES Buffer | Thermo Fisher Scientific | Cat#15630080 |
| N2 Supplement | Thermo Fisher Scientific | Cat#17502-048 |
| Dispase | Thermo Fisher Scientific | Cat#17105-o41 |
| Acutase | Thermo Fisher Scientific | Cat#A11105-01 |
| Collagen Type I, rat tail | EMD Millipore | Cat#08-115 |
| Transwell 24 mm Polyester Membrane Inserts, 6 well plate | Corning | Cat#3450 |
| Deep Well Plate, 6 well | BD | Cat#355467 |
| Ahlstrom Filter Papers—Grade 222 | Fisher Scientific | Cat#09-790-49J |
| 1,2-Dioctanoyl-sn-glycerol | Cayman Chemicals | Cat#62225 |
| F12 Media | Invitrogen | Cat#11755-054 |
| 1x DMEM | Invitrogen | Cat#11965-084 |
| Fetal Bovine Serum (FBS) | HyClone | Cat#SH30071.03 |
| Adenine | Sigma-Aldrich | Cal#A2786-5G |
| Cholera toxin | EMD Millipore | Cat#227035 |
| Hydrocortisone | Sigma-Aldrich | Cat#H0888-1G |
| Fungizone (Amphotericin B) | Omega Scientific | Cat#FG-70 |
| Insulin, human recombinant | Invitrogen | Cat#12585-014 |
| EGF | Sigma-Aldrich | Cat#1257-0.1MG |
| RNAlater | Thermo Fisher Scientific | Cat#AM7020 |
| Critical Commercial Assays | | |
| Quantitect SYBR Green | Qiagen | Cat#204145 |
| Nucleospin RNA | Macherey-Nagel | Cat#740955 |
| SuperScript VILO cDNA synthesis kit | Thermo Fisher Scientific | Cal#11754250 |
| Click-iT EdU Alexa Fluor 488 Imaging Kit | Invitrogen | Cat#C10337 |
| Experimental Models: Cell Lines | | |
| Human: H1 ES cells (passage 42) | CCHMC Pluripotent Stem cell core/WiCell Research Institute | NIH hESC-10-0043 |
| Human: H9 ES cells (passage 30) | CCHMC Pluripotent Stem cell core/WiCell Research Institute | NIH hESC-10-0062 |
| Human: iPS65.8 iPS cells (passage 44) | CCHMC Pluripotent Stem cell core | |
| Human: iPS72.3 iS cells (passage 35) | CCHMC Pluripotent Stem cell core | |
| Human: iPS263.10 iPS cells (passage 30) | | |
| Human: WTC: CRISPRi-SOX2 iPS cells (passage 43) | Conklin lab | Mandegar et al. 2016 |
| Experimental Models: Organisms/Strains | | |
| Mouse: Foxa2tm2.1(cre/Esr1*)Moon/J | The Jackson Laboratory | JAX: 008494 |
| Mouse: B6.:129S-Sox2trm1(cre/ERT2)Hoch/J | The Jackson Laboratory | JAX: 017593 |
| Mouse: Sox2tm1.1Lan/J | Lang Lab | JAX: 013093) |
| *Xenopus laevis* | | |
| Oligonucleotides | | |
| sox2- UTR MO: CTGGCAGAGCG-GAATCAGTTTCCCA | GeneTools | N/A (synthesized) |
| sox2- ATO MO: AGCTCGGTCTCCATCATGCTGTAC | GeneTools | N/A (synthesized) |
| control MO: CCTCTTACCTCAGTTACAATTTATA | GeneTools | N/A (synthesized) |
| See Table S1 for qRT-PCR primers. | IDT DNA | N/A (synthesized) |
| Recombinant DNA | | |
| pINDUCER20 | Ciccia et al._ 2011 | Addgene plasmid 44012 |

| Resources Table | | |
|---|---|---|
| Software and Algorithms | | |
| Imans | While | N/A |
| NIS Elements | Nikon | N/A |
| Computational Suite for Bioinformaticians and Biologists version 2.1 (CSBB v2.1) | | https://sourceforge.net/projects/csbb-v2-1/ |
| Gene Set Enrichment Analysis (GSEA) | | Subramanian et al, 2005 |
| PRISMv9 graphing and statistical software | GraphPad Software | N/A |

RNA Sequencing and Analysis

Whole-transcriptome RNA sequencing of anterior foregut cultures and HEOs (n=3 per condition or time point) was performed by the DNA sequencing and Genotyping Core Facility on an Illumina Hi-Seq 2500 platform from a Poly (A) and TruSeq library generated from isolated total RNA. RNA sequencing parameters were 75 bp single-end sequencing at a depth of 10M reads per samples. Fastq read files for each sample were obtained and then aligned using the Computational Suite for Bioinformaticians and Biologists version 2.1 (CSBB-v2.1, https://sourceforge.net/projects/csbb-v2-1/). Raw transcript counts and normalized transcripts per million (TPM) values were obtained and analyzed for differential expression with CSBB-v2.1 and for Gene Set Enrichment Analysis (GSEA, Subramanian et al., 2005). For differential expression, statistical and biological significance was set at $P<0.05$, $FDR<0.05$, log fold-change>1, with a minimum of 3 transcript counts in 3 of the 6 samples. For heatmap visualization and hierarchical clustering analysis, Morpheus (https://software.broadinstitute.org/morpheus/) was used.

Anterior foregut transcriptome analyses were cross-referenced with SOX2 and SMAD1 ChIP-seq peaks from GEO sets (GSE61475, Tsankov et al., 2015; GSE47058, Watanabe et al., 2014) using HOMER to obtain lists of genes whose expression is potentially regulated by these transcription factors. Peak cutoff distance was set at 50 kb from the transcription start site of any particular gene.

HEO analyses were compared to previously published RNA-seq samples on in vitro generated organoids (intestine and gastric), EPC2 cultures, and biopsies from the ENCODE Roadmap project, which including the following tissues: skin, esophagus, small intestine, stomach, colon, and lung. To compare in-house data with public data, Applicant used Upper Quantile [between-Lane Normalization] from EDASEQ [http://bioconductor.org/packages/release/bioc/vignettes/EDASeq/inst/doc/EDASeq.pdf]. Applicant used to CSBB's [Computational Suite for Bioinformaticians and Biologists] version 3.0 [https://github.com/csbbcompbio/CSBB-v3.0] UpperQuantile module. Applicant generated a matrix of expression of genes across in-house and public samples and quantile-normalized using CSBB-v3.0's UpperQuantile module. Then, Applicant log 2 transformed the quantile normalized matrix in R. Log 2

Transformed Matrix was Used for all Downstream Analysis

Applicant also used SVA [https://bioconductor.org/packages/release/bioc/vignettes/sva/inst/doc/sva.pdf] on the log 2 transformed—quantile normalized matrix to check if there are any latent variables/surrogate variables to correct. Applicant found no surrogate variables to correct for. This approach gave Applicant confidence that Upper-Quantile normalization followed by Log 2 transform is robust enough to remove batch and sequencing effects from the data.

Quantification and Statistical Analysis

For experiments involving spheroid patterning, organoid outgrowth, and raft experiments, "n" represents the number of replicates performed in each experiment (1 well of 3-7 organoids or 30-50 spheroids were collected for each replicate in matrigel culture, all samples from 1 well of an organotypic raft culture are considered a single replicate). For animal experiments, "n" represents the number of embryos analyzed. All data quantification is represented as the mean±SD. To compare the various conditions tested in spheroid patterning and organoid outgrowth, t-tests with 2-tailed distribution not assuming equal (i.e. un-equal) variance was used in Microsoft Excel, where $*p\leq0.05$, $p\leq0.01$, $*p\leq0.001$, and $****p\leq0.0001$.

Details for Quantification and Statistical Analysis for FIGS. 1-7

FIG. 1: For 1H, a minimum of 20 spheroids from two experiments were assessed. For all qPCR results, the data is representative of a minimum of 2 separate experiments with n=3 wells (50-100 spheroids in each well) for each experiment. RA experiments were replicated in both H1 and iPS263.10 cell lines.

Figures 6H, 6I, 6J, 6K:
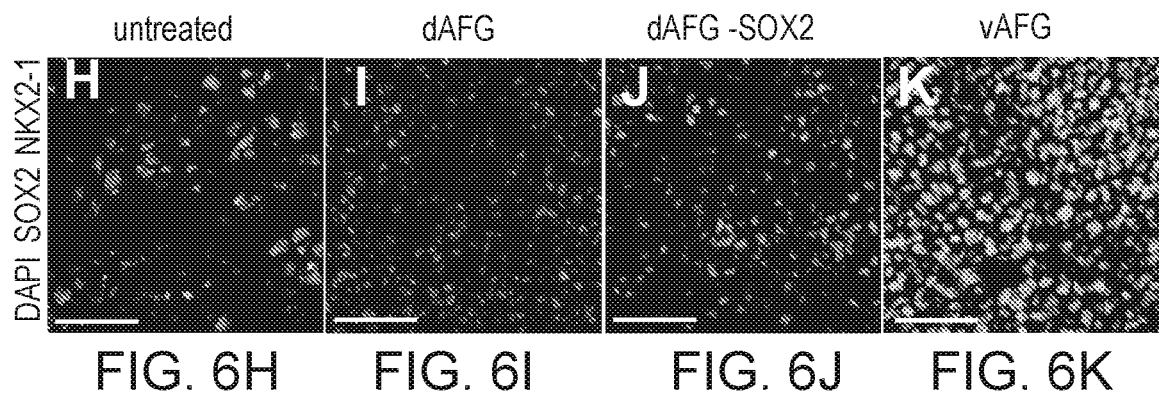
Figures 1, 6H, 6I, 6J, 6K:
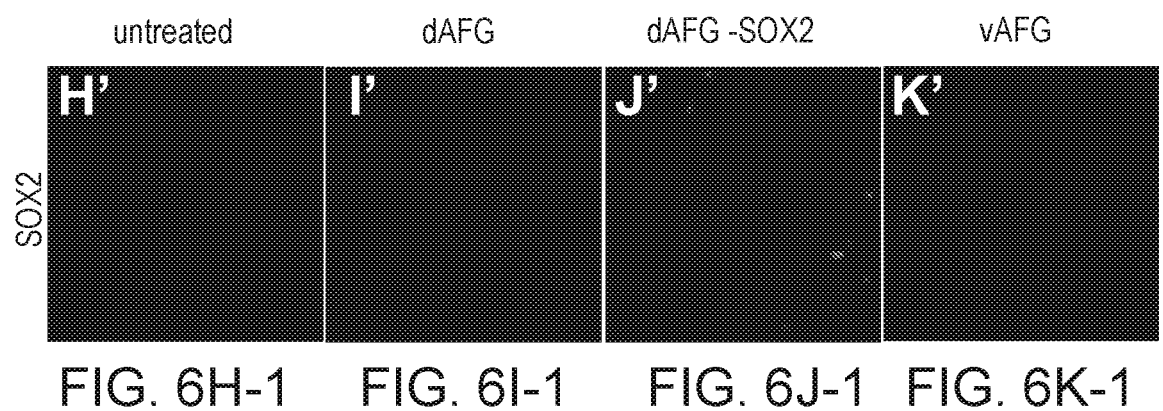
Figures 2, 6H, 6I, 6J, 6K:
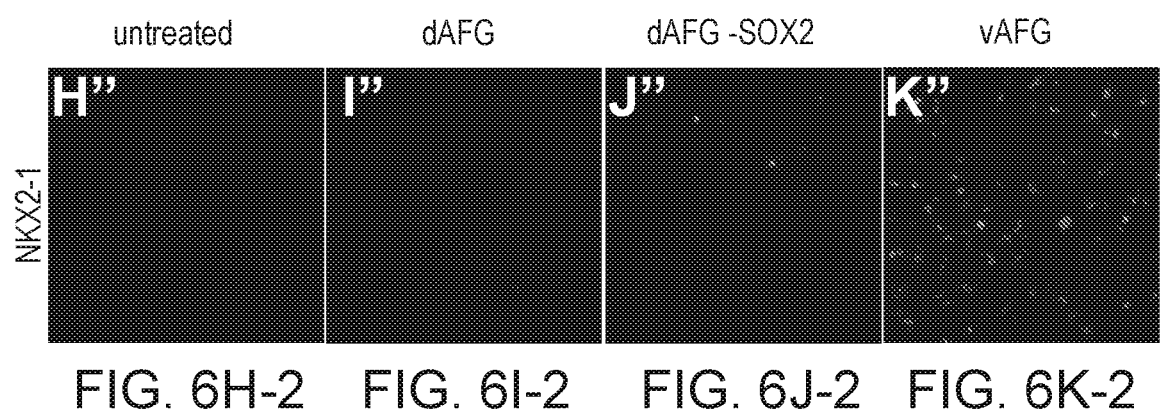
Figure 6L:
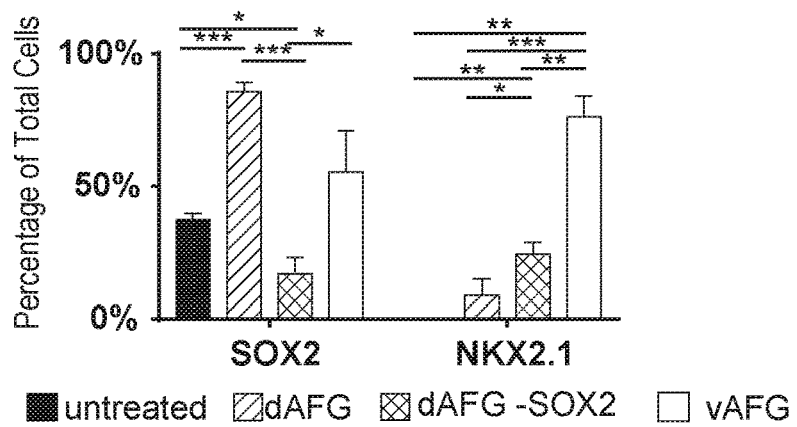
Figures 6M, 6N:
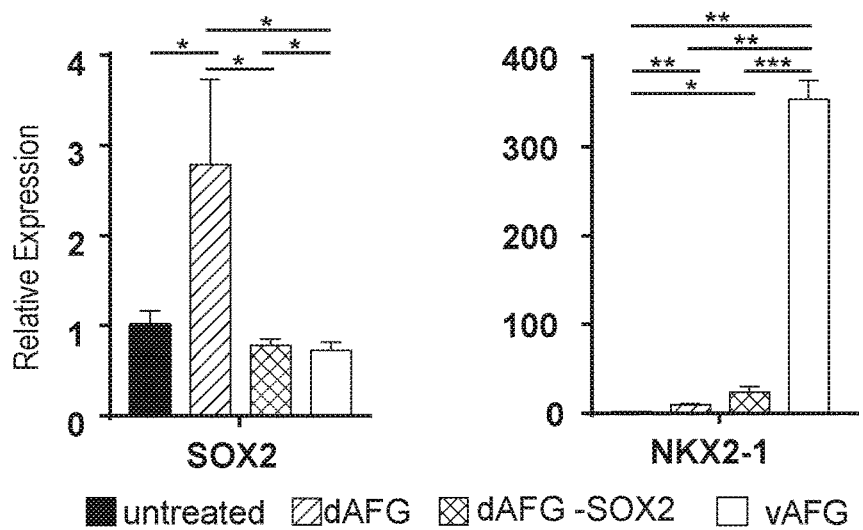
Figures 6S, 6T:
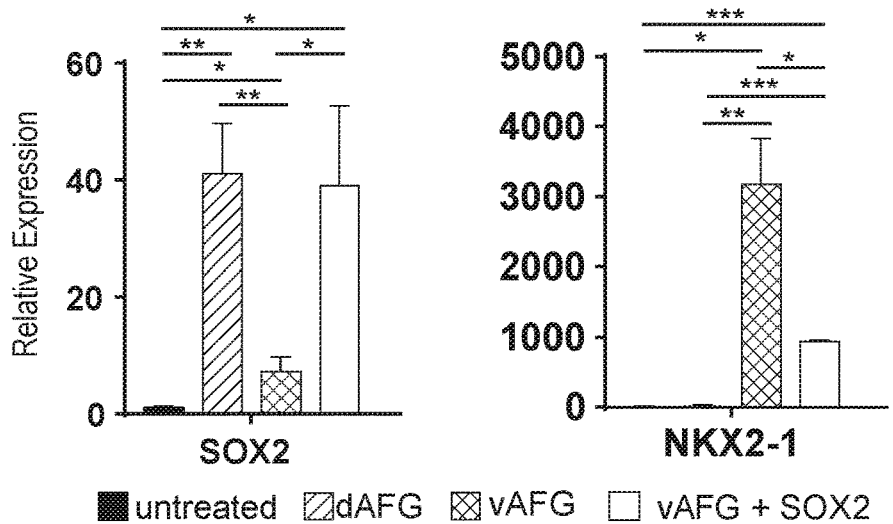
Figures 6O, 6P, 6Q, 6R:
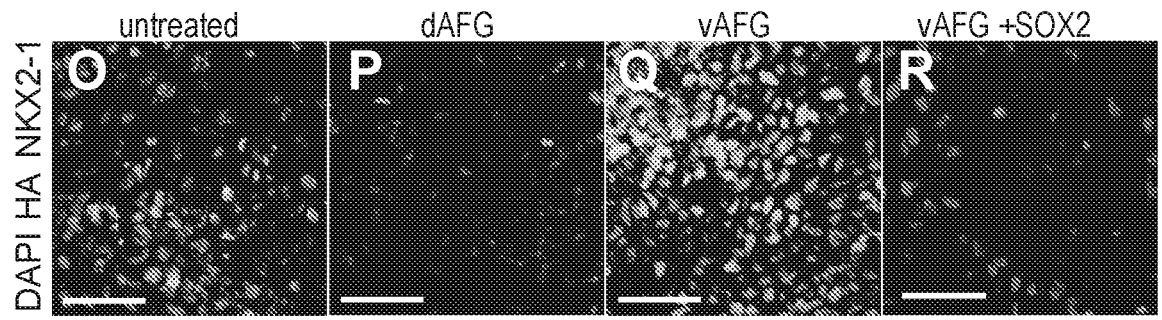
Figures 1, 6O, 6P, 6Q, 6R:
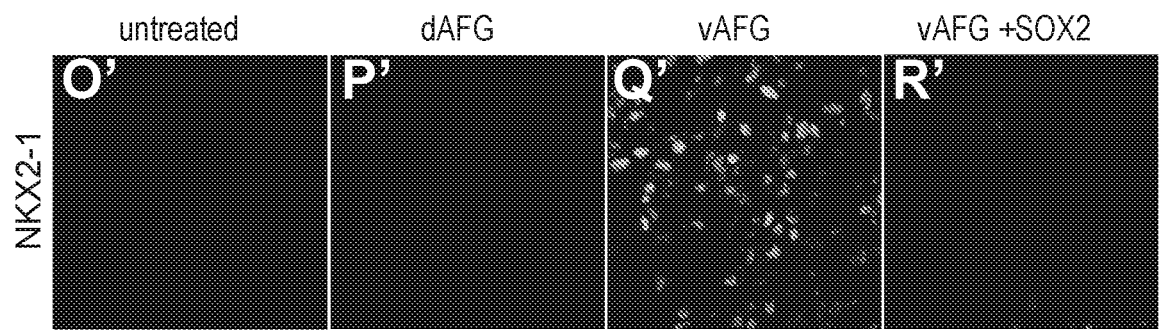

FIG. 2: The data is representative of 2 separate experiments with n=3 wells (averaging 30-50 spheroids per well) in each experiment utilizing the H1 hESC line.

FIG. 3: Generation of organoids is representative of 40+ experiments across 4 hES and iPS cell lines: H1, iPS 65.8, iPS 72.3, iPS 263.10. The qPCR data is representative of 2 separate experiments with n=3 wells (3-12 organoids per well) and were compared to n=5 patient biopsy samples.

FIG. 4: n=2-4 wells for the HEOs to organotypic raft culture experiment. n=6-10 organoids at each time-point for the EdU experiment. n=5 patient esophageal biopsy samples. Experiments were done in the H1 hESC line.

FIG. 5: For Sox2-DE-LOF embryos, n=3 embryos of each genotype at E9.5, and n=2 embryos for each analysis type for each genotype at E11.5. For Sox2 driven Sox2 cKO embryos, n=3 embryos analyzed for IF of each stage of tamoxifen administration and corresponding stage harvest.

FIG. 6: All data from the human PSC-derived cultures are representative of 3 separate experiments with n=3 wells for each condition per experiment.

Data and Software Availability

The accession number for the data generated is Gene Expression Omnibus (GEO): GSE112886. This includes the organoid outgrowth comparison (1 versus 2-month human esophageal organoids, FIG. 3) as well as the SOX2-knockdown experiment in dorsal and ventral anterior foregut cultures (FIG. 7 and FIG. 14A-14D).

ChIP-seq data of SOX2 and SMAD1 ChIP-seq peaks were downloaded from the public database GEO with accession numbers GSE61475 (Tsankov et al., 2015) and GSE47058 (Watanabe et al., 2014), respectively. RNA-seq data of biopsies and EPC2 cultures were downloaded from the public database GEO. The accession numbers for the samples are: GSM1120313 and GSM1120314 (small intestine), GSM1010946 and GSM1120308 (lung), GSM1120307 and GSM11010960 (stomach), GSM1120315 and GSM1010974 (large intestine), GSM1010956 and GSM1120303 (esophagus), GSM2343841 and GSM234564 (lower leg skin), and GSM1592609-GSM1592611 (EPC2 day 0 cultures). The complete RNA-seq processing pipeline was done using Computational Suite for Bioinformaticians and Biologists version 2.1 (CSBB-v2.1) and is available at https://sourceforge.net/projects/csbb-v2-1/.

Disease States

With the advent of the human esophageal organoid models described herein, Applicant sought to apply this system to study various diseases that affect the esophagus. Applicant examined the role of Sox2 in the patterning and separation of the anterior foregut and formation of the esophagus. Though esophageal atresia is mainly focused on the proper resolution of the esophageal and respiratory tracts, its sequalae in human patients go far beyond this primary issue. This is because the treatment for esophageal atresia is surgery to fix the anatomical defect; however, the underlying mechanisms that led to the primary defect and how they may compromise the proper development of the esophagus (and respiratory tract) are not addressed. Among the many genes that are associated with esophageal atresia, the role of two genes, Sox2 and a Fanconi anemia gene (FANCA), in esophageal development, are discussed herein.

Previous studies have examined the role of Sox2 in esophageal development and homeostasis. In the Sox2 hypomorphic embryos, the esophagus of mutant embryos where foregut separation occurred had altered properties, including lack of expression of stratified squamous epithelial markers p63 and Krt14, as well as expression of gastric and intestinal markers (Que et al., 2007). However, interpreting these results in terms of Sox2's role in early versus later esophageal development is challenging to decipher, as these changes could be a result of early mispatterning in the mutant foregut as opposed to a continued requirement for Sox2 to drive esophageal growth and maturation. Studies in the adult esophagus do suggest that Sox2 continues to play a role past the developmental stage. Sox2 expressing cells in the esophagus are critical for maintaining homeostasis, and when ablated, this leads to the complete loss of the basal layers and atypical cells residing in the esophagus (Arnold et al., 2011). Aside from just serving as a marker of basal cells in the adult esophagus, Sox2 overexpression in the esophagus results in expansion of the basal compartment and decreased differentiation of the suprabasal layers (Liu et al., 2013). Apart from the esophagus, Sox2 plays a homeostatic role in other endodermal organs. In the trachea, loss of Sox2 postnatally leads to less proliferation and a decreased proportion of basal (less p63+), ciliated, and Clara cells (Que et al., 2009). However, in the adult stomach, it appears that Sox2 is dispensable for homeostasis of the tissue, though it may have tumor suppressive roles (Sarkar et al., 2016). Despite this, the role of Sox2 in the developing esophagus (post-foregut-separation) has yet to be carefully examined, which may yield insights into the other issues of patients with esophageal atresia.

Fanconi anemia is recessive disorder (for any particular FANC complementation group gene) and is also associated with esophageal atresia, among other GI defects, though these GI issues occur in only a subset of patients (i.e. low penetrance) (Fausett and Klingensmith, 2012). Some patients do not have major congenital defects, though many patients have defects, which span across multiple organ systems. In various patients, in addition to the hematological issues, the presenting defects have similarities with the VACTERL association of symptoms, which consist of vertebral, anal, cardiac, trachea-esophageal, renal, and limb defects (Auerbach, 2009). Of all the FANC complementation group genes that cause Fanconi anemia, the most common are FANCA, FANCC, and FANCG (Auerbach, 2009; Nebert et al., 2016). There is a thought that the Shh signaling pathway may be involved in Fanconi anemia, based on the similarity of symptoms in Shh mutants and Fanconi anemia (Lubinsky, 2015). However, virtually nothing is known about how esophageal atresia develops in some cases of Fanconi anemia. An obstacle to understanding how esophageal atresia develops in Fanconi anemia patients is that mouse models of Fanconi anemia do not recapitulate most of the developmental abnormalities (Bakker et al., 2013). Thus, using human organoid models of development may provide a breakthrough in understanding the pathogenesis of various GI malformations in Fanconi anemia.

In addition to the congenital disease esophageal atresia, Applicant are also interested in the later diseases affecting the esophagus, such as Barrett's esophagus. Barrett's esophagus (or Barrett's metaplasia) is a condition where the stratified squamous epithelium of the esophagus transforms into a columnar (intestinal-like) epithelium, which predisposes the patient towards esophageal adenocarcinoma (De Jonge et al., 2014). The mechanism underlying this transformation is actively being studied, and there are multiple hypotheses concerning the cell-of-origin of this ectopic columnar epithelium. Of these, the more likely models include transformation of esophageal cells into intestinal-like cells, transformation of the transitional epithelium at the gastroesophageal junction, and transformation of submucosal glands (Jiang et al., 2017; Leedham et al., 2008; Wang et al., 2010).

Previous studies testing this hypothesis have found that acid and bile salts upregulate Cdx1 and Cdx2 in cultured esophageal cells, potentially by regulating the Cdx2 promoter (Huo et al., 2010; Kazumori et al., 2006, 2009; Liu et al., 2007). Additionally, in culture, acid and bile salts lead to downregulation of stratified squamous epithelial genes (Ghatak et al., 2013). However, Cdx2 induction alone does not appear to be able to fully transform esophageal cells, though it can result in mild downregulation of some stratified squamous epithelial genes, upregulate some intestinal genes (Muc2, Villin), and mildly alters the epithelial morphology (Kong et al., 2011; Liu et al., 2007). BMP activation, alone or in combination with Cdx2, appears to have a stronger effect to downregulate stratified squamous epithelial genes in the mouse esophagus and cultured human esophageal cells, though these alterations are still far from the full transformation into a columnar epithelium, by morphology or gene expression (Mari et al., 2014). Other signaling pathways, such as Wnt and Notch, may be altered in esophageal cells exposed to bile acids (Chen et al., 2012). Notch inhibition leads to some changes in cultured esophageal cells, including downregulation of stratified squamous epithelial genes, upregulation of columnar epithelial genes, and increased intercellular spaces in the basal compartment (Kasagi et al., 2018; Vega et al., 2014). However, from these studies, it is unclear which signaling pathways contribute to the pathogenesis of Barrett's metaplasia as opposed to simply being changed as a result of all the other morphological changes. Accordingly, HEOs may allow rapid combinatorial screening of these suspected signaling pathways in a more biologically relevant model.

Another disease affecting the pediatric and adult esophagus is eosinophilic esophagitis, which is a chronic immune-mediated disease that causes difficulty feeding or food impaction, vomiting, and abdominal pain. The diseased esophagus undergoes some changes, including esophageal strictures from fibrosis and muscle wall thickening, basal cell hyperplasia and dilated intercellular spaces in the epithelium, and the hallmark finding of high levels of eosinophils in the esophageal epithelium (Furuta and Katzka, 2015). It is classically thought that an impaired barrier and exposure to certain antigens initiate and then maintain the disease, as the inflamed esophagus recruits immune cells and further maintains the impaired barrier (Caldwell et al., 2017; Furuta and Katzka, 2015).

The recruited type 2 helper T-cells (and other immune cells) secrete multiple cytokines, which cause broad changes in the esophageal epithelium and surrounding layers. In the epithelium, IL-13 upregulates eotaxin-3 (or CCL26), a chemokine that attracts eosinophils. In addition to CCL26 and other target inflammatory genes, IL-13 exposure results in basal cell hyperplasia in the mouse esophagus, and downregulation of differentiated stratified squamous epithelial markers (such as FLG, IVL, SPRR family of proteins) (Blanchard et al., 2010; Jiang et al., 2015; K C et al., 2015; Rochman et al., 2017). Air-liquid interface cultures of esophageal keratinocytes treated with IL-13 also display decreased transepithelial electrical resistance (TEER), demonstrating barrier dysfunction (D'Mello et al., 2016; Davis et al., 2016; Wu et al., 2018).

Results

The Role of Sox2 in Later Esophageal Development

To examine the role of Sox2 in the development and maturation of the esophagus (post-separation of the esophagus from the respiratory tract), Applicant utilized the same mouse model as with the previous chapter to conditionally knockout Sox2 in Sox2 expressing cells. Applicant mated female Sox2$^{fl/f}$ mice to male Sox2$^{CreERT2/+}$ mice and either the dams were gavaged with tamoxifen at E11.5 and E14.5 or the pups at P1 were injected with tamoxifen, which were then harvested several days post-gavage to examine the effects of Sox2 loss in the esophagus at various developmental stages (FIG. 1A). Earlier loss of Sox2 (gavage at E11.5) results in delayed stratification at E14.5, as evident by the mostly simple columnar epithelium in the esophagus of the conditional knockout compared to the wild-type, which has stratified to 2 layers at this stage (FIG. 1B). Later knockout of Sox2 (E14.5 gavage) results in a somewhat smaller esophagus, though stratification appears normal. Finally, early postnatal knockout of Sox2 (P1) appears to have no gross changes to the esophagus (FIG. 1B). In these embryos where Sox2 was knocked-out after separation of the anterior foregut, there was no immediate re-expression of Nkx2-1 in the esophagus, though the E11.5 gavaged embryos had a few cells in the esophagus expressing Nkx2-1 at E17.5 (FIG. 1B,1E)

Because the most obvious changes occurred only in the E11.5 gavaged embryos, Applicant looked more carefully at these esophagi at E17.5 for various patterning and differentiation markers. Grossly, the esophageal epithelium appeared less folded (upon itself) and had a larger average luminal diameter. Besides the confirmatory loss of Sox2, the basal layer of the Sox2 knockout esophagus appears normal—it expresses p63 and Krt14 and lacks Krt8 expression (FIG. 1C). However, the suprabasal layer is obviously altered: Krt13 is absent while Krt8 is robustly expressed; there are proliferating (Ki67+) positive cells, which is not present in the wild-type esophagus; and, the epithelial morphology persists as a columnar epithelium (FIG. 1C-D). However, Applicant did not find evidence of Muc2 or Muc5ac production, though further future analysis (such as Alcian blue staining) may reveal mucous generation (data not shown). Aside from the few cells that express Nkx2-1 in the Sox2 knocked-out esophagus, other key intestinal and gastric markers were not expressed in either wild-type of Sox2 knockout esophagi (FIG. 1E). In addition to the critical role Sox2 plays in early patterning, these data directly demonstrate the necessity of Sox2 for proper esophageal development and maturation after the separation of the esophagus from the respiratory tract.

Fanconi's Anemia and Early Esophageal Development

In addition to Sox2, various other genes are associated with esophageal atresia, and the mechanisms that underlie foregut defects resulting from mutations in some of these genes are unknown. Loss of a Fanconi anemia complementation group gene can result in multiple issues with variable penetrance, including GI issues like atresias (esophageal, duodenal, anal), CNS defects, renal defects, and growth abnormalities (Auerbach, 2009; De Jong et al., 2010). To begin to understand how these genes result in esophageal atresia, Applicant sought to model the effects of a FANCA deficiency in esophageal development using HEOs.

Figure 2C:
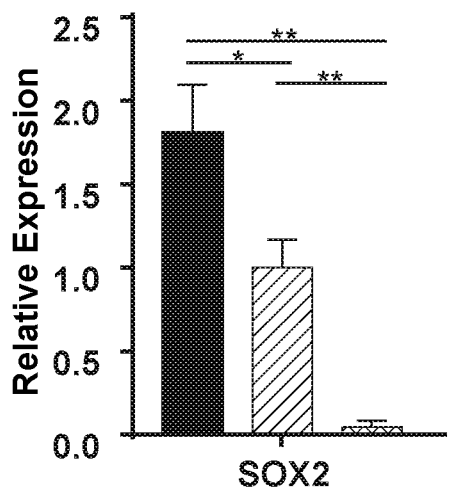
Figure 2D:
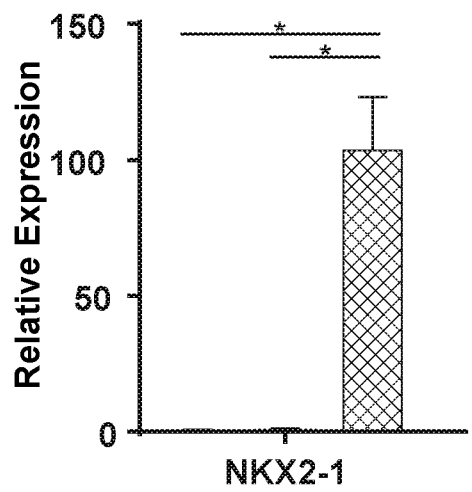
Figure 2E:
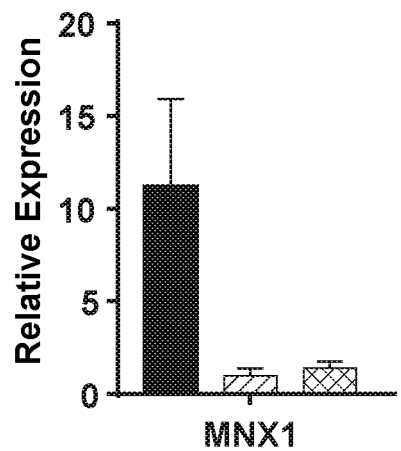
Figure 2F:
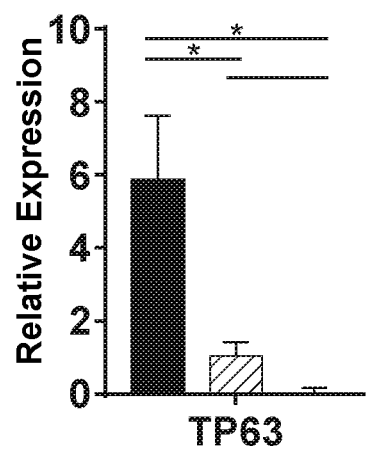
Figure 2G:
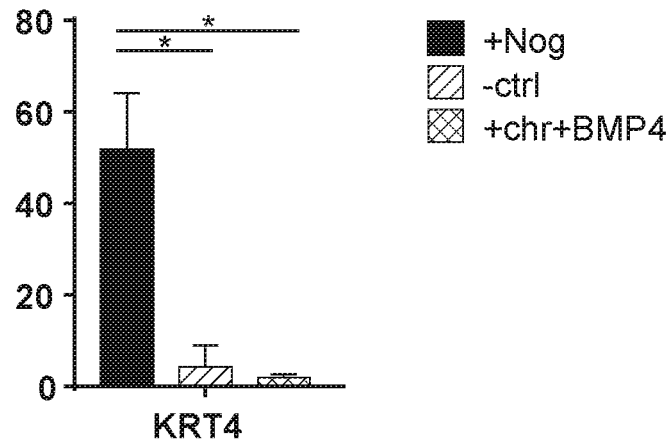
Figures 2H, 2I:
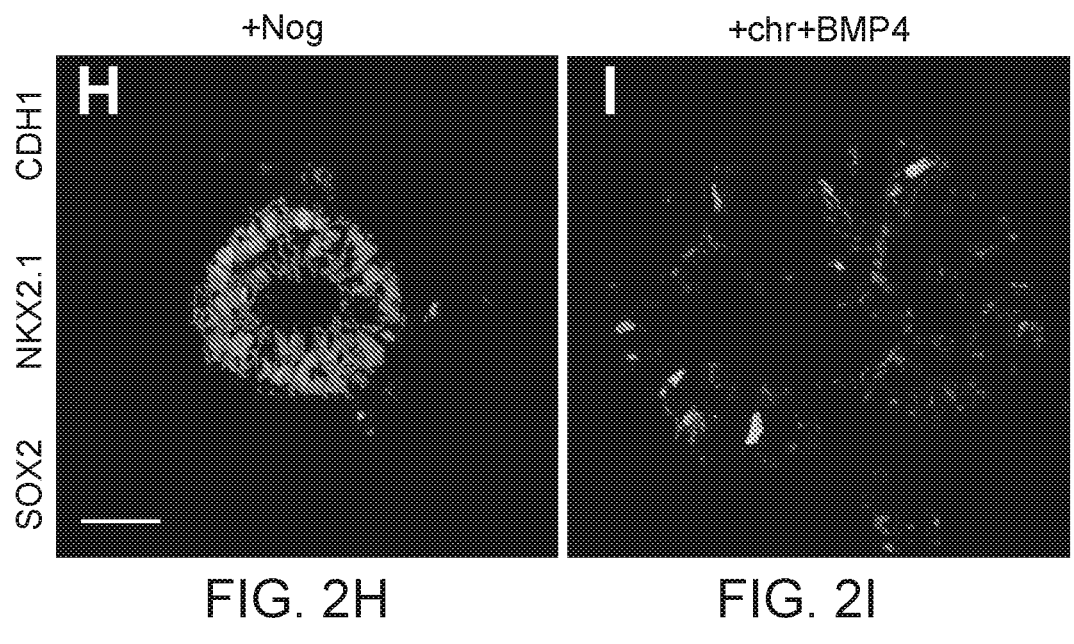

Applicant used an iPSC line generated from a patient lacking FANCA that can be maintained/rescued using a dox-inducible FANCA construct. This line could successfully generate HEOs using described herein with or without doxycycline treatment (FIG. 2A). Foregut patterning did not appear to be altered in the low or absent expression of FANCA (FIG. 2B). Upon outgrowth (2-4 weeks) of the dorsal anterior foregut spheroids into HEOs, the FANCA-deficient organoids appear to consistently be smaller than the "control"/rescued (+dox) organoids (FIG. 2C, 2F). However, FANCA-deficient HEOs have increased numbers of KI67+ cells compared to control HEOs at 1 month (FIG. 2D, 2G). There appears to be no difference in cell death (by cleaved Caspase 3 staining) in either condition (data not shown). Additionally, Applicant did not find a significant difference in the expression of stratified squamous epithelial markers between the two conditions (data not shown). To confirm that organoids responded to doxycycline treatment and expressed FANCA, Applicant probed for FANCA and response of FANCD2 to hydroxyurea treatment when FANCA is present. Western blotting clearly revealed knockout and rescue of FANCA without or with doxycycline treatment, respectively, and a shift in FANCD2 protein size upon doxycycline and hydroxyurea treatment (FIG. 2E).

Modeling Barrett's Esophagus Using HEOs

In addition to studying early defects in foregut and esophageal development, Applicant also wanted to apply HEOs to model later diseases affecting the esophagus, such as Barrett's metaplasia. There has been a lot of work trying to identify the cell-of-origin and to understand the mechanisms that result in the transformation of the stratified squamous epithelium into an intestinal (columnar) epithelium. However, because of the challenges in accurately modeling the human pathological process in mice, it is believed that using an HEO model can serve as a complementary approach to understanding how Barrett's esophagus develops.

Applicant started by focusing on early development of the foregut and esophagus. Applicant utilized a dox-inducible CDX2 construct that is stably transduced in hPSCs, which are then used to generate HEOs (FIG. 3A-3B). First, anterior foregut (AFG) cultures were treated for 1 day with doxycycline at varying doses to gauge the appropriate concentration required to induce CDX2 in most cells, which seemed to saturate around 100-500 ng/mL (FIG. 3C-3E). Interestingly, SOX2 expression was not repressed by brief (24 hour) induction of CDX2 in anterior foregut cells, suggesting that CDX2 (alone) does not directly repress SOX2 transcription (FIG. 3C-3D).

Figure 8A:
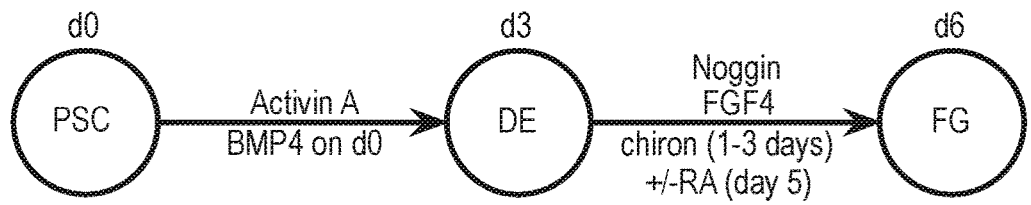
FIGS. 8A-8V. Modulating the duration of Wnt and retinoic acid signaling to coordinate foregut patterning across the anterior-posterior axis. (8A) Schematic depicting the experimental protocol to pattern foregut spheroids along the anterior-posterior axis using CHIR99021 (chiron, or chr) and retinoic acid (RA). (8B-8G) qPCR analysis of day 6 spheroids resulting from varying the duration of chiron treatment with or without retinoic acid treatment for (B) the anterior and posterior foregut marker HNF1B, (8C-8D) the posterior foregut markers PROX1 and HNF6, (8E) the hindgut marker CDX2, (8F-8G) and the pharyngeal markers PAX9 and OTX2. (8H-8N) A comparison of chiron versus Wnt3a treatment on endoderm by qPCR analysis of (8H) the foregut marker SOX2, (8I) HNF1B, PROX1, HNF6, and CDX2, (8J) Wnt target genes AXIN2, LEF1, and TCF1, and (8K) epithelial and neural marker CDH1 and NESTIN, respectively. Spheroids generated with one day of chiron treatment have same gene expression profile as those generated with 2 days of Wnt3a. (8L-8N) Brightfield imaging of nascent spheroids resulting from chiron versus Wnt3a treatments show that the efficiency of generating spheroids is unaffected in the different conditions. (8O-8R) Analysis of day 9 spheroids resulting from altering the duration of retinoic acid treatment starting on day 5. qPCR analysis of (8O) retinoic acid targets HOXA1, HOXB1, CYP26C1. (8S) Schematic depicting experimental protocol for modulating retinoic acid signaling using the synthesis inhibitor DEAB. (8T-8U) qPCR analysis of (8T) foregut markers at day 6, (8U) dorsal anterior foregut markers SOX2 and TP63 (ΔN isoform) at day 9, and (8V) RA targets HOXA1 and HOXB1 at day 9. Scale bar=500 μm in (8L-8N) and 50 μm in (8P-8R). Error bars indicate SD. *p<0.05, p<0.01, and *p<0.001 for two-tailed t-test.
Figure 8B:
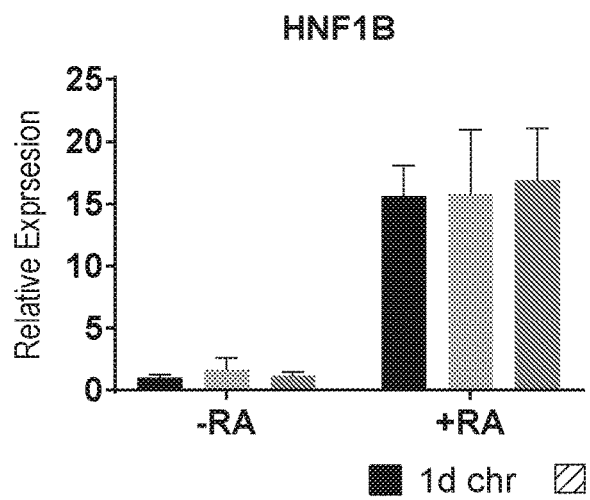
Figure 8C:
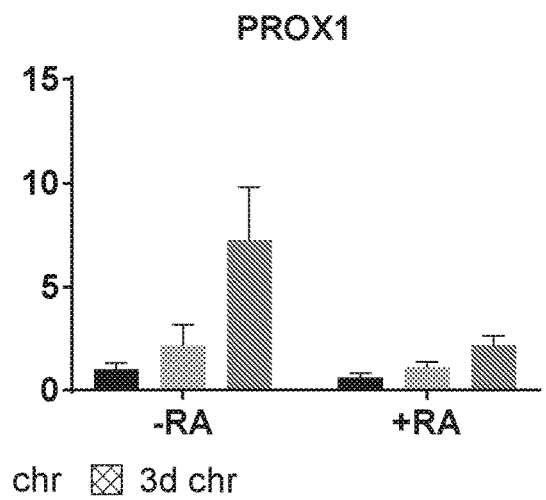
Figure 8D:
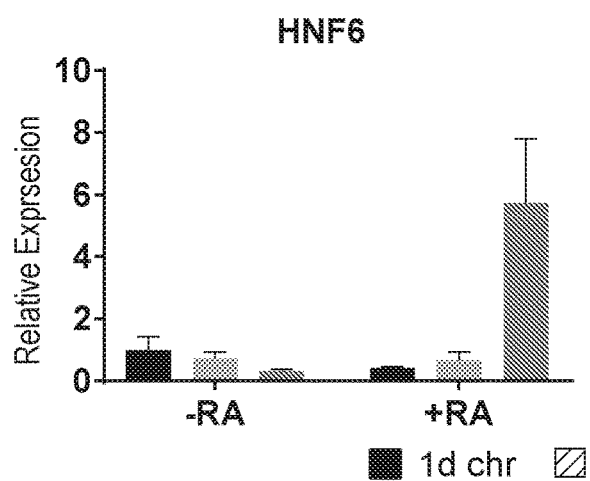
Figure 8E:
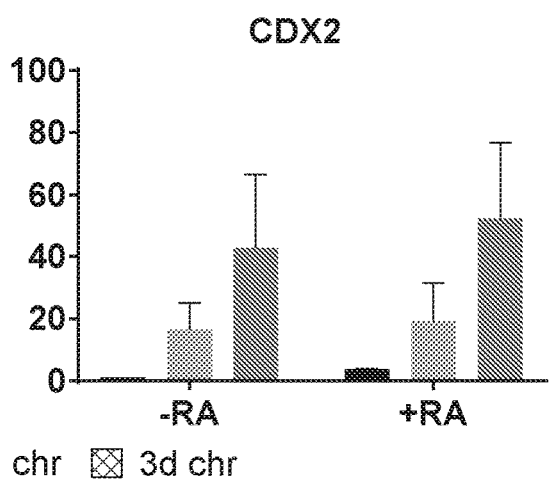
Figures 8F, 8G:
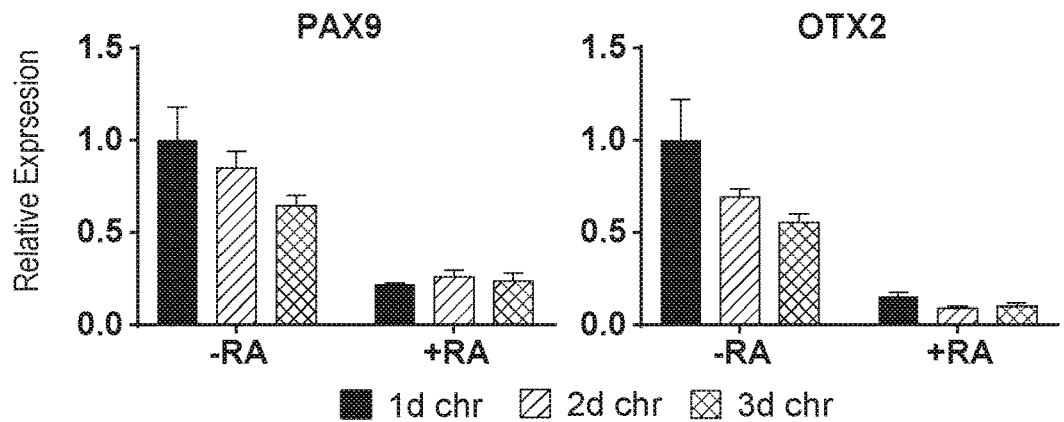
Figure 8H:
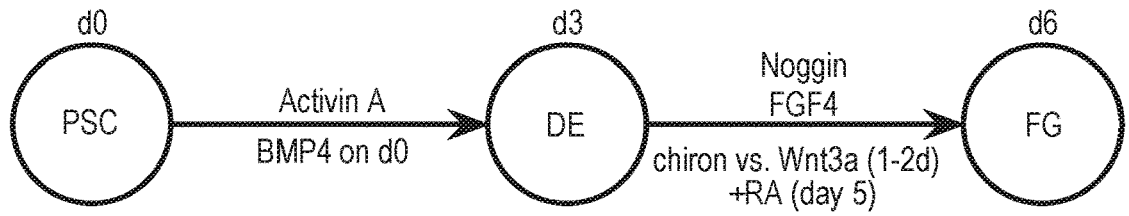
Figures 8I, 8J:
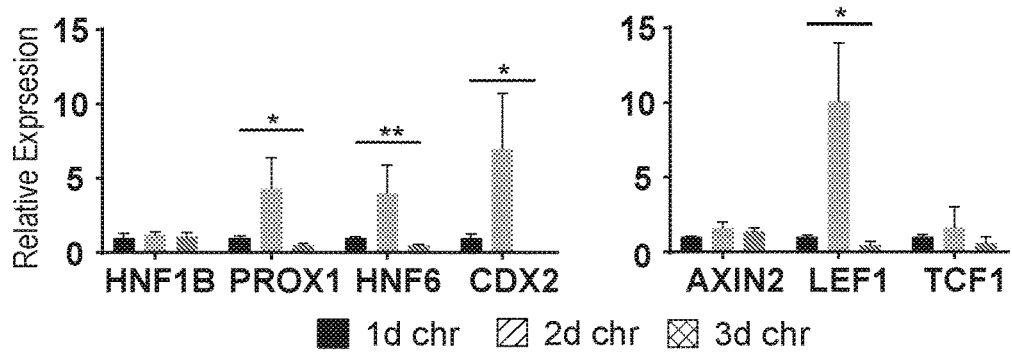
Figure 8K:
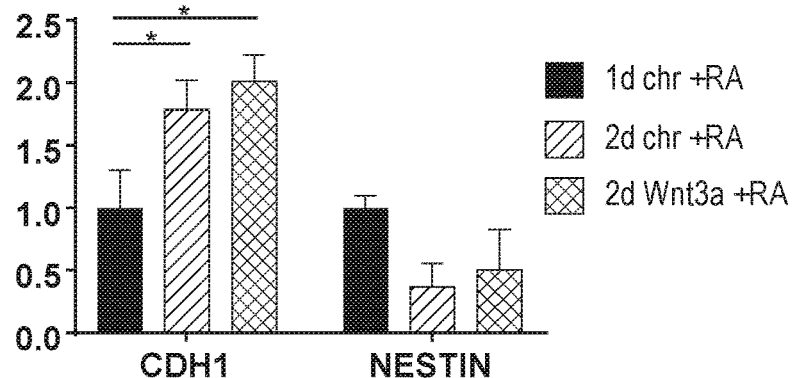
Figure 8L:
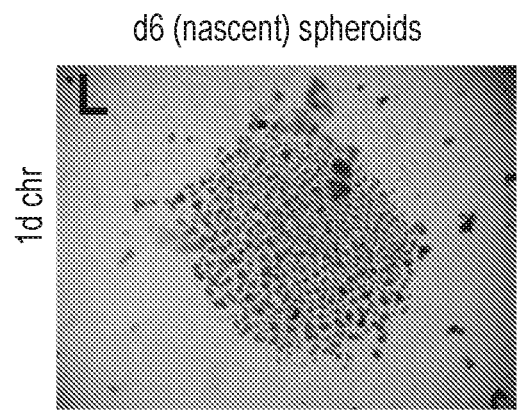
Figure 8M:
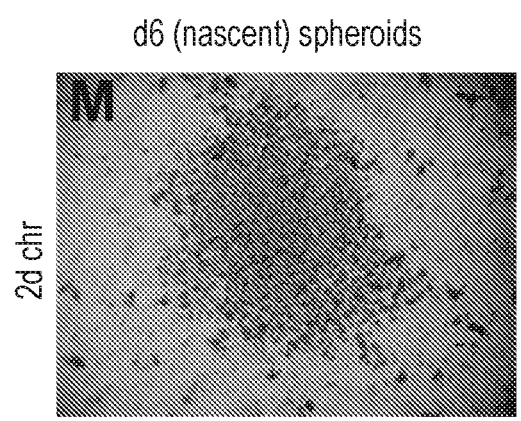
Figure 8N:
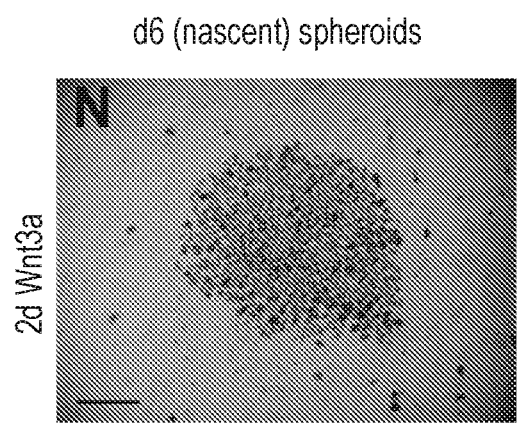
Figure 8O:
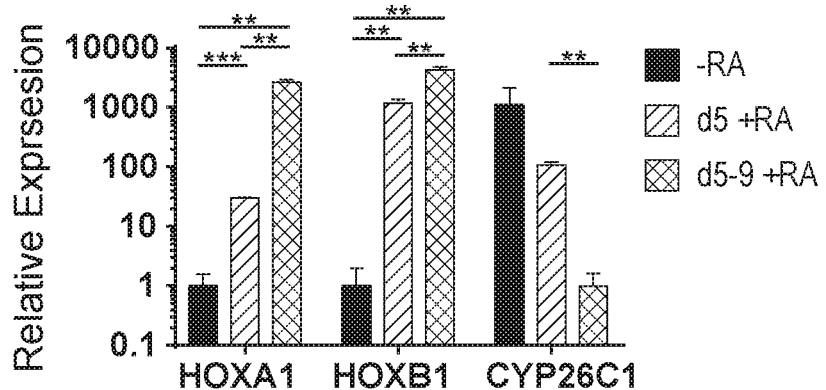
Figures 8P, 8Q, 8R:
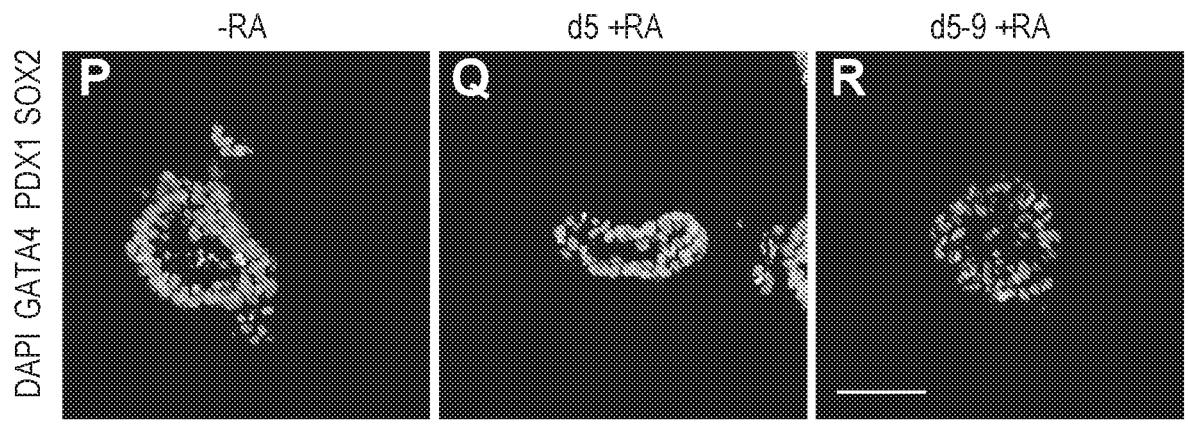
Figures 1, 8P, 8Q, 8R:
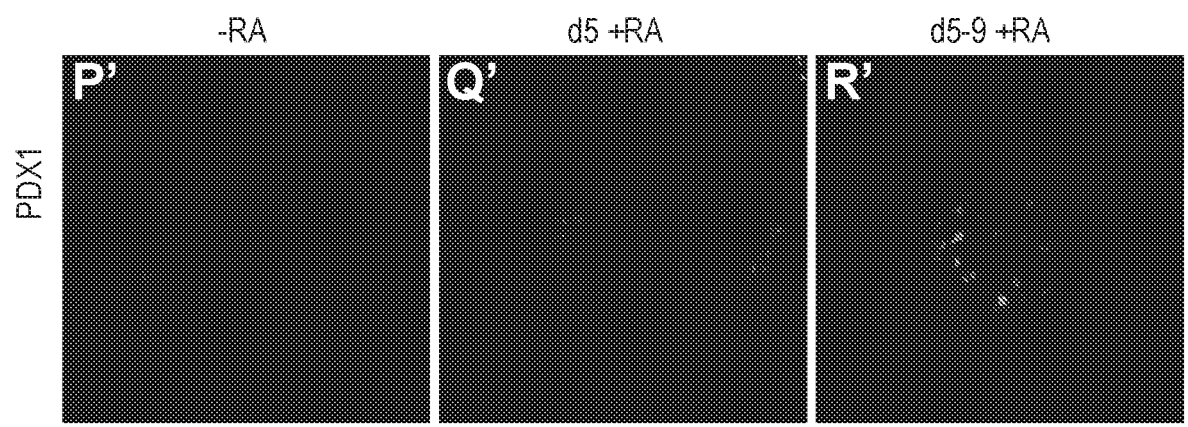
Figure 8S:
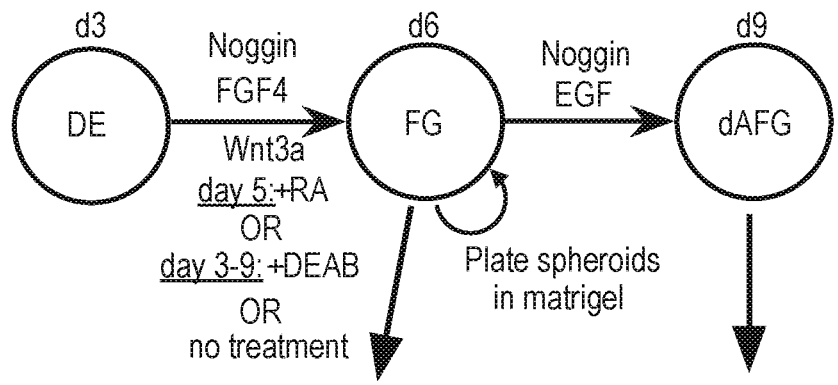
Figure 8T:
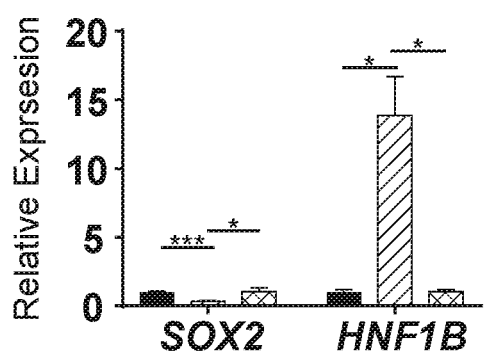
Figure 8U:
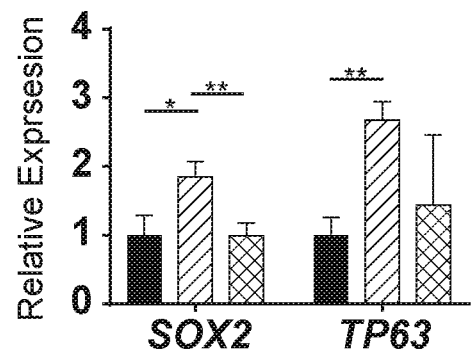
Figure 8V:
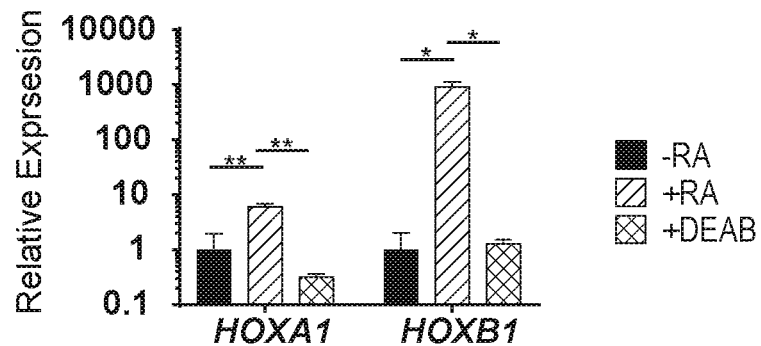

Continuing doxycycline treatment for the first month in HEOs outgrowth resulted in HEOs upregulating some intestinal markers, such as CDX1 and CDH17, while MUC2 remained unchanged (FIG. 3G-3J). The stratified squamous marker p63 was repressed, and SOX2 appears modestly downregulated, which is consistent with earlier results in the day 6 anterior foregut cultures (FIG. 3D, 3K-3L). Additionally, stratified squamous markers KRT5 and KRT13 were unchanged by CDX2 induction in the developing HEOs (data not shown). To further examine the regulatory interplay between these two primary transcription factors—SOX2 in the foregut and CDX2 in the hindgut—Applicant induced SOX2 in the human intestinal organoids (HIOs) (FIG. 8A-8B). In these cultures, Applicant found that treatment of HIOs with SOX2 resulted in upregulation of stratified squamous markers p63 and KRT13 (mildly), as well as downregulation of CDH17 and CDX2 (FIG. 8C-E,8G-8H). In the SOX2-induced HIOs, there is also upregulation of CLDN18, a marker expressed in the stomach, though it is important to note that some variability exists in control HIOs (FIG. 8C, data not shown). PDX1, a distal stomach or proximal intestine marker, trends towards downregulation with SOX2-induction, though its expression is also often variable in control HIOs (FIG. 8F). Together, these data suggest that while SOX2 exerts a stronger effect to inhibit the mid/hindgut fate, CDX2 alone is unable to robustly repress the foregut/esophageal fate during early development.

To determine whether the regulatory actions of CDX2 persist later in development (or in the HEO protocol) when plasticity is classically thought to be increasingly limited, Applicant grew HEOs to 6 weeks of age and treated with doxycycline for 8 days (FIG. 4A). In this case, SOX2 and p63 were downregulated in response to CDX2 induction, though there were some HEOs that minimally responded and/or had minimal CDX2 induction (FIG. 4B-4E, data not shown). Due to the variability in the CDX2-inducible system, Applicant opted for an analysis at the cellular resolution. Applicant counted and binned cells into 3 categories: uninduced, CDX2-low (induced), and CDX2-high (induced) (FIG. 4F-4G). Restricting the analysis to the basal cells, both SOX2 and p63 are strongly repressed in CDX2-high basal cells, while many cells can co-express SOX2 or p63 with CDX2 in CDX2-low basal cells (FIG. 4H-4I). This suggests that if all cells expressed CDX2 at high levels, these key esophageal transcription factors would be effectively repressed.

To further examine the role of CDX2 in repressing the esophageal (stratified squamous) epithelial identity, Applicant examined differentiated markers of the esophagus with CDX2-induction as well as in conjunction with DAPT, a Notch (γ-secretase) inhibitor (FIG. 5A). HES5, a target gene of Notch signaling in the esophagus, is downregulated upon DAPT addition (FIG. 5F). KRT5 is downregulated with CDX2-induction, and further downregulated with DAPT addition, as evident by some organoids completely losing KRT5 expression (FIG. 5B,5H). KRT13 is also downregulated, though there does not appear to be a synergistic effect with DAPT treatment (FIG. 5C). More differentiated markers IVL and CRNN are downregulated in CDX2-induced HEOs with or without DAPT treatment (FIG. 5D,5H). Finally, CDH17 appears to be modestly upregulated with CDX2-induction, though it was rare to find organoids that had visible protein expression of CDH17 (FIG. 5E,5H). This suggests that CDX2 is able to repress stratified squamous epithelial markers, with inhibition of Notch minimally adding to this effect.

Figure 9A:
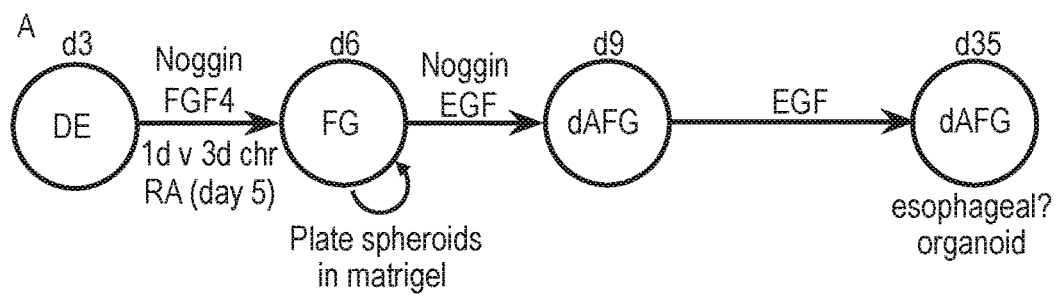
FIGS. 9A-9R. Early modulation of Wnt and retinoic acid signaling affects later differentiation into human esophageal organoids. (9A) Schematic depicting the experimental protocol to generate organoids starting with foregut spheroids treated with chiron for 1 or 3 days. (9B-9C) qPCR analysis of day 35 (1-month-old) organoids for (9B) stratified squamous epithelial markers KRT5, KRT13, and KRT13, and (9C) posterior foregut markers GATA4 and PDX1. (9D-9C) Analysis of day 35 (1-month-old) organoids resulting from altering the duration of retinoic acid treatment starting on day 5. qPCR analysis of (9D) anterior foregut basal transcription factors SOX2 and AN isoform of TP63, (9E) antral stomach and pancreas marker PDX1, and (9F) stratified squamous epithelial markers KRT5, KRT13, and IVL. Immunofluorescence analysis of one-month old organoids with (9G-9I) SOX2 and p63, (9J-9L) KRT13, and (9M-9O) PDX1. (9P) Schematic depicting experimental protocol for modulating retinoic acid signaling using the synthesis inhibitor DEAB. (9Q-9R) qPCR analysis of day 35 organoids of (9Q) esophageal basal markers SOX2 and TP63, (9R) stratified squamous epithelial markers KRT5, KRT13, and IVL. These data is representative of 2 separate experiments with n=3 wells in each experiment. Scale bar=100 μm. Error bars indicate SD. *p<0.05 and **p<0.01 for two-tailed t-test.
Figure 9B:
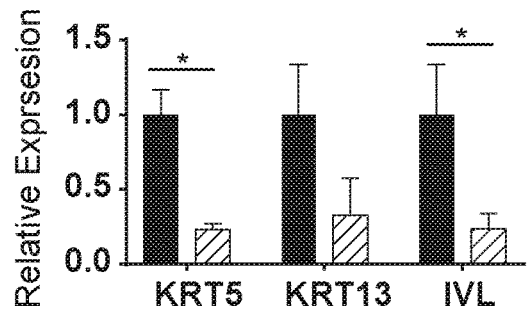
Figure 9C:
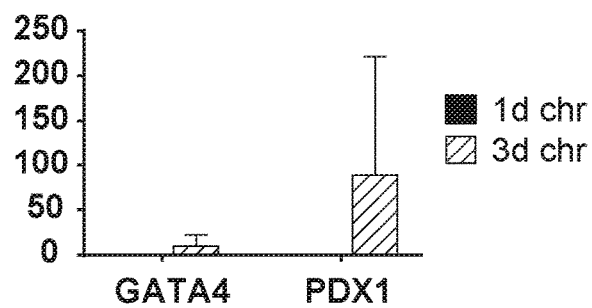
Figures 9D, 9E:
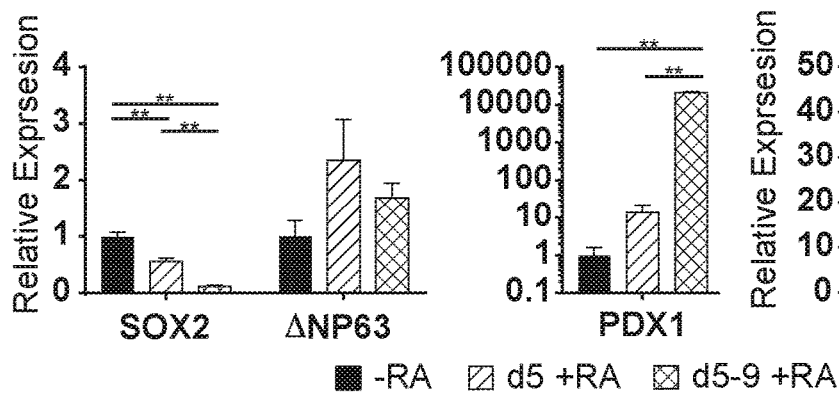
Figure 9F:
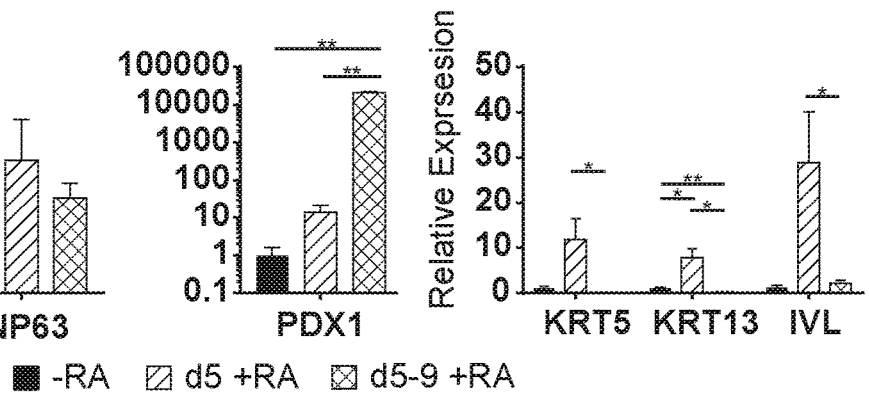
Figures 9G, 9H, 9I:
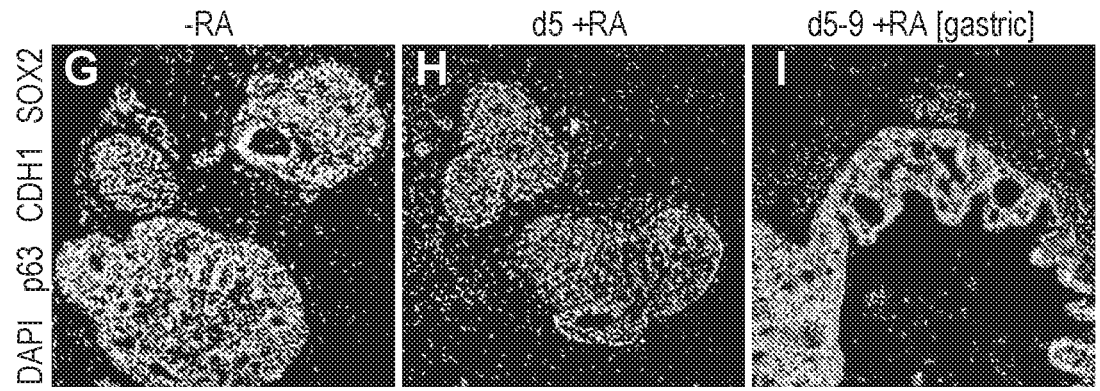
Figures 9J, 9K, 9L:
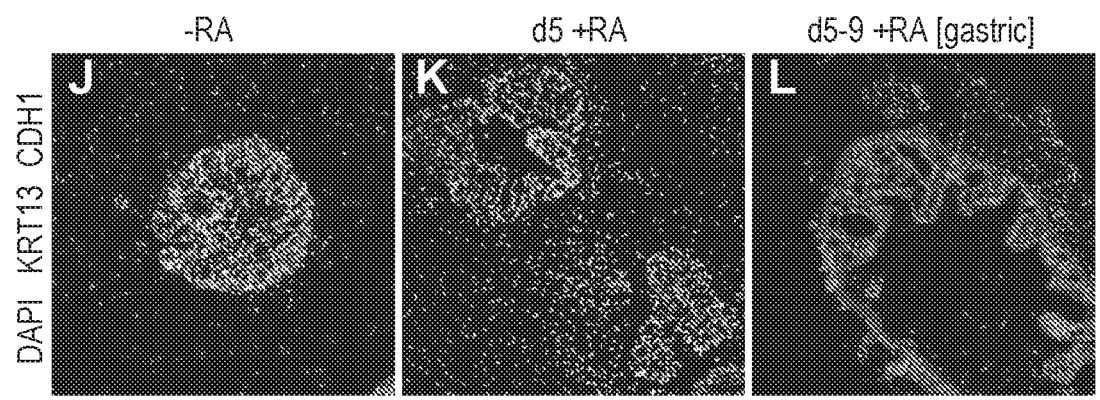
Figures 9M, 9N, 9O:
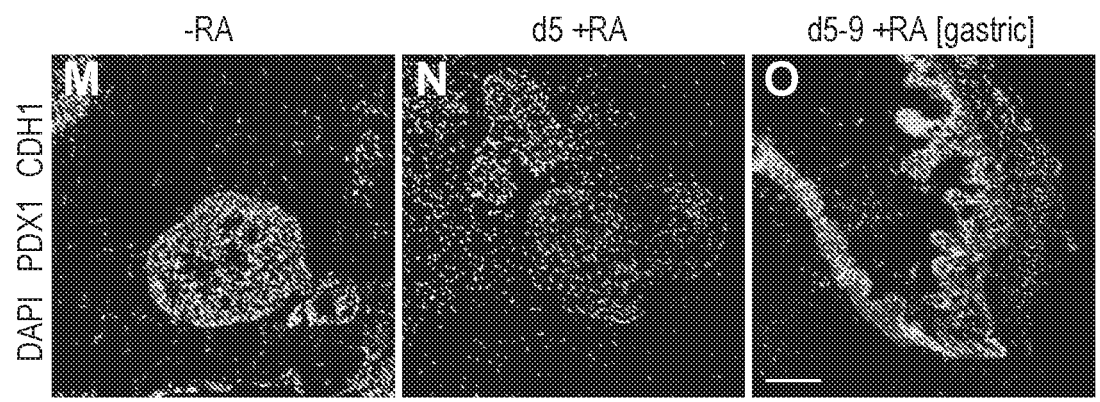
Figure 9P:
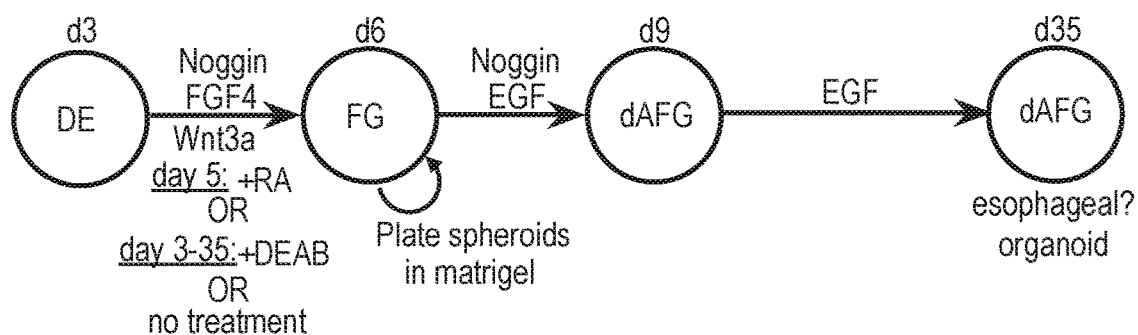
Figures 9Q, 9R:
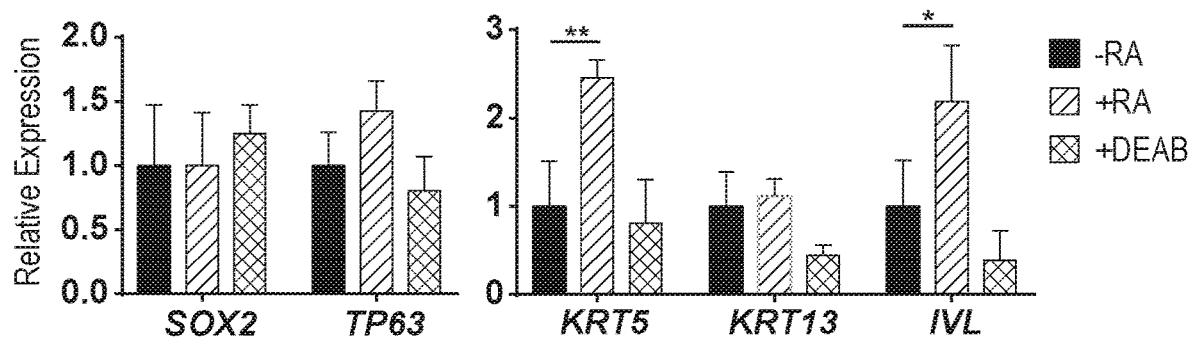
Figure 10A:
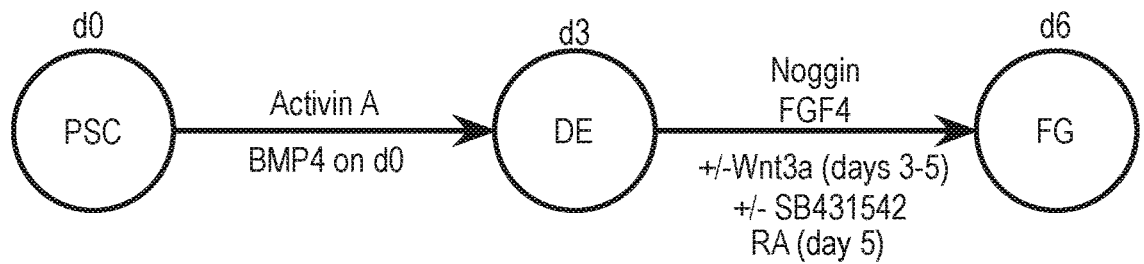
FIGS. 10A-10J. TGFβ inhibition is not required to pattern foregut into anterior foregut spheroids in these culture conditions. (10A) Schematic depicting the experimental protocol to test the requirement of TGFβ signaling in anterior-posterior patterning of the foregut. (10B-10F) qPCR analysis on day 6 anterior foregut spheroids treated with and without Wnt3a and TGFβ inhibitor (SB431542, 10 μM) treatment for (10B-10C) foregut marker SOX2 and hindgut marker CDX2, (10D) foregut marker HNF1B, and (10E-10F) posterior foregut markers PROX1 and HNF6. (10G) Schematic depicting the experimental protocol to test the competency of anterior foregut spheroids treated with and without Wnt3a or the TGFβ inhibitor SB431542 to respond to respiratory induction. (H-J) Analysis of day 9 spheroids for NKX2-1 by (10H-10I) immunofluorescence and (10J) qPCR. Scale bar=50 μm. Error bars indicate SD. *p<0.05 and **p<0.01 for two-tailed t-test.
Figure 10B:
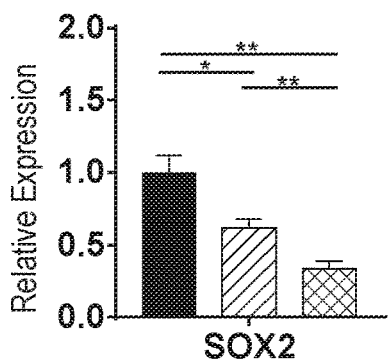
Figure 10C:
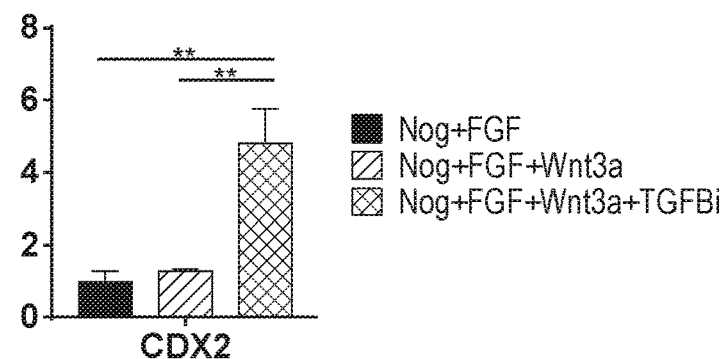
Figure 10D:
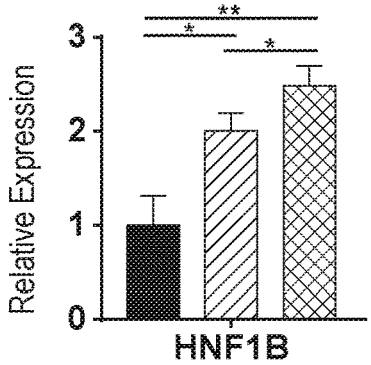
Figure 10E:
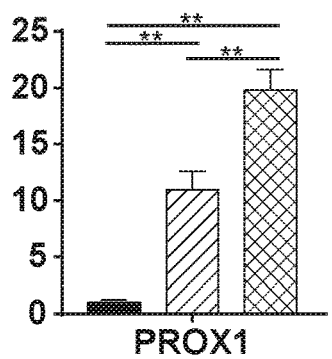
Figure 10F:
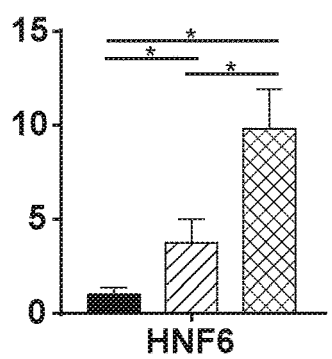
Figure 10G:
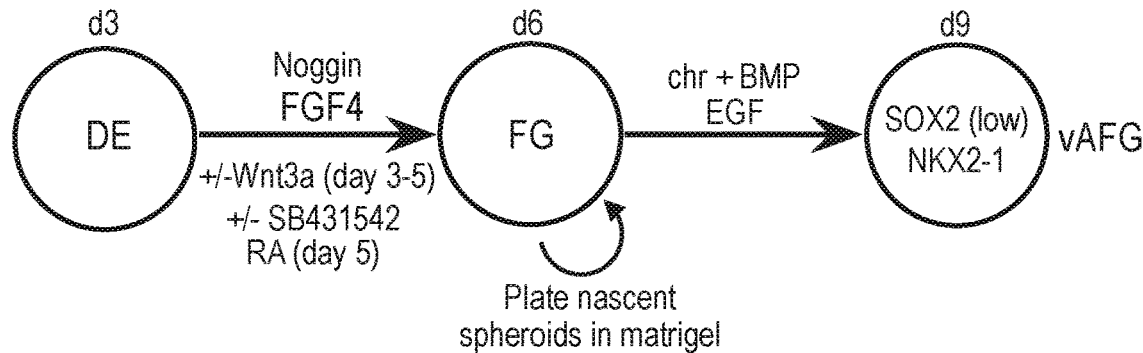
Figure 10H:
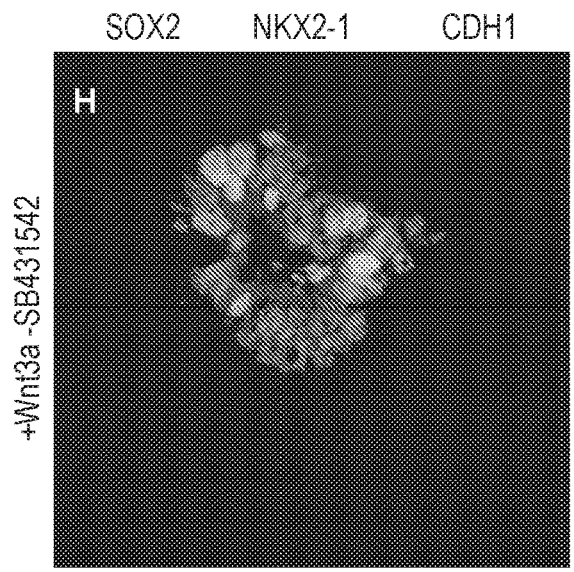
Figure 10I:
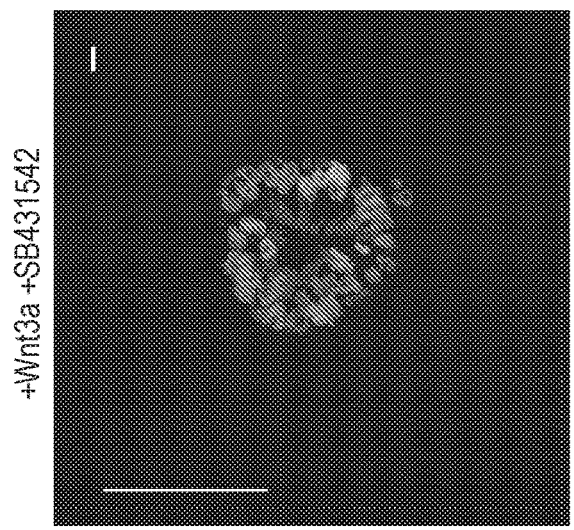
Figure 10J:
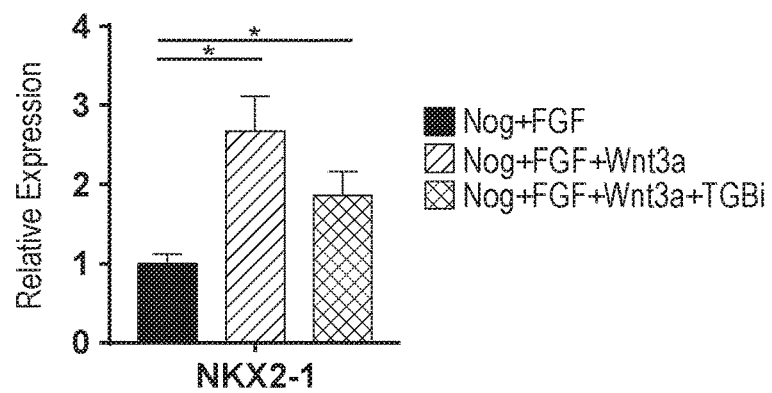
Figure 11E:
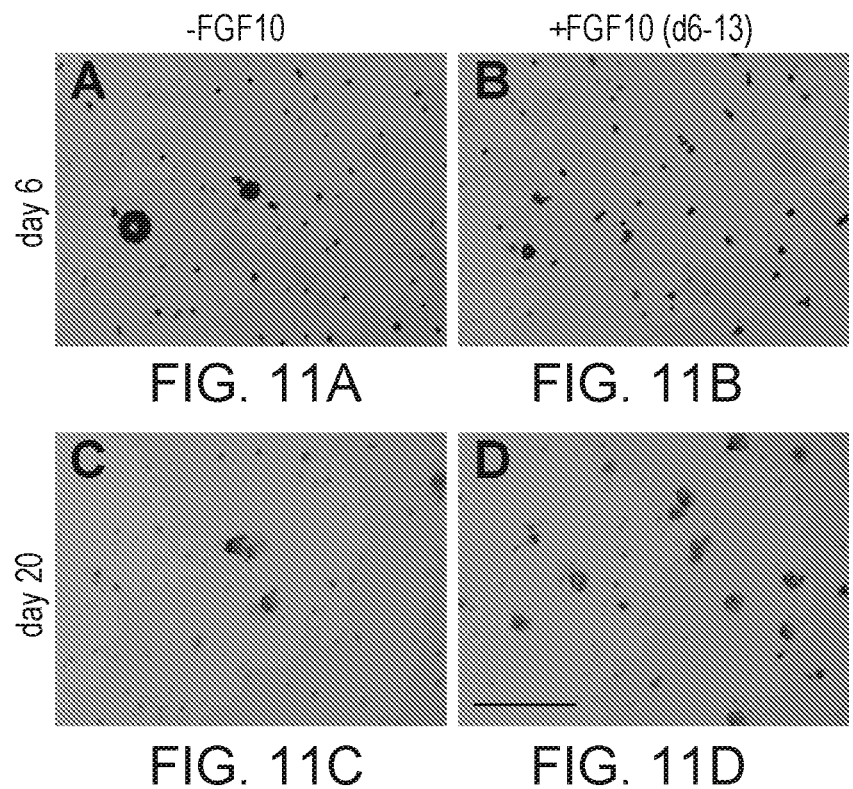
FIGS. 11A-11CC. Robust outgrowth of human esophageal organoids and a comparison to mouse embryonic esophageal development. (11A-11E) Improved spheroid outgrowth efficiency of organoids treated with FGF10 from day 6-13 as analyzed by (A-D) brightfield imaging and (11E) quantification of the images. (11F-11Q) Comparative analysis by immunofluorescence staining of mouse embryonic esophagi at E12.5 (11F, 11J, 11N) and E14.5 (11G, 11K, 11O) and human esophageal organoids (HEOs) at 2 weeks (11H, 11L, 11P) and 3 weeks (11I, 11M, 11Q). (R11) Gene expression of stratified squamous epithelial markers in mouse esophagi across time; public data acquired from GEO dataset GSE34728 (Chen et al. 2012). (11S) qPCR analysis of various time points during differentiation of definitive endoderm to human esophageal organoids for stratified squamous epithelial markers. (11T) Quantification of day 62 HEOs for % area of epithelia positive for KRT5 and KRT13. Each point is an individual organoid, and subpanels "a" and "b" are representative images of different organoids depicted in this graph. (11U) Quantification of day 62 HEOs for % epithelial nuclei positive for SOX2 and p63. Each point is an individual organoid. (11V-11CC) Immunofluorescence analysis of 1-month old HEOs across different cell lines tested, examining esophageal enriched markers SOX2 and p63 (11V-11Y), and KRT13 (11Z-11CC). Scale bar=500 μm in (11A-11D), 50 μm in (11F-11Q, 11V-11CC), and 100 μm in (11T-11U). Error bars indicate SD. *p<0.05, p<0.01, and *p<0.001 for two-tailed t-test.
Figure 11E:
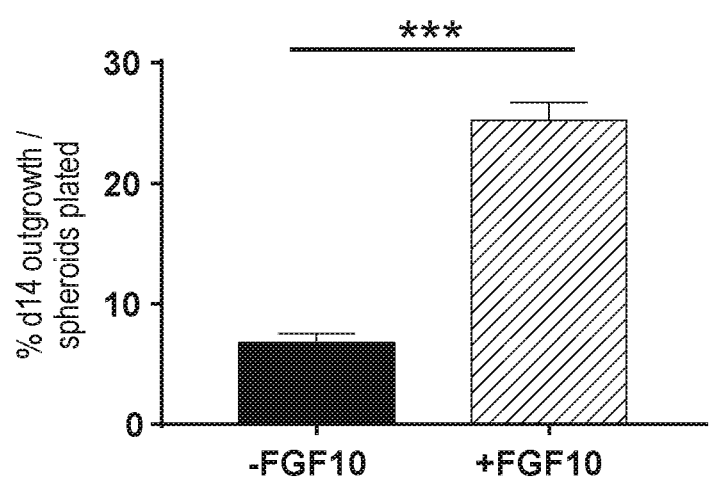
Figure 11R:
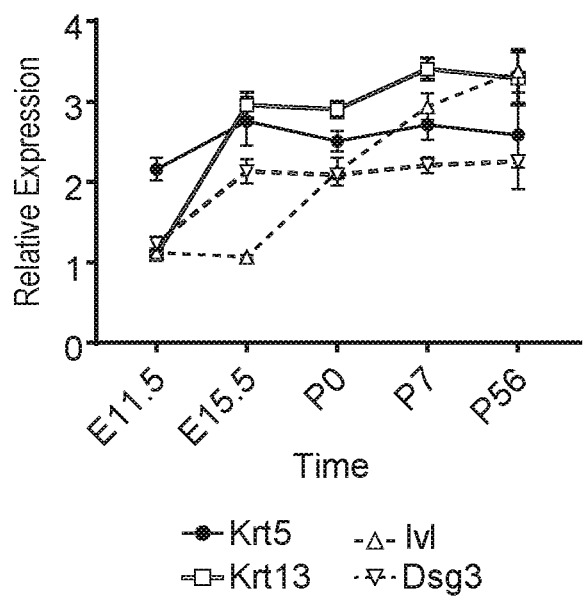
Figure 11S:
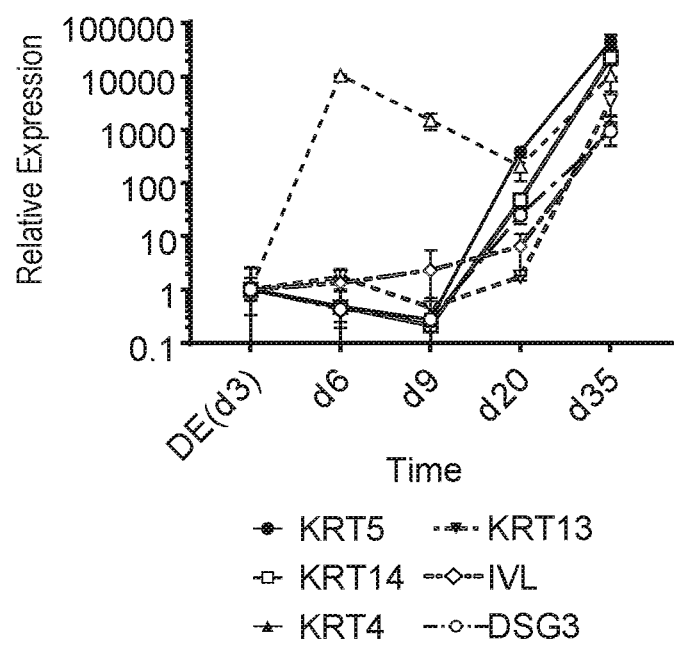
Figure 11T:
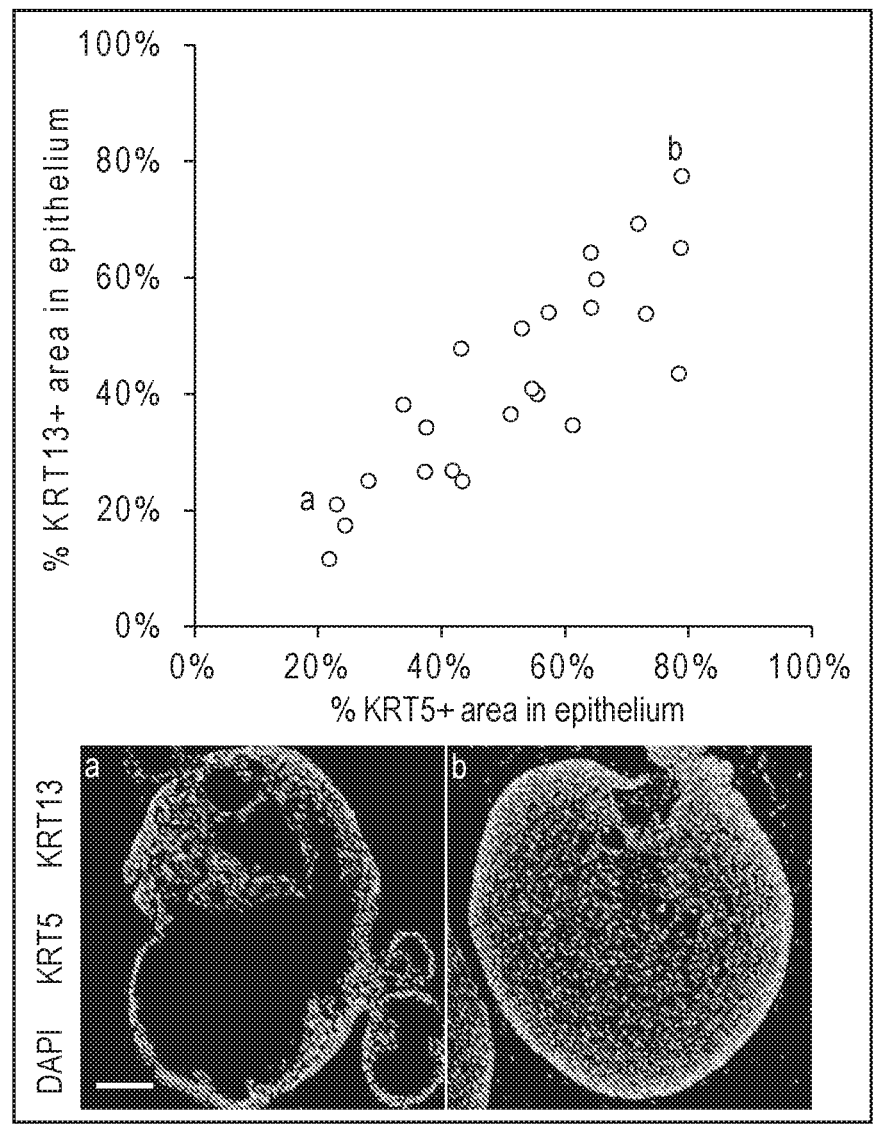
Figure 11U:
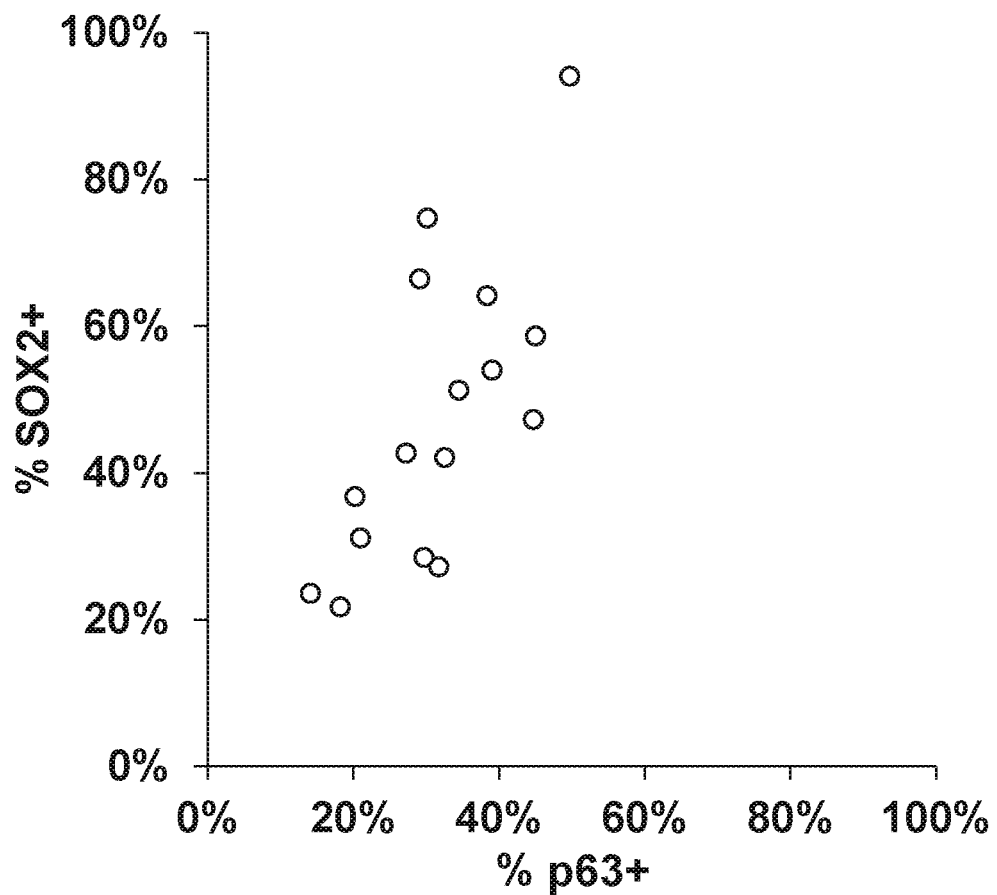
Figures 1, 12A:
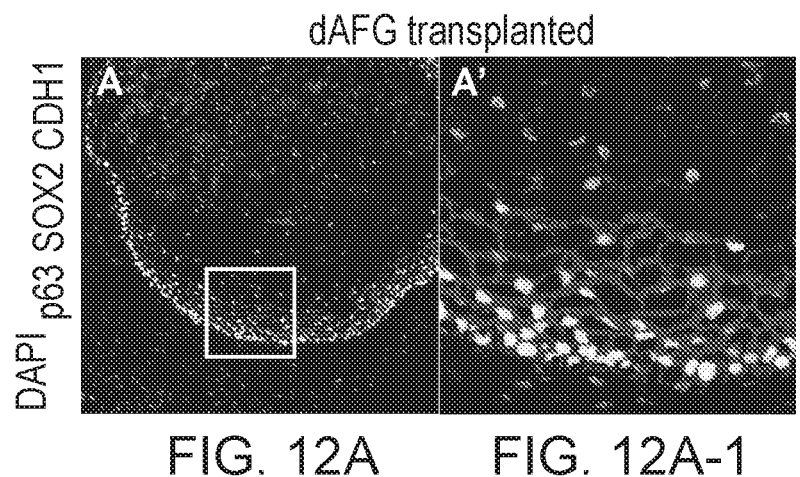
FIGS. 12A-12R. Alternate methods of human esophageal organoid maturation and expansion. (12A-12F) Analysis of HEOs grown for 2 months after transplantation into immunodeficient mice's kidney capsules by (12A-12E) Immunofluorescence images for early (KRT8) and differentiated (KRT13, KRT14, and IVL) esophageal specific markers, and (12F) H&E. (12G-12R) Analysis of HEOs mechanically passaged (dissociated and re-cultured) twice. (12G-12N) IF images of passaged organoids for (12G-12H) transcription factors SOX2 and p63, (12I-12J) immature (KRT8) and basal marker (KRT14), (12K-12L) basal (KRT5) and suprabasal (KRT13) markers, and (12M-12N) suprabasal differentiated markers KRT4, CRNN, and IVL. (12O-12R) qPCR analysis comparing passaged HEOs to normal HEOs and gastric organoids (hAGO) for (12O) transcription markers SOX2 and TP63, (12P) stratified squamous markers KRT5, KRT13, IVL, and (12Q-12R) patterning markers for lung (NKX2-1), stomach (GATA4), and intestine (GATA4 and CDX2). *p<0.05, p<0.01, and *p<0.001 for two-tailed t-test.
Figures 1, 12B:
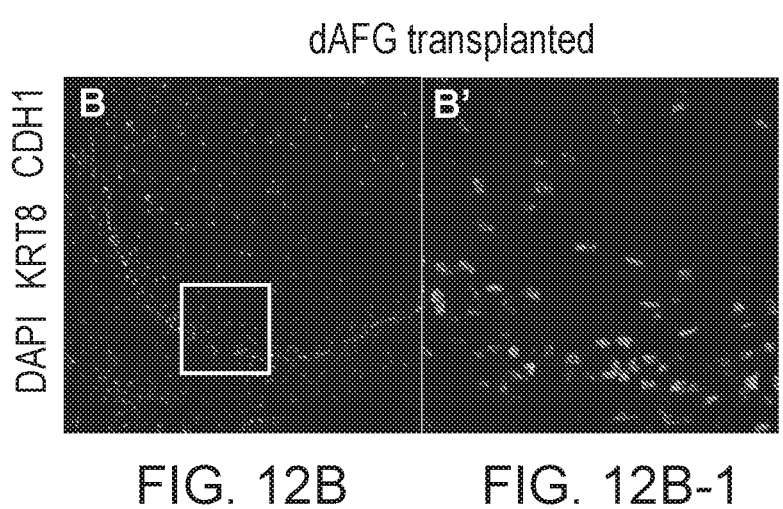
Figures 1, 12C:
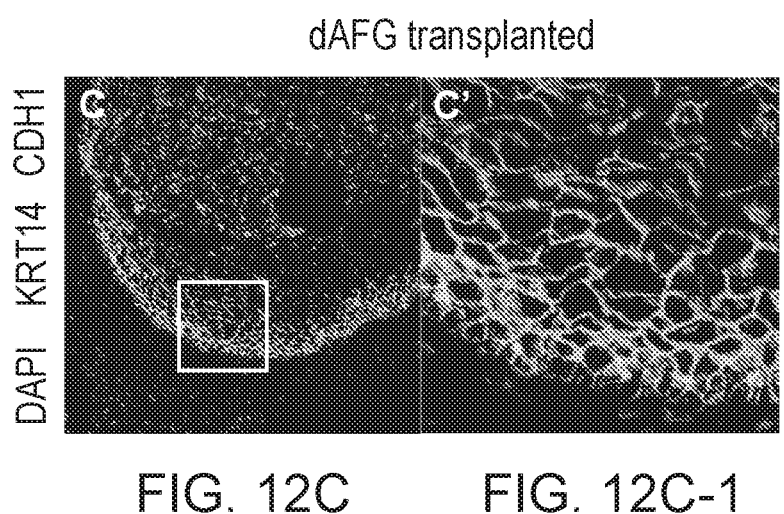
Figures 1, 12D:
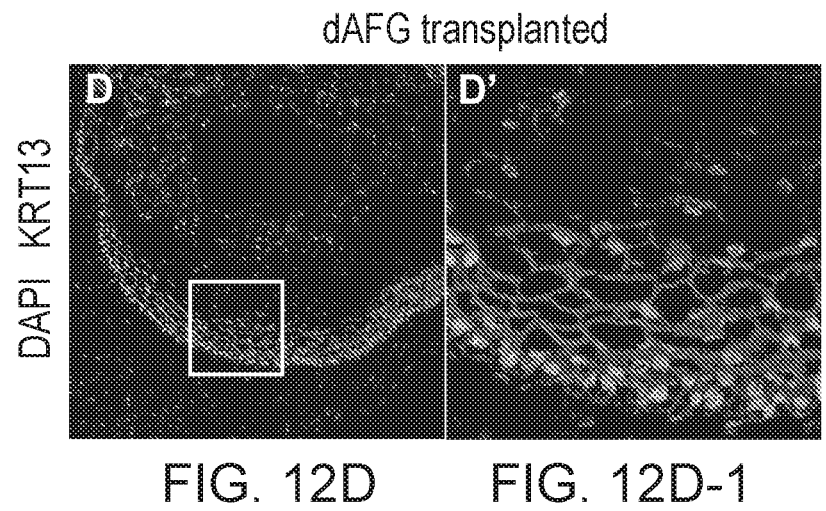
Figures 1, 12E:
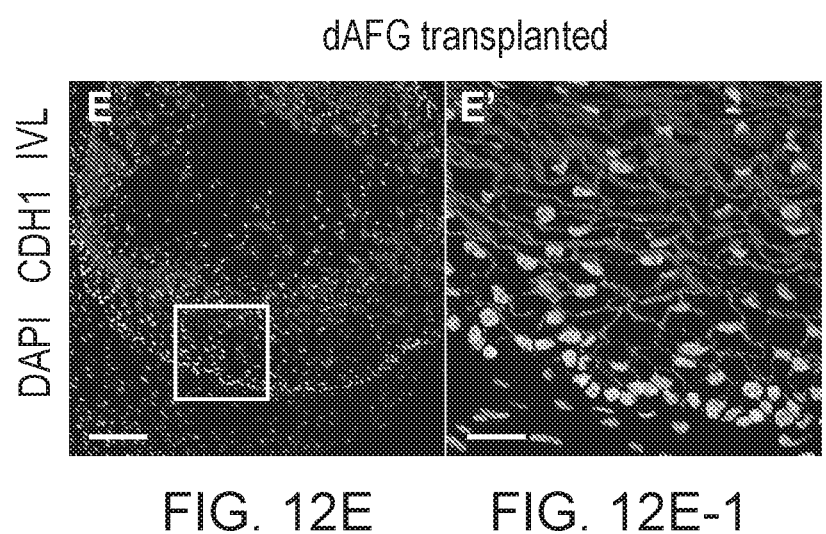
Figures 1, 12F:
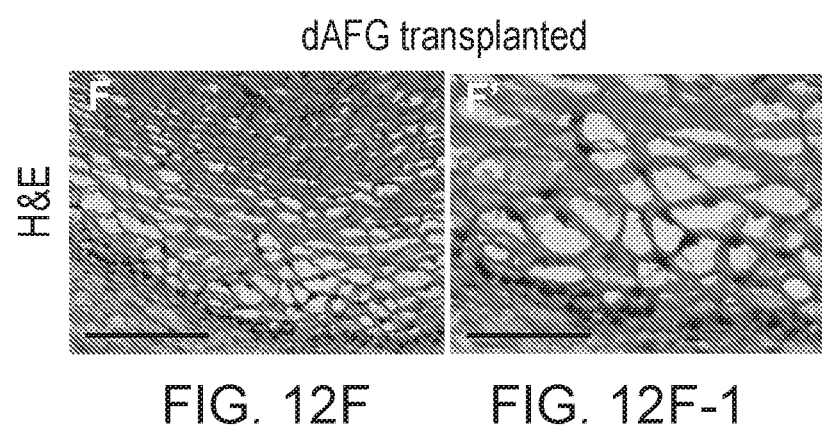

Because BMP signaling has been implicated in the transformation of esophageal into intestinal cells, Applicant also examined the effects of BMP signaling in HEOs (FIG. 9A) (Mari et al., 2014). Treating 6-week-old HEOs with BMP4 for additional 2 weeks results in loss of stratification and expression of differentiation markers (FIG. 9B, 9G-9J). The remaining basal cells have active BMP signaling (pSMAD1/5/9+) and express p63, but loss expression of SOX2 (FIG. 9B, 9D-9E). Additionally, there was minimal EdU incorporation in BMP4 treated HEOs, meaning that cell turnover has dramatically slowed down (FIG. 9B-9C). CDX2 expression was unchanged in BMP4 treated HEOs, though CDX2-induction results in downregulation of ID1, a BMP target (FIG. 5G, data not shown). Together, this suggests that BMP signaling may reinforce the downregulation of stratified squamous epithelium by counteracting the dampening in BMP signaling when CDX2 is induced.

Modeling Eosinophilic Esophagitis Using HEOs

Finally, Applicant tested whether HEOs could be used to model eosinophilic esophagitis, an inflammatory disease affecting the esophagus. Applicant focused on the epithelial response to IL-13, a cytokine known to enact broad changes in the esophagus, to validate HEOs in modeling eosinophilic esophagitis. Applicant treated 6-8-week-old HEOs with IL-13 for various durations and examined multiple properties of the HEOs (FIG. 6A). First, Applicant validated the response of target genes CCL26, CDH26, CAPN14, and SERPINB4 to a short duration of IL-13 treatment (FIG. 6B-6E). Extended treatment with IL-13 maintained upregulation of some target genes SERPINB13 and CDH26 (FIG. 6F). In addition to the upregulation of these target genes, EdU incorporation was increased in the basal-most p63+ cells, suggesting that the basal cells are more proliferative with extended exposure to IL-13 (FIG. 6G-6H).

Applicant next looked at the morphology and differentiation of the stratified squamous epithelium upon treatment with IL-13. HEOs treated with IL-13 downregulated late differentiation and structural proteins DSG1, IVL, and CRNN, though the control organoids had significant variability in the expression of these differentiated markers by RNA (FIG. 7A-7D). Additionally, the epithelium had dilated intercellular spaces suprabasally, and using electron microscopy, there were increased spaces between individual cells and a decrease in cell-cell contacts (FIG. 7A,7G). These data suggest that, for the most part, HEOs respond as expected to IL-13 treatments when compared to other model systems.

Figure 7L:
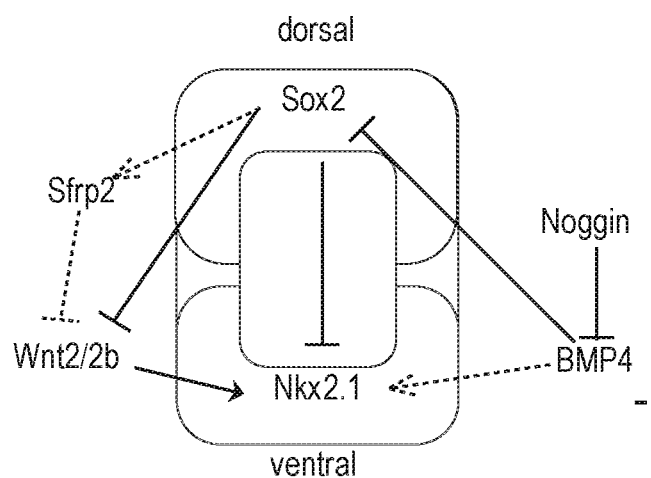

Lastly, because BMP signaling has also been implicated in eosinophilic esophagitis, particularly that the BMP antagonist follistatin is downregulated in the diseased esophagus, Applicant examined whether BMP activation can reverse some aspects of the disease process (Jiang et al., 2015). However, unlike the mouse esophagus induced with IL-13, HEOs did not upregulate BMP antagonists NOG and FST (FIG. 7E-F) (Jiang et al., 2015). This is reflected by the mild increase in BMP target gene ID3 to IL-13 (and BMP4) treatment (FIG. 7L). Despite this, upon treatment of HEOs with IL-13 and BMP4 compared to just IL-13, the expression of SOX2 and PTCH1 normalizes back to control (FIG. 7H,7K). IL-13 targets CCL26 and CDH26 were also downregulated with BMP4 addition (FIG. 7I-7J). However, stratified squamous markers KRT5, KRT13, IVL, and CRNN were not consistently altered with the addition of BMP4 and IL-13 compared to IL-13 treatment alone (data not shown). Thus, BMP signaling activation may reverse or counter some aspects of the disease process induced by IL-13.

The results shared some similarities with previously published experiments. In contrast to the hypomorphic Sox2 model, which had low Sox2 levels for the entirety of embryonic development, Applicant was able to carefully examine when and for which processes are Sox2 necessary in esophageal development. Thus, Applicant was able to distinguish that the basal layer of the esophagus appeared intact in mid-embryonic (E11.5) knockout of Sox2 by expression of Krt14 and p63, while the esophagus in earlier knockouts (E8.5) or in hypomorphic Sox2 embryos had reduced/absent expression of these proteins (Que et al., 2007). The result may be due to the establishment of p63 expression in the esophagus by the time of the later Sox2 knockout, which then p63 alone may be able to maintain basal development. Another difference between the global Sox2 hypomorphs and mid-embryonic Sox2 knockout was that the later Sox2 knockout esophagi did not appear to acquire a different tissue identity (intestine, gastric, respiratory), suggesting that establishment of the esophageal fate has been set by E11.5. Interestingly, the results also show that Sox2 loss at E11.5 resulted in loss of suprabasal differentiation and increased suprabasal proliferation, which is similar to how Sox2 may suppress proliferation during stomach development (Hagey et al., 2018). Late-embryonic or early-postnatal knockout of Sox2 appeared to have minimal effect on the esophagus, which suggest that Sox2 may not play a major role in the adult esophagus, more closely resembling the stomach compared to the trachea (Que et al., 2009; Sarkar et al., 2016). Therefore, though the esophageal fate may be set by mid-embryonic development, the results demonstrate that continued Sox2 expression after initial patterning of the anterior foregut is required for proper esophageal differentiation and maturation. However, longer-term studies with more mice as well as injury models may uncover a later role for Sox2 in the late embryonic and post-natal esophagus.

For the other diseases, Fanconi anemia, Barrett's esophagus, and eosinophilic esophagitis, Applicant attempted to use HEOs to model the changes in the esophagus. In trying to model esophageal atresia in Fanconi anemia with HEOs, a primary obstacle is that only a minority of patients with Fanconi anemia have GI malformations. The particular patient used to generate the iPS line in this study did not have esophageal atresia, though FANCA mutations have been linked to esophageal atresia (Feng et al., 2018). Because loss of FANCA results in increased sensitivity to DNA damage, Applicant examined cell death (by cleaved Caspase 3 staining), but found no difference (or more precisely, no significant amount of cell death in either case), which may be expected since Applicant did not add any chemotherapeutic agents. Interestingly, despite the smaller size of the FANCA-deficient HEOs, there were more proliferative cells compared to control HEOs, which is similar to the results found in FANCA-deficient skin keratinocytes in culture (Hoskins et al., 2009). Apart from this difference though, Applicant did not find changes in differentiation. One caveat with using HEOs to model esophageal atresia is that the culture conditions may compensate for or complement the deficiency, which could bypass the majority of the disease process. Additionally, the analysis at the 1-month time point may be too late in that the deficiency may have had most of its effects in the earlier stages of the protocol.

Applicant next sought to model Barrett's esophagus using HEOs. In the older HEOs, Applicant found that CDX2-induction leads to downregulation of some stratified squamous markers, which contrasts the minimal changes that resulted in a similar experiment performed in an esophageal keratinocyte line (EPC2) (Mari et al., 2014). Applicant's results aligned with the inability of CDX2-induction to robustly upregulate of intestinal genes, suggesting the requirement of additional factors, as shown by using a DNA-methyltransferase inhibitor in other models (Kong et al., 2009, 2011; Mari et al., 2014). Notch inhibition only appeared to mildly (or negligibly) add to this transformation in the HEOs, unlike a previous study using organotypic raft cultures (Vega et al., 2014). Applicant similarly found that BMP activation also downregulates stratified squamous genes, although in our case, this may be mediated by the cell cycle arrest of the stem/progenitor cells (Mari et al., 2014).

Applicant also induced CDX2 and SOX2 in the HEO or HIO differentiation protocols (respectively) to examine the transcriptional network that regulates this switch between fates. Consistent with studies in mice, SOX2 induction in HIOs downregulate CDX2 and upregulate genes of various foregut lineages, p63, KRT13, and CLDN18, though the epithelium still is predominantly columnar (Kuzmichev et al., 2012). Interestingly, brief CDX2 induction in early foregut cultures does not directly regulate/repress SOX2 expression, and it has been shown in the early endoderm that some SOX2+ CDX2+ double-positive cells exist (Sherwood et al., 2009). However, extending cultures and CDX2-induction to early (or late) HEOs results in repression of SOX2 and p63, suggesting CDX2 may alter downstream targets that then regulate SOX2 and p63. Also, beginning CDX2-induction early results in significant upregulation of CDH17, unlike later CDX2-induction, suggesting that there is some plasticity earlier on which is lost as the organoids mature. Thus, this suggests that multiple changes are required to fully transform an esophageal epithelium into intestinal epithelium, or vice-versa. Alternatively, the cells that give rise to the metaplasia in Barrett's esophagus may not be the stratified squamous epithelium.

Finally, modeling the epithelial changes in eosinophilic esophagitis using HEOs may be done. Treating HEOs with IL-13 resulted in similar responses using IL-13 treated air-liquid interface (ALI) esophageal cultures, such as downregulation of differentiated stratified squamous epithelial genes (Blanchard et al., 2010; K C et al., 2015). Additionally, the increased proliferation in IL-13 treated HEOs may indicate the start of basal cell hyperplasia, though, in HEOs, the actual thickening of the basal layer is difficult to assess and may not occur, as the organoid would be able to freely expand being suspended in three-dimensional culture. Similar to other studies, signs of barrier dysfunction can be observed, including the increased intercellular spaces and downregulation of DSG1, though barrier function was not directly assessed through measuring the transepithelial electrical resistance (TEER) as in ALI cultures (D'Mello et al., 2016; Davis et al., 2016; Kasagi et al., 2018). Thus, it appears that HEOs respond expectedly to IL-13 treatment.

Various signaling pathways that might be misregulated in eosinophilic esophagitis were investigated. In human biopsies of eosinophilic esophagitis and an experiment where IL-13 was misexpressed in the mouse esophagus, BMP signaling was reduced and the BMP antagonist, follistatin, was upregulated (Jiang et al., 2015). However, Applicant found a mild, but opposite, change in BMP antagonists and BMP activation in HEOs treated with IL-13. Interestingly though, BMP activation in IL-13 treated HEOs reverses some changes that occur in HEOs treated with IL-13 alone, as evident by downregulation SOX2 and some IL-13 target genes. Additionally, using PTCH1 as a read-out for hedgehog signaling activity, IL-13 treatment upregulates PTCH1 (Robbins et al., 2012). This potential increase in hedgehog signaling may be linked to the increase in proliferation and decreased differentiation of the epithelium, which resembles a study with Ptch1 mutant mouse esophagi and in esophageal squamous cell carcinoma (van Dop et al., 2012). Through modeling these select esophageal pathologies, Applicant has demonstrated that HEOs can be used as a complementary model to better understand the mechanisms underlying these and hopefully other diseases affecting the esophagus.

Materials and Methods

Mice

Wild-type and mutant mice were used for studies on foregut and esophageal development. Sox2$^{fl/fl}$ mice were obtained from Richard Lang's lab (Shaham et al., 2009), and Sox2CreER (stock #017593, Arnold et al., 2011) were obtained from The Jackson Laboratory. Pregnant dams were gavaged at various stages with tamoxifen at 0.12 mg/g mouse to activate the CreER at appropriate stages. Mice were housed in the animal facility at Cincinnati Children's Hospital Medical Center (CCHMC) in accordance with NIH Guidelines for the Care and Use of Laboratory animals. Animals were maintained on a 12 hour light-dark cycle with access to water and standard chow ad libitum. Healthy animals were used for all experiments. All experiments were performed under the approval of the Institutional Animal Care and Use Committee of CCHMC (protocols IACUC2016-0004).

Human ESC/IPSC and Maintenance

Human embryonic stem cell (hESC) line H1 (WA01, male) were purchased from WiCell. iPSC line iPS106 was generated in-house and approved by the institutional review board at CCHMC. All hPSCs were maintained on feeder-free cultures: cells were plated on hESC-qualified Matrigel (BD Biosciences, San Jose, Calif.) and maintained at 37° C. with 5% $CO_2$ with daily replacement of mTeSR1 media (STEMCELL Technologies, Vancouver, Canada); cells were passaged routinely every 4 days using Dispase (STEMCELL Technologies). The HA-tagged SOX2, CDX2, or FANCA dox-inducible lines were generated by first cloning the human SOX2 ORF, CDX2 ORF, or FANCA ORF into pINDUCER20 (respectively) (Addgene #44012, Meerbrey et al., 2011). Next, lentivirus was generated with help of the Viral Vector Core Facility at CCHMC. The lentivirus for HA-SOX2 and CDX2 were transduced into hESCs with 2 µL of virus; these lines were maintained on selection with mTeSR1 and G418 (500 µg mL-1, ThermoFisher Scientific). The lentivirus for FANCA were transduced prior to the iPS106 line generation, as FANCA is required for maintenance of hPSC properties. The hESC H1 line (and transduced derivatives) was used in all experiments excluding Fanconi Anemia modeling in HEOs, which used the iPS106 line.

Differentiation of Anterior Foregut Cultures and Spheroids

Confluent hPSC cultures were treated with Acutase (STEMCELL Technologies) to resuspend as single cells in mTeSR1 and Y-27632 (10 µM, Tocris) and plated on Matrigel. On the following day, differentiation into definitive endoderm was carried out as previously described (McCracken et al., 2014). Briefly, cells were treated with Activin A (100 ng mL-1, R&D systems, Minneapolis, Minn.) and BMP4 (50 ng mL-1, R&D systems) on the first day in RPMI 1640 media (Life Technologies). Cells in the following two days were treated with only Activin A (100 ng mL-1) in RPMI 1640 with increasing concentrations 0.2% and 2% of HyClone defined fetal bovine serum (dFBS, GE Healthcare Life Sciences).

For the generation of anterior foregut spheroids, from definitive endoderm, cells were treated with Wnt3a (500 ng mL-1, R&D systems) for 2 days, and FGF4 (500 ng mL-1, R&D systems), Noggin (200 ng mL-1) for 3 days in RPMI 1640 with 2% dFBS. Three-dimensional culture and differentiation of anterior foregut spheroids into human esophageal organoids were obtained as described above.

Immunofluoresence Analysis

Tissue cultures were fixed with 4% paraformaldehyde at either room temperature for 15 minutes (for monolayer cultures), or 4° C. for overnight (for organoids). Tissues were thoroughly washed in PBS and stained for monolayer cultures, while organoids were thoroughly washed and then left in 30% sucrose overnight, embedded in OCT compound (VWR), and sectioned at a thickness of 8 µm. Slides were then permeabilized with 0.5% TritonX-100 in PBS for 10 minutes, blocked in 5% normal donkey serum (Jackson ImmunoResearch) for 1 hour minimum, and incubated in primary antibody overnight at 4° C. On the next day, slides were thoroughly washed in PBS, incubated in secondary antibody (at 1:500) for 1 hour, and then thoroughly washed again. For EdU visualization, the Click-iT EdU Alexa Fluor 488 Imaging Kit (Invitrogen) was used prior to blocking. Antibodies and dilutions used are shown in Table 1.

RNA Isolation and qPCR

Monolayer cultures and organoids were harvested in total, including the plated/embedding matrigel. Total RNA was isolated using the NucleoSpin RNA kit (Macherey-Nagel) and reverse transcribed to cDNA using the SuperScript VILO cDNA synthesis kit (ThermoFisher Scientific). For qRT-PCR, Applicant used Quantitect SYBR-Green master mix (Qiagen) and ran the reaction on a QuantStudio 6 machine (ThermoFisher Scientific). Primers used are shown in Table 2.

REFERENCES

Andl, C. D., Mizushima, T., Nakagawa, H., Oyama, K., Harada, H., Chruma, K., Herlyn, M., and Rustgi, A. K. (2003). Epidermal growth factor receptor mediates increased cell proliferation, migration, and aggregation in esophageal keratinocytes in vitro and in vivo. Journal of Biological Chemistry, 278(3), 1824-1830. https://doi.org/10.1074/jbc.M209148200

Arnold, K., Sarkar, A., Yram, M. A., Polo, J. M., Bronson, R., Sengupta, S., Seandel, M., Geijsen, N., and Hochedlinger, K. (2011). Sox2+ Adult Stem and Progenitor Cells Are Important for Tissue Regeneration and Survival of Mice. Cell Stem Cell, 9(4), 317-329. https://doi.org/10.1016/j.stem.2011.09.001 Bamberger, C., Pollet, D., and Schmale, H. (2002). Retinoic acid inhibits downregulation of DeltaNp63alpha expression during terminal differentiation of human primary keratinocytes. The Journal of Investigative Dermatology, 118(1), 133-8. https://doi.org/10.1046/j.0022-202x.2001.01649.x Bayha, E., Jorgensen, M. C., Serup, P., and Grapin-Botton, A. (2009). Retinoic acid signaling organizes endodermal organ specification along the entire antero-posterior axis. PloS One, 4(6), e5845. https://doi.org/10.1371/journal.pone.0005845

Chen, H., Li, J., Li, H., Hu, Y., Tevebaugh, W., Yamamoto, M., Que, J., and Chen, X. (2012). Transcript profiling identifies dynamic gene expression patterns and an important role for Nrf2/Keap1 pathway in the developing mouse esophagus. PloS One, 7(5), e36504. https://doi.org/10.1371/journal.pone.0036504

Chen, Y.-W., Huang, S. X., de Carvalho, A. L. R. T., Ho, S.-H., Islam, M. N., Volpi, S., Notarangelo, L. D., Ciancanelli, M., Casanova, J.-L., Bhattacharya, J., Liang, A. F., et al. (2017). A three-dimensional model of human lung development and disease from pluripotent stem cells. Nature Cell Biology, 19(5), 542-549. https://doi.org/10.1038/ncb3510

Chen, Y., Shi, L., Zhang, L., Li, R., Liang, J., Yu, W., Sun, L., Yang, X., Wang, Y., Zhang, Y., and Shang, Y. (2008). The Molecular Mechanism Governing the Oncogenic Potential of SOX2 in Breast Cancer. Journal of Biological Chemistry, 283(26), 17969-17978. https://doi.org/10.1074/jbc.M802917200

D'Amour, K. a, Agulnick, A. D., Eliazer, S., Kelly, O. G., Kroon, E., and Baetge, E. E. (2005). Efficient differentiation of human embryonic stem cells to definitive endoderm. Nature Biotechnology, 23(12), 1534-1541. https://doi.org/10.1038/nbt1163

Daniely, Y., Liao, G., Dixon, D., Linnoila, R. I., Lori, A., Randell, S. H., Oren, M., and Jetten, A. M. (2004). Critical role of p63 in the development of a normal esophageal and tracheobronchial epithelium. American Journal of Physiology. Cell Physiology, 287(1), C171-C181. https://doi.org/10.1152/ajpcell.00226.2003 Davenport, C., Diekmann, U., Budde, I., Detering, N., and Naujok, O. (2016). The Anterior-Posterior Patterning of Definitive Endoderm Generated from Human Embryonic Stem Cells Depends on the Differential Signaling of Retinoic Acid, Wnt- and BMP-Signaling. Stem Cells, 34(11), 2635-2647. https://doi.org/10.1002/stem.2428

Dessimoz, J., Opoka, R., Kordich, J. J., Grapin-Botton, A., and Wells, J. M. (2006). FGF signaling is necessary for establishing gut tube domains along the anterior-posterior axis in vivo. Mechanisms of Development, 123(1), 42-55. https://doi.org/10.1016/j.mod.2005.10.001

DeWard, A. D., Cramer, J., and Lagasse, E. (2014). Cellular heterogeneity in the mouse esophagus implicates the presence of a nonquiescent epithelial stem cell population. Cell Reports, 9(2), 701-11. https://doi.org/10.1016/j.celrep.2014.09.027

Domyan, E. T., Ferretti, E., Throckmorton, K., Mishina, Y., Nicolis, S. K., and Sun, X. (2011). Signaling through BMP receptors promotes respiratory identity in the foregut via repression of Sox2. Development (Cambridge, England), 138(5), 971-981. https://doi.org/10.1242/dev.053694

Doupe, D. P., Alcolea, M. P., Roshan, A., Zhang, G., Klein, a. M., Simons, B. D., and Jones, P. H. (2012). A Single Progenitor Population Switches Behavior to Maintain and Repair Esophageal Epithelium. Science, 337(6098), 1091-1093. https://doi.org/10.1126/science.1218835

Dye, B. R., Dedhia, P. H., Miller, A. J., Nagy, M. S., White, E. S., Shea, L. D., and Spence, J. R. (2016). A bioengineered niche promotes in vivo engraftment and maturation of pluripotent stem cell derived human lung organoids. ELife, 5(September2016). https://doi.org/10.7554/eLife.19732

Dye, B. R., Hill, D. R., Ferguson, M. A., Tsai, Y.-H., Nagy, M. S., Dyal, R., Wells, J. M., Mayhew, C. N., Nattiv, R., Klein, O. D., White, E. S., et al. (2015). In vitro generation of human pluripotent stem cell derived lung organoids. ELife, 4, e05098. https://doi.org/10.7554/eLife.05098

Fantes, J., Ragge, N. K., Lynch, S.-A., McGill, N. I., Collin, J. R. O., Howard-Peebles, P. N., Hayward, C., Vivian, A. J., Williamson, K., van Heyningen, V., and FitzPatrick, D. R. (2003). Mutations in SOX2 cause anophthalm ia. Nature Genetics, 33(4), 461-463. https://doi.org/10.1038/ng1120

Fausett, S. R., Brunet, L. J., and Klingensmith, J. (2014). BMP antagonism by Noggin is required in presumptive notochord cells for mammalian foregut morphogenesis. Developmental Biology, 391(1), 111-24. https://doi.org/10.1016/j.ydbio.2014.02.008

Goss, A. M., Tian, Y., Tsukiyama, T., Cohen, E. D., Zhou, D., Lu, M. M., Yamaguchi, T. P., and Morrisey, E. E. (2009). Wnt2/2b and beta-catenin signaling are necessary and sufficient to specify lung progenitors in the foregut. Developmental Cell, 17(2), 290-8. https://doi.org/10.1016/j.devcel.2009.06.005

Green, M. D., Chen, A., Nostro, M.-C., d'Souza, S. L., Schaniel, C., Lemischka, I. R., Gouon-Evans, V., Keller, G., and Snoeck, H.-W. (2011). Generation of anterior foregut endoderm from human embryonic and induced pluripotent stem cells. Nature Biotechnology, 29(3), 267-72. https://doi.org/10.1038/nbt.1788 Harris-Johnson, K. S., Domyan, E. T., Vezina, C. M., and Sun, X. (2009). beta-Catenin promotes respiratory progenitor identity in mouse foregut. Proceedings of the National Academy of Sciences of the United States of America, 106(38), 16287-92. https://doi.org/10.1073/pnas.0902274106

Hoskins, E. E., Morris, T. A., Higginbotham, J. M., Spardy, N., Cha, E., Kelly, P., Williams, D. A., Wikenheiser-Brokamp, K. A., Duensing, S., and Wells, S. I. (2009). Fanconi anemia deficiency stimulates HPV-associated hyperplastic growth in organotypic epithelial raft culture. Oncogene, 28(5), 674-685. https://doi.org/10.1038/onc.2008.416

Jho, E., Zhang, T., Domon, C., Joo, C.-K., Freund, J.-N., and Costantini, F. (2002). Wnt/beta-catenin/Tcf signaling induces the transcription of Axin2, a negative regulator of the signaling pathway. Molecular and Cellular Biology, 22(4), 1172-83. https://doi.org/10.1128/MCB.22.4.1172

Kalabis, J., Oyama, K., Okawa, T., Nakagawa, H., Michaylira, C. Z., Stairs, D. B., Figueiredo, J., Mahmood, U., Diehl, J. A., Herlyn, M., and Rustgi, A. K. (2008). A subpopulation of mouse esophageal basal cells has properties of stem cells with the capacity for self-renewal and lineage specification. Journal of Clinical Investigation, (118), 3860-3869. https://doi.org/10.1172/JCI35012

Kalabis, J., Wong, G. S., Vega, M. E., Natsuizaka, M., Robertson, E. S., Herlyn, M., Nakagawa, H., and Rustgi, A. K. (2012). Isolation and characterization of mouse and human esophageal epithelial cells in 3D organotypic culture. Nature Protocols, 7(2), 235-246. https://doi.org/10.1038/nprot.2011.437

Kasagi, Y., Chandramouleeswaran, P. M., Whelan, K. A., Tanaka, K., Giroux, V., Sharma, M., Wang, J., Benitez, A. J., DeMarshall, M., Tobias, J. W., Hamilton, K. E., et al. (2018). The Esophageal Organoid System Reveals Functional Interplay Between Notch and Cytokines in Reactive Epithelial Changes. Cmgh, 5(3), 333-352. https://doi.org/10.1016/j.jcmgh.2017.12.013

Kearns, N. a, Genga, R. M. J., Ziller, M., Kapinas, K., Peters, H., Brehm, M. a, Meissner, A., and Maehr, R. (2013). Generation of organized anterior foregut epithelia from pluripotent stem cells using small molecules. Stem Cell Research, 11(3), 1003-12. https://doi.org/10.1016/j.scr.2013.06.007

Kormish, J. D., Sinner, D., and Zorn, A. M. (2010). Interactions between SOX factors and Wnt/beta-catenin signaling in development and disease. Developmental Dynamics: An Official Publication of the American Association of Anatomists, 239(August 2009), 56-68. https://doi.org/10.1002/dvdy.22046 Li, H., Zhou, H., Fu, X., and Xiao, R. (2016). Directed differentiation of human embryonic stem cells into keratinocyte progenitors in vitro: an attempt with promise of clinical use. In vitro Cellular & Developmental Biology—Animal, 52(8), 885-893. https://doi.org/10.1007/s11626-016-0024-2

Longmire, T. a, Ikonomou, L., Hawkins, F., Christodoulou, C., Cao, Y., Jean, J. C., Kwok, L. W., Mou, H., Rajagopal, J., Shen, S. S., Dowton, A. a, et al. (2012). Efficient derivation of purified lung and thyroid progenitors from embryonic stem cells. Cell Stem Cell, 10(4), 398-411. https://doi.org/10.1016/j.stem.2012.01.019

Lustig, B., Jerchow, B., Sachs, M., Weiler, S., Pietsch, T., Karsten, U., van de Wetering, M., Clevers, H., Schlag, P. M., Birchmeier, W., and Behrens, J. (2002). Negative feedback loop of Wnt signaling through upregulation of conductin/axin2 in colorectal and liver tumors. Molecular and Cellular Biology, 22(4), 1184-93. https://doi.org/10.1128/MCB.22.4.1184

Mandegar, M. A., Huebsch, N., Frolov, E. B., Shin, E., Truong, A., Olvera, M. P., Chan, A. H., Miyaoka, Y., Holmes, K., Spencer, C. I., Judge, L. M., et al. (2016). CRISPR Interference Efficiently Induces Specific and Reversible Gene Silencing in Human iPSCs. Cell Stem Cell, 18(4), 541-553. https://doi.org/10.1016/j.stem.2016.01.022

Matt, N., Ghyselinck, N. B., Wendling, O., Chambon, P., and Mark, M. (2003). Retinoic acid-induced developmental defects are mediated by RARβ/RXR heterodimers in the pharyngeal endoderm. Development, 130 (10), 2083-2093. https://doi.org/10.1242/dev 0.00428

McCauley, H. A., and Wells, J. M. (2017). Pluripotent stem cell-derived organoids: using principles of developmental biology to grow human tissues in a dish. Development, 144(6), 958-962. https://doi.org/10.1242/dev.140731

McCracken, K. W., Aihara, E., Martin, B., Crawford, C. M., Broda, T., Treguier, J., Zhang, X., Shannon, J. M., Montrose, M. H., and Wells, J. M. (2017). Wnt/β-catenin promotes gastric fundus specification in mice and humans. Nature, 541(7636), 182-187. https://doi.org/10.1038/nature21021

McCracken, K. W., Catá, E. M., Crawford, C. M., Sinagoga, K. L., Schumacher, M., Rockich, B. E., Tsai, Y.-H., Mayhew, C. N., Spence, J. R., Zavros, Y., and Wells, J. M. (2014). Modelling human development and disease in pluripotent stem-cell-derived gastric organoids. Nature, 516(7531), 400-404. https://doi.org/10.1038/nature13863

McLin, V. a, Rankin, S. a, and Zorn, A. M. (2007). Repression of Wnt/beta-catenin signaling in the anterior endoderm is essential for liver and pancreas development. Development (Cambridge, England), 134(12), 2207-17. https://doi.org/10.1242/dev 0.001230

Meerbrey, K. L., Hu, G., Kessler, J. D., Roarty, K., Li, M. Z., Fang, J. E., Herschkowitz, J. I., Burrows, A. Ciccia, A., Sun, T., Schmitt, E. M., et al. (2011). The pINDUCER lentiviral toolkit for inducible RNA interference in vitro and in vivo. Proceedings of the National Academy of Sciences of the United States of America, 108(9), 3665-3670. https://doi.org/10.1073/pnas.1019736108

Múnera, J. O., Sundaram, N., Rankin, S. A., Hill, D., Watson, C., Mahe, M., Vallance, J. E., Shroyer, N., Sinagoga, K. L., Zarzoso-Lacoste, A., Hudson, J. R., et al. (2017). Differentiation of Human Pluripotent Stem Cells into Colonic Organoids via Transient Activation of BMP Signaling. Cell Stem Cell, 21(1), 51-64.e6. https://doi.org/10.1016/j.stem.2017.05.020

Niederreither, K., Subbarayan, V., Dolle, P., and Chambon, P. (1999). Embryonic retinoic acid synthesis is essential for early mouse post-implantation development. Nature Genetics, 21(4), 444-448. https://doi.org/10.1038/7788

Park, E. J., Sun, X., Nichol, P., Saijoh, Y., Martin, J. F., and Moon, A. M. (2008). System for tamoxifen-inducible expression of Cre-recombinase from the Foxa2 locus in mice. Developmental Dynamics, 237(2), 447-453. https://doi.org/10.1002/dvdy.21415

Que, J., Choi, M., Ziel, J. W., Klingensmith, J., and Hogan, B. L. M. (2006). Morphogenesis of the trachea and esophagus: current players and new roles for noggin and Bmps. Differentiation, 74(7), 422-437. https://doi.org/10.1111/j.1432-0436.2006.00096.x Que, J., Okubo, T., Goldenring, J. R., Nam, K.-T., Kurotani, R., Morrisey, E. E., Taranova, O., Pevny, L. H., and Hogan, B. L. M. (2007). Multiple dose-dependent roles for Sox2 in the patterning and differentiation of anterior foregut endoderm. Development (Cambridge, England), 134(13), 2521-31. https://doi.org/10.1242/dev.003855

Rankin, S. A., Han, L., McCracken, K. W., Kenny, A. P., Anglin, C. T., Grigg, E. A., Crawford, C. M., Wells, J. M., Shannon, J. M., and Zorn, A. M. (2016). A Retinoic Acid-Hedgehog Cascade Coordinates Mesoderm-Inducing Signals and Endoderm Competence during Lung Specification. Cell Reports, 16(1), 66-78. https://doi.org/10.1016/J.CELREP.2016.05.060

Rankin, S. a, Gallas, A. L., Neto, A., Gomez-Skarmeta, J. L., and Zorn, A. M. (2012). Suppression of Bmp4 signaling by the zinc-finger repressors Osr1 and Osr2 is required for Wnt/β-catenin-mediated lung specification in *Xenopus*. Development (Cambridge, England), 139(16), 3010-20. https://doi.org/10.1242/dev.078220

Rosekrans, S. L., Baan, B., Muncan, V., and van den Brink, G. R. (2015). Esophageal development and epithelial homeostasis. American Journal of Physiology—Gastrointestinal and Liver Physiology, 309(4), G216-228. https://doi.org/10.1152/ajpgi.00088.2015

Shaham, O., Smith, A. N., Robinson, M. L., Taketo, M. M., Lang, R. a, and Ashery-Padan, R. (2009). Pax6 is essential for lens fiber cell differentiation. Development (Cambridge, England), 136(15), 2567-2578. https://doi.org/10.1242/dev.032888

Sherwood, R. I., Chen, T.-Y. A., and Melton, D. (2009). Transcriptional dynamics of endodermal organ formation. Developmental Dynamics: An Official Publication of the American Association of Anatomists, 238(1), 29-42. https://doi.org/10.1002/dvdy.21810

Sinner, D., Kordich, J. J., Spence, J. R., Opoka, R., Rankin, S., Lin, S. J., Jonatan, D., Zorn, A. M., and Wells, J. M. (2007). Sox17 and Sox4 differentially regulate beta-catenin/T-cell factor activity and proliferation of colon carcinoma cells. Molecular and Cellular Biology, 27(22), 7802-7815. https://doi.org/10.1128/MCB.02179-06

Sive, H., Grainger, R., and Harland, R. (2000). Early Development of *Xenopus laevis*: A Laboratory Manual. Cold Spring Harbor, N.Y.: Cold Spring Harbor Laboratory Press.

Spence, J. R., Mayhew, C. N., Rankin, S. a, Kuhar, M. F., Vallance, J. E., Tolle, K., Hoskins, E. E., Kalinichenko, V. V, Wells, S. I., Zorn, A. M., Shroyer, N. F., and Wells, J. M. (2011). Directed differentiation of human pluripotent stem cells into intestinal tissue in vitro. Nature, 470(7332), 105-109. https://doi.org/10.1038/nature09691

Stevens, M. L., Chaturvedi, P., Rankin, S. A., Macdonald, M., Jagannathan, S., Yukawa, M., Barski, A., and Zorn, A. M. (2017). Genomic integration of Wnt/β-catenin and BMP/Smad1 signaling coordinates foregut and hindgut transcriptional programs. Development, 144(7), 1283-1295. https://doi.org/10.1242/dev.145789

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: A knowledge-based approach for interpreting genome-wide expression profiles. Proceedings of the National Academy of Sciences, 102(43), 15545-15550. https://doi.org/10.1073/pnas.0506580102

Tiso, N., Filippi, A., Pauls, S., Bortolussi, M., and Argenton, F. (2002). BMP signalling regulates anteroposterior endoderm patterning in zebrafish. Mechanisms of Development, 118(1-2), 29-37. Retrieved from http://www.ncbi.nlm.nih.gov/pubmed/12351167

Tsankov, A. M., Gu, H., Akopian, V, Ziller, M. J., Donaghey, J., Amit, I., Gnirke, A., and Meissner, A. (2015). Transcription factor binding dynamics during human ES cell differentiation. Nature, 518(7539), 344-9. https://doi.org/10.1038/nature14233

Van Raay, T. J., Moore, K. B., Iordanova, I., Steele, M., Jamrich, M., Harris, W. A., and Vetter, M. L. (2005). Frizzled 5 signaling governs the neural potential of progenitors in the developing *Xenopus* retina. Neuron, 46(1), 23-36. https://doi.org/10.1016/j.neuron.2005.02.023

Wang, Z., Done, P., Cardoso, W. V., and Niederreither, K. (2006). Retinoic acid regulates morphogenesis and patterning of posterior foregut derivatives. Developmental Biology, 297(2), 433-445. https://doi.org/10.1016/j.ydbio.2006.05.019

Watanabe, H., Ma, Q., Peng, S., Adelmant, G., Swain, D., Song, W., Fox, C., Francis, J. M., Pedamallu, C. S., DeLuca, D. S., Brooks, A. N., et al. (2014). SOX2 and p63 colocalize at genetic loci in squamous cell carcinomas. Journal of Clinical Investigation, 124(4), 1636-1645. https://doi.org/10.1172/JCI71545 Williamson, K. a., Hever, A. M., Rainger, J., Rogers, R. C., Magee, A., Fiedler, Z., Keng, W. T., Sharkey, F. H., McGill, N., Hill, C. J., Schneider, A., et al. (2006). Mutations in SOX2 cause anophthalmia-esophageal-genital (AEG) syndrome. Human Molecular Genetics, 15(9), 1413-1422. https://doi.org/10.1093/hmg/ddl064

Woo, J., Miletich, I., Kim, B.-M., Sharpe, P. T., and Shivdasani, R. a. (2011). Barx1-mediated inhibition of Wnt signaling in the mouse thoracic foregut controls tracheo-esophageal septation and epithelial differentiation. PLoS One, 6(7), e22493. https://doi.org/10.1371/journal.pone.0022493

Zhang, Y., Jiang, M., Kim, E., Lin, S., Liu, K., Lan, X., and Que, J. (2016). Development and Stem Cells of the Esophagus. Seminars in Cell & Developmental Biology, 66, 25-35. https://doi.org/10.1016/j.semcdb.2016.12.008

Zhou, C., Yang, X., Sun, Y., Yu, H., Zhang, Y., and Jin, Y. (2016). Comprehensive profiling reveals mechanisms of SOX2-mediated cell fate specification in human ESCs and NPCs. Cell Research, 26(2), 171-189. https://doi.org/10.1038/cr.2016.15

Zorn, A. M., and Wells, J. M. (2007). Molecular Basis of Vertebrate Endoderm Development. In International Review of Cytology (Vol. 259, pp. 49-111). https://doi.org/10.1016/S0074-7696(06)59002-3 Zorn, A. M., and Wells, J. M. (2009). Vertebrate Endoderm Development and Organ Formation. Annual Review of Cell and Developmental Biology, 25(1), 221-251. https://doi.org/10.1146/annurev.cellbio.042308.113344

Arnold, K., Sarkar, A., Yram, M. A., Polo, J. M., Bronson, R., Sengupta, S., Seandel, M., Geijsen, N., and Hochedlinger, K. (2011). Sox2+Adult Stem and Progenitor Cells Are Important for Tissue Regeneration and Survival of Mice. Cell Stem Cell, 9(4), 317-329. https://doi.org/10.1016/j.stem.2011.09.001

Auerbach, A. D. (2009). Fanconi anemia and its diagnosis. Mutation Research—Fundamental and Molecular Mechanisms of Mutagenesis, 668(1-2), 4-10. https://doi.org/10.1016/j.mrfmmm.2009.01.013

Bakker, S. T., de Winter, J. P., and Riele, H. t. (2013). Learning from a paradox: recent insights into Fanconi anaemia through studying mouse models. Disease Models & Mechanisms, 6(1), 40-47. https://doi.org/10.1242/dmm.009795

Blanchard, C., Stucke, E. M., Burwinkel, K., Caldwell, J. M., Collins, M. H., Ahrens, A., Buckmeier, B. K., Jameson, S. C., Greenberg, A., Kaul, A., Franciosi, J. P., et al. (2010). Coordinate Interaction between IL-13 and Epithelial Differentiation Cluster Genes in Eosinophilic Esophagitis. The Journal of Immunology, 184(7), 4033-4041. https://doi.org/10.4049/jimmunol.0903069

Caldwell, J. M., Paul, M., and Rothenberg, M. E. (2017). Novel immunologic mechanisms in eosinophilic esophagitis. Current Opinion in Immunology, 48, 114-121. https://doi.org/10.1016/j.coi.2017.08.006

Chen, X., Jiang, K., Fan, Z., Liu, Z., Zhang, P., Zheng, L., Peng, N., Tong, J., and Ji, G. (2012). Aberrant expression of Wnt and Notch signal pathways in Barrett's esophagus. Clinics and Research in Hepatology and Gastroenterology, 36(5), 473-483. https://doi.org/10.1016/j.clinre.2012.06.001

D'Mello, R. J., Caldwell, J. M., Azouz, N. P., Wen, T., Sherrill, J. D., Hogan, S. P., and Rothenberg, M. E. (2016). LRRC31 is induced by IL-13 and regulates kallikrein expression and barrier function in the esophageal epithelium. Mucosal Immunology, 9(3), 744-756. https://doi.org/10.1038/mi.2015.98

Davis, B. P., Stucke, E. M., Khorki, M. E., Litosh, V. A., Rymer, J. K., Rochman, M., Travers, J., Kottyan, L. C., and Rothenberg, M. E. (2016). Eosinophilic esophagitis-linked calpain 14 is an IL-13—induced protease that mediates esophageal epithelial barrier impairment. JCI Insight, 1(4). https://doi.org/10.1172/jci.insight.86355

De Jong, E. M., Felix, J. F., De Klein, A., and Tibboel, D. (2010). Etiology of esophageal atresia and tracheoesophageal fistula: "Mind the gap." Current Gastroenterology Reports, 12(3), 215-222. https://doi.org/10.1007/s11894-010-0108-1

De Jonge, P. J. F., Van Blankenstein, M., Grady, W. M., and Kuipers, E. J. (2014). Barrett's oesophagus: Epidemiology, cancer risk and implications for management. Gut, 63(1), 191-202. https://doi.org/10.1136/gutjnl-2013-305490

Fausett, S. R., and Klingensmith, J. (2012). Compartmentalization of the foregut tube: developmental origins of the trachea and esophagus. Wiley Interdisciplinary Reviews. Developmental Biology, 1(2), 184-202. https://doi.org/10.1002/wdev.12

Feng, Y., Chen, R., Da, M., Qian, B., and Mo, X. (2018). Identification of rare heterozygous missense mutations in FANCA in esophageal atresia patients using next generation sequencing. Gene, 661(January), 182-188. https://doi.org/10.1016/j.gene.2018.03.097

Furuta, G. T., and Katzka, D. A. (2015). Eosinophilic Esophagitis. New England Journal of Medicine, 373(17), 1640-1648. https://doi.org/10.1056/NEJMra1502863

Ghatak, S., Reveiller, M., Toia, L., Ivanov, A., Godfrey, T. E., and Peters, J. H. (2013). Bile acid at low pH reduces squamous differentiation and activates EGFR signaling in esophageal squamous cells in 3-D culture. Journal of Gastrointestinal Surgery: Official Journal of the Society for Surgery of the Alimentary Tract, 17(10), 1723-31. https://doi.org/10.1007/s11605-013-2287-1

Hagey, D. W., Klum, S., Kurtsdotter, I., Zaouter, C., Topcic, D., Andersson, O., Bergsland, M., and Muhr, J. (2018). SOX2 regulates common and specific stem cell features in the CNS and endoderm derived organs. PLOS Genetics, 14(2), e1007224. https://doi.org/10.1371/journal.pgen.1007224

Huo, X., Zhang, H. Y., Zhang, X. I., Lynch, J. P., Strauch, E. D., Wang, J. Y., Melton, S. D., Genta, R. M., Wang, D. H., Spechler, S. J., and Souza, R. F. (2010). Acid and Bile Salt-Induced CDX2 Expression Differs in Esophageal Squamous Cells From Patients With and Without Barrett's Esophagus. Gastroenterology, 139(1), 194-203.e1. https://doi.org/10.1053/j.gastro.2010.03.035

Jiang, M., Ku, W., Zhou, Z., Dellon, E. S., Falk, G. W., Nakagawa, H., Wang, M., Liu, K., Wang, J., Katzka, D. a, Peters, J. H., et al. (2015). BMP-driven NRF2 activation in esophageal basal cell differentiation and eosinophilic esophagitis. The Journal of Clinical Investigation, 125(14), 1-12. https://doi.org/10.1172/JCI78850DS1

Jiang, M., Li, H., Zhang, Y., Yang, Y., Lu, R., Liu, K., Lin, S., Lan, X., Wang, H., Wu, H., Zhu, J., et al. (2017). Transitional basal cells at the squamous-columnar junction generate Barrett's oesophagus. Nature, 550(7677), 529-533. https://doi.org/10.1038/nature24269

Kasagi, Y., Chandramouleeswaran, P. M., Whelan, K. A., Tanaka, K., Giroux, V., Sharma, Wang, J., Benitez, A. J., DeMarshall, M., Tobias, J. W., Hamilton, K. E., et al. (2018). The Esophageal Organoid System Reveals Functional Interplay Between Notch and Cytokines in Reactive Epithelial Changes. Cmgh, 5(3), 333-352. https://doi.org/10.1016/j.jcmgh.2017.12.013

Kazumori, H., Ishihara, S., and Kinoshita, Y. (2009). Roles of caudal-related homeobox gene Cdx1 in oesophageal epithelial cells in Barrett's epithelium development. Gut, 58(5), 620-628. https://doi.org/10.1136/gut.2008.152975

Kazumori, H., Ishihara, S., Rumi, M. A. K., Kadowaki, Y., and Kinoshita, Y. (2006). Bile acids directly augment caudal related homeobox gene Cdx2 expression in oesophageal keratinocytes in Barrett's epithelium. Gut, 55(1), 16-25. https://doi.org/10.1136/gut.2005.066209

KC, K., Rothenberg, M. E., and Sherrill, J. D. (2015). In vitro model for studying esophageal epithelial differentiation and allergic inflammatory responses identifies keratin involvement in eosinophilic esophagitis. PloS One, 10(6), e0127755. https://doi.org/10.1371/journal.pone.0127755

Kong, J., Crissey, M. A., Funakoshi, S., Kreindler, J. L., and Lynch, J. P. (2011). Ectopic Cdx2 expression in murine esophagus models an intermediate stage in the emergence of Barrett's esophagus. PLoS ONE, 6(4), 1-12. https://doi.org/10.1371/journal.pone.0018280

Kong, J., Nakagawa, H., Isariyawongse, B. K., Funakoshi, S., Silberg, D. G., Rustgi, A. and Lynch, J. P. (2009). Induction of intestinalization in human esophageal keratinocytes is a multistep process. Carcinogenesis, 30(1), 122-130. https://doi.org/10.1093/carcin/bgn227

Kuzmichev, A. N., Kim, S. K., D'Alessio, A. C., Chenoweth, J. G., Wittko, I. M., Campanati, and McKay, R. D. (2012). Sox2 acts through Sox21 to regulate transcription in pluripotent and differentiated cells. Current Biology, 22(18), 1705-1710. https://doi.org/10.1016/j.cub.2012.07.013

Leedham, S. J., Preston, S. L., McDonald, S. A. C., Elia, G., Bhandari, P., Poller, D., Harrison, R., Novelli, M. R., Jankowski, J. A., and Wright, N. A. (2008). Individual crypt genetic heterogeneity and the origin of metaplastic glandular epithelium in human Barrett's oesophagus. Gut, 57(8), 1041-1048. https://doi.org/10.1136/gut.2007.143339

Liu, K., Jiang, M., Lu, Y., Chen, H., Sun, J., Wu, S., Ku, W.-Y., Nakagawa, H., Kita, Y., Natsugoe, S., Peters, J. H., et al. (2013). Sox2 Cooperates with Inflammation-Mediated Stat3 Activation in the Malignant Transformation of Foregut Basal Progenitor Cells. Cell Stem Cell, 12(3), 304-315. https://doi.org/10.1016/j.stem.2013.01.007

Liu, T., Zhang, X., So, C. K., Wang, S., Wang, P., Yan, L., Myers, R., Chen, Z., Patterson, A. P., Yang, C. S., and Chen, X. (2007). Regulation of Cdx2 expression by promoter methylation, and effects of Cdx2 transfection on morphology and gene expression of human esophageal epithelial cells. Carcinogenesis, 28(2), 488-496. https://doi.org/10.1093/carcin/bgl176

Lubinsky, M. (2015). Sonic Hedgehog, VACTERL, and Fanconi anemia: Pathogenetic connections and therapeutic implications. American Journal of Medical Genetics, Part A, 167(11), 2594-2598. https://doi.org/10.1002/ajmg.a.37257

Mari, L., Milano, F., Parikh, K., Straub, D., Everts, V., Hoeben, K. K., Fockens, P., Buttar, N. S., and Krishnadath, K. K. (2014). A pSMAD/CDX2 complex is essential for the intestinalization of epithelial metaplasia. Cell Reports, 7(4), 1197-1210. https://doi.org/10.1016/j.celrep.2014.03.074

Meerbrey, K. L., Hu, G., Kessler, J. D., Roarty, K., Li, M. Z., Fang, J. E., Herschkowitz, J. I., Burrows, A. E., Ciccia, A., Sun, T., Schmitt, E. M., et al. (2011). The pINDUCER lentiviral toolkit for inducible RNA interference in vitro and in vivo. Proceedings of the National Academy of Sciences, 108(9),3665-3670. https://doi.org/10.1073/pnas.1019736108

Nebert, D. W., Dong, H., Bruford, E. A., Thompson, D. C., Joenje, H., and Vasiliou, V. (2016). Letter to the editor for "Update of the human and mouse Fanconi anemia genes." Human Genomics, 10(1), 25. https://doi.org/10.1186/s40246-016-0081-3

Que, J., Luo, X., Schwartz, R. J., and Hogan, B. L. M. (2009). Multiple roles for Sox2 in the developing and adult mouse trachea. Development (Cambridge, England), 136(11), 1899-1907. https://doi.org/10.1242/dev.034629

Robbins, D. J., Fei, D. L., and Riobo, N. A. (2012). The Hedgehog Signal Transduction Network. Science Signaling, 5(246), re6-re6. https://doi.org/10.1126/scisignal.2002906

Rochman, M., Travers, J., Miracle, C. E., Bedard, M. C., Wen, T., Azouz, N. P., Caldwell, J. M., KC, K., Sherrill, J. D., Davis, B. P., Rymer, J. K., et al. (2017). Profound loss of esophageal tissue differentiation in patients with eosinophilic esophagitis. Journal of Allergy and Clinical Immunology, 140(3), 738-749.e3. https://doi.org/10.1016/j.jaci.2016.11.042

Sarkar, A., Huebner, A. J., Sulahian, R., Anselmo, A., Xu, X., Flattery, K., Desai, N., Sebastian, C., Yram, M. A., Arnold, K., Rivera, M., et al. (2016). Sox2 Suppresses Gastric Tumorigenesis in Mice. Cell Reports, 16(7), 1929-1941. https://doi.org/10.1016/j.celrep.2016.07.034 van Dop, W. a., Rosekrans, S. L., Uhmann, a., Jaks, V., Offerhaus, G. J. a., van den Bergh Weerman, M. a., Kasper, M., Heijmans, J., Hardwick, J. C. H., Verspaget, H. W., Hommes, D. W., et al. (2012). Hedgehog signalling stimulates precursor cell accumulation and impairs epithelial maturation in the murine oesophagus. Gut, 62(3), 348-57. https://doi.org/10.1136/gutjnl-2011-301141

Vega, M. E., Giroux, V. V., Natsuizaka, M., Liu, M., Klein-Szanto, A. J., Stairs, D. B., Nakagawa, H., Wang, K. K., Wang, T. C., Lynch, J. P., and Rustgi, A. K. (2014). Inhibition of notch signaling enhances transdifferentiation of the esophageal squamous epithelium towards a Barrett's-like metaplasia via KLF4. Cell Cycle, 13(24), 3857-3866. https://doi.org/10.4161/15384101.2014.972875

Wang, D. H., Clemons, N. J., Miyashita, T., Dupuy, A. J., Zhang, W., Szczepny, A., Corcoran-Schwartz, I. M., Wilburn, D. L., Montgomery, E. A., Wang, J. S., Jenkins, N. A., et al. (2010). Aberrant Epithelial-Mesenchymal Hedgehog Signaling Characterizes Barrett's Metaplasia. Gastroenterology, 138(5), 1810-1822.e2. https://doi.org/10.1053/j.gastro.2010.01.048

Wu, L., Oshima, T., Li, M., Tomita, T., Fukui, H., Watari, J., and Miwa, H. (2018). Filaggrin and tight junction proteins are crucial for IL-13-mediated esophageal barrier dysfunction. American Journal of Physiology-Gastrointestinal and Liver Physiology, ajpgi.00404.2017. https://doi.org/10.1152/ajpgi.00404.2017

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of making an esophageal organoid (EO), comprising
   a. contacting a definitive endoderm with a BMP signaling pathway inhibitor, a Wnt signaling pathway activator, an FGF signaling pathway activator, and retinoic acid (RA), for a first period of time to form an anterior foregut culture, wherein said anterior foregut culture expresses SOX2 and HNFIB;
   b. contacting said anterior foregut culture with a BMP signaling pathway inhibitor, and an EGF signaling pathway activator for a second period of time sufficient to form a dorsal anterior foregut (dAFG) spheroid, wherein said dAFG spheroid expresses SOX2 and TP63 but does not express PDX1, PAX9, or NKX2.1;
   c. culturing said dAFG spheroid for a third period of time sufficient to allow formation of an esophageal organoid (EO), wherein said culturing is carried out in the presence of the EGF signaling pathway activator, and wherein the EO comprises a luminal structure.

2. The method of claim 1, wherein said BMP signaling pathway inhibitor is selected from Noggin, Dorsomorphin, LDN189, DMH-1, and combinations thereof.

3. The method of claim 1 wherein said BMP signaling pathway inhibitor is present at a concentration of about 50 to about 1500 ng/ml.

4. The method of claim 1, wherein said Wnt signaling pathway activator is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSK3β inhibitor, BIO, LY2090314, SB-216763, lithium, porcupine inhibitors IWP, LGK974, C59, SFRP inhibitor WAY-316606, beta-catenin activator DCA and combinations thereof.

5. The method of claim 1, wherein the concentration of said Wnt signaling pathway activator is about 50 to about 1500 ng/ml.

6. The method of claim 1, wherein the concentration of said FGF signaling pathway activator is about 50 to about 1500 ng/ml.

7. The method of claim 1, wherein said first period of time is about 2-4 days.

8. The method of claim 1, wherein said second period is 2-4 days.

9. The method of claim 1, wherein said third period is about 21 days to about 90 days.

10. The method of claim 1, wherein said definitive endoderm is derived from a pluripotent stem cell.

11. The method of claim 1, wherein said definitive endoderm is derived by contacting a pluripotent stem cell with molecules selected from Activin, the BMP subgroups of the TGF-beta superfamily of growth factors; Nodal, Activin A, Activin B, BMP4, Wnt3a, and a combinations thereof.

12. The method of claim 1, wherein said BMP signaling pathway inhibitor is Noggin.

13. The method of claim 1, wherein said step c is carried out for a period of time sufficient for the formation of a stratified epithelium lacking KRT8.

14. The method of claim 1, wherein said step c is carried out for a period of time sufficient for the formation a stratified squamous epithelium expressing regional keratins.

15. The method of claim 1, further comprising contacting the anterior foregut culture of step a) or the spheroid of step b) with a matrix selected from collagen, basement membrane matrix, and a combination thereof.

16. A composition comprising the EO produced by the method of claim 1, wherein said EO comprises a luminal structure and is characterized by being free of cornification.

17. A human esophageal organoid (HEO) composition, wherein said HEO composition comprises a luminal structure and is free of cornification and one or more of submucosal glands, transition zones, vasculature, immune cells, and submucosal layers.

18. The method of claim 1, wherein said definitive endoderm is a definitive endoderm monolayer, wherein greater than 90% of the cells in the DE monolayer co-express FOXA2 and SOX17.

19. The method of claim 1, wherein culturing said dAFG spheroid for the third period of time further comprises culturing in the presence of an FGF signaling pathway activator.

20. The method of claim 19, wherein said FGF signaling pathway activator is selected from the group consisting of FGF1, FGF2, FGF3, FGF4, FGF1O, FGF1 1, FGF12, FGF13, FGF14, FGF15, FGF16, FGF1 7, FGF18, FGF19, FGF20, FGF21, FGF22, FGF23, and combinations thereof.

21. The method of claim 20, wherein said FGF signaling pathway activator is FGF1O.

22. The method of claim 1, wherein said Wnt signaling pathway activator is CHIR9902 1.

23. The method of claim 1, wherein said anterior foregut culture does not express PROX1 and HNF6.

24. The method of claim 1, further comprising the step of enzymatically dissociating the EO to release progenitor cells, wherein said EO is at an age of about 3 weeks to about 10 weeks.

25. The method of claim 24, further comprising the step of expanding said progenitor cells in a monolayer.

* * * * *

SEQUENCE LISTING

<160> NUMBER OF SEQ ID NOS: 82

<210> SEQ ID NO 1
<211> LENGTH: 20
<212> TYPE: DNA
<213> ORGANISM: Artificial Sequence
<220> FEATURE:
<223> OTHER INFORMATION: DSG3 human forward primer

<400> SEQUENCE: 1
cgtggttgtc tccgctagaa                                            20

<210> SEQ ID NO 2
<211> LENGTH: 20
<212> TYPE: DNA
<213> ORGANISM: Artificial Sequence
<220> FEATURE:
<223> OTHER INFORMATION: DSG3 human reverse primer

<400> SEQUENCE: 2
ccgaggtagc attgagggtt                                            20

<210> SEQ ID NO 3
<211> LENGTH: 20
<212> TYPE: DNA
<213> ORGANISM: Artificial Sequence
<220> FEATURE:
<223> OTHER INFORMATION: KRT5 human forward primer

<400> SEQUENCE: 3
ctggtccaac tccttctcca                                            20

<210> SEQ ID NO 4
<211> LENGTH: 20
<212> TYPE: DNA
<213> ORGANISM: Artificial Sequence
<220> FEATURE:
<223> OTHER INFORMATION: KRT5 human reverse primer

<400> SEQUENCE: 4
ggagctcatg aacaccaagc                                            20

<210> SEQ ID NO 5
<211> LENGTH: 20
<212> TYPE: DNA
<213> ORGANISM: Artificial Sequence
<220> FEATURE:
<223> OTHER INFORMATION: FOXE1 human forward primer

<400> SEQUENCE: 5
cgacaacccc aaaaagtggc                                            20

<210> SEQ ID NO 6
<211> LENGTH: 20
<212> TYPE: DNA
<213> ORGANISM: Artificial Sequence
<220> FEATURE:
<223> OTHER INFORMATION: FOXE1 human reverse primer

<400> SEQUENCE: 6
gcccagtagt tgcccttacc                                            20

<210> SEQ ID NO 7
<211> LENGTH: 20
<212> TYPE: DNA
<213> ORGANISM: Artificial Sequence

```
<220> FEATURE:
<223> OTHER INFORMATION: TBX1 human forward primer

<400> SEQUENCE: 7
gtctatgtgg acccacgcaa                                              20

<210> SEQ ID NO 8
<211> LENGTH: 20
<212> TYPE: DNA
<213> ORGANISM: Artificial Sequence
<220> FEATURE:
<223> OTHER INFORMATION: TBX1 human reverse primer

<400> SEQUENCE: 8
ctgcgtgatc cgatggttct                                              20

<210> SEQ ID NO 9
<211> LENGTH: 19
<212> TYPE: DNA
<213> ORGANISM: Artificial Sequence
<220> FEATURE:
<223> OTHER INFORMATION: SFRP2 human forward primer

<400> SEQUENCE: 9
ccaccgagga agctccaaa                                               19

<210> SEQ ID NO 10
<211> LENGTH: 20
<212> TYPE: DNA
<213> ORGANISM: Artificial Sequence
<220> FEATURE:
<223> OTHER INFORMATION: SFRP2 human reverse primer

<400> SEQUENCE: 10
ttcaggtccc tttcggacac                                              20

<210> SEQ ID NO 11
<211> LENGTH: 20
<212> TYPE: DNA
<213> ORGANISM: Artificial Sequence
<220> FEATURE:
<223> OTHER INFORMATION: SOX2 human forward primer

<400> SEQUENCE: 11
gcttagcctc gtcgatgaac                                              20

<210> SEQ ID NO 12
<211> LENGTH: 20
<212> TYPE: DNA
<213> ORGANISM: Artificial Sequence
<220> FEATURE:
<223> OTHER INFORMATION: SOX2 human reverse primer

<400> SEQUENCE: 12
aaccccaaga tgcacaactc                                              20

<210> SEQ ID NO 13
<211> LENGTH: 20
<212> TYPE: DNA
<213> ORGANISM: Artificial Sequence
<220> FEATURE:
<223> OTHER INFORMATION: PAX9 human forward primer

<400> SEQUENCE: 13
ggtagggtaa ggagccatgc                                              20
```

```
<210> SEQ ID NO 14
<211> LENGTH: 20
<212> TYPE: DNA
<213> ORGANISM: Artificial Sequence
<220> FEATURE:
<223> OTHER INFORMATION: PAX9 human reverse primer

<400> SEQUENCE: 14
ctggagcagg aagccaagta                                                   20

<210> SEQ ID NO 15
<211> LENGTH: 20
<212> TYPE: DNA
<213> ORGANISM: Artificial Sequence
<220> FEATURE:
<223> OTHER INFORMATION: GATA4 human forward primer

<400> SEQUENCE: 15
tagccccaca gttgacacac                                                   20

<210> SEQ ID NO 16
<211> LENGTH: 17
<212> TYPE: DNA
<213> ORGANISM: Artificial Sequence
<220> FEATURE:
<223> OTHER INFORMATION: GATA4 human reverse primer

<400> SEQUENCE: 16
gtcctgcaca gcctgcc                                                      17

<210> SEQ ID NO 17
<211> LENGTH: 20
<212> TYPE: DNA
<213> ORGANISM: Artificial Sequence
<220> FEATURE:
<223> OTHER INFORMATION: KRT13 human forward primer

<400> SEQUENCE: 17
aggtgaagat ccgtgactgg                                                   20

<210> SEQ ID NO 18
<211> LENGTH: 19
<212> TYPE: DNA
<213> ORGANISM: Artificial Sequence
<220> FEATURE:
<223> OTHER INFORMATION: KRT13 human reverse primer

<400> SEQUENCE: 18
gttgttttca atggtggcg                                                    19

<210> SEQ ID NO 19
<211> LENGTH: 20
<212> TYPE: DNA
<213> ORGANISM: Artificial Sequence
<220> FEATURE:
<223> OTHER INFORMATION: KRT14 human forward primer

<400> SEQUENCE: 19
ggcctgctga gatcaaagac                                                   20

<210> SEQ ID NO 20
<211> LENGTH: 19
<212> TYPE: DNA
<213> ORGANISM: Artificial Sequence
<220> FEATURE:
<223> OTHER INFORMATION: KRT14 human reverse primer
```

```
<400> SEQUENCE: 20
tctgcagaag gacattggc                                                 19

<210> SEQ ID NO 21
<211> LENGTH: 20
<212> TYPE: DNA
<213> ORGANISM: Artificial Sequence
<220> FEATURE:
<223> OTHER INFORMATION: IVL human forward primer

<400> SEQUENCE: 21
ctgcctcagc cttactgtga                                                20

<210> SEQ ID NO 22
<211> LENGTH: 21
<212> TYPE: DNA
<213> ORGANISM: Artificial Sequence
<220> FEATURE:
<223> OTHER INFORMATION: IVL human reverse primer

<400> SEQUENCE: 22
ggaggaggaa cagtcttgag g                                              21

<210> SEQ ID NO 23
<211> LENGTH: 20
<212> TYPE: DNA
<213> ORGANISM: Artificial Sequence
<220> FEATURE:
<223> OTHER INFORMATION: LEF1 human forward primer

<400> SEQUENCE: 23
cactgtaagt gatgaggggg                                                20

<210> SEQ ID NO 24
<211> LENGTH: 20
<212> TYPE: DNA
<213> ORGANISM: Artificial Sequence
<220> FEATURE:
<223> OTHER INFORMATION: LEF1 human reverse primer

<400> SEQUENCE: 24
tggatctctt tctccaccca                                                20

<210> SEQ ID NO 25
<211> LENGTH: 20
<212> TYPE: DNA
<213> ORGANISM: Artificial Sequence
<220> FEATURE:
<223> OTHER INFORMATION: TCF1 human forward primer

<400> SEQUENCE: 25
gacttgacca tcttcgccac                                                20

<210> SEQ ID NO 26
<211> LENGTH: 21
<212> TYPE: DNA
<213> ORGANISM: Artificial Sequence
<220> FEATURE:
<223> OTHER INFORMATION: TCF1 human reverse primer

<400> SEQUENCE: 26
cctcaaagag ctggagaacc t                                              21

<210> SEQ ID NO 27
```

```
<211> LENGTH: 23
<212> TYPE: DNA
<213> ORGANISM: Artificial Sequence
<220> FEATURE:
<223> OTHER INFORMATION: HNF1B human forward primer

<400> SEQUENCE: 27
tcacagatac cagcagcatc agt                                              23

<210> SEQ ID NO 28
<211> LENGTH: 19
<212> TYPE: DNA
<213> ORGANISM: Artificial Sequence
<220> FEATURE:
<223> OTHER INFORMATION: HNF1B human reverse primer

<400> SEQUENCE: 28
gggcatcacc aggcttgta                                                   19

<210> SEQ ID NO 29
<211> LENGTH: 20
<212> TYPE: DNA
<213> ORGANISM: Artificial Sequence
<220> FEATURE:
<223> OTHER INFORMATION: PROX1 human forward primer

<400> SEQUENCE: 29
ggcattgaaa aactcccgta                                                  20

<210> SEQ ID NO 30
<211> LENGTH: 20
<212> TYPE: DNA
<213> ORGANISM: Artificial Sequence
<220> FEATURE:
<223> OTHER INFORMATION: PROX1 human reverse primer

<400> SEQUENCE: 30
acagggctct gaacatgcac                                                  20

<210> SEQ ID NO 31
<211> LENGTH: 20
<212> TYPE: DNA
<213> ORGANISM: Artificial Sequence
<220> FEATURE:
<223> OTHER INFORMATION: HNF6 human forward primer

<400> SEQUENCE: 31
tgttgcctct atccttccca                                                  20

<210> SEQ ID NO 32
<211> LENGTH: 19
<212> TYPE: DNA
<213> ORGANISM: Artificial Sequence
<220> FEATURE:
<223> OTHER INFORMATION: HNF6 human reverse primer

<400> SEQUENCE: 32
ggaggatgtg gaagtggct                                                   19

<210> SEQ ID NO 33
<211> LENGTH: 18
<212> TYPE: DNA
<213> ORGANISM: Artificial Sequence
<220> FEATURE:
<223> OTHER INFORMATION: PDX1 human forward primer

<400> SEQUENCE: 33
```
cgtccgcttg ttctcctc                                                18

<210> SEQ ID NO 34
<211> LENGTH: 20
<212> TYPE: DNA
<213> ORGANISM: Artificial Sequence
<220> FEATURE:
<223> OTHER INFORMATION: PDX1 human reverse primer

<400> SEQUENCE: 34
cctttcccat ggatgaagtc                                              20

<210> SEQ ID NO 35
<211> LENGTH: 20
<212> TYPE: DNA
<213> ORGANISM: Artificial Sequence
<220> FEATURE:
<223> OTHER INFORMATION: DeltaN isoform human forward primer

<400> SEQUENCE: 35
agccagaaga aaggacagca                                              20

<210> SEQ ID NO 36
<211> LENGTH: 21
<212> TYPE: DNA
<213> ORGANISM: Artificial Sequence
<220> FEATURE:
<223> OTHER INFORMATION: DeltaN isoform human reverse primer

<400> SEQUENCE: 36
tcgtgtactg tggctcacta a                                            21

<210> SEQ ID NO 37
<211> LENGTH: 21
<212> TYPE: DNA
<213> ORGANISM: Artificial Sequence
<220> FEATURE:
<223> OTHER INFORMATION: RFX6 human forward primer

<400> SEQUENCE: 37
ccagtttttg agctaagcga a                                            21

<210> SEQ ID NO 38
<211> LENGTH: 20
<212> TYPE: DNA
<213> ORGANISM: Artificial Sequence
<220> FEATURE:
<223> OTHER INFORMATION: RFX6 human reverse primer

<400> SEQUENCE: 38
tggcatcaaa gagagcagtg                                              20

<210> SEQ ID NO 39
<211> LENGTH: 19
<212> TYPE: DNA
<213> ORGANISM: Artificial Sequence
<220> FEATURE:
<223> OTHER INFORMATION: MNX1 human forward primer

<400> SEQUENCE: 39
ctgcctaaga tgcccgact                                               19

<210> SEQ ID NO 40
<211> LENGTH: 18
<212> TYPE: DNA

```
<213> ORGANISM: Artificial Sequence
<220> FEATURE:
<223> OTHER INFORMATION: MNX1 human reverse primer

<400> SEQUENCE: 40
agctgctggc tggtgaag                                                 18

<210> SEQ ID NO 41
<211> LENGTH: 18
<212> TYPE: DNA
<213> ORGANISM: Artificial Sequence
<220> FEATURE:
<223> OTHER INFORMATION: NKX2-1 (TTF1) human forward primer

<400> SEQUENCE: 41
ctcatgttca tgccgctc                                                 18

<210> SEQ ID NO 42
<211> LENGTH: 19
<212> TYPE: DNA
<213> ORGANISM: Artificial Sequence
<220> FEATURE:
<223> OTHER INFORMATION: NKX2-1 (TTF1) human reverse primer

<400> SEQUENCE: 42
gacaccatga ggaacagcg                                                19

<210> SEQ ID NO 43
<211> LENGTH: 19
<212> TYPE: DNA
<213> ORGANISM: Artificial Sequence
<220> FEATURE:
<223> OTHER INFORMATION: CDH1 (E-CAD) human forward primer

<400> SEQUENCE: 43
gaccggtgca atcttcaaa                                                19

<210> SEQ ID NO 44
<211> LENGTH: 19
<212> TYPE: DNA
<213> ORGANISM: Artificial Sequence
<220> FEATURE:
<223> OTHER INFORMATION: CDH1 (E-CAD) human reverse primer

<400> SEQUENCE: 44
ttgacgccga gagctacac                                                19

<210> SEQ ID NO 45
<211> LENGTH: 20
<212> TYPE: DNA
<213> ORGANISM: Artificial Sequence
<220> FEATURE:
<223> OTHER INFORMATION: AXIN2 human forward primer

<400> SEQUENCE: 45
ctggtgcaaa gacatagcca                                               20

<210> SEQ ID NO 46
<211> LENGTH: 20
<212> TYPE: DNA
<213> ORGANISM: Artificial Sequence
<220> FEATURE:
<223> OTHER INFORMATION: AXIN2 human reverse primer

<400> SEQUENCE: 46
agtgtgaggt ccacggaaac                                               20
```

<210> SEQ ID NO 47
<211> LENGTH: 20
<212> TYPE: DNA
<213> ORGANISM: Artificial Sequence
<220> FEATURE:
<223> OTHER INFORMATION: KRT4 human forward primer

<400> SEQUENCE: 47
cctgagatcc agaaagtccg                                               20

<210> SEQ ID NO 48
<211> LENGTH: 20
<212> TYPE: DNA
<213> ORGANISM: Artificial Sequence
<220> FEATURE:
<223> OTHER INFORMATION: KRT4 human reverse primer

<400> SEQUENCE: 48
ttccatttgg tctccaggac                                               20

<210> SEQ ID NO 49
<211> LENGTH: 22
<212> TYPE: DNA
<213> ORGANISM: Artificial Sequence
<220> FEATURE:
<223> OTHER INFORMATION: CDX2 human forward primer

<400> SEQUENCE: 49
ctggagctgg agaaggagtt tc                                            22

<210> SEQ ID NO 50
<211> LENGTH: 24
<212> TYPE: DNA
<213> ORGANISM: Artificial Sequence
<220> FEATURE:
<223> OTHER INFORMATION: CDX2 human reverse primer

<400> SEQUENCE: 50
attttaacct gcctctcaga gagc                                          24

<210> SEQ ID NO 51
<211> LENGTH: 20
<212> TYPE: DNA
<213> ORGANISM: Artificial Sequence
<220> FEATURE:
<223> OTHER INFORMATION: NESTIN human forward primer

<400> SEQUENCE: 51
gagggaagtc ttggagccac                                               20

<210> SEQ ID NO 52
<211> LENGTH: 19
<212> TYPE: DNA
<213> ORGANISM: Artificial Sequence
<220> FEATURE:
<223> OTHER INFORMATION: NESTIN human reverse primer

<400> SEQUENCE: 52
aagatgtccc tcagcctgg                                                19

<210> SEQ ID NO 53
<211> LENGTH: 20
<212> TYPE: DNA
<213> ORGANISM: Artificial Sequence
<220> FEATURE:

<223> OTHER INFORMATION: HOXA1 human forward primer

<400> SEQUENCE: 53
gtacggctac ctgggtcaac                                               20

<210> SEQ ID NO 54
<211> LENGTH: 20
<212> TYPE: DNA
<213> ORGANISM: Artificial Sequence
<220> FEATURE:
<223> OTHER INFORMATION: HOXA1 human reverse primer

<400> SEQUENCE: 54
acttgggtct cgttgagctg                                               20

<210> SEQ ID NO 55
<211> LENGTH: 20
<212> TYPE: DNA
<213> ORGANISM: Artificial Sequence
<220> FEATURE:
<223> OTHER INFORMATION: HOXB1 human forward primer

<400> SEQUENCE: 55
aacccaccca agacagcgaa                                               20

<210> SEQ ID NO 56
<211> LENGTH: 21
<212> TYPE: DNA
<213> ORGANISM: Artificial Sequence
<220> FEATURE:
<223> OTHER INFORMATION: HOXB1 human reverse primer

<400> SEQUENCE: 56
cgcgcttctt ctgcttcatt c                                             21

<210> SEQ ID NO 57
<211> LENGTH: 20
<212> TYPE: DNA
<213> ORGANISM: Artificial Sequence
<220> FEATURE:
<223> OTHER INFORMATION: CYP26C1 human forward primer

<400> SEQUENCE: 57
gttcccttca gtggcctacg                                               20

<210> SEQ ID NO 58
<211> LENGTH: 20
<212> TYPE: DNA
<213> ORGANISM: Artificial Sequence
<220> FEATURE:
<223> OTHER INFORMATION: CYP26C1 human reverse primer

<400> SEQUENCE: 58
acagccgact ccttcagctc                                               20

<210> SEQ ID NO 59
<211> LENGTH: 22
<212> TYPE: DNA
<213> ORGANISM: Artificial Sequence
<220> FEATURE:
<223> OTHER INFORMATION: OTX2 human forward primer

<400> SEQUENCE: 59
ggaagcactg tttgccaaga cc                                            22

```
<210> SEQ ID NO 60
<211> LENGTH: 22
<212> TYPE: DNA
<213> ORGANISM: Artificial Sequence
<220> FEATURE:
<223> OTHER INFORMATION: OTX2 human reverse primer

<400> SEQUENCE: 60
ctgttgttgg cggcacttag ct                                              22

<210> SEQ ID NO 61
<211> LENGTH: 21
<212> TYPE: DNA
<213> ORGANISM: Artificial Sequence
<220> FEATURE:
<223> OTHER INFORMATION: CRNN human forward primer

<400> SEQUENCE: 61
tgtgattgtg aaccccacg a                                                21

<210> SEQ ID NO 62
<211> LENGTH: 20
<212> TYPE: DNA
<213> ORGANISM: Artificial Sequence
<220> FEATURE:
<223> OTHER INFORMATION: CRNN human reverse primer

<400> SEQUENCE: 62
gcactctcgc tcagtgtctt                                                 20

<210> SEQ ID NO 63
<211> LENGTH: 22
<212> TYPE: DNA
<213> ORGANISM: Artificial Sequence
<220> FEATURE:
<223> OTHER INFORMATION: TMPRSS11A human forward primer

<400> SEQUENCE: 63
gtctcctggt tcacttccta gt                                              22

<210> SEQ ID NO 64
<211> LENGTH: 22
<212> TYPE: DNA
<213> ORGANISM: Artificial Sequence
<220> FEATURE:
<223> OTHER INFORMATION: TMPRSS11A human reverse primer

<400> SEQUENCE: 64
gtgttgcttt gtccgaaatt gt                                              22

<210> SEQ ID NO 65
<211> LENGTH: 22
<212> TYPE: DNA
<213> ORGANISM: Artificial Sequence
<220> FEATURE:
<223> OTHER INFORMATION: TMPRSS11D human forward primer

<400> SEQUENCE: 65
gcagtcacca tagctctact tg                                              22

<210> SEQ ID NO 66
<211> LENGTH: 23
<212> TYPE: DNA
<213> ORGANISM: Artificial Sequence
<220> FEATURE:
<223> OTHER INFORMATION: TMPRSS11D human reverse primer
```

```
<400> SEQUENCE: 66
ccactcaaag tcctgtattc ctg                                      23

<210> SEQ ID NO 67
<211> LENGTH: 21
<212> TYPE: DNA
<213> ORGANISM: Artificial Sequence
<220> FEATURE:
<223> OTHER INFORMATION: CPHA (PPIA) human forward primer

<400> SEQUENCE: 67
cccaccgtgt tcttcgacat t                                        21

<210> SEQ ID NO 68
<211> LENGTH: 22
<212> TYPE: DNA
<213> ORGANISM: Artificial Sequence
<220> FEATURE:
<223> OTHER INFORMATION: CPHA (PPIA) human reverse primer

<400> SEQUENCE: 68
ggacccgtat gctttaggat ga                                       22

<210> SEQ ID NO 69
<211> LENGTH: 20
<212> TYPE: DNA
<213> ORGANISM: Artificial Sequence
<220> FEATURE:
<223> OTHER INFORMATION: ID1 human forward primer

<400> SEQUENCE: 69
ctgctctacg acatgaacgg                                          20

<210> SEQ ID NO 70
<211> LENGTH: 22
<212> TYPE: DNA
<213> ORGANISM: Artificial Sequence
<220> FEATURE:
<223> OTHER INFORMATION: ID1 human reverse primer

<400> SEQUENCE: 70
gaaggtccct gatgtagtcg at                                       22

<210> SEQ ID NO 71
<211> LENGTH: 20
<212> TYPE: DNA
<213> ORGANISM: Artificial Sequence
<220> FEATURE:
<223> OTHER INFORMATION: ID3 human forward primer

<400> SEQUENCE: 71
gagaggcact cagcttagcc                                          20

<210> SEQ ID NO 72
<211> LENGTH: 22
<212> TYPE: DNA
<213> ORGANISM: Artificial Sequence
<220> FEATURE:
<223> OTHER INFORMATION: ID3 human reverse primer

<400> SEQUENCE: 72
tccttttgtc gttggagatg ac                                       22

<210> SEQ ID NO 73
<211> LENGTH: 20
```

```
<212> TYPE: DNA
<213> ORGANISM: Artificial Sequence
<220> FEATURE:
<223> OTHER INFORMATION: HES5 human forward primer

<400> SEQUENCE: 73
gaaaaaccga ctgcggaagc                                              20

<210> SEQ ID NO 74
<211> LENGTH: 20
<212> TYPE: DNA
<213> ORGANISM: Artificial Sequence
<220> FEATURE:
<223> OTHER INFORMATION: HES5 human reverse primer

<400> SEQUENCE: 74
gacgaaggct tgctgtgct                                               20

<210> SEQ ID NO 75
<211> LENGTH: 20
<212> TYPE: DNA
<213> ORGANISM: Artificial Sequence
<220> FEATURE:
<223> OTHER INFORMATION: FST human forward primer

<400> SEQUENCE: 75
tgccacctga gaaaggctac                                              20

<210> SEQ ID NO 76
<211> LENGTH: 25
<212> TYPE: DNA
<213> ORGANISM: Artificial Sequence
<220> FEATURE:
<223> OTHER INFORMATION: FST human reverse primer

<400> SEQUENCE: 76
tcttcacagg actttgcttt gatac                                        25

<210> SEQ ID NO 77
<211> LENGTH: 20
<212> TYPE: DNA
<213> ORGANISM: Artificial Sequence
<220> FEATURE:
<223> OTHER INFORMATION: NOG human forward primer

<400> SEQUENCE: 77
tggtggacct catcgaacac                                              20

<210> SEQ ID NO 78
<211> LENGTH: 20
<212> TYPE: DNA
<213> ORGANISM: Artificial Sequence
<220> FEATURE:
<223> OTHER INFORMATION: NOG human reverse primer

<400> SEQUENCE: 78
atgaagcctg ggtcgtagtg                                              20

<210> SEQ ID NO 79
<211> LENGTH: 27
<212> TYPE: DNA
<213> ORGANISM: Artificial Sequence
<220> FEATURE:
<223> OTHER INFORMATION: CCL26 human forward primer

<400> SEQUENCE: 79
```

-continued

```
aactccgaaa caattgtgac tcagctg                                            27

<210> SEQ ID NO 80
<211> LENGTH: 24
<212> TYPE: DNA
<213> ORGANISM: Artificial Sequence
<220> FEATURE:
<223> OTHER INFORMATION: CCL26 human reverse primer

<400> SEQUENCE: 80
gtaactctgg gaggaaacac cctc                                               24

<210> SEQ ID NO 81
<211> LENGTH: 21
<212> TYPE: DNA
<213> ORGANISM: Artificial Sequence
<220> FEATURE:
<223> OTHER INFORMATION: CDH26 human forward primer

<400> SEQUENCE: 81
tgcttttctt gttgcgatgc t                                                  21

<210> SEQ ID NO 82
<211> LENGTH: 19
<212> TYPE: DNA
<213> ORGANISM: Artificial Sequence
<220> FEATURE:
<223> OTHER INFORMATION: CDH26 human reverse primer

<400> SEQUENCE: 82
cttgccataa ccccagctc                                                     19
```